United States Patent
Stein et al.

(10) Patent No.: US 7,659,281 B2
(45) Date of Patent: *__Feb. 9, 2010__

(54) HMG-COA REDUCTASE INHIBITORS

(75) Inventors: Philip D. Stein, Pennington, NJ (US);
Steven P. Seitz, Swarthmore, PA (US);
David J. Carini, Wallingford, CT (US);
Yan Shi, Flourtown, PA (US); Jeffrey A. Robl, Newtown, PA (US); Jay A. Markwalder, New London, PA (US);
Chunhong He, Boothwyn, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 106 days.

This patent is subject to a terminal disclaimer.

(21) Appl. No.: 11/789,335

(22) Filed: Apr. 24, 2007

(65) Prior Publication Data

US 2007/0249583 A1 Oct. 25, 2007

Related U.S. Application Data

(60) Provisional application No. 60/794,733, filed on Apr. 25, 2006.

(51) Int. Cl.
*A01N 43/42* (2006.01)
*A61K 31/44* (2006.01)
*C07D 221/18* (2006.01)
*C07D 221/22* (2006.01)

(52) U.S. Cl. .................................. 514/279; 546/26

(58) Field of Classification Search .................. None
See application file for complete search history.

(56) References Cited

U.S. PATENT DOCUMENTS

| | | | |
|---|---|---|---|
| 4,906,624 A | 3/1990 | Chucholowski et al. |
| 4,925,852 A | 5/1990 | Kesseler et al. |
| 5,006,530 A | 4/1991 | Angerbauer et al. |
| 5,169,857 A | 12/1992 | Angerbauer et al. |
| 5,177,080 A | 1/1993 | Angerbauer et al. |
| 5,686,433 A | 11/1997 | Robl |
| 5,753,675 A | 5/1998 | Wattanasin |
| 6,620,821 B2 * | 9/2003 | Robl ........................... 514/290 |
| 6,627,636 B2 | 9/2003 | Robl |
| 6,812,345 B2 | 11/2004 | Robl et al. |
| 6,875,867 B2 | 4/2005 | Brodfuehrer et al. |

FOREIGN PATENT DOCUMENTS

| | | |
|---|---|---|
| EP | 0306929 A2 | 3/1989 |
| EP | 0307342 A2 | 3/1989 |
| EP | 0325129 A2 | 7/1989 |
| EP | 0325130 A2 | 7/1989 |
| EP | 0491226 A | 6/1992 |
| EP | 0444533 A | 6/1997 |
| EP | 0818197 A | 1/1998 |

OTHER PUBLICATIONS

"Fibric Acid", http://medical-dictionary.thefreedictionary.com/fibric+acid, accessed Dec. 30, 2008.*
Sietsema et al. Expert Opinion on Investigational Drugs, 1994, 3(12), 1255-76.*
J. Robl et al., "Phosphorous Containing Inhibitors of HMG-CoA Reductase. 2. [1]Synthesis and Biological Activities of a Series of Substituted Pyridines Containing A Hydroxyphosphinyl Moiety[2]", J. Med. Chem., 34, 2804-2815, 1991.

* cited by examiner

*Primary Examiner*—James O Wilson
*Assistant Examiner*—Noble Jarrell
(74) *Attorney, Agent, or Firm*—Burton Rodney

(57) ABSTRACT

Compounds are provided of the following structure are HMG CoA reductase inhibitors and thus are active in inhibiting cholesterol biosynthesis, modulating blood serum lipids, for example, lowering LDL cholesterol and/or increasing HDL cholesterol, and treating hyperlipidemia and dyslipidemia, hypercholesterolemia, hypertriglyceridemia and atherosclerosis

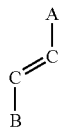

wherein variables A and B are defined herein.

8 Claims, No Drawings

HMG-COA REDUCTASE INHIBITORS

This application claims the benefit of U.S. provisional application Ser. No. 60/794,733 filed Apr. 25, 2006, the contents of which are herein incorporated by reference.

FIELD OF THE INVENTION

The present invention relates to pyridine-containing compounds and pharmaceutical compositions useful as hypocholesterolemic and hypolipidemic agents. More particularly, this invention concerns (1) certain inhibitors of the enzyme 3-hydroxy-3-methylglutaryl-coenzyme A reductase (HMG-CoA reductase) that include a pyridine-containing nucleus attached by means of a linker to an HMG-binding domain sidechain, (2) pharmaceutical compositions containing such compounds and (3) a method of lowering blood serum cholesterol levels and modulating blood serum lipids employing such pharmaceutical compositions.

BRIEF DESCRIPTION OF THE INVENTION

In one aspect of the invention, compounds are provided having the formula

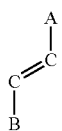

1 wherein
A is chosen from

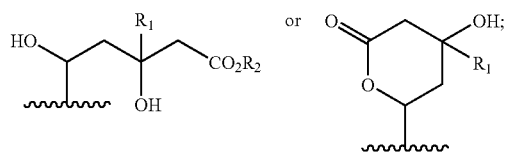

B is chosen from

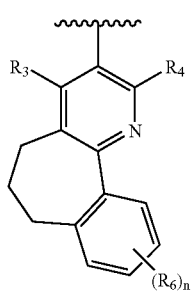

B1

-continued

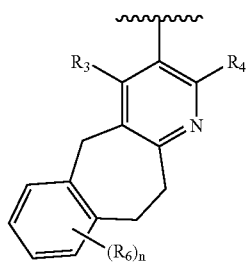

B2

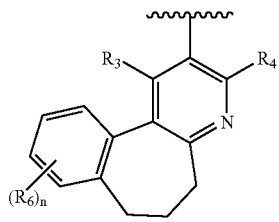

B3

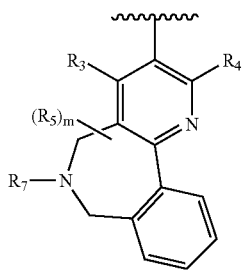

B4

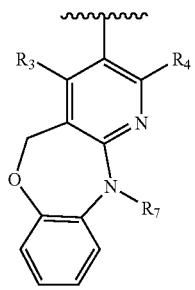

B5

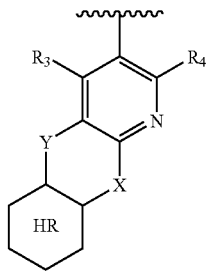

B6

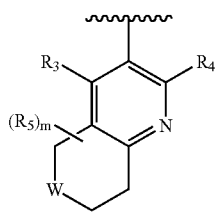

B7

-continued

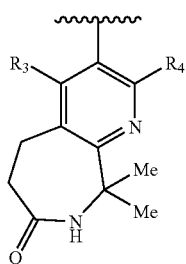

wherein
n is 1 or 2;
m is 0, 1 or 2;
X is a direct bond or

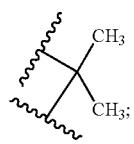

Y is
$(CH_2)_2$,
$(CH_2)_3$,
$(CH_2)_4$,

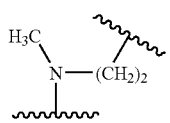

where the N-atom is attached to

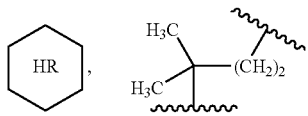

where the quaternary C-atom is attached to

or —$CH_2$—O—$CH_2$; and

is a heterocyclic ring;

with respect to ring system B6,

B8
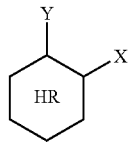

represents a heterocyclo ring and linking groups X and Y which is selected from the following:

| Combination | Y (attached to atom labeled*) |  | X (attached to atom labeled**) |
|---|---|---|---|
| B6a | —$(CH_2)_3$— |  | Direct bond |
| B6b | —$(CH_2)_3$— | 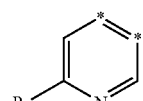 | Direct bond |
| B6c | —$(CH_2)_3$— | 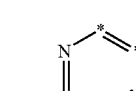 | Direct bond |
| B6d | —$(CH_2)_2$— | 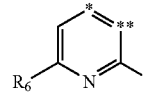 | Direct bond |
| B6e | —$(CH_2)_3$— | 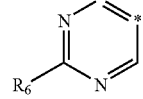 | Direct bond |
| B6f | 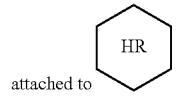 wherein the N-atom is attached to 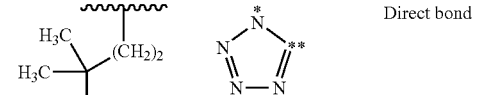 | 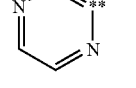 | Direct bond |
| B6g |  | | Direct bond |

-continued

| Combination | Y (attached to atom labeled*) | HR (ring) | X (attached to atom labeled**) |
|---|---|---|---|
| B6h | —(CH$_2$)$_2$— | tetrazole (*N, N, N, N**) | Direct bond |
| B6i | —(CH$_2$)$_3$— | tetrazole | Direct bond |
| B6j | —(CH$_2$)$_4$— | tetrazole | Direct bond |
| B6k | —(CH$_2$)$_2$— | tetrazole (N*, N**) | C(CH$_3$)$_2$ (gem-dimethyl) |
| B6l | —CH$_2$—O—CH$_2$— | pyrrolidinone (*N**, C=O) | Direct bond |
| B6m | —CH$_2$—O—CH$_2$— | pyrazole (*N, N**) | Direct bond |
| B6n | —CH$_2$—O—CH$_2$— | triazole (*N, N**, N) | Direct bond |
| B6o | —(CH$_2$)$_3$— | triazole with R$_6$—N | Direct bond |
| B6p | —(CH$_2$)$_3$— | triazole with N—R$_6$ | Direct bond |
| B6q | —(CH$_2$)$_3$— | oxo-imidazole with R$_6$ | Direct bond |
| B6r | —(CH$_2$)$_2$— | oxadiazole (*N, N**, O, N) | Direct bond |

Note: when B6 is B6b, B6c, B6d or B6e and R6 is OH, the structures may be drawn herein or below as one or the other of the tautomers:

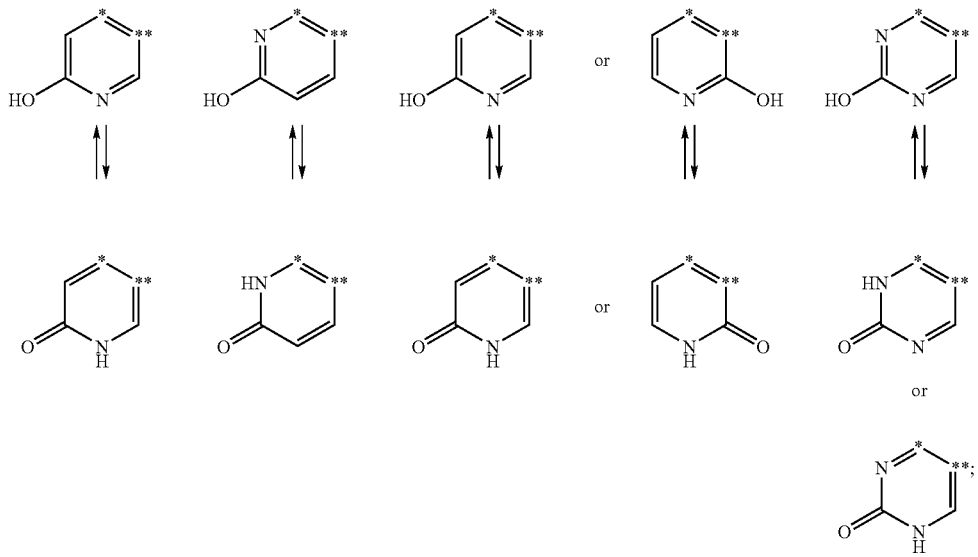

when B is B1,
R$_6$ (a substituent in the benzo ring) is, when n=1,
nitro,
—N(H)C(O)NR$_8$R$_9$,
—N(H)C(O)CH$_2$NMe$_2$,
—N(H)C(O)NH$_2$
tetrazole linked through its carbon atom and which is optionally substituted by methyl,
methyl substituted with either N(H)SO$_2$Me or N(H)C(O)NHMe,
SO$_2$N(H)R$_{10}$,
C(O)N(H)R$_{11}$,
—N=C(NH$_2$)NH$_2$ or

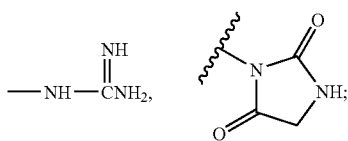

or
R$_6$ is identical at each occurrence and is, when n=2,
CN,
CO$_2$H,
COOMe; or
R$_6$ is, when R$_3$ is 3-carboxy-4-fluorophenyl and n=1 or 2,
H,
alkyl,
alkenyl,
alkynyl,
cycloalkyl,
aryl,
heterocyclo, or
an alkyl substitutent as defined hereinafter;

when B is B2,
R$_6$ is
N(H)C(O)N(H)R$_{12}$, or
tetrazole attached through its carbon atom and which is optionally substituted by methyl;

when B is B3,
R$_6$ is NC(O)N(H)R$_{13}$;

when B is B4,
m is 0 or 1,
R$_5$ is oxo, and
R$_7$ is
H,
C(O)alkyl,
C(O)heterocyclo,
C(O)NR$_{14}$R$_{15}$, or
SO$_2$alkyl;

when B is B5,
R$_7$ is SO$_2$alkyl;

when B is B6b,
R$_6$ is
OH,
Oalkyl,
H,
CN,
C(O)NH$_2$, or
CO$_2$H;

when B is B6c,
R$_6$ is
OH,
heterocyclo,
NR$_{14}$R$_{15}$,
N(H)SO$_2$R$_{16}$,
N(H)C(O)N(H)R$_{16}$,
CO$_2$H,
C(O)NR$_{14}$R$_{15}$,
C(O)NH-heterocyclo, or
C(O)heterocyclo;

when B is B6d,
one of R$_6$ or R$_{6a}$ is OH, and
the other is H;

when B is B6e,
R$_6$ is
H,
alkyl,
NR$_{14}$R$_{15}$,
Oalkyl,
NH—CN,
OH,
C(O)NR$_{14}$R$_{15}$, or
COOH;

when B is B6o, B6p or B6q,
R$_6$ is R$_{17}$;

when B is B7,
W is

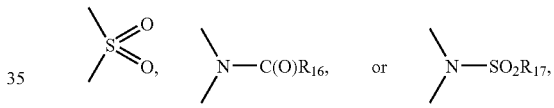

m=0, 1 or 2, and
R$_5$ is alkyl;
R$_1$ and R$_2$ are independently selected from H or lower alkyl;
R$_3$ and R$_4$ are independently selected from
H,
alkyl,
alkenyl,
alkynyl,
cycloalkyl,
aryl, or
heterocyclo (wherein the attachment atom in the heterocyclo group is a carbon);
R$_8$ is H, or methyl;
R$_9$ is
alkyl (which is optionally substituted by one or more groups independently selected from
carboxy,
methylamino,
dimethylamino,
aminoalkyl,
and/or hydroxyl,
alkyl substituted by carboxy and amino, or
heterocyclo;
R$_{10}$ is
H,
alkyl which is optionally substituted with one or more groups independently selected from
hydroxy,
dimethylamino and/or 4-morpholino, SO$_2$Me,
C(O)Me, or
C(O)NHMe;
R$_{11}$ is
alkyl (which is substituted with dimethylamino),
MeO,
SO$_2$Me, or
heterocyclo such as

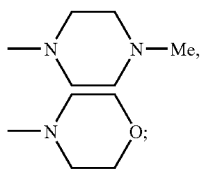 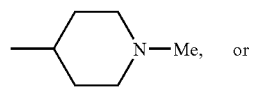

R$_{12}$ is alkyl which is optionally substituted with one or more groups independently selected from carboxy, and/or hydroxy, or is heterocyclo;
R$_{13}$ is alkyl substituted by carboxy;
R$_{14}$ and R$_{15}$ are each independently
H,
alkyl, or
cycloalkyl;
R$_{16}$ is
alkyl,
cycloalkyl,
alkenyl,
alkynyl,
aryl, or
heterocyclo;
R$_{17}$ is
alkyl,
cycloalkyl, or
aryl;

and including pharmaceutically acceptable salts thereof, esters thereof, prodrug esters thereof, and all stereoisomers thereof.

Preferred are compounds of formula 1 of the invention wherein
R$_1$ is H;
the A group is a free acid, a physiologically acceptable and hydrolyzable ester or δ lactone thereof, or an alkali metal salt, alkaline earth metal salt or an amine salt or an amino acid salt;
C═C is trans;
R$_3$ is aryl;
R$_4$ is alkyl or cycloalkyl; and
B is B1 or B4.

More preferred are a subset of the preferred compounds of formula 1 wherein
R$_3$ is 4-fluorophenyl or 3-carboxy-4-fluorophenyl;
R$_4$ is isopropyl;
the stereochemistry of the heptenoic acid chain (i.e., the A-C═C fragment of formula 1) is (3-R, 5-S); and
B is B1 or B4.

Another aspect of the invention provides pharmaceutical compositions useful as hypolipidemic or hypocholesterolemic agents, or hypotriglyceridemic agents, or anti-Alzheimer's agents, or anti-osteoporosis agents as well as other uses as described herein, which contain a hypolipidemic or hypocholesterolemic or hypotriglyceridemic or anti-Alzheimer's disease or anti-osteoporosis amount, or other therapeutically effective amount (depending upon use) of a compound of formula 1 in accordance with this invention, in combination with a pharmaceutically acceptable carrier.

Another aspect of the invention provides a method of inhibiting cholesterol biosynthesis or lowering blood serum cholesterol levels and/or modulating blood serum cholesterol levels such as lowering LDL cholesterol and/or increasing HDL cholesterol, and/or lowering triglycerides, or treating dyslipidemia, mixed dyslipidemia, hyperlipidemia, hypercholesterolemia, hypo α-lipoproteinemia, LDL Pattern B, LDL Pattern A, hyperlipoproteinemia or hypertriglyceridemia, and other aberrations of apolipoprotein B metabolism, or reducing levels of Lp(a), or treating or preventing other cholesterol-related diseases, or treating or preventing or reversing progression of atherosclerosis, or preventing or treating Alzheimer's disease, or preventing or treating osteoporosis and/or osteopenia, or reducing inflammatory markers such as C-reactive protein, or preventing or treating low grade vascular inflammation, or preventing or treating stroke, or preventing or treating dementia, or preventing and treating coronary heart disease (including primary and secondary prevention of myocardial infarction), or preventing or treating stable and unstable angina, or primary prevention of coronary events, or secondary prevention of cardiovascular events, or preventing or treating peripheral vascular disease, preventing or treating peripheral arterial disease, or preventing or treating acute vascular syndromes, or preventing or reducing the risk of undergoing myocardial revascularization procedures, or preventing or treating microvascular diseases such as nephropathy, neuropathy, retinopathy and nephrotic syndrome or preventing or treating hypertension in a patient in need of such treatment by administering a therapeutically effective amount of a compound of structure 1 or pharmaceutical composition containing same in accordance with the present invention as defined above.

In addition, in another aspect of the invention, a method is provided for preventing or treating diabetes, especially Type 2 diabetes, and related diseases such as insulin resistance, hyperglycemia, hyperinsulinemia, elevated blood levels of fatty acids or glycerol, obesity, Syndrome X, diabetic complications, dysmetabolic syndrome, and related diseases, and sexual dysfunction, wherein a therapeutically effective amount of a compound of structure 1 or composition containing same is administered to a patient in need of treatment.

In addition, in still another aspect of the invention, a method is provided for preventing and treating malignant lesions (such as ductal carcinoma in situ of the breast and lobular carcinoma in situ of the breast), premalignant lesions (such as fibroadenoma of the breast and prostatic intraepithelial neoplasia (PIN), gastrointestinal malignencies, liposarcomas and various other epithelial tumors (including breast, prostate, colon, ovarian, gastric and lung), cancer-induced asthenia (fatigue), irritable bowel syndrome, Crohn's disease, gastric ulceritis, and gallstones, and HIV infection, other infectious diseases, drug-induced lipodystrophy, and proliferative diseases such as psoriasis, wherein a therapeutically effective amount of a compound of structure 1 or a composition containing same is administered to a human patient in need of treatment.

In addition, in yet another aspect of the invention, a method is provided for improving coagulation homeostasis including reducing plasminogen activating inhibitor (PAI)-1 activity, reducing fibrinogen, and/or reducing platelet aggregation, and/or improving endothelial function, wherein a therapeutically effective amount of a compound of structure 1 or a composition containing same is administered to a patient in need of treatment.

In addition, in another aspect of the invention, a method is provided for treating cholesterol related diseases, diabetes and related diseases, cardiovascular diseases, cerebrovascular diseases as defined above and hereinafter and other diseases as set out above, wherein a therapeutically effective amount of a combination of a compound of structure 1 and a hypolipidemic agent, and/or lipid modulating agent and/or antidiabetic agent and/or cardiovascular agent, cerebrovascular agent, and/or other type of therapeutic agent, is administered to a patient in need of treatment.

In the above methods of the invention wherein a combination is administered, the compound of structure 1 will be employed in a weight ratio to the other therapeutic agent (depending upon its mode of operation) within the range from about 0.01:1 to about 500:1, preferably from about 0.5:1 to about 100:1.

DETAILED DESCRIPTION OF THE INVENTION

The compounds of the invention are useful in inhibiting the enzyme HMG-CoA reductase, and are useful as hypocholesterolemic agents, dyslipidemic agents, hypolipidemic agents, hypotriglyceridemic agents, anti-Alzheimer's disease agents, and antiosteoporosis agents as well as other uses as described herein.

The term "coronary events" as employed herein refers to myocardial infarction, myocardial revascularization procedures, angina, cardiovascular death and acute coronary syndrome.

The term "cardiovascular diseases or events" as employed herein refers to atherosclerosis of the coronary arteries, myocardial infarction, including primary MI and secondary MI, recurrent myocardial infarction, angina pectoris (including stable and unstable angina), congestive heart failure, and sudden cardiac death.

The term "cerebrovascular diseases or events" as employed herein refers to cerebral infarction or stroke (caused by vessel blockage or hemorrhage), or transient ischemia attack (TIA), syncope, atherosclerosis of the intracranial and/or extracranial arteries, and the like.

The term "cholesterol-related diseases" as employed herein refers to diseases involving elevated levels of LDL cholesterol, diseases involving regulation of LDL receptors, diseases involving reduced levels of HDL cholesterol, dyslipidemia, hyperlipidemia, elevated LDL Pattern B, elevated LDL Pattern A, hypercholesterolemia, hypo α-lipoproteinemia (low HDL cholesterol syndrome), hyperlipoproteinemia, elevated Lp(a) levels, hypertriglyceridemia, other aberrations of apolipoprotein B metabolism, heterozygous familial, presumed familial combined and non-familial (non-FH) forms of primary hypercholesterolemia (including Frederickson Types IIa and IIb), cholesterol ester storage disease, and cholesterol ester transfer protein disease, and related diseases.

The conditions, diseases, and maladies collectively referenced to as "Syndrome X" or Dysmetabolic Syndrome (as detailed in Johansson, $J.\ Clin.\ Endocrinol.\ Metab.$, 1997, 82:727-734, and other publications) include hyperglycemia and/or prediabetic insulin resistance syndrome, and is characterized by an initial insulin resistant state generating hyperinsulinemia, dyslipidemia, and impaired glucose tolerance, which can progress to Type II diabetes, characterized by hyperglycemia, which can progress to diabetic complications.

The term "diabetes and related diseases" refers to Type II diabetes, Type I diabetes, impaired glucose tolerance, obesity, hyperglycemia, Syndrome X, dysmetabolic syndrome, diabetic complications and hyperinsulinemia.

The conditions, diseases and maladies collectively referred to as "diabetic complications" include retinopathy, neuropathy and nephropathy, and other known complications of diabetes.

The term "other type(s) of therapeutic agents" as employed herein refers to one or more antidiabetic agents (other than compounds of formula 1), one or more anti-obesity agents, and/or one or more lipid-lowering agents, one or more lipid modulating agents (including anti-atherosclerosis agents), other types of anti-atherosclerosis agents, and/or one or more antiplatelet agents, one or more agents for treating hypertension, one or more anti-cancer drugs, one or more agents for treating arthritis, one or more anti-osteoporosis agents, one or more agents for treating immunomodulatory diseases, and/or one or more agents for treating anorexia nervosa.

The term "lipid-modulating" agent as employed herein refers to agents which lower LDL and/or raise HDL and/or lower triglycerides and/or lower total cholesterol and/or other known mechanisms for therapeutically treating lipid disorders.

The term "other types of anti-atherosclerosis agents" as employed herein refers to conventional anti-atherosclerosis agents including lipoxygenase inhibitors, ACAT inhibitors, PPARα agonists, dual PPARα/γ agonists, CETP inhibitors, antioxidants, PPAR δ agonists, phospholipase inhibitors including PLA-2 inhibitors and/or other known anti-atherosclerotic agents.

The terms pharmaceutically acceptable "salt" and "salts" refer to basic salts formed with inorganic and organic bases. Such salts include ammonium salts; alkali metal salts, such as lithium, sodium and potassium salts; alkaline earth metal salts, such as calcium and magnesium salts; and other salts, such as zinc and aluminum; salts with organic bases, such as amine salts (e.g., diethanolamine, ethylenediamine, t-butylamine, t-octylamine, dicyclohexylamine, benzathine, N-methyl-D-glucamine, tris-(hydroxymethyl)aminomethane (TRIS), methylamine, dehydroabietylamine and hydrabamine salts); and salts with amino acids like arginine, lysine and the like; and zwitterions, the so-called "inner salts". Non-toxic, pharmaceutically acceptable salts are preferred, although other salts are also useful, e.g., in isolating or purifying the product. Preferred are sodium and calcium salts.

The term pharmaceutically acceptable "salt" and "salts" also includes acid addition salts. These are formed, for example, with strong inorganic acids, such as mineral acids, for example sulfuric acid, phosphoric acid or a hydrohalic acid such as HCl or HBr, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methanesulfonic acid or p-toluenesulfonic acid.

Unless otherwise indicated, the term "alkyl" or "alk" as employed herein alone or as part of another group includes both straight and branched chain hydrocarbons, containing 1 to 20 carbons, preferably 1 to 10 carbons, more preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Lower alkyl refers to such groups containing 1-6 carbon atoms. Unless specified otherwise, alkyl groups may be optionally substituted with 1 or more 'alkyl substituents' which may be the same or different at each occurrence. These substituents may occur at any place and in any combination that provides a stable compound. These substituents may be halogen, nitro, cyano, $OR_{22}$, alkyl which may be substituted with one or more occurrences of $R_{23}$, alkenyl which may be substituted with one or more occurrences of $R_{23}$, alkynyl which may be substituted with one or more occurrences of $R_{23}$, cycloalkyl which may be substituted with one or more occurrences of $R_{23}$, aryl which may be substituted with one or more occurrences of $R_{23}$, heterocyclo which may be substituted with one or more occurrences of $R_{23}$, $SR_{22}$, $SO_2R_{22}$, $COOR_{22}$, $C(O)R_{22}$, $CONR_{24}R_{25}$, $SO_2NR_{24}R_{25}$, $SO_2N(H)C(O)R_{22}$, $SO_2N(H)CO_2R_{22}$ wherein $R_{22}$ is not H, $NR_{24}R_{25}$, $N(R_{24})SO_2R_{25}$, $N(R_{24})C(O)_mR_{25}$ (m=1,2), $N(R_{24})C(O)NR_{25}R_{26}$, $N(R_{24})SO_2NR_{25}R_{26}$, $OC(O)R_{22}$, $OC(O)OR_{22}$, $OC(O)NR_{25}R_{26}$, $C(O)N(H)SO_2NR_{25}R_{26}$, $C(O)N(H)SO_2R_{25}$, oxo (or keto, i.e. =O), thioxo (i.e., =S), imino (i.e., $=NR_{27}$), $NR_{27}-C(=NR_{28})R_{29}$, $NR_{27}-C(=NR_{28})NR_{29}R_{30}$, $C(=NR_{27})NR_{28}R_{29}$, $OC(=NR_{27})NR_{28}R_{29}$, $OC(=NR_{27})R_{28}$, $C(=NR_{27})R_{28}$, $C(=NR_{27})OR_{22}$;

$R_{22}$ is selected from H, $C_1$-$C_8$ alkyl, $C_2$-$C_8$ alkenyl, $C_2$-$C_8$ alkynyl, $C_3$-$C_8$ cycloalkyl, $C_6$-$C_{10}$ aryl, or $C_1$-$C_9$ heterocyclo each of which may be substituted with 1 to 3 independent occurrences of $R_{23}$;

$R_{24}$, $R_{25}$, and $R_{26}$ are selected from $C_1$-$C_8$ alkyl, $C_2$-$C_8$ alkenyl, $C_2$-$C_8$ alkynyl, $C_3$-$C_8$ cycloalkyl, $C_6$-$C_{10}$ aryl, or $C_1$-$C_9$ heterocyclo each of which may be substituted with 1 to 3 independent occurrences of $R_{23}$, or $R_{24}$ and $R_{25}$, or $R_{24}$ and $R_{26}$ or $R_{25}$ and $R_{26}$ may be joined by an alkylene or an alkenylene chain to form a 5- to 8-membered heterocyclo ring which is defined as for heterocyclo wherein the substitutents may be one or more occurrences of $R_{23}$;

$R_{27}$, $R_{28}$, $R_{29}$, or $R_{30}$ are independently selected from H, nitro, cyano, OH, $O(C_1$-$C_6$ alkyl), $C(O)R_{22}$, $C(O)NR_{24}R_{25}$, $CO_2R_{22}$ (with the proviso that $R_{22}$ is not H), $SO_2R_{22}$, $SO_2NR_{24}R_{25}$, $C_1$-$C_8$ alkyl, $C_2$-$C_8$ alkenyl, $C_2$-$C_8$ alkynyl, $C_3$-$C_8$ cycloalkyl, $C_6$-$C_{10}$ aryl, or $C_1$-$C_9$ heterocyclo or $R_{27}$ and $R_{28}$ or $R_{27}$ and $R_{29}$ or $R_{27}$ and $R_{30}$ or $R_{28}$ and $R_{29}$ or $R_{28}$ and $R_{30}$ or $R_{29}$ and $R_{30}$ may be joined by an alkylene or alkenylene chain to form a 5-8 membered ring that may be optionally substituted with one or more occurrences of $R_{23}$;

$R_{23}$ is selected from halogen, nitro, cyano, $OR_{31}$, alkyl optionally substituted with halogen, cycloalkyl optionally substituted with halogen, aryl optionally substituted with halogen, hydroxy, nitro, methoxy, trifluoromethyl, cyano, carbomethoxy, $CONH_2$, or CHO, heterocyclo optionally substituted with halogen, hydroxy, nitro, methoxy, trifluoromethyl, cyano, carbomethoxy, $CONH_2$, or CHO, $SR_{31}$, $CO_2R_{31}$, $C(O)R_{31}$, $CONR_{32}R_{33}$, $SO_2NR_{32}R_{33}$, $NR_{32}R_{33}$, $N(R_{32})SO_2R_{33}$, $N(R_{32})C(O)_mR_{33}$ (m=1,2), $N(R_{32})C(O)NR_{33}R_{34}$, $N(R_{32})SO_2NR_{33}R_{34}$, $OC(O)R_{31}$, $OC(O)OR_{31}$, $SO_2R_{31}$, $SO_2N(H)C(O)R_{31}$, $SO_2N(H)CO_2R_{31}$ wherein $R_{31}$ is not H, $C(O)N(H)SO_2NR_{32}R_{33}$, $C(O)N(H)SO_2R_{31}$, $OC(O)NR_{32}R_{33}$, $NR_{35}-C(=NR_{36})R_{37}$, $NR_{35}-C(=NR_{36})OR_{31}$, $NR_{35}-C(=NR_{36})NR_{37}R_{38}$, $C(=NR_{35})NR_{36}R_{37}$, $OC(=NR_{35})R_{36}$, $OC(=NR_{35})NR_{36}R_{37}$, $C(=NR_{35})OR_{31}$;

$R_{31}$ is selected from unsubstituted alkyl, alkenyl, unsubstituted alkynyl, unsubstituted cycloalkyl, unsubstituted aryl, unsubstituted heterocyclo;

$R_{32}$, $R_{33}$ and $R_{34}$ are selected from unsubstituted alkyl, unsubstituted alkenyl, unsubstituted alkynyl, unsubstituted cycloalkyl, unsubstituted aryl, unsubstituted heterocyclo, or $R_{32}$ and $R_{33}$ or $R_{32}$ and $R_{34}$ or $R_{33}$ and $R_{34}$ may be joined by an unsubstituted alkylene or unsubstituted alkenylene chain to form a 5-8 membered unsubstituted heterocyclo ring; and $R_{35}$, $R_{36}$, $R_{37}$, $R_{38}$ are selected from nitro, cyano, unsubstituted alkyl, unsubstituted alkenyl, unsubstituted alkynyl, unsubstituted cycloalkyl, unsubstituted aryl, unsubstituted heterocyclo, or $R_{35}$ and $R_{36}$, or $R_{35}$ and $R_{37}$ or $R_{35}$ and $R_{38}$ or $R_{36}$ and $R_{37}$ or $R_{36}$ and $R_{38}$ or $R_{37}$ and $R_{38}$ may be joined by an unsubstituted alkylene chain or unsubstituted alkenylene chain to form a 5- to 8-membered unsubstituted heterocyclo ring.

Unless otherwise indicated, the term "cycloalkyl" as employed herein alone or as part of another group includes saturated or partially unsaturated (i.e. containing one or more carbon-carbon double bonds) cyclic hydrocarbon groups containing 1 to 3 rings, containing a total of 3 to 20 carbons forming the ring(s), preferably 3 to 10 carbons, forming the ring. Polycyclic systems may contain fused or bridged rings or both. In addition, the cycloalkyl group may be fused to 1 or 2 aryl rings. Examples include cyclopropyl, cyclobutyl, cyclopentyl, cyclohexyl, cycloheptyl, cyclooctyl, cyclodecyl and cyclododecyl, cyclohexenyl,

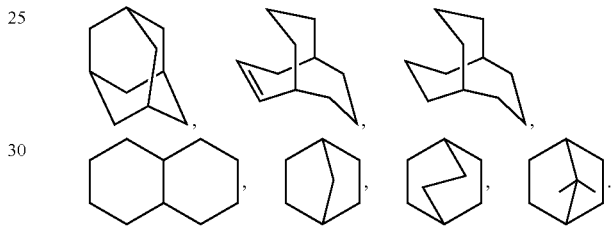

Cycloalkyl groups may be substituted with 1 or more 'cycloalkyl substituents' which may be the same or different at each occurrence. These substituents may occur at any place in any combination that provides a stable compound. These substituents may be any of the substituents for alkyl set out above.

The term "alkanoyl" as used herein alone or as part of another group refers to alkyl linked to a carbonyl group.

Unless otherwise indicated, the term "alkenyl" as used herein by itself or as part of another group refers to straight or branched chain radicals of 2 to 20 carbons, preferably 2 to 12 carbons, and more preferably 2 to 8 such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. Lower alkenyl refers to such groups containing 2-6 carbon atoms. Alkenyl groups may be optionally substituted with 1 or more 'alkenyl substituents' which may be the same or different at each occurrence. These substituents may occur at any place in any combination that provides a stable compound. These substituents may be any of those set out for substitutents for alkyl as defined above.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. Lower alkynyl refers to such groups containing 1-6 carbon atoms. Alkynyl groups may be optionally substituted with 1 or more 'alkynyl substituents' which may be the same or different at each occurrence. These substitutents may occur at any place in any combination that provides a stable compound. These substitutents may be any of the substitutents for alkyl as set out above.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring. Aryl groups may be substituted with 1 or more 'aryl substitutents' which may be the same or different at each occurrence. These substitutents may occur at any place in any combination that provides a stable compound. These substitutents may be any of the substitutents set out for alkyl as defined above.

Unless otherwise indicated, the term "lower alkoxy", "alkoxy", "aryloxy", "aralkoxy" or "heterocycloalkoxy" as employed herein alone or as part of another group includes any of the above alkyl, aralkyl, aryl, or heterocyclo groups linked to an oxygen atom.

Unless otherwise indicated, the term "acyl" as employed herein by itself or part of another group, as defined herein, refers to an organic radical linked to a carbonyl

group; examples of acyl groups include any of the $R^1$ groups attached to a carbonyl, such as alkanoyl, alkenoyl, aroyl, aralkanoyl, heteroaroyl, cycloalkanoyl, heterocycloalkanoyl and the like.

Unless otherwise indicated, the term "heterocyclo" as used herein alone or as part of another group refers to a monocyclic or multicyclic ring system wherein one or more of the ring atoms are elements other than carbon. Preferred systems have 1 to 4 of the atoms independently selected from N, O or S. The ring system may be unsaturated, partially saturated, fully saturated or aromatic. Heterocyclo groups containing more than one ring may be fused or bridged. Heteroatoms may be optionally oxidized. Attachment may be through any available atom in the ring system. Heterocyclo groups may be optionally substituted with 1 or more 'heterocyclo substitutents' which may be the same or different at each occurrence. These substitutents may occur at any place in any combination that provides a stable compound. These substitutents may be any of the substitutents for alkyl as set out above.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides. The heteroaryl group may optionally include 1 to 4 substitutents such as any of the substitutents set out above for alkyl. Examples of heteroaryl groups include the following:

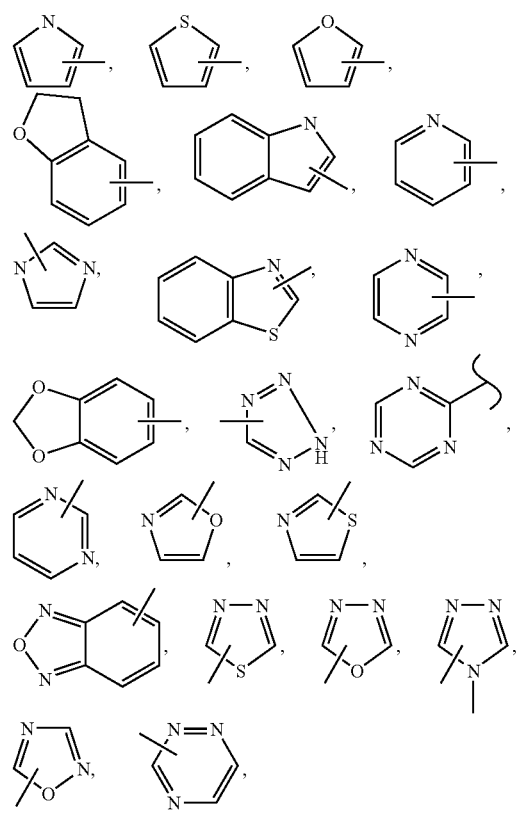

and the like.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_r$ (where r is 1, 2 or 3), such as

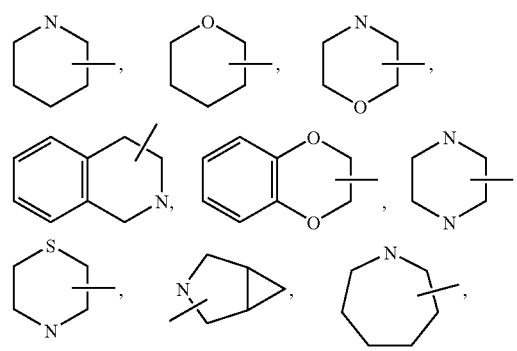

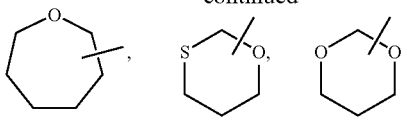

and the like. The above groups may include 1 to 4 substitutents such as alkyl, halo, oxo and/or any of the alkyl substitutents set out herein. In addition, any of the cycloheteroalkyl rings can be fused to a cycloalkyl, aryl, heteroaryl or cycloheteroalkyl ring.

As defined above, alkyl, alkenyl, alkynyl, cycloalkyl, aryl, and heterocyclo groups may be attached through one or more single bonds to one or more attachment atoms. In addition, these groups may be attached by double bonds to attachment atoms, and these groups may be referred to as 'alkylidene', 'alkenylidene', 'alkynylidene', 'cycloalkylidene' or 'heterocyclidene' groups. Examples include methylidene ($=CH_2$), ethylidene ($=CHCH_3$), ethenylidene ($=C=CH_2$), cyclohexylidene

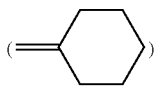

and 2-pyranylidene

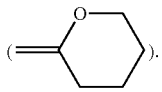

These groups may be substituted as described above for alkyl, alkenyl, alkynyl, cycloalkyl, and heterocyclo.

All stereoisomers of the compounds of the instant invention are contemplated, either in admixture or in pure or substantially pure form. The compounds of the present invention can have asymmetric centers at any of the carbon atoms including any one or the R substitutents. Consequently, compounds of formula 1 can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

The compounds of formula 1 of the invention can have asymmetric centers at certain of the nitrogen or sulfur atoms. Consequently, these isomers or mixtures thereof are part of the present invention.

The compounds of formula 1 of the invention may also display other instances of chirality, such as atropisomerism. Thus, these isomers or mixtures thereof are part of the invention.

The compounds of formula 1 of the invention may also contain varying amounts of isotopes of carbon, hydrogen, nitrogen, oxygen, sulfur, halogen, etc.; such as $^{13}C$, $^{14}C$, deuterium, tritium, $^{15}N$, $^{18}O$, $^{128}I$, etc. Some of the isotopic content is naturally occurring, but the compounds of the present invention may be enriched or depleted in one or more of these. Thus, these isotopes or mixtures thereof are part of the invention.

The term "prodrug esters" as employed herein includes esters and carbonates formed by reacting one or more hydroxyls of compounds of formula 1 with alkyl, alkoxy, or aryl substituted acylating agents employing procedures known to those skilled in the art to generate acetates, pivalates, methylcarbonates, benzoates and the like. In addition, the term includes prodrug esters which are known in the art for carboxylic acid esters such as methyl, ethyl, benzyl and the like.

Examples of such prodrug esters include

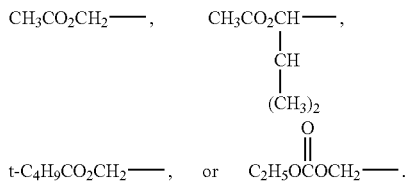

Other examples of suitable prodrug esters include

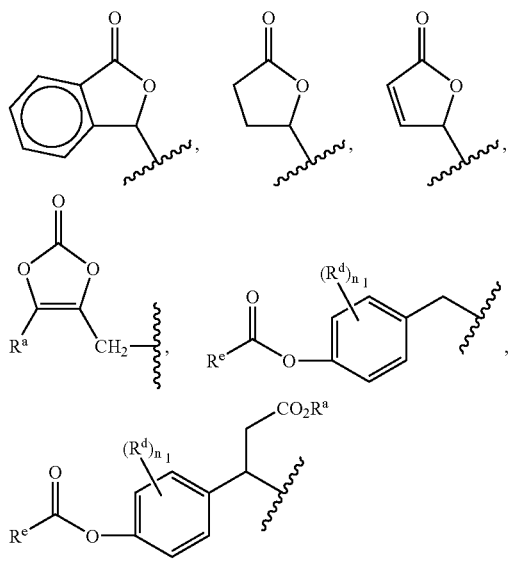

wherein $R^a$ can be H, alkyl (such as methyl or t-butyl), arylalkyl (such as benzyl) or aryl (such as phenyl); $R^d$ is H, alkyl, halogen or alkoxy, $R^e$ is alkyl, aryl, arylalkyl or alkoxyl, and $n_1$ is 0, 1 or 2.

Compounds of formula 1 of the invention may be prepared by the following methods. Those skilled in the art will recognize that other reagents, catalysts, reaction conditions, solvents, etc. may be used to effect the transformations outlined in the following schemes. In addition, those skilled in the art will recognize common functional group transformations among the more specialized reactions in the schemes. These common transformations (e.g., amide formation, hydrolysis, acylation, sulfonylation, esterification, hydrogenation/hydrogenolysis, etc.) may be accomplished those skilled in the art with a variety of reagents, catalysts, reaction conditions, and solvents already known to them. Additional functional groups and substitutents as specified for compounds of formula 1 may be readily incorporated using modifications and extensions of the methods described. Such steps are common organic transformations and are known to those skilled in the art of organic synthesis.

The compounds of the invention (i.e., formula 1) are synthesized by first constructing the pyridine ring from acyclic and/or simpler cyclic precursors and then appending the A group of formula 1 in protected form. Before, during or after these key processes, functional groups, substitutents and protecting groups are added/modified/removed as needed.

For many compounds of the invention, this pyridine ring-forming strategy requires a ketone precursor.

Synthesis of Ketone Intermediates

The syntheses of ketone precursors for compounds of formula 1 wherein B is B1 or B2 or B3 are shown in Schemes 1a-1d. The starting materials are commercially available or are compounds known to those skilled in the art.

As seen in Scheme 1a, nitration of known compound 1-1 using fuming nitric acid in sulfuric acid provides nitro intermediate 1-2 which is hydrogenated and acetylated in one step using hydrogen, palladium on carbon, and acetic anhydride in acetic acid solvent at elevated temperature to provide intermediate acid 1-3. Acid 1-3 is cyclized and deacylated by heating in phosphoric acid to provide 1-4. Intermediate 1-4 is converted to 1-5 by heating with benzyl bromide, potassium carbonate, and potassium iodide in dimethylformamide.

Another ketone precursor was prepared from 1-4 as shown in Scheme 1b. Intermediate 1-4 is treated with isoamyl nitrite and copper (II) chloride in acetonitrile to provide 1-6.

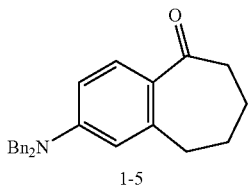
1-5

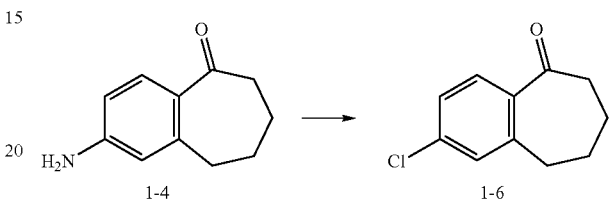
1-4      1-6

SCHEME 1b

A further ketone precursor is prepared as shown in Scheme 1c from known bromide 1-7. Bromide 1-7 is treated with the lithium anion of tert-butyl acetate to provide diester 1-8. Dieckmann cyclization and acid mediated hydrolysis/decarboxylation of 1-8 provides 1-9.

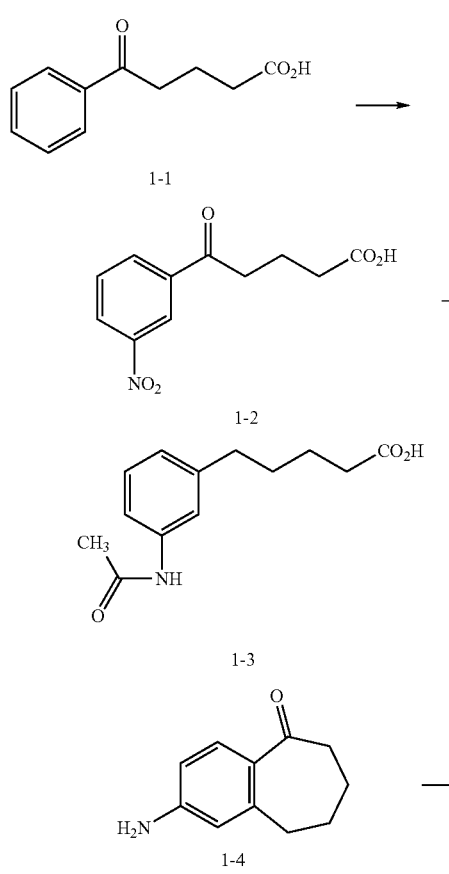

SCHEME 1a

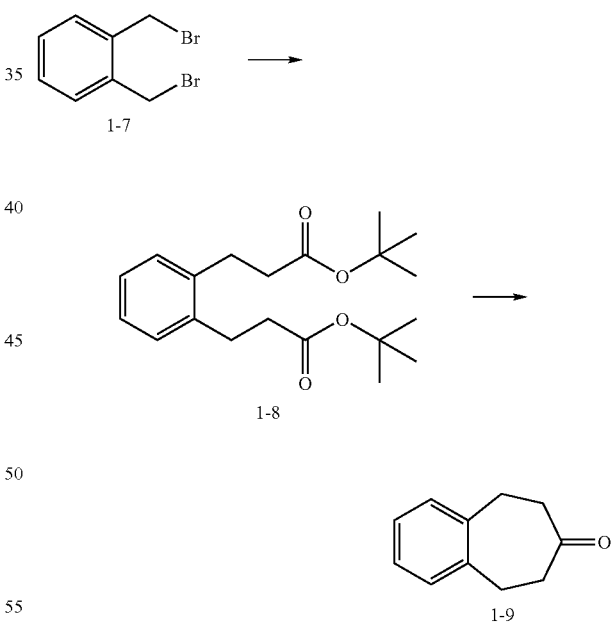

SCHEME 1c

Another ketone precursor, 1-13, is prepared from the commercially available ketone 1-10 by a multistep 1,2-carbonyl transposition as outlined in Scheme 1d. Lithium aluminum hydride (LAH) reduction of 1-10 provides carbinol 1-11 which is dehydrated using p-toluenesulfonic acid to provide hydrocarbon 1-12. Sequential epoxidation of 1-12 with m-chloroperoxybenzoic acid, LAH-mediated epoxide opening and Jones oxidation of the resultant carbinol provides ketone 1-13.

SCHEME 1d

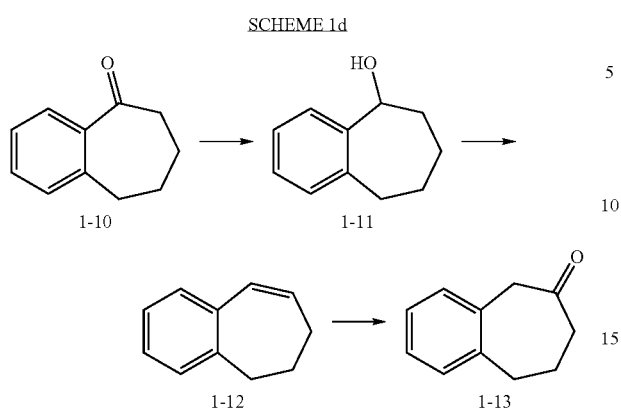

Heterocyclic ketone precursors required for the synthesis of compounds of the invention of formula 1 wherein B is B6 also begins from commercially available materials or compounds known to those skilled in the art.

As shown in Scheme 2a, intermediate 2-2, prepared from acetal 2-1 and isopropyl isocyanate, is converted to 2-3 by treatment with trifluoroacetic acid. Alkylation of 2-3 using sodium hydride and ethyl 5-bromopentanoate provides 2-4 which is then hydrolyzed with lithium hydroxide in THF/water. The resultant acid, 2-5, is cyclized to provide ketone 2-6 using polyphosphoric acid at elevated temperature.

SCHEME 2a

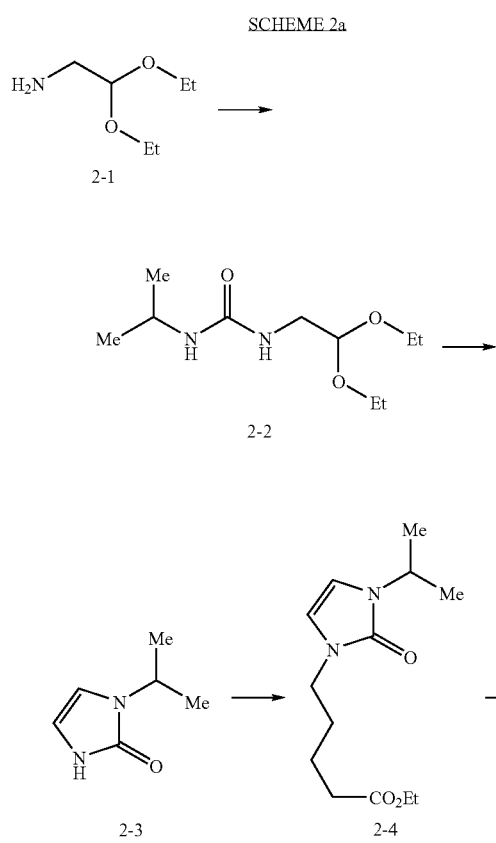

For the synthesis of a related ketone precursor, 2-10, ethyl glycinate (2-7) is utilized. The procedure outlined in Scheme 2b is similar to that in Scheme 2a except that benzyl isocyanate is used and the conversion of ester 2-8 to imidazolone 2-9 is initiated by a reduction with diisobutylaluminum hydride (DIBAL).

SCHEME 2b

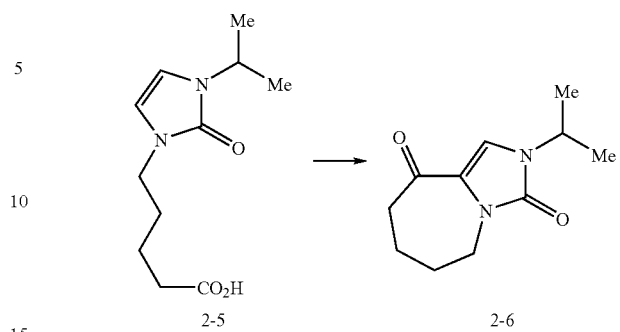

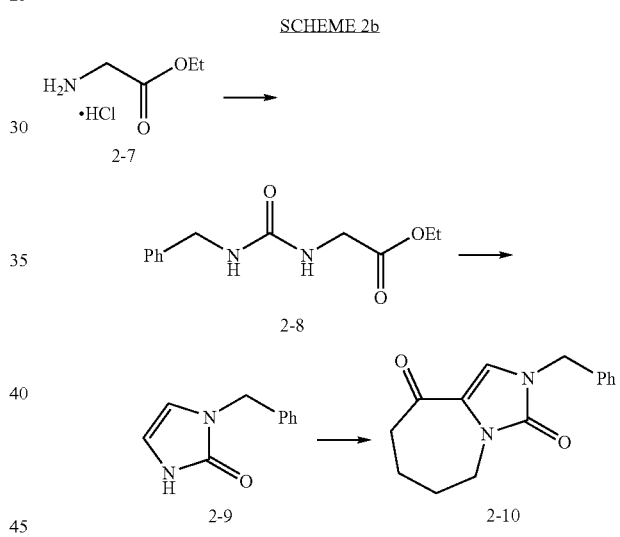

An additional group of ketone precursors are prepared as shown in Schemes 3a-3f from 1,3-cycloheptanedione (3-1). As shown in Scheme 3a, 1,3-cycloheptanedione is converted to 3-2 by treatment with N,N-dimethylformamide dimethyl acetal at elevated temperature. Subsequent treatment of 3-2 with S-methylisothiourea hemisulfate and triethylamine provides pyrimidine 3-3.

SCHEME 3a

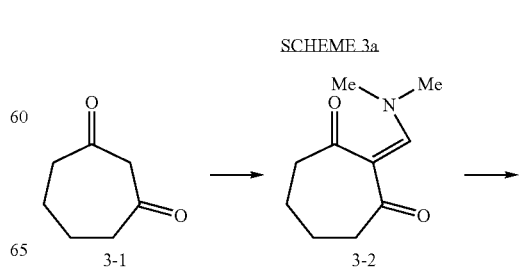

Two additional ketone precursors are prepared as summarized in Scheme 3b. Intermediate 3-2 is treated with methyl hydrazine in methanol below room temperature to provide a mixture of 3-4 and 3-5 which are separated by crystallization.

A further ketone precursor is also prepared from 3-2. As shown in Scheme 3c, 3-2 is treated with acetamidine hydrochloride to provide 3-6.

A further ketone precursor is prepared as outlined in Scheme 3d. Treatment of 1,3-cycloheptanedione with oxalyl chloride and dimethylformamide in methylene chloride provides intermediate 3-7. Treatment of 3-7 with cyanoacetamide in the presence of sodium hydride provides 3-8. Treatment of this latter intermediate first with N,N-dimethylformamide dimethyl acetal (to effect cyclization) and then with mineral acid at elevated temperature (to effect nitrile hydrolysis/decarboxylation) provides pyridone 3-9. Methylation of 3-9 using methyl iodide and silver carbonate provides 3-10.

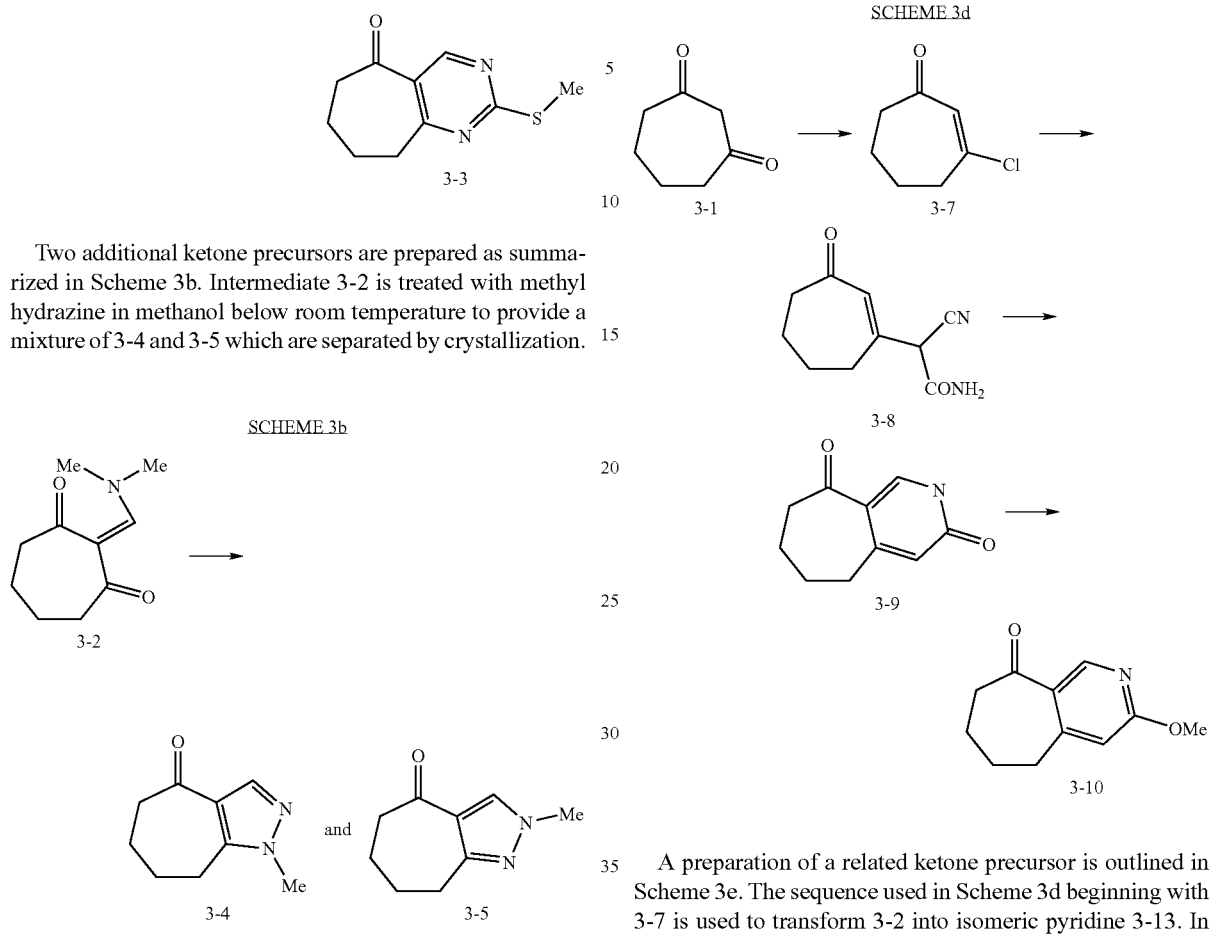

A preparation of a related ketone precursor is outlined in Scheme 3e. The sequence used in Scheme 3d beginning with 3-7 is used to transform 3-2 into isomeric pyridine 3-13. In Scheme 3d, the decarboxylation step is accomplished using copper powder in quinoline.

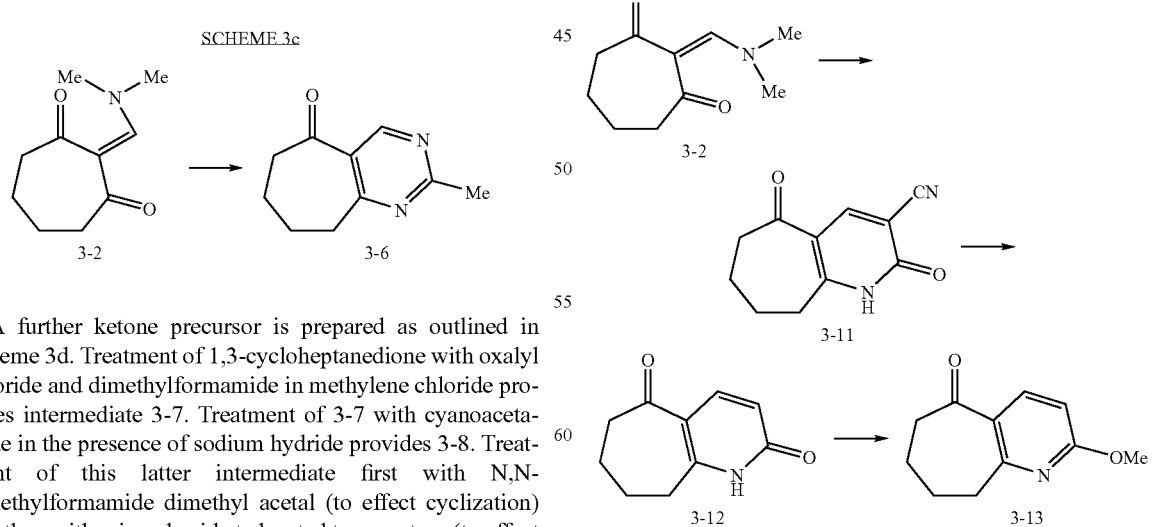

As shown in Scheme 3f, 1,3-cyclohexanedione is transformed into 3-14 using the steps outlined in Scheme 3d.

SCHEME 3f

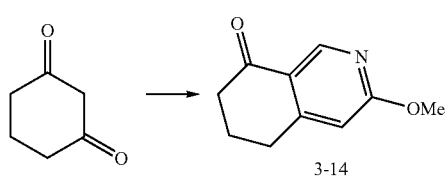

3-14

A pyrazine ketone precursor, 4-3, is prepared from commercially available pyrazine 4-1 as shown Scheme 4a. Displacement of the bromine atom in 4-1 with 4-(methylamino) butanoic acid followed by treatment of the adduct with (trimethylsilyl)diazomethane to effect esterification provides ester 4-2. Dieckmann cyclization of 4-2 using potassium tert-butoxide followed by decarbomethoxylation using DMSO-water at elevated temperature provides pyrazine 4-3.

SCHEME 4a

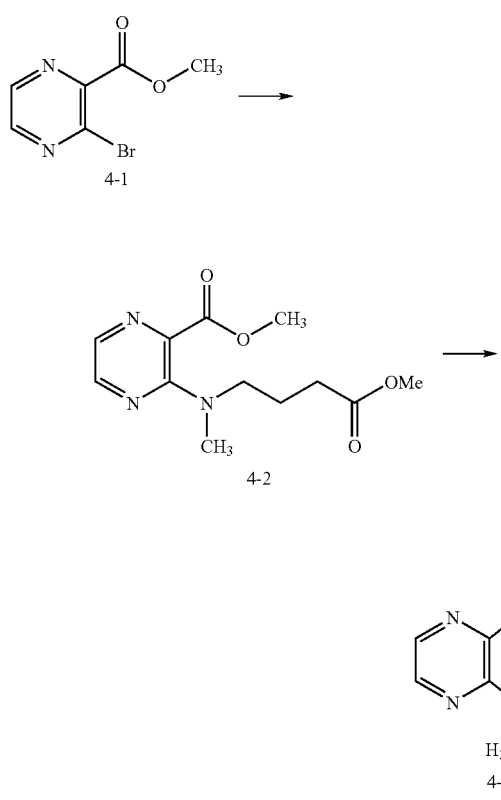

Several tetrazole-based ketone precursors are prepared as summarized in Schemes 5a-d. As shown in Scheme 5a, commercially available tetrazole 5-1 is transformed using a multistep sequence to provide 5-4. Metallation of 5-1 with n-butyllithium followed by condensation with benzaldehyde and acetylation of the adduct using acetyl chloride provides acetate 5-2. Treatment of 5-2 with potassium tert-butoxide provides 5-3 which is treated in turn with ozone in methanol to provide 5-4 after a reductive workup with dimethyl sulfide.

SCHEME 5a

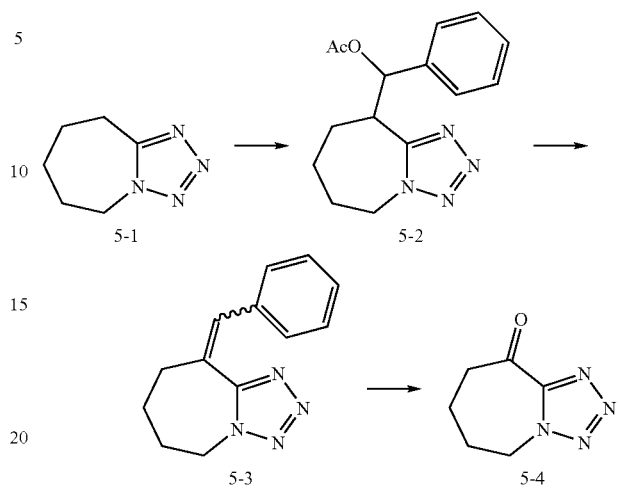

In a similar fashion, outlined in Scheme 5b, commercially available tetrazole 5-5 and known tetrazole 5-7 are converted to intermediates 5-6 and 5-8, respectively.

SCHEME 5b

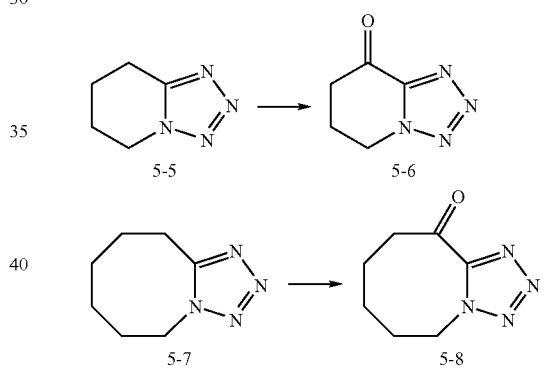

A further ketone precursor, 5-10, is prepared from known acetal 5-9. As shown in Scheme 5c, treatment of 5-9 with silicon tetrachloride and sodium azide in acetonitrile provides tetrazole 5-10.

SCHEME 5c

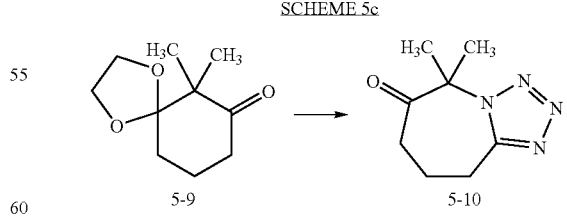

A still further ketone precursor is prepared as shown in Scheme 5d. Intermediate 5-11 is prepared from 2,2-dimethylcyclohexanone using the method described in Scheme 5c. Intermediate 5-11 is transformed into 5-12 using the sequence of steps outlined in Scheme 5a.

SCHEME 5d

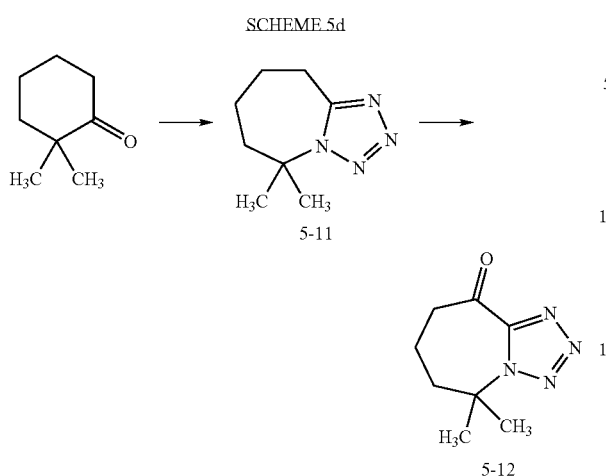

Scheme 6 lists additional commercially available or known ketones which serve as precursors to compounds of the invention wherein B is B1, B6, B7 or B8.

SCHEME 6

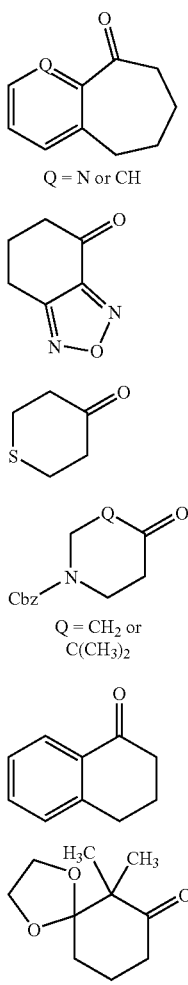

Pyridine Ring Construction

The ketone precursors described in Schemes 1-6 are used in the pyridine forming steps as described in Scheme 7 to form the polycyclic cores of the invention compounds wherein B is B1, B2, B3, B6, B7 and B8. In Scheme 7, intermediates 1-5, 1-6, 1-9, 1-13, 2-6, 2-10, 3-3, 3-4, 3-5, 3-6, 3-10, 3-13, 3-14, 4-3, 5-4, 5-6, 5-8, 5-9, 5-10, 5-12 as well as the other commercially available and known carbocyclic/heterocyclic ketones listed in Scheme 6 are depicted generically as intermediate 7-1.

Referring to Scheme 7, treatment of the generic ketone 7-1 with a base such as sodium or lithium bis(trimethylsilyl) amide and a 1,3-dicarbonyl compound, 7-2, provides an adduct, 7-3, which is cyclized to provide pyridine 7-4. The cyclizations are effected using either ammonium acetate in an alcoholic solvent in the presence of copper bromide (optionally in the presence of an acid such as p-toluenesulfonic acid), or using ammonium acetate in acetic acid in the presence of copper acetate. In some cases, the pyridine formation is effected in a stepwise manner: isolated adduct 7-3 is treated with a source of ammonia (optionally in the presence of a copper salt and/or an acid source such as p-toluenesulfonic acid) and then subsequently with an oxidizing agent such as 2,3-dichloro-5,6-dicyano-1,4-benzoquinone or ceric ammonium nitrate. In some cases, air or oxygen can be the oxidant either in the sequential or stepwise method.

SCHEME 7

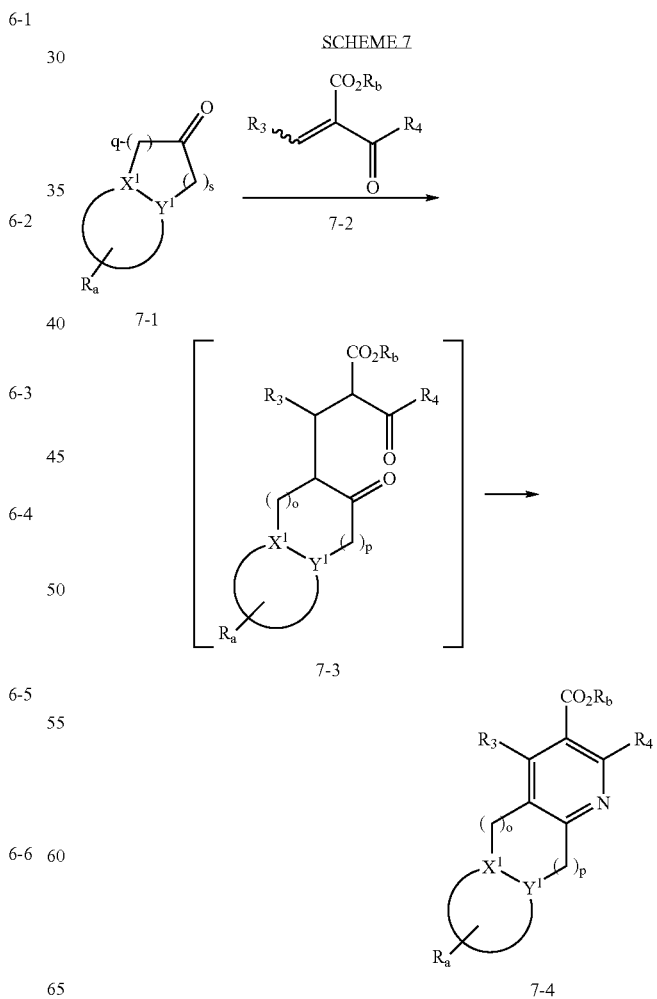

$R_a$=$R_6$ or H or $NBn_2$;

$R_b$=lower alkyl or arylalkyl such as benzyl;

q is an integer from 1 to 5;

s is an integer from 0 to 3 (q and s are chosen so that q+s=3 to 5);

o is an integer from 0 to 4; and p is an integer from 0 to 3, provided that at least one of o and p is other than 0.

In Scheme 7 and subsequent schemes, $R_a$ is $R_6$ or $R_{6a}$ as defined for compound 1 or may be alternate substitutents found in the intermediates shown in the schemes, such as halogen, dibenzylamine, carbobenzyloxy (CBz), methylthio or benzyl; $X^1$ and $Y^1$ may be carbon or nitrogen, or $X^1$ may be —C—N(CH$_3$)— wherein the C atom is at the ring fusion position and the N-atom which carries a methyl substitutent is attached to the $(CH_2)_q$ group, so that the generic structure 7-1 includes ketones such as 4-3 and the like.

The polycyclic cores present in some compounds of structure 1 wherein B is B4 are prepared starting with the sequence shown in Schemes 8a and 8b. Condensation of ethyl cyanoacetate with a beta-ketoester, 8-1, provides 8-2. Intermediate 8-3 is prepared from 8-2 by catalytic reduction of the nitrile group in the presence of mineral acid and protection of the resultant amine with a tert-butoxycarbonyl (BOC) group. Finally, 8-3 is transformed into triflate 8-4 by treatment with triflic anhydride in the presence of pyridine or triethylamine.

ketoester, 8-5, malononitrile and an aldehyde provides dihydropyridone 8-6. Subsequent oxidation of 8-6 with 2,3-dichloro-5,6-dicyano-1,4-benzoquinone provides 8-2.

SCHEME 8b

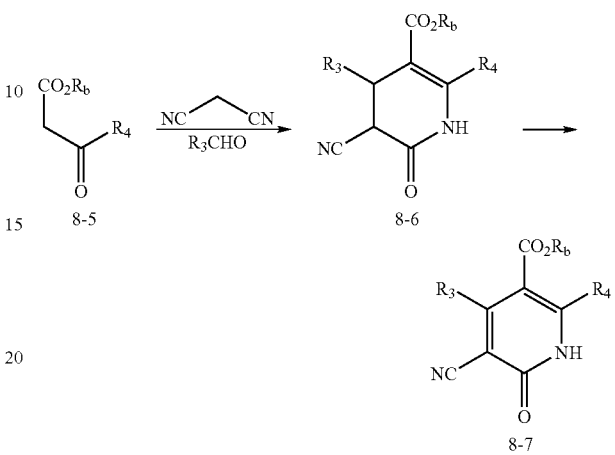

The next step in the construction of the polycyclic core of compounds of the invention wherein B is B4 is outlined in Schemes 9a and 9b. In Scheme 9a, Suzuki coupling of 8-4 with (2-formylphenyl)boronic acid followed by treatment of the adduct with trifluoroacetic acid provides 9-1. Reduction of 9-1 with sodium borohydride and protection as BOC provides intermediate 9-3 (via 9-2).

SCHEME 9a

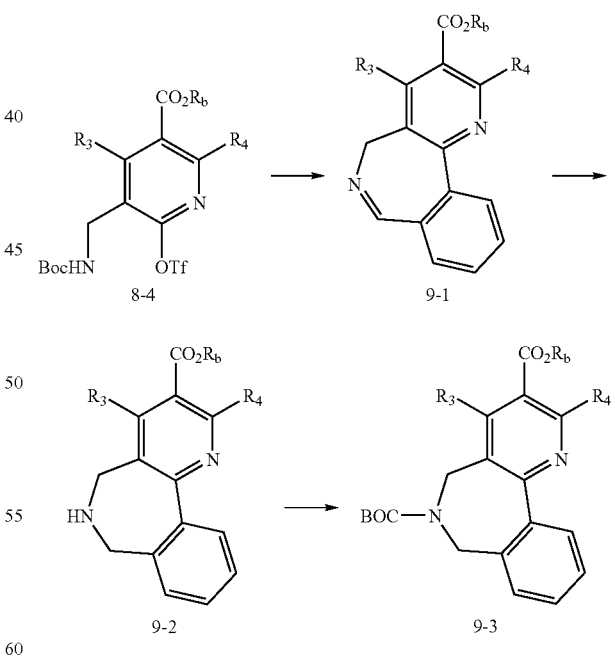

SCHEME 8a

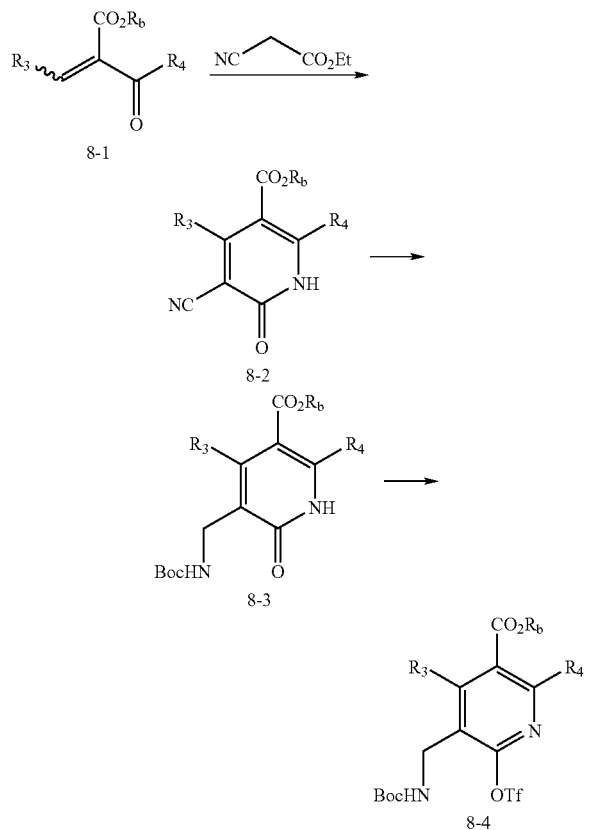

Scheme 8b shows an alternate preparation of 8-2. A piperidine-catalyzed 3-component coupling reaction of a beta- Another synthesis of advanced intermediates for invention compounds 1 wherein B is B4 begins with the sequence shown in Scheme 9b. Intermediate 8-4 is reduced using steps outlined in Scheme 11a and the resultant carbinol, 9-4, is subjected to a Suzuki coupling reaction employing 2-cyanobenzeneboronic acid to provide 9-5. Subsequent simultaneous hydrolysis of $X^2$ to a carboxy group and removal of the BOC group (aqueous hydrochloric acid) and lactam formation (WSC/HOBt) using procedures known to those skilled in the art provides 9-6.

SCHEME 9b

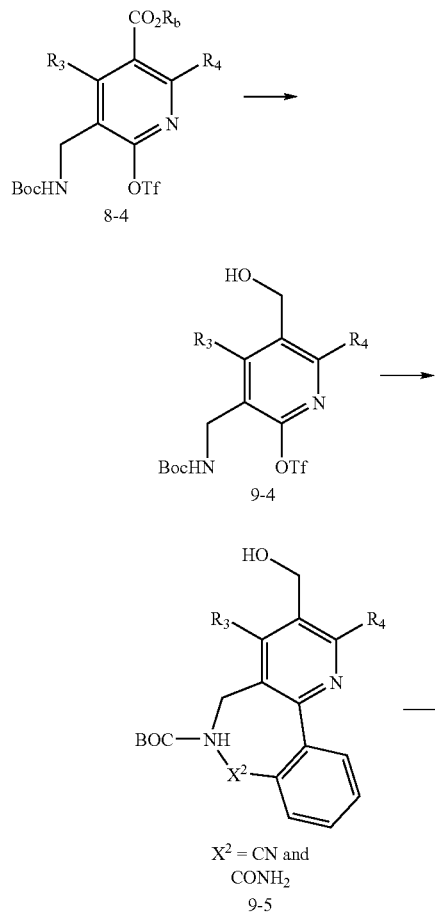

Compounds of the invention 1 wherein B is B5 and some compounds wherein B is B6 begin with the series of reactions shown in Schemes 10a and 10b. As seen in Scheme 10a, aminopyridine 10-1 is converted to fluoride 10-2 by diazotization and fluoride displacement using sodium nitrite and fluoroboric acid. Reduction of the less hindered ester group with a hydride reducing agent such as LAH and subsequent halogenation using carbon tetrabromide and triphenylphosphine provides 10-4.

SCHEME 10a

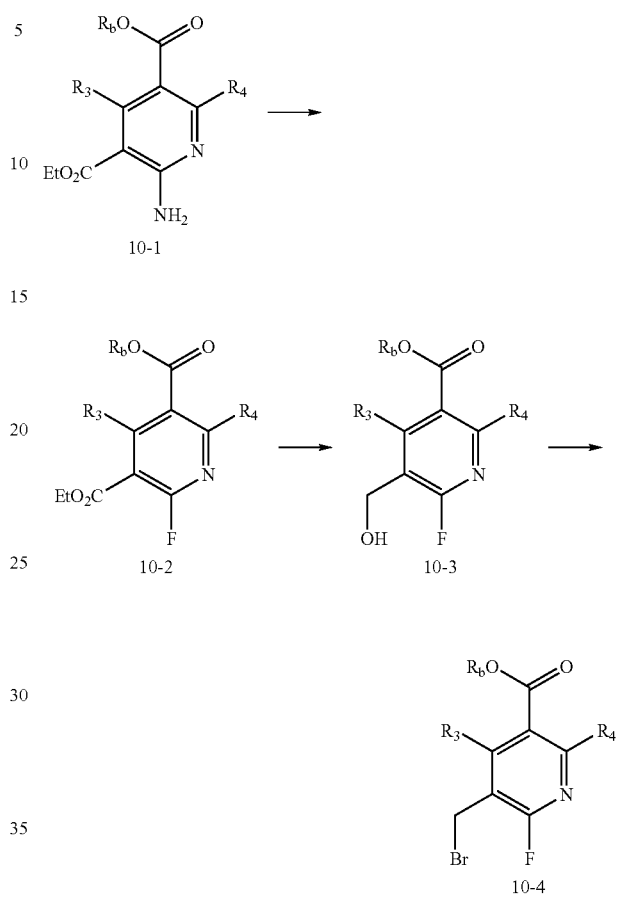

As seen in Scheme 10b, reaction of fluoropyridine 10-4 with a heterocyclic alcohol or a phenol, generically shown as 10-5, in the presence of a base such as sodium hydride or potassium carbonate provides adduct 10-6. (A reactive functional group or atom in 10-5 is optionally protected as shown by the generic protecting group Prot.) Removal of the protecting group (such as BOC by TFA or SEM by fluoride ion) is followed by cyclization to provide intermediate 10-7. A base such as sodium hydride or tetrabutylammonium fluoride is used to facilitate the cyclization reaction.

SCHEME 10b

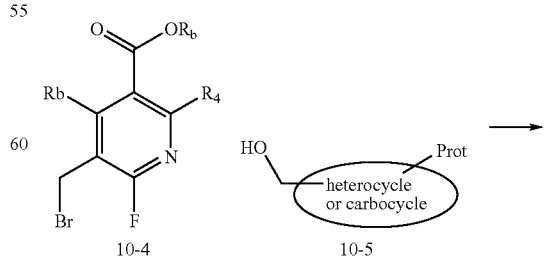

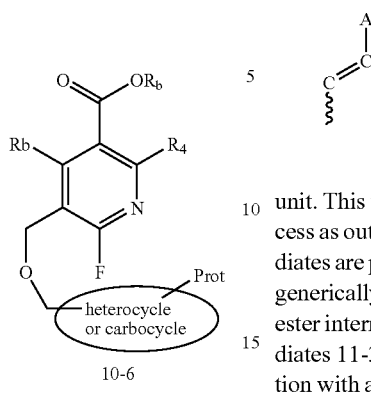

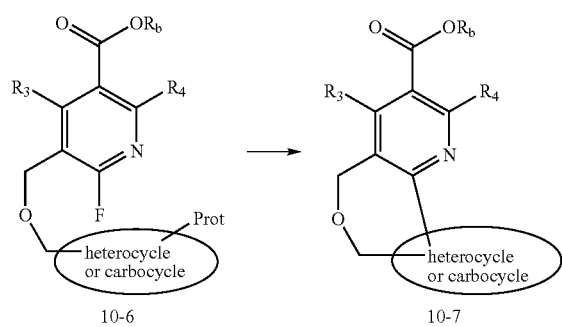

Modifications to the Polycyclic Structures

An additional step in the syntheses of the compounds of the invention from the preceding intermediates is the introduction of the unit. This transformation is accomplished in a multistep process as outlined in Schemes 11a-c. All the preceding intermediates are prepared as esters or as alcohols and they are shown generically in Scheme 11a as 11-1 and 11-3, respectively. The ester intermediates 11-1 are converted to the alcohol intermediates 11-3 by several means. One method was direct reduction with a hydride reducing agent such as lithium aluminum hydride, lithium borohydride, DIBAL, LithAl, RedAl, and the like. In another method the ester group is first subjected to a basic hydrolysis (using a tetraalkylammonium hydroxide salt, potassium trimethylsilanol, sodium or potassium hydroxide, and the like) or other cleavage agent (boron tribromide) to produce acid 11-2. Acid 11-2 is then converted to an acid chloride (such as with oxalyl chloride and the like) and then reduced with a hydride reducing agent such as sodium borohydride or others previously mentioned. The intermediate alcohol 11-3 is oxidized to the aldehyde, 11-5, using Dess-Martin periodinane, a buffered TEMPO/KBr/NaOCl system, tetrapropylammonium perruthenate/N-methylmorpholine-N-oxide, and the like. Also shown in Scheme 11a is an optional protection/deprotection step; that is, the interconversion of 11-3 and 11-4. This optional step is advantageous for some compounds of the invention wherein the presence of the free alcohol group is unwanted. Those skilled in the art will recognize that a variety of protecting groups and procedures can be used to accomplish this interconversion. In general, silyl protecting groups (such as tert-butyldimethylsilyl which are removed by treatment with fluoride), and ester groups (such as benzoate and acetate which are removed by hydrolysis or reduction) are useful.

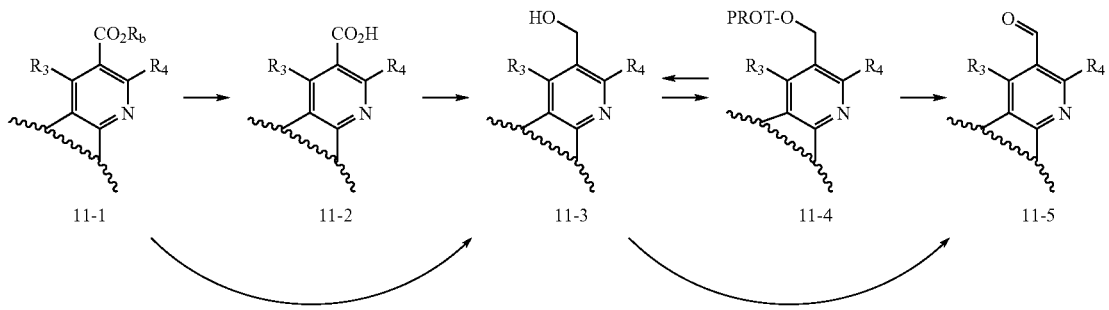

As shown in Scheme 11b, aldehyde 11-5 is allowed to react with sulfone 11-6 in the presence of a base such as lithium or sodium bis(trimethylsilyl)amide to produce 11-7. In Scheme 11b and in following schemes, the stereochemistry of the heptenoic acid chain is depicted as (3-R, 5-S); however, the methods described can be used to prepare other stereoisomers or mixtures.

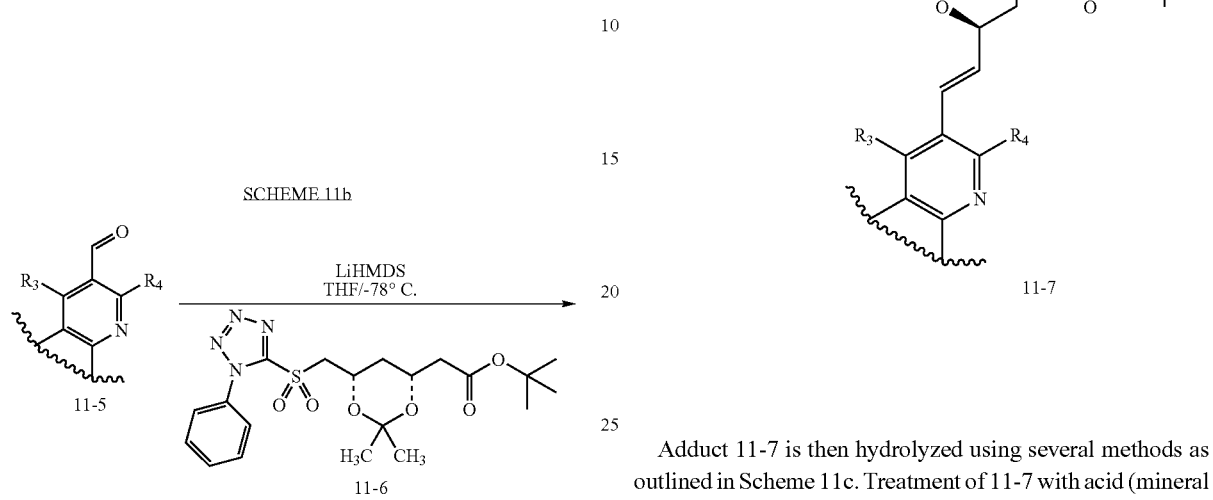

Adduct 11-7 is then hydrolyzed using several methods as outlined in Scheme 11c. Treatment of 11-7 with acid (mineral acid, or TFA, and the like) produces lactone 11-8 which, when treated with aqueous base provides invention compound 1 as a salt or as the acid form after neutralization. Alternatively, treatment of 11-7 with acid under different conditions (for example, p-toluenesulfonic acid in methanol) serves to convert 11-7 to diol ester 11-9. Ester 11-9 is transformed to 11-8 or compound 1a of the invention by acid or base treatment.

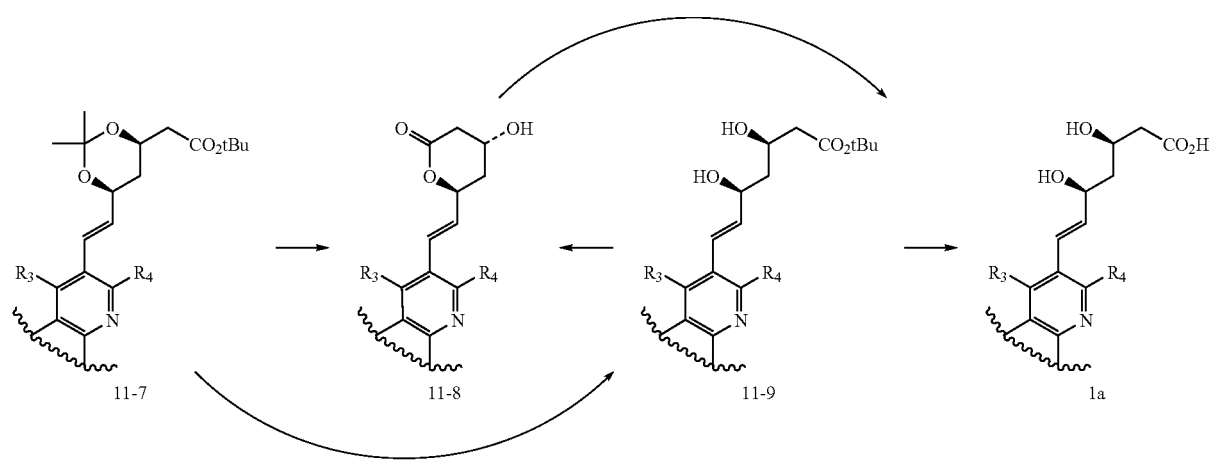

For some compounds of the invention the final steps of the synthesis also involves introduction of additional functional groups and/or modification of groups already present (collectively, functional group transformations). These modifications are done at various stages of the synthesis. Many of the reagents, reactants, solvents and reaction conditions used for functional group transformations are familiar to those skilled in the art of organic synthesis. Some others are presented in the following schemes.

In some compounds of the invention wherein B is B1 electrophilic aromatic substitution is used to introduce sulfonyl, nitro, or bromo substitutents.

Introduction of a sulfonyl group is accomplished using the steps outlined in Scheme 12. Intermediate 12-1, prepared from intermediate 6-1 (X=CH) as described in Scheme 7, is subjected to electrophilic sulfonation using chlorosulfonic acid in trifluoroacetic acid to provide intermediate 12-2. Using common functional group transformations, intermediate 12-2 is condensed with a variety of amines to produce a sulfonamide intermediate which in turn is subjected to a reduction using a hydride reducing agent such as lithium aluminum hydride or DIBAL-H as described in Scheme 11a to produce carbinol 12-3. Oxidation of 12-3 is described in Scheme 11a provided aldehyde 12-4. Intermediate 12-4 is converted to compounds of the invention as described in Schemes 11b and 11c.

Intermediate 13-1, obtained from 12-4 using the steps described in Scheme 11b, is used to prepare other compounds of the invention. Using common functional group transformations as shown in Scheme 13, the sulfonamide group is sulfonylated with methanesulfonyl chloride, acylated with acetyl chloride or reacted with an isocyanate such as methyl isocyanate to form a derivative, 13-2. Conversion of 13-2 to compounds 1b of the invention is accomplished using steps described in Scheme 11c.

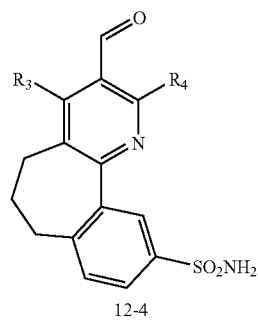

12-4

SCHEME 12

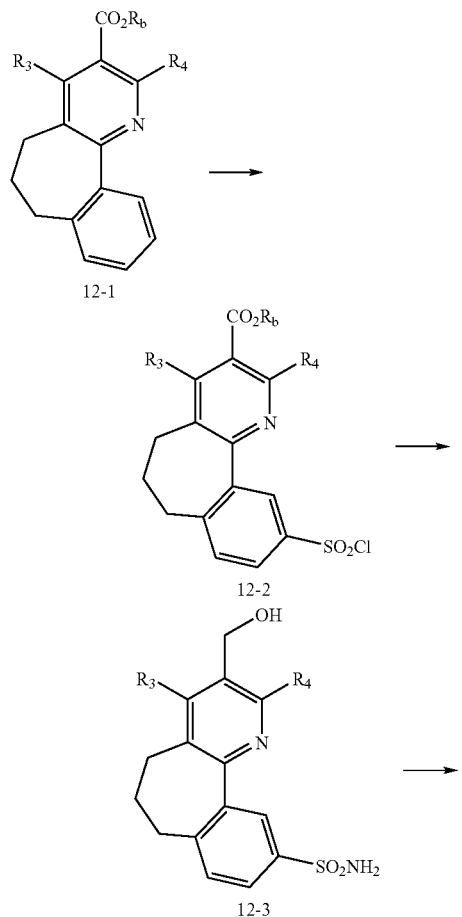

SCHEME 13

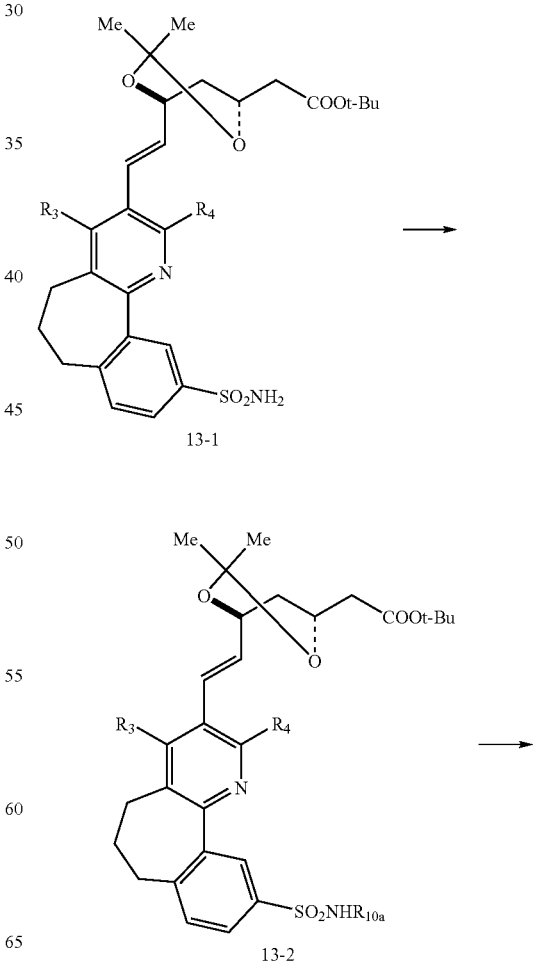

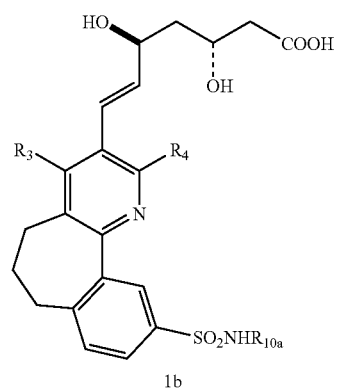

1b $R_{10a} = R_{10}$ and preferably SO$_2$Me, C(O)Me, C(O)NHMe, (CH$_2$)$_x$NMe$_2$, (CH$_2$)$_x$—N⏜O, (CH$_2$)$_x$OH, x = 1 to 8

Introduction of a bromo group into 12-1 is used to prepare additional compounds of the invention as shown in Schemes 14a and 14b. Exposure of 12-1 to bromine and aluminum chloride followed by reduction of the halogenated product with DIBAL-H provides an aryl bromide which is treated with zinc cyanide and a palladium catalyst to provide 14-1 (along with 14-2). The nitrile group of intermediate 14-1 is subjected to base hydrolysis. The resultant carboxylic acid is esterified with methyl iodide and cesium carbonate to provide ester 14-3. Transformation of 14-2 and 14-3 to invention compounds is accomplished using steps described in Schemes 11a-11c.

Additional compounds of the invention were prepared as shown in Scheme 14b from ester 14-4 which is prepared from 14-3 using steps described in Schemes 11a and 11b. The methyl ester group of intermediate 14-4 is subjected to mild base hydrolysis using lithium hydroxide and transformed to an amide functionality using an amine and a peptide coupling reagent, such as BOP [(benzotriazol-1-yl)oxy-tris(dimethylamino)phosphonium hexafluorophosphate]. The resultant intermediate, 14-5, is converted to compound 1c of the invention using steps described in Scheme 11c.

SCHEME 14b

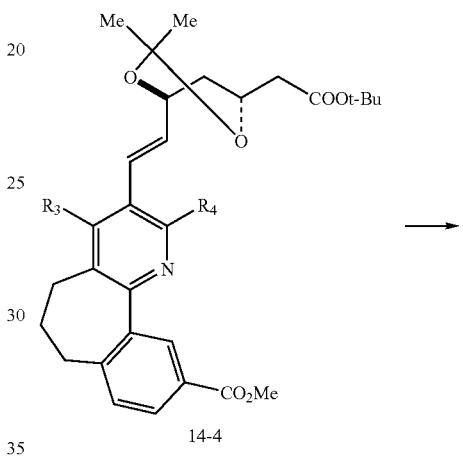

14-4

SCHEME 14a

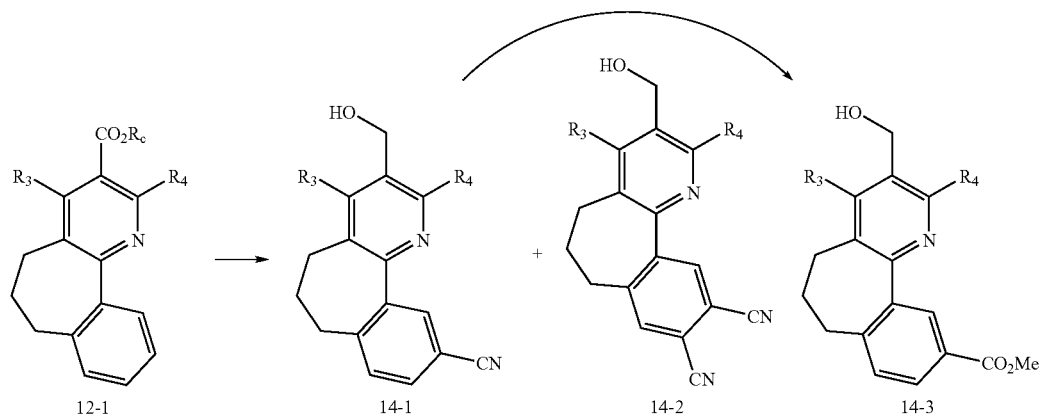

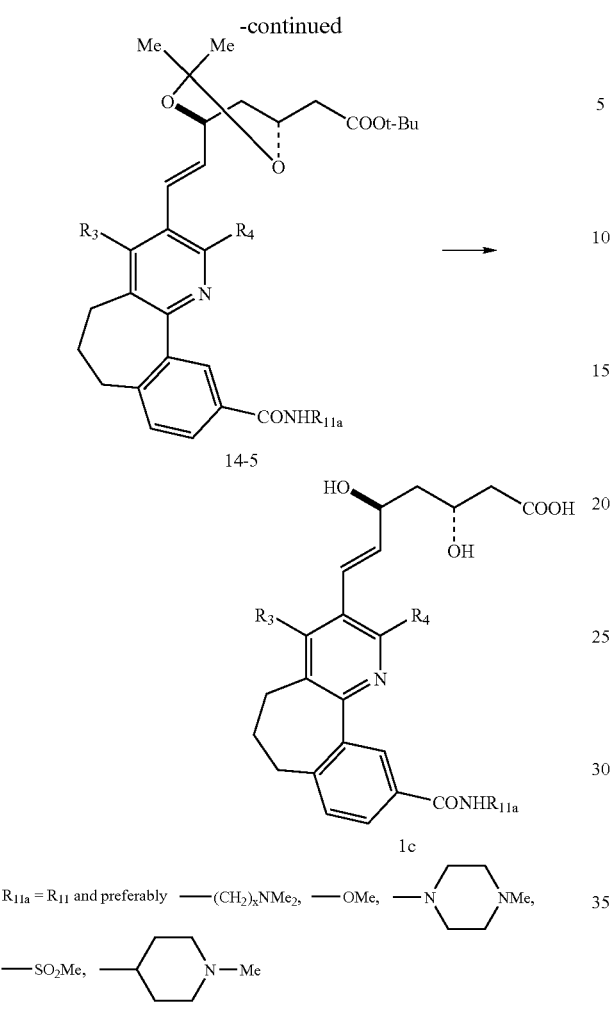

14-5

1c

R$_{11a}$ = R$_{11}$ and preferably —(CH$_2$)$_x$NMe$_2$, —OMe, —N⟨piperazine⟩NMe, —SO$_2$Me, —⟨piperidine⟩N—Me Starting another series of transformations, ester 12-1 is reduced and protected as the benzoate using steps shown in Scheme 11a. As seen in Scheme 15a, the resultant benzoate, 15-1, is treated with bromine and aluminum chloride to form 15-2. Transformation of 15-2 to 15-3 is effected with zinc cyanide and a palladium catalyst. Treatment of 15-3 with lithium aluminum hydride removes the benzoate group and reduces the nitrile group to an aminomethyl group which is protected using 2-(trimethylsilyl)ethyl 4-nitrophenyl carbonate to produce intermediate 15-4.

SCHEME 15a

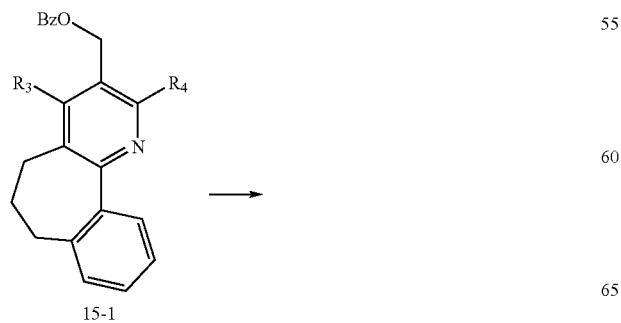

15-1

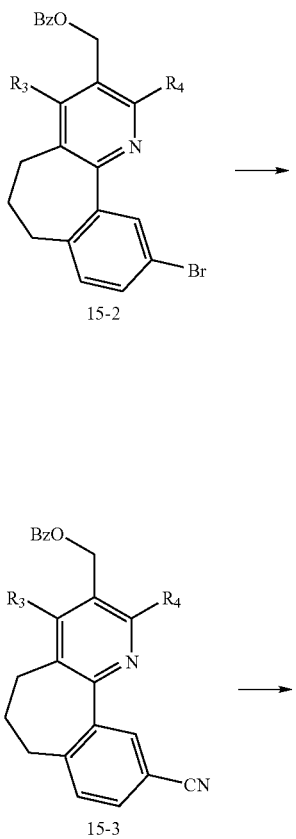

15-2

15-3

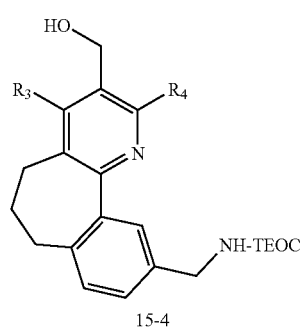

15-4

Intermediate 15-4 is converted to 15-5 using steps described in Schemes 11a and 11b. As outlined in Scheme 15b, the TEOC group is removed from the resultant intermediate 15-5 with fluoride ion and the amine is functionalized with methanesulfonyl chloride or methylisocyanate to provide 15-6. Conversion of 15-6 to compound 1d of the invention is accomplished using steps described in Scheme 11c provided.

SCHEME 15b
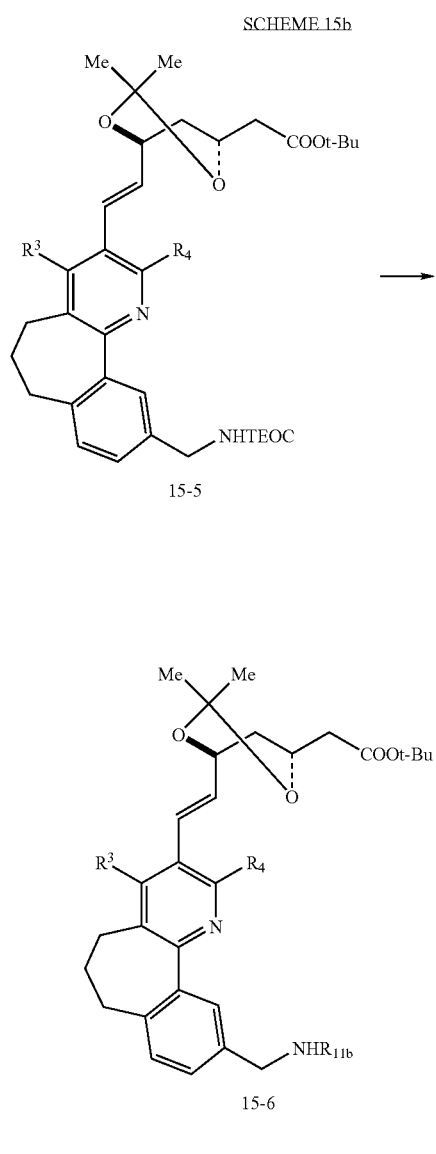
Introduction of a nitro group is used to prepare additional invention compounds. As outlined in Scheme 16a, ester 12-1 is transformed into aldehyde 16-1 using steps described in Scheme 11a. Aldehyde 16-1 is nitrated with fuming nitric acid in nitromethane to provide 16-2. Intermediate 16-2 is transformed into 16-3 using the steps described in Scheme 11b.
SCHEME 16a
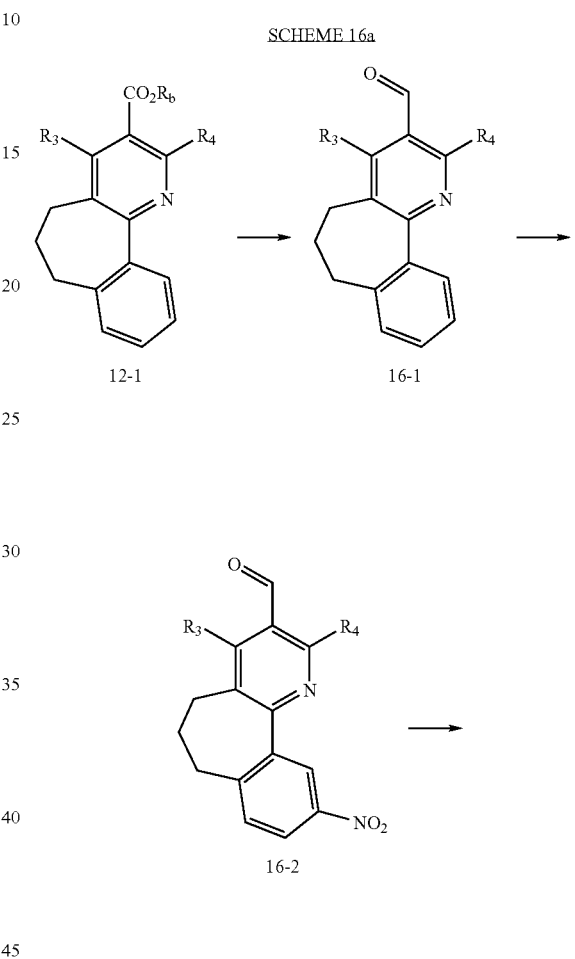
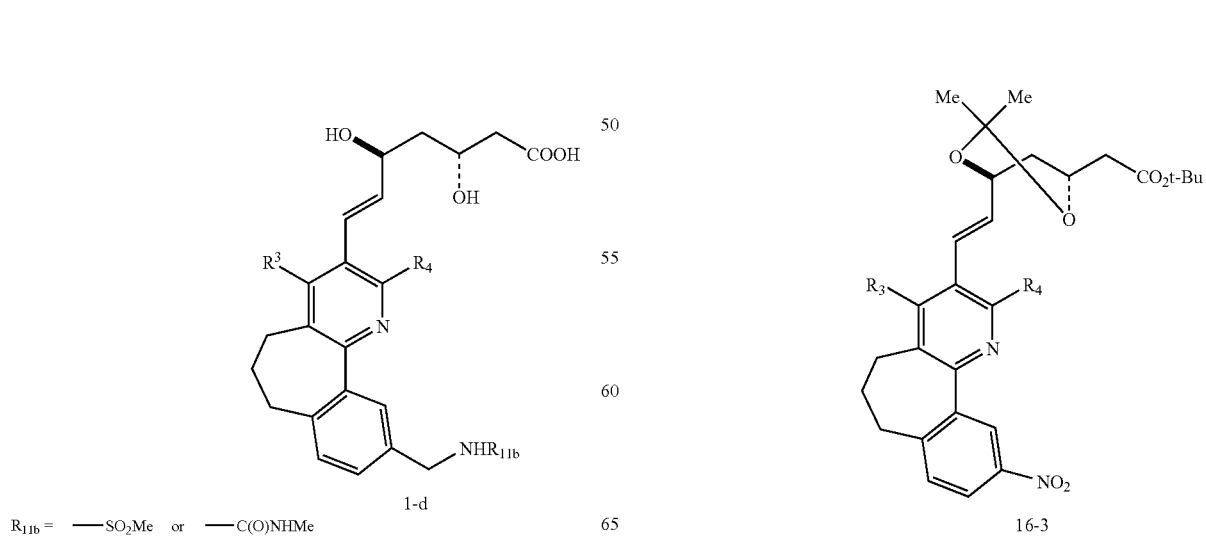

As shown in Scheme 16b, reduction of 16-3 with zinc provides an amine which is further transformed to provide intermediate 16-4 using common functional group transformations. For example, the amine is condensed with an isocyanate to form a urea; with p-nitrophenyl chloroformate to form a reactive carbamate which may further react with amines to also provide a urea; or with a carboxylic acid chloride to form an amide. Transformation of 16-4 using steps described in Scheme 11c provides compound 1e of the invention.

SCHEME 16b

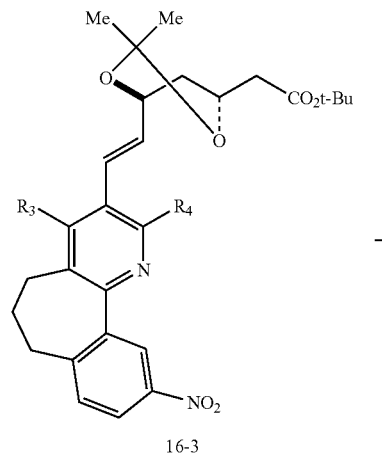

16-3

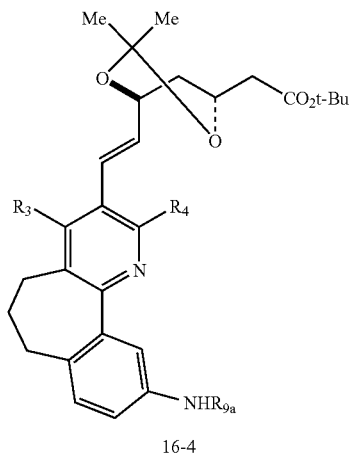

16-4

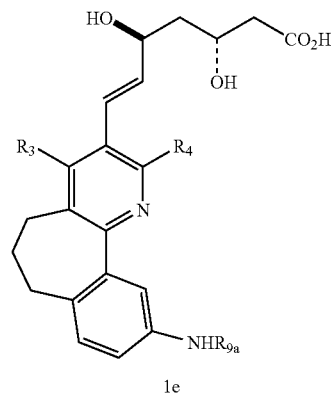

1e $R_{9a}$ = Cl—CH$_2$C(=O)—, COCH$_2$NMe$_2$, CONR$_8$R$_{9b}$ (where R$_{9b}$ is the same as R$_9$ and may include alkyl substituted by methoxycarbonyl)

Additional compounds of the invention are derived from bromo intermediates. As shown in Scheme 17, ester 12-1 is converted to dibromide 17-1 using bromine and aluminum chloride. Dibromide 17-1 is transformed into 17-2 using the steps outlined in Schemes 11a and 11b followed by carbonylation/esterification using palladium acetate and carbon monoxide in methanol. Diester 17-2 is converted to compound 1f of the invention using steps described in Scheme 11c.

SCHEME 17

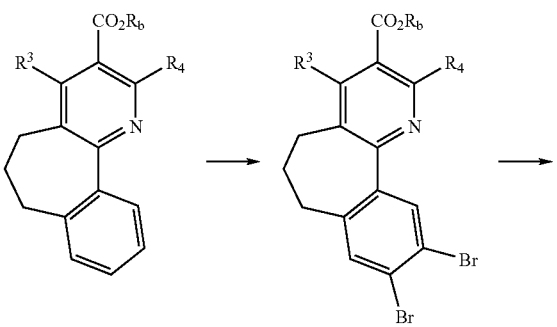

12-1     17-1

-continued

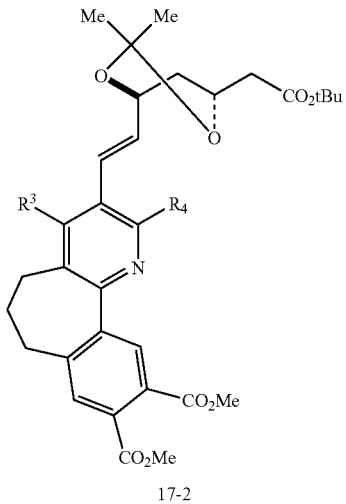

17-2

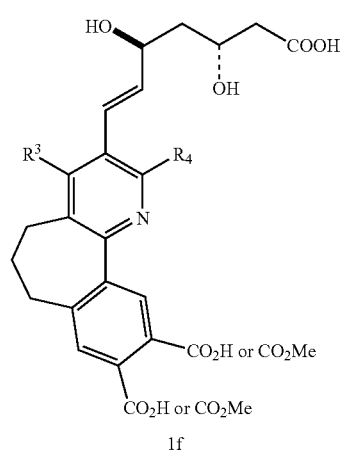

1f

SCHEME 18

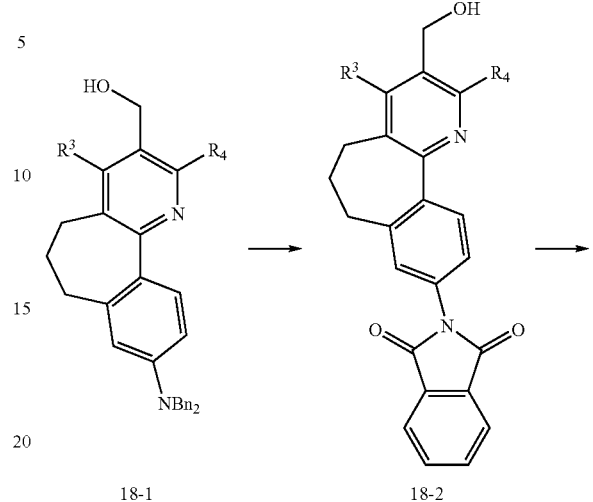

18-1            18-2

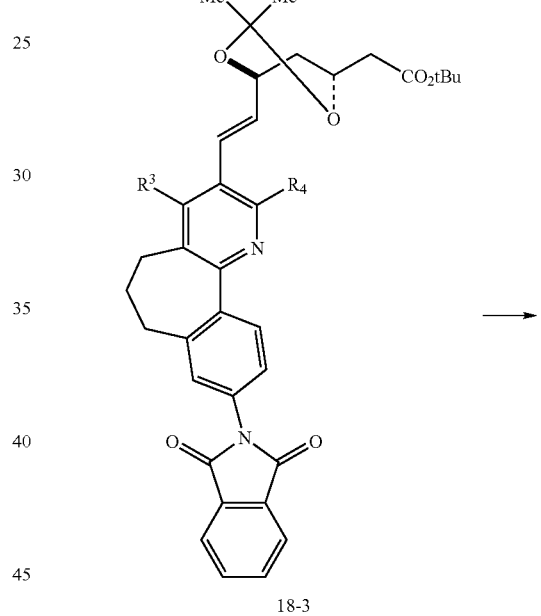

18-3

18-4

From dibenzylamine intermediate 1-5, using procedures described in Schemes 7 and 11a, intermediate 18-1 is prepared. As seen in Scheme 18, intermediate 18-1 is debenzylated using palladium and ammonium formate and the resultant amine is protected as a phthalate using N-carbethoxyphthalimide to provide intermediate 18-2. Intermediate 18-2 is transformed into 18-3 using steps outlined in Schemes 11a and 11b. The amine group of 18-3 is deprotected with hydrazine to produce intermediate 18-4. Using steps described in Scheme 16 and other common functional group transformations familiar to those skilled in the art and then steps outlined in Scheme 1c, intermediate 18-4 is transformed to compounds of the invention 1g.

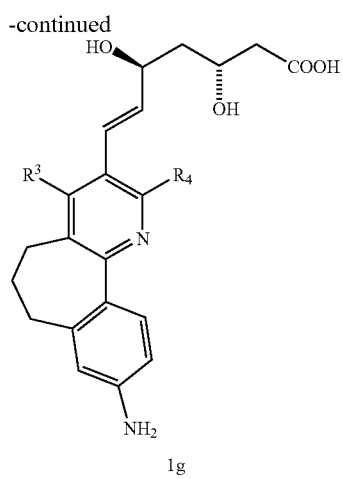

1g

From intermediate halide 1-6, using the procedures described in Schemes 7 and 11a, intermediate 19-1 is prepared. As shown in Scheme 19a, intermediate 19-1 is transformed to 19-2 using zinc cyanide and a palladium catalyst. Base hydrolysis of the nitrile and methylation of the resultant carboxylic acid group using methyl iodide and potassium carbonate provides intermediate 19-3. Intermediate 19-3 is transformed into 19-4 using steps outlined in Schemes 11a and 11b. Intermediate 19-4 is transformed to compounds of the invention using steps outlined in Schemes 11c. Intermediate 19-2 is also transformed to invention compounds using steps described in Schemes 11b and 11c. Intermediate 19-2 is also transformed into 19-5 using steps described in Schemes 11a and 11b.

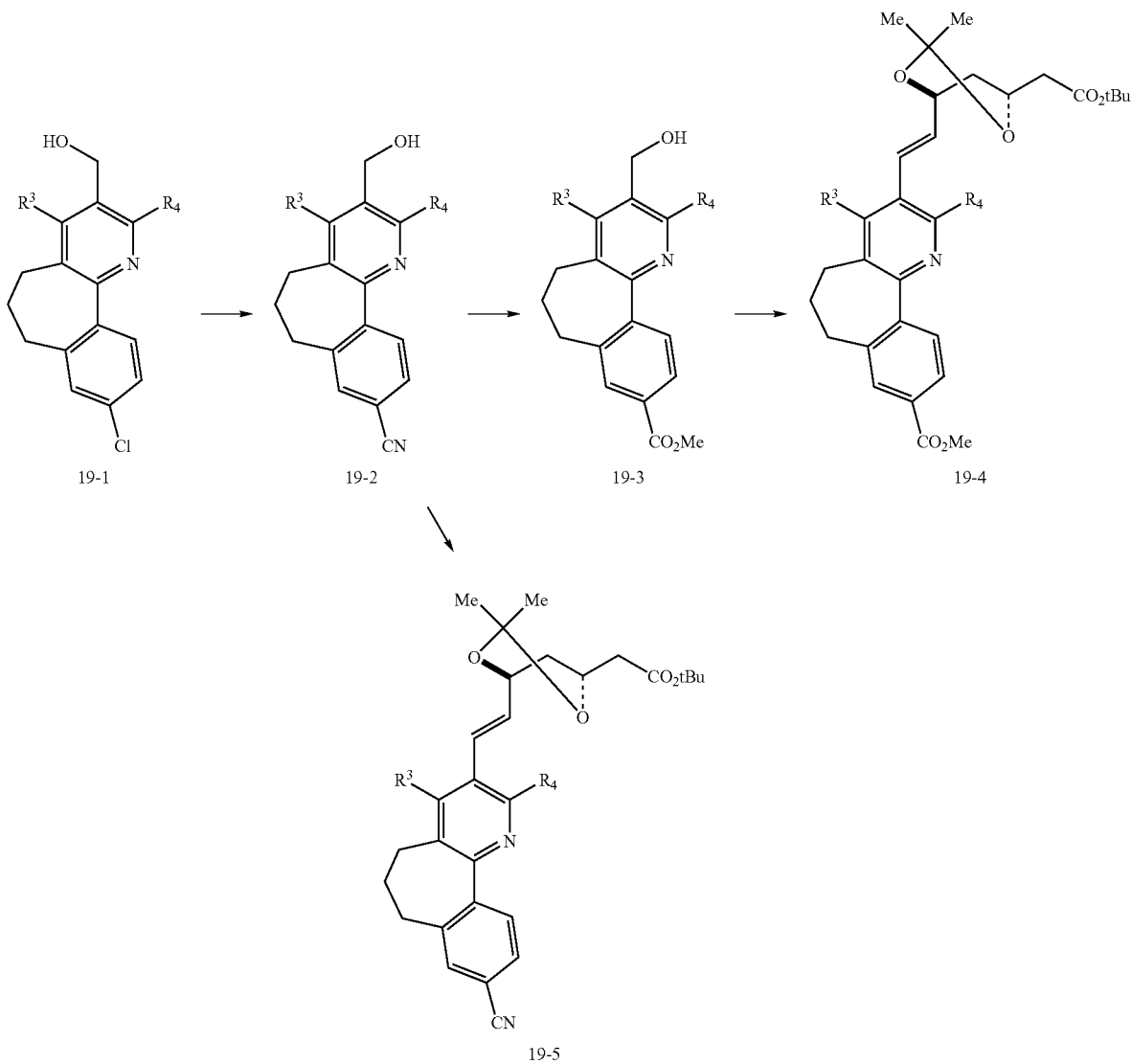

SCHEME 19a

Ester 19-4 is converted to additional compounds of the invention as shown in Scheme 19b. The ester group of 19-4 is hydrolyzed using aqueous lithium hydroxide and the resultant carboxylic acid is converted to an amide with an amine and HBTU (O-benzotriazol-1-yl-N,N,N',N'-tetramethyluronium hexafluorophosphate) to provide intermediate (19-6). Intermediate 19-6 provides invention compound 1h of the invention using steps outlined in Scheme 11c.

SCHEME 19b

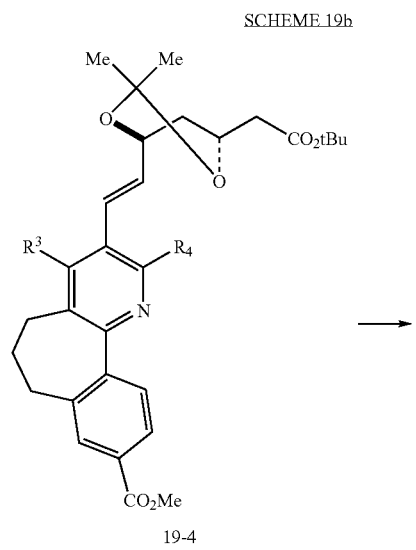

19-4

-continued

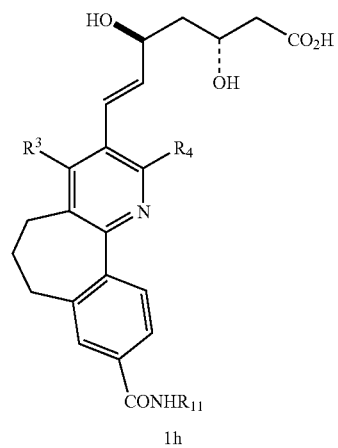

1h

Further, intermediate 19-5 is treated with trimethylstannyl azide in hot toluene to produce tetrazole 19-7. Tetrazole 19-7 is methylated using methyl iodide and sodium carbonate in dimethylsulfoxide to produce intermediate 19-8 and 19-9. Tetrazoles 19-7, 19-8, and 19-9 are transformed to compound 1i of the invention using steps described in Scheme 11c.

Using steps described in Schemes 19a and 19c, intermediate 14-1 was transformed into invention compounds 1 wherein B is B1 and $R_6$ is tetrazole linked through its carbon atom and optionally substituted with methyl.

Sequentially using the bromination step described in Scheme 15a, the reduction described in Scheme 11a, the cyanide displacement described in Scheme 15a, the oxidation and coupling reactions described in Schemes 11a and 11b, the tetrazole forming steps described in Scheme 19c and the steps described in Scheme 11c, intermediate 1-9 is transformed to compounds of the invention wherein B is B2 and $R_6$ is tetrazole linked through its carbon atom and optionally substituted by methyl.

SCHEME 19c

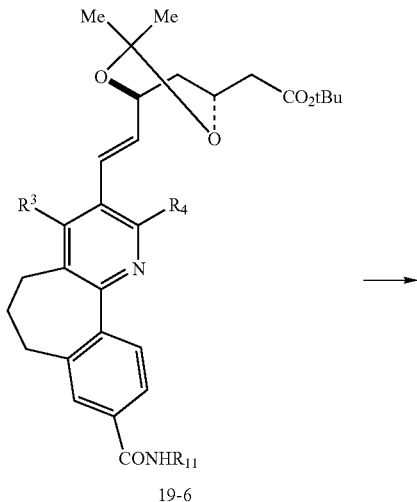

19-5

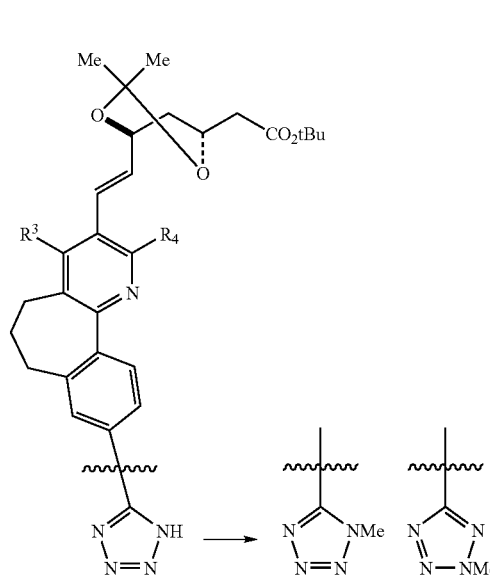

1i

Additional compounds of the invention are prepared as shown in the Scheme 20. Intermediate 12-1 (wherein $R_3$ is 4-fluorophenyl) is converted to intermediate 20-1 using the methods described in Scheme 11a. Intermediate 20-1 is metallated with n-butyllithium and carboxylated to provide an intermediate which is subjected to Fischer esterification (and concomitant removal of the silyl protecting group) to provide pendant ester 20-2. Using steps described in Schemes 11a and 11b, intermediate 20-2 provides 20-3 which is converted to compound 1j of the invention using steps described in Scheme 11c.

SCHEME 20

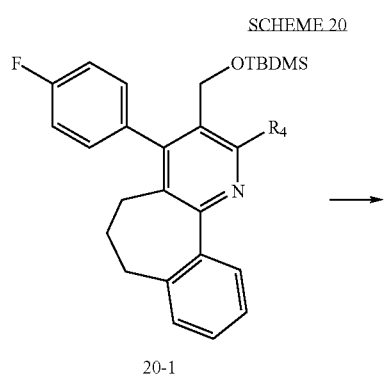

20-1

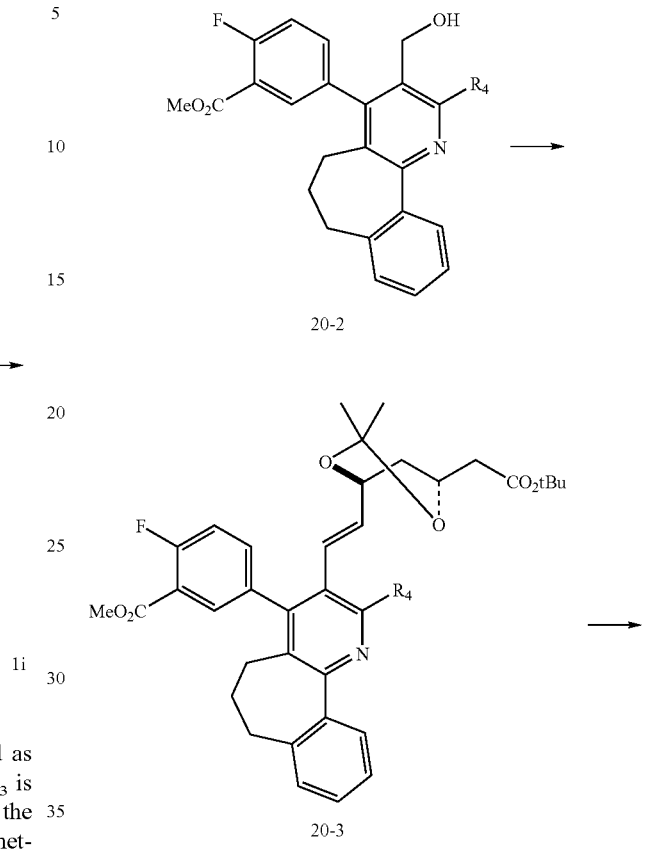

Using steps described in Schemes 7, 16a and 16b intermediates 1-9 and 1-13 are transformed into compounds of structure 1 in which B is B2 and B3.

Intermediate 9-3 is transformed into compounds of the invention (wherein B is B4 and $R_7$ is H) using steps described in Schemes 11a-c.

Intermediate 9-2 is sulfonylated with methanesulfonyl chloride or acetylated with an acetyl chloride and the resultant products are transformed to provide invention compounds wherein B is B4 and $R_7$ is acetyl or methanesulfonyl using steps described in Schemes 11a-c.

As shown in Scheme 21, intermediate 9-2 is reduced using steps described in Scheme 11a and the resultant aminocarbinol is protected (as the 2-(trimethylsilyl)ethoxycarbonyl (TEOC)) to provide intermediate 21-1. Intermediate 21-1 is transformed into 21-2 using steps described in Schemes 11a and 11b. Next, intermediate 21-2 is transformed to 21-3 using fluoride ion. Intermediate 21-3 is condensed with isocyanates, carbamoyl chlorides or acid chlorides (e.g. mesyl chloride) to provide intermediates which are transformed to provide compound 1k of the invention using steps described in Scheme 11c.

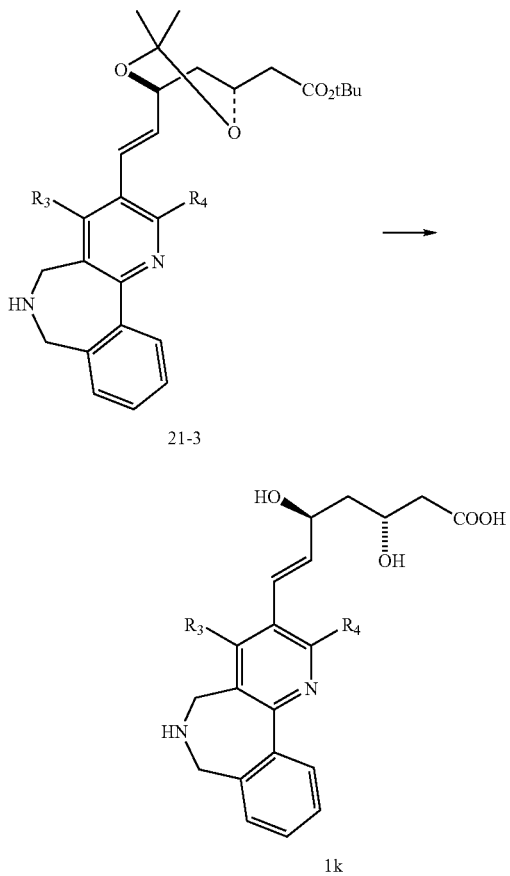

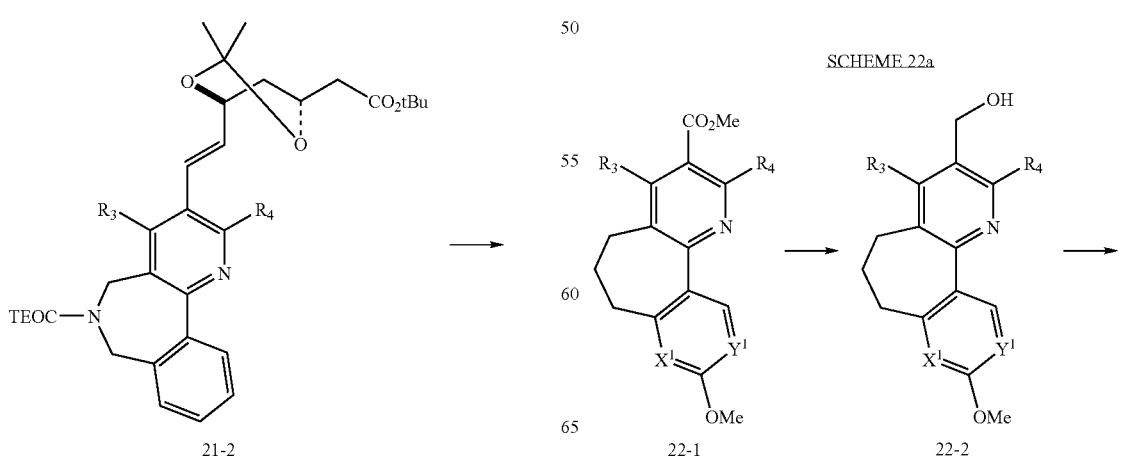

Intermediate 9-6 is transformed into compounds of the invention using steps described in Schemes 11a-c.

Intermediates 2-6, 2-10 and 6-1 (wherein X=N) are converted to compounds of the invention wherein B is B6 using steps described in Schemes 7 and 11a-11c.

Referring to Scheme 22a, intermediates 3-10 and 3-13 are converted to intermediates 22-1, 22-2, 22-3 and 224 using steps described in Schemes 7 and 11a-b. Intermediate 22-4 is converted to compounds of the invention 11 using steps described in Scheme 11c.

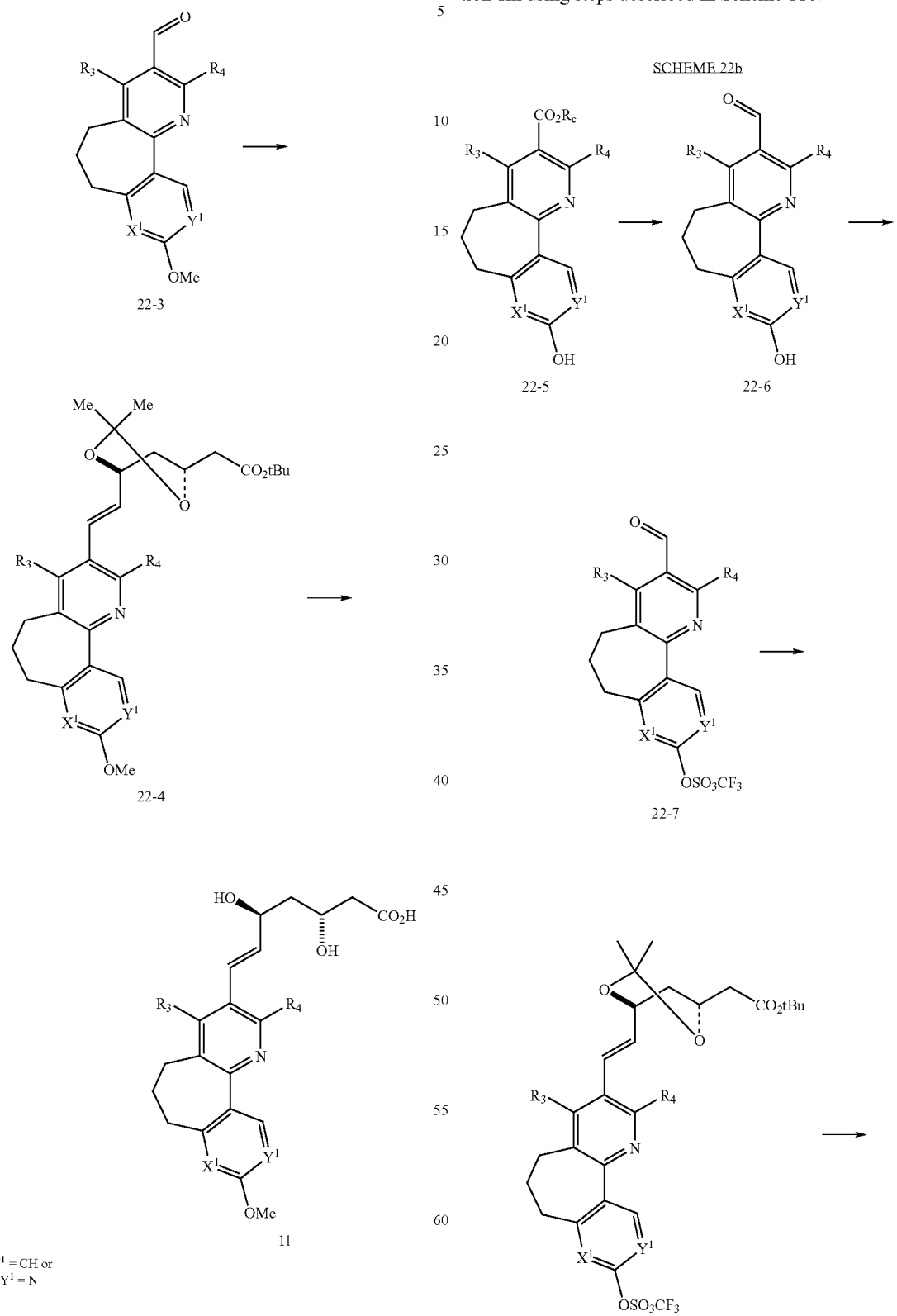
intermediate 22-6. Reaction of 22-6 with triflic anhydride provides 22-7 which provides 22-8 using steps described in Scheme 11b which is converted to compounds of the invention 1m using steps described in Scheme 11c.
Referring to Scheme 22b, intermediate 22-1 is transformed into intermediate 22-5 using aqueous HBr. Subsequent treatment of 22-5 using steps described in Scheme 11a provides

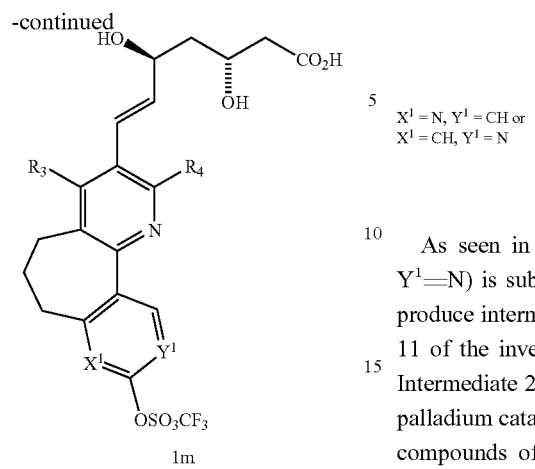

$X^1 = N, Y^1 = CH$ or
$X^1 = CH, Y^1 = N$

As seen in Scheme 22c, intermediate 22-8a ($X^1$=CH, $Y^1$=N) is subjected to a palladium catalyzed reduction to produce intermediate 22-9 which is converted to compound 11 of the invention using steps described in Scheme 11c. Intermediate 22-8 is also converted to nitrile 22-10 (using a palladium catalyst and zinc cyanide) which in turn provided compounds of the invention 1n using steps described in Scheme 11c.

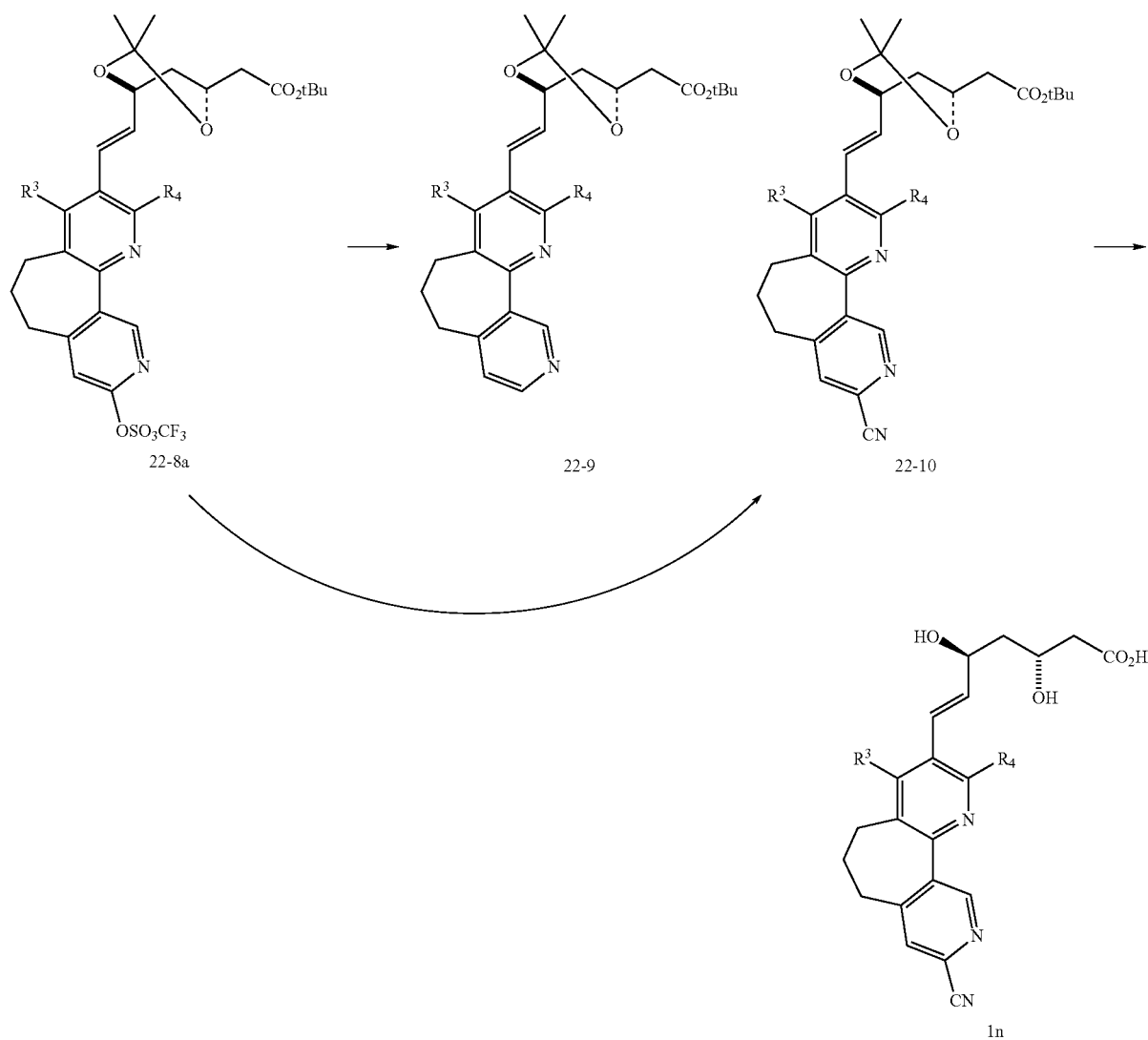

Referring to Scheme 22d, using steps described in Scheme 11b, intermediate 22-6 is transformed into intermediate 22-11 which produces compounds of the invention 1o using the methods described in Scheme 11c.

Referring to Scheme 22e, intermediate 22-5 is transformed to bromide 22-12 using phosphorous oxybromide in toluene. Transformation of 22-12 using steps described in Schemes 11a-b provides 22-14.

SCHEME 22d

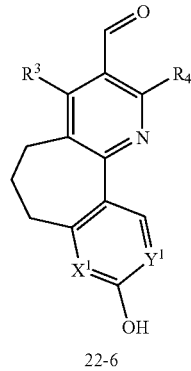

22-6

SCHEME 22e

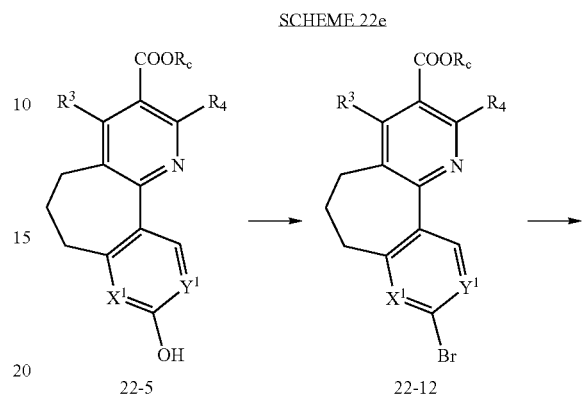

22-5     22-12

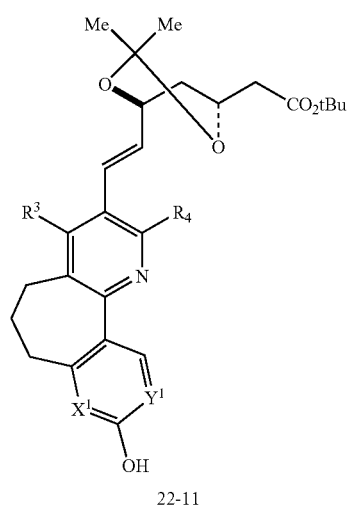

22-11

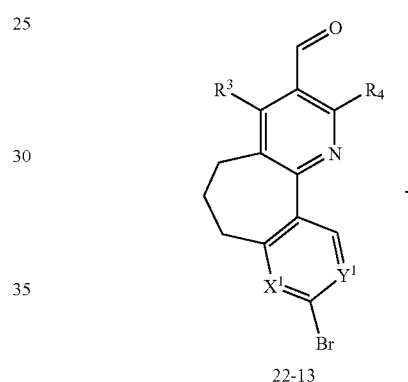

22-13

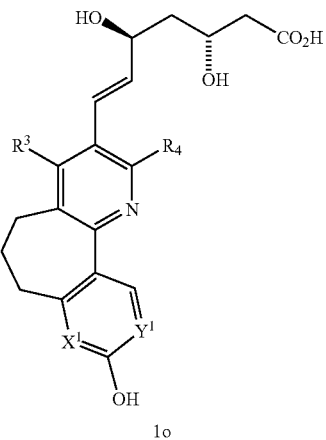

1o

X¹ = N, Y¹ = CH or
X¹ = CH, Y¹ = N

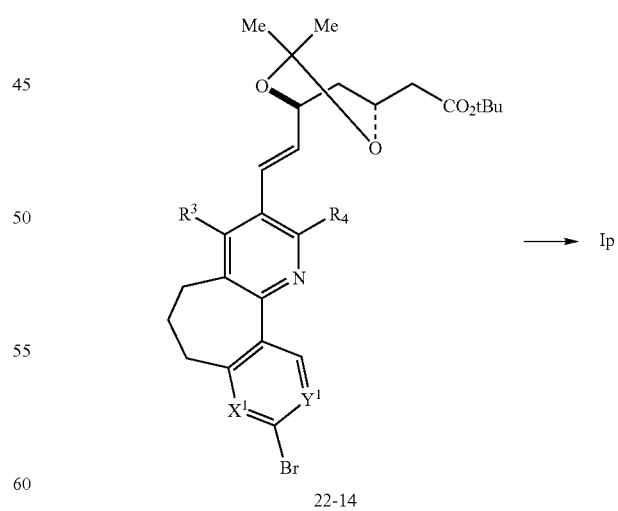

22-14

X¹ = N, Y¹ = CH or
X¹ = CH, Y¹ = N

Referring to Scheme 22f, the bromine atom of intermediate 22-14 is replaced by a carbomethoxy group by carbonylation and esterification under palladium catalysis; or is replaced by an amino group by reaction with an amine; or is converted to a cyano group with zinc cyanide and a palladium catalyst to provide intermediates 22-15, 22-16, and 22-17, respectively. Intermediate 22-16 is transformed to compounds of the invention 1p using steps described in Scheme 11c. Treatment of intermediate 22-17 sequentially with trifluoroacetic acid, urea/hydrogen peroxide, and acetone serves to convert the nitrile group to a carboxamide group and remove the protecting groups and then employing procedures as described above to provide compounds 1q of the invention.

SCHEME 22f

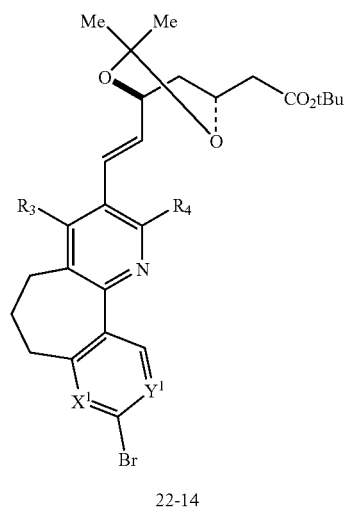

22-14

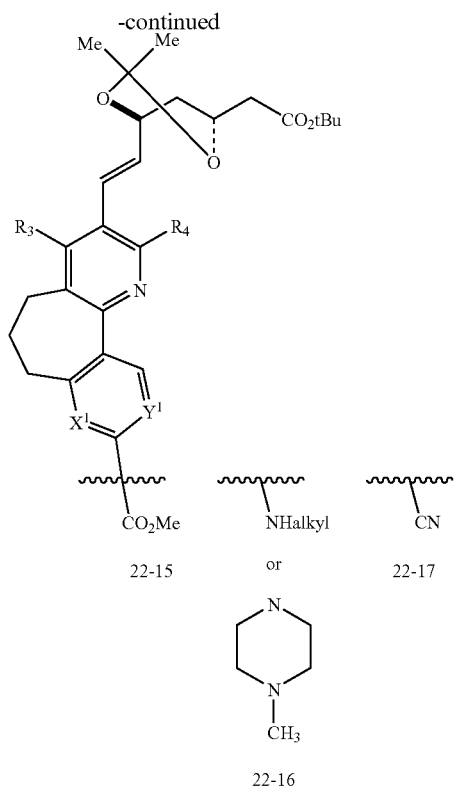

22-15

22-16

22-17

$X^1 = N, Y^1 = CH$ or $X^1 = CH, Y^1 = N$

Referring to Scheme 22g, intermediate 22-15 is subjected to mild base hydrolysis to provide intermediate 22-18. Acid 22-18 is treated with an amine under amide-forming conditions (for example, BOP reagent and diisopropylethylamine in tetrahydrofuran and dimethylformamide) to provide intermediate 22-19. Both 22-18 and 22-19 are converted to compound 1r of the invention using steps described in Scheme 11c.

SCHEME 22g

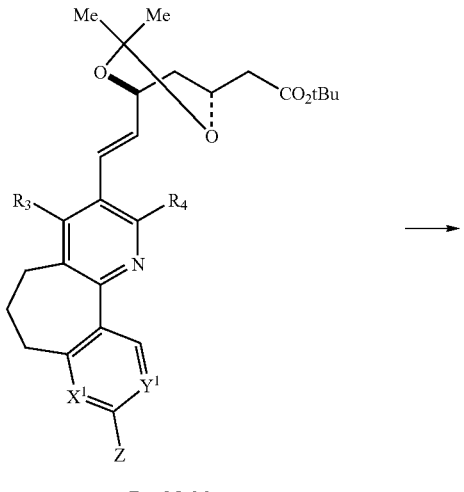

$Z = CO_2Me$ 22-15

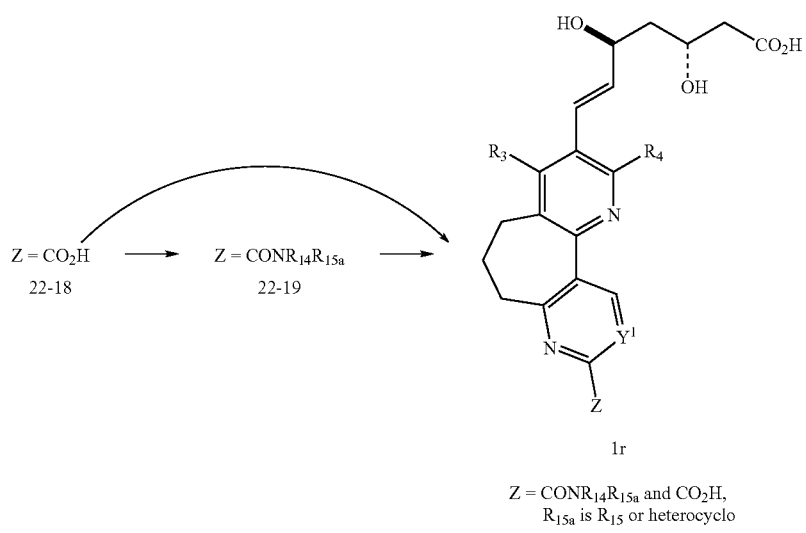

$X^1 = N, Y^1 = CH$ or $X^1 = CH, Y^1 = N$

Referring to Scheme 22h, intermediate 22-18 is treated with diphenylphosphoryl azide and triethylamine to provide isocyanate 22-20. This intermediate is treated with tert-butanol to provide a mixture of BOC-amine 22-21 and amine 22-22 or is isolated and treated with an amine to provide 22-23. Transformation of 22-21, 22-22 and 22-23 using steps described in Scheme 11c provides compounds of the invention 1s.

SCHEME 22h

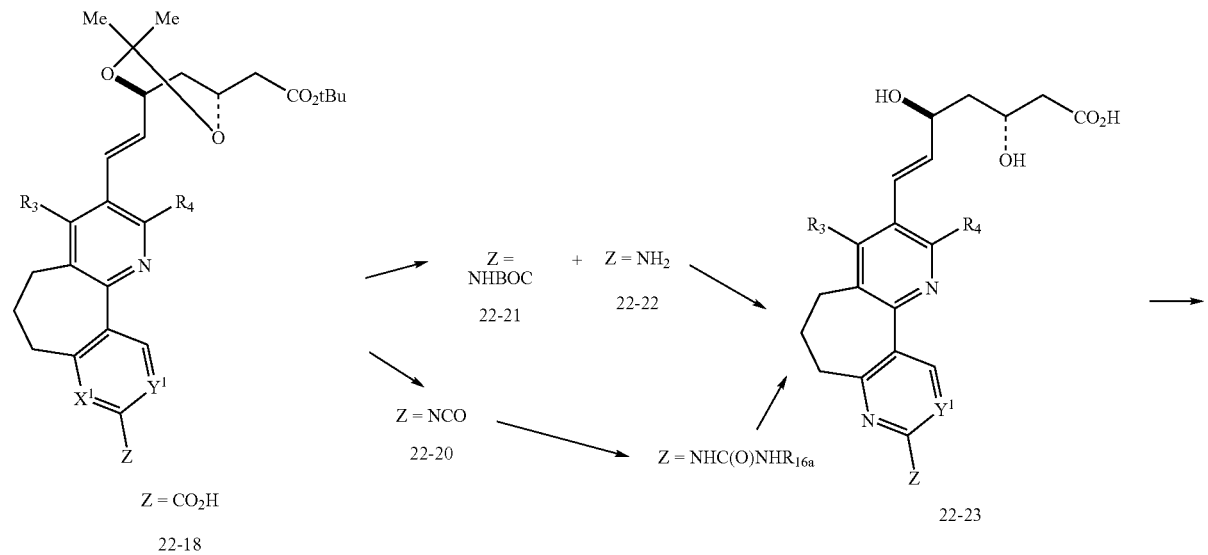

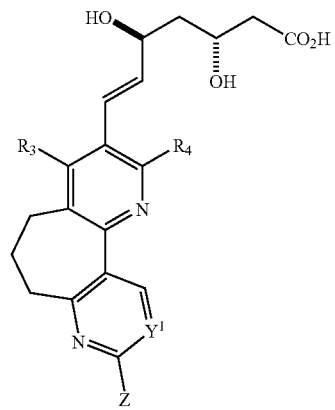

1s $X^1 = N, Y^1 = CH$ or $X^1 = CH, Y^1 = N$ $Z = NHC(O)NHR_{16a}$ and $NH_2$ $R_{16a}$ is alkyl or substituted alkyl Referring to Scheme 22i, treatment of 22-22 with methanesulfonyl chloride and triethylamine and then steps described in Scheme 11c provides compound 1t of the invention.

Referring to Scheme 23a, using the methods described in Scheme 7 and the reduction described in Scheme 11a, intermediate 23-1 is transformed into intermediate 23-2. Methylthiopyrimidine intermediate 23-2 is desulfurized using Raney Nickel to produce intermediate 23-3 which is transformed into compound 1u of the invention using steps described in Schemes 11a-c.

SCHEME 22i

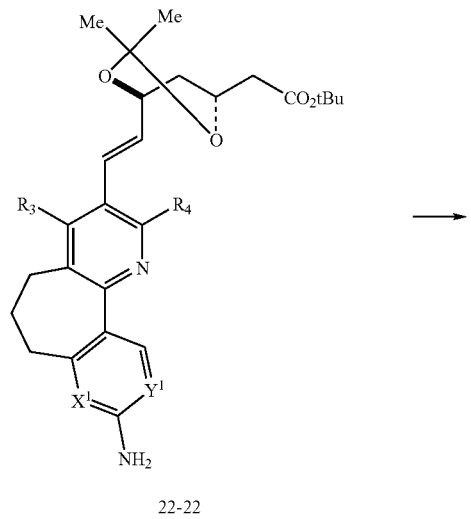

22-22

SCHEME 23a

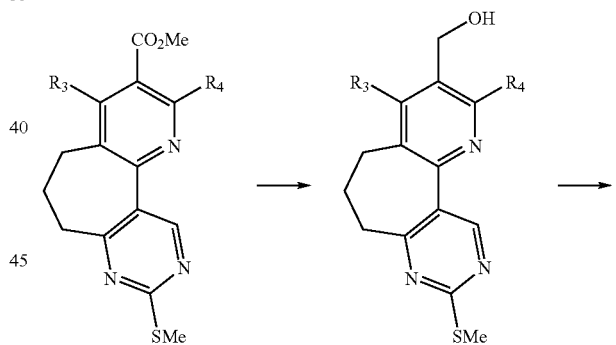

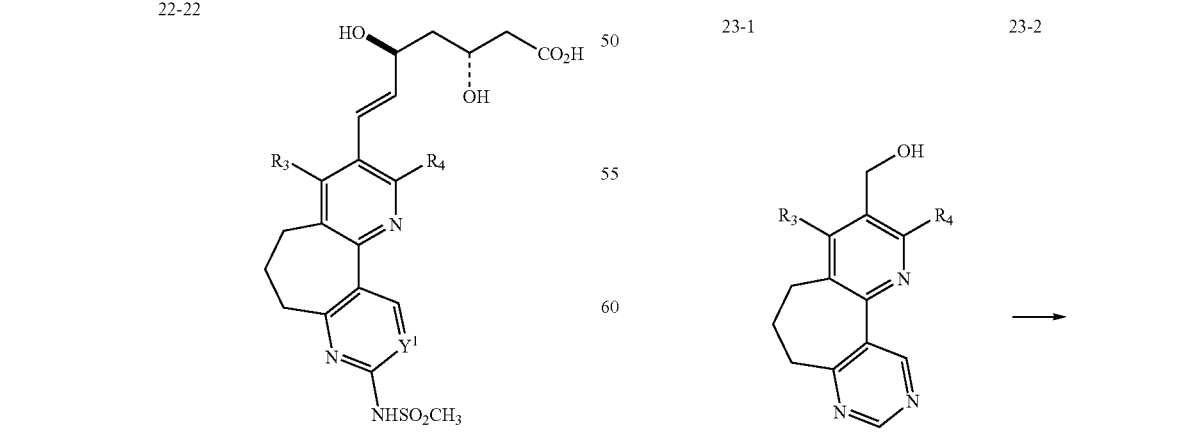

$X = N, Y = CH$ or $X = CH, Y = N$

1t

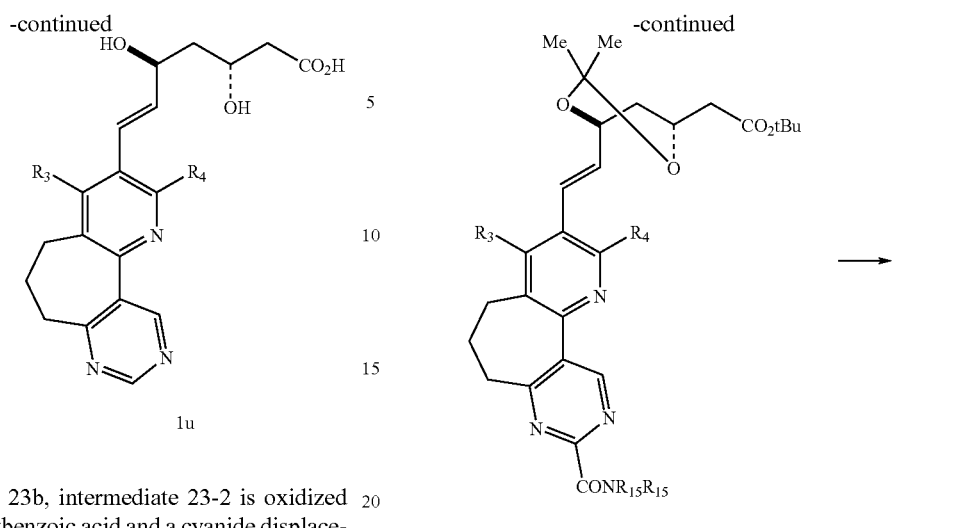

Referring to Scheme 23b, intermediate 23-2 is oxidized with meta-chloroperoxybenzoic acid and a cyanide displacement of the resultant sulfone group produces intermediate 23-4. Hydrolysis of 23-4 with aqueous sodium hydroxide followed by Fischer esterification and steps described in Schemes 11a and 11b produces intermediate 23-5. Ester 23-5 is treated with an amine to produce 23-6 which is transformed to compounds of the invention 1v using the methods described in Scheme 11c.

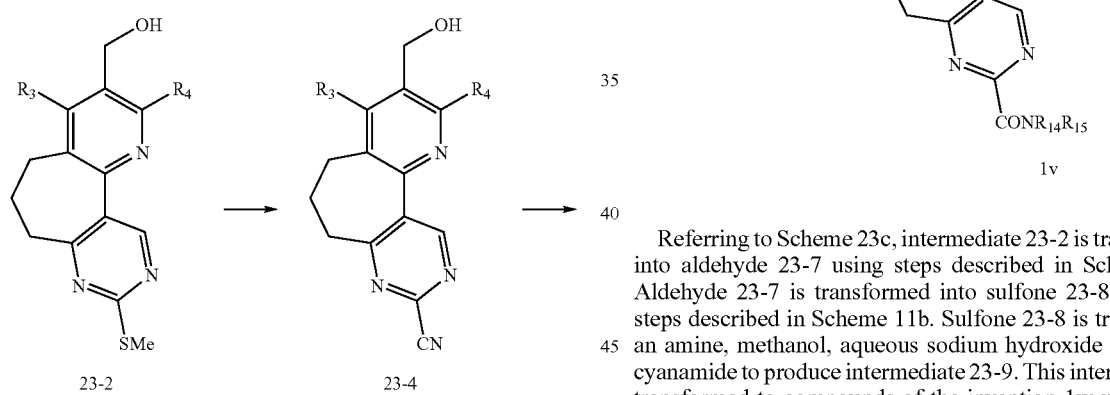

Referring to Scheme 23c, intermediate 23-2 is transformed into aldehyde 23-7 using steps described in Scheme 11a. Aldehyde 23-7 is transformed into sulfone 23-8 using the steps described in Scheme 11b. Sulfone 23-8 is treated with an amine, methanol, aqueous sodium hydroxide or sodium cyanamide to produce intermediate 23-9. This intermediate is transformed to compounds of the invention 1w using steps described in Scheme 11c.

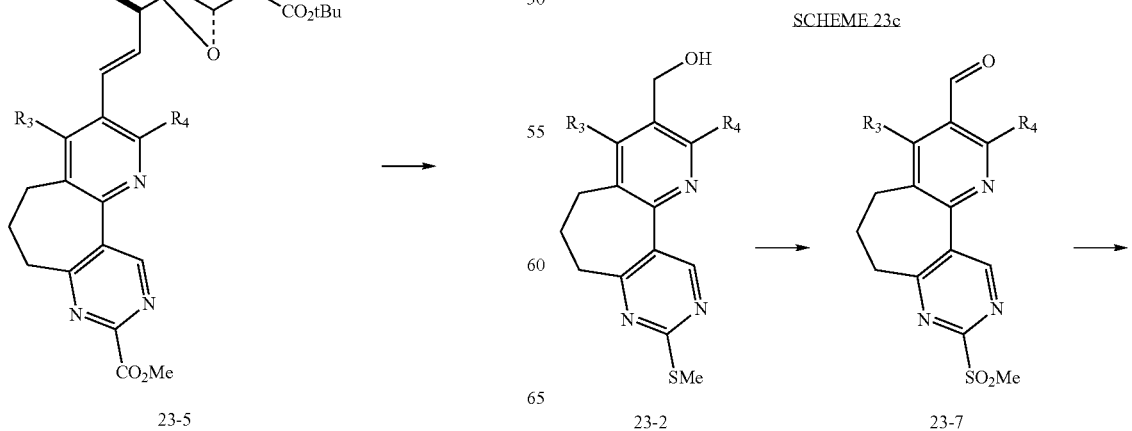

-continued

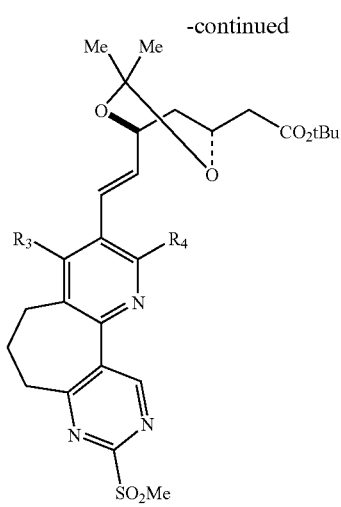

23-8

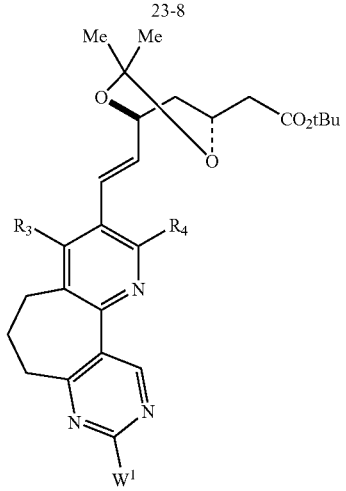

$W^1 = NR_{14}R_{15}$, OH, OMe, N(H)CN 23-9

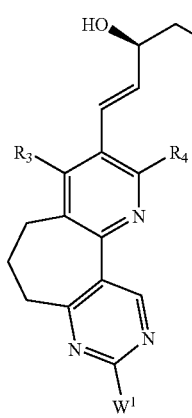

1w

Methylpyrazole intermediates 3-4 and 3-5 and methylpyrimidine 3-6 are transformed to compounds of the invention using steps described in Schemes 7 and 11a-c.

Referring to Scheme 24, transformation of methylpyrazole intermediate 3-5 using steps as described in Schemes 7 and 11a and protection as the t-butyldimethylsilyl (TBS) ether produces intermediate 24-1. Metallation/carboxylation using n-butyllithium and carbon dioxide and Fischer esterification provides intermediate 24-2. Intermediate 24-2 provides compounds of the invention 1x using steps described in Schemes 11a-c.

SCHEME 24

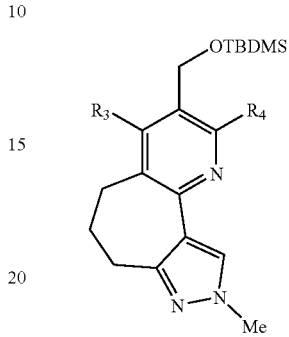

24-1

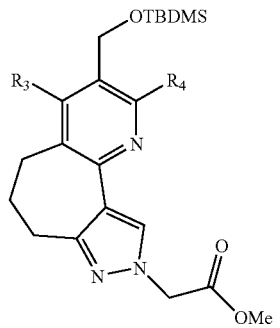

24-2

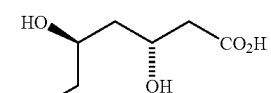

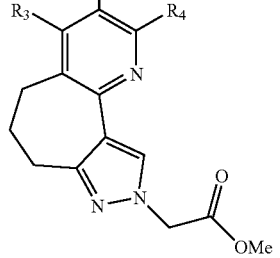

1x

Intermediates of type 4-3, 5-4, 5-6, 5-8, 5-9, and 5-12 are transformed to compounds of the invention using the steps described in Schemes 7 and 11a-c.

Referring to Scheme 25, pyridine ring formation using steps described in Scheme 7 transforms intermediate 6-6 into ester 25-1. Reduction and acetylation produces acetate 25-2. Beckman rearrangement of the derivative oxime produces 25-3. Hydrolysis produces a carbinol, 25-4, which is elaborated and deprotected to form compounds of the invention 1y using the methods described in Schemes 11a-c.

SCHEME 25

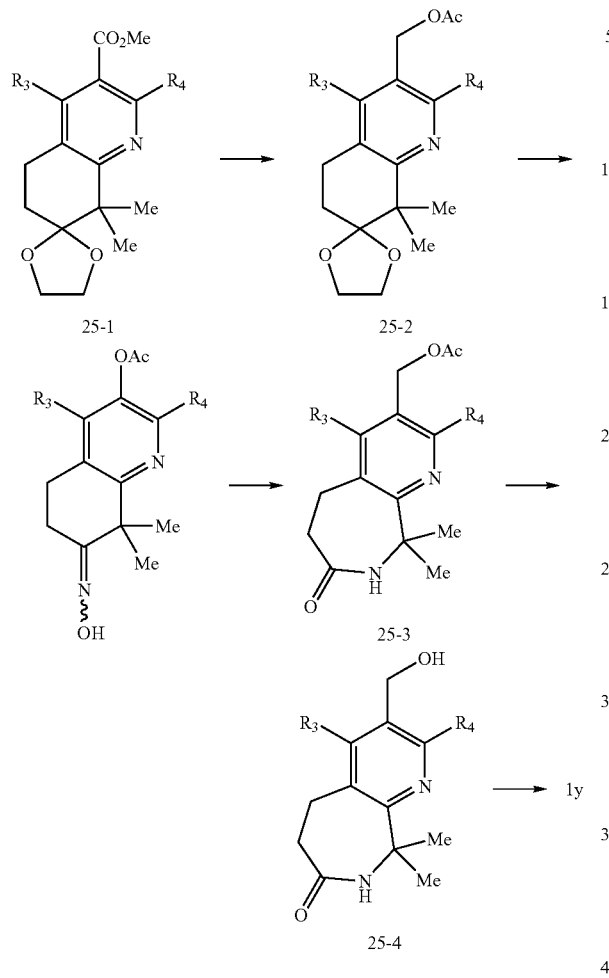

SCHEME 26

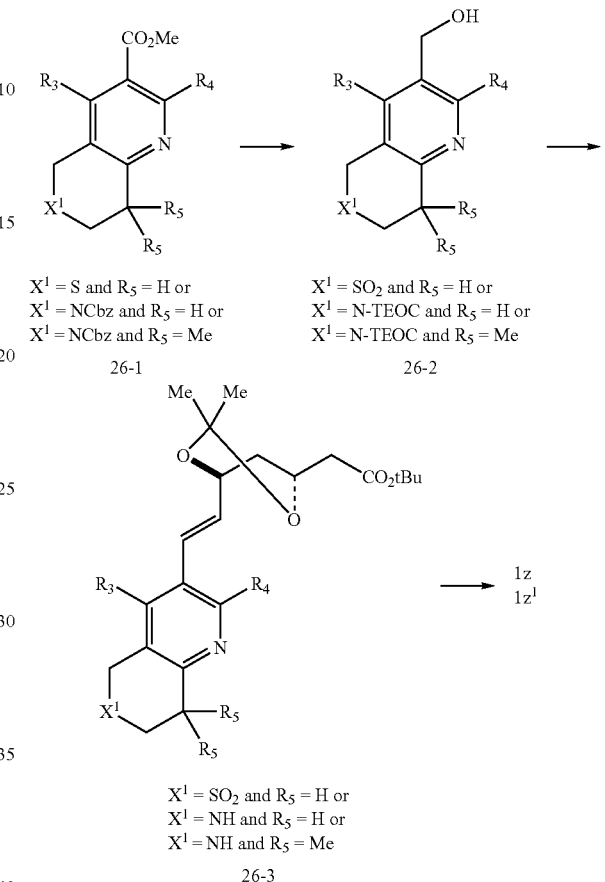

Referring to Scheme 26, compounds of the invention wherein B is B7 are prepared from intermediates 6-3 and 6-4. Using steps described in Scheme 7, these intermediates are transformed into intermediate 26-1. Reduction of intermediate 26-1 wherein $X^1$ is S and R is H using steps described in Scheme 11a, and oxidation using meta-chloroperoxybenzoic acid provides intermediate 26-2 wherein $X^1$ is $SO_2$ and R is H. Hydrogenolysis of the CBZ group of 26-1 wherein $X^1$ is N-Cbz and R is H or Me using palladium on carbon and cyclohexadiene, reduction using steps described in Scheme 11a and protection of the NH group as the 2-(trimethylsilyl) ethoxycarbonyl (TEOC) derivative provides 26-2 wherein $X^1$ is N-TEOC and R is H or Me. Transformation of 26-2 wherein $X^1$ is $SO_2$ and R is H using steps described in Scheme 11a-b produces intermediate 26-3 wherein $X^1$ is $SO_2$ and R is H. Transformation of intermediate 26-2 wherein $X^1$ is N-TEOC and R is H or Me using steps described in Scheme 11a-b followed by removal of the TEOC group by treatment with tetrabutylammonium fluoride produces intermediate 26-3 wherein $X^1$ is NH and R is H or Me. Intermediate 26-3 wherein W is $SO_2$ and R is H is transformed compounds of the invention 1z wherein B is B7, W is $SO_2$ and R is H using steps outlined in Scheme 11c. Intermediate 26-3 wherein $X^1$ is NH and R is H or Me is acylated with acetyl chloride, methoxyacetyl chloride, or acetoxyacetyl chloride; or sulfonylated with methanesulfonyl chloride and the resulting intermediates are transformed compounds of the invention $1z^1$ wherein B is B7 and R is H or Me and W is $NC(O)R_{16}$ and $NSO_2R_{17}$ using steps outlined in Scheme 11c.

It will be appreciated that the designation

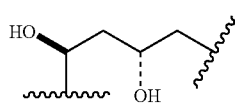

as employed herein is used interchangeably with

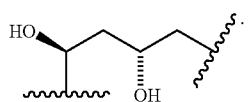

Compounds containing dihydroxy acid HMG-CoA binding domain side chains may be prepared in homochiral form, which is preferred, or may be prepared as racemic or diastereomeric mixtures (3R*, 5S*) and may later be resolved to obtain the (3R, 5S) isomer.

The compounds of the invention are inhibitors of 3-hydroxy-3-methyl-glutaryl coenzyme A (HMG-CoA) reductase and thus are useful in inhibiting cholesterol biosynthesis and/or in lowering triglycerides, in a manner similar to atorvastatin, pravastatin, simvastatin, lovastatin, cerivastatin, rosuvastatin, fluvastatin, pitavastatin, and the like.

A further aspect of the invention is a pharmaceutical composition containing at least one of the compounds of formula 1 of the present invention in association with a pharmaceutical vehicle or diluent. The pharmaceutical composition can be formulated employing conventional solid or liquid vehicles of diluents and pharmaceutical additives of a type appropriate to the mode of desired administration. The compounds can be administered by an oral route, for example, in the form of tablets, capsules, granules or powders, or they can be administered by a parenteral route in the form of injectable preparations. Such dosage forms contain from 0.1 to 1500 mg of active compound per dosage, for use in the treatment. The dose to be administered depends on the unitary dose, the symptoms, and the age and the body weight of the patient.

The compounds of the invention can be administered in a similar manner as known compounds suggested for use in inhibiting cholesterol biosynthesis, such as pravastatin, lovastatin, simvastatin, rosuvastatin, atorvastatin, cerivastatin, fluvastatin, pitavastatin, and the like, in mammalian species such as humans, dogs, cats and the like. Thus, the compounds of the invention may be administered in an amount from about 0.1 to 500 mg in a single dose or in the form of individual doses from 1 to 4 times per day, preferably 0.5 to 200 mg daily or in sustained release form.

The HMG CoA reductase inhibitors of formula 1 may be employed in combination with all therapeutic agents which are useful in combination with HMG CoA reductase inhibitors.

Thus, where desired, the compounds of structure 1 may be used in combination with one or more hypolipidemic agents or lipid-lowering agents, or lipid agents, or lipid modulating agents, and/or one or more other types of therapeutic agents including antidiabetic agents, anti-obesity agents, antihypertensive agents, platelet aggregation inhibitors, anti-Alzheimer's agents, anti-dementia agents, anti-osteoporosis agents, and/or hormone replacement therapeutic agents, and/or other therapeutic agents, and/or other cardiovascular agents (including anti-anginal agents, anti-arrhythmic agents, anti-atherosclerosis agents, anti-inflammatory agents, anti-platelet agents, anti-heart failure agents), anti-cancer agents, anti-infective agents, hormone replacement agents, growth hormone secretagogues, selective androgen receptor modulators (SARMs), and/or other therapeutic agents which may be administered orally in the same dosage form or in a separate oral dosage form, or by injection.

The hypolipidemic agent or lipid-lowering agent or other lipid agent or lipid modulating agent which may be optionally employed in combination with the compounds of formula 1 of the invention may include 1, 2, 3 or more MTP inhibitors, HMG CoA reductase inhibitors, squalene synthetase inhibitors, PPAR α agonists, PPAR dual α/γ agonists, PPAR δ agonists, fibric acid derivatives, ACAT inhibitors, lipoxygenase inhibitors, cholesterol absorption inhibitors, ileal Na+/bile acid cotransporter inhibitors, upregulators of LDL receptor activity, cholesteryl ester transfer protein inhibitors, bile acid sequestrants, and/or nicotinic acid and derivatives thereof.

MTP inhibitors employed herein include MTP inhibitors disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. Pat. No. 5,962,440. Preferred are each of the preferred MTP inhibitors disclosed in each of the above patents and applications.

All of the above U.S. Patents and applications are incorporated herein by reference.

Most preferred MTP inhibitors to be employed in accordance with the present invention include preferred MTP inhibitors as set out in U.S. Pat. Nos. 5,739,135 and 5,712, 279, and U.S. Pat. No. 5,760,246.

The most preferred MTP inhibitor is 9-[4-[4-[[2-(2,2,2-Trifluoroethoxy)benzoyl]amino]-1-piperidinyl]butyl]-N-(2, 2,2-trifluoroethyl)-9H-fluorene-9-carboxamide

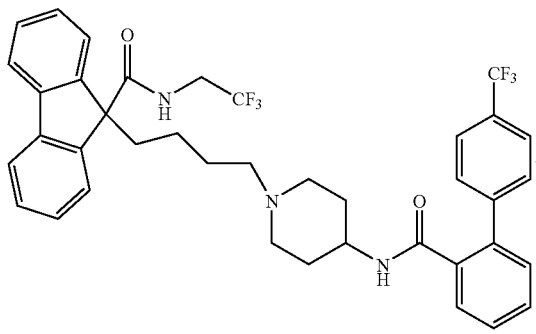

The squalene synthetase inhibitors suitable for use herein include, but are not limited to, α-phosphono-sulfonates disclosed in U.S. Pat. No. 5,712,396, those disclosed by Biller et al., J. Med. Chem., 1988, Vol. 31, No. 10, pp. 1869-1871, including isoprenoid (phosphinyl-methyl)phosphonates as well as other known squalene synthetase inhibitors, for example, as disclosed in U.S. Pat. Nos. 4,871,721 and 4,924, 024 and in Biller, S. A., Neuenschwander, K., Ponpipom, M. M., and Poulter, C. D., Current Pharmaceutical Design, 2, 1-40 (1996).

In addition, other squalene synthetase inhibitors suitable for use herein include the terpenoid pyrophosphates disclosed by P. Ortiz de Montellano et al., J. Med. Chem., 1977, 20, 243-249, the farnesyl diphosphate analog A and presqualene pyrophosphate (PSQ-PP) analogs as disclosed by Corey and Volante, J. Am. Chem. Soc., 1976, 98, 1291-1293, phosphinylphosphonates reported by McClard, R. W. et al., J.A.C.S., 1987, 109, 5544 and cyclopropanes reported by Capson, T. L., Ph.D. dissertation, June, 1987, Dept. Med. Chem. U of Utah, Abstract, Table of Contents, pp. 16, 17, 40-43, 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, fenofibrate, probucol and gemfibrozil being preferred, bile acid sequestrants such as cholestyramine, colestipol and DEAE-Sephadex (Secholex®, Policexide®) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (ER niacin, Niaspan), acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, Drugs of the Future 24, 9-15 (1999), (Avasimibe); "The ACAT inhibitor, C1-1011 is effective in the prevention and regression of aortic fatty streak area in hamsters", Nicolosi et al., Atherosclerosis (Shannon, Irel). (1998), 137(1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al., Bioorg. Med. Chem. Lett. (1996), 6(1), 47-50; "ACAT inhibitors: physiologic mechanisms for hypolipidemic and anti-atherosclerotic activities in experimental animals", Krause et al., Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al., Curr. Med. Chem. (1994), 1(3), 204-25; "Inhibitors of acyl-CoA: cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al., Chemtracts: Org. Chem. (1995), 8(6), 359-62, or TS-962 (Taisho Pharmaceutical Co. Ltd.), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd.) and LY295427 (Eli Lilly).

The hypolipidemic agent may be a cholesterol absorption inhibitor preferably Schering-Plough's SCH48461 (ezetimibe) as well as those disclosed in Atherosclerosis 115, 45-63 (1995) and J. Med. Chem. 41, 973 (1998).

The other lipid agent or lipid-modulating agent may be a cholesteryl transfer protein inhibitor (CETP) such as Pfizer's CP-529,414 (torcetrapib) as well as those disclosed in WO/0038722 and in EP 818448 (Bayer) and EP 992496, and Pharmacia's SC-744 and SC-795 as well as CETi-1 and JTT-705.

The hypolipidemic agent may be an ileal $Na^+$/bile acid cotransporter inhibitor such as disclosed in Drugs of the Future, 24, 425-430 (1999).

The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201;

a beta-lactam cholesterol absorption inhibitor such as disclosed in EP 675714;

an HDL upregulator such as an LXR agonist, a PPAR α-agonist and/or an FXR agonist;

an α-glucosidase inhibitor, an aldose reductase inhibitor and/or an LDL catabolism promoter such as disclosed in EP 1022272;

a sodium-proton exchange inhibitor such as disclosed in DE 19622222;

an LDL-receptor inducer or a steroidal glycoside such as disclosed in U.S. Pat. No. 5,698,527 and GB 2304106;

an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E;

isoniazid as disclosed in WO 97/35576;

a cholesterol absorption inhibitor, an HMG-CoA synthase inhibitor, or a lanosterol demethylase inhibitor as disclosed in WO 97/48701;

a PPAR δ agonist for treating dyslipidemia;

a PPAR α agonist for treating dyslipidemia;

a dual PPAR α/γ agonist such as muraglitazar (Bristol Myers-Squibb), tesaglitazar (AstraZeneca) or MK-767 (Merck/Kyorin/Banyu);

or a sterol regulating element binding protein-I (SREBP-1) as disclosed in WO 2000/050574, for example, a sphingolipid, such as ceramide, or neutral sphingomyelenase (N-SMase) or fragment thereof.

Preferred hypolipidemic agents are cholesterol absorption inhibitors such as ezetimibe, cholesterol ester transfer protein (CETP) inhibitors such as torcetrapib and JTT-705, dual PPAR α/δ agonists such as muraglitazar and tesaglitazar, as well as niacin and/or cholestagel.

The above-mentioned U.S. patents are incorporated herein by reference. The amounts and dosages employed will be as indicated in the Physician's Desk Reference and/or in the patents set out above or as otherwise known in the art.

The compounds of formula 1 of the invention will be employed in a weight ratio to the hypolipidemic agent (where present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent or other lipid agent or lipid modulating agent will be as disclosed in the various patents and applications discussed above.

The dosages and formulations for the other hypolipidemic agent or other lipid agent or lipid modulating agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 200 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The anti-atherosclerotic agent includes a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties," Brit. J. Pharmacology (1997) 120, 1199-1206, and Cornicelli et al., "15-Lipoxygenase and its Inhibition: A Novel Therapeutic Target for Vascular Disease", Current Pharmaceutical Design, 1999, 5, 11-20.

The compounds of formula 1 and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The antidiabetic agent which may be optionally employed in combination with the HMG-CoA reductase inhibitor of formula 1 may be 1, 2, 3 or more antidiabetic agents or antihyperglycemic agents including insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, aP2 inhibitors, PPAR α/γ dual agonists, dipeptidyl peptidase IV (DP4) inhibitors, SGLT2 inhibitors, glycogen phosphorylase inhibitors, and/or meglitinides, and/or glucagon-like peptide-1 (GLP-1), and/or a PTP-1B inhibitor (protein tyrosine phosphatase-1B inhibitor), as well as insulin and slow release insulin (Basulin™ (Flamel)).

The antidiabetic agent may be an oral antihyperglycemic agent preferably a biguanide such as metformin or phenformin or salts thereof, preferably metformin HCl.

Where the antidiabetic agent is a biguanide, the compounds of structure 1 will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of structure 1 will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure 1 will be employed in a weight ratio to the glucosidase inhibitor within the range from about 0.01:1 to about 100:1, preferably from about 0.05:1 to about 10:1.

The compounds of structure 1 may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Wellcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of structure 1 will be employed in a weight ratio to the thiazolidinedione in an amount within the range from about 0.01:1 to about 100:1, preferably from about 0.05:1 to about 10:1.

The sulfonyl urea and PPAR γ agonists in amounts of less than about 150 mg oral antidiabetic agent may be incorporated in a single tablet with the compounds of structure 1.

The compounds of structure 1 may also be employed in combination with a antihyperglycemic agent such as insulin or slow release insulin (Basulin™), or with glucagon-like peptide-1 (GLP-1) or mimetic such as GLP-1 (1-36) amide, GLP-1 (7-36) amide, GLP-1 (7-37) (as disclosed in U.S. Pat. No. 5,614,492 to Habener, the disclosure of which is incorporated herein by reference), as well as AC2993 (Amylin) and LY-315902 (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the PPAR anti-diabetic agent may be employed in amounts within the range from about 0.01 to about 2000 mg/day which may be administered in single or divided doses one to four times per day.

Where present insulin and other anti-diabetic agents as set out above may be employed in formulations, amounts and dosing as indicated by the Physician's Desk Reference.

Where present GLP-1 peptides or mimetics may be administered in oral buccal formulations, by nasal administration or parenterally as described in U.S. Pat. Nos. 5,346,701 (TheraTech), 5,614,492 and 5,631,224 which are incorporated herein by reference.

The antidiabetic agent or other lipid agent may also be a PPAR modulator such as a PPAR α/γ dual agonist such as tesaglitazar (Astra/Zeneca), muraglitazar (Bristol Myers-Squibb), MK-767 (Merck/Kyorin/Banyu), GW-409544 (Glaxo-Wellcome), KRP297 (Kyorin Merck) as well as those disclosed by Murakami et al., "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841-1847 (1998), and in U.S. application Ser. No. 09/664,598, filed Sep. 18, 2000, the disclosure of which is incorporated herein by reference, employing dosages as set out therein, which compounds designated as preferred are preferred for use herein.

The antidiabetic agent may be an SGLT2 inhibitor such as disclosed in U.S. Pat. Nos. 6,414,126 and 6,515,117, employing dosages as set out therein. Preferred are the compounds designated as preferred in the above patents.

The antidiabetic agent may be an aP2 inhibitor such as disclosed in U.S. Pat. No. 6,548,529, employing dosages as set out herein. Preferred are the compounds designated as preferred in the above patent.

The antidiabetic agent may be a DPP4 inhibitor such as disclosed in U.S. Pat. No. 6,395,767, U.S. Pat. No. 6,573,287, U.S. Pat. No. 6,395,767 (BMS-477118 (preferred), BMS- 471211 and BMS 538,305), WO99/38501, WO99/46272, WO99/67279 (PROBIODRUG), WO99/67278 (PROBIODRUG), WO99/61431 (PROBIODRUG), NVP-LAF-237, NVP-DPP728A (1-[[[2-[(5-cyanopyridin-2-yl)amino]ethyl] amino]acetyl]-2-cyano-(S)-pyrrolidine) (Novartis) as disclosed by Hughes et al., Biochemistry, 38(36), 11597-11603, 1999, TSL-225 (tryptophyl-1,2,3,4-tetrahydro-isoquinoline-3-carboxylic acid (disclosed by Yamada et al., Bioorg. & Med. Chem. Lett. 8 (1998) 1537-1540, 2-cyanopyrrolidides and 4-cyanopyrrolidides as disclosed by Ashworth et al., Bioorg. & Med. Chem. Lett., Vol. 6, No. 22, pp. 1163-1166 and 2745-2748 (1996) employing dosages as set out in the above references.

The meglitinide which may optionally be employed in combination with the compound of formula 1 of the invention may be repaglinide or Starlix® (Novartis), nateglinide (Novartis) or KAD1229 (PF/Kissei), with repaglinide being preferred.

The antidiabetic compound may be a melanocortin receptor agonist such as a spiropiperidine as disclosed in WO 99/64002.

The HMG CoA reductase inhibitor of formula 1 will be employed in a weight ratio to the meglitinide, PPAR modulator such as a PPAR γ agonist, PPAR α agonist, PPAR δ agonist or antagonist, PPAR α/γ dual agonist, aP2 inhibitor, DP4 inhibitor or SGLT2 inhibitor or other antidiabetic agent within the range from about 0.01:1 to about 100:1, preferably from about 0.05:1 to about 10:1.

The other type of therapeutic agent which may be optionally employed with the HMG CoA reductase inhibitor of formula 1 may be 1, 2, 3 or more of an anti-obesity agent including a beta 3 adrenergic agonist, a lipase inhibitor, a serotonin and/or dopamine modulator/mimic, norepinephrine (NE) modulator/mimic, an aP2 inhibitor, a thyroid receptor beta drug, a PTP-1B inhibitor, an anorectic agent, a PPAR modulator including PPAR γ antagonists, PPAR α agonists, PPAR δ antagonists, a CCKA agonist, a leptin inhibitor such as a leptin receptor activator, a neuropeptide Y antagonist, a melanocortin-4-receptor (MC4R) agonist, a CB-1 inverse agonist, a fatty acid oxidation upregulator or inducer (such as Famoxin® Genset), a 5-HT2c agonist, and an acetyl CoA carboxylase (ACC) inhibitor.

The beta 3 adrenergic agonist which may be optionally employed in combination with a compound of formula I may be AJ9677 (Takeda/Dainippon), L750355 (Merck), or CP331648 (Pfizer) or other known beta δ agonists as disclosed in U.S. Pat. Nos. 5,541,204, 5,770,615, 5,491,134, 5,776,983 and 5,488,064, with AJ9677, L750,355 and CP331648 being preferred.

The neuropeptide Y antagonists which may be optionally employed in combination with a compound of formula 1 include those described in WO 01/13917 (BMS) or in U.S. Pat. No. 6,218,408 (Synaptic) and in WO 01/14376 (Banyu).

The lipase inhibitor which may optionally be employed in combination with a compound of formula 1 may be orlistat or ATL-962 (Alizyme), with orlistat being preferred.

The serotonin and dopoamine modulator/mimic and/or norepinephrine modulator/mimic which may be optionally employed in combination with a compound of formula 1 may be sibutramine.

The anorectic agent which may be optionally employed in combination with a compound of formula 1 may be topiramate, Axokine® (Regeneron) (analogue of Ciliary Neurotrophic Factor) dexamphetamine, phentermine, phenylpropanolamine or mazindol, with dexamphetamine or topiramate being preferred.

The thyroid receptor beta compound which may be optionally employed in combination with a compound of formula 1 may be a thyroid receptor ligand as disclosed in WO97/21993 (U. Cal SF), WO99/00353 (KaroBio), and U.S. Provisional Application 60/183,223 filed Feb. 17, 2000, with compounds of the KaroBio applications and the above U.S. provisional application being preferred.

Examples of the ACC inhibitors which may be employed include those described in WO 03/072197.

Examples of the CB-1 inverse agonists which may be employed include SR-141716 (Sanofi) and FLV-319 (Folvay).

Examples of the 5-HT2c agonists which may be employed include compounds as disclosed in WO 00/77010.

The CCKA agonists which may be employed herein include Glaxo-SmithKline's GI-181,771 and Sanofi's SR146,131.

The PTP-1B inhibitor which may be an anti-obesity and/or an antidiabetic agent include those disclosed in WO 99/58521, WO 99/58518, WO 99/58522 and WO 99/61435.

The anti-obesity agent employed may also be Pfizer's P57 or CP-644,673 (licensed from Phytopharm).

The various anti-obesity agents described above may be employed in the same dosage form with the compound of formula 1 or in different dosage forms, in dosages and regimens as generally known in the art or in the PDR.

The antihypertensive agents which may be employed in combination with the HMG CoA reductase inhibitors of the invention include ACE inhibitors, angiotensin II receptor antagonists, MR agonist, NEP inhibitors such as candoxatril, NEP/ACE inhibitors, as well as calcium channel blockers (such as verapamil and amlodipine besylate), T-channel calcium antagonists (such as mibefradil), β-adrenergic blockers, diuretics, α-adrenergic blockers (such as doxazosin mesylate and terazosin HCl), dual action receptor antagonists (DARA), heart failure drugs such as digoxin, and other types of antihypertensive agents.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al. mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenyl-butyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Preferred ACE inhibitors are captopril, fosinopril, enalapril, lisinopril, cetapril, cilazapril, indalapril, spirapril, perindopril, ceranapril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366,973, 5,225,401, 4,722,810, 5,223,516, 4,749,688, U.S. Pat. No. 5,552,397, U.S. Pat. No. 5,504,080, U.S. Pat. No. 5,612,359,U.S. Pat. No. 5,525,723, European Patent Application 0599,444, 0481,522, 0599,444, 0595,610, European Patent Application 0534363A2, 534,396 and 534,492, and European Patent Application 0629627A2.

Preferred are those NEP/ACE inhibitors and dosages thereof which are designated as preferred in the above patents/applications which U.S. patents are incorporated herein by reference; most preferred are omapatrilat, gemopatrilat ([S[(R*,R*)]-hexahydro-6-[(2-mercapto-1-oxo-3-phenylpropyl)amino]-2,2-dimethyl-7-oxo-1H-azepine-1-acetic acid) and CGS 30440.

The angiotensin II receptor antagonist (also referred to herein as angiotensin II antagonist or AII antagonist) suitable for use herein includes, but is not limited to, irbesartan, losartan, valsartan, candesartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

It will be appreciated that preferred dosages of ACE inhibitor and AII antagonist will be as set out in the latest edition of the Physician's Desk Reference (PDR).

Dual action receptor antagonists (DARA) suitable for use herein include those disclosed in U.S. application Ser. No. 09/513,779, filed Feb. 25, 2000, and Ser. No. 09/604,322, filed Jun. 26, 2000.

Other examples of preferred antihypertensive agents suitable for use herein include omapatrilat (Vanlev®), gemopatrilat, amlodipine besylate (Norvasc®), prazosin HCl (Minipress®), verapamil, nifedipine, diltiazem, felodipine, nisoldipine, isradipine, nicardipine, beta blockers such as nadolol, atenolol (Tenormin®), sotalol, terazosin, doxazosin, carvedilol, and propranolol, and clonidine HCl (Catapres®).

Diuretics which may be employed in combination with compounds of formula 1 include hydrochlorothiazide, torasemide, furosemide, spironolactone, and indapamide.

Antiplatelet agents which may be employed in combination with compounds of formula 1 of the invention include aspirin, clopidogrel, ticlopidine, dipyridamole, CS-747, (Lilly), abciximab, tirofiban, eptifibatide, anagrelide, and ifetroban, with clopidogrel and aspirin being preferred.

Anti-thrombotic agents which may be employed in combination with compounds of formula 1 of the invention include melagatran and ximelagatran (Exanta™ Astra Zeneca), warfarin and Factor Xa inhibitors such as razaxaban.

The antihypertensive agents, diuretics and antiplatelet drugs may be employed in amounts as indicated in the PDR. Ifetroban may be employed in amounts as set out in U.S. Pat. No. 5,100,889.

Anti-Alzheimer's agents or anti-dementia agents suitable for use herein with the HMG CoA reductase inhibitors of the invention include tacrine HCl (Cognex®) and donepezil (Aricept®), as well as γ-secretase inhibitors, β-secretase inhibitors and/or antihypertensive agents. Dosages employed will be as set out in the PDR.

Antiosteoporosis agents suitable for use herein in combination with the HMG CoA reductase inhibitors of the invention include parathyroid hormone or bisphosphonates, such as MK-217 (alendronate) (Fosamax®) as well as Ca receptor agonists and progestin receptor agonists. Dosages employed will be as set out in the PDR.

The hormone replacement therapeutic agents, where present, will be employed in dosages as set out in the latest edition of the PDR. Examples of such agents include selective estrogen receptor modulators (SERMs) such as raloxifen, tamoxifen or lasoxifen.

The HMG CoA reductase compound of the invention may also be employed in combination with a tyrosine kinase inhibitor such as disclosed in WO 2000/053605.

The selective androgen receptor modulator (SARM) suitable for use herein may be LGD-2226 (Ligand) or those compounds disclosed in WO 03/011824.

The antiarrhythmic agents suitable for use herein include β-blockers as set out herein including sotalol and amioderome, calcium channel blockers as set out herein including verapamil, nifedipine, amlodipine-besylate, and diltiazem, which may also be used in combination with a debrillator device such as a pace maker;

coenzyme Q sub. 10 such as disclosed in U.S. Pat. Nos. 5,316,765, 4,933,165, 4,929,437;

an agent that upregulates type III endothelial cell nitric acid syntase such as disclosed in WO 2000/003746;

a chondroprotective compound such as a polysulfated glycosaminoglycan (PSGAG), glucosamine, chondroitin sulfate (CS), hyaluronic acid (HA), pentosan polysulfate (PPS), doxycycline or minocycline, such as disclosed in EP 970694;

a cyclooxygenase (COX)-2 inhibitor, such as celecoxib (Celebrex® (Searle)) or rofecoxib (Vioxx® (Merck)) or a glycoprotein IIa/IIIb receptor antagonist such as disclosed in WO 99/45913 and tirofiban or abciximab;

a 5-HT reuptake inhibitor such as disclosed in WO 99/44609;

anti-anginal agents such as vasodilators, for example, isosorbide dinitrate, or nitroglycerin;

a growth hormone secretagogue such as disclosed in U.S. application Ser. No. 09/662,448, filed Sep. 14, 2000, and U.S. Provisional application 60/203,335, filed May 11, 2000, and MK-677 (Merck), Pfizer's CP-424391 and Lilly's LY 444,711;

anti-atherosclerosis agents such as ACAT inhibitors and lipoxygenase inhibitors as described herein and phospholipase inhibitors;

anti-infective agents such as quinolones, for example, ciprofloxacin, ofloxacin, and Tequin® (Bristol-Myers Squibb), macrolides such as erythromycin and clarithromycin (Biaxin® (Abbott)), and azithromycin (Zithromax (Pfizer)); or an immunosuppressant (for use in transplantations) such as cyclosporine, mycophenolate mofetil, azathioprine and the like.

As used herein, the phrase "antineoplastic agent" refers to compounds which prevent cancer cells from multiplying. In general, the antineoplastic agents used herein prevent cancer cells from multiplying by: (1) interfering with the cell's ability to replicate DNA, or (2) inducing apoptosis in the cancerous cells.

Examples of antineoplastic agents which are suitable for use in combinations of this invention include, but are not limited to, microtuble-stabilizing agents such as the taxanes, for example, paclitaxel (also known as Taxol®), docetaxel (also known as Taxotere®), 7-O-methylthio-methylpaclitaxel (disclosed in U.S. Pat. No. 5,646,176), 3'-tert-butyl-3'-N-tert-butyloxycarbonyl-4-deacetyl-3'-dephenyl-3'-N-debenzoyl-4-O-methoxycarbonyl-paclitaxel (disclosed in U.S. Ser. No. 60/179,965 filed on Feb. 3, 2000, and example 17 herein), C-4 methyl carbonate paclitaxel (disclosed in WO 94/14787), the epothilone, such as epothilone A, epothilone B, epothilone C, epothilone D, desoxyepothilone A, desoxyepothilone B, [1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17-oxabicyclo[14.1.0]hepta-decane-5,9-dione (disclosed in WO 99/02514), [1S-[1R*,3R*(E),7R*,10S*,11R*,12R*,16S*]]-3-[2-[2-(aminomethyl)-4-thiazolyl]-1-methylethenyl]-7,11-di-hydroxy-8,8,10,12,16-pentamethyl-4,17-dioxabi-cyclo[14.1.0]-heptadecane-5,9-dione (disclosed in U.S. Ser. No. 09/506,481 filed on Feb. 17, 2000, and examples 7 and 8 herein), and derivatives thereof; microtuble-disruptor agents; alkylating agents; anti-metabolites; epidophyllotoxin; an antineoplastic enzyme; a topoisomerase inhibitor; procarbazine; mitoxantrone; platinum coordination complexes; biological response modifiers; growth inhibitors; hormonal/antihormonal therapeutic agents; and haematopoietic growth factors.

Other classes of antineoplastic agents suitable for use in the method of the present invention include, but are not limited to, the anthracycline family of drugs, the vinca drugs, the mitomycins, the bleomycins, the cytotoxic nucleosides, discodermolide, the pteridine family of drugs, diynenes, aromatase inhibitors, and the podophyllotoxins. Particularly useful members of those classes not previously mentioned include, for example, doxorubicin, carminomycin, daunorubicin, aminopterin, methotrexate, methopterin, dichloro-methotrexate, mitomycin C, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine, leurosine, and the like. Other useful antineoplastic agents include estramustine, cisplatin, carboplatin, cyclophosphamide, bleomycin, tamoxifen, ifosfamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons, and interleukins.

It will be appreciated that unless otherwise specified the dosage regiment for therapeutic agents used in combination with the compounds of the invention will be as specified in the PDR.

In carrying out the method of the invention for treating hypercholesterolemia, hyperlipidemia, hyperlipoproteinemia, hypertriglyceridemia, or atherosclerosis, and related diseases, or Alzheimer's disease or osteoporosis, or other disclosures as set out hereinbefore, a pharmaceutical composition will be employed containing the compounds of structure 1, with or without other cholesterol lowering agents, osteoporosis agents, Alzheimer's agents, antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders and the like. The compounds can be administered to mammalian species including humans, monkeys, dogs, etc. by an oral route, for example, in the form of tablets, capsules, beads, granules or powders, or they can be administered by a parenteral route in the form of injectable preparations, or they can be administered intranasally or in transdermal patches. Typical solid formulations will contain from about 0.1 to about 500 mg of a compound of formula 1. The dose for adults is preferably between 0.5 and 1,000 mg per day, which can be administered in a single dose or in the form of individual doses from 1-4 times per day and also single dose once weekly (5 to 1000 mg).

A typical injectable preparation is produced by aseptically placing 250 mg of compounds of structure 1 into a vial, aseptically freeze-drying and sealing. For use, the contents of the vial are mixed with 2 mL of physiological saline, to produce an injectable preparation.

Abbreviations

The following abbreviations are employed in the Examples and elsewhere herein:
μL=microliter
Ac=acetyl
AcCN=acetonitrile
AIBN=2,2'-azobisisobutyronitrile
API=active pharmaceutical ingredient or atmospheric pressure ionization
aq.=aqueous
Bn=benzyl
Boc=tert-butoxycarbonyl
BOP=((1-benzotriazolyl)oxy)-tris-(dimethylamino)phosphonium hexafluorophosphate
bp=boiling point
brine=saturated aqueous sodium chloride
Cbz=carbobenzyloxy or carbobenzoxy or benzyloxycarbonyl
DDQ=2,3-Dichloro-5,6-dicyano-1,4-benzoquinone
DEAD=diethyl azodicarboxylate
Dess-Martin periodinane=1,1,1-tris(acetyloxy)-1,1-dihydro-1,2-Benziodoxol-3(1H)-one
DI water=dionized water
DIBAL or DIBAL-H or DIBAH=diisobutylaluminum hydride
DIPEA=diisopropylethylamine
DMF=N,N-dimethylformamide
DMP=1,1,1-tris(acetyloxy)-1,1-dihydro-1,2-Benziodoxol-3(1H)-one
DMPU=1,3-dimethyl-3,4,5,6-tetrahydro-2(1H)-pyrimidinone
Dppf=1,1'-bis(diphenylphosphino)ferrocene
EDAC=3-ethyl-3'-(dimethylamino)propyl-carbodiimide hydrochloride (or 1-[(3-(dimethyl)amino)propyl])-3-ethylcarbodiimide hydrochloride)
EDCI=1-[3-(dimethylamino)propyl]-3-ethylcarbodiimide hydrochloride.
ESI=electrospray ionization
Et=ethyl
Et$_2$NH=diethylamine FMOC=fluorenylmethoxycarbonyl
g=gram(s)
h or hr=h(s)
HBTU=O-benzotriazol-1-yl-N,N,N',N'-tetramethyluronium hexafluorophosphate
HOAc or AcOH=acetic acid
HOAT=1-hydroxy-7-azabenzotriazole
HOBT=1-hydroxybenzotriazole
HPLC=high performance liquid chromatography
i-Bu=iso-butyl
KF=Karl Fisher titration
L=liter
LC/MS=high performance liquid chromatography/mass spectrometry
LDA=lithium diisopropylamide
LiHMDS=lithium bis(trimethylsilyl)amide
$LiN(TMS)_2$=Lithium bis(trimethylsilyl)amide
LRMS=low resolution mass spectrometry
mCPBA=m-chloroperbenzoic acid
Me=methyl
meq=milliequivalent
mg=milligram(s)
min=minute(s)
mL=milliliter
mmol=millimole(s)
mol=mole(s)
mp=melting point
MS or Mass Spec=mass spectrometry
MTBE=methyl t-butyl ether
NaHMDS=sodium bis(trimethylsilyl)amide
n-BuLi=n-butyllithium
NMM=N-methyl morpholine
NMO=methylmorpholine N-oxide
NMR=nuclear magnetic resonance
OTf=trifluoromethanesulfonate, triflate
Pd/C=palladium on carbon
Ph=phenyl
$PPh_3$=triphenylphosphine
PS—PB—CHO=1% Cross linked polystyrene with (4-formyl-3-methoxyphenoxy)methyl linker.
$PtO_2$=platinum oxide
PTSH=N-phenylthiotetrazole
PyBOP reagent=benzotriazol-1-yloxy-tripyrrolidino phosphonium hexafluorophosphate
Red-AL=sodium bis(2-methoxyethoxy)aluminum hydride
RT, rt=room temperature
sat or sat'd=saturated
TBAF=tetrabutylammonium fluoride
t-Bu or tBu=tert-butyl
TBDMS=tert-butyldimethylsilyl
TEA=triethylamine
TEMPO=2,2,6,6-tetramethyl-1-piperidinyloxy free radical
TEOC=2-(trimethylsilyl)ethoxycarbonyl
Tf=trifluoromethanesulfonyl
TFA=trifluoroacetic acid
TFFH=Tetramethylfluoroformamidinium hexafluorophosphate.
THF=tetrahydrofuran
TLC=thin layer chromatography
TMS=trimethylsilyl
TPAP=tetrapropylammonium perruthenate
Triflate=trifluoromethanesulfonate
WSC=1-[3-(dimethylamino)propyl]-3-ethylcarbodiimide hydrochloride.

The following RP-HPLC and LC-MS methods were employed:

Method 1: Phenomenex ODS S5 column, 4.6 mm×30 mm; 5 mL/min; detection at 220 nm; solvent A=90:10 water:methanol, solvent B=10:90 water:methanol (both containing 0.1% trifluoroacetic acid); 0% B to 100% B (2 min linear gradient) and then hold.

Method 2: column—YMC-ODS S5 column, 4.6×50 mm; detection at 220 nm; flow rate 5 mL/min; solvent—A: 10:90 methanol:water (containing 0.1% trifluoroacetic acid), B: 90:10 methanol:water (containing 0.1% trifluoroacetic acid); 4 min linear gradient from 0-100% B then hold.

Method 3: column—YMC-ODS-A (S5) 4.6 mm×50 mm column; detection at 220 nm; flow-4 mL/min; solvent—A=10:90 methanol:water+0.2% phosphoric acid, B=90:10 methanol:water+0.2% phosphoric acid; linear gradient, 0% B to 100% B over 4 min and 100% B for 2 min.

Method 4: column—YMC-ODS, 4.6 mm×50 mm; detection at 220 nm; flow rate 4 mL/min; solvent—A=90:10 water:methanol+0.1% trifluoroacetic acid, B=10:90 water:methanol+0.1% trifluoroacetic acid; linear gradient 0% B to 100% B over 4 min.

Method 5: column—Phenomenex Luna (S5) 4.6 mm×30 mm column; detection at 220 nm; flow-5 mL/min; solvent—A=10:90 methanol:water+0.1% acid, B=90:10 methanol:water+0.1% trifluoroacetic acid; linear gradient, 0% B to 100% B over 2 min and 100% B for 2 min.

Method 6: column: Dynamax −60 Å, C18, 4.6×250 mm; detection at 254 nm; flow rate: 1 mL/min; 20 min linear gradient from 10:90 acetonitrile:water (0.05% trifluoroacetic acid) to 90:10 acetonitrile:water (0.05% trifluoroacetic acid) followed by 10 min at 90:10 acetonitrile:water (0.05% trifluoroacetic acid).

Method 7: column—YMC ODS-A (S5) 4.6 mm×33 mm column; detection at 220 nm; flow-5 mL/min; solvent—A=10:90 methanol:water+0.2% phosphoric acid, B=90:10 methanol:water+0.2% phosphoric acid; linear gradient, 0% B to 100% B over 2 min and 100% B for 1 min.

Method 8: column YMC S-5 ODS CombiScreen, 4.6×50 mm; detection at 254 nm; flow rate 4 mL/min; 4 min linear gradient from 10:90 methanol:water (containing 0.2% phosphoric acid) to 90:10 methanol:water (containing 0.2% phosphoric acid)

Method 9: column XTerra, 4.6 mm×30 mm; detection at 220 nm; flow rate 5 mL/min; solvent—A=90:10 water:methanol containing 0.1% trifluoroacetic acid, B=10:90 water:methanol containing 0.1% trifluoroacetic acid; linear gradient 0% B to 100% B over 2 min, then hold.

Method 10: column YMC-ODS, 4.6 mm×50 mm; detection at 220 nm; flow rate 2 mL/min; solvent—A=90:10 water:methanol+0.1% trifluoroacetic acid, B=10:90 water:methanol+0.1% trifluoroacetic acid; isocratic elution 20% B over 5 min.

EXAMPLES

The following Examples represent preferred embodiments of the invention. Compound names cited in the Examples are—or are consistent with—Chemical Abstracts nomenclature.

Example 1

6-Heptenoic acid, 7-[4-(4-fluorophenyl)-6,7-dihydro-10-[(methylamino)sulfonyl]-2-(1-methylethyl)-5H-benzo[6,7]cyclohepta[1,2-b]pyridin-3-yl]-3,5-dihydroxy-, (3R,5S,6E)-

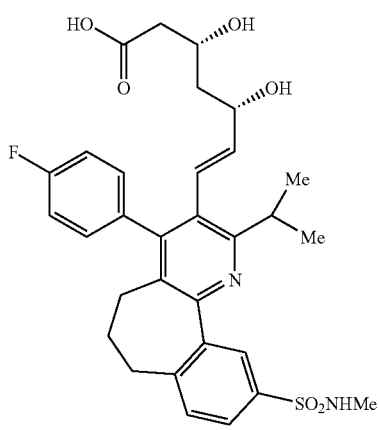

Part A:

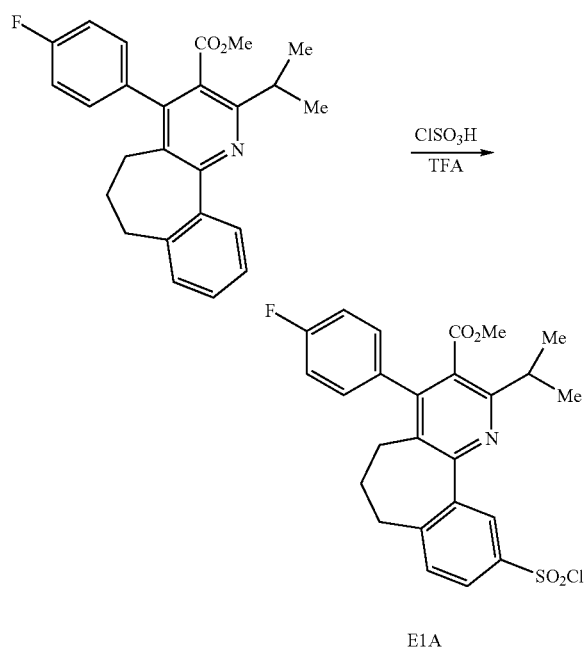

To a stirred solution of 1.95 g (5.00 mmol) of methyl 4-(4-fluorophenyl)-6,7-dihydro-2-(1-methylethyl)-5H-benzo[6,7]cyclohepta[1,2-b]pyridine-3-carboxylate (prepared as described in P. R. Brodfuehrer, T. R. Sattelberg, J. Kant, X. Qian, "Process for Preparing Chiral Diol Sulfones and Dihydroxy Acid HMG CoA Reductase Inhibitors" PCT Int. Appl. WO 2002/098854, 20021212) in 20 mL of trifluoroacetic acid was added 2.8 mL (50 mmol) of chlorosulfuric acid. The solution was stirred for 20 min at reflux, cooled to ambient temperature, and then slowly quenched into 500 mL of a rapidly-stirred saturated aqueous sodium bicarbonate solution. The resulting precipitate was collected by filtration, rinsed with water, and dried to afford 1.73 g (71%) of E1A as an off-white powder: LRMS m/z 488 (M+H)$^+$; R$_f$ (25% ether-hexanes) 0.38.

Part B:

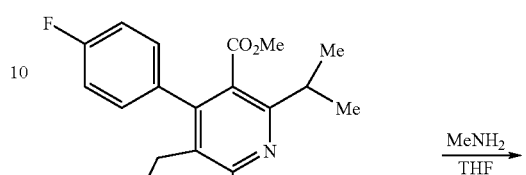

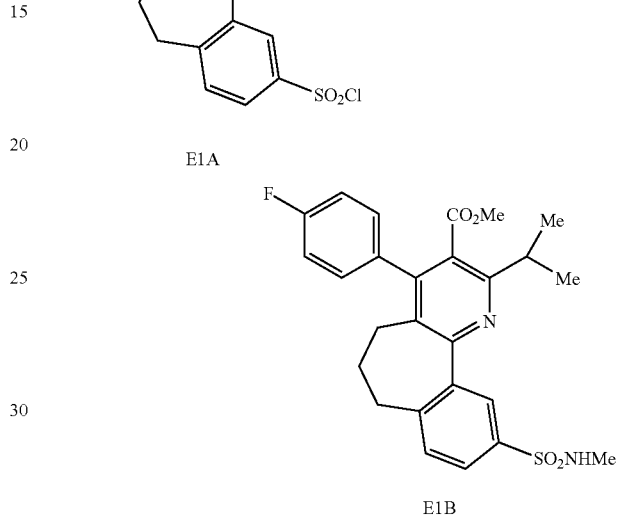

To a stirred solution of 0.10 g (0.21 mmol) of E1A in 8 mL of tetrahydrofuran was added 0.5 mL of 40% aqueous methylamine. The solution was stirred for 15 min and was then made acidic with 10% aqueous acetic acid. This mixture was extracted twice with ethyl acetate. The combined organic phases were washed (brine), dried (MgSO$_4$), and concentrated under reduced pressure. The residue was chromatographed on silica gel (gradient elution with 1:1 ether-hexanes then ether) to afford, after removal of solvent, 0.060 g (60%) of sulfonamide E1B as a white powder: LRMS m/z 483 (M+H)$^+$; HPLC (method 3) t$_R$=4.13 min.

Part C:

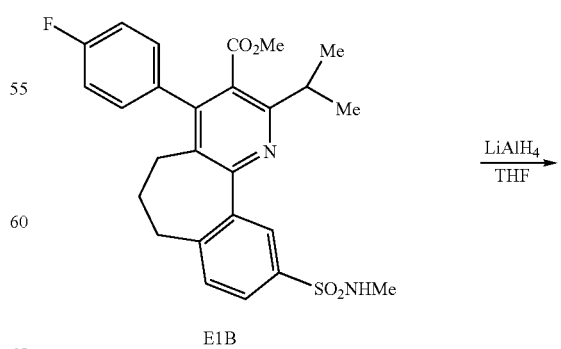

-continued

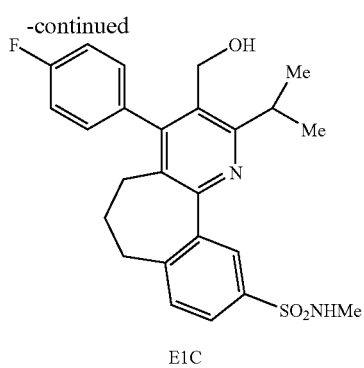

E1C

To a stirred solution of 0.048 g (0.1 mmol) of E1B in 1 mL of tetrahydrofuran was added 1 mL of 1 M LiAlH$_4$ in THF. The solution was stirred for 15 min at ambient temperature, treated with an additional 1 mL of 1 M LiAlH$_4$ in THF, and stirred for 1 h at reflux. The reaction was cooled to ambient temperature and treated dropwise with 0.076 mL of water, 0.076 mL of 15% aqueous NaOH, then 0.240 mL of water. The mixture was stirred for 30 min, and then diluted with dichloromethane and treated with MgSO$_4$. This mixture was stirred for 30 min longer and filtered. Evaporation of solvent afforded 44 mg (97%) of alcohol E1C as a glass: LRMS m/z 455 (M+H)$^+$; HPLC (method 3) $t_R$=3.60 min.

Part D:

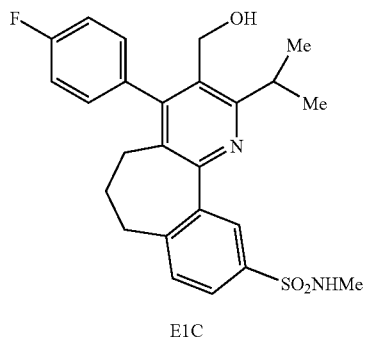

E1C

1) DMP wet CH$_2$Cl$_2$
2) NaHMDS, THF, -78° C.

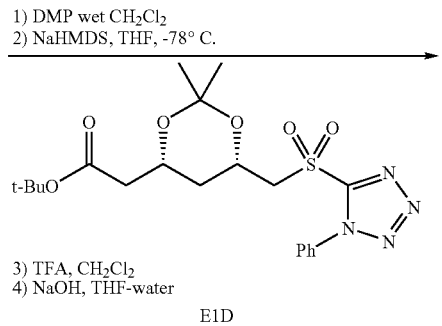

3) TFA, CH$_2$Cl$_2$
4) NaOH, THF-water

E1D

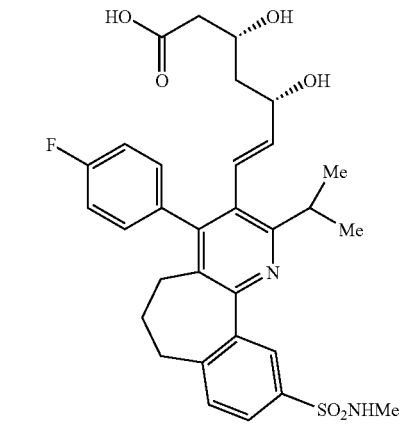

Ex. 1 title compound

A stirred solution of 54 mg (0.12 mmol) of E1C and 66 mg (0.15 mmol) of Dess-Martin periodinane in 3 mL of dichloromethane was treated dropwise over 10 min with a colloid consisting of 0.004 mL of water dispersed in 3 mL of dichloromethane. The solution was stirred for an additional 15 min, diluted with ether, and washed with 1:1 saturated aqueous NaHCO$_3$-10% aqueous sodium thiosulfate. The organic phase was washed (brine), dried (MgSO$_4$), and concentrated under reduced pressure. The residue was dissolved in 3 mL of tetrahydrofuran and treated with 72 mg (0.16 mmol) of E1D (1,1-dimethylethyl 2,4,6-trideoxy-3,5-O-(1-methylethylidene)-6-[(1-phenyl-1H-tetrazol-5-yl)sulfonyl]-D-erythro-hexonate, Chemical Abstracts 9CI nomenclature). The solution was cooled to −78° C. and treated with 0.32 mL of 1 M LiHMDS in tetrahydrofuran, dropwise over 20 seconds. The solution was stirred for 15 min at −78° C., warmed to ambient temperature, and quenched with 10% aqueous acetic acid. The mixture was extracted with ether. The organic extract was washed (brine), dried (MgSO$_4$), and concentrated under reduced pressure. The crude product was chromatographed on silica gel (gradient elution with 1:1 ether-hexanes then 3:1 ether-hexanes). Concentration of the product-containing fractions under reduced pressure afforded a glass. This material was dissolved in 2 mL of dichloromethane and treated with 2 ml of trifluoroacetic acid. The solution was stirred for 2.5 h then concentrated under reduced pressure. The residue was dissolved in 2 mL of tetrahydrofuran and treated with 0.6 mL of 0.5 M aqueous sodium hydroxide. The solution was stirred for 2 h, and most of the tetrahydrofuran was removed under a stream of nitrogen. The resulting solution was eluted through a C18-silica cartridge (10% methanol-water then methanol). Lyophilization of the product-containing fractions afforded 16 mg (23%) of the title compound as the sodium salt as a white powder: LRMS m/z 583 (M+H)$^+$; HPLC (method 3) $t_R$=3.39 min.

Example 2

6-Heptenoic acid, 7-[10-(aminosulfonyl)-4-(4-fluorophenyl)-6,7-dihydro-2-(1-methylethyl)-5H-benzo[6,7]cyclohepta[1,2-b]pyridin-3-yl]-3,5-dihydroxy-, (3R,5S,6E)-

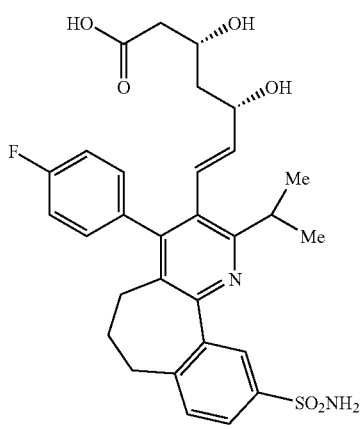

Part A:

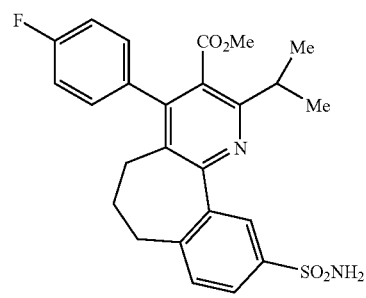

E2A

E2A was prepared in 60% yield from E1A and ammonium hydroxide using the procedure described in Example 1 Part B: LRMS m/z 469 (M+H)$^+$; HPLC (method 3) $t_R$=3.92 min.

Part B:

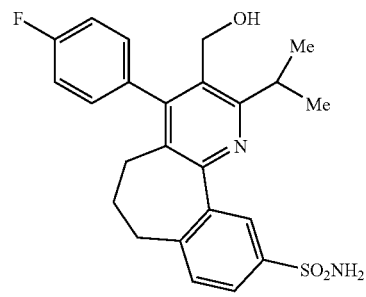

E2B

E2B was prepared in 44% yield from E2A using the procedure described in Example 1 Part C: $^1$H NMR (CDCl$_3$, 300 MHz) δ 8.35 (d, 1H, J=1.8 Hz), 7.89 (dd, 1H, J=7.9, 1.8 Hz), 7.38 (d, 1H, J=8.1 Hz), 7.13-7.27 (m, 4H), 4.90 (br. s, <2H (possible rapid exchange with residual water in sample)), 4.48 (s, 2H), 3.45-3.60 (m, 1H), 2.65 (t, 2H, J=6.5 Hz), 2.00-2.16 (m, 4H), 1.41 (d, 6H, J=6.6 Hz); R$_f$ (25% ether-hexanes) 0.18.

Part C:

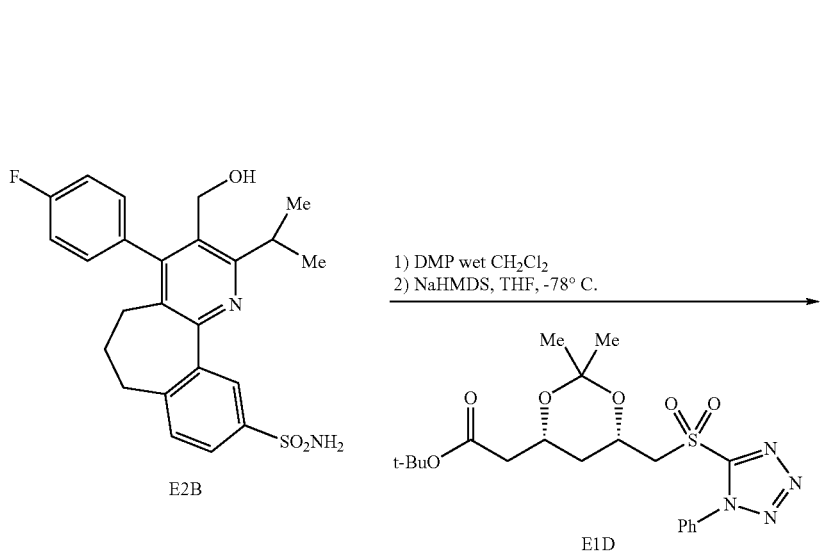

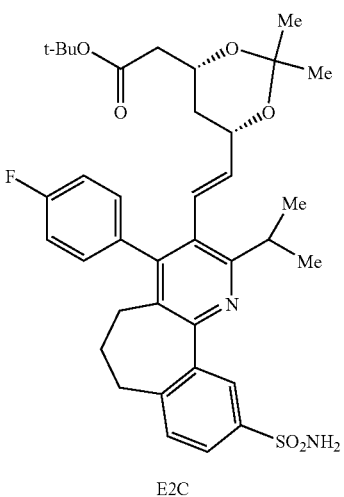

A stirred solution of 200 mg (0.46 mmol) of E2B and 265 mg (0.60 mmol) of Dess-Martin periodinane in 3 mL of dichloromethane was treated dropwise over 10 min with a colloid consisting of 0.009 mL of water in 3 mL of dichloromethane. The solution was stirred for an additional 15 min, diluted with ether, and washed with 1:1 saturated aqueous NaHCO$_3$-10% aqueous sodium thiosulfate. The organic phase was washed (brine), dried (MgSO$_4$), and concentrated under reduced pressure. The residue was dissolved in 3 mL of tetrahydrofuran and treated with 160 mg (0.35 mmol) of E1D. The solution was cooled to −78° C. and treated with 0.32 mL of 1 M LiHMDS in tetrahydrofuran, dropwise over 20 seconds. The solution was stirred for 20 min at −78° C., warmed to ambient temperature, and quenched with 10% aqueous acetic acid. The mixture was extracted with ether, and the organic extract was washed (brine), dried (MgSO$_4$), and concentrated under reduced pressure. The residue was chromatographed on silica gel (gradient elution with 3% methanol-chloroform then 5% methanol-chloroform). Concentration of the product-containing fractions under reduced pressure afforded 135 mg (49%) of E2C as a foam: LRMS m/z 665 (M+H)$^+$; HPLC (method 3) t$_R$=4.51 min.

Part D:

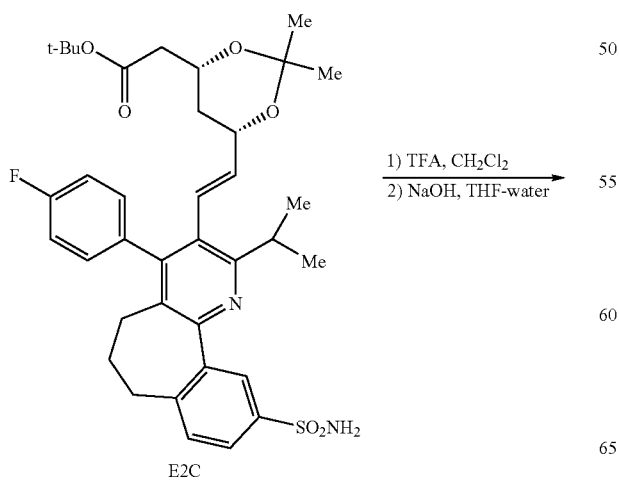

-continued

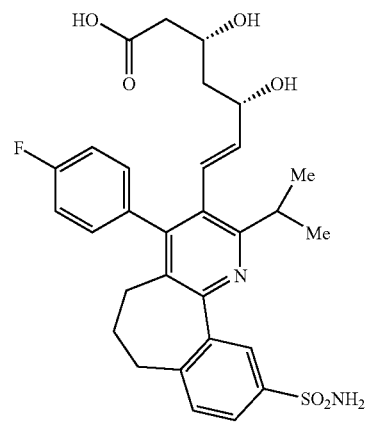

Ex. 2 title compound

To a stirred solution of 25 mg (0.038 mmol) of E2C in 2 mL of dichloromethane was added 2 ml of trifluoroacetic acid. The solution was stirred for 2.5 h then concentrated under reduced pressure. The residue was dissolved in 2 mL of tetrahydrofuran and treated with 0.2 mL of 0.5 M aqueous sodium hydroxide. The solution was stirred for 1 h, and most of the tetrahydrofuran was removed under a stream of nitrogen. The resulting solution was eluted through a C 18-silica cartridge (10% methanol-water then methanol). Lyophilization of the product-containing fractions afforded 16 mg (76%) of the sodium salt of the title compound as a white powder: LRMS m/z 569 (M+H)$^+$; HPLC (method 3) t$_R$=3.05 min.

Example 3

6-Heptenoic acid, 7-[10-[(acetylamino)sulfonyl]-4-(4-fluorophenyl)-6,7-dihydro-2-(1-methylethyl)-5H-benzo[6,7]cyclohepta[1,2-b]pyridin-3-yl]-3,5-dihydroxy-, (3R,5S,6E)-

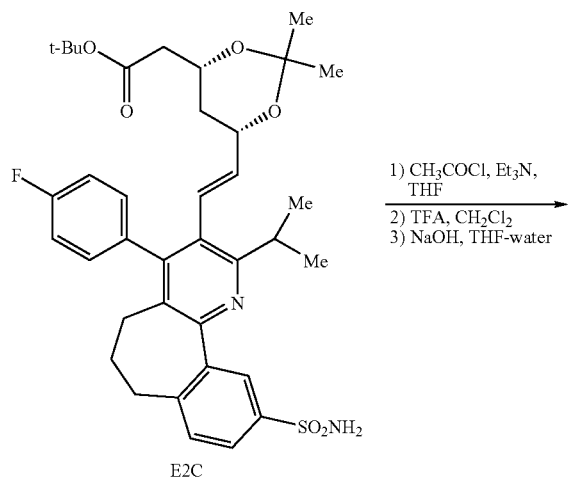

Ex. 3 title compound

To a stirred solution of 20 mg (0.030 mmol) of E2C in 3 mL of dichloromethane was added 0.02 ml of triethylamine followed by 0.010 ml of acetyl chloride. The solution was stirred for 30 min, diluted with ether, and washed with 10% aqueous acetic acid. The organic phase was washed (brine), dried (MgSO$_4$), concentrated under reduced pressure. The residue was chromatographed on silica gel (elution with 50% ether-hexanes then ether). Concentration of the product-containing fractions afforded an oil. This oil was dissolved in 2 mL of dichloromethane and treated with 2 mL of trifluoroacetic acid. The solution was stirred for 2.5 h and then evaporated under reduced pressure. The residue was dissolved in 2 mL of tetrahydrofuran and treated with 0.2 mL of 0.5 M aqueous sodium hydroxide. The solution was stirred for 1 h, and most of the tetrahydrofuran was removed under a stream of nitrogen. The resulting solution was eluted through a C 18-silica cartridge (10% methanol-water then methanol). Lyophilization of the product-containing fractions afforded 12 mg (61%) of the disodium salt of the title compound as a white powder: LRMS m/z 611 (M+H)$^+$; HPLC (method 3) t$_R$=3.35 min.

Example 4

6-Heptenoic acid, 7-[4-(4-fluorophenyl)-6,7-dihydro-10-[[[(methylamino)carbonyl]amino]sulfonyl]-2-(1-methylethyl)-5H-benzo[6,7]cyclohepta[1,2-b]pyridin-3-yl]-3,5-dihydroxy-, (3R,5S,6E)-

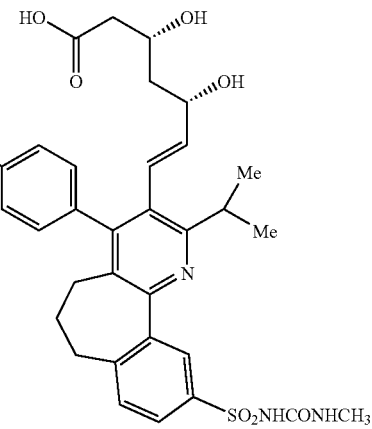

Part A:

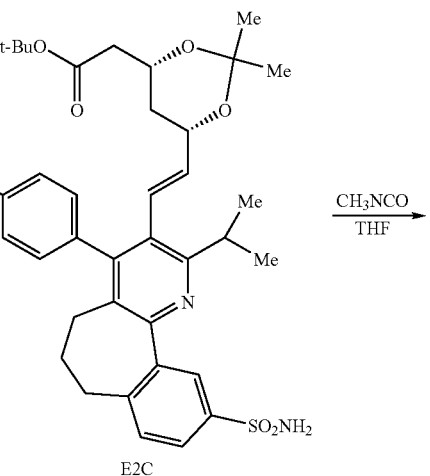

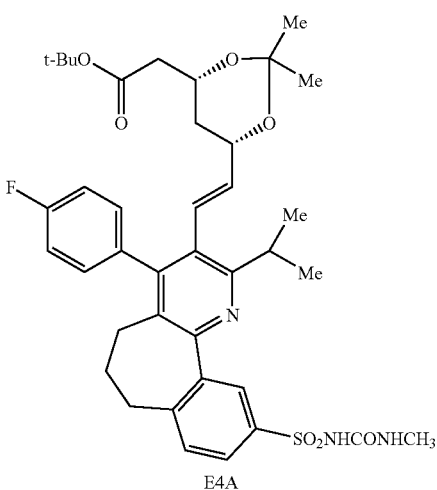

E4A extracted with ether. The organic extract was washed (brine), dried (MgSO₄), and concentrated under reduced pressure. Chromatography of the residue on silica gel (elution with 1:1 ether-hexanes) afforded, after evaporation of solvent, 21 mg (96%) of E4A as a foam: LRMS m/z 720 (M−H)⁻; $R_f$ (25% ether-hexanes) 0.30.

Part B:

Ex. 4 title compound

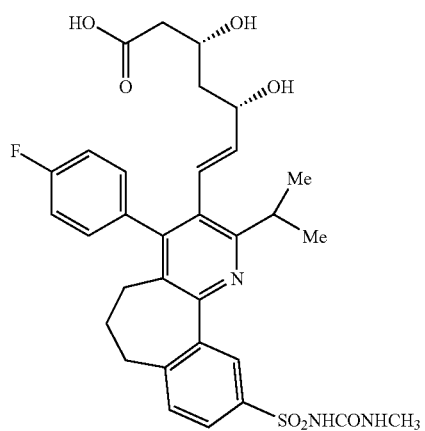

The title compound was prepared as the disodium salt in 51% yield from E4A using the same described in Example 2 Part D: LRMS m/z 626 (M+H)⁺; HPLC (method 3) $t_R$=3.22 min.

Example 5

6-Heptenoic acid, 7-[10-[[[3-(dimethylamino)propyl]amino]sulfonyl]-4-(4-fluorophenyl)-6,7-dihydro-2-(1-methylethyl)-5H-benzo[6,7]cyclohepta[1,2-b]pyridin-3-yl]-3,5-dihydroxy-, (3R,5S,6E)-

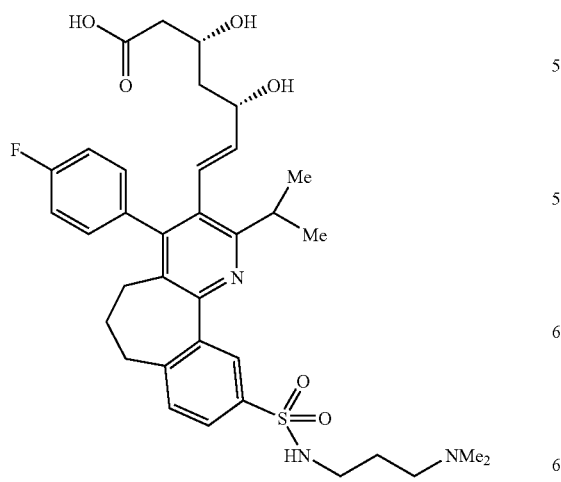

Part A:

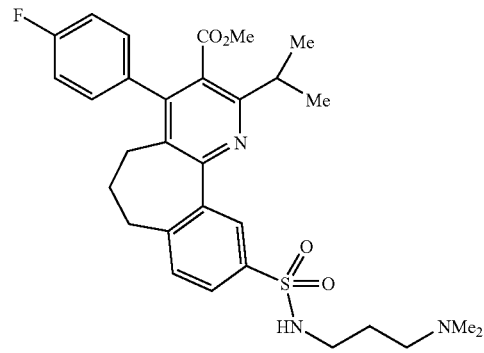

E5A was prepared in 73% yield from E1A and N,N-dimethyl-1,3-propanediamine using the procedure described in Example 1 Part B with the exception that the product was not chromatographed: LRMS m/z 554 (M+H)⁺; $R_f$(85:10:5 chloroform-methanol-acetic acid) 0.27.

Part B:

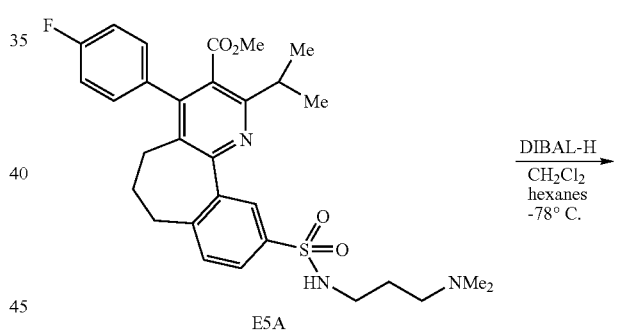

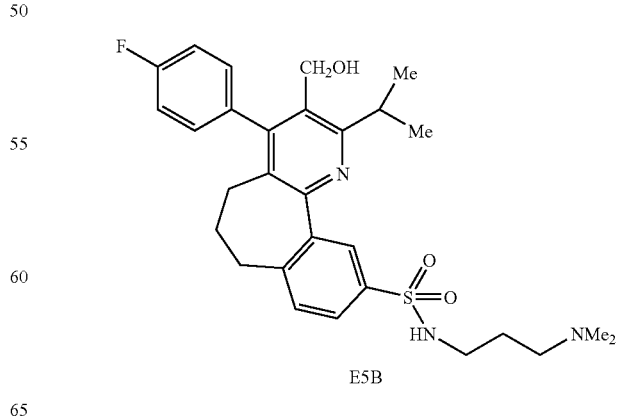

To a stirred, cooled (−78° C.) solution of the E5A in 3 mL of dichloromethane was added 2 mL of 1 M diisobutylaluminum hydride in hexanes. The solution was stirred for 1 h, diluted with ethyl acetate, and treated with saturated aqueous sodium potassium tartrate. This mixture was stirred for 1 h, the phases were separated, and the organic phase was dried (MgSO$_4$) and concentrated under reduced pressure to provide 157 mg (73%) of E5B as a foam: $^1$H NMR (CDCl$_3$, 300 MHz) δ 9.92 (s, 1H), 8.33 (d, 1H, J=1.8 Hz), 7.91 (dd, 1H, J=7.9, 1.8 Hz), 7.42 (d, 1H, J=8.0 Hz), 7.15-7.30 (m, 4H), 3.90-4.03 (m, 1H), 3.22 (t, 2H J=5.9 Hz), 2.65-2.85 (m, 4H), 1.86-2.26 (m, 6H), 1.38 (d, 6H, J=6.6 Hz); R$_f$ (85:10:5 chloroform-methanol-acetic acid) 0.19.

Part C:

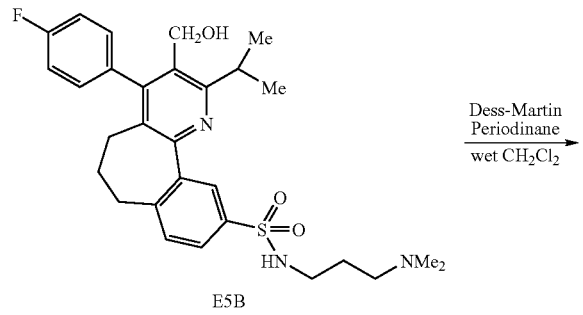

E5B

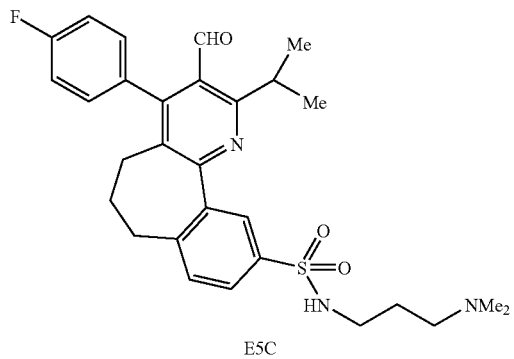

E5C

A stirred solution of 150 mg (0.27 mmol) of E5B and 170 mg (0.40 mmol) of Dess-Martin periodinane in 7 mL of dichloromethane was treated dropwise over 15 min with a colloid consisting of 0.007 mL of water in 6 mL of dichloromethane. The solution was stirred for an additional 15 min, diluted with ether, and washed with 1:1 saturated aqueous NaHCO$_3$-10% aqueous sodium thiosulfate. The organic phase was washed (brine), dried (MgSO$_4$), and concentrated under reduced pressure to afford 134 mg (89%) of E5C as a foam: $^1$H NMR (CDCl$_3$, 300 MHz) δ 9.92 (s, 1H), 8.33 (d, 1H, J=1.8 Hz), 7.91 (dd, 1H, J=7.9, 1.8 Hz), 7.42 (d, 1H, J=8.0 Hz), 7.15-7.30 (m, 4H), 3.90-4.03 (m, 1H), 3.22 (t, 2H J=5.9 Hz), 2.65-2.85 (m, 4H), 1.86-2.26 (m, 6H), 1.38 (d, 6H, J=6.6 Hz); R$_f$ (85:10:5 chloroform-methanol-acetic acid) 0.33.

Part D:

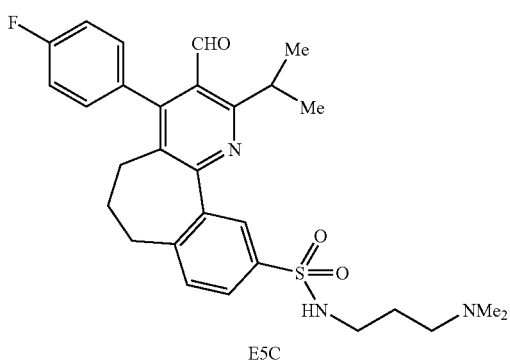

E5C

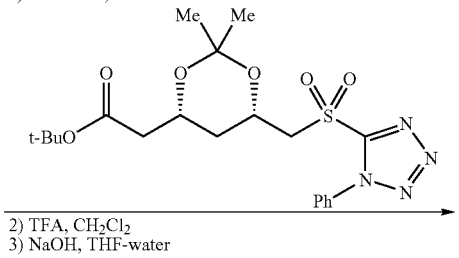

1) NaHMDS, THF
2) TFA, CH$_2$Cl$_2$
3) NaOH, THF-water

-continued

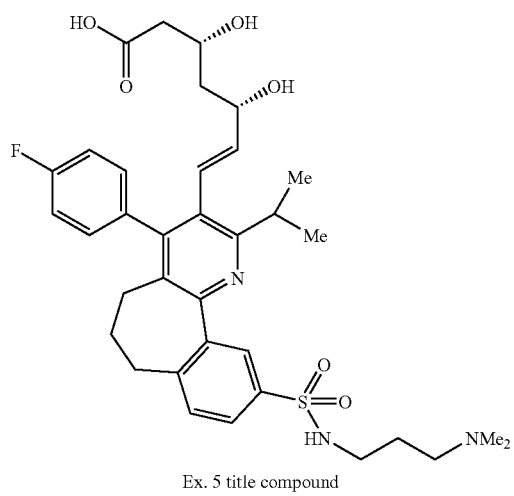

Ex. 5 title compound

A stirred solution of 125 mg (0.23 mmol) of E5C in 3 mL of tetrahydrofuran was treated with 113 mg (0.25 mmol) of E1D. The solution was cooled to −78° C. and treated with 0.50 mL of 1 M LiHMDS in tetrahydrofuran, dropwise over 20 seconds. The solution was stirred for 15 min at −78° C., warmed to ambient temperature, and quenched with 10% aqueous acetic acid. The mixture was extracted with ether, and the organic extract was washed (brine), dried (MgSO$_4$), and concentrated under reduced pressure. This material was dissolved in 2 mL of dichloromethane and treated with 2 ml of trifluoroacetic acid. The solution was stirred for 2.5 h then concentrated under reduced pressure. The residue was dissolved in 2 mL of tetrahydrofuran and treated with 0.6 mL of 0.5 M aqueous sodium hydroxide. The solution was stirred for 2 h, and most of the tetrahydrofuran was removed under a stream of nitrogen. The resulting solution was eluted through a C18-silica cartridge (10% methanol-water then methanol). Lyophilization of the product-containing fractions afforded 53 mg (35%) of the title compound as the sodium salt as a white powder: LRMS m/z 654 (M+H)$^+$; HPLC (method 3) $t_R$=3.04 min.

Example 6

6-Heptenoic acid, 7-[4-(4-fluorophenyl)-6,7-dihydro-2-(1-methylethyl)-10-[[(methylsulfonyl)amino]sulfonyl]-5H-benzo[6,7]cyclohepta[1,2-b]pyridin-3-yl]-3,5-dihydroxy-, (3R,5S,6E)-

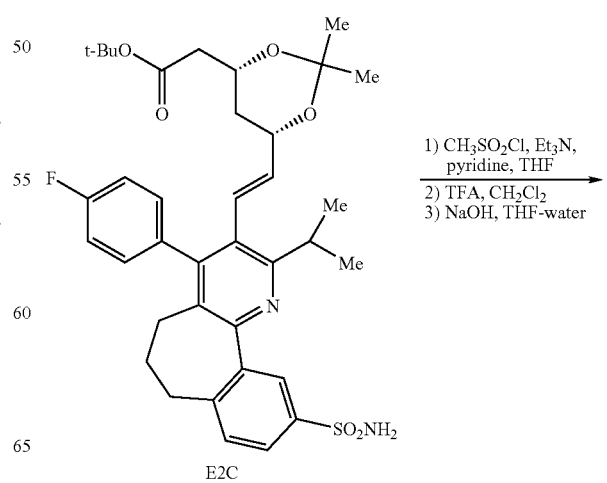

E2C

1) CH$_3$SO$_2$Cl, Et$_3$N, pyridine, THF
2) TFA, CH$_2$Cl$_2$
3) NaOH, THF-water

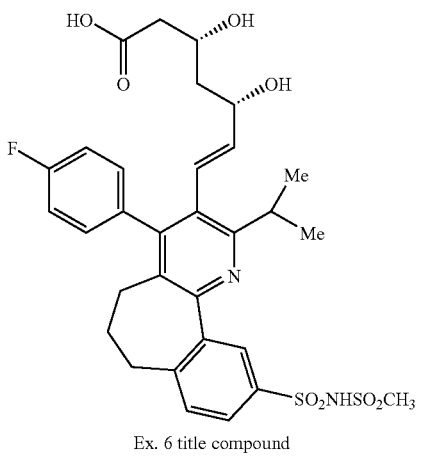

Ex. 6 title compound

To a stirred, cooled (0° C.) solution of 30 mg (0.045 mmol) of E2C in 2 mL of 1:1 ether-dichloromethane were sequentially added 0.1 mL of pyridine, 0.02 mL of methanesulfonyl chloride, and 0.1 mL of triethylamine. The solution was stirred overnight, diluted with ether, and washed with 10% aqueous acetic acid. The organic phase was washed (brine), dried (MgSO$_4$), and concentrated under reduced pressure to afford a glass. This glass was dissolved in 2 mL of dichloromethane and treated with 2 mL of trifluoroacetic acid. The solution was stirred for 2.5 h and then evaporated under reduced pressure. The residue was dissolved in 2 mL of tetrahydrofuran and treated with 0.2 mL of 0.5 M aqueous sodium hydroxide. The solution was stirred for 1 h, and most of the tetrahydrofuran was removed under a stream of nitrogen. The resulting solution was eluted through a C18-silica cartridge (10% methanol-water then methanol). Lyophilization of the product-containing fractions afforded 14 mg (48%) of the title compound as the disodium salt as a white powder: $^1$H NMR (CDCl$_3$, 300 MHz) δ 8.30 (d, 1H, J=1.8 Hz), 7.90 (dd, 1H, J=7.9, 2.0 Hz), 7.36 (d, 1H, J=8.1 Hz), 7.15-7.24 (m, 4H), 6.44 (dd, 1H J=16.3, 1.3 Hz), 5.41 (dd, 1H, J=16.4, 6.4 Hz), 4.17-4.24 (m, 1H), 3.69-3.80 (m, 1H), 3.44-3.55 (m, 1H), 2.96 (s, 3H), 2.63 (t, 2H J=6.8 Hz), 1.99-2.33 (m, 6H), 1.46-1.58 (m, 1H), 1.32 (d, 6H, J=7.0 Hz), 1.21-1.34 (m, 1H).

Example 7

6-Heptenoic acid, 7-[10-[[[2-(dimethylamino)ethyl]amino]sulfonyl]-4-(4-fluorophenyl)-6,7-dihydro-2-(1-methylethyl)-5H-benzo[6,7]cyclohepta[1,2-b]pyridin-3-yl]-3,5-dihydroxy-, (3R,5S,6E)-

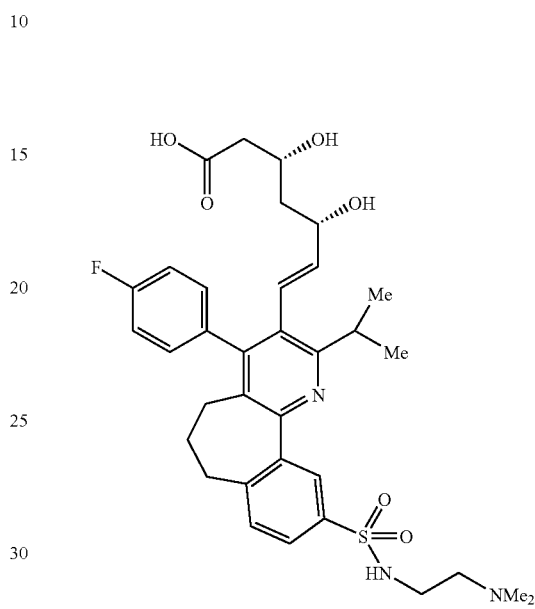

Part A:

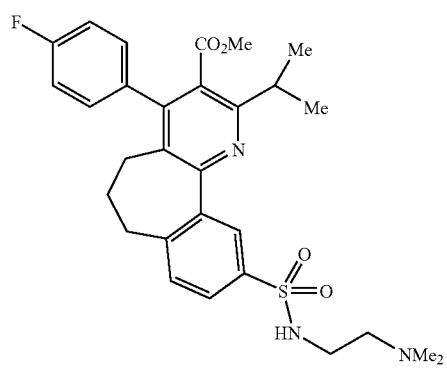

E7A

E7A was prepared in 55% yield from E1A and N,N-dimethylethylenediamine using the procedure described in Example 1 Part B with the exception that the chromatography step was omitted.

Part B:

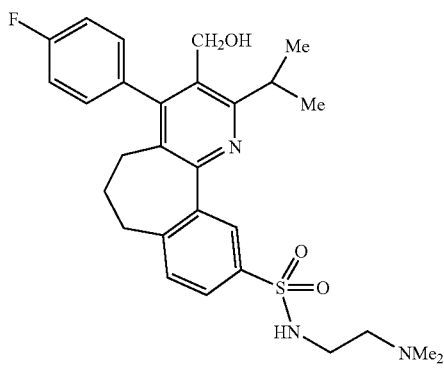

E7B was prepared in 92% yield from E7A using the procedure described in Example 5 Part B: $^1$H NMR (CDCl$_3$, 300 MHz) δ 8.21 (d, 1H, J=1.9 Hz), 7.76 (dd, 1H, J=7.7, 1.9 Hz), 7.29 (d, 1H, J=7.9 Hz), 7.05-7.21 (m, 4H), 4.40 (s, 2H), 3.40-3.51 (m, 1H), 3.03 (t, 2H J=5.7 Hz), 2.57 (t, 2H, J=6.6 Hz), 2.36 (t, 2H, J=5.6 Hz), 2.08 (s, 6H), 1.93-2.04 (m, 4H), 1.86-2.26 (m, 6H), 1.31 (d, 6H, J=6.6 Hz); R$_f$ (75:25:5 chloroform-methanol-acetic acid) 0.53.

Part C:

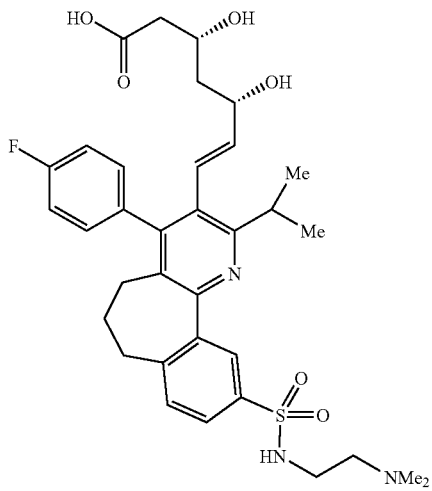

Ex. 7 title compound

The title compound was prepared as the sodium salt from E7B using the procedure described in Example 1 Part D: $^1$H NMR (CD$_3$OD, 300 MHz) δ 8.20 (d, 1H, J=1.9 Hz), 7.81 (dd, 1H, J=7.9, 2.0 Hz), 7.46 (d, 1H, J=8.1 Hz), 7.13-7.22 (m, 4H), 6.42 (d, 1H, J=16.1), 5.41 (dd, 1H, J=16.2, 6.6 Hz), 4.17-4.24 (m, 1H), 3.68-3.78 (m, 1H), 3.47-3.57 (m, 1H), 3.03 (t, 2H, J=7.0 Hz), 2.65 (t, 2H, J=6.4 Hz), 2.42 (t, 2H, J=7.0 Hz), 1.99-2.31 (m, 12H), 1.45-1.58 (m, 1H), 1.31 (d, 6H, J=6.9 Hz), 1.21-1.32 (m, 1H).

Example 8

6-Heptenoic acid, 7-[4-(4-fluorophenyl)-6,7-dihydro-2-(1-methylethyl)-10-[[[2-(4-morpholinyl)ethyl]amino]sulfonyl]-5H-benzo[6,7]cyclohepta[1,2-b]pyridin-3-yl]-3,5-dihydroxy-, (3R,5S,6E)-

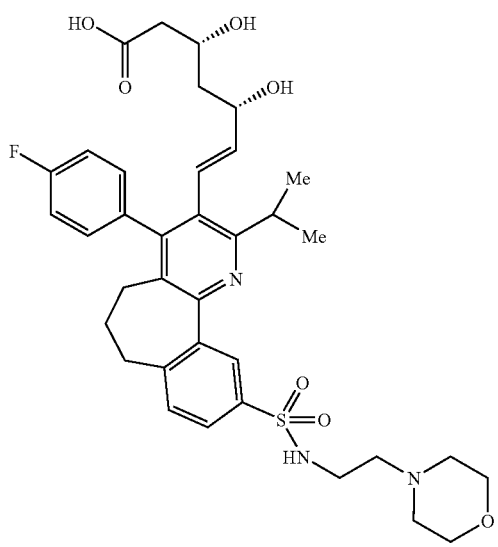

Part A:

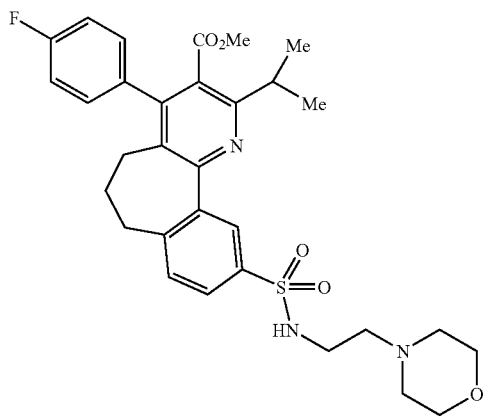

E8A was prepared in 70% yield from E1A and 4-(2-aminoethyl)morpholine using the procedure described in Example 1 Part A with the modification that the chromatography step was omitted. The crude product was dissolved in hot methanol and precipitated with water to afford E8A as a white powder: LRMS m/z 582 (M+H)$^+$; R$_f$ (80:15:5 chloroform-methanol-acetic acid) 0.64.

Part B:

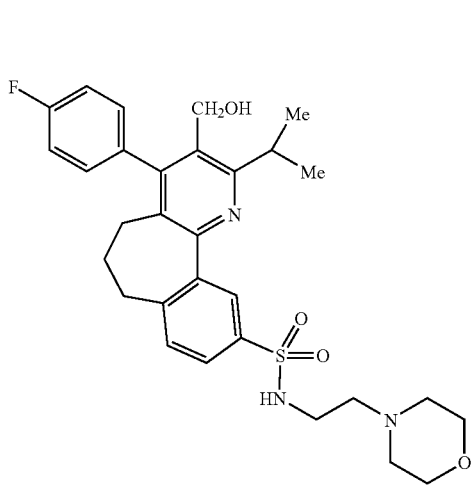

E8B

E8B was prepared in 70% yield from E8A using the procedure described in Example 5 Part B: LRMS m/z 554 (M+H)$^+$; R$_f$ (80:15:5 chloroform-methanol-acetic acid) 0.58.

Part C:

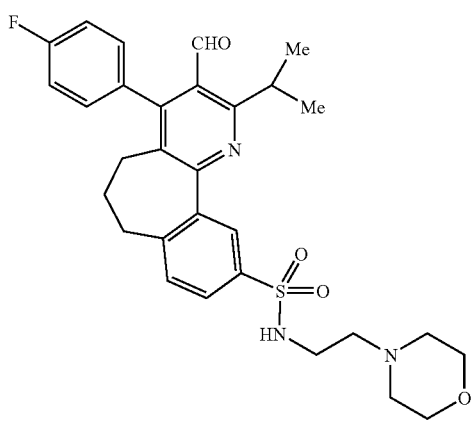

E8C

E8C was prepared in 90% yield from E8B using the procedure described in Example 5 Part C: R$_f$ (85:10:5 chloroform-methanol-acetic acid) 0.65.

Part D:

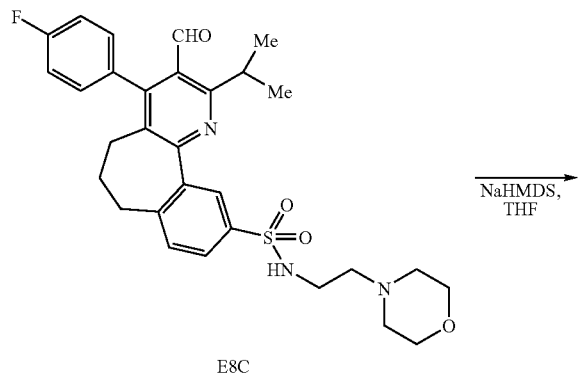

NaHMDS, THF

-continued

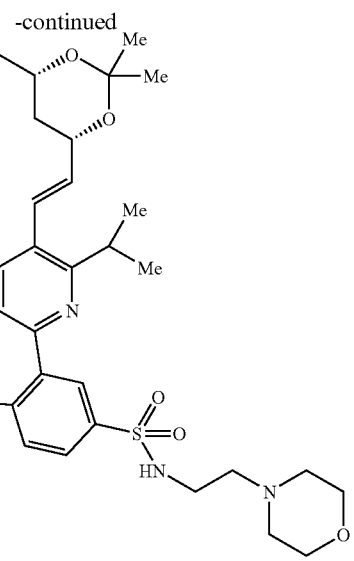

E8D

E8C (115 mg, 0.21 mmol) was dissolved in 4 mL of tetrahydrofuran and treated with 120 mg (0.27 mmol) of E1D. The solution was cooled to −78° C. and treated with 0.60 mL of 1 M LiHMDS in tetrahydrofuran, dropwise over 30 seconds. The solution was stirred for 15 min at −78° C., warmed to 0° C., and quenched with saturated aqueous NaHCO$_3$. The mixture was extracted with ether, and the organic extract was washed (brine), dried (MgSO$_4$), and concentrated under reduced pressure. The crude product was purified by reverse-phase HPLC (Phenomenex C18-silica Luna 75 mm×30 mm, 65% methanol-water to 100% methanol over 6 min). Concentration of the product-containing fractions afforded 66 mg (41%) of E8D as a foam: LRMS m/z 778 (M+H)$^+$.

Part E:

Ex. 8 title compound

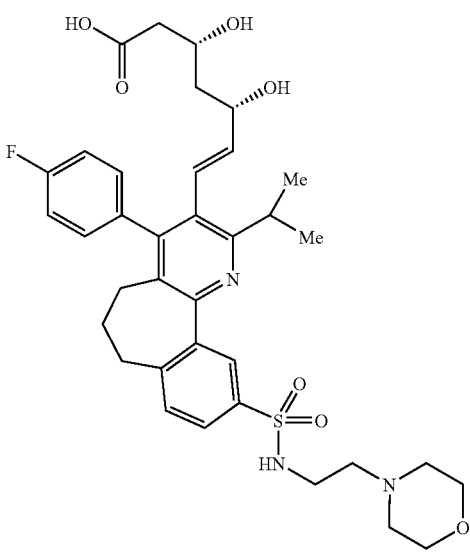

The title compound was prepared from 30 mg of E8D using the procedure described in Example 2 Part D. The compound was purified by reverse-phase HPLC (Phenomenex C18-silica Luna 60 mm×21 mm; 20% methanol-water then a linear gradient to 100% methanol over 4 min; Flow=9.9 mL/min).

Concentration of the product-containing fractions afforded 16 mg (54%) of the title compound as the sodium salt as a white powder: LRMS m/z 682 (M+H)+; HPLC (method 3) $t_R$=3.07 mm.

Example 9

6-Heptenoic acid, 7-[4-(4-fluorophenyl)-6,7-dihydro-10-[[(3-hydroxypropyl)amino]sulfonyl]-2-(1-methylethyl)-5H-benzo[6,7]cyclohepta[1,2-b]pyridin-3-yl]-3,5-dihydroxy-, (3R,5S,6E)-

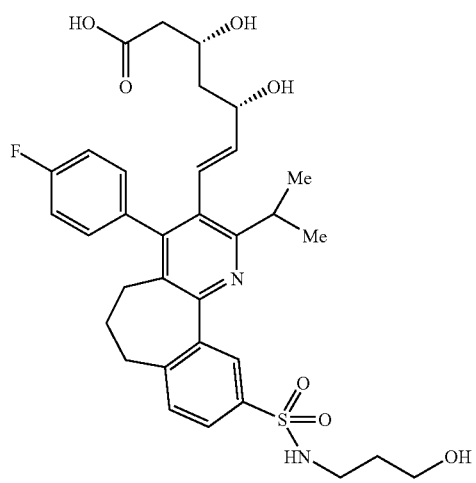

The title compound was prepared as the sodium salt from E1A and 3-aminopropanol using the method described in Example 1: LRMS m/z 627 (M+H)+; HPLC (method 3) $t_R$=3.28 min.

Example 10

6-Heptenoic acid, 7-[9,10-dicyano-4-(4-fluorophenyl)-6,7-dihydro-2-(1-methylethyl)-5H-benzo[6,7]cyclohepta[1,2-b]pyridin-3-yl]-3,5-dihydroxy-, (3R,5S,6E)-

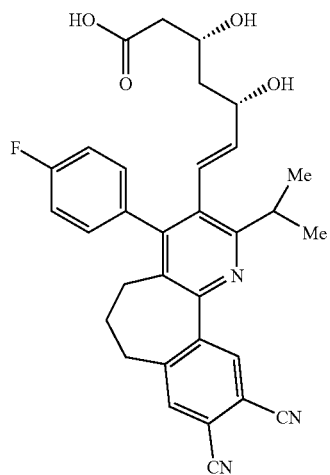

Part A:

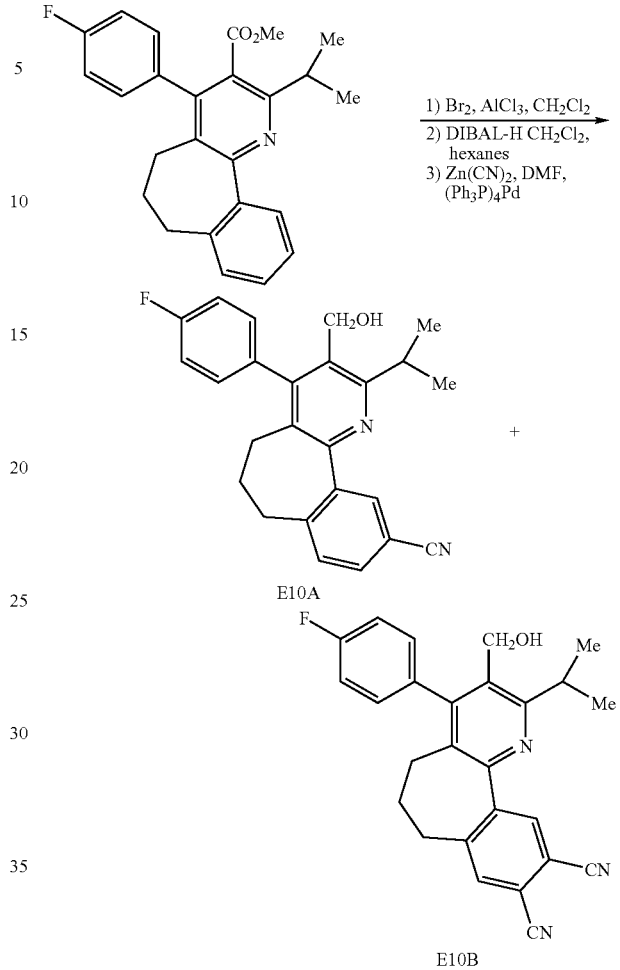

To a stirred solution of 9.0 g (23.1 mmol) of methyl 4-(4-fluorophenyl)-6,7-dihydro-2-(1-methylethyl)-5H-benzo[6,7]cyclohepta[1,2-b]pyridine-3-carboxylate in 100 mL of dichloromethane was added 12.3 g (92 mmol) of aluminum trichloride. The solution was stirred for 1 min and then treated with 4.7 mL (92 mmol) of bromine over 5 min. The red solution was stirred for 30 min, quenched carefully with water, and the phases were then separated. The aqueous phase was extracted with ether, and the combined organic phases were washed with 1:1-saturated aqueous sodium bicarbonate: 10% aqueous sodium thiosulfate, water, and brine. The organic phase was dried (MgSO$_4$) and evaporated under reduced pressure. The residue was crystallized from tetrahydrofuran-cyclohexane to afford 5.25 g (47%) of an approximately 9:1 mixture consisting of monobromo:dibromo ester products. This mixture was dissolved in 33 mL of dichloromethane, cooled to −78° C. and treated with 32 mL of 1 M diisobutylaluminum hydride in hexanes. The solution was stirred for 1 h at −78° C. and then removed from the cold bath. The reaction was quenched by sequential addition of ethyl acetate, methanol, and then saturated aqueous sodium potassium tartrate. The phases were stirred together for 1 h and separated. The organic phase was dried (MgSO$_4$) and concentrated to afford 5.08 g (100% yield) of an approximately 9:1 mixture of monobromo:dibromo carbinol products. This mixture was dissolved in 15 mL of dimethylformamide and the solution was degassed by three freeze-thaw cycles under vacuum. The solution was treated with 1.76 g (15 mmol) of zinc (II) cyanide followed by 300 mg of tetrakis (triphenylphosphine)palladium (0). The mixture was heated to 90° C. for 1 h. The dimethylformamide was removed under vacuum, and the residue was chromatographed on silica gel (gradient elution with 3:1 hexanes-ether then 2:1 ether-hexanes) to afford, after removal of solvent, 4.00 g (90%) of E10A and 360 mg (8%) E10B. For E10A: $^1$H NMR (CDCl$_3$, 300 MHz) δ 8.12 (d, 1H, J=1.5 Hz), 7.61 (dd, 1H, J=7.6, 1.8 Hz), 7.32 (d, 1H, J=7.7 Hz), 7.14-7.28 (m, 4H), 4.48 (s, 2H), 3.45-3.59 (m, 1H), 2.64 (t, 2H J=6.6 Hz), 2.00-2.17 (m, 4H), 1.40 (d, 6H, J=6.5 Hz); LRMS m/z 387 (M+H)$^+$; HPLC (method 3): $t_R$=4.14 min, $R_f$ (50% ether-hexanes) 0.35. For E10B: LRMS m/z 412 (M+H)$^+$; $R_f$ (50% ether-hexanes) 0.15.

Part B:

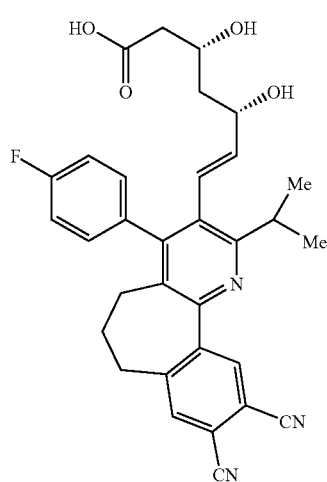

Ex. 10 title compound

The title compound was prepared as the sodium salt in 34% yield from E10B using the procedure described in Example 1 Part D: LRMS m/z 540 (M+H)$^+$; HPLC (method 3) $t_R$=4.05 min.

Example 11

6-Heptenoic acid, 7-[10-[[[2-(dimethylamino)ethyl] amino]carbonyl]-4-(4-fluorophenyl)-6,7-dihydro-2-(1-methylethyl)-5H-benzo[6,7]cyclohepta[1,2-b] pyridin-3-yl]-3,5-dihydroxy-, (3R,5S,6E)-

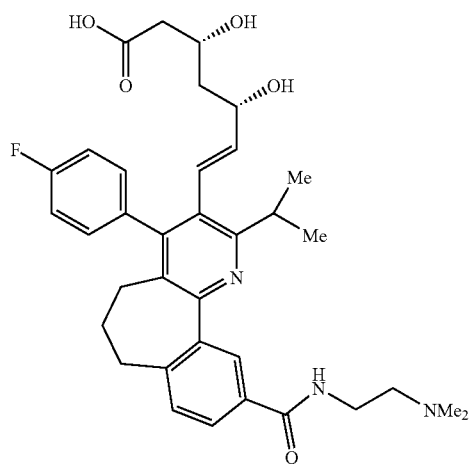

Part A:

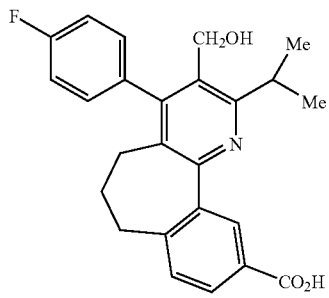

E11A

A stirred solution of 4.00 g (10.4 mmol) of E10A in 65 mL of ethanol was treated with 80 mL of 1 M aqueous sodium hydroxide, and the solution was stirred overnight at reflux. The reaction was stirred for 3 h longer at reflux during which time approximately 50 mL of solvent was allowed to boil off. Finally, 10 mL of 50% aqueous sodium hydroxide was added, and the reaction was stirred for another 3 h at reflux. The mixture was cooled and acidified to pH 4.5 with glacial acetic acid. This mixture was extracted with ether, and then ethyl acetate. The combined organic extracts were washed with water and then brine. The solution was dried (MgSO$_4$) and concentrated to afford 4.20 g (~quantitative yield) of E11A as a colorless solid: LRMS m/z 406 (M+H)$^+$; HPLC (method 3) $t_R$=3.61 min.

Part B:

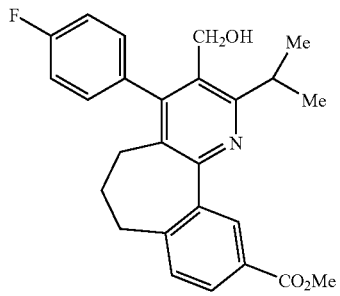

E11B

To a stirred solution of 2.76 g (6.81 mmol) of E11A in 25 mL of dimethylsulfoxide was added 2.6 g (8.0 mmol) of cesium carbonate followed by 0.5 mL (8.0 mmol) of iodomethane. The solution was stirred for 25 min and treated with an additional 0.5 mL of iodomethane. After stirring for an additional 2.5 h the reaction was diluted with water and extracted twice with ether. The combined organic extracts were washed with water then brine, dried (MgSO$_4$), and concentrated under reduced pressure. Chromatography of the residue on silica gel (gradient elution with 2:1 hexanes-ether then ether) afforded, after removal of solvent, 2.65 g (93%) of E11B as a foam: $^1$H NMR (CDCl$_3$, 300 MHz) δ 8.46 (d, 1H, J=1.9 Hz), 8.02 (dd, 1H, J=7.7, 1.9 Hz), 7.13-7.31 (m, 5H), 4.48 (d, 2H, J=5.2 Hz), 3.95 (s, 3H), 3.43-3.59 (m, 1H), 2.63 (t, 2H, J=6.8 Hz), 1.97-2.15 (m, 4H), 1.42 (d, 6H, J=6.6 Hz), 1.36 (t, 1H, J=5.3 Hz); $R_f$ (50% ether-hexanes) 0.61.

Part C:

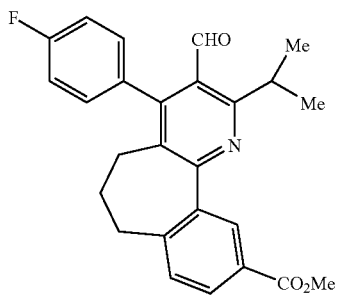

E11C

E11C was prepared in 85% yield from E11B using the procedure described in Example 5 Part C: $^1$H NMR (CDCl$_3$, 300 MHz) δ 9.90 (s, 1H), 8.50 (d, 1H, J=1.5 Hz), 8.06 (dd, 1H, J=7.7, 1.8 Hz), 7.33 (d, 1H, J=8.0 Hz), 7.15-7.28 (m, 4H), 3.90-4.00 (m, 4H), 2.67 (t, 2H, J=6.8 Hz), 2.05-2.22 (m, 4H), 1.39 (d, 6H, J=6.6 Hz).

Part D:

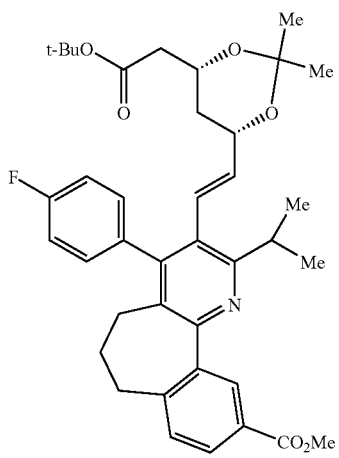

E11D

E11D was prepared in 93% yield from E11C using the procedure described in Example 8 Part D: LRMS m/z 644 (M+H)$^+$; HPLC (method 3) $t_R$=5.00 min.

Part E:

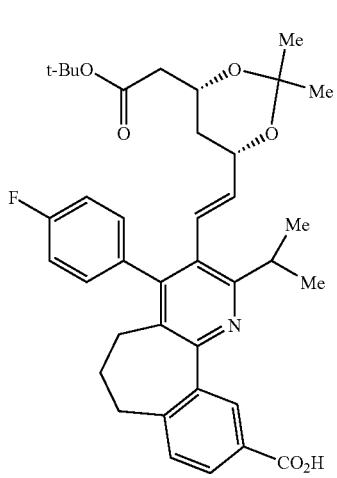

E11E

To a stirred solution of 3.20 g (4.97 mmol) of E11D in 70 mL of tetrahydrofuran and 9 mL of methanol was added 600 mg (14.3 mmol) of lithium hydroxide monohydrate in 60 mL of water. The mixture was heated to provide a slightly cloudy solution which was stirred overnight at ambient temperature. The reaction was quenched by the addition of 15 mL of 1 M aqueous HCl, and the resulting mixture was extracted twice with ether. The combined organic extracts were washed with brine, dried (MgSO$_4$), and chromatographed on silica gel (gradient elution with 3:1 hexanes-ether then 2:1 ether-hexanes) to afford, after concentration, 2.78 g (89%) of E11E as a colorless solid: LRMS m/z 630 (M+H)$^+$; HPLC (method 3) $t_R$=4.69 min.

Part F:

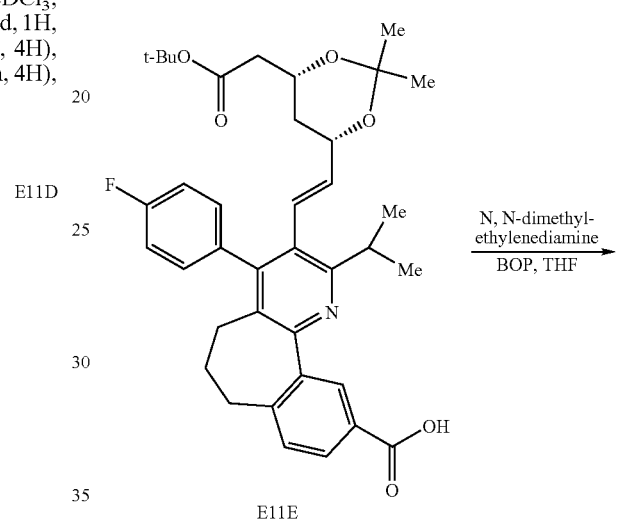

E11E

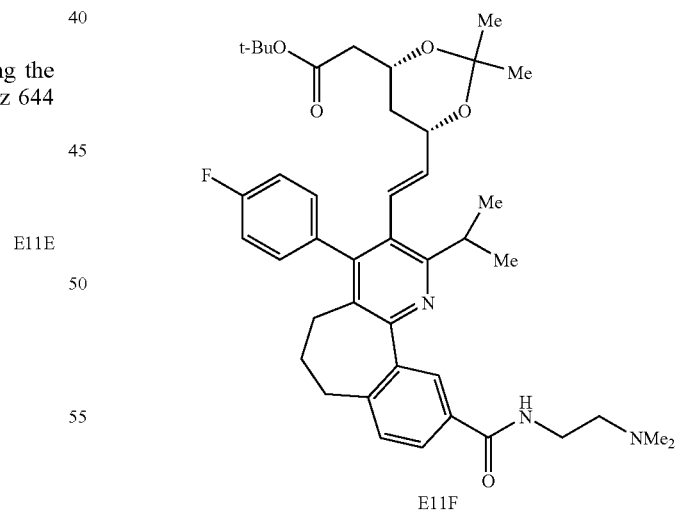

E11F

To a stirred solution of 3.30 g (5.24 mmol) of E11E in 30 mL of tetrahydrofuran and 2 mL of dimethylformamide was added 2.34 mL (21.0 mmol) of N,N-dimethylethylenediamine. The solution was treated with 2.54 g (5.6 mmol) of (benzotriazol-1-yl)oxy-tris(dimethylamino)phosphonium hexafluorophosphate, and the reaction was stirred for 6 h. The reaction was diluted with ether and washed with water, saturated aqueous sodium bicarbonate, water, and brine. The solution was dried (MgSO$_4$) and concentrated under reduced pressure to afford 3.39 g (92%) of E11F as an off-white foam: LRMS m/z 700 (M+H)$^+$; HPLC (method 3) $t_R$=4.16 min.

Part G:

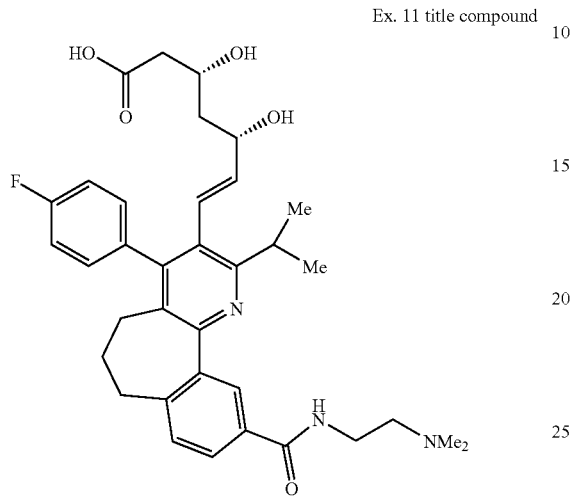

Ex. 11 title compound

The title compound was prepared as the sodium salt from E11F using the procedure described in Example 2 Part D. The product was purified by reverse-phase HPLC (Phenomenex C18-silica Luna 60 mm×21 mm; 20% methanol-water then to 100% methanol over 4 min; Flow=9.9 mL/min): LRMS m/z 604 (M+H)$^+$; HPLC (method 3) $t_R$=2.65 min.

Example 12

6-Heptenoic acid, 7-[10-[[[3-(dimethylamino)propyl]amino]carbonyl]-4-(4-fluorophenyl)-6,7-dihydro-2-(1-methylethyl)-5H-benzo[6,7]cyclohepta[1,2-b]pyridin-3-yl]-3,5-dihydroxy-, (3R,5S,6E)-

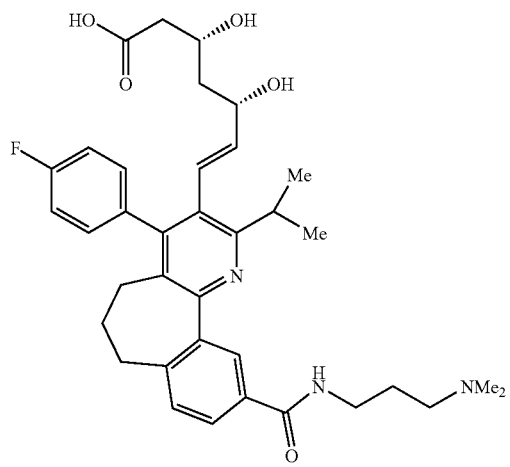

Part A:

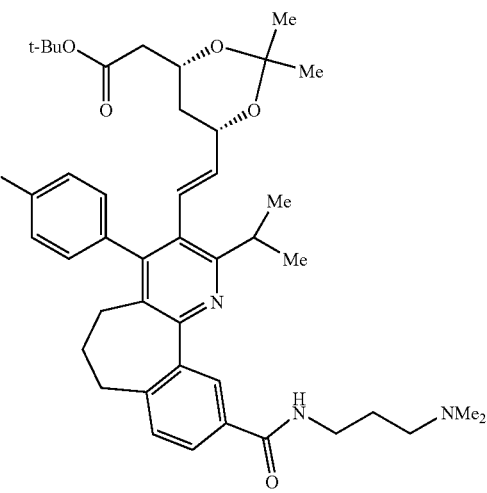

E12A

E12A was prepared in 75% yield from E11E and N,N-dimethyl-1,3-propanediamine using the procedure described in Example 11 Part F: R$_f$ (85:10:5 chloroform-methanol-acetic acid) 0.57.

Part B:

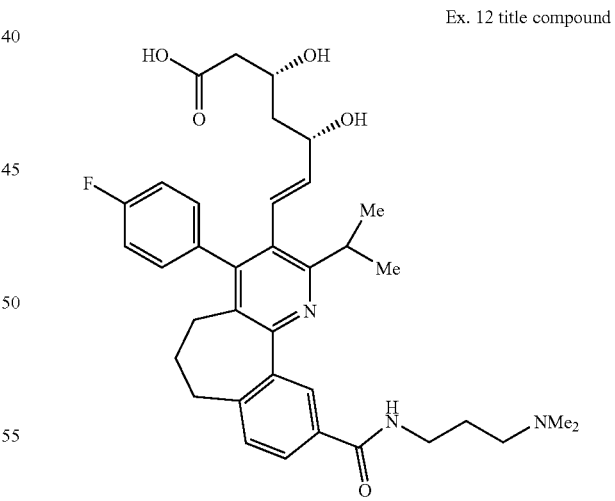

Ex. 12 title compound

The title compound was prepared in 92% yield from E12A as the sodium salt using the procedure described in Example 2 Part D. The product was purified by reverse-phase HPLC (Phenomenex C18-silica Luna 60 mm×21 mm; 20% methanol-water then up to 100% methanol over 4 min; Flow=9.9 mL/min): LRMS m/z 618 (M+H)$^+$; HPLC (method 3) $t_R$=2.69 min.

Example 13

6-Heptenoic acid, 7-[4-(4-fluorophenyl)-6,7-dihydro-10-[(methoxyamino)carbonyl]-2-(1-methylethyl)-5H-benzo[6,7]cyclohepta[1,2-b]pyridin-3-yl]-3,5-dihydroxy-, (3R,5S,6E)-

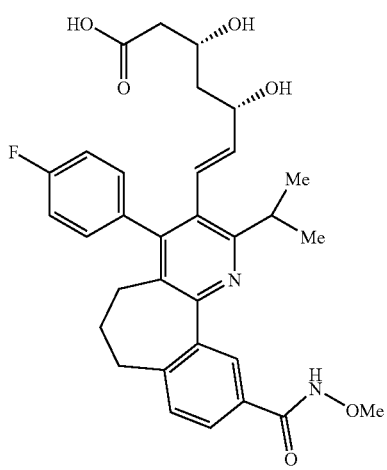

Part A:

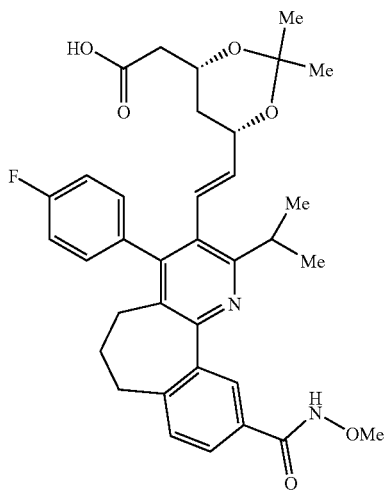

E13A

E13A was prepared in 100% yield from E11E, and O-methylhydroxylamine (generated in situ from 2 equivalents of O-methylhydroxylamine hydrochloride and 4 equivalents of diisopropylethylamine) using the procedure described in Example 11 Part F: LRMS m/z 659 (M+H)⁺; R$_f$ (50% ether-hexanes) 0.05.

Part B:

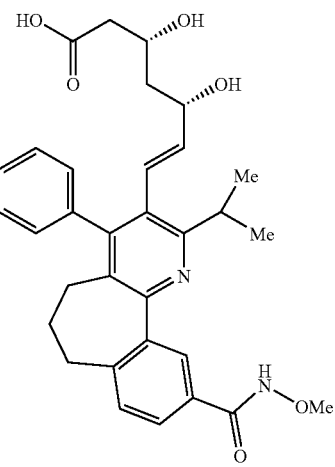

Ex. 13 title compound

The title compound was prepared in 90% yield as the sodium salt from E13A using the procedure described in Example 2 Part D. The crude product was purified by reverse-phase HPLC (Phenomenex C18-silica Luna 60 mm×21 mm; 20% methanol-water then up to 100% methanol over 4 min; Flow=9.9 mL/min): LRMS m/z 561 (M−H)⁻; HPLC (method 3) t$_R$=3.07 min.

Example 14

6-Heptenoic acid, 7-[4-(4-fluorophenyl)-6,7-dihydro-2-(1-methylethyl)-10-[[[(4-methyl-1-piperazinyl)amino]carbonyl]-5H-benzo[6,7]cyclohepta[1,2-b]pyridin-3-yl]-3,5-dihydroxy-, (3R,5S,6E)-

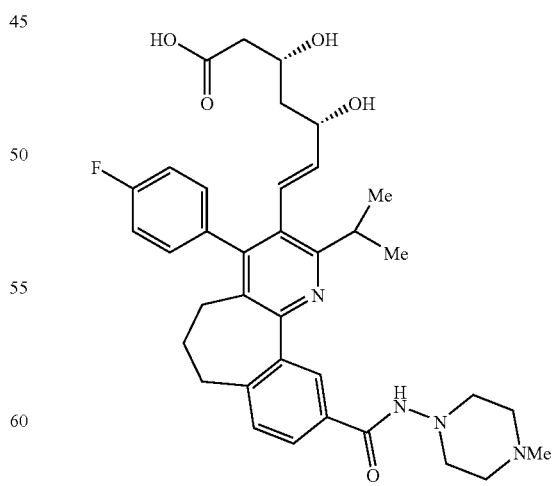

Part A:

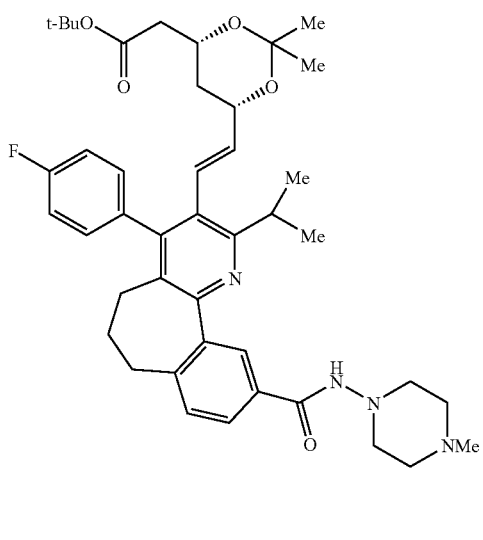

E14A

E14A was prepared in 100% yield from E11E and 1-amino-4-methylpiperazine using the procedure described in Example 11 Part F: LRMS m/z 727 (M+H)+.

Part B:

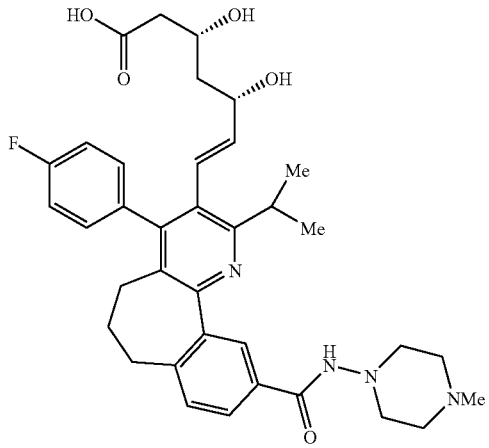

Ex. 14 title compound

The title compound was prepared in 64% yield as the sodium salt from E14A using the procedure described in Example 2 Part D. The crude product was purified by reverse-phase HPLC (Phenomenex C18-silica Luna 60 mm×21 mm; 20% methanol-water then up to 100% methanol over 4 min; Flow=9.9 mL/min): LRMS m/z 631 (M+H)+.

Example 15

6-Heptenoic acid, 7-[4-(4-fluorophenyl)-6,7-dihydro-2-(1-methylethyl)-10-[[(methylsulfonyl)amino]carbonyl]-5H-benzo[6,7]cyclohepta[1,2-b]pyridin-3-yl]-3,5-dihydroxy-, (3R,5S,6E)-

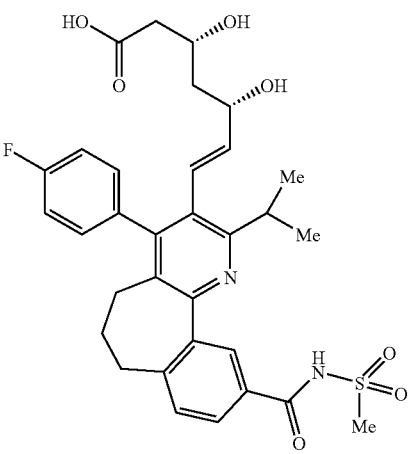

Part A:

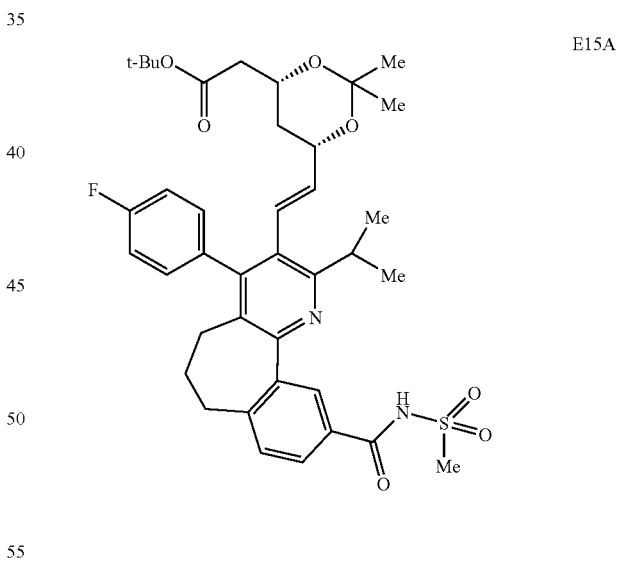

E15A

To a stirred solution of 30 mg (0.05 mmol) of E11E in 2 mL of dichloromethane were sequentially added 15 mg (0.15 mmol) of methanesulfonamide, 18 mg (0.15 mmol) of 4-(dimethylamino)pyridine, and 30 mg (0.15 mmol) of 1-(3-(dimethylamino)propyl)-3-ethylcarbodiimide. The reaction was stirred overnight at ambient temperature, diluted with 1:1 ether-ethyl acetate, and washed sequentially with 1 M aqueous HCl, water, and brine. The solution was dried (MgSO4), and concentrated under reduced pressure to afford 35 mg (100% yield) of E15A as a foam: LRMS m/z 707 (M+H)+; $R_f$ (80:15:5 chloroform-methanol-acetic acid) 0.89.

Part B:

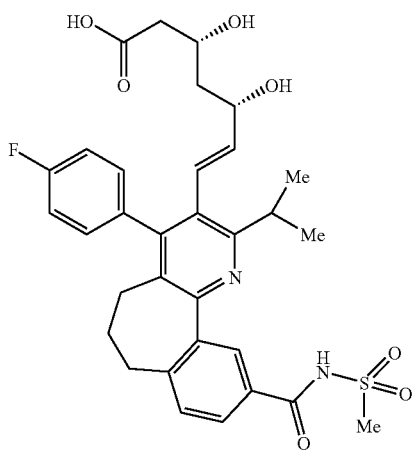

Ex. 15 title compound

The title compound was prepared in 93% yield from E15A as the disodium salt using the procedure described in Example 2 Part D. The crude product was purified by reverse-phase HPLC (Phenomenex C18-silica Luna 60 mm×21 mm; 20% methanol-water then up to 100% methanol over 4 min; Flow=9.9 mL/min): LRMS m/z 611 (M+H)$^+$; HPLC (method 3) $t_R$=3.17 min.

Example 16

6-Heptenoic acid, 7-[4-(4-fluorophenyl)-6,7-dihy-dro-10-[[[(methylamino)carbonyl]amino]methyl]-2-(1-methylethyl)-5H-benzo[6,7]cyclohepta[1,2-b]pyridin-3-yl]-3,5-dihydroxy-, (3R,5S,6E)-

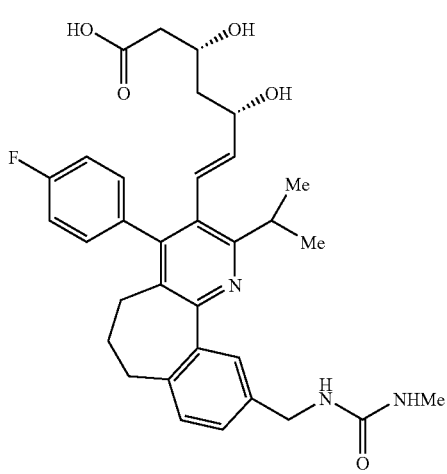

Part A:

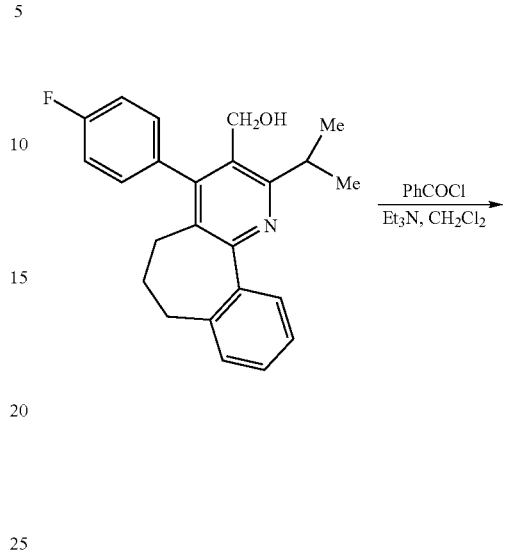

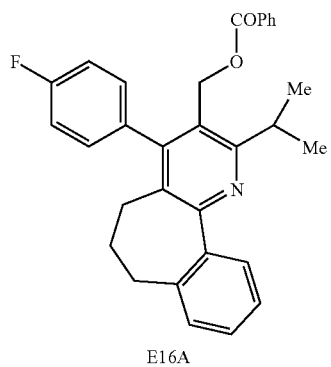

E16A

To a stirred, cooled (−20° C.) solution of 723 mg (2.00 mmol) of 4-(4-fluorophenyl)-6,7-dihydro-2-(1-methyl-ethyl)-5H-benzo[6,7]cyclohepta[1,2-b]pyridine-3-methanol and 0.42 mL (2.1 mmol) of triethylamine in 10 mL of dichloromethane was added 0.29 mL (2.1 mmol) of benzoyl chloride. The solution was warmed to ambient temperature, treated with 10 mg of 4-(dimethylamino)pyridine, and stirred overnight. The reaction was diluted with 30 mL of 1:1 ether-hexanes and washed sequentially with dilute aqueous acetic acid, water, saturated aqueous sodium bicarbonate, and brine. The solution was dried (MgSO$_4$), concentrated under reduced pressure, and the residue was chromatographed on silica gel (gradient elution with 3:1 hexanes-ether then ether). Concentration of the product-containing fractions afforded 460 mg (92%) of E16A as a colorless foam: LRMS m/z 466 (M+H)$^+$; HPLC (method 3) $t_R$=5.00 min.

Part B:

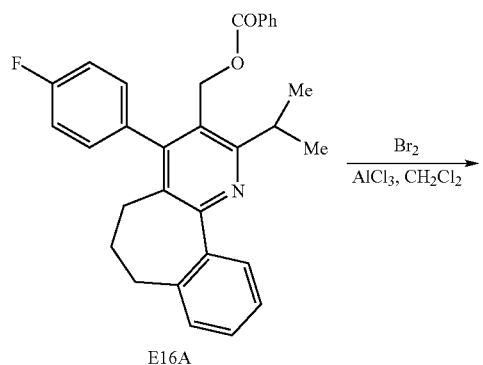

E16A

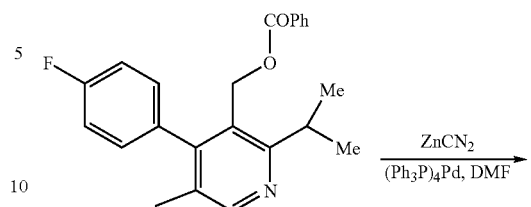

E16B

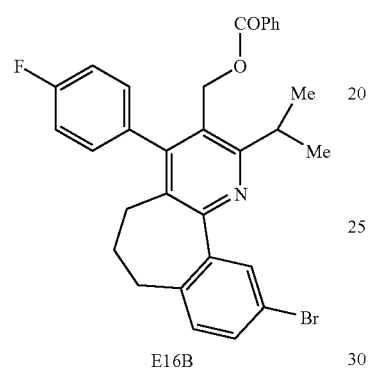

E16B

Part C:

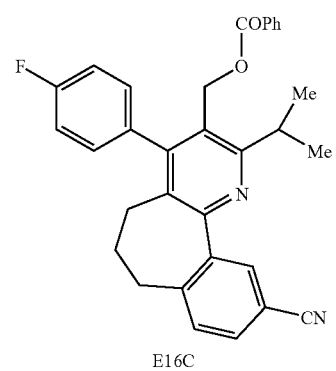

E16C

A solution of 200 mg (0.43 mmol) of E16A in 4 mL of dichloromethane was treated with 120 mg (0.90 mmol) of aluminum trichloride and then with 0.050 mL (0.9 mmol) of bromine. The solution was stirred for 30 min, cooled to 0° C., and quenched with saturated aqueous sodium bicarbonate. This mixture was diluted with 1:1 ether-ethyl acetate and washed sequentially with 10% aqueous sodium thiosulfate, 2% aqueous acetic acid, water, and brine. The organic phase was then dried (MgSO$_4$), concentrated under reduced pressure, and chromatographed on silica gel (gradient elution with 20% ether-hexanes then 40% ether-hexanes). Concentration of the product-containing fractions afforded 460 mg (92%) of E16B as a colorless foam: LRMS m/z 544 (M+H)$^+$; HPLC (method 3) t$_R$=5.59 min.

A solution of 700 mg (1.29 mmol) of E16B in 5 mL of dimethylformamide was de-gassed by performing three freeze-thaw cycles under vacuum. The solution was treated with 176 mg (1.5 mmol) of zinc (II) cyanide followed by 100 mg of tetrakis (triphenylphosphine)palladium (0), and the mixture was heated to 90° C. for 1.5 h. The dimethylformamide was removed under vacuum, and the residue was chromatographed on silica gel (gradient elution with 3:1 hexanes-ether then 2:1 ether-hexanes) to afford, after removal of solvent, 581 mg (92%) of E16C as a colorless foam: LRMS m/z 491 (M+H)$^+$; HPLC (method 3) t$_R$=4.89 min.

Part D:

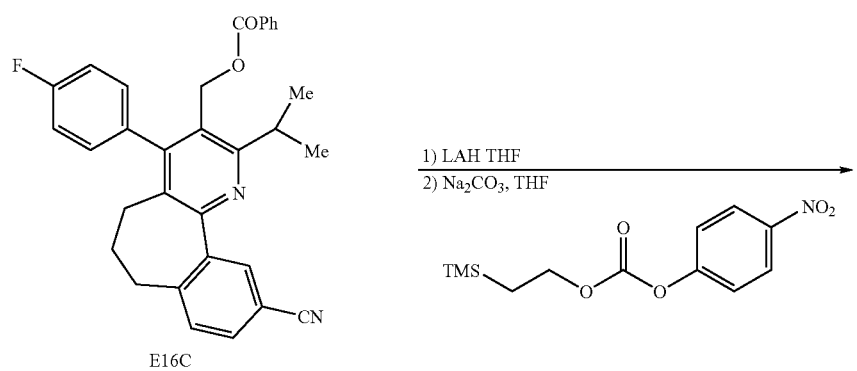

E16C

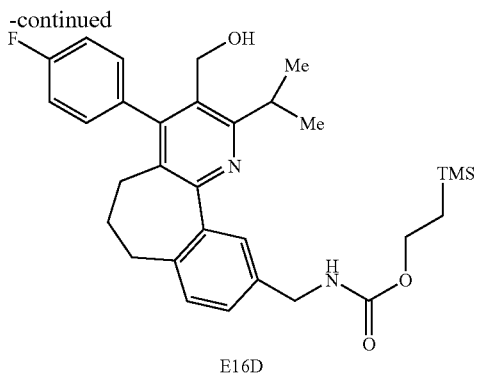

E16D

To a stirred solution of 245 mg (0.50 mmol) of E16C in 4 mL of ether and 2 mL of tetrahydrofuran was added 5.0 mL (5.0 mmol) of a 1 M solution of lithium aluminum hydride in tetrahydrofuran. The solution was stirred overnight, heated to reflux, then allowed to cool to ambient temperature over 1 h. The reaction was quenched using the method of Fieser. The resulting mixture was treated with ether and MgSO$_4$, stirred for 30 min and then filtered. The filtrate was concentrated under reduced pressure to provide an oil. This material was dissolved in 6 mL of tetrahydrofuran and treated with 3 mL of 2 M aqueous sodium carbonate and then 156 mg (0.55 mmol) of 2-(trimethylsilyl)ethyl p-nitrophenylcarbonate. This mixture was stirred for 5 h at ambient temperature, diluted with water, and extracted with ether. The organic extract was washed with dilute aqueous sodium carbonate, 10% aqueous acetic acid, then brine, dried (MgSO$_4$) and concentrated under reduced pressure. Chromatography on silica gel (gradient elution with 2:1 hexanes-ether then ether) afforded, after removal of solvent, 581 mg (92%) of E16D as a colorless foam: R$_f$ (50% ether-hexanes) 0.30.

Part E:

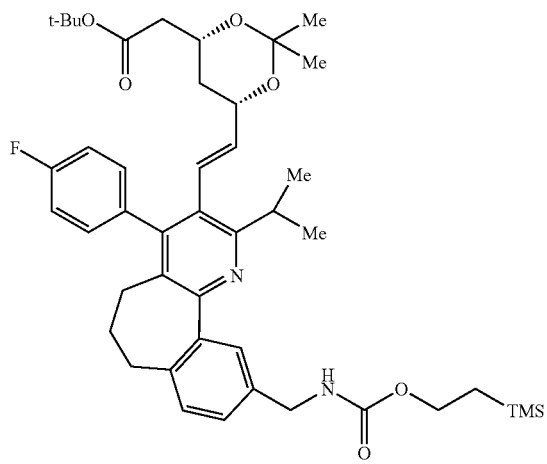

E16E

E16E was prepared from E16D in 86% yield using the procedure described in Example 2 Part C: LRMS m/z 759 (M+H)$^+$; HPLC (method 3) t$_R$=4.94 min.

Part F:

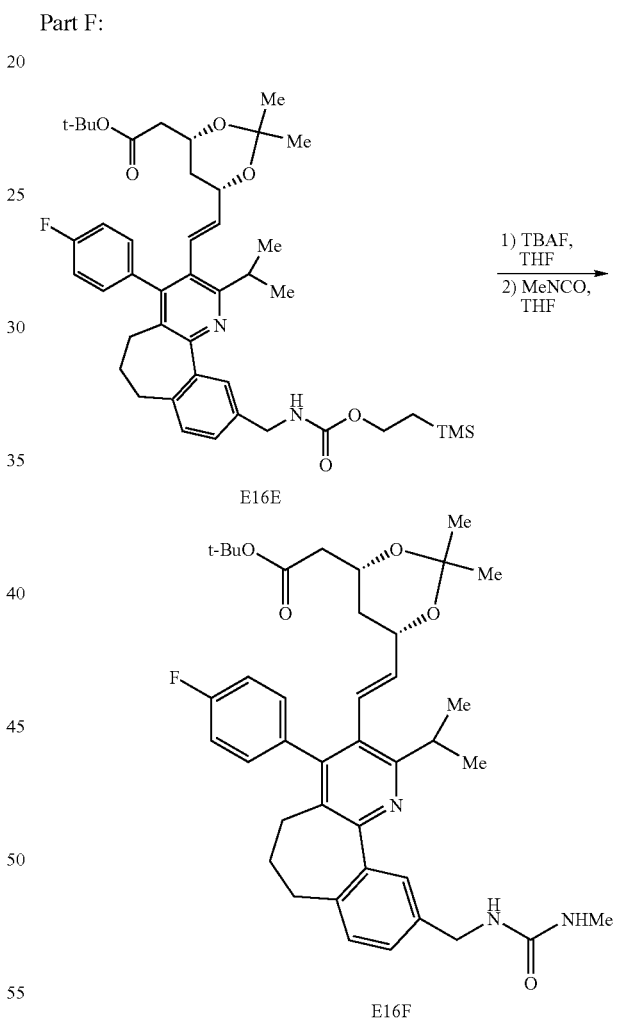

To a stirred solution of 75 mg (0.099 mmol) of E16E in 1 mL of dimethylformamide was added 0.5 mL of 1 M tetrabutylammonium fluoride in tetrahydrofuran. The solution was stirred for 4 h, diluted with ethyl acetate, and washed with water then brine. The organic phase was dried (MgSO$_4$), and concentrated under reduced pressure. The residue was dissolved in 2 mL of tetrahydrofuran, and treated with 0.10 mL of methyl isocyanate. The reaction was stirred for 2 days, during which time most of the solvent evaporated. The residue was chromatographed on silica gel (gradient elution with 1:1 hexanes-ethyl acetate, then ethyl acetate) to afford, after removal of solvent, 36 mg (54%) of E16F as an amorphous solid: $R_f$ (ether) 0.12.

Part G:

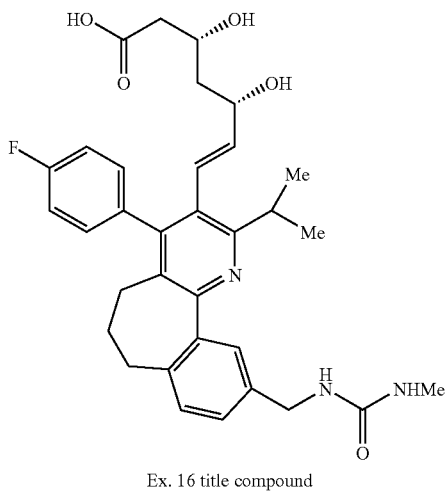

Ex. 16 title compound

The title compound was prepared as the sodium salt in 61% yield from E16F using the procedure described in Example 2 Part D. The crude product was purified by reverse-phase HPLC (Phenomenex C18-silica Luna 60 mm×21 mm; 20% methanol-water then up to 100% methanol over 4 min; Flow=9.9 mL/min): LRMS m/z 576 (M+H)$^+$; HPLC (method 3) $t_R$=2.95 min.

Example 17

6-Heptenoic acid, 7-[4-(4-fluorophenyl)-6,7-dihydro-2-(1-methylethyl)-10-[[(methylsulfonyl)amino]methyl]-5H-benzo[6,7]cyclohepta[1,2-b]pyridin-3-yl]-3,5-dihydroxy-, (3R,5S,6E)-

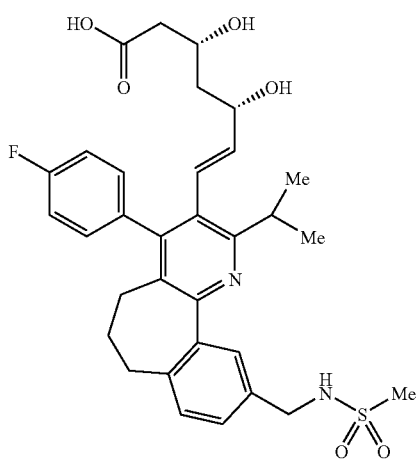

Part A:

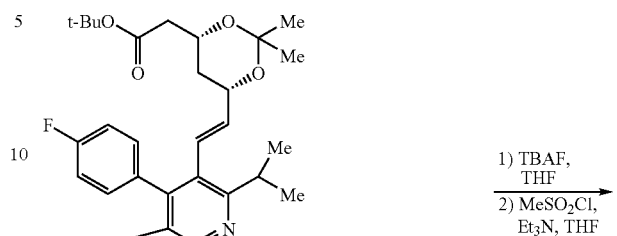

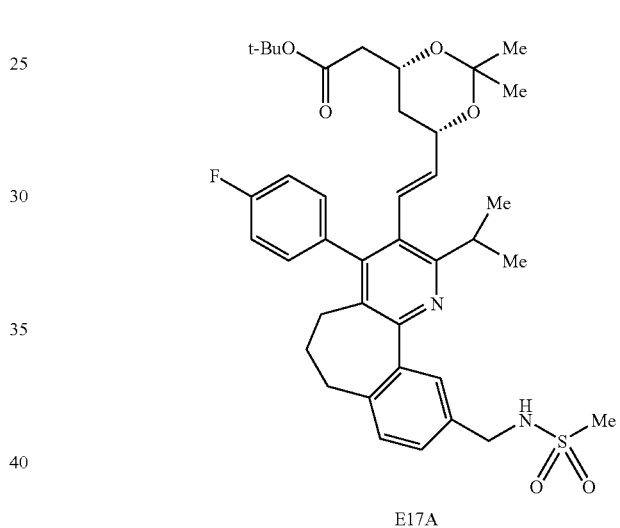

E17A

To a stirred solution of 75 mg (0.099 mmol) of E16E in 1 mL of dimethylformamide was added 0.5 mL of 1 M tetrabutylammonium fluoride in tetrahydrofuran. The solution was stirred for 4 h, diluted with ethyl acetate, and washed with water and then brine. The organic phase was dried (MgSO$_4$) and concentrated under reduced pressure. The residue was dissolved in 2 mL of dichloromethane and treated with 0.05 mL of triethylamine and 0.040 mL of methanesulfonyl chloride. The reaction was stirred for 4 h and concentrated. The residue was chromatographed on silica gel (gradient elution with 1:1 hexanes-ethyl acetate then ethyl acetate) to afford, after removal of solvent, 45 mg (66%) of sulfonamide E17A as an amorphous solid: $^1$H NMR (CDCl$_3$, 300 MHz) δ 7.78 (d, 1H, J=1.9 Hz), 7.32 (dd, 1H, J=7.9, 2.0 Hz), 7.24 (d, 1H, J=8.1 Hz), 7.00-7.19 (m, 4H), 6.33 (d, 1H, J=16.1 Hz), 5.41 (dd, 1H, J=16.1, 5.9 Hz), 4.72-4.83 (br. m, 1H), 4.42 (d, 2H, J=5.8 Hz), 4.15-4.32 (m, 2H), 3.36-3.47 (m, 1H), 2.94 (s, 3H), 2.56-2.62 (m, 2H), 2.42 (t, 2H, J=7.0 Hz), 2.32 (ABX, 2H, $J_{AB}$=15.2 Hz, $J_{AX}$=7.2 Hz, $J_{BX}$=6.3 Hz, Δν~45 Hz), 1.94-2.19 (m, 4H), 1.32-1.51 (m, 17H).

Part B:

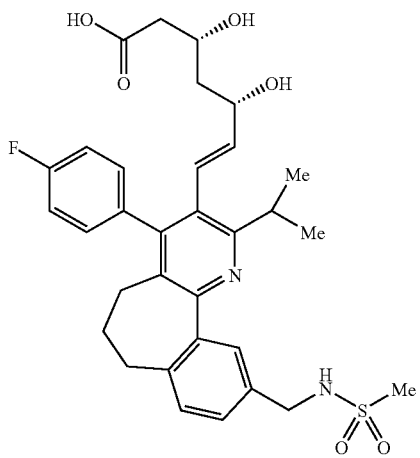

Ex. 17 title compound

The title compound was prepared as the sodium salt in 39% yield from E17A using the procedure described in Example 2 Part D. The crude product was purified by reverse-phase HPLC (Phenomenex C18-silica Luna 60 mm×21 mm; 20% methanol-water then up to 100% methanol over 4 min; Flow=9.9 mL/min): LRMS m/z 597 (M+H)$^+$; $R_f$ (2% acetic acid-ethyl acetate) 0.67.

Example 18

5H-benzo[6,7]cyclohepta[1,2-b]pyridine-9,10-dicarboxylic acid, 3-[(1E,3S,5R)-6-carboxy-3,5-dihydroxy-1-hexenyl]-4-(4-fluorophenyl)-6,7-dihydro-2-(1-methylethyl)-, 9,10-dimethyl ester

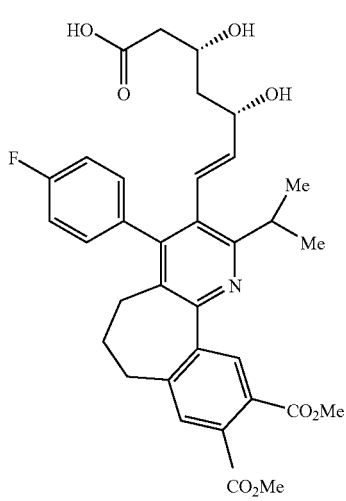

Part A:

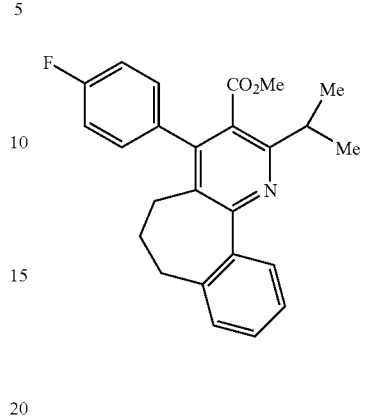

1) $Br_2$, $AlCl_3$, $CH_2Cl_2$
2) DIBAL-H, $CH_2Cl_2$, -78° C.
3) Dess-Martin periodinane wet $CH_2Cl_2$
4) sulfone E1D, LiHMDS THF, -78° C.
5) Pd(OAc)$_2$, dppf, CO, Et$_3$N MeOH, DMF, 60° C.

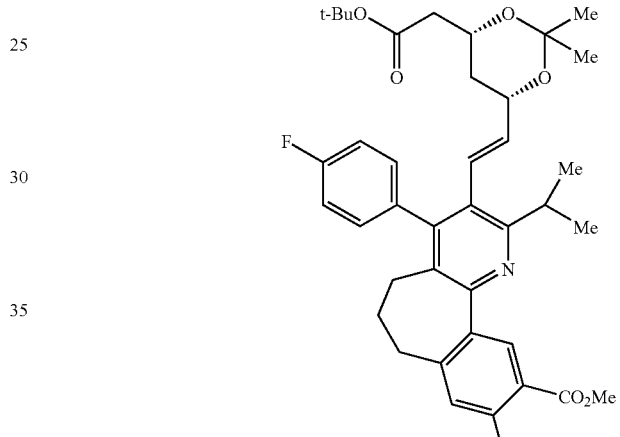

E18A

To a stirred solution of 4.7 g (12 mmol) of methyl 4-(4-fluorophenyl)-6,7-dihydro-2-(1-methylethyl)-5H-benzo[6,7]cyclohepta[1,2-b]pyridine-3-carboxylate in 50 mL of dichloromethane was added 6.4 g (48 mmol) of aluminum trichloride. The solution stirred for 1 min and then treated with 2.5 mL (48 mmol) of bromine over 5 min The red solution was stirred for 30 min, quenched carefully with water, and the phases were then separated. The aqueous phase was extracted with ether and the combined organic phases were washed with 1:1 saturated aqueous sodium bicarbonate: 10% aqueous sodium thiosulfate, water, and brine. The organic phase was dried (MgSO$_4$) and evaporated under reduced pressure. Crystallization from tetrahydrofuran-cyclohexane afforded 2.75 g (47%) of an 85:15 mixture consisting of monobromo- and dibromo-esters. This mixture was dissolved in 33 mL of dichloromethane, cooled to –78° C. and treated with 32 mL of 1 M diisobutylaluminum hydride in hexanes. The solution was stirred for 1 h at –78° C. and then removed from the cold bath. The reaction was quenched by sequential addition of ethyl acetate, methanol, then saturated aqueous sodium potassium tartrate. The phases were stirred together for 1 h and separated. The organic phase was dried (MgSO$_4$) and concentrated to afford 2.50 g (99%) of an 85:15 mixture of monobromo- and dibromo-carbinols. This mixture was oxidized to provide 2.30 g of a mixture of aldehydes using the procedure described in Example 5 Part C. The crude aldehyde mixture was converted into 1.33 g of a mixture of bromoesters using the procedure described in Example 8 Part D. This mixture was dissolved in 4 mL of methanol and 10 mL of dimethylformamide and treated with 110 mg (0.20 mmol) of diphenylphosphinoferrocene, 23 mg (0.10 mmol) of palladium (II) acetate, and 0.55 mL (4.0 mmol) of triethylamine. The mixture was purged three times with carbon monoxide and then was heated to 60° C. for 18 h. The reaction was diluted with ethyl acetate, washed twice with water, dried (MgSO$_4$), and concentrated under reduced pressure. The residue was chromatographed on silica gel (gradient elution with 1:1 ether-hexanes then ether) to afford, after removal of solvent, 140 mg (10%) of E18A as a colorless foam: $^1$H NMR (CDCl$_3$, 300 MHz) δ 8.18 (s, 1H), 7.59 (s, 1H), 7.04-7.13 (m, 4H), 6.33 (d, 1H, J=16.1 Hz), 5.29 (dd, 1H, J=16.1, 6.2 Hz), 4.16-4.32 (m, 2H), 3.94 (s, 3H), 3.91 (s, 3H), 3.36-3.47 (m, 1H), 2.65 (t, 2H, J=6.0 Hz), 2.33 (ABX, 2H, J$_{AB}$=15.2 Hz, J$_{AX}$=7.0 Hz, J$_{BX}$=6.2 Hz, Δv~44 Hz), 1.98-2.18 (m, 4H), 0.82-1.46 (m, 23H).

Part B:

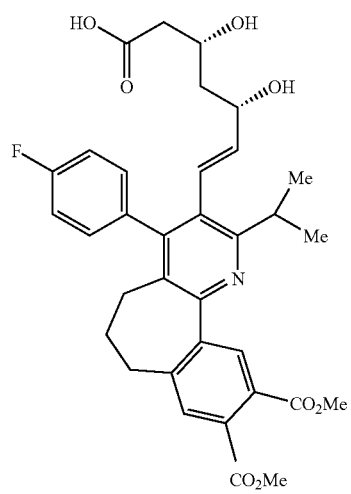

Ex. 18 title compound

The title compound was prepared as the sodium salt from E18A using the procedure described in Example 2 Part D. The crude product was purified by reverse-phase HPLC (Phenomenex C18-silica Luna 60 mm×21 mm; 20% methanol-water then up to 100% methanol over 4 min; Flow=9.9 mL/min): LRMS m/z 606 (M+H)$^+$; HPLC (method 3) t$_R$=3.93 min.

Example 19

5H-benzo[6,7]cyclohepta[1,2-b]pyridine-9,10-dicarboxylic acid, 3-[(1E,3S,5R)-6-carboxy-3,5-dihydroxy-1-hexenyl]-4-(4-fluorophenyl)-6,7-dihydro-2-(1-methylethyl)-

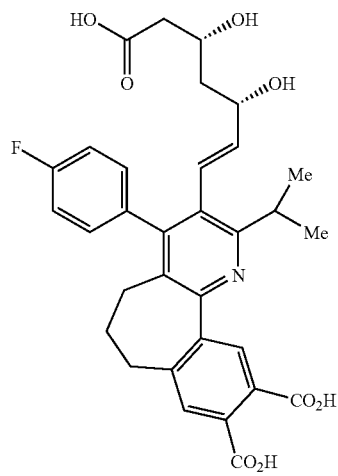

Ex. 19 title compound

The title compound was prepared as the trisodium salt from E18A using the procedure described in Example 2 Part D with the modification that the final base hydrolysis reaction was run overnight with a 10-fold excess of sodium hydroxide. The crude product was purified by reverse-phase HPLC (Phenomenex C18-silica Luna 60 mm×21 mm; 20% methanol-water then up to 100% methanol over 4 min; Flow=9.9 mL/min): LRMS m/z 578 (M+H)$^+$; HPLC (method 3) t$_R$=3.15 min.

Example 20

6-Heptenoic acid, 7-[4-(4-fluorophenyl)-6,7-dihydro-2-(1-methylethyl)-10-nitro-5H-benzo[6,7]cyclohepta[1,2-b]pyridin-3-yl]-3,5-dihydroxy-, (3R,5S, 6E)-

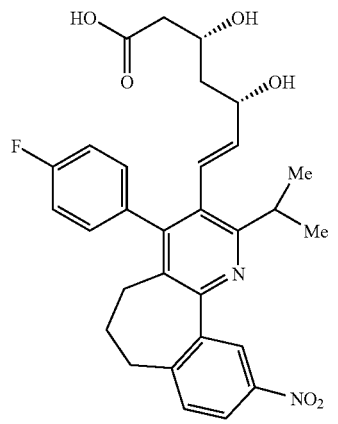

Part A:

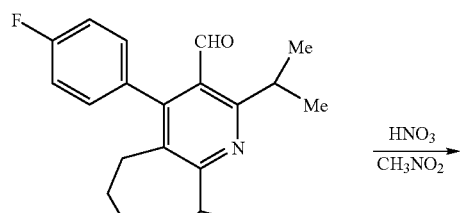

To a stirred, cooled (0° C.) suspension of 3.6 g (10 mmol) of 4-(4-fluorophenyl)-6,7-dihydro-2-(1-methylethyl)-5H-benzo[6,7]cyclohepta[1,2-b]pyridine-3-carboxaldehyde (prepared as described in the reference cited in Ex 1 pt. A) in 15 mL of nitromethane was added 20 mL of fuming 90% nitric acid. The reaction was warmed to ambient temperature and stirred for 16 h. Thin-layer chromatography indicated the presence of a trace of starting material, so the reaction was treated with an additional 2 mL of fuming 90% nitric acid. The mixture was warmed with a heat gun to approximately 50° C. and stirred for an additional 1 h at ambient temperature. Column chromatography on silica gel (gradient elution with 9:1 hexanes-ether then 1:1 hexanes-ether) afforded, after removal of solvent, 3.04 g (75%) of E20A: LRMS m/z 405 (M+H)$^+$; R$_f$ (10% ethyl acetate-hexanes) 0.31.

Part B:

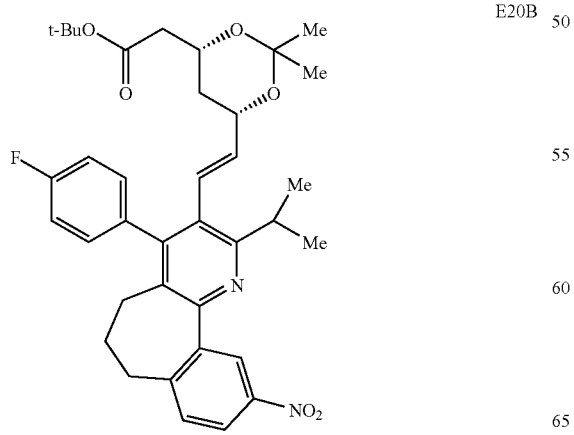

E20B was prepared in 93% yield from E20A using the procedure described in Example 8 Part D. The crude product was purified by chromatography on silica gel (gradient elution with 9:1 hexanes-ether then 1:1 hexanes-ether) to afford E20B: LRMS m/z 631 (M+H)$^+$; R$_f$ (15% ethyl acetate-hexanes) 0.27.

Part C:

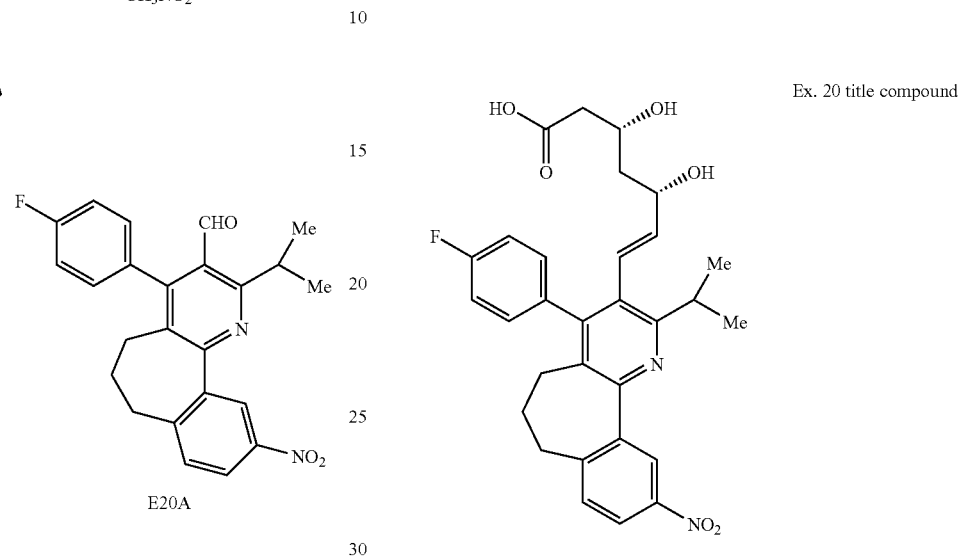

Ex. 20 title compound

The title compound was prepared in 76% yield from E20B using the procedure described in Example 2 Part D: LRMS m/z 535 (M+H)$^+$; HPLC (method 3) t$_R$=4.23 min.

Example 21

6-Heptenoic acid, 7-[4-(4-fluorophenyl)-6,7-dihydro-10-[[(methylamino)carbonyl]amino]-2-(1-methylethyl)-5H-benzo[6,7]cyclohepta[1,2-b]pyridin-3-yl]-3,5-dihydroxy-, (3R,5S,6E)-

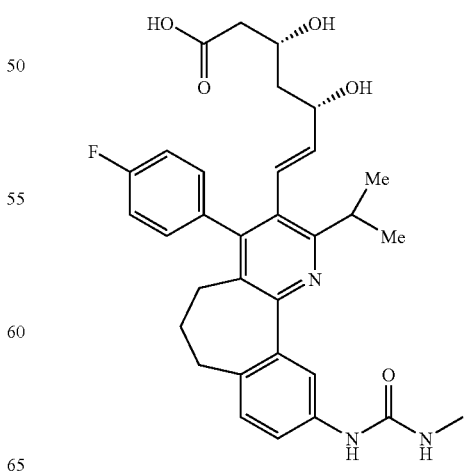

Part A:

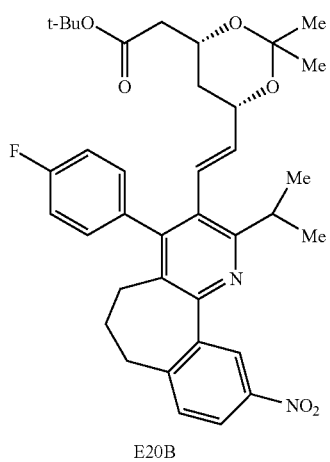

E20B

To a stirred solution of 631 mg (1.00 mmol) of E20B in 15 mL of ethanol was added a solution of 220 mg of calcium chloride in 2 mL of water. The resultant solution was treated with 1.31 g of zinc dust and then was heated to reflux for 30 min. The reaction was cooled, filtered, diluted with ether, and washed with saturated aqueous sodium bicarbonate and then brine. The organic solution was dried and concentrated under reduced pressure. The residue was purified by chromatography on silica gel (gradient elution with 1:1 hexanes-ether then ether) to afford a white solid which was crystallized from ethyl acetate-hexanes to afford 302 mg (51%) of E21A as a colorless solid: LRMS m/z 601 (M+H)$^+$; R$_f$ (50% ether-hexanes) 0.16.

Part B:

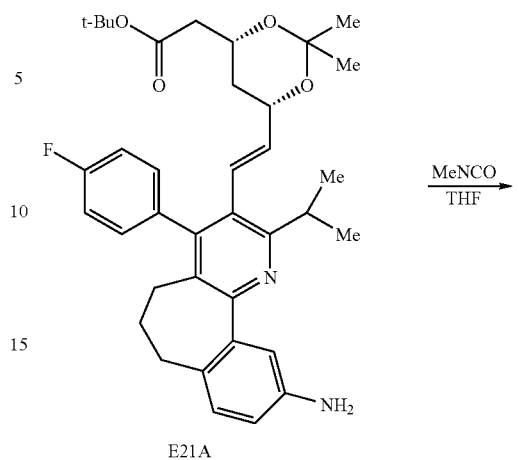

E21A

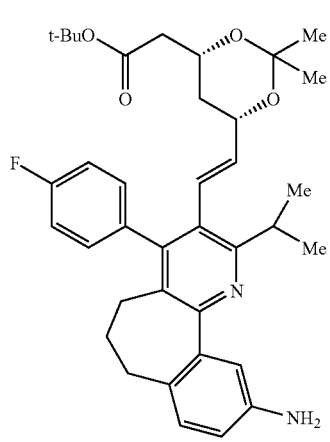

E21A

E21B

To a stirred solution of 58 mg (0.11 mmol) of E21A in 1 mL of tetrahydrofuran was added 0.020 mL of methyl isocyanate. The solution was stirred for 16 h at ambient temperature, heated to reflux, and treated with water. The resulting precipitate was filtered, rinsed with water, and briefly air-dried to afford 74 mg (100%) of E21B as a colorless solid: LRMS m/z 658 (M+H)$^+$; HPLC (method 3) t$_R$=4.26 min.

Part C:

Ex. 21 title compound

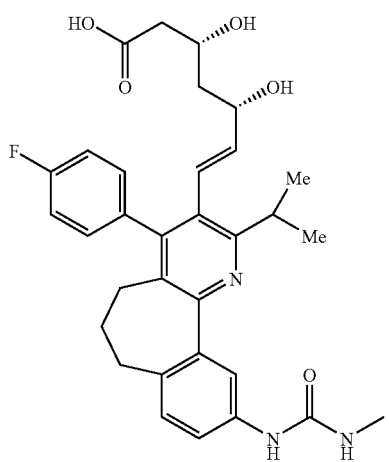

The title compound was prepared as the sodium salt from E21B using the procedure described Example 2 Part D: LRMS m/z 562 (M+H)$^+$; HPLC (method 3) $t_R$=2.99 min.

Example 22

6-Heptenoic acid, 7-[4-(4-fluorophenyl)-6,7-dihydro-2-(1-methylethyl)-10-[[[(4-methyl-1-piperazinyl)amino]carbonyl]amino]-5H-benzo[6,7]cyclohepta[1,2-b]pyridin-3-yl]-3,5-dihydroxy-, (3R,5S, 6E)-

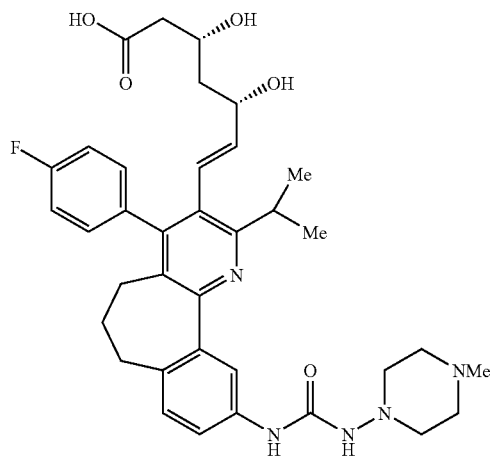

Part A:

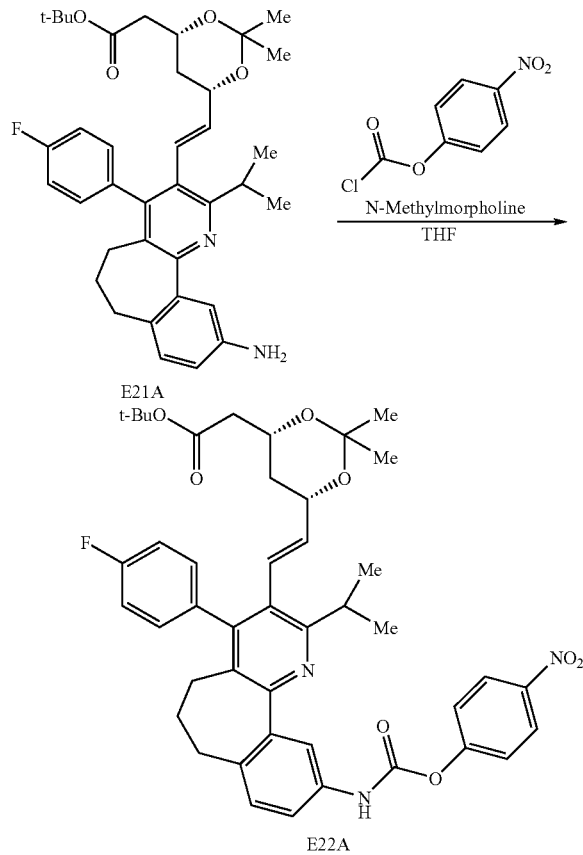

To a stirred solution of 120 mg (0.20 mmol) of E21A in 2 mL of tetrahydrofuran was added 0.033 mL (0.30 mmol) of 4-methylmorpholine followed by 40 mg (0.22 mmol) of p-nitrophenyl chloroformate. The solution was stirred for 1 h, treated with a drop of 1-methyl-4-(2-aminoethyl)piperazine and diluted with ether. The solution was washed sequentially with dilute aqueous acetic acid then brine, dried (MgSO$_4$), and concentrated under reduced pressure. Column chromatography of the residue on silica gel (gradient elution with 2:1 hexanes-ether then ether) afforded, after removal of solvent, 140 mg (92%) of E22A: R$_f$ (50% ether-hexanes) 0.43.

Part B:

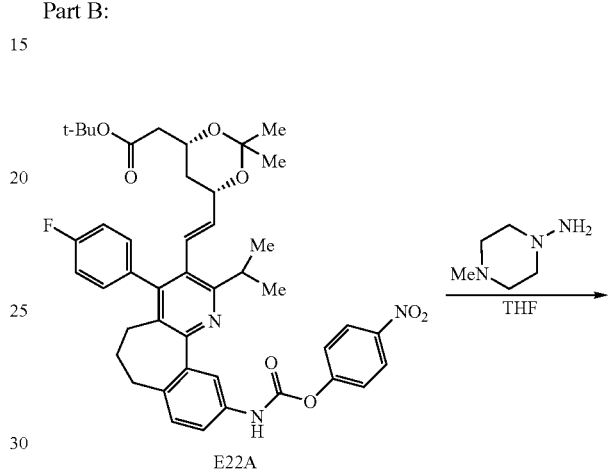

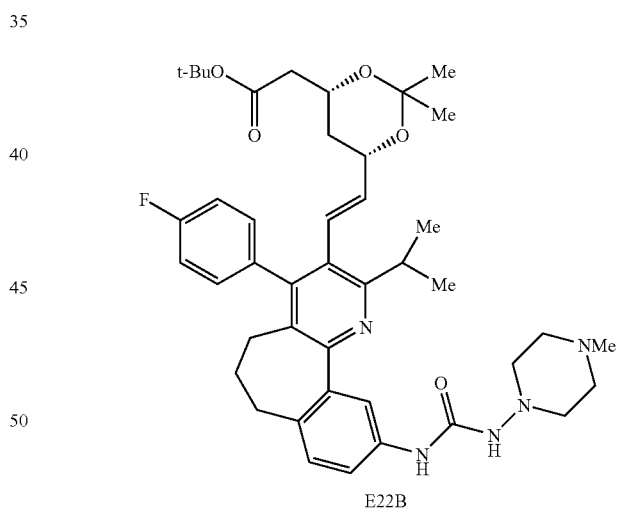

To a stirred solution of 30 mg (0.039 mmol) of E22A in 1 mL of tetrahydrofuran was added 0.020 mL of 1-amino-4-methylpiperazine. The solution was stirred for 10 min, treated with 1 mL of dimethylsulfoxide, and stirred for an additional 15 min. The reaction was diluted with 2:1 ether-ethyl acetate and washed sequentially with saturated aqueous sodium bicarbonate (twice) and brine. The solution was dried (MgSO$_4$) and concentrated under reduced pressure to afford 26 mg (90%) of E22B as an oil: LRMS m/z 742 (M+H)$^+$; R$_f$ (85:10:5 chloroform-methanol-acetic acid) 0.49.

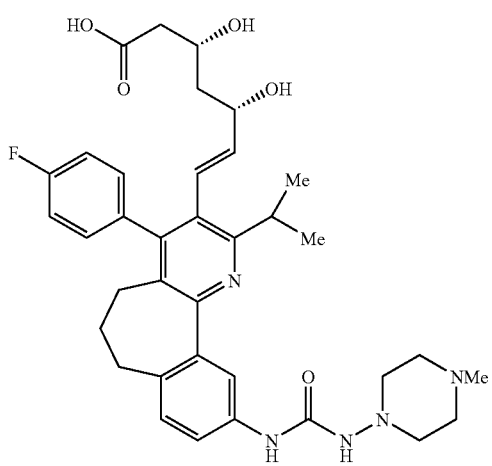

Ex. 22 title compound

Part C:

The title compound was prepared in 40% yield from E22B using the procedure described in Example 2 Part D. The crude product was purified by reverse-phase HPLC (Phenomenex C18-silica Luna 60 mm×21 mm; 20% methanol-water then up to 100% methanol over 4 min; Flow=9.9 mL/min). Concentration of the product-containing fractions afforded the sodium salt of the title compound as a white powder: LRMS m/z 646 (M+H)$^+$; HPLC (method 3) $t_R$=3.04 min.

Example 23

6-Heptenoic acid, 7-[10-[[[[2-(dimethylamino)ethyl]amino]carbonyl]amino]-4-(4-fluorophenyl)-6,7-dihydro-2-(1-methylethyl)-5H-benzo[6,7]cyclohepta[1,2-b]pyridin-3-yl]-3,5-dihydroxy-, (3R,5S,6E)-

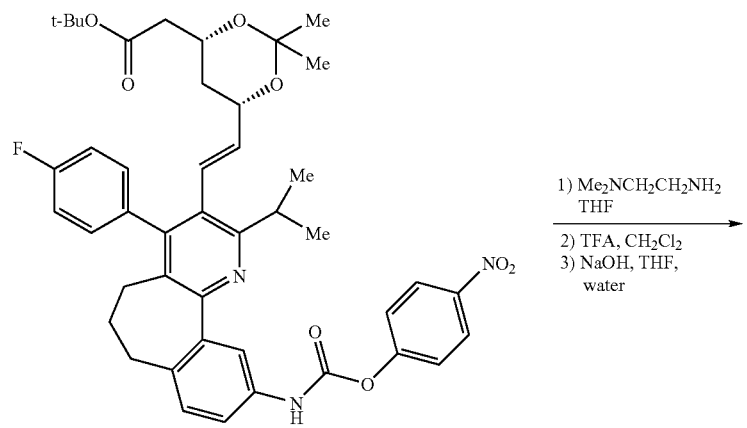

E22A

1) Me$_2$NCH$_2$CH$_2$NH$_2$
   THF
2) TFA, CH$_2$Cl$_2$
3) NaOH, THF, water

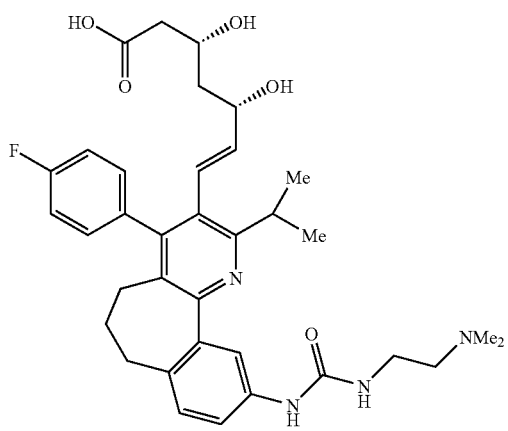

Ex. 23 title compound

To a stirred solution of 45 mg (0.059 mmol) of E22A in 2 mL of tetrahydrofuran was added 0.020 mL of N,N-dimethylethylenediamine. The solution was stirred for 10 min, treated with 0.3 mL of dimethylsulfoxide, and stirred for an additional 15 min. The reaction was diluted with 2:1 ether-ethyl acetate and washed sequentially with saturated aqueous sodium bicarbonate (twice) and brine. The solution was dried (MgSO$_4$) and concentrated under reduced pressure. The residue was dissolved in 2 mL of dichloromethane and treated with 2 ml of trifluoroacetic acid. The solution was stirred for 2.5 h and then concentrated under reduced pressure. The residue was dissolved in 2 mL of tetrahydrofuran and treated with 0.2 mL of 0.5 M aqueous sodium hydroxide. The solution was stirred for 1 h, and most of the tetrahydrofuran was removed under a stream of nitrogen. The crude product was purified by reverse-phase HPLC (Phenomenex C18-silica Luna 60 mm×21 mm; 20% methanol-water then up to 100% methanol over 4 min; Flow=9.9 mL/min). Concentration of the product-containing fractions afforded 26 mg (68%) of the title compound as the sodium salt as a white powder: LRMS m/z 619 (M+H)$^+$; HPLC (method 3) t$_R$=2.60 min.

Example 24

6-Heptenoic acid, 7-[4-(4-fluorophenyl)-6,7-dihydro-2-(1-methylethyl)-10-[[[methyl[2-(methylamino)ethyl]amino]carbonyl]amino]-5H-benzo[6,7]cyclohepta[1,2-b]pyridin-3-yl]-3,5-dihydroxy-, (3R,5S,6E)-

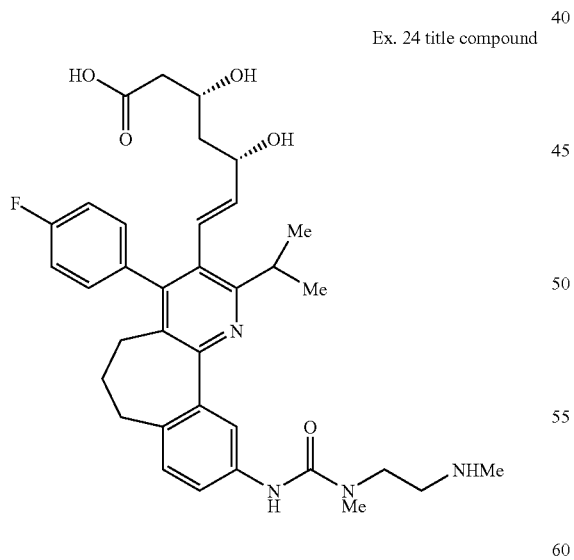

Ex. 24 title compound

The title compound was prepared in 63% yield from E22A and N,N'-dimethylethylenediamine using the procedure described in Example 23: LRMS m/z 619 (M+H)$^+$.

Example 25

6-Heptenoic acid, 7-[10-[[[(carboxymethyl)amino]carbonyl]amino]-4-(4-fluorophenyl)-6,7-dihydro-2-(1-methylethyl)-5H-benzo[6,7]cyclohepta[1,2-b]pyridin-3-yl]-3,5-dihydroxy-, (3R,5S,6E)-

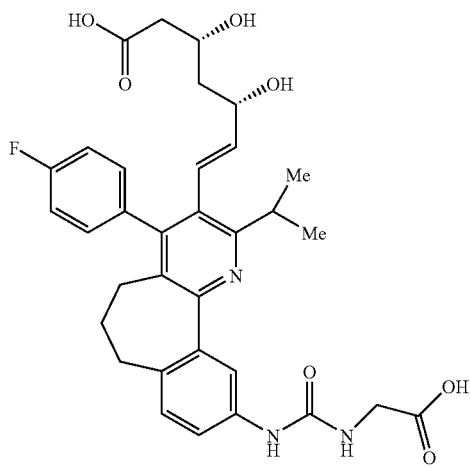

Part A:

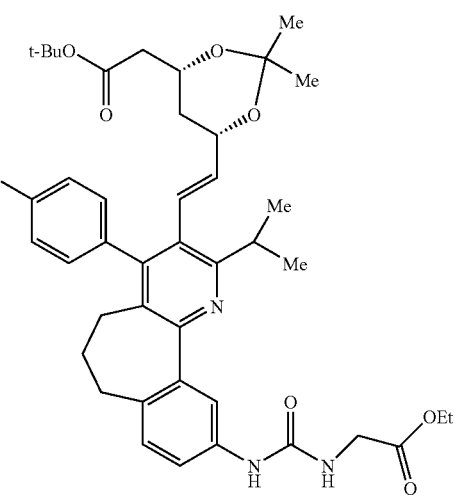

E25A

E25A was prepared in quantitative yield from E21A and ethyl isocyanatoacetate using the procedure described in Example 21 Part B: LRMS m/z 730 (M+H)$^+$; HPLC (method 3) t$_R$=4.36 min.

Part B:

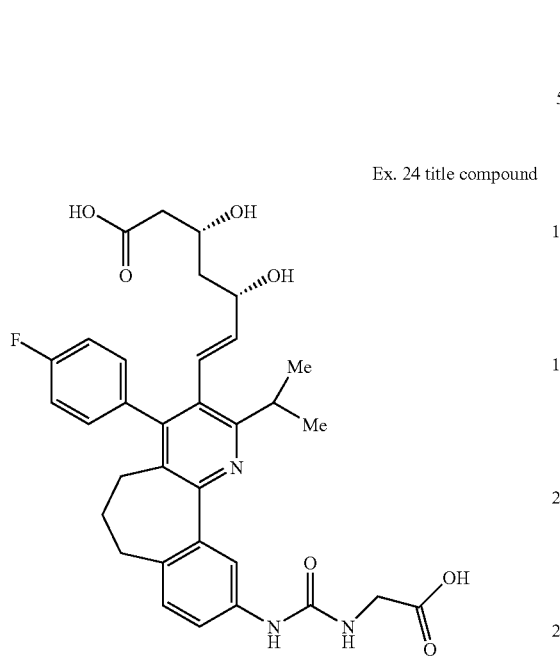

Ex. 24 title compound

The title compound was prepared as the disodium salt in 96% yield from E25A using the procedure described in Example 22 Part C: LRMS m/z 604 (M−H)⁻, HPLC (method 3) $t_R$=2.93 min.

Example 26

6-Heptenoic acid, 7-[10-(2,5-dioxo-1-imidazolidinyl)-4-(4-fluorophenyl)-6,7-dihydro-2-(1-methylethyl)-5H-benzo[6,7]cyclohepta[1,2-b]pyridin-3-yl]-3,5-dihydroxy-, (3R,5S,6E)-

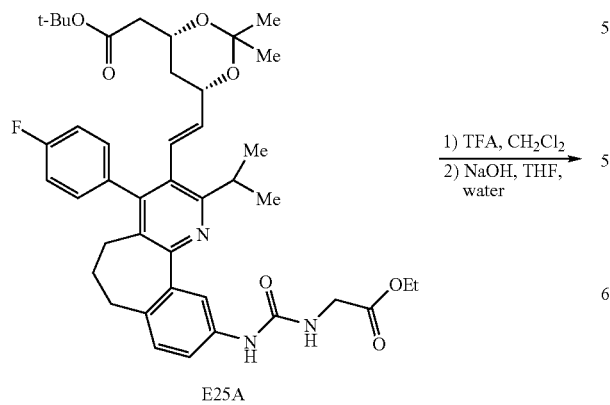

E25A

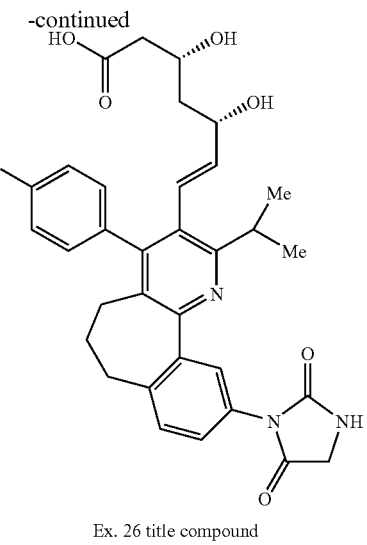

Ex. 26 title compound

To a stirred solution of 28 mg (0.038 mmol) of E25A in 2 mL of dichloromethane was added 2 mL of trifluoroacetic acid. The solution was stirred for 2.5 h, concentrated under reduced pressure, and coevaporated three times with ether. The residue was dissolved in 2 mL of tetrahydrofuran and treated with 0.1 mL of water and 0.06 mL of 1 M aqueous sodium hydroxide. The solution was stirred for 15 min and was then purified by reverse-phase HPLC (Phenomenex C18-silica Luna 60 mm×21 mm; 20% methanol-water then up to 100% methanol over 4 min; Flow=9.9 mL/min). Lyophilization of the product-containing fractions afforded 13 mg (57%) of the title compound as the sodium salt as a white powder: LRMS m/z 588 (M+H)⁺; HPLC (method 3) $t_R$=2.84 min.

Example 27

6-Heptenoic acid, 7-[10-[[(dimethylamino)acetyl]amino]-4-(4-fluorophenyl)-6,7-dihydro-2-(1-methylethyl)-5H-benzo[6,7]cyclohepta[1,2-b]pyridin-3-yl]-3,5-dihydroxy-, (3R,5S,6E)-

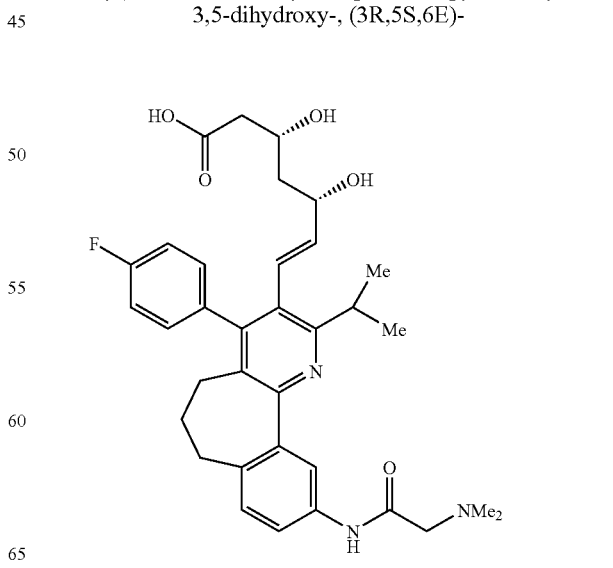

Part A:

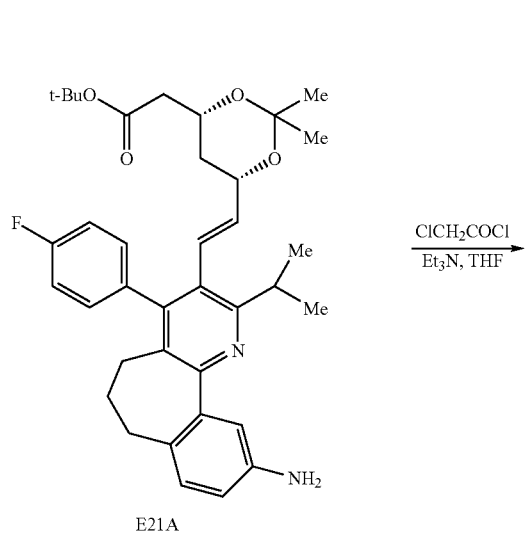

Part B:

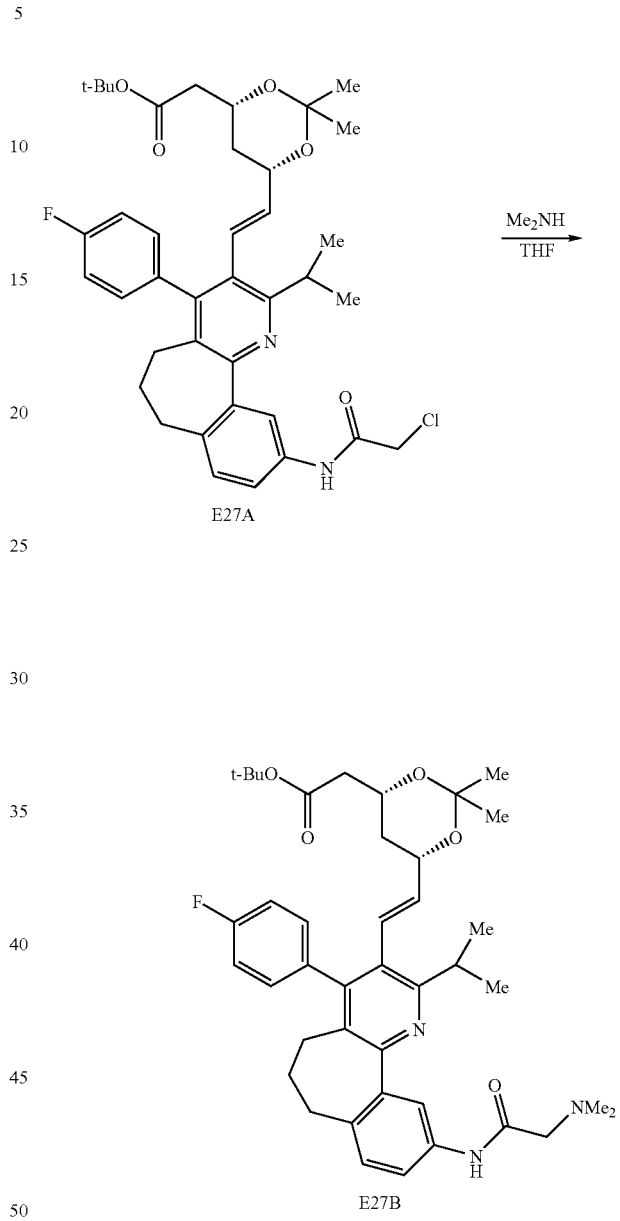

To a stirred solution of 300 mg (0.50 mmol) of aniline E21A in 5 mL of tetrahydrofuran were added sequentially 0.11 mL (0.80 mmol) of triethylamine and 0.048 mL (0.60 mmol) of chloroacetyl chloride. The solution was stirred for 10 min then poured into dilute aqueous acetic acid. This mixture was extracted with ether and the organic extract was washed with saturated aqueous sodium bicarbonate and then brine. The solution was dried (MgSO$_4$) and concentrated under reduced pressure to afford 334 mg (99%) of amide E27A as a foam: R$_f$ (50% ether-hexanes) 0.40.

To a stirred solution of 34 mg (0.05 mmol) of E27A in 2 mL of tetrahydrofuran was added 0.1 mL of 40% aqueous dimethylamine. The solution was stirred for 20 min at ambient temperature and was then warmed to reflux for 1 h. The solution was cooled, diluted with ethyl acetate, and washed with 1:1:1 water-brine-saturated aqueous sodium bicarbonate. The organic phase was dried (MgSO$_4$) and concentrated under reduced pressure to afford E27B as a foam: LRMS m/z 686 (M+H)$^+$.

Part C:

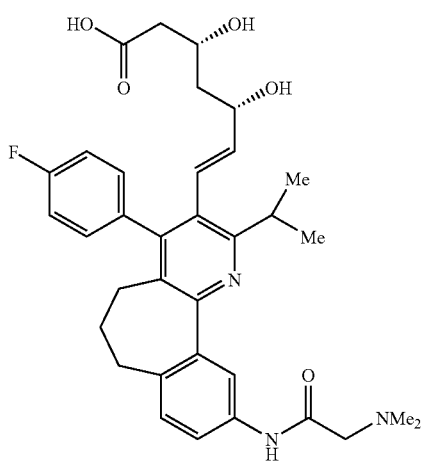

Ex. 27 title compound

The title compound was prepared in 53% yield from E27B using the procedure described in Example 22 Part C: LRMS m/z 590 (M+H)$^+$; HPLC (method 3) $t_R$=2.57 min.

Example 28

6-Heptenoic acid, 7-[4-(4-fluorophenyl)-6,7-dihydro-9-[[(methylamino)carbonyl]amino]-2-(1-methylethyl)-5H-benzo[6,7]cyclohepta[1,2-b]pyridin-3-yl]-3,5-dihydroxy-, (3R,5S,6E)-

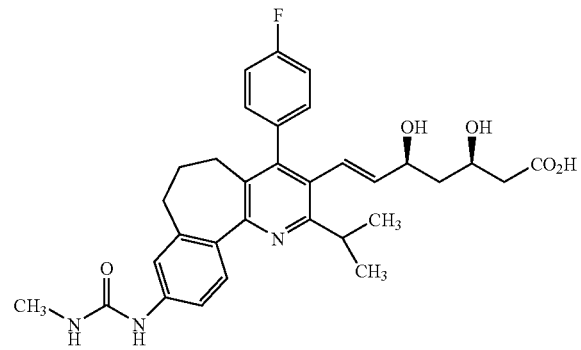

Part A:

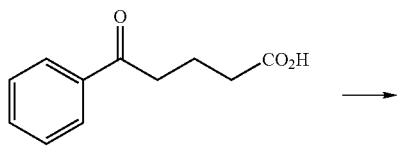

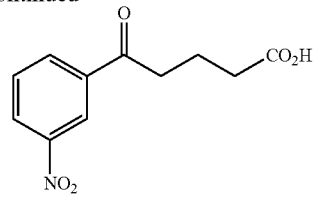

E28A

To a well-stirred mixture of fuming nitric acid (670 mL) and concentrated sulfuric acid (335 mL) at −10° C. was added 4-benzoylbutyric acid (333 g, 1730 mmol) in portions such that the reaction temperature was held at −10-0° C. [Note: temperature control is critical as the reaction is exothermic.] Total addition time was 1.0 h. Following the addition, the reaction mixture was stirred for 0.5 h at 0° C. The mixture then was poured slowly into a vigorously stirred slurry of water-ice/water. After the ice had completely melted the resulting solids were recovered by filtration, washed twice with water, and dried to afford 298 g of the crude product, which was employed in Part B without further purification or characterization.

Part B:

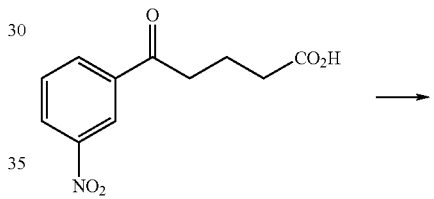

E28A

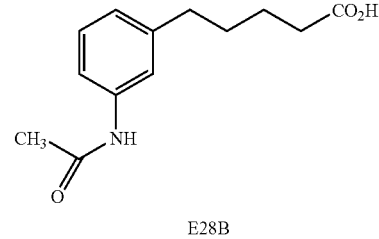

E28B

A mixture of E28A (298 g, 1250 mmol), 30 g of 10% palladium/carbon, acetic acid (2400 mL), and acetic anhydride (600 mL) under hydrogen gas (1 atm) was heated slowly to 50° C. External heating was discontinued, but the reaction temperature continued to rise to 75° C. After ~4 h the reaction temperature had returned to 65° C. Heating was resumed, and the mixture was stirred at 65° C. for 4 h. At this point an additional 30 g of 10% palladium/carbon was added to the mixture as a slurry in 150 mL of acetic acid. The resulting mixture was stirred at 65° C. for an additional 20 h. After cooling, the mixture was filtered and the filtrate was concentrated under vacuum to 300-400 mL. The resulting solution was diluted by the rapid addition of 1600 mL of water at 70-80° C., and the mixture was allowed to cool slowly. During the cooling, small portions of ethanol were added as necessary to prevent oiling out of the crude product. When the mixture had reached room temperature the resulting precipitate was recovered by filtration and washed with 500 mL of 80:20 water/ethanol and then dried to provide 101.4 g (25% overall yield for 2 steps) of E28B: NMR (300 MHz, DMSO-d$_6$) δ 11.95 (br s, 1H), 9.79 (br s, 1H), 7.34 (m, 2H), 7.12 (t, 1H, J=7.5 Hz), 6.80 (d, 1H, J=7.5 Hz), 2.47 (t, 2H, J=7.0 Hz), 2.17 (t, 2H, J=7.0 Hz), 1.96 (s, 3H), 1.47 (m, 4H).

Part C:

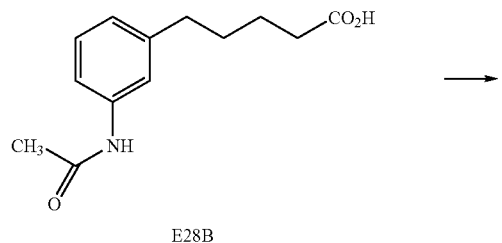

E28B

To mechanically-stirred polyphosphoric acid (2000 g) at 100° C. was added in portions over several min E28B (93.2 g, 396 mmol). The mixture then was stirred at 100° C. for 3 h. At this point external heating was discontinued. While the reaction mixture was still hot water-ice was added in small portions such that the temperature remained at 80-100° C. [Note: this addition is initially very exothermic. External cooling was employed as needed to help keep the temperature in the desired range.] The addition of water-ice was continued until the total reaction volume was ~4500 mL. By this time the mixture had cooled to 0-10° C. With external cooling, 50% aqueous sodium hydroxide solution was added at a rate such that the reaction temperature remained at <35° C. This addition was continued until the aqueous mixture reached pH 3-4. The mixture then was extracted with ethyl acetate. The combined extracts were washed with saturated aqueous sodium bicarbonate solution and brine, dried over anhydrous sodium sulfate, filtered, and concentrated under vacuum. Column chromatography of the residue on silica gel (elution: 0-5% diethyl ether/methylene chloride), followed by crystallization of the material from methylene chloride/hexane, provided 58.5 g (84%) of E28C: NMR (300 MHz, CDCl$_3$) δ 7.69 (d, 1H, J=8.5 Hz), 6.57 (d of d, 1H, J=8.5, 2.2 Hz), 6.47 (d, 1H, J=2.2 Hz), 2.84 (m, 2H), 2.69 (m, 2H), 1.81 (m, 4H).

Part D:

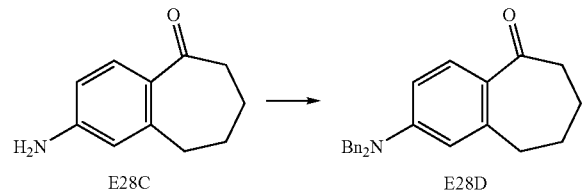

E28C                     E28D

A mixture of E28C (74.3 g, 420 mmol), benzyl bromide (151 mL, 1270 mmol), potassium carbonate (176 g, 1270 mmol), potassium iodide (7.0 g, 42 mmol), and dimethylformamide (1000 mL) was stirred at 85° C. for 168 h. After cooling, the mixture was filtered, and the filtrate was concentrated under vacuum. The residue was dissolved in ethyl acetate, and the solution was washed with water (×4) and brine, dried over anhydrous sodium sulfate, filtered, and concentrated under vacuum to ~250 mL of total volume. The resulting solution was warmed gently on a steam-bath and diluted by the slow addition of 1000 mL of hexane. The solution then was allowed to cool to room temperature, and the resulting precipitate was recovered by filtration, washed with hexane, and dried under vacuum to furnish 117 g (78%) of E28D: NMR (300 MHz, CDCl$_3$) δ 7.74 (d, 1H, J=8.5 Hz), 7.37-7.21 (m, 10H), 6.64 (d of d, 1H, J=8.5, 2.5 Hz), 6.50 (d, 1H, J=2.5 Hz), 4.69 (s, 4H), 2.81 (m, 2H), 2.68 (m, 2H), 1.81 (m, 4H).

Part E:

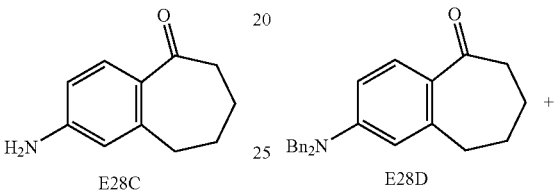

E28D

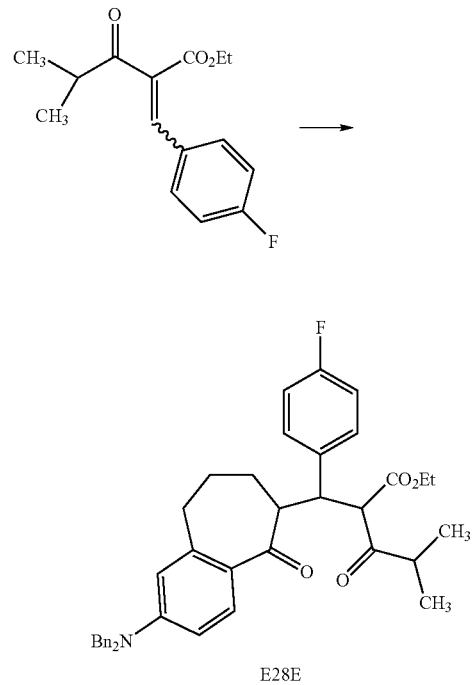

E28E

To a solution of 1.00 M sodium hexamethyldisilazide/tetrahydrofuran (366 mL, 366 mmol) in tetrahydrofuran (400 mL) at −78° C. was added dropwise a solution of E28D (130 g, 366 mmol) in tetrahydrofuran (400 mL) at such a rate that the reaction temperature did not exceed −70° C. Following the addition, the mixture was stirred at −78° C. for 0.5 h. To the reaction mixture then was added a solution of ethyl 2-[(4-fluorophenyl)methylene]-4-methyl-3-oxo-pentanoate (96.7 g, 366 mmol) in tetrahydrofuran (200 mL), and the resulting mixture was stirred at −78° C. for 3 h. The reaction was quenched by the addition of acetic acid (22.0 mL, 384 mmol).

The mixture was allowed to warm to room temperature and then was concentrated under vacuum to give crude E28E as a mixture of diastereomers, which was immediately employed in Part F without further purification or characterization.

Part F:

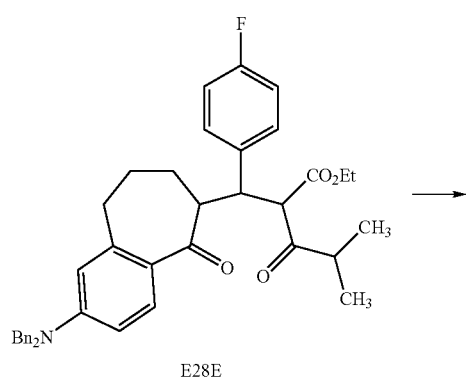

E28E

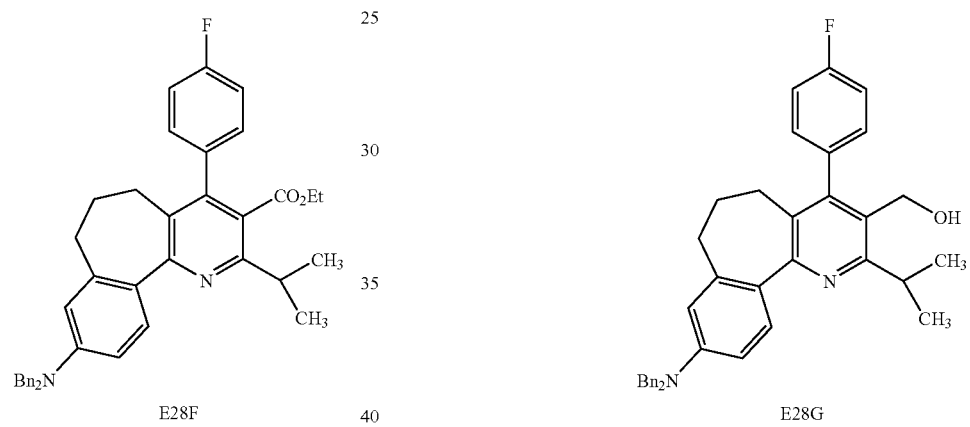

E28F

The crude product from Part E was dissolved in acetic acid (1600 mL). To this solution was added ammonium acetate (226 g, 2930 mmol) and copper(II)acetate monohydrate (292 g, 1460 mmol), and the reaction mixture was refluxed for 12 h. The mixture was allowed to cool to ~50° C. and was then filtered. The solids were slurried in warm acetic acid (40-50° C.), and the resulting mixture was filtered. This process was repeated until the desired product was not detected in the filtrate by thin-layer chromatography. The combined filtrates were allowed to cool to room temperature and then were concentrated under vacuum. The residue was dissolved in ethyl acetate, and the resulting mixture was washed with aqueous ammonia, water, and then brine, dried over anhydrous sodium sulfate, filtered, and concentrated under vacuum. Column chromatography of the residue on silica gel (elution: 2-10% ethyl acetate/hexane), followed by crystallization of the product from hexane, afforded 165 g (75% overall yield for Parts E and F) of E28F: NMR (300 MHz, CDCl$_3$) δ 7.67 (d, 1H, J=8.5 Hz), 7.37-7.29 (m, 12H), 7.09 (m, 2H), 6.78 (d of d, 1H, J=8.5, 2.5 Hz), 6.60 (d, 1H, J=2.5 Hz), 4.70 (s, 4H), 4.01 (quart., 2H, J=7.5 Hz), 3.15 (sept., 1H, J=7.0 Hz), 2.50 (m, 2H), 2.22 (m, 2H), 2.01 (m, 2H), 1.34 (d, 6H, J=7.0 Hz), 0.99 (t, 3H, J=7.5 Hz).

Part G:

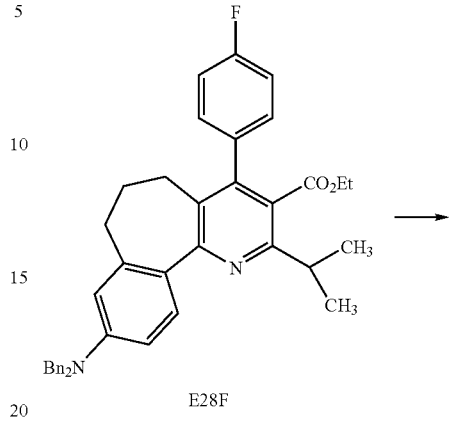

To a solution of E28F (165 g, 275 mmol) in tetrahydrofuran (1000 mL) at 0° C. was added 1.00 M lithium aluminum hydride in tetrahydrofuran (825 mL, 825 mmol) at a rate such that the temperature of the reaction mixture did not exceed 10° C. The resulting mixture was stirred at 0° C. for 1 h and then at room temperature for 20 h. To the mixture then was added dropwise 33 mL of water, followed by 33 mL of 15% aqueous sodium hydroxide solution, followed by another 99 mL of water. The resulting slurry was filtered, and the solids were washed with diethyl ether. The combined filtrates were concentrated under vacuum, and the residue was dissolved in methylene chloride. This solution was washed with brine, dried over anhydrous sodium sulfate, filtered, and concentrated under vacuum. Column chromatography of the residue on silica gel (elution: 5-20% ethyl acetate/hexane), followed by crystallization of the product from 1-chlorobutane/hexane, provided 144 g (94%) of E28G: NMR (300 MHz, CDCl$_3$) δ 7.68 (d, 1H, J=8.5 Hz), 7.37-7.22 (m, 12H), 7.14 (m, 2H), 6.78 (d of d, 1H, J=8.5, 2.5 Hz), 6.59 (d, 1H, J=2.5 Hz), 4.69 (s, 4H), 4.44 (m, 2H), 3.48 (sept., 1H, J=7.0 Hz), 2.47 (m, 2H), 2.13 (m, 2H), 1.94 (m, 2H), 1.37 (d, 6H, J=7.0 Hz).

Part H:

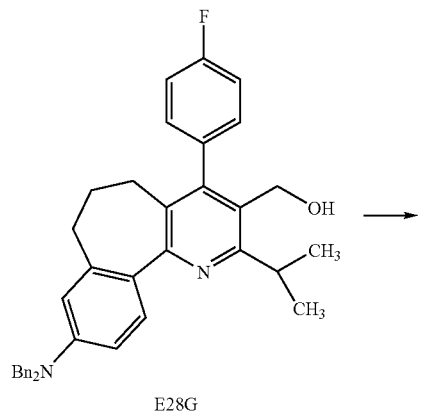

Part I:

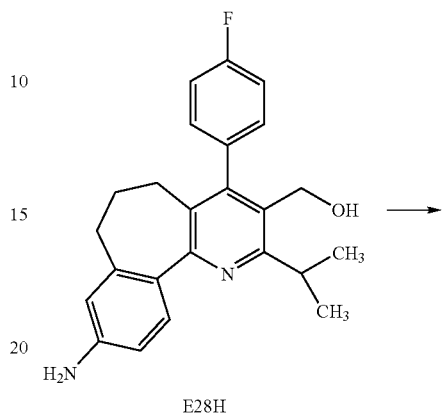

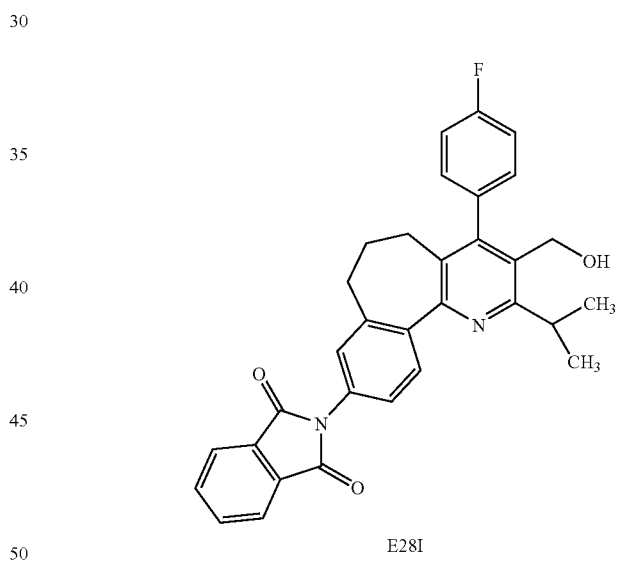

A mixture of E28G (144 g, 260 mmol), ammonium formate (165 g, 2600 mmol), and 10% palladium/carbon in ethyl acetate (600 mL) and methanol (800 mL) was heated near or at a gentle reflux for 4 h in order to maintain control of the rate of gas evolution from the reaction. After cooling to room temperature the mixture was filtered. The filtrate with diluted with 1000 mL of diethyl ether, washed with water (×2) and brine, dried over anhydrous sodium sulfate, filtered, and concentrated under vacuum. Finally, the crude product was recrystallized from t-butyl methyl ether to furnish 82 g (84%) of E28H: NMR (300 MHz, CDCl$_3$) δ 7.66 (d, 1H, J=8.5 Hz), 7.23 (m, 2H), 7.15 (m, 2H), 6.72 (d of d, 1H, J=8.5, 2.5 Hz), 6.54 (d, 1H, J=2.5 Hz), 4.45 (d, 2H, J=4.8 Hz), 3.75 (br s, 2H), 3.50 (sept., 1H, J=7.0 Hz), 2.50 (m, 2H), 2.11 (m, 2H), 1.97 (m, 2H), 1.39 (d, 6H, J=7.0 Hz).

A mixture of E28H (17.0 g, 45 mmol), N-carbethoxyphthalimide (12.0 g, 55 mmol), and chloroform (200 mL) was refluxed for 60 h. After cooling, the reaction mixture was concentrated under vacuum. Column chromatography of the residue on silica gel (elution: 0-10% ethyl acetate/methylene chloride) afforded 20.0 g (87%) of E28I: NMR (300 MHz, CDCl$_3$) δ 7.98 (m, 3H), 7.81 (m, 2H), 7.48 (d of d, 1H, J=8.5, 2.5 Hz), 7.30-7.26 (m, 3H), 7.17 (m, 2H), 4.49 (d, 2H, J=4.6 Hz), 3.54 (sept., 1H, J=7.0 Hz), 2.64 (m, 2H), 2.18 (m, 2H), 2.04 (m, 2H), 1.41 (d, 6H, J=7.0 Hz).

Part J:

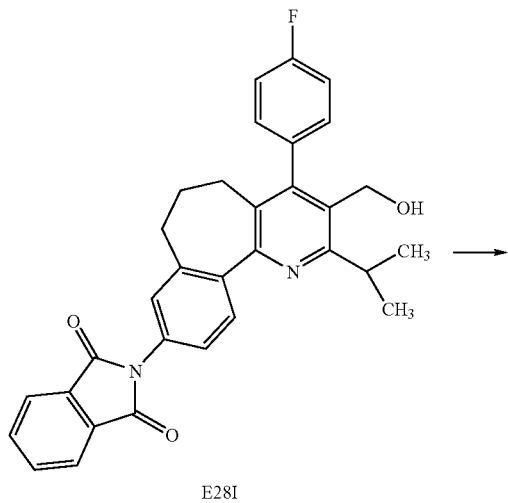
E28I

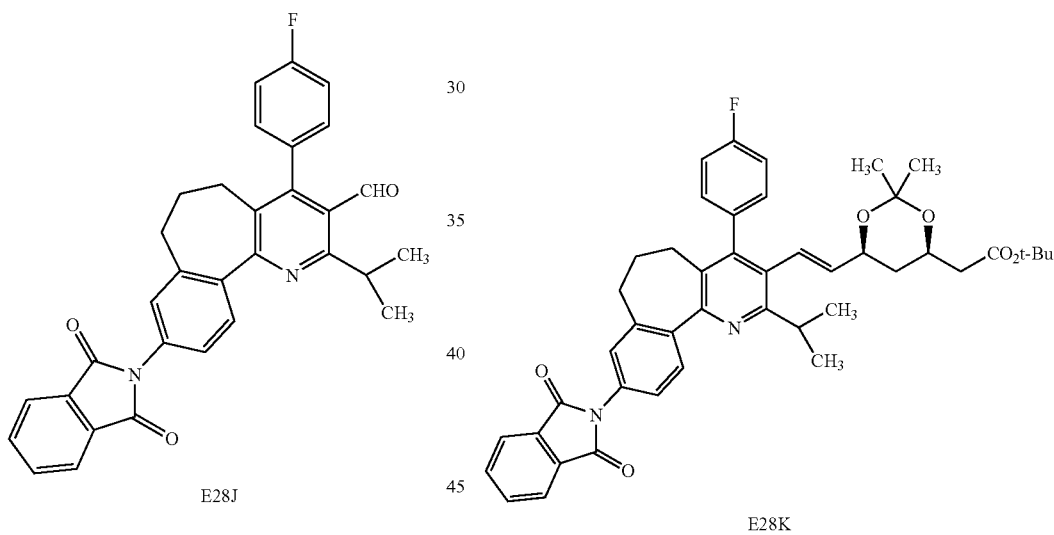
E28J

Part K:

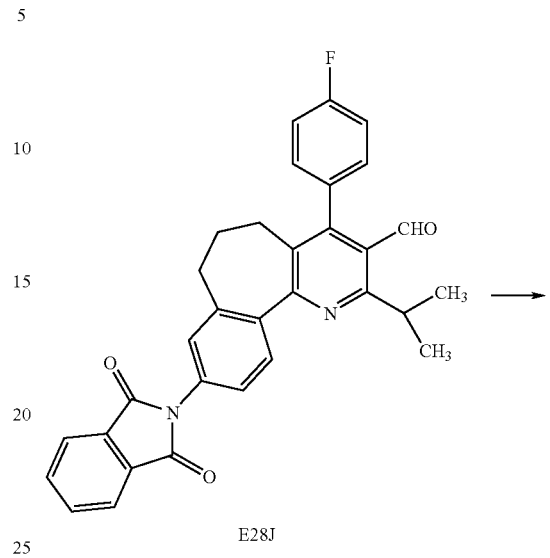
E28J

E28K

To a well-stirred mixture of E28I (20.0 g, 39.5 mmol) and activated, powdered, 4 Å molecular sieves (50 g) in methylene chloride (400 mL) at room temperature was added N-methylmorpholine-N-oxide (14.0 g, 120 mmol) and tetrapropylammonium perruthenate (1.00 g, 2.85 mmol). The resulting mixture was stirred for ~1 h while the reaction was monitored by thin-layer chromatography. When the reaction was complete, the mixture was filtered. The filtrate was washed with aqueous sodium bisulfate solution, saturated aqueous sodium bicarbonate solution, and brine, dried over anhydrous sodium sulfate, filtered, and concentrated under vacuum. Column chromatography of the residue on silica gel (elution: 5-20% ethyl acetate/hexane) furnished 18.0 g (90%) of E28J: NMR (300 MHz, CDCl$_3$) δ 9.90 (s, 1H), 8.05-7.97 (m, 3H), 7.82 (m, 2H), 7.52 (d of d, 1H, J=8.5, 2.5 Hz), 7.36 (d, 1 H, J=2.5 Hz), 7.30-7.17 (m, 4H), 3.96 (sept., 1H, J=7.0 Hz), 2.68 (m, 2H), 2.27 (m, 2H), 2.13 (m, 2H), 1.38 (d, 6H, J=7.0 Hz).

To a solution of E28J (18.0 g, 35.6 mmol) and E1D (17.6 g, 38.0 mmol) in tetrahydrofuran (300 mL) at –78° C. was added 1.00 M lithium hexamethyldisilazide in tetrahydrofuran (38.0 mL, 38.0 mmol) dropwise over ~1 h. Following the addition, the reaction mixture was allowed to warm to –50° C. over 1.5 h. It then was cooled back to –78° C. and was quenched by the addition of aqueous ammonium chloride solution. The resulting mixture was allowed to warm to room temperature, diluted with ethyl acetate, washed with saturated sodium bicarbonate solution and brine, dried over anhydrous sodium sulfate, filtered, and then concentrated under vacuum to 50-70 mL total volume. This solution was diluted by the slow addition of 300 mL of hexane, and the resulting precipitate was recovered by filtration. Finally, the crude product was recrystallized from acetonitrile/water to provide 21.5 g (82%) of E28K: LRMS (ESI, pos. ion spectrum) m/z 731 (M+H)$^+$.

Part L:

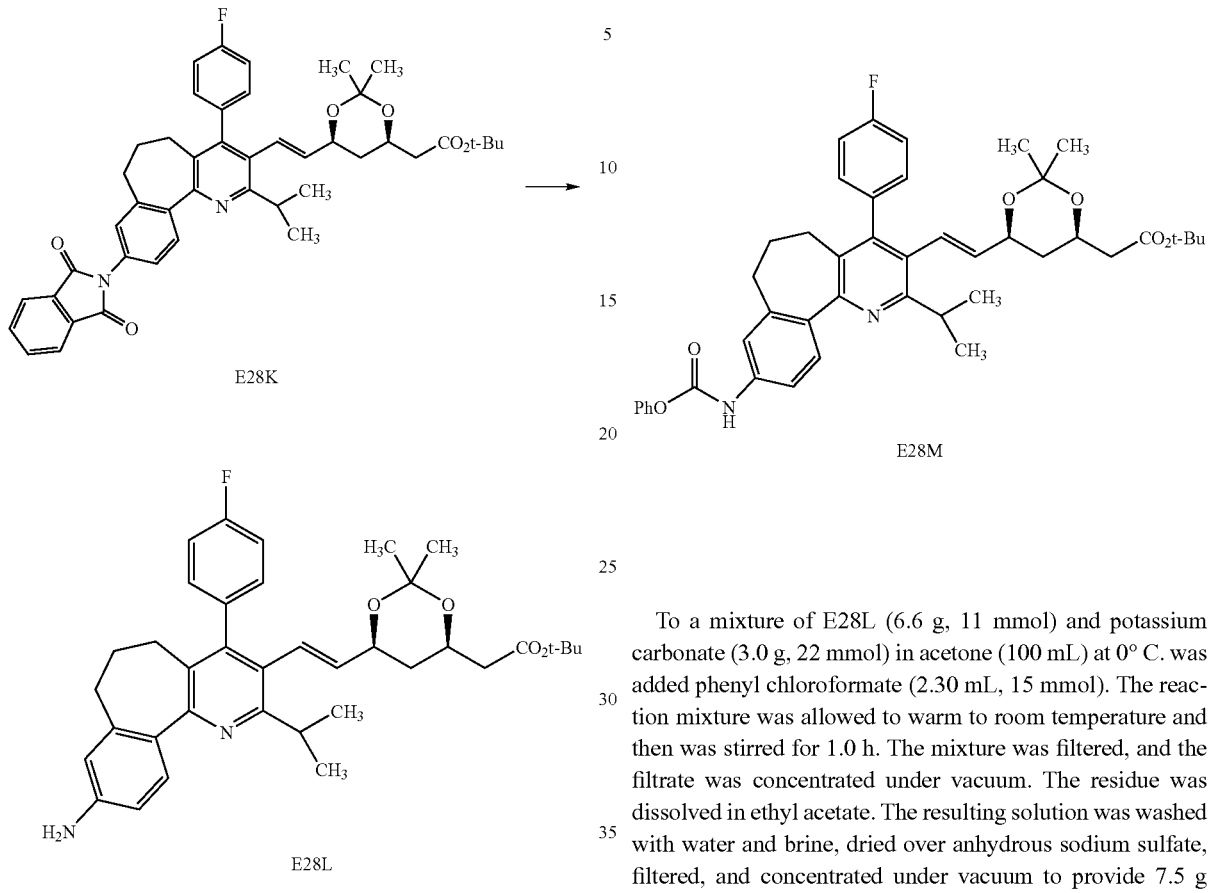

A solution of E28K (21.5 g, 29.4 mmol) and hydrazine monohydrate (20.0 mL, 410 mmol) in ethanol (500 mL) was refluxed for 1.5 h. After cooling to room temperature, the reaction mixture was filtered, and the filtrate was concentrated under vacuum. Column chromatography of the residue on silica gel (elution: 20% ethyl acetate/methylene chloride) furnished 17.5 g (99%) of E28L: LRMS (ESI, pos. ion spectrum) m/z 601 (M+H)$^+$.

Part M:

To a mixture of E28L (6.6 g, 11 mmol) and potassium carbonate (3.0 g, 22 mmol) in acetone (100 mL) at 0° C. was added phenyl chloroformate (2.30 mL, 15 mmol). The reaction mixture was allowed to warm to room temperature and then was stirred for 1.0 h. The mixture was filtered, and the filtrate was concentrated under vacuum. The residue was dissolved in ethyl acetate. The resulting solution was washed with water and brine, dried over anhydrous sodium sulfate, filtered, and concentrated under vacuum to provide 7.5 g (95%) of E28M: LRMS (ESI, pos. ion spectrum) m/z 721 (M+H)$^+$.

Part N:

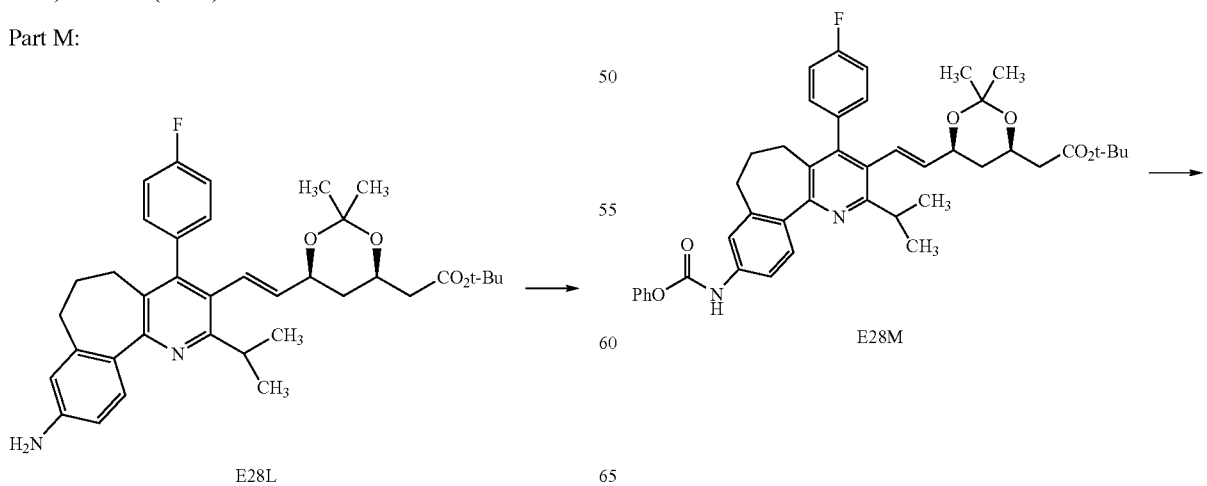

-continued

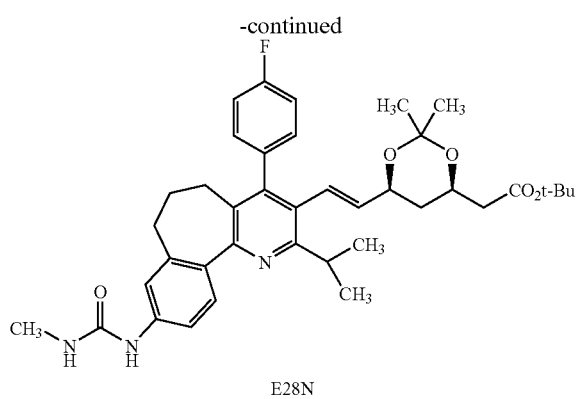

E28N

To a solution of E28M (0.080 g, 0.11 mmol) and triethylamine (0.15 mL, 1.1 mmol) in dimethyl sulfoxide (3 mL) at room temperature was added 1.0 M methylamine in tetrahydrofuran (1.0 mL, 1.0 mmol), and the resulting mixture was stirred at 60° C. for 1.0 h. After cooling to room temperature, the reaction mixture was diluted with ethyl acetate, and the solution was washed with water and brine, dried over anhydrous sodium sulfate, filtered, and concentrated under vacuum. Column chromatography of the residue (elution: 40% ethyl acetate/methylene chloride) afforded 0.060 g (82%) of E28N: LRMS (ESI, pos. ion spectrum) m/z 658 (M+H)$^+$.

Part O:

To a solution of E28N (0.060 g, 0.09 mmol) in methylene chloride (2 mL) at room temperature was added trifluoroacetic acid (2 mL). The reaction mixture was stirred for 1.0 h at room temperature and then was concentrated under vacuum. The residue was dissolved in methylene chloride. This solution then was washed with pH 7.0 phosphate buffer and brine, dried over anhydrous sodium sulfate, filtered, and concentrated under vacuum to furnish 0.052 g of crude product, which was employed in the Part P without further purification or characterization.

Part P:

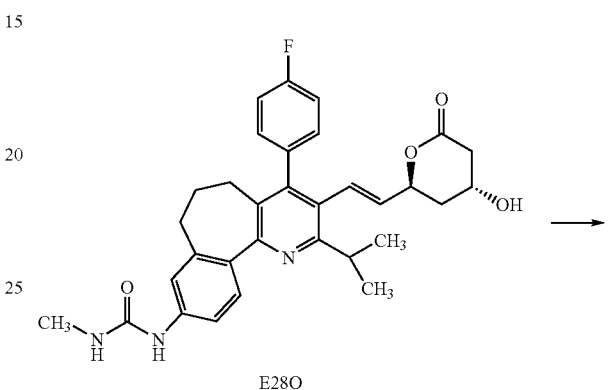

E28O

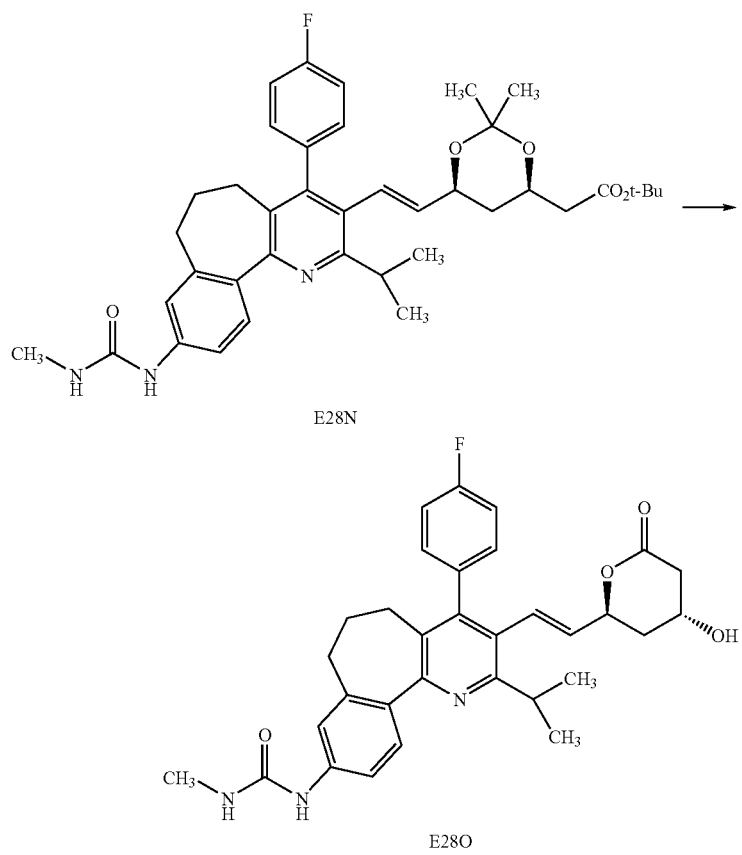

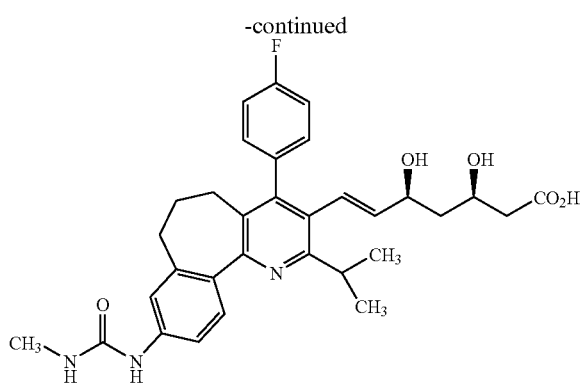

Ex. 28 title compound

To a solution of the crude product from Part O in tetrahydrofuran (5 mL) at room temperature was added dropwise an excess of 0.10 M aqueous sodium hydroxide solution. This addition was continued until the mixture reached ~pH 13. The reaction mixture was stirred at room temperature for 16 h, adjusted to pH 7-8 by the addition of 0.10 M hydrochloric acid, and then concentrated under vacuum. The crude product was purified by flash chromatography on a C-18 reverse-phase cartridge (elution: 0-50% methanol/water). The product-containing fractions were combined and then concentrated under vacuum. The residue was dissolved in ~2 mL of water, and the product was isolated by lyophilization to provide 0.040 g (75% overall yield for Parts O and P) of the title compound as its sodium salt: LRMS (ESI, pos. ion spectrum) m/z 562 (M+H)$^+$; HPLC (Method 6) $t_R$=13.8 min.

Examples 29 to 40

The following Examples were prepared employing the procedures described in Example 28:

| Ex. | Structure | Characterization |
|---|---|---|
| 29 | 6-Heptenoic acid, 7-[9-[(aminocarbonyl)amino]-4-(4-fluorophenyl)-6,7-dihydro-2-(1-methylethyl)-5H-benzo[6,7]cyclohepta[1,2-b]pyridin-3-yl]-3,5-dihydroxy-, (3R,5S,6E)- | HPLC (method 6) $t_R$ = 12.5 min<br>LRMS (ESI, pos. ion spectrum) m/z 548 (M + H)$^+$ |
| 30 | 6-Heptenoic acid, 7-[9-[[[[2-(dimethylamino)ethyl]amino]carbonyl]amino]-4-(4-fluorophenyl)-6,7-dihydro-2-(1-methylethyl)-5H-benzo[6,7]cyclohepta[1,2-b]pyridin-3-yl]-3,5-dihydroxy-, (3R,5S,6E)- | HPLC (method 6) $t_R$ = 16.4 min<br>LRMS (ESI, pos. ion spectrum) m/z 619 (M + H)$^+$ |

-continued

| Ex. | Structure | Characterization |
|---|---|---|
| 31 | 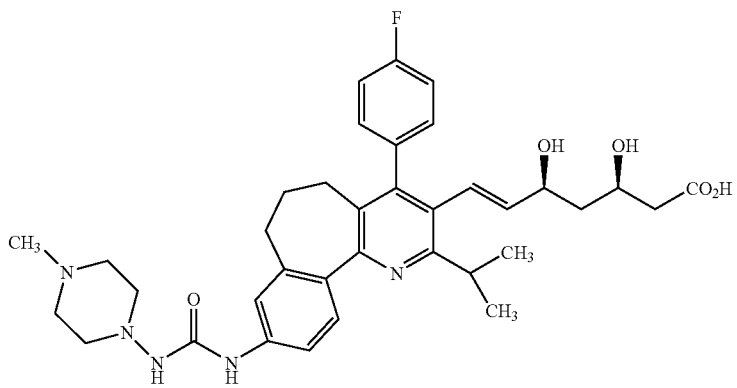 6-Heptenoic acid, 7-[4-(4-fluorophenyl)-6,7-dihydro-2-(1-methylethyl)-9-[[[(4-methyl-1-piperazinyl)amino]carbonyl]amino]-5H-benzo[6,7]cyclohepta[1,2-b]pyridin-3-yl]-3,5-dihydroxy-, (3R,5S,6E)- | HPLC (method 6) $t_R$ = 15.9 min<br>LRMS (ESI, pos. ion spectrum) m/z 646 $(M + H)^+$ |
| 32 | 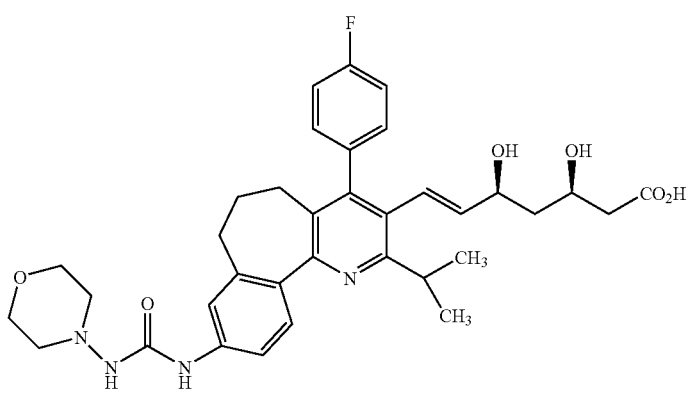 6-Heptenoic acid, 7-[4-(4-fluorophenyl)-6,7-dihydro-2-(1-methylethyl)-9-[[[(4-morpholinylamino)carbonyl]amino]-5H-benzo[6,7]cyclohepta[1,2-b]pyridin-3-yl]-3,5-dihydroxy-, (3R,5S,6E)- | HPLC (method 6) $t_R$ = 14.7 min<br>LRMS (ESI, pos. ion spectrum) m/z 633 $(M + H)^+$ |
| 33 | 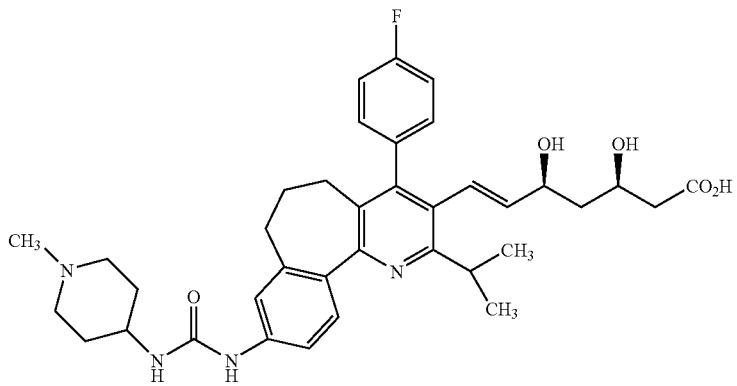 6-Heptenoic acid, 7-[4-(4-fluorophenyl)-6,7-dihydro-2-(1-methylethyl)-9-[[[(1-methyl-4-piperidinyl)amino]carbonyl]amino]-5H-benzo[6,7]cyclohepta[1,2-b]pyridin-3-yl]-3,5-dihydroxy-, (3R,5S,6E)- | HPLC (method 6) $t_R$ = 16.7 min<br>LRMS (ESI, pos. ion spectrum) m/z 645 $(M + H)^+$ |

| Ex. | Structure | Characterization |
|---|---|---|
| 34 | 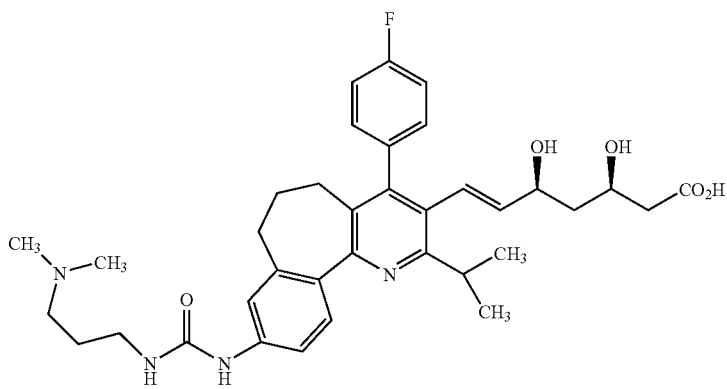

6-Heptenoic acid, 7-[9-[[[[3-(di-methylamino)propyl]amino]carbonyl]amino]-4-(4-fluoro-phenyl)-6,7-dihydro-2-(1-methylethyl)-5H-ben-zo[6,7]cyclohepta[1,2-b]pyridin-3-yl]-3,5-di-hydroxy-, (3R,5S,6E)- | HPLC (method 6) $t_R$ = 16.3 min<br>LRMS (ESI, pos. ion spectrum) m/z 633 $(M + H)^+$ |
| 35 | 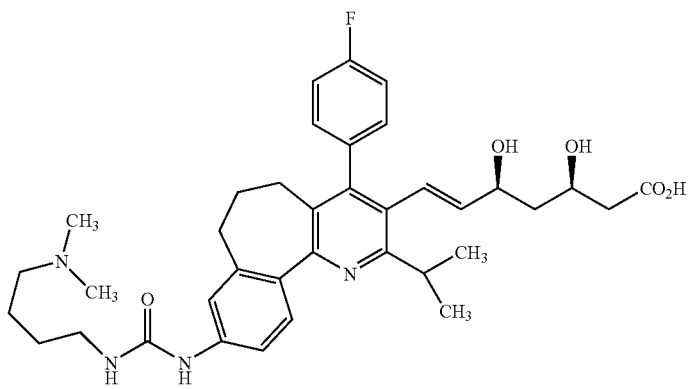

6-Heptenoic acid, 7-[9-[[[[4-(di-methylamino)butyl]amino]carbonyl]amino]-4-(4-fluoro-phenyl)-6,7-dihydro-2-(1-methylethyl)-5H-ben-zo[6,7]cyclohepta[1,2-b]pyridin-3-yl]-3,5-di-hydroxy-, (3R5S,6E)- | HPLC (method 6) $t_R$ = 15.5 min<br>LRMS (ESI, pos. ion spectrum) m/z 647 $(M + H)^+$ |
| 36 | 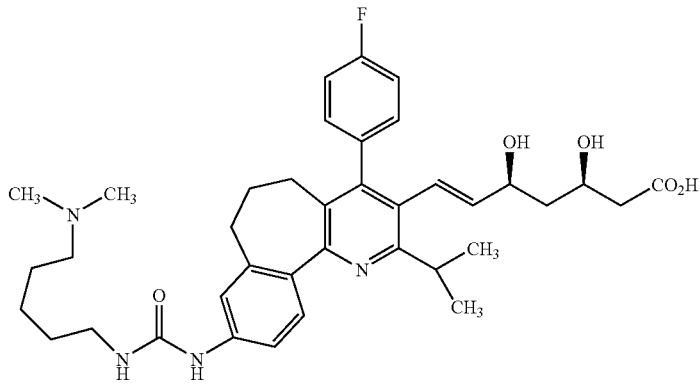

6-Heptenoic acid, 7-[9-[[[[5-(di-methylamino)pentyl]amino]carbonyl]amino]-4-(4-fluoro-phenyl)-6,7-dihydro-2-(1-methylethyl)-5H-ben-zo[6,7]cyclohepta[1,2-b]pyridin-3-yl]-3,5-di-hydroxy-, (3R,5S,6E)- | HPLC (method 6) $t_R$ = 16.5 min<br>LRMS (ESI, pos. ion spectrum) m/z 661 $(M + H)^+$ |

| Ex. | Structure | Characterization |
|---|---|---|
| 37 | 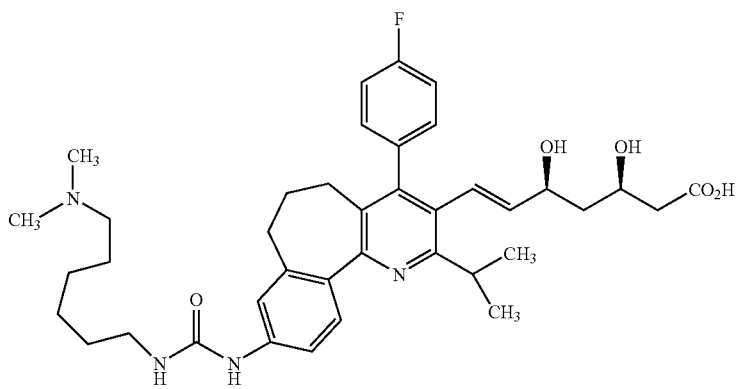<br>6-Heptenoic acid, 7-[9-[[[[6-(di-methylamino)hexyl]amino]carbonyl]amino]-4-(4-fluoro-phenyl)-6,7-dihydro-2-(1-methylethyl)-5H-ben-zo[6,7]cyclohepta[1,2-b]pyridin-3-yl]-3,5-di-hydroxy-, (3R,5S,6E)- | HPLC (method 6) $t_R$ = 17.0 min<br>LRMS (ESI, pos. ion spectrum) m/z 675 $(M + H)^+$ |
| 38 | 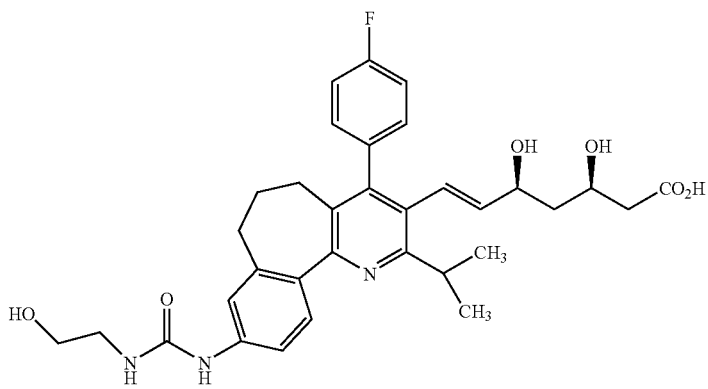<br>6-Heptenoic acid, 7-[4-(4-fluorophenyl)-6,7-di-hydro-9-[[[(2-hydroxy-ethyl)amino]carbonyl]amino]-2-(1-methyl-ethyl)-5H-benzo[6,7]cyclohepta[1,2-b]pyri-din-3-yl]-3,5-dihydroxy-, (3R,5S,6E)- | HPLC (method 6) $t_R$ = 12.6 min<br>LRMS (ESI, pos. ion spectrum) m/z 592 $(M + H)^+$ |
| 39 | 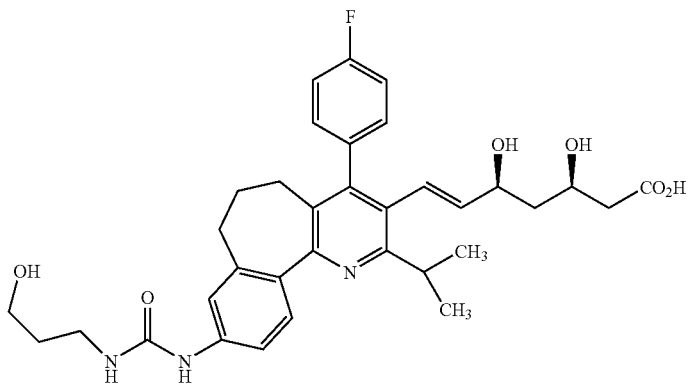<br>6-Heptenoic acid, 7-[4-(4-fluorophenyl)-6,7-di-hydro-9-[[[(3-hydroxy-propyl)amino]carbonyl]amino]-2-(1-methyl-ethyl)-5H-benzo[6,7]cyclohepta[1,2-b]pyri-din-3-yl]-3,5-dihydroxy-, (3R,5S,6E)- | HPLC (method 6) $t_R$ = 12.8 min<br>LRMS (ESI, pos. ion spectrum) m/z 606 $(M + H)^+$ |

| Ex. | Structure | Characterization |
|---|---|---|
| 40 | 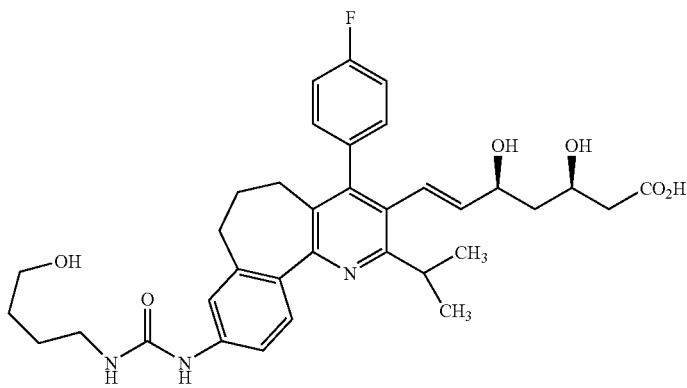

6-Heptenoic acid, 7-[4-(4-fluorophenyl)-6,7-di-hydro-9-[[[(4-hydroxy-butyl)amino]carbonyl]amino]-2-(1-methyl-ethyl)-5H-benzo[6,7]cyclohepta[1,2-b]pyridin-3-yl]-3,5-dihydroxy-, (3R,5S,6E)- | HPLC (method 6) $t_R$ = 13.2 min
LRMS (ESI, pos. ion spectrum) m/z 620 (M + H)$^+$ |

Example 41

6-Heptenoic acid, 7-[9-[[[(carboxymethyl)amino]carbonyl]amino]-4-(4-fluorophenyl)-6,7-dihydro-2-(1-methylethyl)-5H-benzo[6,7]cyclohepta[1,2-b]pyridin-3-yl]-3,5-dihydroxy-, (3R,5S,6E)-

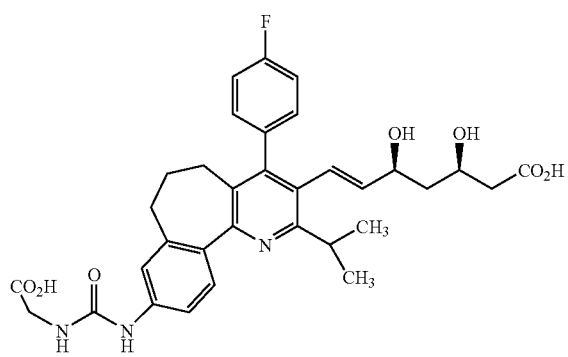

Part A:

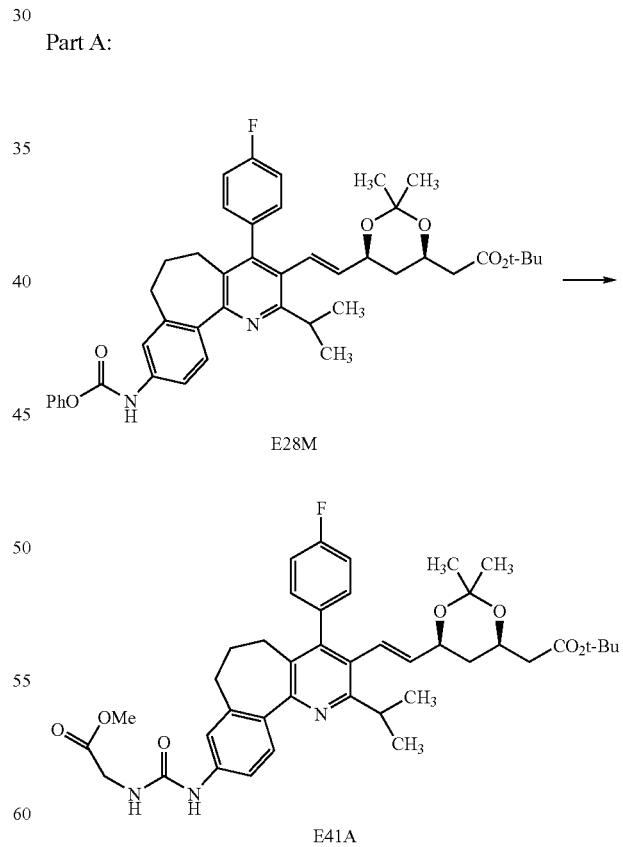

E41A was prepared from E28M and methyl glycinate hydrochloride employing the procedure described in Example 28 Part N: LRMS (ESI, pos. ion spectrum) m/z 716 (M+H)$^+$.

Part B:

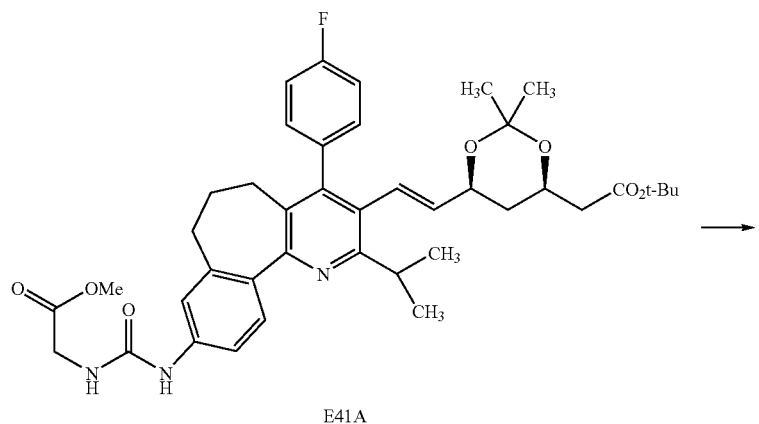

E41A

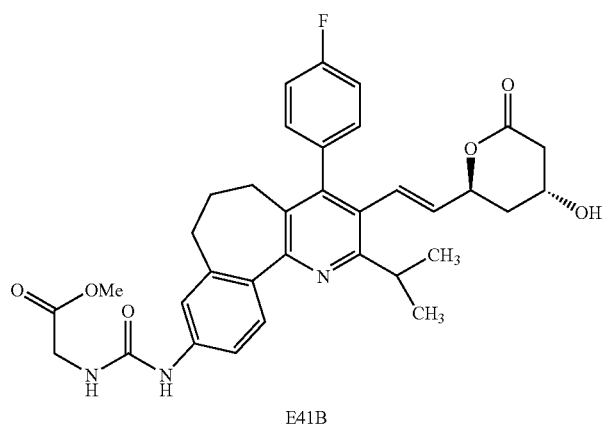

E41B

E41B was prepared from E41A employing the procedure described in Example 28 Part O. In this instance the crude product was purified by column chromatography on silica gel (with 40% ethyl acetate/methylene chloride as eluant): LRMS (ESI, pos. ion spectrum) m/z 602 (M+H)$^+$.

Part C:

-continued

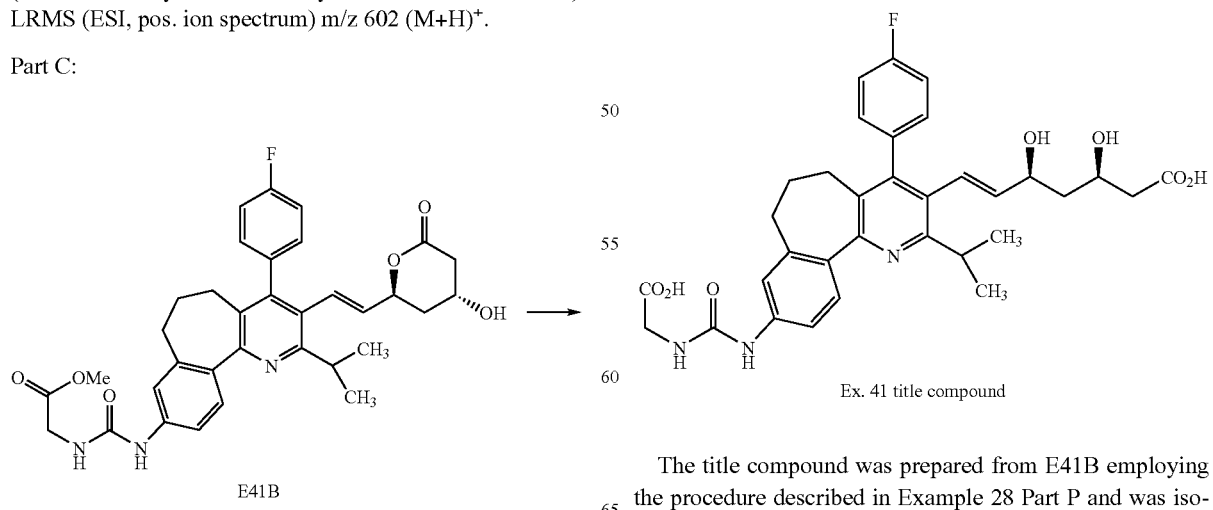

E41B

Ex. 41 title compound

The title compound was prepared from E41B employing the procedure described in Example 28 Part P and was isolated as its disodium salt: LRMS (ESI, pos. ion spectrum) m/z 606 (M+H)$^+$; HPLC (Method 6) $t_R$=12.5 min.

175
Example 42

6-Heptenoic acid, 7-[9-[[[[(1S)-5-amino-1-carboxy-pentyl]amino]carbonyl]amino]-4-(4-fluorophenyl)-6,7-dihydro-2-(1-methylethyl)-5H-benzo[6,7]cyclohepta[1,2-b]pyridin-3-yl]-3,5-dihydroxy-, (3R,5S,6E)-

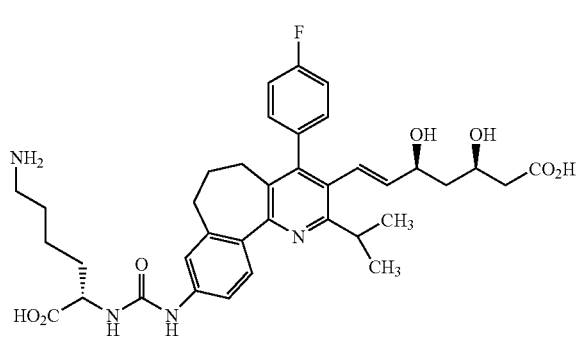

This example was prepared from E28M and N-ε-Boc-L-lysine, methyl ester hydrochloride employing the procedures described in Example 28 Parts N to P and isolated as its disodium salt: LRMS (ESI, pos. ion spectrum) m/z 677 (M+H)$^+$; HPLC (Method 6) $t_R$=12.5 min.

176
Example 43

6-Heptenoic acid, 7-[9-(2,5-dioxo-1-imidazolidinyl)-4-(4-fluorophenyl)-6,7-dihydro-2-(1-methylethyl)-5H-benzo[6,7]cyclohepta[1,2-b]pyridin-3-yl]-3,5-dihydroxy-, (3R,5S,6E)-

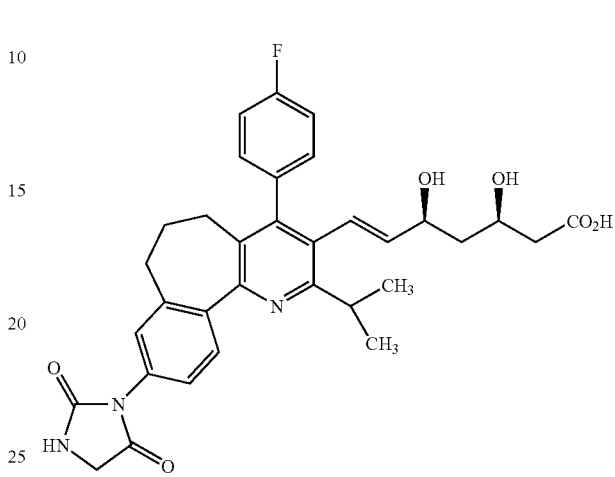

Part A:

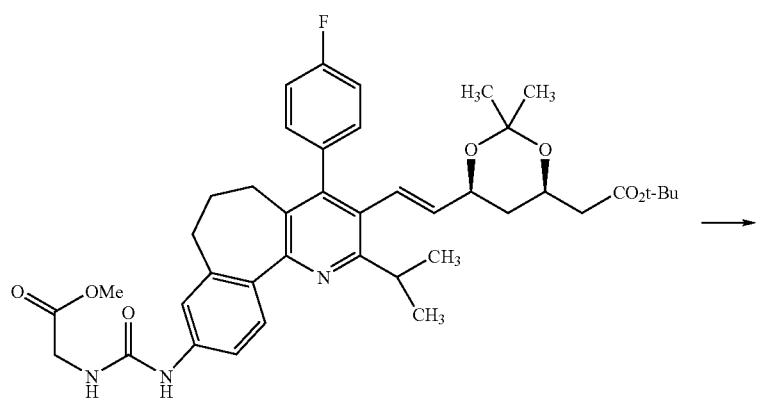

E41A

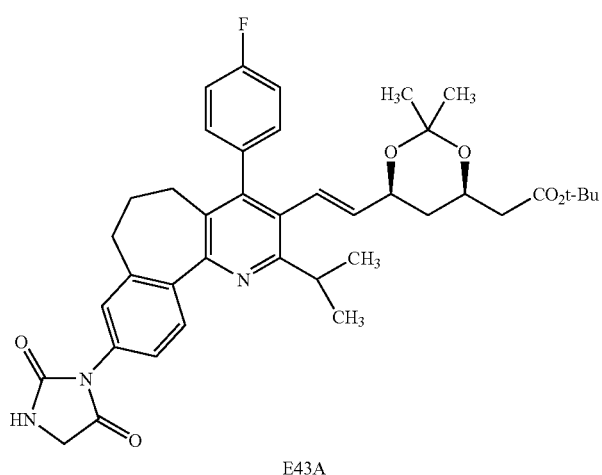

E43A

To a solution of E41A (0.15 g, 0.20 mmol) in tetrahydrofuran (2 mL) and tert-butanol (2 mL) at room temperature was added sodium tert-butoxide (0.030 g, 0.30 mmol), and the resulting mixture was stirred for 2 h. The mixture was diluted with methylene chloride, washed with water and brine, dried over anhydrous sodium sulfate, filtered, and concentrated under vacuum. Column chromatography of the residue on silica gel (elution: 20% ethyl acetate/methylene chloride) afforded 0.050 g (37%) of E43A: LRMS (ESI, pos. ion spectrum) m/z 684 (M+H)+.

Part B:

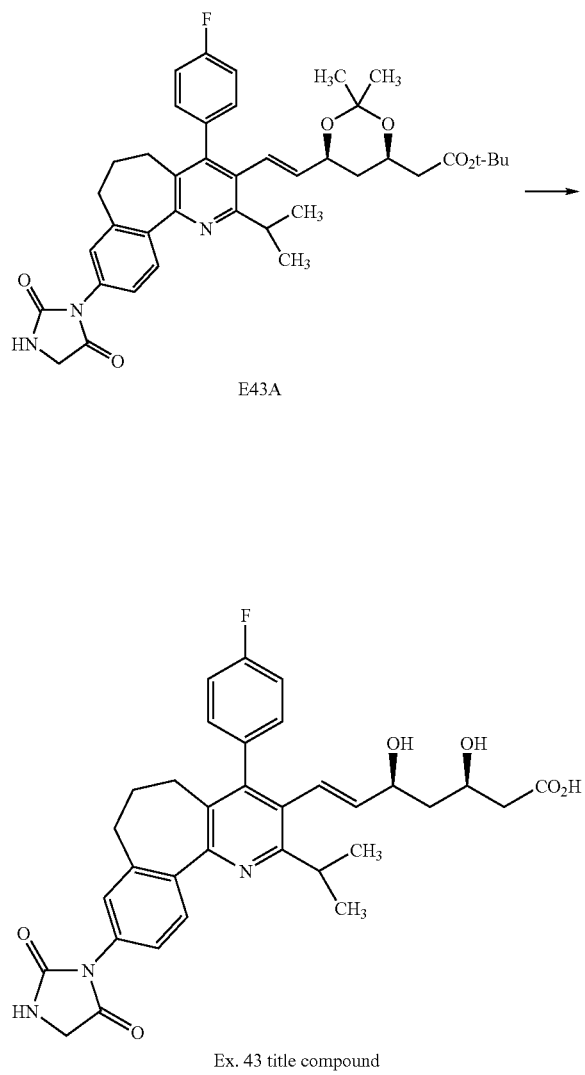

E43A

Ex. 43 title compound

The title compound was prepared from E43A employing the procedures described in Example 28 Parts O and P and isolated as its sodium salt: LRMS (ESI, pos. ion spectrum) m/z 588 (M+H)+; HPLC (Method 6) $t_R$=12.9 min.

Example 44

6-Heptenoic acid, 7-[9-[(diaminomethylene)amino]-4-(4-fluorophenyl)-6,7-dihydro-2-(1-methylethyl)-5H-benzo[6,7]cyclohepta[1,2-b]pyridin-3-yl]-3,5-dihydroxy-, (3R,5S,6E)-

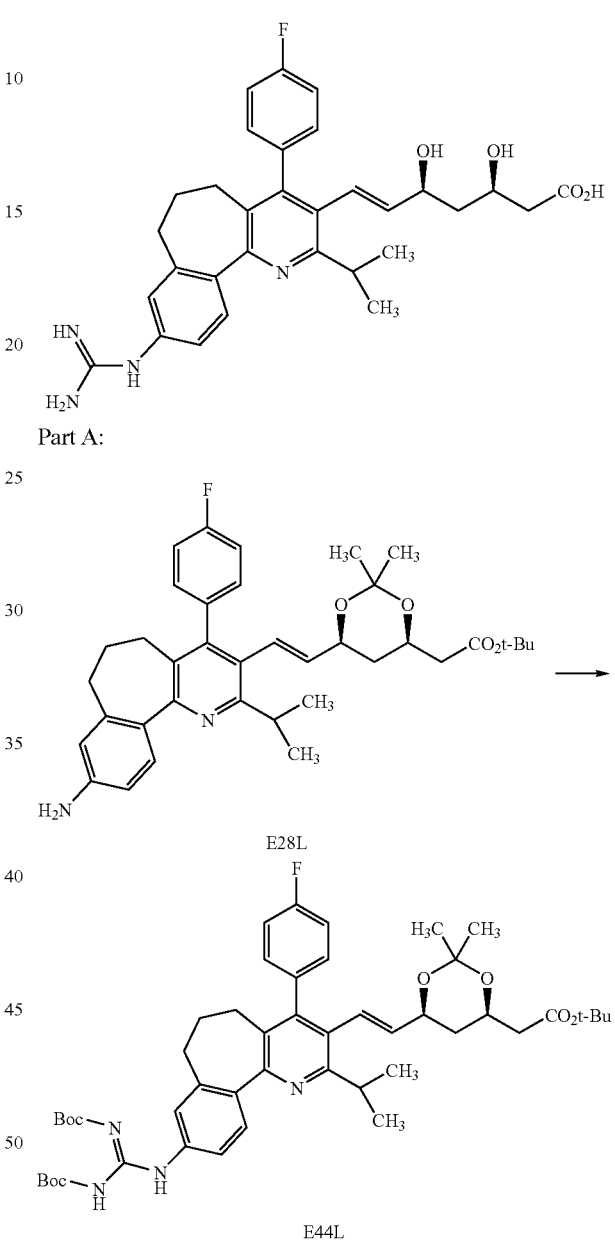

Part A:

E28L

E44L

To a mixture of E28L (0.100 g, 0.17 mmol) and N,N'-bis(tert-butoxycarbonyl)-S-methylisothiourea (0.052 g, 0.18 mmol) in dimethylformamide (2.0 mL) at 0° C. was added triethylamine (0.15 mL, 1.1 mmol) and mercury(II) chloride (0.055 g, 0.20 mmol). The resulting mixture was stirred at 0° C. for 3 h and then at room temperature for 16 h. The mixture then was diluted with ethyl acetate and filtered. The filtrate was washed with water and brine, dried over anhydrous sodium sulfate, filtered, and concentrated under vacuum. Column chromatography of the residue on silica gel (elution: 30% ethyl acetate/methylene chloride) furnished 0.12 g (86%) of E44A: LRMS (ESI, pos. ion spectrum) m/z 843 (M+H)+.

Part B:

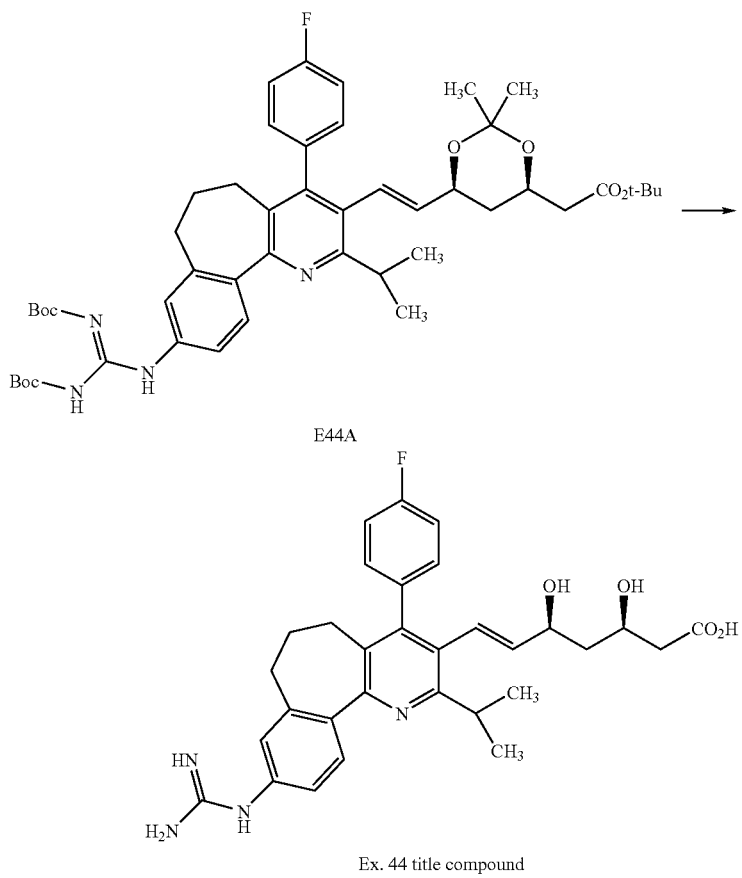

E44A

Ex. 44 title compound

The title compound was prepared from E44A employing the procedures described in Example 28 Parts O and P and isolated as its sodium salt: LRMS (ESI, pos. ion spectrum) m/z 547 (M+H)$^+$; HPLC (Method 6) $t_R$=13.7 min.

Example 45

6-Heptenoic acid, 7-[9-[[[2-(dimethylamino)ethyl]amino]carbonyl]-4-(4-fluorophenyl)-6,7-dihydro-2-(1-methylethyl)-5H-benzo[6,7]cyclohepta[1,2-b]pyridin-3-yl]-3,5-dihydroxy-, (3R,5S,6E)-

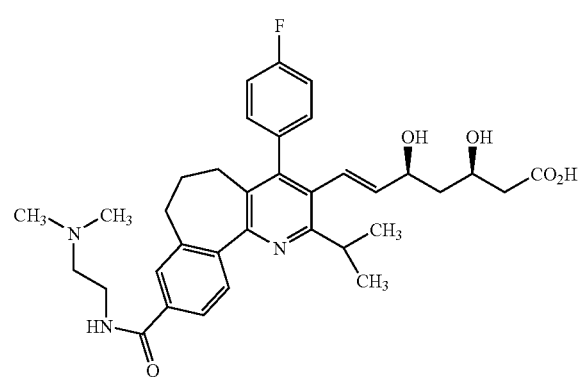

Part A:

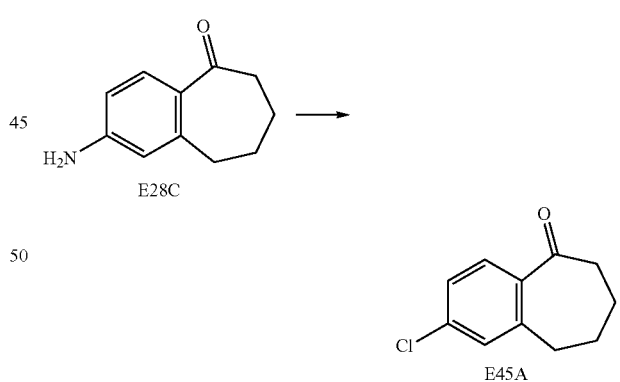

To a well-stirred mixture of anhydrous copper(II) chloride (12.4 g, 92 mmol) and isoamyl nitrite (15.5 mL, 115 mmol) in acetonitrile (300 mL) at 65° C. was added dropwise over 0.2 h a solution of E28C (13.5 g, 77 mmol) in acetonitrile (80 mL). The resulting mixture was stirred at 65° C. for 1.0 h. After cooling the reaction mixture was poured into 500 mL of 10% hydrochloric acid, and the resulting mixture was extracted with diethyl ether. The combined extracts were washed with water (×3) and brine, dried over anhydrous sodium sulfate, filtered, and concentrated under vacuum. Column chromatography on silica gel (elution: 1-10% diethyl ether/hexane) furnished 12.2 g (81%) of E45A: NMR (300 MHz, CDCl₃) δ 7.68 (d, 1H, J=8.4 Hz), 7.28 (d of d, 1H, J=1.9 Hz), 7.21 (d, 1H, J=1.9 Hz), 2.91 (m, 2H), 2.73 (m, 2H), 1.94-1.76 (m, 4H), 1.59 (s, 3H).

Part B:

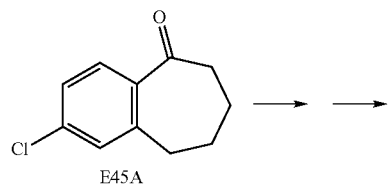

E45A

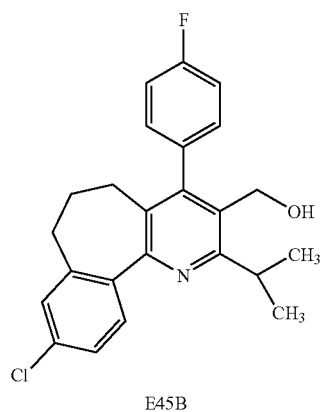

E45B

E45B was prepared from E45A employing the procedures described in Example 28 Parts E-G: NMR (300 MHz, CDCl₃) δ 7.77 (d, 1H, J=8.0 Hz), 7.37 (d of d, 1H, J=8.0, 2.2 Hz), 7.27-7.12 (m, 5H), 4.47 (s, 2H), 3.52 (sept., 1H, J=7.0 Hz), 2.56 (t, 2H, J=6.8 Hz), 2.11 (t, 2H, J=6.8 Hz), 2.00 (quint., 2H, J=6.8 Hz), 1.40 (d, 6H, J=7.0 Hz).

Part C:

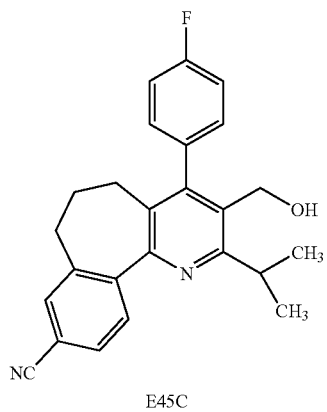

E45C

A mixture of E45B (12.1 g, 30.5 mmol), tris(dibenzylideneacetone)dipalladium(0) (2.80 g, 3.05 mmol), 1,1'-bis(diphenylphosphino)ferrocene (3.40 g, 6.10 mmol), zinc powder (0.80 g, 12.2 mmol), and zinc cyanide (4.20 g, 35.8 mmol) in N,N-dimethylacetamide (100 mL) was stirred at 150° C. for 24 h. After cooling, the reaction mixture was diluted with ethyl acetate and then filtered. The filtrate was washed with water, aqueous ammonia, water, and then brine; dried over anhydrous sodium sulfate; filtered; and concentrated under vacuum. Column chromatography of the residue on silica gel (elution: 20% ethyl acetate/hexane) afforded 10.4 g (88%) of E45C: NMR (300 MHz, CDCl₃) δ 7.93 (d, 1H, J=8.0 Hz), 7.70 (d of d, 1H, J=8.0, 2.2 Hz), 7.53 (d, 1H, J=2.2 Hz), 7.27-7.15 (m, 4H), 4.49 (d, 2H, J=5.1 Hz), 3.54 (sept., 1H, J=7.0 Hz), 2.61 (t, 2H, J=6.6 Hz), 2.15-2.02 (m, 4H), 1.39 (d, 6H, J=7.0 Hz).

Part D:

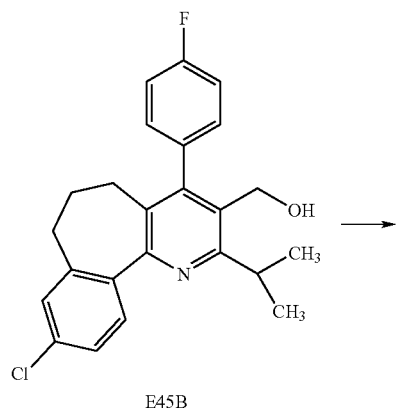

E45B

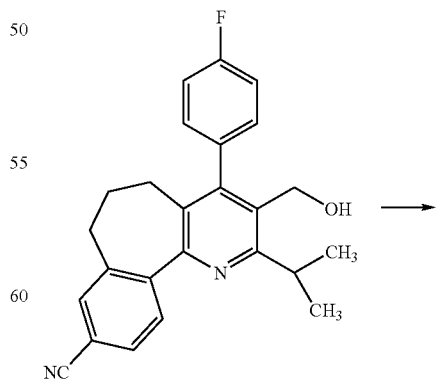

E45C

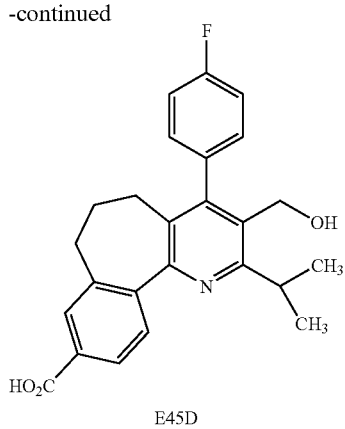

E45D

A mixture of E45C (10.4 g, 27 mmol), 25% aqueous sodium hydroxide solution (25 mL), and ethanol (250 mL) was refluxed for 18 h. After cooling, the mixture was diluted with ~200 mL of water, and the resulting solution was acidified (~pH 2) by the addition of conc. hydrochloric acid. The resulting precipitate was recovered by filtration, washed with water, and dried to furnish 10.9 g (quantitative) of E45D: NMR (300 MHz, DMSO-$d_6$) δ 7.92 (d of d, 1H, J=8.0, 1.8 Hz), 7.82 (d, 1H, J=1.8 Hz), 7.75 (d, 1H, J=8.0 Hz), 7.35-7.23 (m, 4H), 4.81 (br s, 1H), 4.18 (s, 2H), 3.53 (sept., 1H, J=7.0 Hz), 2.53 (m, 2H), 2.14 (m, 4H), 1.25 (d, 6H, J=7.0 Hz).

Part E:

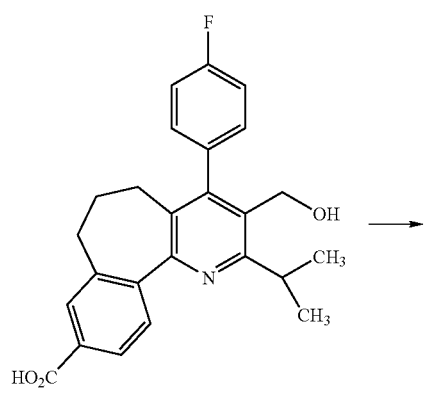

E45D

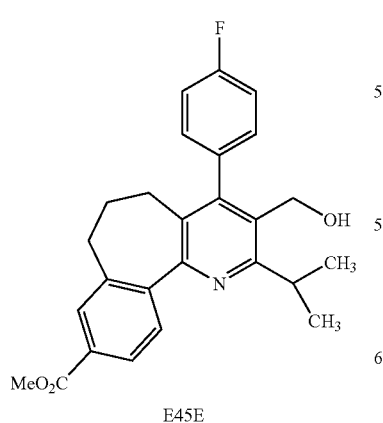

E45E

To a mixture of E45D (10.9 g, 27 mmol) and potassium carbonate (12.0 g, 87 mmol) in dimethylformamide (200 mL) at 0° C. was added iodomethane (8.00 mL, 128 mmol). The reaction mixture was stirred at room temperature for 1.0 h. The mixture then was filtered, and the filtrate was concentrated under vacuum. The residue was dissolved in ethyl acetate, and the resulting solution was washed with water and brine, dried over anhydrous sodium sulfate, filtered, and concentrated. The crude product was recrystallized from ethyl acetate/hexane to provide 11.0 g (98%) of E45E: NMR (300 MHz, DMSO-$d_6$) δ 7.94 (d of d, 1H, J=8.0, 1.8 Hz), 7.85 (d, 1H, J=1.8 Hz), 7.77 (d, 1H, J=8.0 Hz), 7.35-7.23 (m, 4H), 4.82 (t, 1H, J=4.4 Hz), 4.19 (d, 2H, J=4.4 Hz), 3.53 (sept., 1H, J=7.0 Hz), 2.54 (m, 2H), 1.93 (m, 4H), 1.25 (d, 6H, J=7.0 Hz).

Part F:

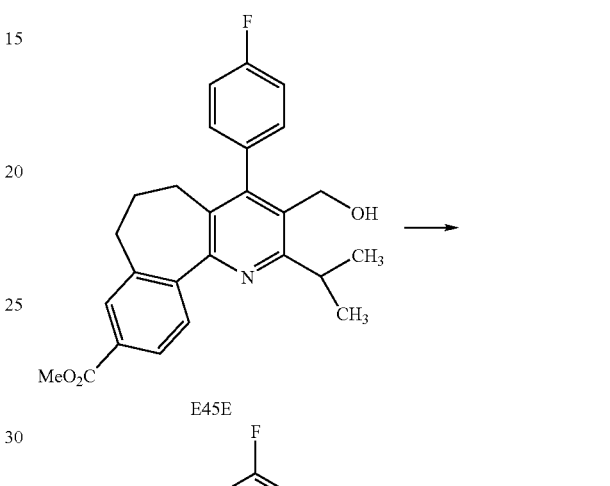

E45E

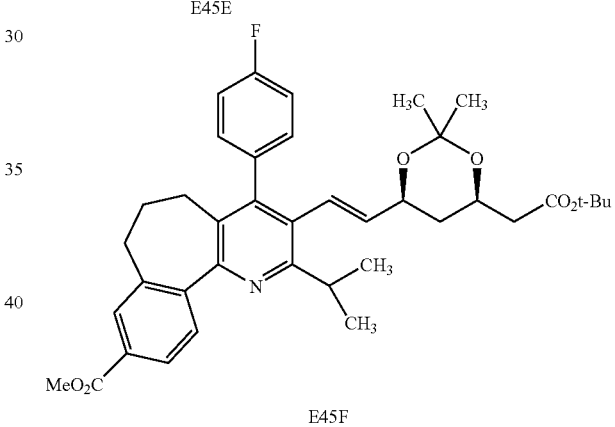

E45F

E45F was prepared from E45E employing the procedures described in Example 28 Parts J and K: LRMS (ESI, pos. ion spectrum) m/z 644 (M+H)$^+$.

Part G:

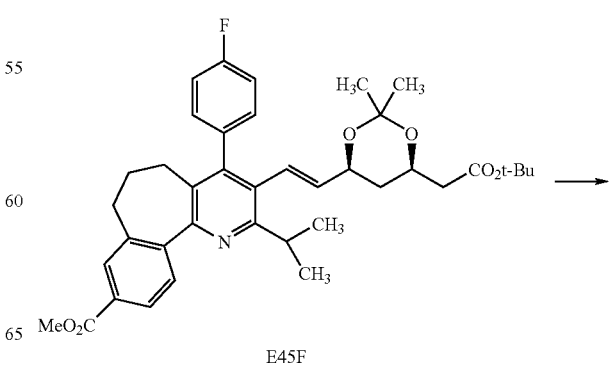

E45F

Part H:

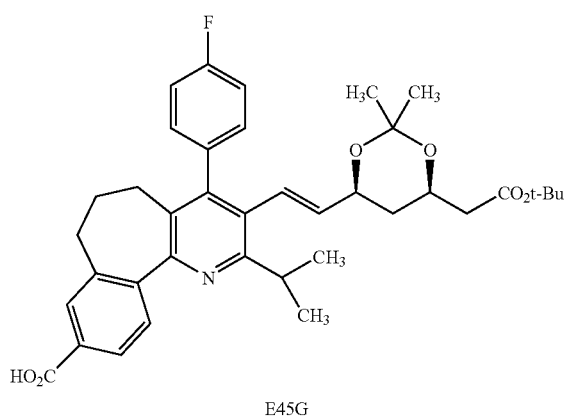

E45G

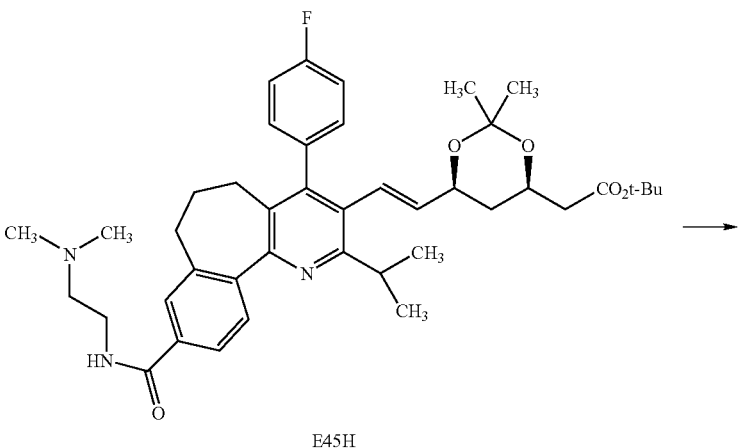

-continued

E45G

To a solution of E45F (6.40 g, 10 mmol) in tetrahydrofuran (80 mL) and methanol (4 mL) at room temperature was added a solution of lithium hydroxide monohydrate (1.26 g, 30 mmol) in water (8 mL), and the resulting mixture was stirred for 48 h. The mixture was concentrated under vacuum to ~25 mL of volume, placed in an ice-water bath, acidified by the addition of 30 mL of 1.00 N hydrochloric acid (~pH 3), and extracted with ethyl acetate. The combined extracts were washed with brine, dried over anhydrous sodium sulfate, filtered, and concentrated under vacuum. Column chromatography of the residue on silica gel (elution: 20% ethyl acetate/methylene chloride) furnished 6.0 g (96%) of E45G: LRMS (ESI, pos. ion spectrum) m/z 630 (M+H)⁺.

To a solution of E45G (0.052 g, 0.082 mmol) and O-benzotriazol-1-yl-N,N,N',N'-tetramethyluronium hexafluorophosphate (0.045 g, 0.12 mmol) in dimethylformamide (1.5 mL) at room temperature were sequentially added triethylamine (0.100 mL, 0.72 mmol) and N,N-dimethylethylenediamine (0.015 mL, 0.14 mmol). The reaction mixture was stirred for 2 h. The mixture then was diluted with ethyl acetate, washed with water (×2) and brine, dried over anhydrous sodium sulfate, filtered, and concentrated under vacuum. Column chromatography of the residue on silica gel (elution: 10% methanol/methylene chloride) afforded 0.050 g (87%) of E45H: LRMS (ESI, pos. ion spectrum) m/z 700 (M+H)⁺.

Part I:

E45H

-continued

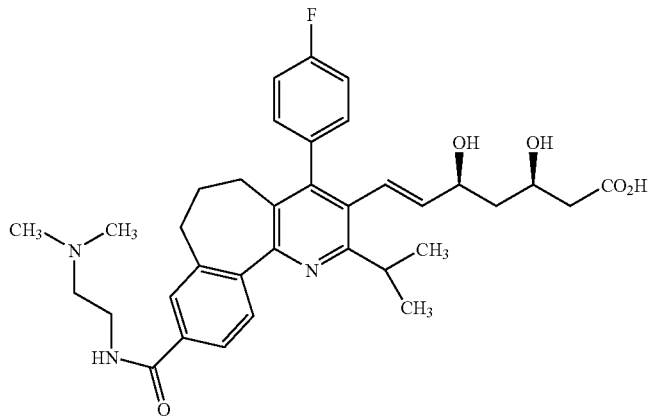

Ex. 45 title compound

The title compound was prepared from E45H employing the procedures described in Example 28, Parts O and P and isolated as its sodium salt: LRMS (ESI, pos. ion spectrum) m/z 604 (M+H)⁺; HPLC (Method 6) $t_R$=15.5 min.

Examples 46 to 49

The following Examples were prepared employing the procedures described in Example 45:

| Ex. | Structure | Characterization |
|---|---|---|
| 46 | 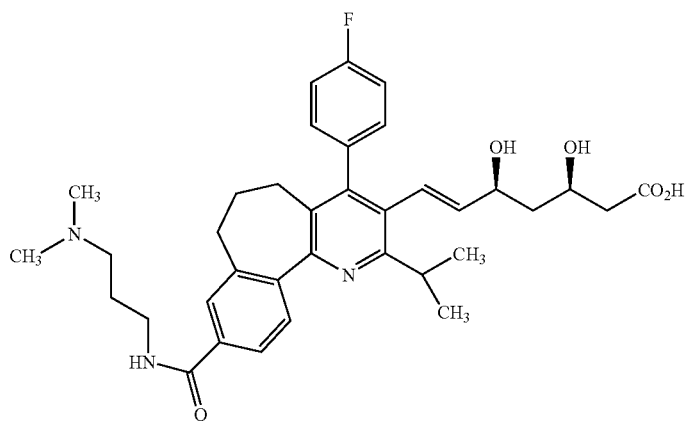<br>6-Heptenoic acid, 7-[9-[[[3-(di-methylamino)propyl]amino]carbonyl]-4-(4-fluoro-phenyl)-6,7-dihydro-2-(1-methylethyl)-5H-ben-zo[6,7]cyclohepta[1,2-b]pyridin-3-yl]-3,5-di-hydroxy-, (3R,5S,6E)- | HPLC (method 6)<br>$t_R$ = 16.2 min<br>LRMS (ESI, pos.<br>ion spectrum) m/z<br>618 (M + H)⁺ |

-continued

| Ex. | Structure | Characterization |
|---|---|---|
| 47 | 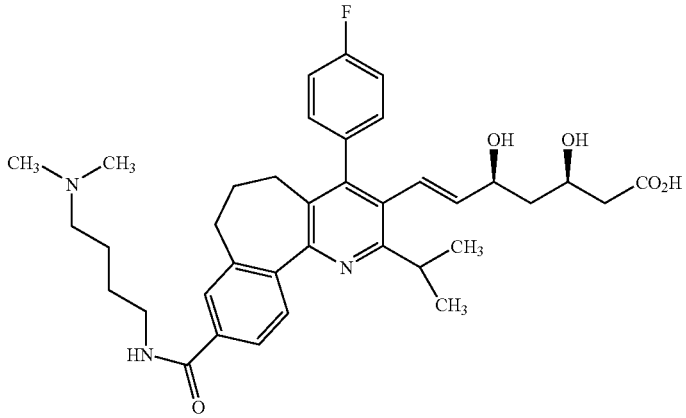<br>6-Heptenoic acid, 7-[9-[[[4-(di-methylamino)butyl]amino]carbonyl]-4-(4-fluoro-phenyl)-6,7-dihydro-2-(1-methylethyl)-5H-ben-zo[6,7]cyclohepta[1,2-b]pyridin-3-yl]-3,5-di-hydroxy-, (3R,5S,6E)- | HPLC (method 6)<br>$t_R$ = 16.2 min<br>LRMS (ESI, pos. ion spectrum) m/z 632 (M + H)$^+$ |
| 48 | 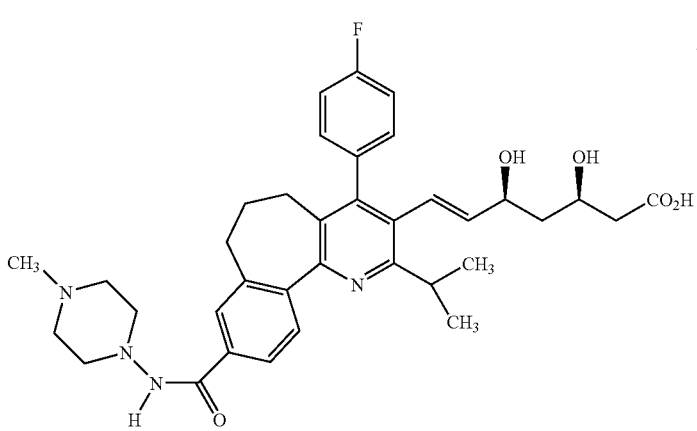<br>6-Heptenoic acid, 7-[4-(4-fluorophenyl)-6,7-dihydro-2-(1-methyl-ethyl)-9-[[(4-methyl-1-pipe-razinyl)amino]carbonyl]-5H-ben-zo[6,7]cyclohepta[1,2-b]pyridin-3-yl]-3,5-di-hydroxy-, (3R,5S,6E)- | HPLC (method 6)<br>$t_R$ = 16.5 min<br>LRMS (ESI, pos. ion spectrum) m/z 631 (M + H)$^+$ |
| 49 | 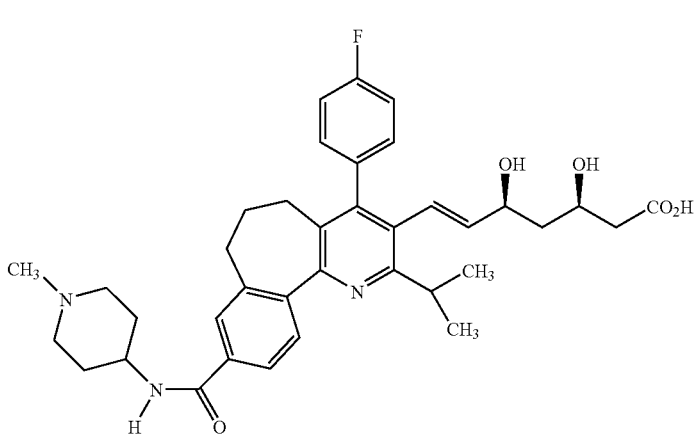<br>6-Heptenoic acid, 7-[4-(4-fluorophenyl)-6,7-dihydro-2-(1-methyl-ethyl)-9-[[(1-methyl-4-pipe-ridinyl)amino]carbonyl]-5H-ben-zo[6,7]cyclohepta[1,2-b]pyridin-3-yl]-3,5-di-hydroxy-, (3R,5S,6E)- | HPLC (method 6)<br>$t_R$ = 16.0 min<br>LRMS (ESI, pos. ion spectrum) m/z 630 (M + H)$^+$ |

Example 50

6-Heptenoic acid, 7-[4-(4-fluorophenyl)-6,7-dihydro-2-(1-methylethyl)-9-(1H-tetrazol-5-yl)-5H-benzo[6,7]cyclohepta[1,2-b]pyridin-3-yl]-3,5-dihydroxy-, (3R,5S,6E)-

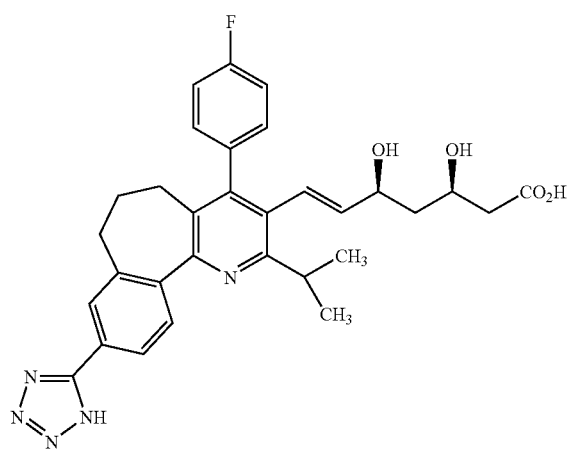

Part A:

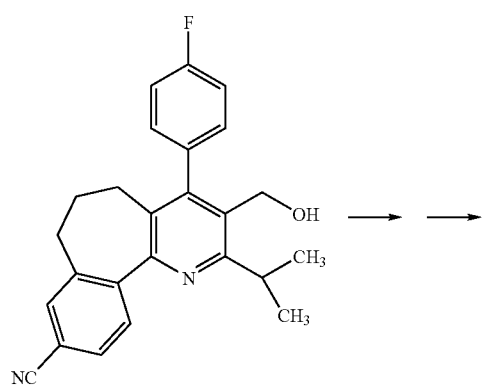
E45C

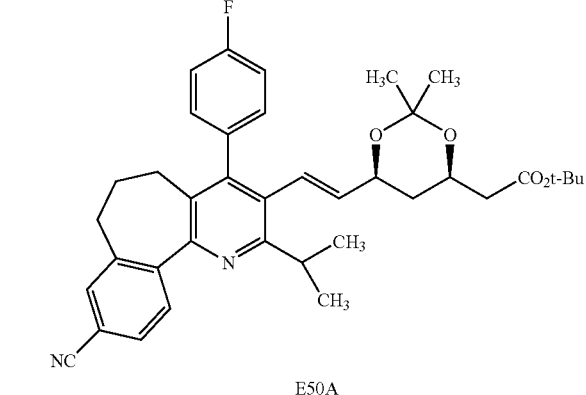
E50A

E50A was prepared from E45C employing the procedures described in Example 28 Parts J and K: LRMS (ESI, pos. ion spectrum) m/z 611 (M+H)+.

Part B:

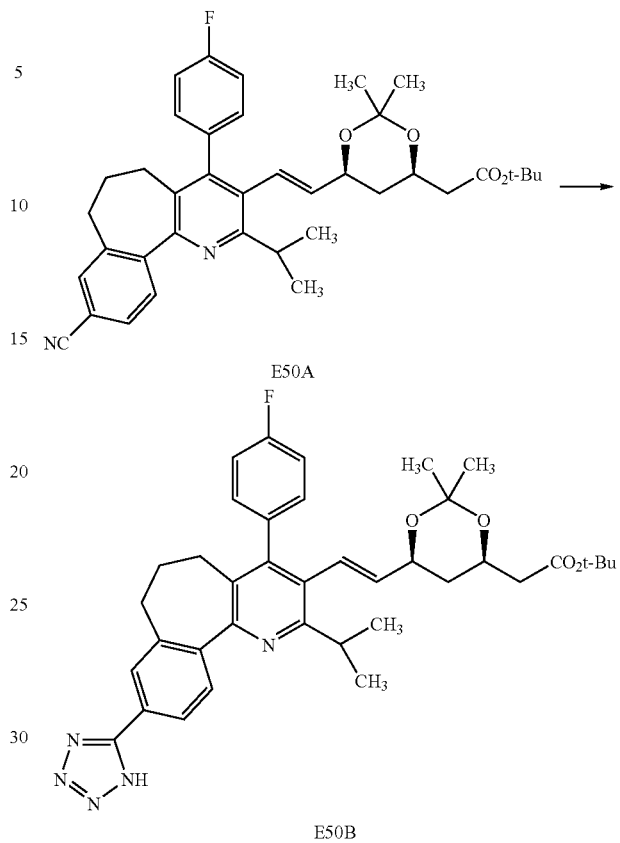
E50A

E50B

A mixture of E50A (1.16 g, 1.90 mmol) and azidotrimethyltin (1.56 g, 7.60 mmol) in toluene (20 mL) was refluxed for 20 h. After cooling, the mixture was filtered. The filtrate was diluted with 80 mL of diethyl ether. This solution was stirred vigorously for several min with an aqueous solution that contained excess potassium fluoride and had been adjusted to ~pH 5 employing 1.00 N hydrochloric acid. The stirring was stopped, and the phases were separated. The organic phase was washed with brine, dried over anhydrous sodium sulfate, filtered, and concentrated under vacuum. The crude product was crystallized from toluene, recovered by filtration, and dried to afford 1.12 g (90%) of E50B: LRMS (ESI, pos. ion spectrum) m/z 654 (M+H)+.

Part C:

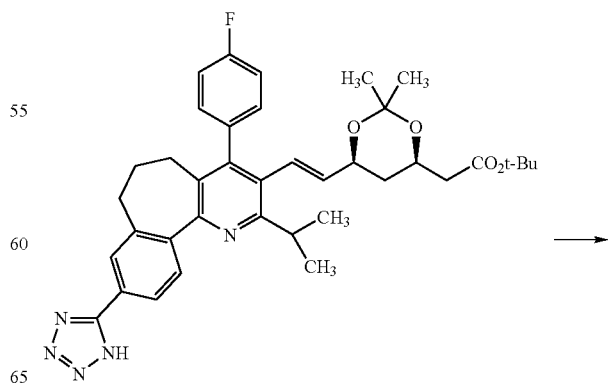
E50B

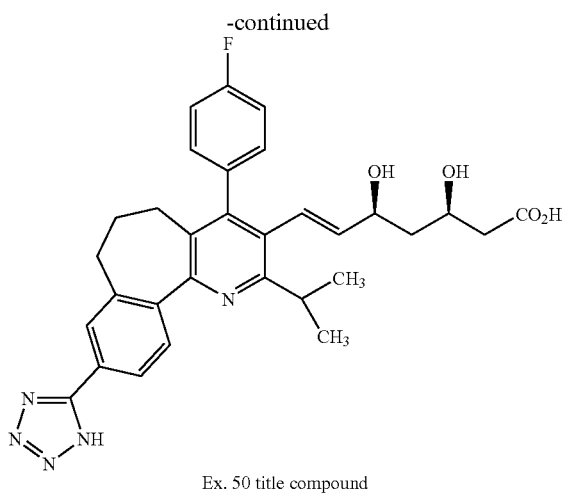

Ex. 50 title compound

The title compound was prepared from E50B employing the procedures described in Example 28 Parts O and P and isolated as its disodium salt: LRMS (ESI, pos. ion spectrum) m/z 558 (M+H)⁺; HPLC (Method 6) $t_R$=13.7 min.

Example 51

6-Heptenoic acid, 7-[4-(4-fluorophenyl)-6,7-dihydro-2-(1-methylethyl)-9-(2-methyl-2H-tetrazol-5-yl)-5H-benzo[6,7]cyclohepta[1,2-b]pyridin-3-yl]-3,5-dihydroxy-, (3R,5S,6E)-

Part A:

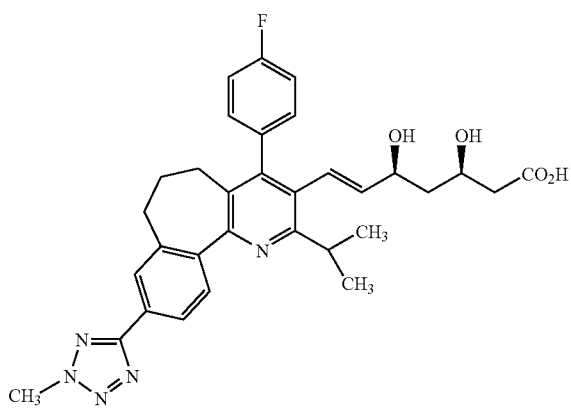

E50B

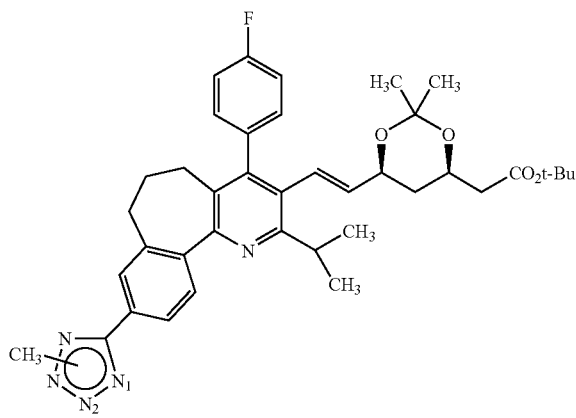

E51A (N²—CH₃)
E51B (N¹—CH₃)

A mixture of E50B (0.65 g, 1.0 mmol), sodium carbonate (0.42 g, 4.0 mmol), iodomethane (0.25 mL, 4.0 mmol), and dimethyl sulfoxide (10 mL) was stirred at room temperature for 4 h. The mixture was diluted with water and then extracted with ethyl acetate. The combined extracts were washed with water (×3) and brine, dried over anhydrous sodium sulfate, filtered, and concentrated under vacuum. Column chromatography of the residue on silica gel (elution: 10-35% ethyl acetate/hexane) furnished 0.43 g (64%) of E51A [LRMS (ESI, pos. ion spectrum) m/z 668 (M+H)⁺] and 0.14 g (21%) of E51B [LRMS (ESI, pos. ion spectrum) m/z 668 (M+H)⁺].

Part B:

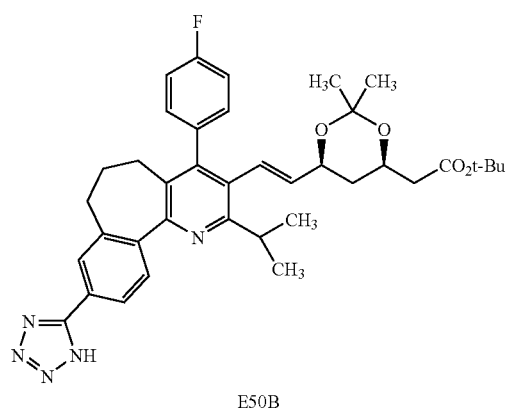

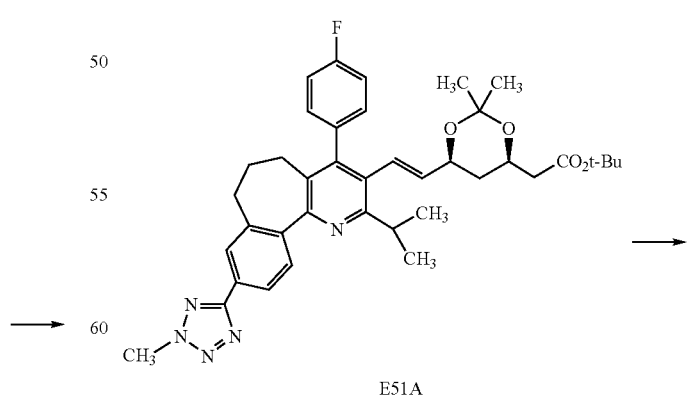

E51A

195

-continued

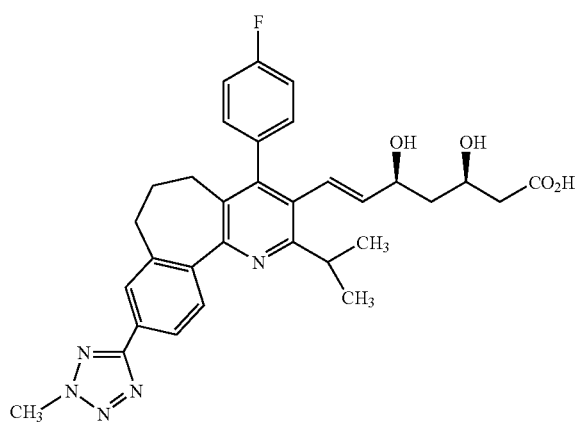

Ex. 51 title compound

The title compound was prepared from E51A employing the procedures described in Example 28 Parts O and P and isolated as its sodium salt: LRMS (ESI, pos. ion spectrum) m/z 572 (M+H)$^+$; HPLC (Method 6) $t_R$=16.7 min.

Example 52

6-Heptenoic acid, 7-[4-(4-fluorophenyl)-6,7-dihydro-2-(1-methylethyl)-9-(1-methyl-1H-tetrazol-5-yl)-5H-benzo[6,7]cyclohepta[1,2-b]pyridin-3-yl]-3,5-dihydroxy-, (3R,5S,6E)-

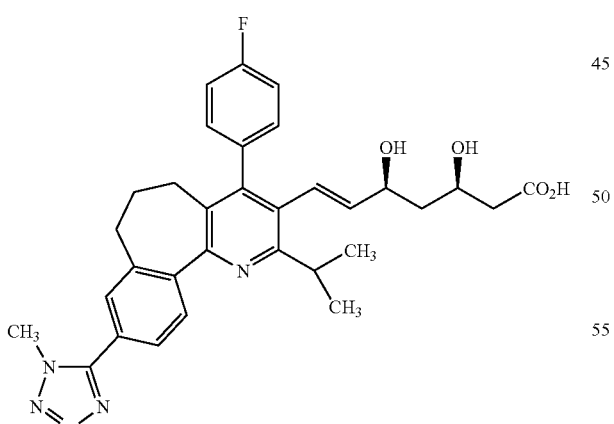

The title compound was prepared from E51B employing the procedures described in Example 28 Parts O and P and isolated as its sodium salt: LRMS (ESI, pos. ion spectrum) m/z 572 (M+H)$^+$; HPLC (Method 6) $t_R$=14.7 min.

196

Example 53

6-Heptenoic acid, 7-[4-(4-fluorophenyl)-6,7-dihydro-2-(1-methylethyl)-10-(2H-tetrazol-5-yl)-5H-benzo[6,7]cyclohepta[1,2-b]pyridin-3-yl]-3,5-dihydroxy-, (3R,5S,6E)-

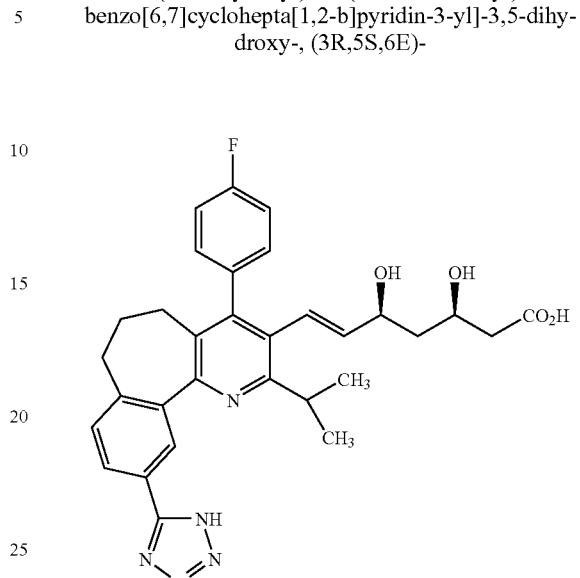

Part A:

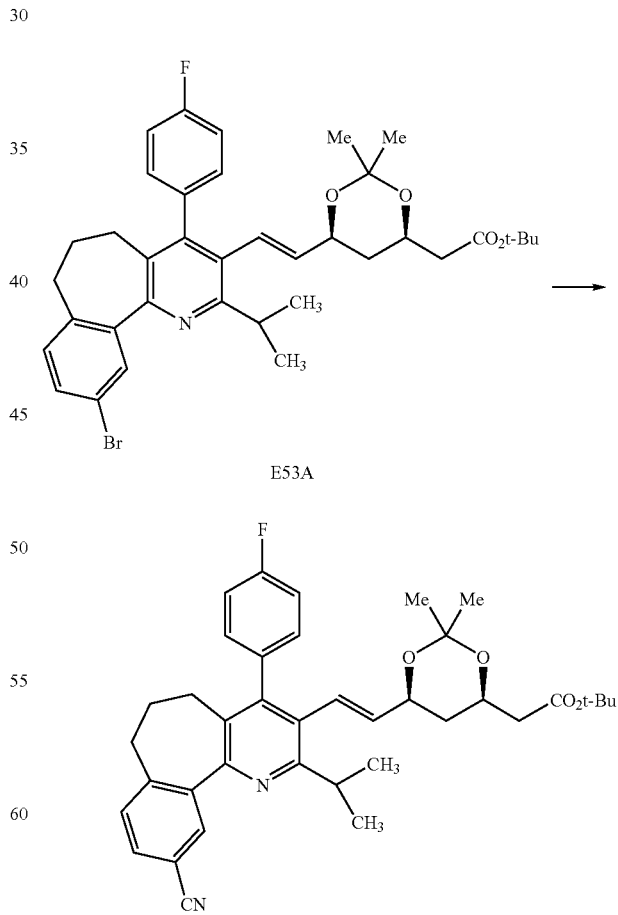

E53A

E53B

A mixture of E53A (0.54 g, 0.80 mmol, prepared from E16B using the steps described in Example 1 Part C and Example 2 Part C), tris(dibenzylideneacetone)dipalladium (0) (0.075 g, 0.08 mmol), 1,1'-bis(diphenylphosphino)ferrocene (0.090 g, 0.16 mmol), and zinc cyanide (0.12 g, 1.00 mmol) in dimethylformamide (8 mL) was stirred at 90° C. for 2 h. After cooling, the reaction mixture was diluted with ethyl acetate and then filtered. The filtrate was washed with water, aqueous ammonia, water, and brine; dried over anhydrous sodium sulfate; filtered; and concentrated under vacuum. Column chromatography of the residue on silica gel (elution: 3-20% ethyl acetate/hexane) afforded 0.32 g (64%) of E53B: LRMS (ESI, pos. ion spectrum) m/z 611 (M+H)$^+$.

Part B:

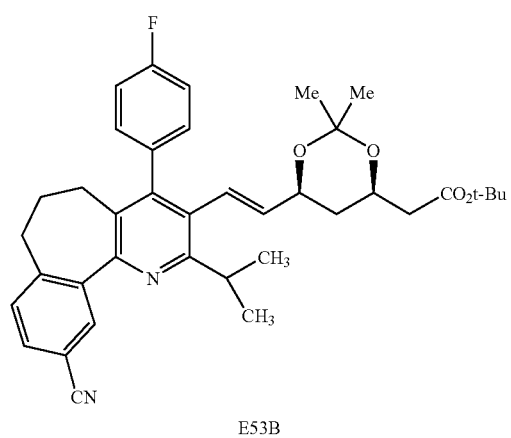

E53B

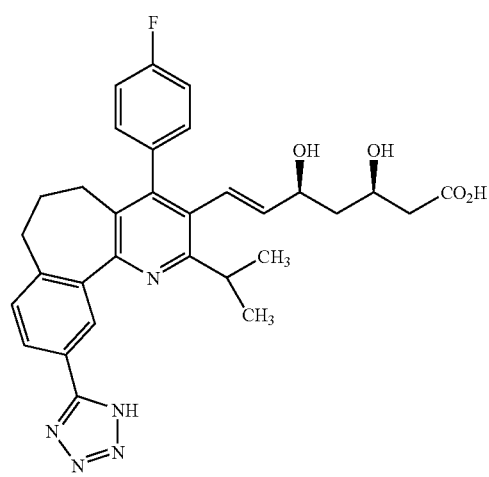

Ex. 53 title compound

The title compound was prepared from E53B employing the procedures described in example 50 Parts B and C and isolated as its disodium salt: LRMS (ESI, pos. ion spectrum) m/z 558 (M+H)$^+$; HPLC (Method 6) $t_R$=14.3 min.

Example 54

6-Heptenoic acid, 7-[4-(4-fluorophenyl)-10,11-dihydro-7-[[(methylamino)carbonyl]amino]-2-(1-methylethyl)-5H-benzo[4,5]cyclohepta[1,2-b]pyridin-3-yl]-3,5-dihydroxy-, (3R,5S,6E)-

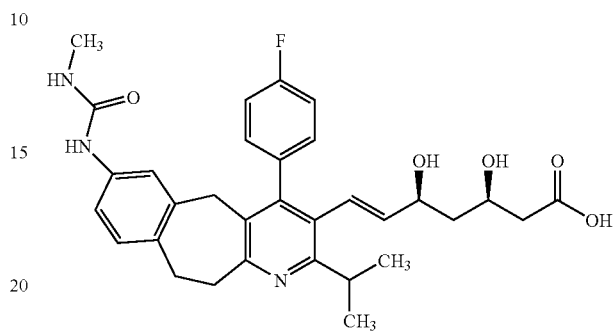

Part A:

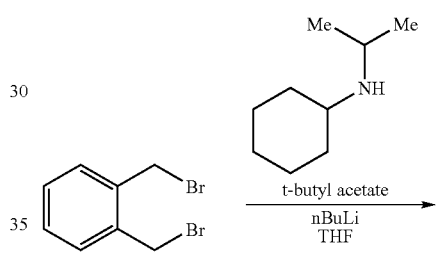

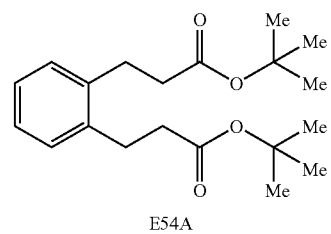

E54A

To a cold solution of isopropylcyclohexylamine (36.7 g, 260 mmol) in tetrahydrofuran (160 mL) at –78° C., was added a 2.5 M solution of n-butyllithium in hexanes (94.2 mL, 236 mmol). The solution was stirred for 20 min at –78° C. then treated dropwise with tert-butyl acetate (30.2 g, 260 mmol) at such a rate that the temperature did not exceed –68° C. After 20 min, a solution of 1,2-bis(bromomethyl)benzene (34 g, 160 mmol) in tetrahydrofuran (70 mL) was introduced. The solution was warmed to –23° C. and stirred at this temperature for 2.5 h. The cooling bath was removed and the solution warmed to room temperature. The reaction was treated with 10% hydrochloric acid (100 mL) and the mixture was poured into brine. The organic layer was separated, dried over sodium sulfate, and concentrated. Flash chromatography of the residue on silica gel eluting with hexanes afforded 38 g (49%) of E54A: $^1$H-NMR (CDCl$_3$, 300 MHz) δ 1.45 (s, 18H), 2.53 (dd, J=6.59, 8.42, 4H), 2.95 (dd, J=7.69, 9.52, 4H), 7.16 (s, 4H).

Part B:

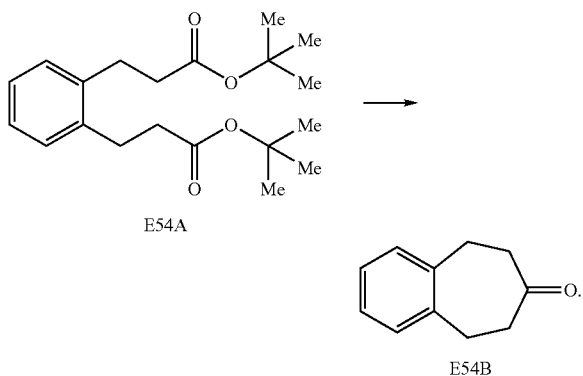

Sodium hydride (60% in mineral oil, 1.2 g, 29.9 mmol) and a catalytic amount of tert-butanol were combined in toluene (100 mL). The solution was brought to reflux and a solution of E54A (10 g, 29.9 mmol) in toluene (30 mL) was added dropwise overnight while maintaining the solution at reflux. After cooling the reaction to room temperature, glacial acetic acid (4 mL) was added dropwise followed by rapid addition of ice water. The layers were separated. The organic layer washed with brine (2×) and water (2×); dried over sodium sulfate; filtered; and concentrated. The crude residue was added to a mixture of methanol (70 mL) and 6 N hydrochloric acid (30 mL) and heated at reflux for 3 h. After cooling to room temperature, the solution was diluted with ethyl acetate and washed with saturated sodium bicarbonate (2×) and brine (2×); dried over sodium sulfate; and concentrated. Column chromatography of the residue on silica gel (10% ethyl acetate/hexanes) afforded 2.5 g (52%) of E54B. $^1$H-NMR (CDCl$_3$, 300 MHz) δ 2.8 (m, 4H), 2.94 (m, 4H), 7.36 (s, 4H).

Part C:

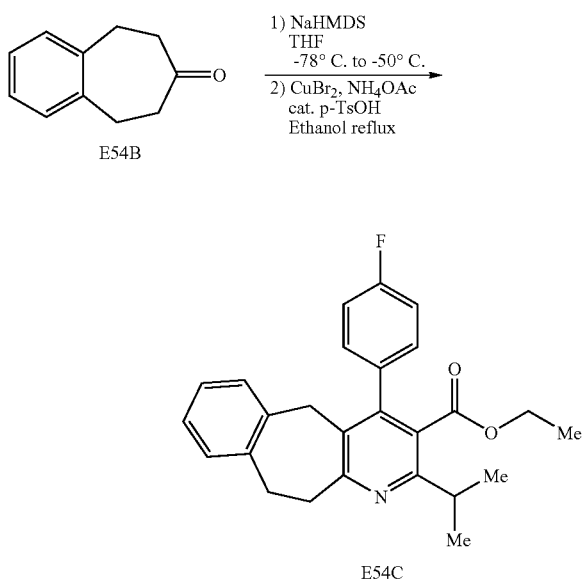

An oven-dried 3-necked flask at −78° C., was purged with nitrogen and charged with anhydrous tetrahydrofuran (20 mL) and sodium bis(trimethylsilyl)amide (1 M in tetrahydrofuran, 19.0 mL, 19.0 mmol). A solution of E54B (3.0 g, 18.9 mmol) in tetrahydrofuran (5 mL) was introduced via cannula and the resultant solution was stirred at −78° C. for 1 h. Ethyl 2-[(4-fluorophenyl)methylene]-4-methyl-3-oxo-pentanoic acid (4.71 g, 17.9 mmol) in tetrahydrofuran (10 mL) was then introduced via cannula and the resultant solution stirred at −78° C. for 30 min and then 0° C. for 30 min. The reaction was quenched with glacial acetic acid (6 mL) and poured into saturated aqueous ammonium chloride. The mixture was extracted with diethyl ether (2×). The combined organic layers were washed with brine (2×), dried over sodium sulfate, filtered, and concentrated. The residue, ammonium acetate (11.3 g, 146.8 mmol), copper(II)bromide (8.36 g, 37.5 mmol) and p-toluenesulfonic acid monohydrate (0.18 g) were combined in ethanol (80 ml) and heated at refluxed for 15 h. After cooling to room temperature, the reaction was concentrated. The crude product was diluted with ethyl acetate. The resultant mixture was poured into a concentrated ammonium hydroxide/ice water solution. The layers were separated, and the organic layer washed with brine (2×), dried over sodium sulfate, filtered, and concentrated. Column chromatography of the residue on silica gel (10% ethyl acetate/hexanes) afforded 4.8 g (64%, 2 steps) of E54C: LRMS (ESI, pos. ion spectrum) m/z 404.4 (M+H)$^+$.

Part D:

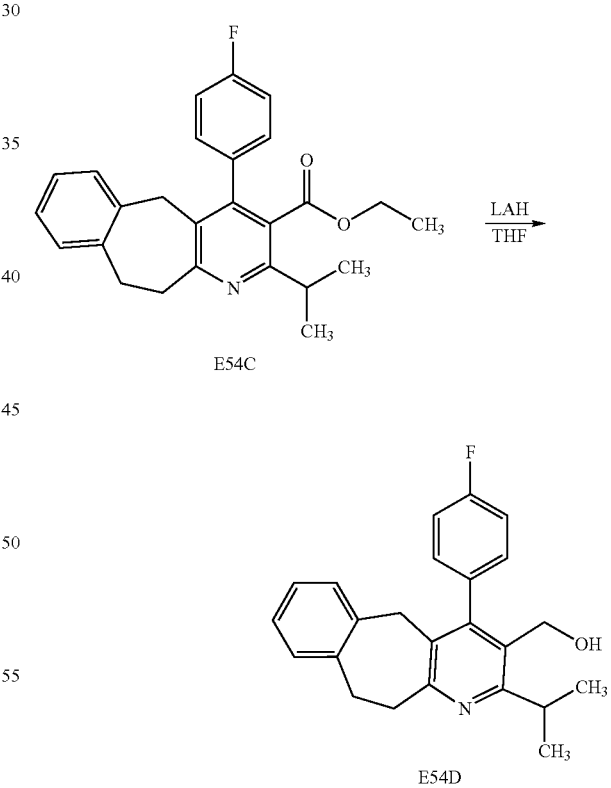

To a solution of E54C (2.2 g, 5.44 mmol) in anhydrous tetrahydrofuran (35 mL) at 0° C. was added 1.0 M lithium aluminum hydride in tetrahydrofuran (11.0 mL, 11.0 mmol). The reaction mixture was stirred at 0° C. for 1 h, warmed to room temperature and stirred for 2 h, and heated at reflux for 25 min. The reaction was then cooled to 0° C. and sequentially, slowly quenched with water (1.0 mL), sodium hydroxide (10% NaOH, 1.0 mL), and water (2.0 mL). The mixture was extracted with diethyl ether (50 mL×2) and filtered. The filter cake was washed with ethyl ether (10 mL) and ethyl acetate (10 mL). The combined organic layers were washed with water (2×) and brine (2×), dried over sodium sulfate, filtered, and concentrated. Flash chromatography of the residue (20% ethyl acetate in hexanes) afforded 1.9 g (87% yield) of E54D: LRMS (ESI, pos. ion spectrum) m/z 362.3 (M+H)⁺.

Part E:

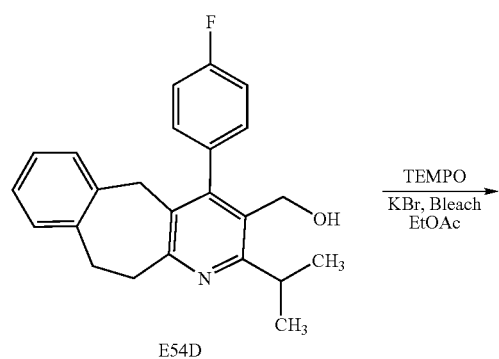

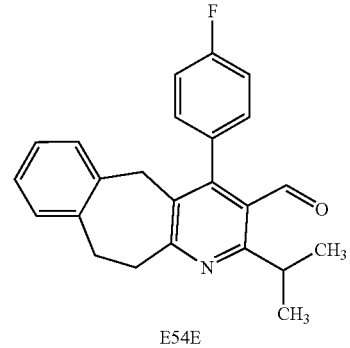

E54D (3.97 g, 11.0 mmol), potassium bromide (0.13 g, 1.1 mmol) in water (2 mL) and TEMPO (17 mg, 0.11 mmol) were combined in ethyl acetate (75 mL). To this solution was slowly added a freshly-prepared pH 9.5 bleach solution (25 mL) while maintaining the temperature between 0° C. and 5° C. After complete addition, the solution was stirred at 0° C. for 20 min and was then diluted with ethyl acetate. The layers were separated and the aqueous layer washed with ethyl acetate (2×). The organic layers were pooled and washed with water (2×) and brine (2×), dried over sodium sulfate, and concentrated. Column chromatography of the residue on silica gel (5% ethyl acetate/hexanes) afforded 2.5 g (65%) of E54E: LRMS (ESI, pos. ion spectrum) m/z 360.3 (M+H)⁺.

Part F:

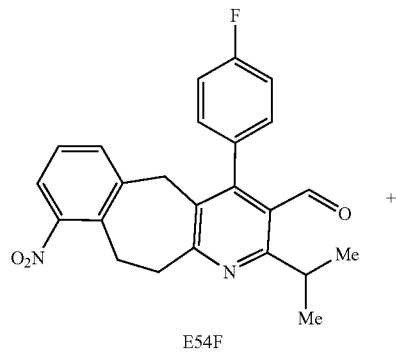

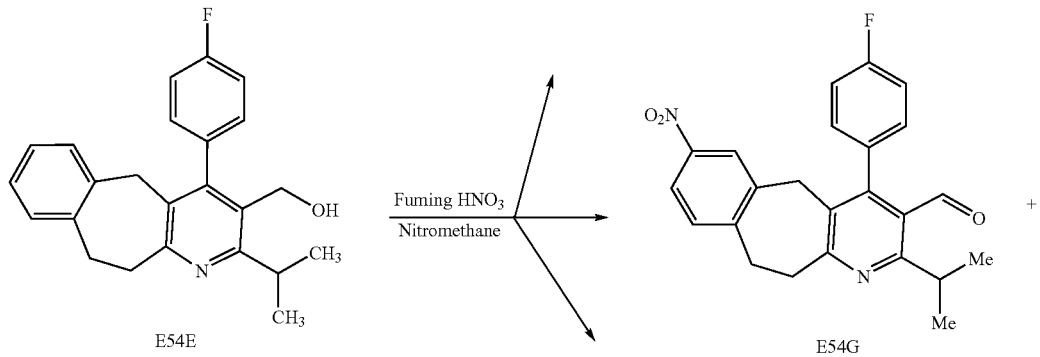

-continued

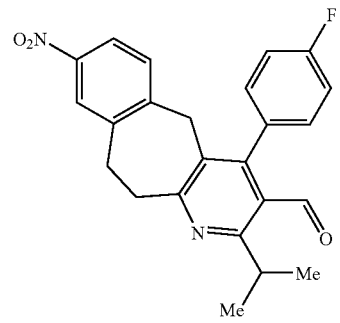

E54H

E54E (2.9 g, 8.08 mmol) was suspended in nitromethane (18 mL) and the mixture was cooled to 0° C. Fuming nitric acid (8 mL) was then introduced and the solution was allowed to warm to room temperature. After stirring for 18 h, the mixture was poured into ice water and extracted with ethyl acetate (2×). The organic layers were pooled and washed with saturated sodium bicarbonate (2×) and brine (2×), dried over sodium sulfate, and concentrated. Column chromatography of the residue on silica gel (10% ethyl acetate/petroleum ether) afforded E54F, E54G and E54H.

Compound E54F: Yield 1.2 g (37%); LRMS (ESI, pos. ion spectrum) m/z 405.3 (M+H)$^+$; $^1$H-NMR (CDCl$_3$, 300 MHz) δ 1.26 (s, 3H), 1.29 (s, 3H), 3.3-3.4 (m, 2H), 3.44-3.49 (m, 2H), 3.87 (s, 2H), 7.12-7.17 (m. 2H), 7.27-7.32 (m, 3H), 7.64 (d, J=2.56. 1H), 7.99 (dd, J=2.2, 5.86, 1H), 9.77 (s, 1H).

Compound E54G: Yield 0.35 g (11%); LRMS (ESI, pos. ion spectrum) m/z 405.3 (M+H)$^+$; $^1$H-NMR (CDCl$_3$, 300 MHz) δ 1.27 (s, 3H), 1.29 (s, 3H), 3.3-3.4 (m, 2H), 3.50-3.52 (m, 2H), 3.87 (s, 2H), 6.87 (d, J=8.06, 1H), 7.10-7.17 (m, 2H), 7.20-7.24 (m, 2H), 7.89 (dd, J=2.2, 8.06, 1H), 8.02 (d, J=2.57, 1H), 9.78 (s, 1H).

Compound E54H: Yield 0.18 g (6%); LRMS (ESI, pos. ion spectrum) m/z 405.3 (M+H)$^+$; $^1$H-NMR (CDCl$_3$, 300 MHz) δ 1.25 (s, 3H), 1.27 (s, 3H), 3.37-3.41 (m, 2H), 3.53-3.57 (m, 2H), 3.87 (s, 2H), 6.97 (d, J=7.32, 1H), 7.13-7.25 (m, 5H), 7.59 (dd, J=1.09, 6.96, 1H), 9.77 (s, 1H).

Part G:

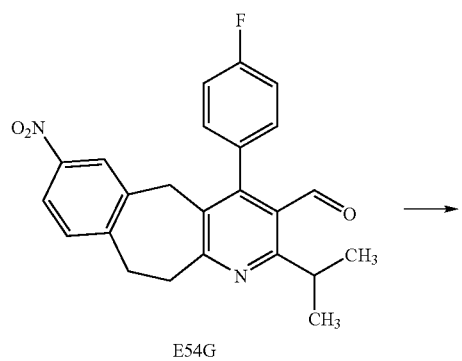

E54G

-continued

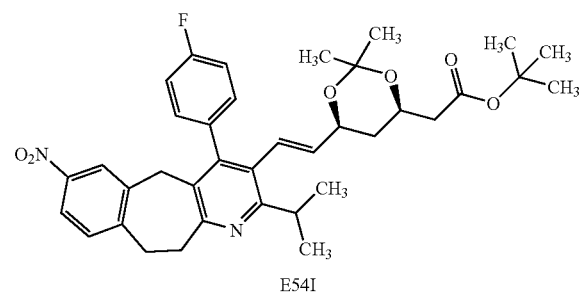

E54I

E54G (1.2 g, 2.98 mmol) and E1D (1.48 g, 3.28 mmol) were combined in tetrahydrofuran (10 mL) and cooled to −78° C. Lithium hexamethylsilylazide (3.3 mL, 3.3 mmol) was added slowly over 20 min. After addition of the base was complete, the solution was stirred at −78° C. for 30 min, warmed to −45° C., cooled to −78° C. and then quenched with concentrated ammonium chloride (2 mL) and water (8 mL). After warming to room temperature, the solution was diluted with ethyl acetate. The organic layer was separated and washed with saturated sodium bicarbonate (2×) and brine (2×), dried over sodium sulfate, and concentrated. Flash chromatography of the residue on silica gel eluting with 20% ethyl acetate/hexanes afforded 1.8 g (96%) of E54I as a white powder: LRMS (ESI, pos. ion spectrum) m/z 631.4 (M+H)$^+$.

Part H:

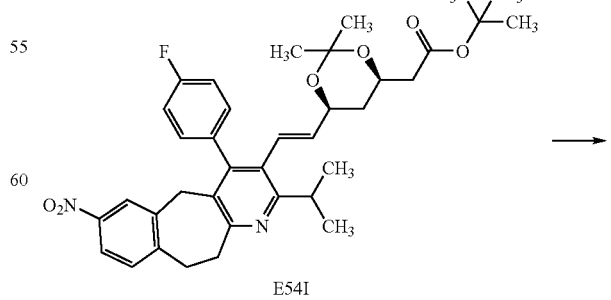

E54I

Part I:

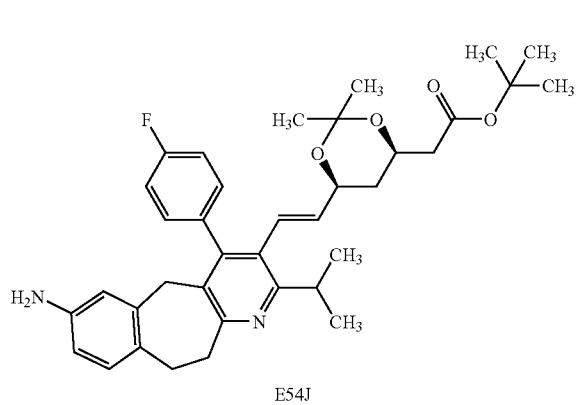

E54I (1.8 g, 2.85 mmol) was dissolved in ethanol (18 mL) and treated with a solution of calcium chloride (0.63 g, 5.7 mmol) in water (3.0 mL). Zinc dust (1.86 g, 28.5 mmol) was added to this solution. The mixture was stirred at reflux for 30 min. After cooling to room temperature, the mixture was filtered and concentrated in vacuo to afford a residue which was dissolved in ethyl acetate and washed with water (2×) and brine (2×), dried over sodium sulfate, filtered, and concentrated. Column chromatography of the residue on silica gel (30% ethyl acetate/hexanes) afforded 1.35 g (79%) of E54J: LRMS (ESI, pos. ion spectrum) m/z 601.4 (M+H)$^+$; $^1$H-NMR (CDCl$_3$, 300 MHz) δ 1.21 (s, 3H), 1.23 (s, 3H), 1.33 (s, 3H), 1.41 (s, 3H), 1.45 (s, 9H), 2.21 (dd, J=6.22, 9.16, 1H), 2.37 (dd, J=6.95, 8.42, 1H), 3.1 (m, 2H), 3.23-3.49 (m, 4H), 3.65 (s, 2H), 4.10-4.26 (m, 3H), 5.15 (dd, J=6.22, 10.26, 1H), 6.08 (d, J=2.19, 1H), 6.19 (d, J=16.85, 1H), 6.49 (dd, J=2.56, 5.49, 1H), 6.92 (d, J=8.05, 1H), 6.96-7.17 (m, 5H).

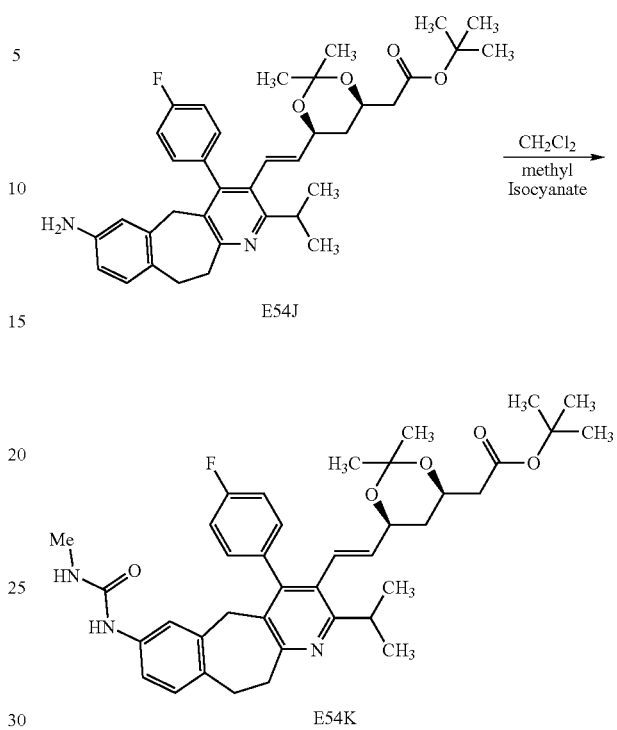

E54J (0.05 g, 0.08 mmol) and methyl isocyanate (0.1 mL, excess) were combined in methylene chloride (2.0 mL) and stirred for 18 h. The solution was diluted with ethyl acetate and washed with water (2×) and brine (2×), dried over sodium sulfate, filtered, and concentrated. Column chromatography of the residue on silica gel afforded 0.038 g (72%) of E54K: LRMS (ESI, pos. ion spectrum) m/z 659.5 (M+H)$^+$.

Part J:

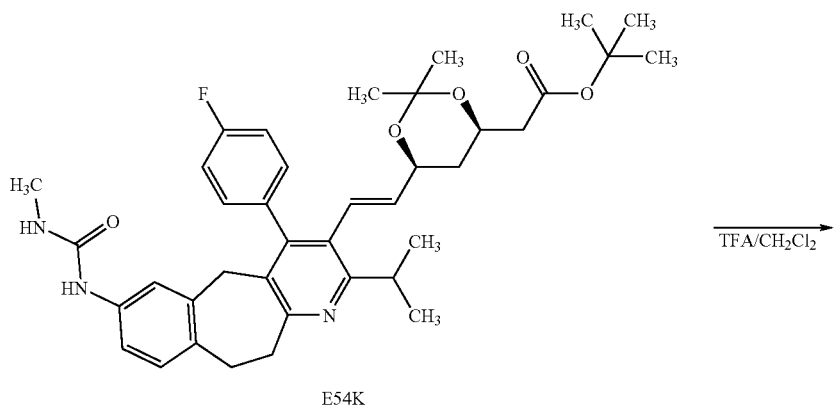

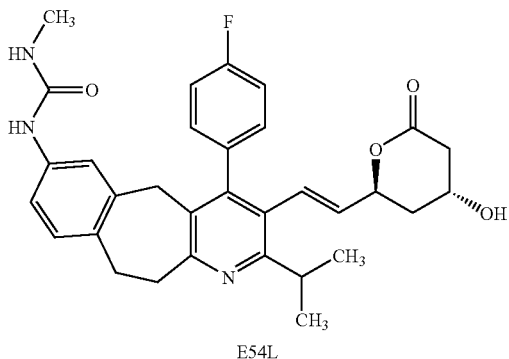

E54L

To a cooled (0° C.) solution of compound E54K (0.025 g, 0.034 mmol) in anhydrous dichloromethane (1.0 mL) was slowly added trifluoroacetic acid (1.0 mL). After the addition was complete, the reaction mixture was stirred at 0° C. for 10 min and at room temperature for 30 min. The solvent was removed in vacuo. The residue was quenched with phosphate solution (pH 7.5, 12 mL) and extracted with dichloromethane (4 mL×2). The combined organic layers were washed with brine (2×), dried over sodium sulfate, filtered and concentrated. Flash silica gel chromatography of the residue afforded 0.020 g (94% yield) of E54L as a white powder.

Part K:

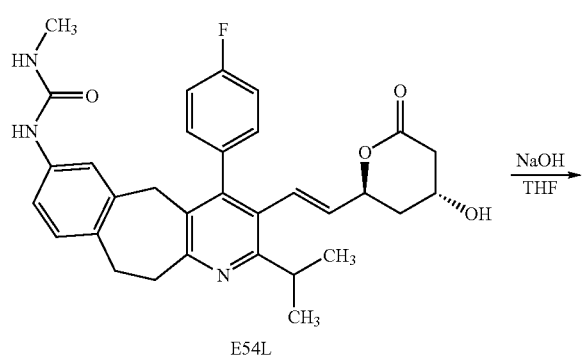

E54L $\xrightarrow{\text{NaOH}}_{\text{THF}}$

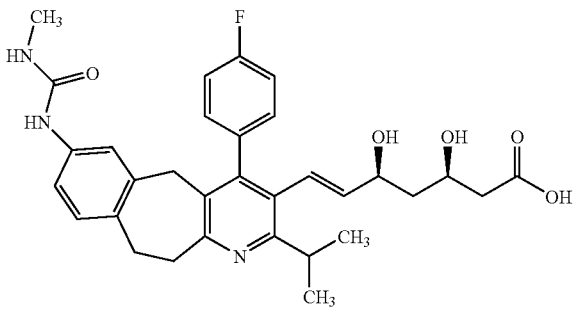

Ex. 54 title compound

To a solution of E54L (0.020 g, 0.03 mmol) in anhydrous tetrahydrofuran (1 mL) at room temperature was added a few drops of aqueous 1 N solution of sodium hydroxide. The reaction was stirred at room temperature for 10 min. The solvent was removed in vacuo and the residue was taken up in water (2 mL). The solution was chromatographed on SP-207 resin eluting with water and then with a gradient of 25%-40% methanol in water. The product-containing fractions were combined and concentrated in vacuo. The residue was dissolved in water and lyophilized to afford 0.017 g (94%) of the title compound as the sodium salt as a white solid: LRMS (ESI, pos. ion spectrum) m/z 562.2 (M+H)$^+$; HPLC (Method 6) $t_R$=12.9 min.

Examples 55 to 60

The following Examples were prepared using the procedures described in Example 54:

| Ex. | Structure | Characterization |
|---|---|---|
| 55 | 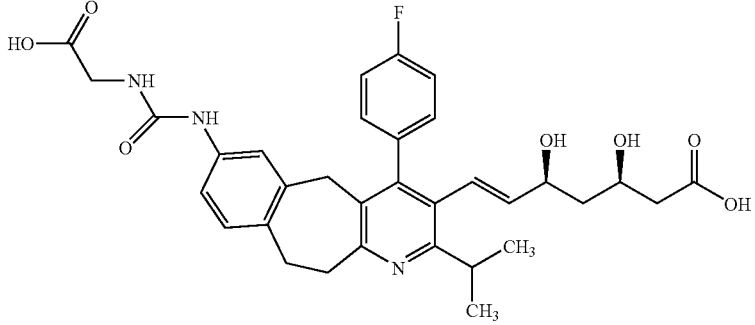<br>6-Heptenoic acid, 7-[7-[[[(carboxymethyl)amino]carbonyl]amino]-4-(4-fluorophenyl)-10,11-dihydro-2-(1-methylethyl)-5H-benzo[4,5]cyclohepta[1,2-b]pyridin-3-yl]-3,5-dihydroxy-, (3R,5S,6E)- | LRMS (ESI, pos. ion spectrum) m/z 606.4 $(M + H)^+$<br>HPLC (Method 6) $t_R$ = 11.6 min |
| 56 | 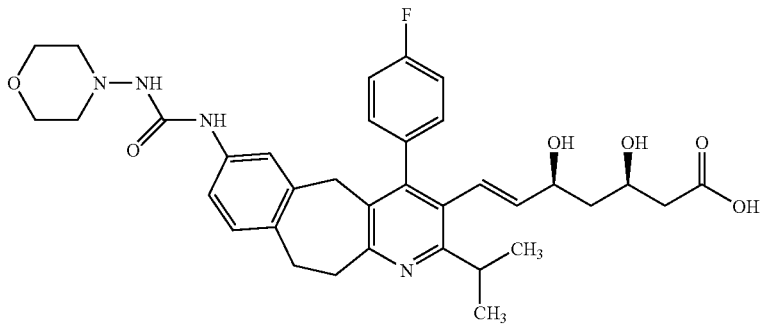<br>6-Heptenoic acid, 7-[4-(4-fluorophenyl)-10,11-dihydro-2-(1-methylethyl)-7-[[(4-morpholinylamino)carbonyl]amino]-5H-benzo[4,5]cyclohepta[1,2-b]pyridin-3-yl]-3,5-dihydroxy-, (3R,5S,6E)- | LRMS (ESI, pos. ion spectrum) m/z 633.4 $(M + H)^+$ |
| 57 | 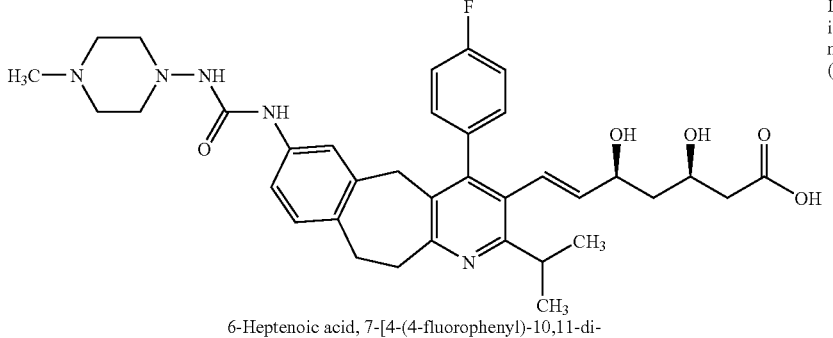<br>6-Heptenoic acid, 7-[4-(4-fluorophenyl)-10,11-dihydro-2-(1-methylethyl)-7-[[[(4-methyl-1-piperazinyl)amino]carbonyl]amino]-5H-benzo[4,5]cyclohepta[1,2-b]pyridin-3-yl]-3,5-dihydroxy-, (3R,5S,6E)- | LRMS (ESI, pos. ion spectrum) m/z 646.3 $(M + H)^+$ |

| Ex. | Structure | Characterization |
|---|---|---|
| 58 | 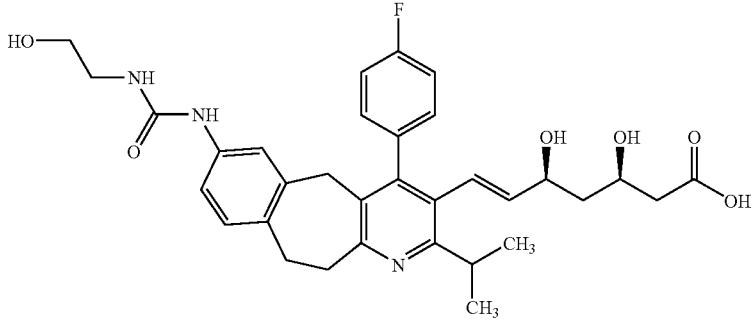<br>6-Heptenoic acid, 7-[4-(4-fluorophenyl)-10,11-di-hydro-7-[[[(2-hydroxy-ethyl)amino]carbonyl]amino]-2-(1-methyl-ethyl)-5H-benzo[4,5]cyclohepta[1,2-b]pyridin-3-yl]-3,5-di-hydroxy-, (3R,5S,6E)- | LRMS (ESI, pos. ion spectrum) m/z 593.3 (M + H)+ |
| 59 | 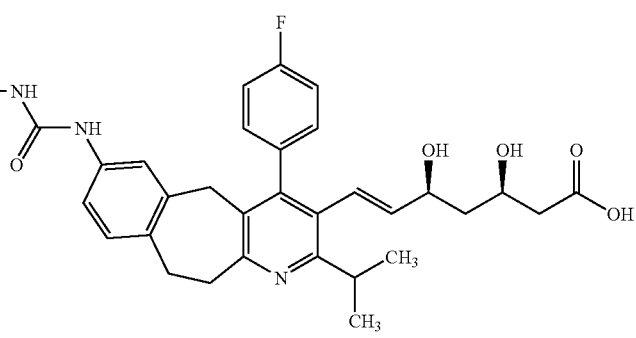<br>6-Heptenoic acid, 7-[4-(4-fluorophenyl)-10,11-di-hydro-7-[[[(3-hydroxy-propyl)amino]carbonyl]amino]-2-(1-methyl-ethyl)-5H-benzo[4,5]cyclohepta[1,2-b]pyridin-3-yl]-3,5-di-hydroxy-, (3R,5S,6E) | LRMS (ESI, pos. ion spectrum) m/z 606.4 (M + H)+ HPLC (Method 6) $t_R$ = 12.2 min |
| 60 | 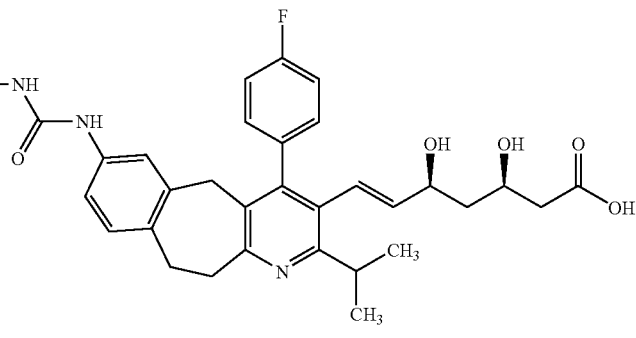<br>6-Heptenoic acid, 7-[4-(4-fluorophenyl)-10,11-di-hydro-7-[[[(4-hydroxy-butyl)amino]carbonyl]amino]-2-(1-methyl-ethyl)-5H-benzo[4,5]cyclohepta[1,2-b]pyridin-3-yl]-3,5-di-hydroxy-, (3R,5S,6E)- | LRMS (ESI, pos. ion spectrum) m/z 620.3 (M + H)+ HPLC (Method 6) $t_R$ = 12.6 min |

Example 61

6-Heptenoic acid, 7-[4-(4-fluorophenyl)-10,11-dihydro-9-[[(methylamino)carbonyl]amino]-2-(1-methylethyl)-5H-benzo[4,5]cyclohepta[1,2-b]pyridin-3-yl]-3,5-dihydroxy-, (3R,5S,6E)-

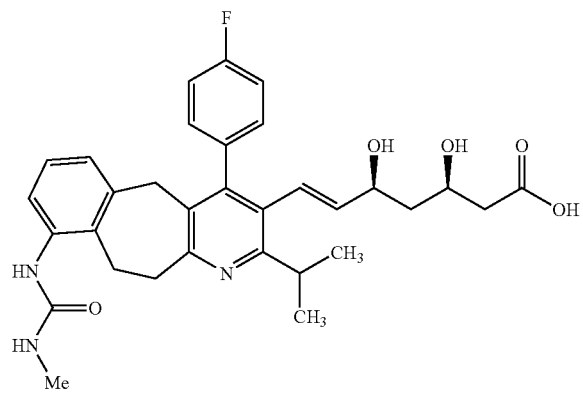

Part A:

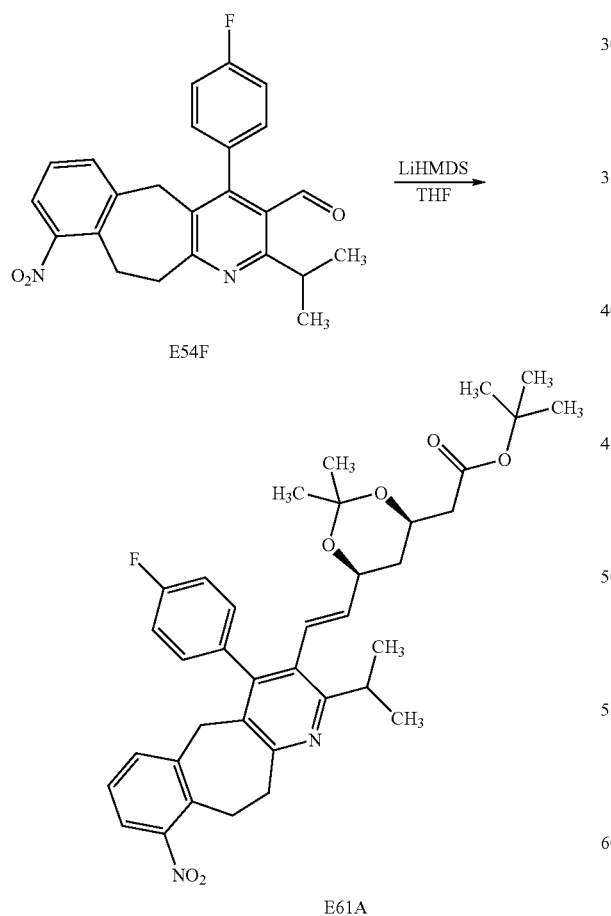

E54F (0.16 g, 0.4 mmol) and E1D (0.16 g, 0.4 mmol) were combined in tetrahydrofuran (6 mL) and cooled to −78° C. lithium hexamethyldisilazide (0.44 mL, 0.44 mmol) was added slowly over 20 min. After complete addition of base, the solution was stirred at −78° C. for 30 min, warmed to −45° C., cooled to −78° C. and quenched with concentrated ammonium chloride (1 mL) and water (4 mL). After warming to room temperature, the solution was diluted with ethyl acetate. The organic layer was separated and washed with saturated sodium bicarbonate (2×), brine (2×), dried over sodium sulfate, and concentrated. Flash chromatography on silica gel eluting with 20% ethyl acetate/hexanes) afforded 0.2 g (80%) of E61A: LRMS (ESI, pos. ion spectrum) m/z 631.4 (M+H)$^+$.

Part B:

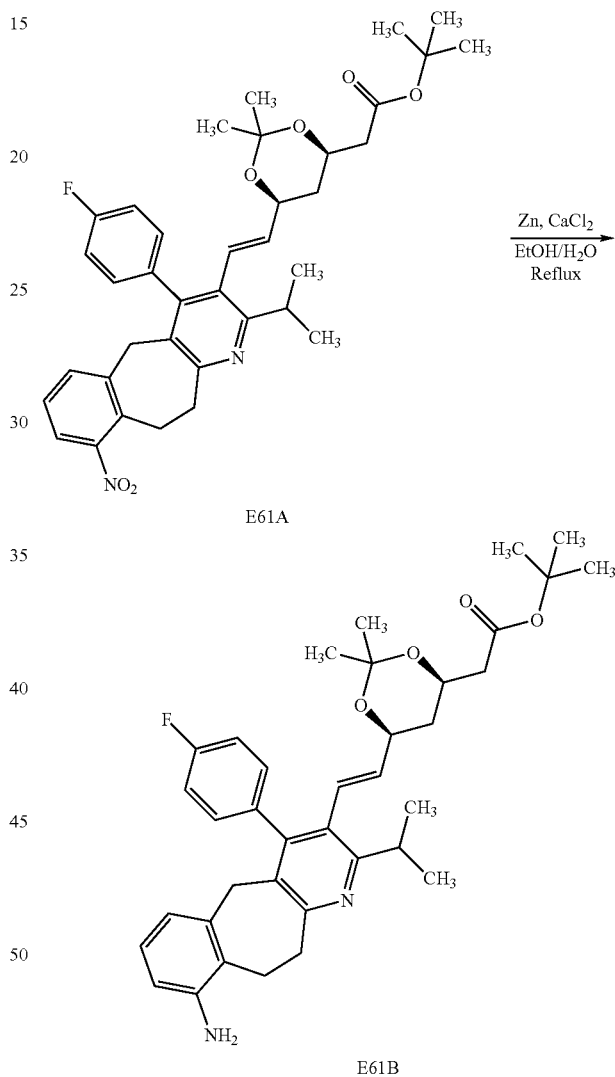

E61A (0.2 g, 0.32 mmol) was dissolved in ethanol (6 mL) and treated with calcium chloride (0.77 g, 0.62 mmol) in water (1.0 mL). To this solution was added zinc dust (0.42 g, 6.4 mmol) and the reaction mixture was stirred at reflux for 30 min. After cooling to room temperature, the mixture was filtered and concentrated in vacuo to afford a residue which was dissolved in ethyl acetate and washed with water (2×), brine (2×), dried over sodium sulfate, filtered, and concentrated. Column chromatography of the residue on silica gel (30% ethyl acetate/hexanes) afforded 0.15 g (78%) of E61B: LRMS (ESI, pos. ion spectrum) m/z 601.4 (M+H)$^+$.

Part C:

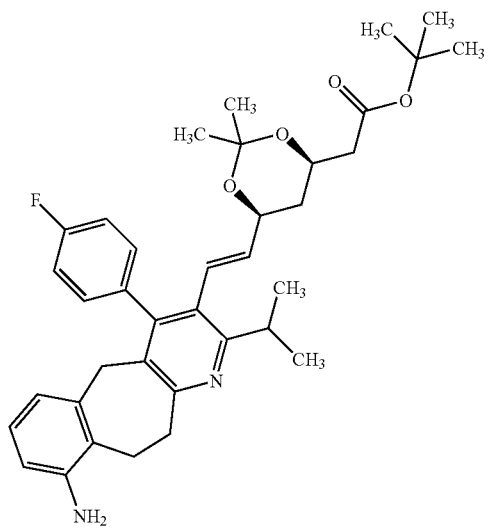

E61B

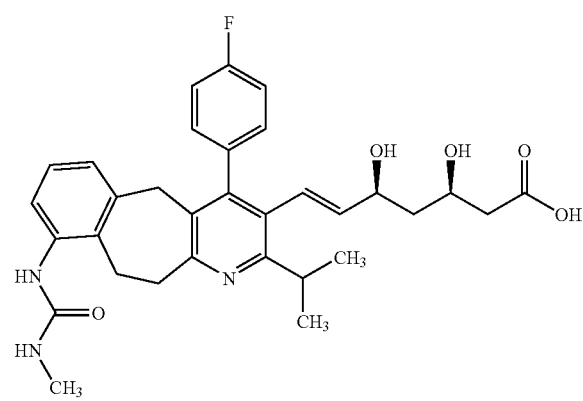

Ex. 61 title compound

The title compound was prepared from E61B employing the procedure described in Example 54 steps I to K: LRMS (ESI, pos. ion spectrum) m/z 584.2 (M+Na)⁺; ¹H-NMR (CDCl₃, 300 MHz) δ 1.33 (s, 3H), 1.45 (s, 6H), 1.61 (m, 4H), 2.21 (dd, J=6.22, 9.16, 1H), 2.40 (dd, J=6.95, 8.06, 1H), 3.14 (m, 2H), 3.67 (s, 2H), 4.14-4.28 (m, 2H), 5.20 (dd, J=5.86, 10.62, 1H), 6.06 (d, J=2.20, 1H), 6.19 (d, J=16.84, 1H), 6.48 (dd, J=2.57, 5.49, 1H), 6.93 (d, J=8.06, 1H), 6.96-7.21 (m, 5H); HPLC (method 6) $t_R$=13.6 min.

Example 62

6-Heptenoic acid, 7-[4-(4-fluorophenyl)-10,11-dihydro-2-(1-methylethyl)-7-(1H-tetrazol-5-yl)-5H-benzo[4,5]cyclohepta[1,2-b]pyridin-3-yl]-3,5-dihydroxy-, (3R,5S,6E)-

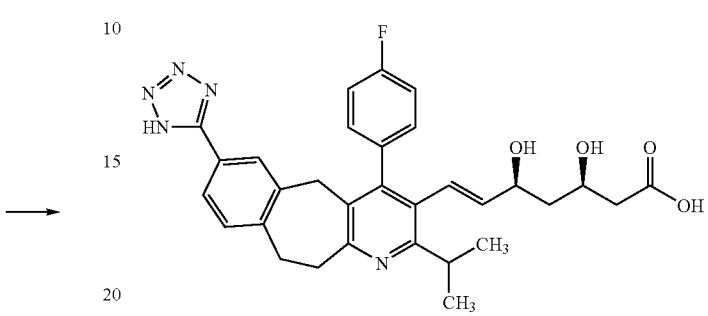

Part A:

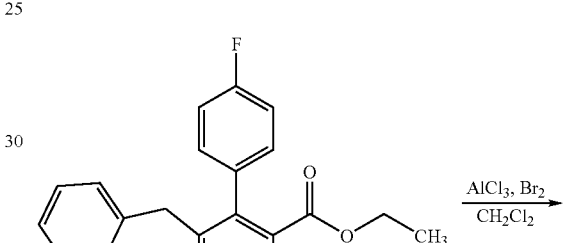

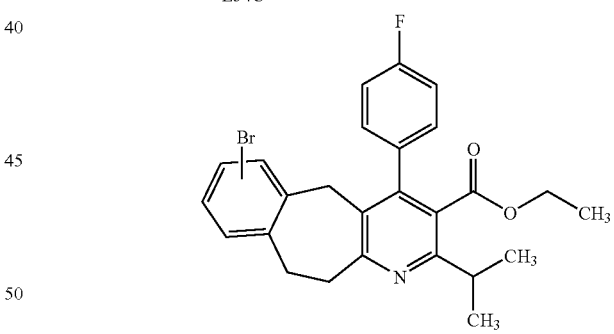

E54C (3.7 g, 9.18 mmol) was dissolved in methylene chloride (50 mL). Aluminum chloride (2.45 g, 18.36 mmol) was slowly added. The solution was stirred at room temperature for 10 min. Bromine (0.94 mL, 18.36 mmol) was slowly introduced over 10 min. The solution was stirred at room temperature overnight and then carefully quenched with 1 N hydrochloric acid (6 mL). The reaction mixture was diluted with diethyl ether; washed with water (2×), sodium thiosulfate (2×), and sodium bicarbonate (2×); dried over sodium sulfate; and concentrated. Column chromatography of the residue on silica gel afforded 2.4 g (55%) of the mixture of monobromides: LRMS (ESI, pos. ion spectrum) m/z 482/484 (M+H)⁺.

Part B:

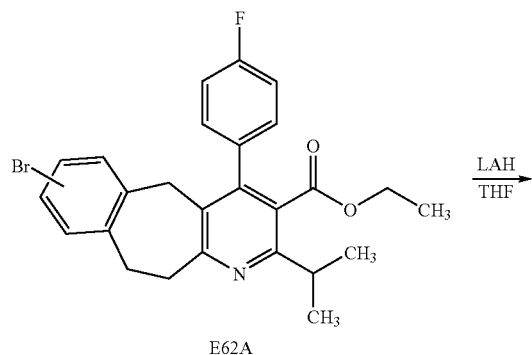
E62A

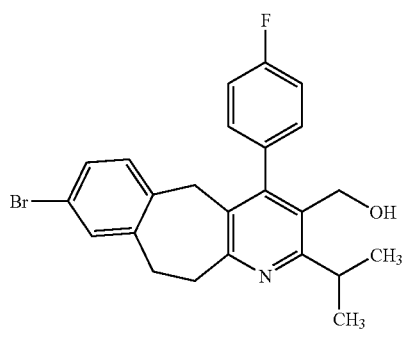
E62B

E62C

Part C:

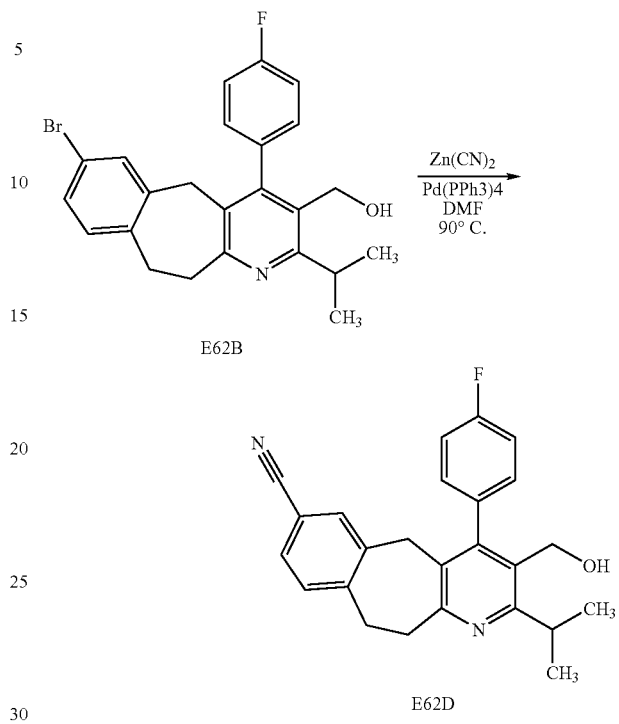
E62B

E62D

E62A (1.4 g, 2.89 mmol) was dissolved in tetrahydrofuran (28 mL) and cooled to 0° C. Lithium aluminum hydride was then slowly added. After the addition was complete, the solution was stirred at 0° C. for 1 h, warmed to room temperature and stirred for 16 h. The reaction mixture was cooled to 0° C. and carefully quenched with water (8 mL), 15% sodium hydroxide (8 mL), and water (15 mL). The resulting mixture was stirred at room temperature for 15 min and was then filtered. The filtrate was concentrated. Column chromatography of the residue afforded 0.8 g (63%) of E62B [LRMS (ESI, pos. ion spectrum) m/z 440.2 (M+H)$^+$] and 0.16 g (13%) of E62C [LRMS (ESI, neg. ion spectrum) m/z 438.3 (M–H)$^-$].

E62B (0.45 g, 1.16 mmol) zinc cyanide (0.19 g, 1.64 mmol), and tetrakis(triphenylphosphine)palladium(0) (0.1 g, 0.09 mmol) were combined in dimethylformamide (5.0 mL). The reaction mixture was degassed repeatedly using the freeze-thaw method. After warming to room temperature, the reaction was heated at 90° C. for 1 h. After cooling to room temperature, the reaction was concentrated in vacuo. The residue was taken up in ethyl acetate and washed with water (2×) and brine (2×), dried over sodium sulfate, filtered, and concentrated. Flash chromatography of the residue on silica gel afforded 0.36 g (91%) of E62D: LRMS (ESI, pos. ion spectrum) m/z 387.3 (M+H)$^+$; $^1$H-NMR (CD$_3$OD, 300 MHz) δ 1.13 (s, 3H), 1.16 (s, 3H), 2.45 (m, 1H), 3.12-3.21 (m, 3H), 3.39 (m, 1H), 3.67 (s, 2H), 4.04 (s, 1H), 4.05 (s, 1H), 4.61 (m, 1H), 6.98 (s, 1H), 7.21 (m, 2H), 7.26-7.38 (m, 3H), 7.52 (dd, J=1.83, 6.22, 1H).

Part D:

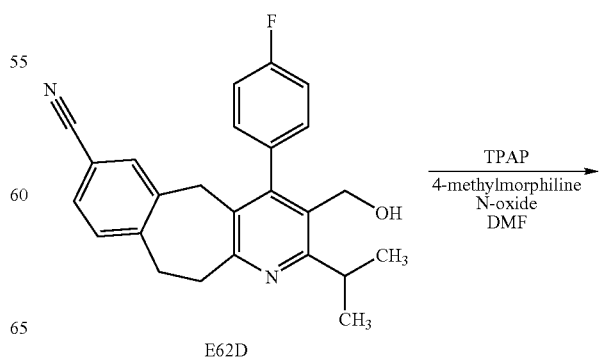
E62D

-continued

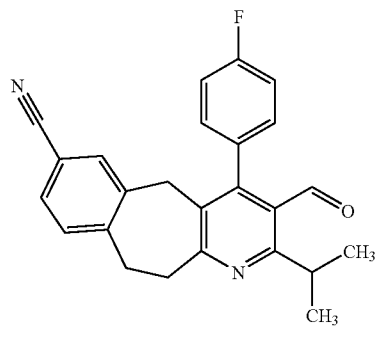

E62E

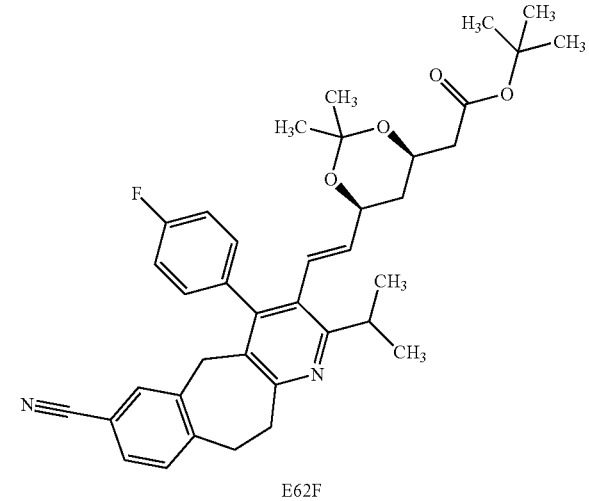

E62F

E62D (0.36 g, 0.93 mmol), tetrapropylammonium perruthenate (0.07 g, mmol), N-methylmorpholine-N-oxide (0.27 g, 2.3 mmol) and powdered, 4 Å molecular sieves (6 g) were combined in a dimethylformamide/methylene chloride mixture (1:2, 21 mL) and stirred at room temperature for 2 h. The mixture was filtered through a pad of Celite®. The filtrate was washed with saturated sodium bicarbonate solution (2×) and brine (2×), dried over sodium sulfate, filtered, and concentrated. Flash chromatography of the residue on silica gel (30% ethyl acetate/hexanes) afforded 0.23 g (63%) of E62E: LRMS (ESI, pos. ion spectrum) m/z 385.3 (M+H)$^+$; $^1$H-NMR (CD$_3$OD, 300 MHz) δ 1.13 (s, 3H), 1.15 (s, 3H), 2.44 (m, 1H), 3.16-3.21 (m, 2H), 3.35 (m, 2H), 3.78 (s, 2H), 7.05 (s, 1H), 7.20-7.26 (m, 2H), 7.29-7.43 (m, 3H), 7.55 (dd, J=1.46, 6.23, 1H), 9.62 (s, 1H).

Part E:

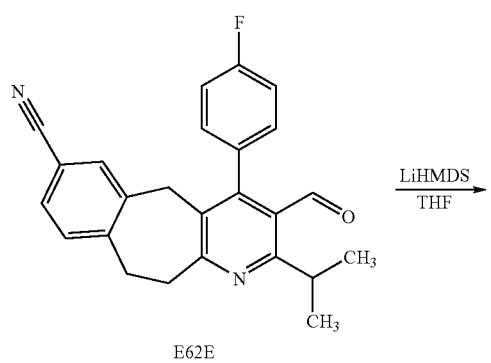

E62E

E62F was prepared from E62E using the procedure described in Example 54 Part G: LRMS (ESI, pos. ion spectrum) m/z 611.3 (M+H)$^+$.

Part F:

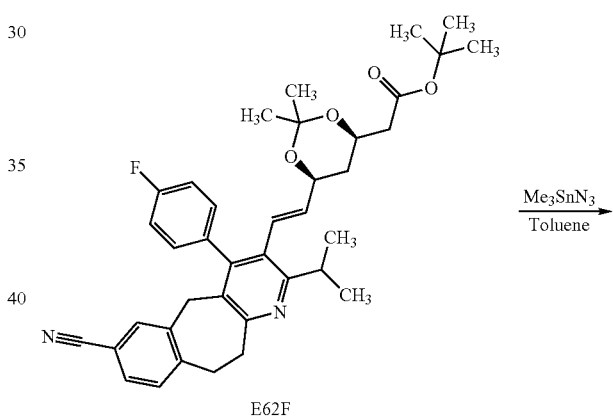

E62F

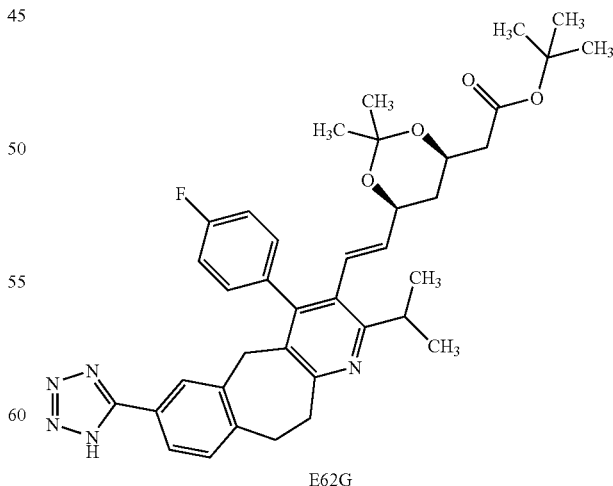

E62G

E62G was prepared from E62F using the procedures described in Example 50 Part B: LRMS (ESI, pos. ion spectrum) m/z 654.3 (M+H)$^+$.

Part G:

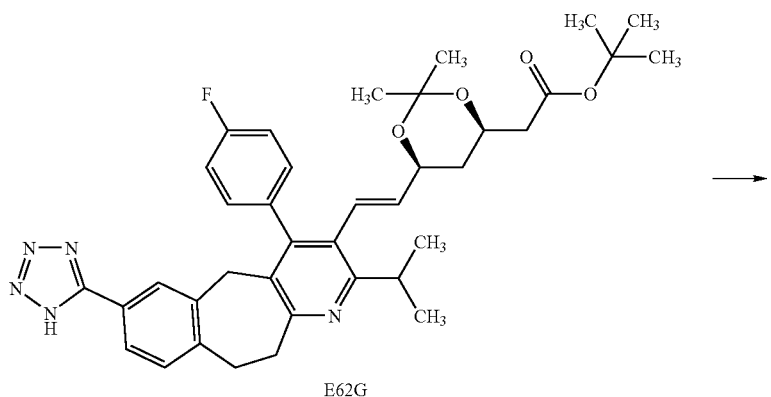

The title compound was prepared as the sodium salt from E62G employing the procedures described in Example 54 Steps J and K: LRMS (ESI, pos. ion spectrum) m/z 558.3 (M+H)$^+$.

Example 63

6-Heptenoic acid, 7-[10-[[[(carboxymethyl)amino]carbonyl]amino]-1-(4-fluorophenyl)-6,7-dihydro-3-(1-methylethyl)-5H-benzo[3,4]cyclohepta[1,2-b]pyridin-2-yl]-3,5-dihydroxy-, (3R,5S,6E)-

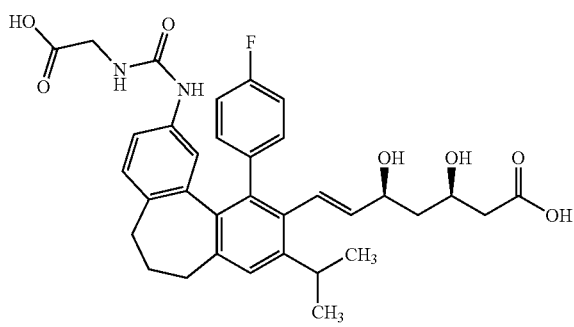

Part A:

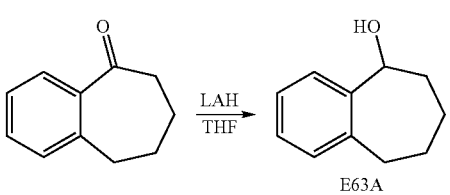

To a solution of 1-benzosuberone (5.0 g, 31.2 mmol) in anhydrous tetrahydrofuran (120 mL) at 0° C. was added 1.0 M lithium aluminum hydride in tetrahydrofuran (62.4 mL, 62.4 mmol). The reaction was stirred at 0° C. for 30 min and then warmed to room temperature and stirred for 2 h. The reaction was then cooled to 0° C. and quenched slowly with water (5.0 mL), then sodium hydroxide (10% NaOH, 10 mL), and then water (10 mL). The mixture was filtered and the filter cake was washed with ethyl acetate (50 mL). The organic layers was then washed with water (10 mL) and brine (10 mL), dried over sodium sulfate, and concentrated to afford 5.35 g of E63A: LRMS (ESI, pos. ion spectrum) m/z 162.3 (M+H)$^+$.

Part B:

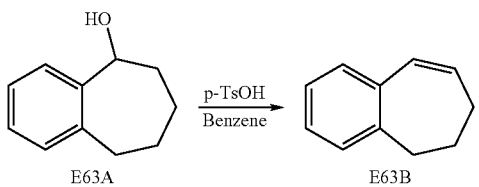

To a solution of E63A (1.0 g, 6.2 mmol) in benzene (25 mL) was added p-toluenesulfonic acid monohydrate (2.5 mg). The flask was fitted with a Dean-Stark trap and the reaction mixture was heated at reflux overnight. After cooling to room temperature, 5% sodium bicarbonate (20 mL) was added to the reaction mixture which was then extracted with diethyl ether (3×). The organic layers were pooled and washed with water (2×) and brine (2×), dried over sodium sulfate, filtered, and concentrated to afford 0.76 g (85%) of E63B: $^1$H-NMR (CDCl$_3$, 300 MHz) δ 1.93-2.01 (m, 2H), 2.4-2.47 (m, 2H), 2.84-2.88 (m, 2H), 5.9 (m, 1H), 6.4 (m, 1H), 7.0-7.17 (m, 4H).

Part C:

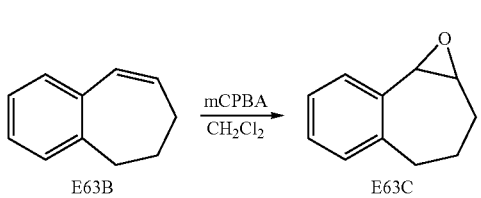

To a solution of E63B (0.44 g, 3.05 mmol) in methylene chloride (10.0 mL) was added m-chloroperbenzoic acid. The reaction was stirred at room temperature overnight. Saturated sodium thiosulfate (10 mL) was added and stirring was maintained for 30 min. The layers were then separated and the organic layer was washed with saturated sodium bicarbonate (2×) and brine (2×), dried over sodium sulfate, filtered and concentrated. Flash chromatography of the residue on silica gel afforded 0.25 g (51%) of E63C: $^1$H-NMR (CDCl$_3$, 300 MHz) δ 1.53-1.90 (m, 3H), 2.15 (m, 1H), 2.71-2.93 (m, 2H), 3.4 (m, 1H), 4.01 (d, J=4.4, 1H), 7.0-7.17 (m, 4H).

Part D:

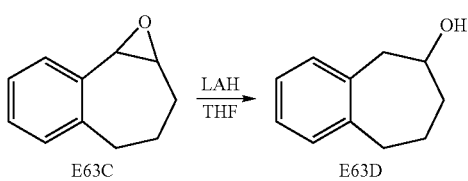

To a solution of E63C (0.25 g, 1.56 mmol) in anhydrous tetrahydrofuran (6.0 mL) at 0° C. was added 1.0 M lithium aluminum hydride in tetrahydrofuran (2.0 mL, 2.0 mmol). The reaction was stirred at 0° C. for 30 min and then warmed to room temperature and stirred for 2 h. The reaction was then cooled to 0° C. and quenched slowly with water (0.2 mL), then sodium hydroxide (10% NaOH, 0.2 mL), and water (0.4 mL). The mixture was filtered and the filter cake was washed with ethyl acetate (10 mL). The organic layers was then washed with water (10 mL) and brine (10 mL), dried over sodium sulfate, filtered, and concentrated to afford 0.2 g (79%) of E63D: LRMS (ESI, pos. ion spectrum) m/z 162.3 (M+H)$^+$.

Part E:

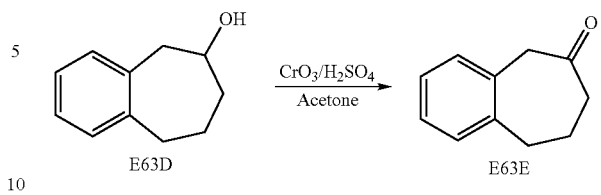

E63D (1.5 g, 9.3 mmol) and Jones reagent (CrO$_3$/H$_2$SO$_4$, 18.6 mmol) were combined in acetone (10 ml) and stirred at room temperature for 2 h. The reaction mixture was then diluted with water and extracted with diethyl ether (2×). The organic layers were pooled and washed with water (2×), brine (2×), dried over sodium sulfate, filtered, and concentrated to afford the crude product which was purified by flash chromatography on silica gel (20% ethyl acetate/hexanes) to afford 1.2 g (97%) of E63E.

Part F:

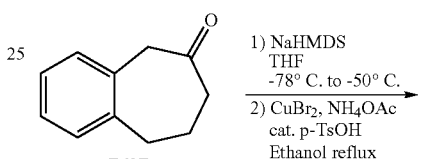

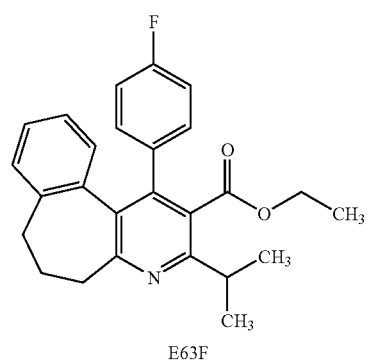

E63F was prepared from E63E using the procedure described in Example 54 Part C. Flash chromatography (10% ethyl acetate in hexanes) afforded 2.2 g (75% yield, 2 steps) of E63F as white powder: LRMS (ESI, pos. ion spectrum) m/z 404.4 (M+H).

Part G:

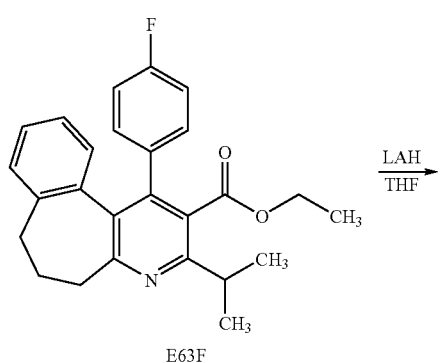

-continued

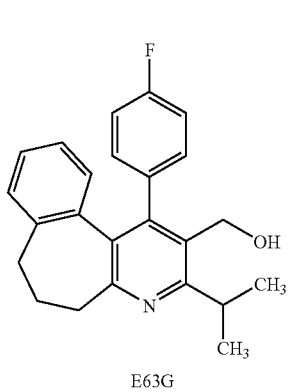

E63G

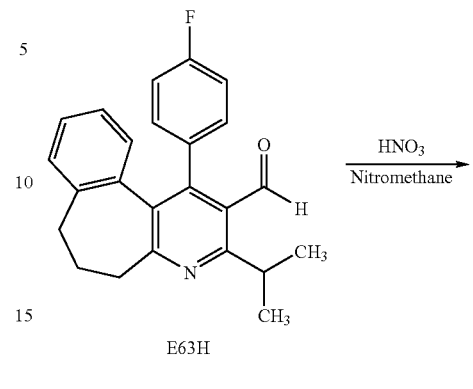

E63H

E63G was prepared from E63F using the procedure described in Example 54 Part D: LRMS (ESI, pos. ion spectrum) m/z 362.3 (M+H).

Part H:

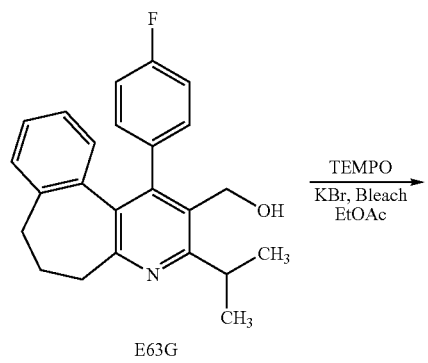

E63G

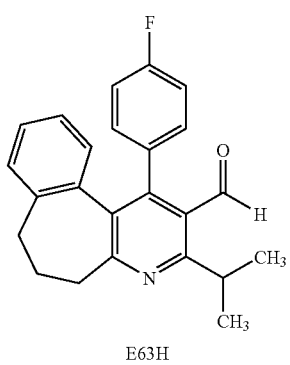

E63H

E63H was prepared from E63G using the procedure described in Example 54 Part E: LRMS (ESI, pos. ion spectrum) m/z 360.3 (M+H).

Part I:

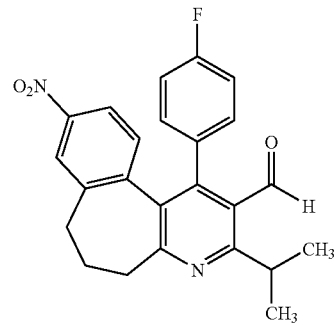

E63I

E63I was prepared from E63H using the procedure described in Example 54 Part F: LRMS (ESI, pos. ion spectrum) m/z 405.3 (M+H).

Part J:

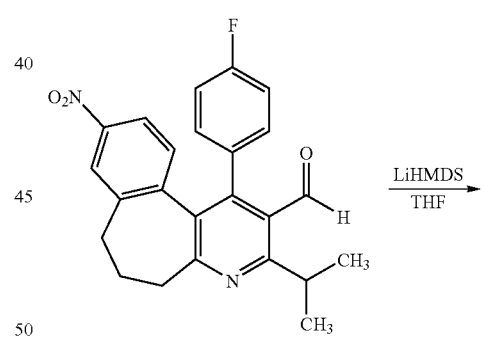

E63I

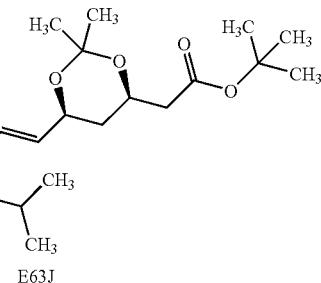

E63J

E63J was prepared from E63I using the procedure described in Example 54 Part G: LRMS (ESI, pos. ion spectrum) m/z 405.3 (M+H).

Part K:
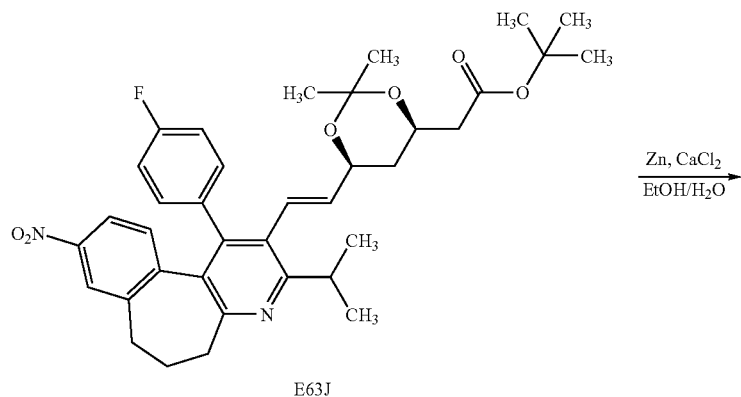
E63K was prepared from E63J using the procedure described in Example 54 Part H: LRMS (ESI, pos. ion spectrum) m/z 601.5 (M+H).
Part L:
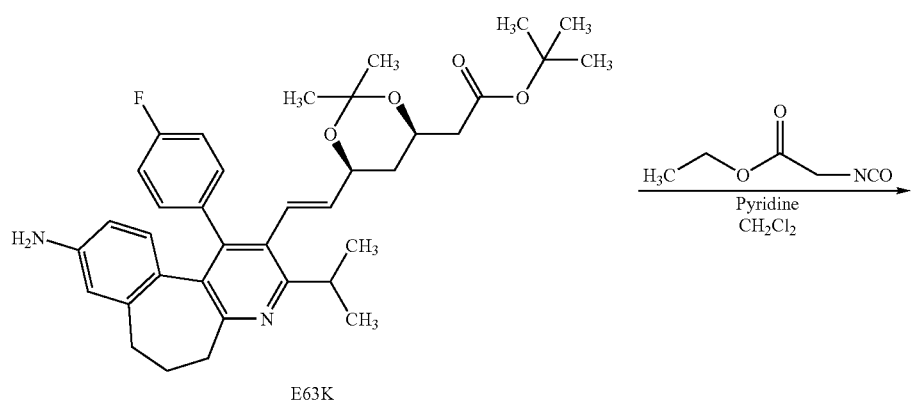

-continued
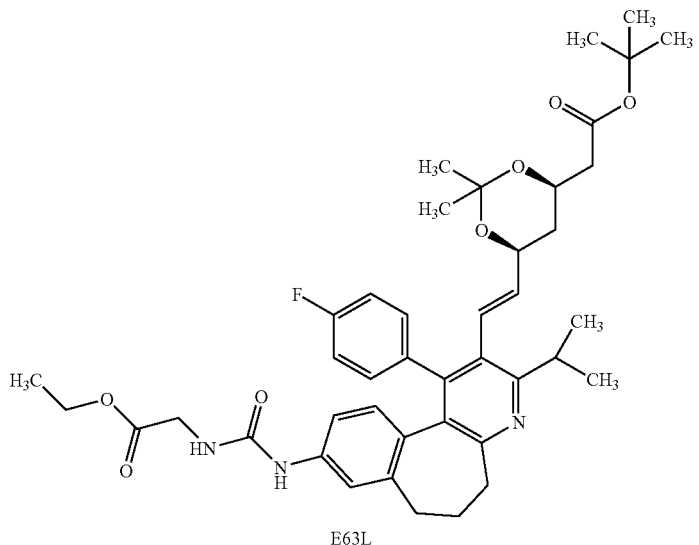
E63L
E63L was prepared from E63K using the procedure described in Example 54 Part I: LRMS (ESI, neg. ion spectrum) m/z 728.5 (M–H).
Part M:
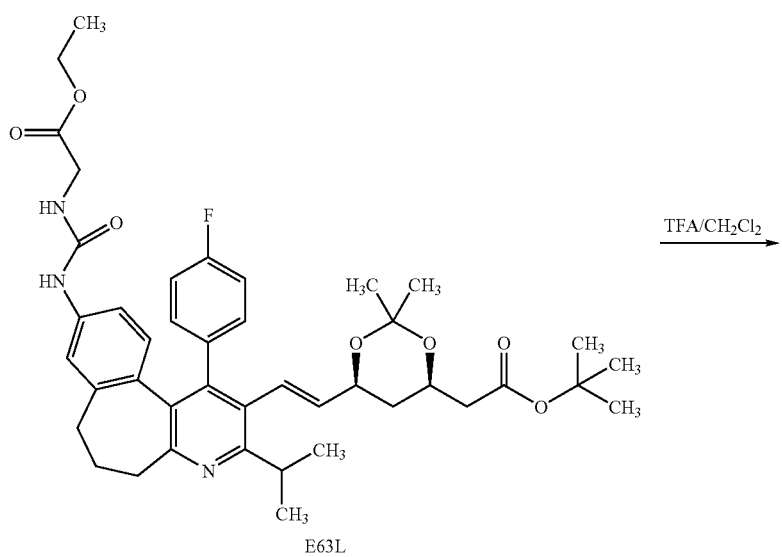
E63L
TFA/CH₂Cl₂ →

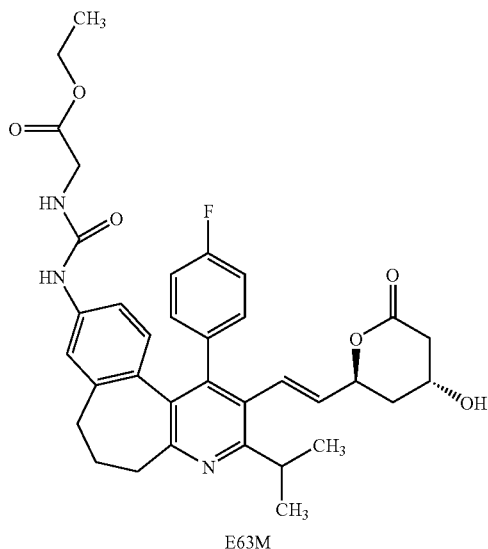
E63M
E63M was prepared from E63K using the procedure described in Example 54 Part J: LRMS (ESI, pos. ion spectrum) m/z 616.5 (M+H).
Part N:
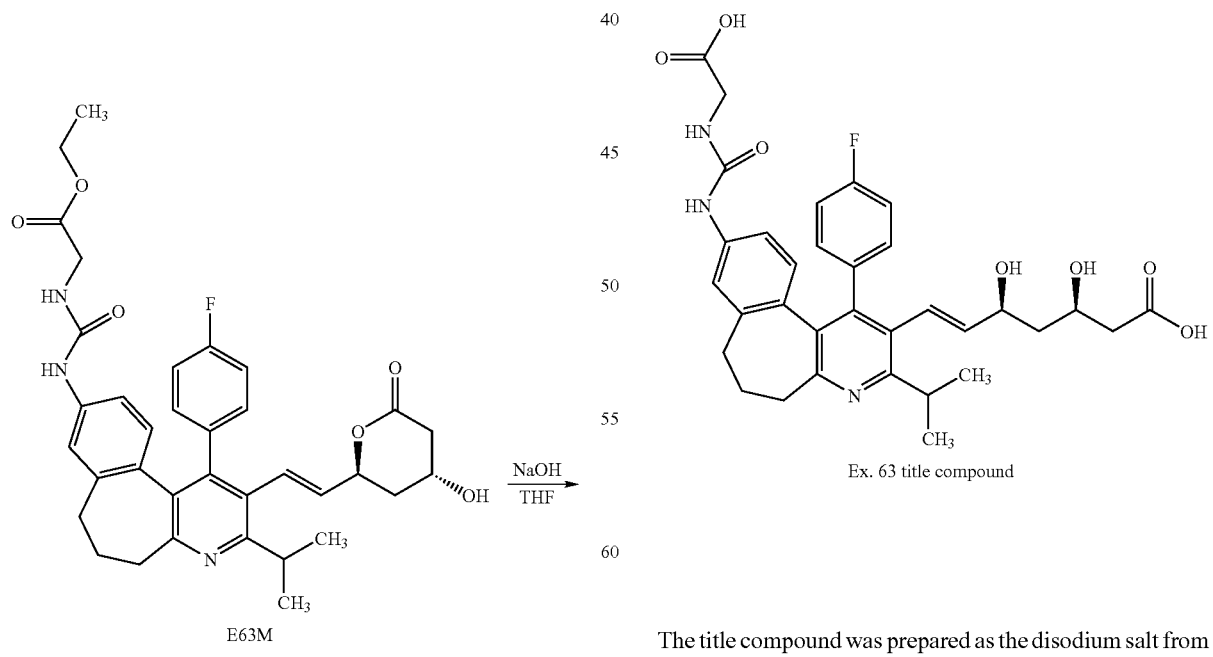
The title compound was prepared as the disodium salt from E63K using the procedure described in Example 54 Part K: LRMS (ESI, pos. ion spectrum) m/z 606.2 (M+H)$^+$; HPLC (method 6) $t_R$=11.6 min.

Example 64

Benzoic acid, 5-[3-[(1E,3S,5R)-6-carboxy-3,5-dihydroxy-1-hexenyl]-6,7-dihydro-2-(1-methylethyl)-5H-benzo[6,7]cyclohepta[1,2-b]pyridin-4-yl]-2-fluoro-

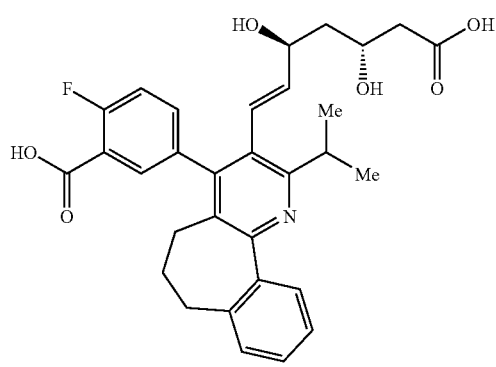

Part A:

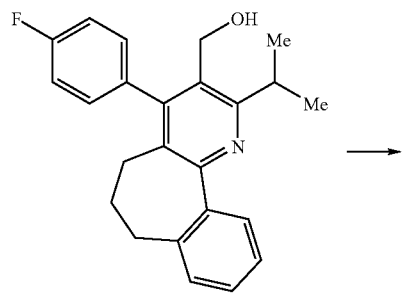

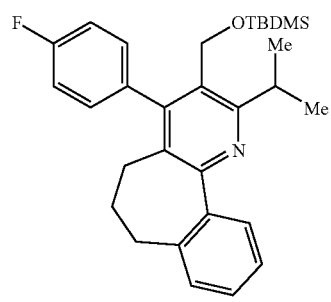

E64A 4-(4-Fluorophenyl)-6,7-dihydro-2-(1-methylethyl)-5H-benzo[6,7]cyclohepta[1,2-b]pyridine-3-methanol (7.6 g, 20 mmol), t-butyldimethylsilyl chloride (15 g, 100 mmol) and imidazole (14 g, 200 mmol) were stirred at ambient temperature in DMF (16 mL). After 2 h, the resultant solid white mass was transferred to a separatory funnel with ether and water. The mixture was extracted with ether (3×300 mL). The combined organic layers were washed with water and brine, dried over MgSO$_4$ and evaporated to afford 18.6 g of crude product. Purification of the residue over silica gel eluting with dichloromethane afforded E64A (9.1 g, 95% yield): HPLC (method 7) t$_R$=3.0 min; LCMS (ESI, pos. ion spectrum) m/z 476 (M+H).

Part B:

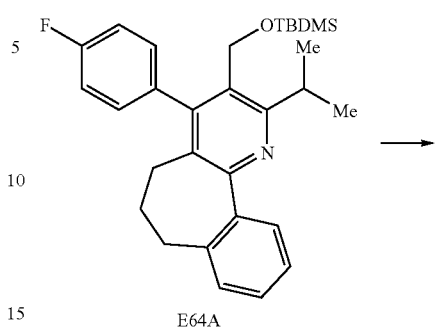

E64A

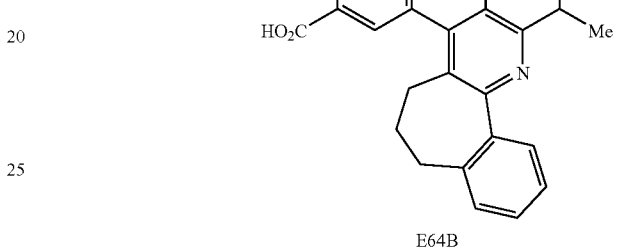

E64B t-Butyllithium (1.7M in hexane, 2.5 mL, 4.2 mmol) was slowly added over 5 min to a stirred solution of E64A (1.95 g, 4.1 mmol) in ether (dry, 60 mL) at −78° C. under nitrogen. After stirring at −78° C. for 2 h, carbon dioxide gas was bubbled through the solution for 5 min. The reaction was removed from the cold bath and stirred at ambient temperature for 20 min. The reaction was cooled to −78° C. and quenched with HCl (6 N, 1 mL). The reaction was warmed to room temperature and was then transferred to a separatory funnel with ether and HCl (0.001 M). The mixture was extracted with ether (2×150 mL). The combined organic layers were washed with brine, dried over MgSO$_4$ and concentrated to afforded 2.0 g of residue. Purification of the residue over silica gel (gradient from dichloromethane to 50% ethyl acetate/dichloromethane containing 1% TFA) afforded 1.25 g (64% yield) of starting material and E64B (0.5 g, 28% yield): HPLC (method 7) t$_R$=2.7 min; LCMS (ESI, pos. ion spectrum) m/z 520 (M+H).

Part C:

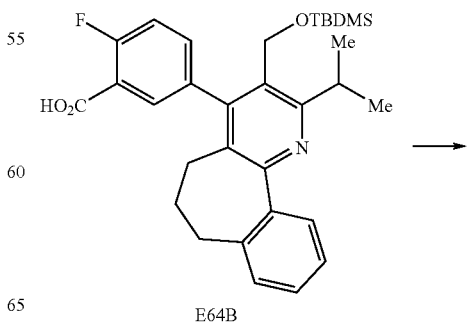

E64B

235

-continued

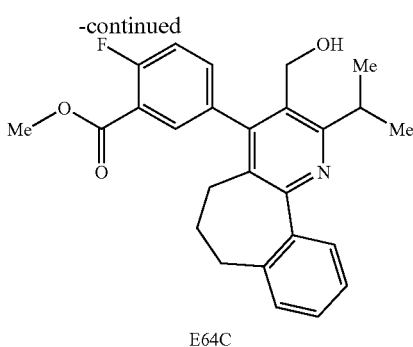

E64C

Sulfuric acid (0.50 mL) was added to a stirred solution of E64B (0.50 g, 0.96 mmol) in methanol (50 mL). The mixture was refluxed for 3 d. The methanol was evaporated in vacuo, and the residue was transferred to a separatory funnel with ethyl acetate and sat. NaHCO$_3$. The mixture was extracted with ethyl acetate (2×40 mL). The combined organic layers were washed with brine, dried over MgSO$_4$ and concentrated to afford 0.27 g (67%) of E64C. This material was used in the next step without further purification: HPLC (method 7) $t_R$=2.2 min; LCMS (ESI, pos. ion spectrum) m/z 420 (M+H).

Part D:

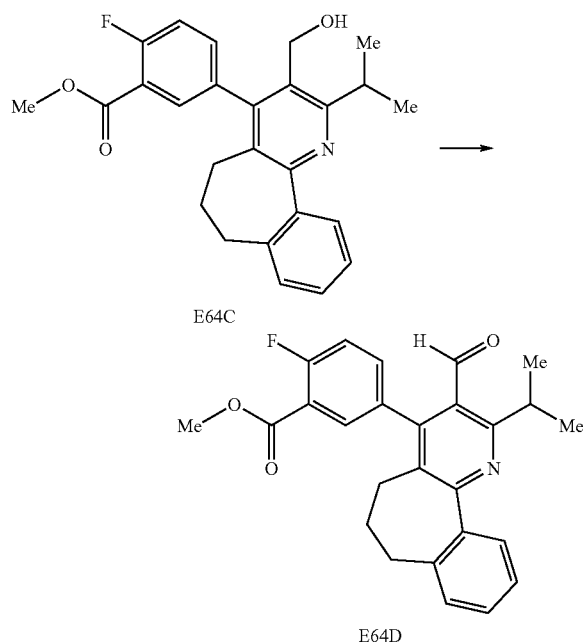

E64C

E64D

Dess-Martin periodinane (0.60 g, 1.3 mmol) was added to a solution of E64C (0.27 g, 0.64 mmol) in dichloromethane (which had been saturated with water, 2.3 mL). The reaction was stirred at ambient temperature for 50 min and the reaction was diluted with ether and Na$_2$S$_2$O$_3$ solution (1.11 g, in 1.8 mL saturated NaHCO$_3$ and 0.6 mL water). The mixture was stirred vigorously for 10 min and was transferred to a separatory funnel with ether. The mixture was extracted with ether (2×30 mL). The combined organic layers were washed with saturated NaHCO$_3$, water, and brine; dried over MgSO$_4$; and concentrated to afford 0.27 g of crude product. The residue was purified over silica gel eluting with dichloromethane to afford E64D (0.15 g, 57% yield): HPLC (method 7) $t_R$=2.6 min; LCMS (ESI, pos. ion spectrum) m/z 418 (M+H).

236

Part E:

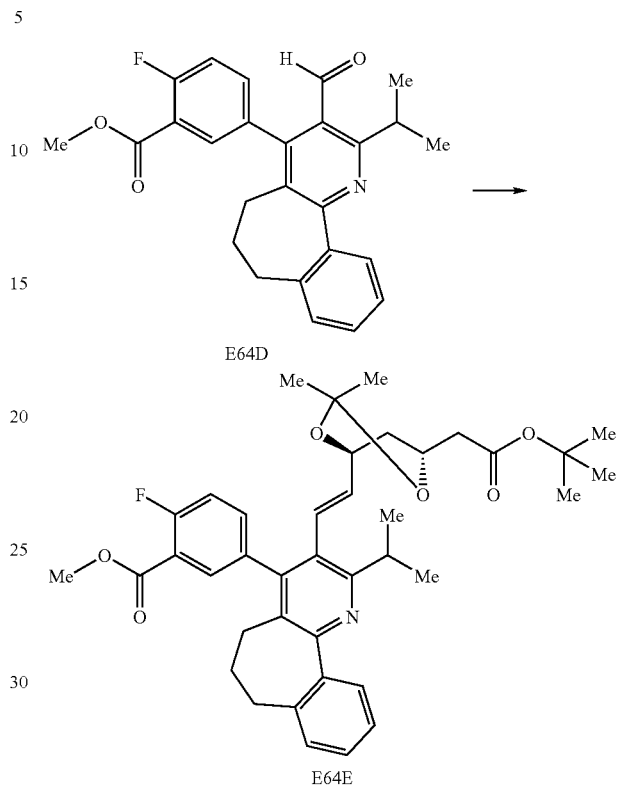

E64D

E64E

Lithium (bis)trimethylsilylamide (1.0M in THF, 0.48 mL, 0.48 mmol) was slowly added over 3 min to a stirred solution of E64D (0.14 g, 0.33 mmol) and E1D (0.18 g, 0.39 mmol) in THF (3.3 mL) at −78° C. The reaction was stirred for 1 h at −78° C. and then was quenched with 25%-saturated ammonium chloride. The mixture was extracted with ethyl acetate. The combined organic layers were washed with saturated NaHCO$_3$, water, and brine; dried over MgSO$_4$; and evaporated to afford 0.25 g of crude product. Purification of the residue over silica gel eluting with ethyl acetate/dichloromethane afforded E64E (0.20 g, 85%): HPLC (method 7) $t_R$=2.7 min; LCMS (ESI, pos. ion spectrum) m/z 644 (M+H).

Part F:

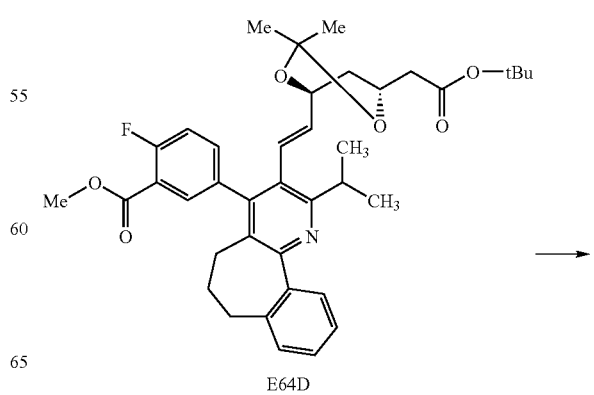

E64D

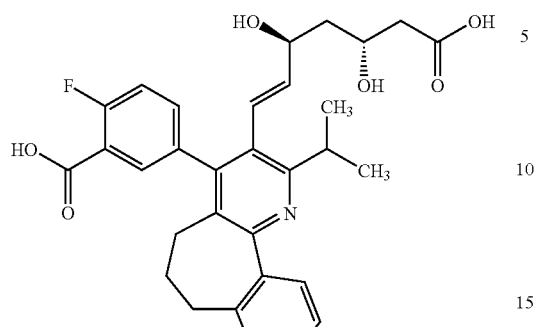

Ex. 64 title compound

A solution of E64D (50 mg, 0.08 mmol) and aqueous hydrochloric acid (6 N, 0.037 mL, 0.22 mmol) in THF (0.30 mL) was stirred at ambient temperature for 65 min. Aqueous sodium hydroxide (1 N, 0.39 mL, 0.39 mmol) was then added and the resultant mixture was stirred vigorously for 5 h. The reaction mixture was evaporated in vacuo and the residue was purified over C-18 silica gel to afford the title compound as the disodium salt (40 mg, 89%): HPLC (method 7) $t_R$=2.0 min; LCMS (ESI, pos. ion spectrum) m/z 534 (M+H).

Example 65

6-Heptenoic acid, 7-[4-(4-fluorophenyl)-6,7-dihydro-2-(1-methylethyl)-5H-pyrido[3,2-d][2]benzazepin-3-yl]-3,5-dihydroxy-, (3R,5S,6E)-

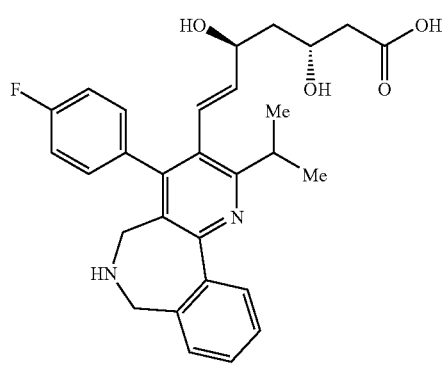

Part A:

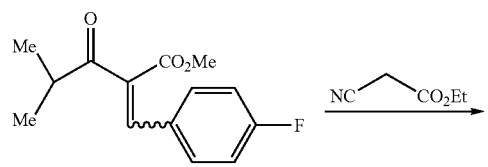

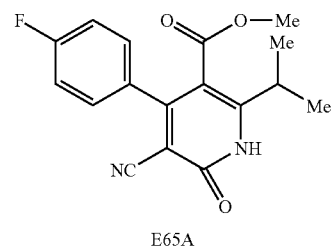

E65A

A mixture of methyl 2-[(4-fluorophenyl)methylene]-4-methyl-3-oxo-pentanoic acid (60 g, 240 mL, 240 mmol), ethyl cyanoacetate (20.4 g, 19.2 mL, 180 mmol) and ammonium acetate (13.8 g, 180 mmol) was heated at 140° C. to 160° C. without a reflux condenser. After 16 h, the reaction was cooled and washed with water. The organic layer was partially purified by silica gel chromatography (ethyl acetate/hexane) to afford 22.4 g of a residue which was recrystallized at 4° C. from ethyl acetate (300 mL) and hexane (300 mL) to afford E65A (3.6 g, 6% yield).

Part B:

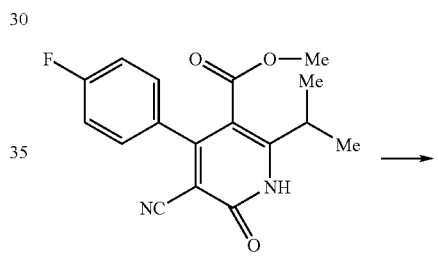

E65A

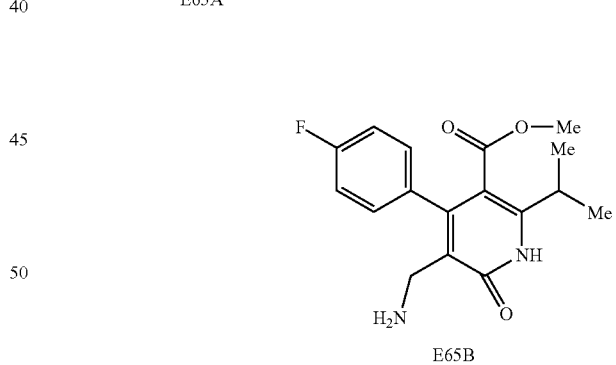

E65B

To a solution of E65A (3.6 g, 11.4 mmol) in ethanol (91 mL) were added HCl (2 N, 5.8 mL, 11.6 mmol) and 10% palladium on carbon (370 mg). The reaction was stirred under 50 psig of hydrogen. After 3 days and 4 days, the reaction was charged with an additional 200- and 400-mg portions of 10% palladium on carbon, respectively. After 5 days, the reaction mixture was filtered through Celite® to afford E65B (3.94 g, 98% yield) as the dihydrochloride salt after evaporation of the solvent: HPLC (method 7) $t_R$=1.52 min; LCMS (ESI, pos. ion spectrum) m/z 318 (M+H).

Part C:

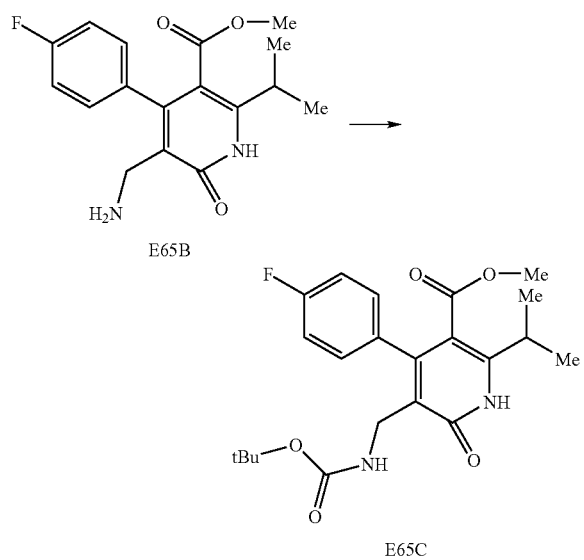

Diisopropylethylamine (3.3 g, 4.6 mL, 23.6 mmol) and a solution of di-tert-butyl dicarbonate (2.75 g, 12.9 mmol) in dichloromethane (14 mL) were sequentially added to a 0° C., stirred solution of E65B (3.9 g, 11.1 mmol) in dichloromethane (48 mL). The reaction was stirred at ambient temperature for 20 h. The mixture was purified by silica gel chromatography using MeOH/dichloromethane to afford E65C (3.93 g, 85%): HPLC (method 7) $t_R$=2.2 min; LCMS (ESI, pos. ion spectrum) m/z 419 (M+H).

Part D:

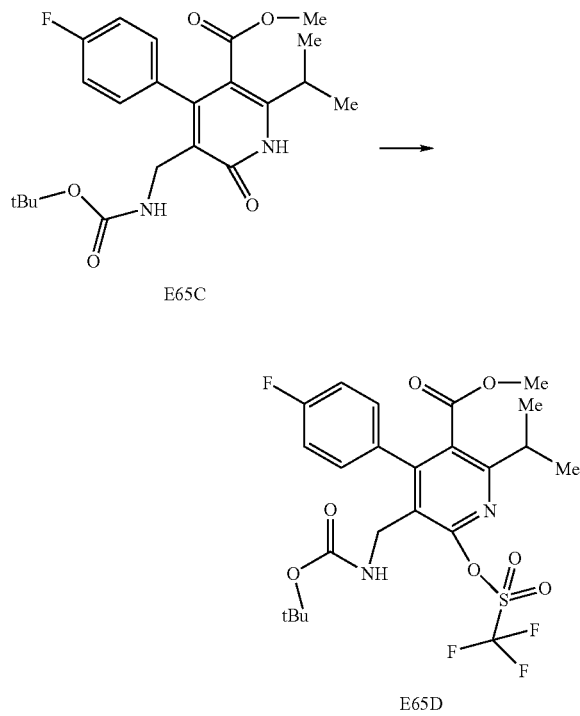

Triflic anhydride (1.7 mL, 10 mmol) was added to a stirred, 0° C. solution of E65C (3.64 g, 8.7 mmol) and pyridine (11.7 mL, 0.14 mol) in dichloromethane (105 mL). The ice bath was removed and the reaction was stirred at ambient temperature for 75 min. The reaction mixture was transferred to a separatory funnel with 2.5% NaHCO$_3$ and dichloromethane. The mixture was extracted with dichloromethane (3×80 mL). The combined organic layers were washed with water (4×50 mL), dried over MgSO$_4$ and concentrated to afford 5.2 g of crude product. Purification of the residue over silica gel eluting with ether containing 1% TEA afforded E65D (4.4 g, 89% yield): HPLC (method 7) $t_R$=2.5 min; LCMS (ESI, pos. ion spectrum) m/z 565 (M+H).

Part E:

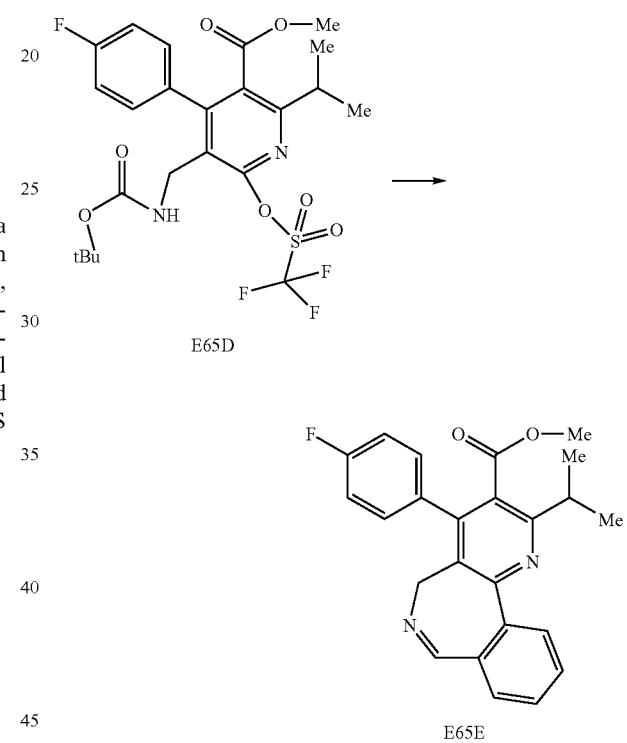

Nitrogen was bubbled through a mixture of E65D (1.37 g, 2.5 mmol), 2 M K$_2$CO$_3$ (2.5 mL, 5.0 mmol), LiCl (210 mg, 5.0 mmol), and 2-formylbenzeneboronic acid (0.75 g, 5.0 mmol) in dioxane (27 mL) for 15 min. Bis(triphenylphosphine)palladium (II) dichloride (216 mg) was then added and the solution was refluxed. After 6 h, the reaction was cooled to room temperature and transferred to a separatory funnel with ethyl acetate and water. The mixture was extracted with ethyl acetate (2×80 mL). The combined organic layers were washed with water and brine, dried over MgSO$_4$ and concentrated to afford 1.86 g of a residue. Trifluoroacetic acid (25 mL) and dichloromethane (50 mL) were added to the residue and the solution was stirred at ambient temperature for 50 min. The mixture was concentrated under reduced pressure. The crude product was purified over silica gel eluting with ethyl acetate/hexane to afford E65E (0.72 g, 74% yield): HPLC (method 7) $t_R$=2.2 min; LCMS (ESI, pos. ion spectrum) m/z 389 (M+H).

Part F:

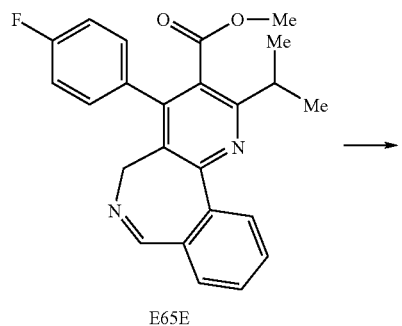

E65E

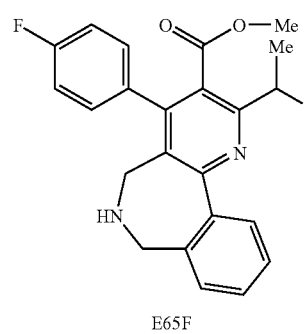

E65F

Sodium borohydride (85 mg, 2.1 mmol) was added portionwise to a 40° C., stirred solution of E65E (0.72 g, 1.8 mmol) in dry methanol (18 mL). The mixture was refluxed for 2 h, cooled to room temperature and transferred to a separatory funnel with ethyl acetate and water. The aqueous layer was adjusted to pH 10 with 2.5 N NaHCO$_3$. The mixture was extracted with ethyl acetate (2×40 mL). The combined organic layers were washed with brine, dried over MgSO$_4$ and concentrated to afford E65F (0.67 g, 93% yield). This material was used in the next step without further purification.

Part G:

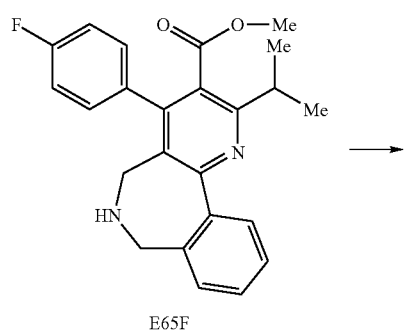

E65F

-continued

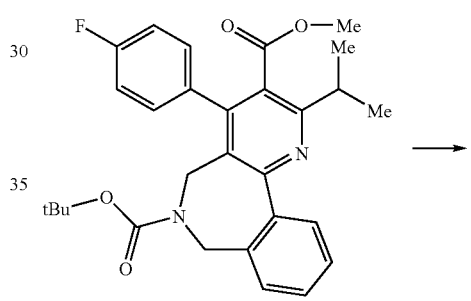

E65G

Diisopropylethylamine (16 mg, 0.025 mL, 0.13 mmol) and a solution of di-tert-butyl dicarbonate (28 mg, 0.12 mmol) in dichloromethane (0.20 mL) were sequentially added to a stirred, 0° C. solution of E65F (43 mg, 0.11 mmol) in dichloromethane (0.5 mL). The reaction was stirred at ambient temperature for 19 h. The reaction was purified by silica gel chromatography (ethyl acetate/dichloromethane) to afford E65G (42 mg, 79%): HPLC (method 7) t$_R$=2.7 min; LCMS (ESI, pos. ion spectrum) m/z 505 (M+H).

Part H:

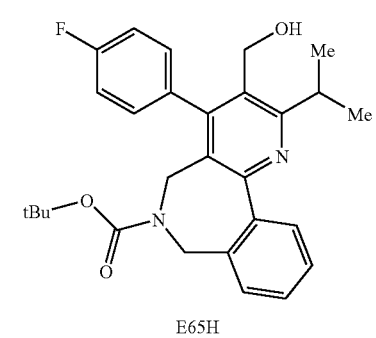

E65G

E65H

Diisobutylaluminum hydride (1.5 M in toluene, 0.19 mL, 0.28 mmol) was added to a stirred, −78° C. solution of E65G (42 mg, 0.08 mmol) in dichloromethane (1.3 mL). The reaction was stirred at −78° C. for 2 h and an additional 0.2 mL (0.30 mmol) of DIBAL-H was added. The reaction was stirred for an additional 1 h at −78° C. and was then quenched with methanol. Saturated Rochelle's salt (0.3 mL) and water (2.0 mL) were added and the mixture was stirred vigorously for 1.5 h. The layers were separated and the aqueous layer was extracted with dichloromethane (3×10 mL). The combined organic layers were dried over MgSO$_4$ and concentrated to afford 43 mg of crude product. Purification of the residue over silica gel eluting with ethyl acetate/dichloromethane provided E65H (26 mg, 71% yield): HPLC (method 7) $t_R$=2.5 min; LCMS (ESI, pos. ion spectrum) m/z 463 (M+H).

Part I:

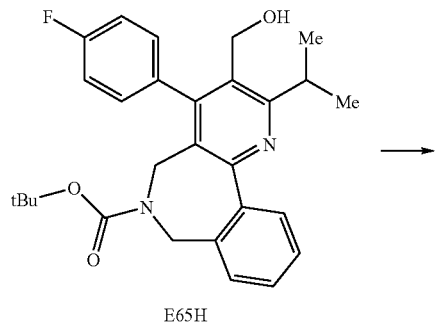

E65H

→

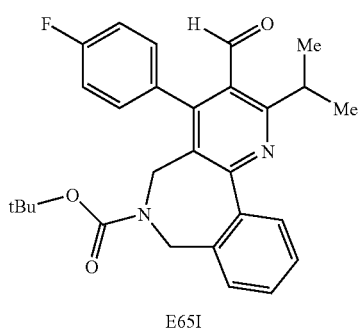

E65I

Dess-Martin periodinane (103 mg, 0.22 mmol) was added to a solution of E65H (52 mg, 0.11 mmol) in water-saturated dichloromethane (0.4 mL). The reaction was stirred at ambient temperature for 1 h and was then diluted with ether. A solution of sodium thiosulfate (0.19 g) in saturated NaHCO₃ (0.30 mL) and water (0.10 mL) was added. After stirring vigorously for 10 min, the reaction mixture was transferred to a separatory funnel. The mixture was extracted with ether (2×15 mL). The combined organic layers were washed with saturated NaHCO₃, water, and brine, dried over Na₂SO₄ and concentrated to afford 48 mg of crude product. Purification of the residue over silica gel eluting with dichloromethane afforded E65I (34 mg, 69% yield): HPLC (method 7) $t_R$=2.66 min; LCMS (ESI, pos. ion spectrum) m/z 461 (M+H).

Part J:

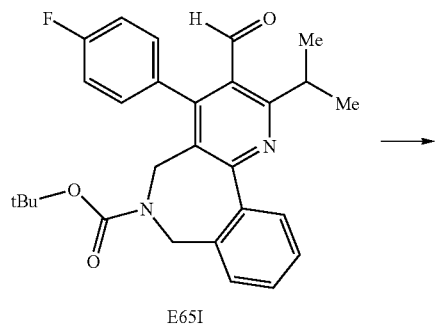

E65I

→

-continued

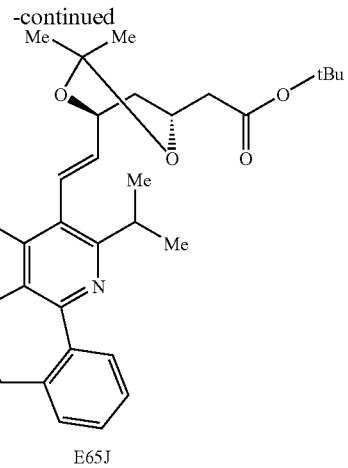

E65J

Lithium (bis)trimethylsilylamide (1.0M in THF, 0.11 mL, 0.11 mmol) was added over 10 min to a stirred, −78° C. solution of E65I (34 mg, 0.074 mmol) and E1D (40 mg, 0.089 mmol) in THF (0.75 mL). The reaction was stirred for 85 min at −78° C. and was quenched with 25%-saturated ammonium chloride. The mixture was extracted with ethyl acetate. The organic layer was washed with saturated NaHCO₃ and brine, dried over Na₂SO4 and concentrated to afford 61 mg of crude product. Purification of the residue over silica gel eluting with ethyl acetate/hexane afforded E65J (45 mg, 89%): HPLC (method 7) $t_R$=3.0 min; LCMS (ESI, pos. ion spectrum) m/z 687 (M+H).

Part K:

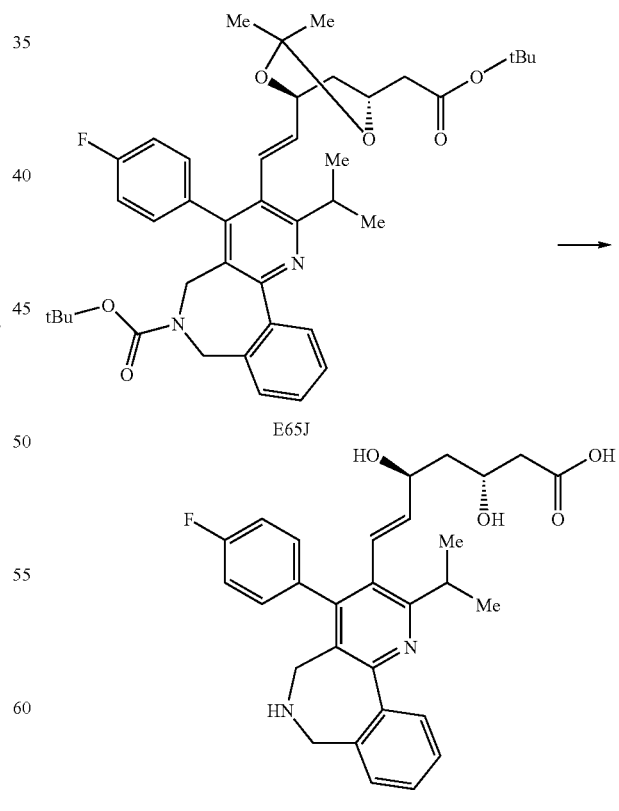

E65J

Ex. 65 title compound

A solution of E65J (45 mg, 0.066 mmol) and aqueous hydrochloric acid (6 N, 0.23 mL, 1.4 mmol) in THF (0.25 mL)

was stirred at ambient temperature for 15 min. Aqueous sodium hydroxide (1 N, 3.3 mL, 3.3 mmol) was then added and the resultant mixture was stirred for 15 min. The reaction mixture was purified over C-18 silica gel to afford the title compound as the sodium salt (26 mg, 76%): HPLC (method 3) $t_R$=2.9 min; LCMS (ESI, pos. ion spectrum) m/z 491 (M+H).

Example 66

6-Heptenoic acid, 7-[4-(4-fluorophenyl)-6,7-dihydro-2-(1-methylethyl)-6-(methylsulfonyl)-5H-pyrido[3,2-d][2]benzazepin-3-yl]-3,5-dihydroxy-, (3R,5S,6E)-

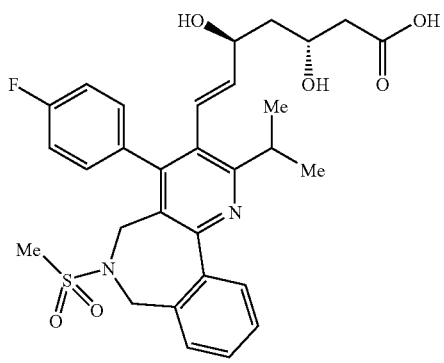

Part A:

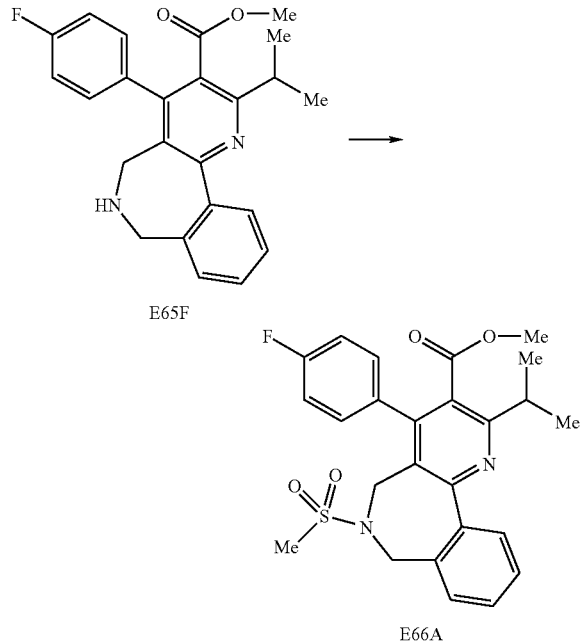

Methanesulfonyl chloride (130 mg, 0.086 mL, 1.1 mmol) and pyridine (0.11 mL, 1.4 mmol) were sequentially added to a stirred solution of E65F (135 mg, 0.35 mmol) in dichloromethane (3.5 mL). Then reaction was stirred at ambient temperature for 2 h. Additional mesyl chloride (0.086 mL) and pyridine (0.11 mL) were added. After an additional 1.5 h, the reaction was transferred to a separatory funnel with dichloromethane and water. The mixture was extracted with dichloromethane (2×20 mL). The combined organic layers were washed with water, dried over MgSO$_4$ and concentrated to afford 0.34 g of crude product. Purification of the residue over silica gel eluting with ethyl acetate/hexane afford E66A (133 mg, 82%): HPLC (method 7) $t_R$=2.4 min; LCMS (ESI, pos. ion spectrum) m/z 469 (M+H).

Part B:

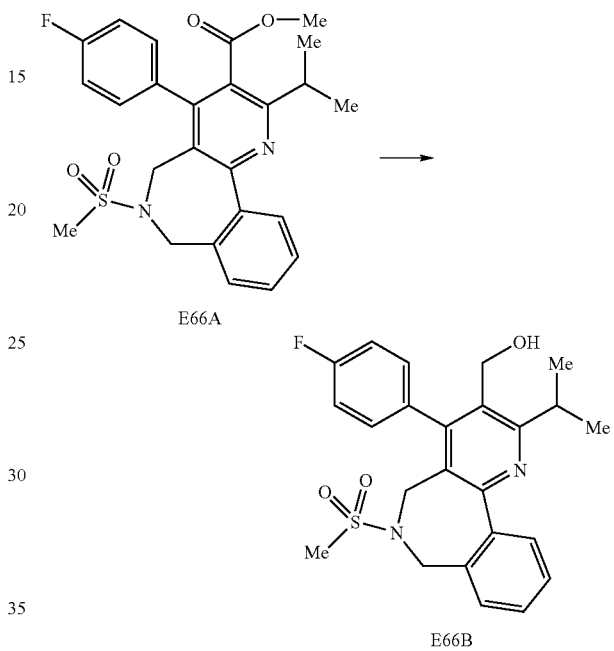

Diisobutylaluminum hydride (1.5 M in toluene, 0.98 mL, 1.5 mmol) was added to a stirred, −78° C. solution of E66A (133 mg, 0.28 mmol) in dichloromethane (4.9 mL). The reaction was stirred at −78° C. for 30 min and was quenched with methanol. Saturated Rochelle's salt (1.0 mL) and water (10 mL) were added and the mixture was stirred vigorously for 1 h. The aqueous layer was extracted with dichloromethane (3×40 mL). The combined organic layers were dried over MgSO$_4$ and concentrated to afford E66B (130 mg, 100% yield) which was used in the next step without further purification: HPLC (method 7) $t_R$=2.2 min; LCMS (ESI, pos. ion spectrum) m/z 441 (M+H).

Part C:

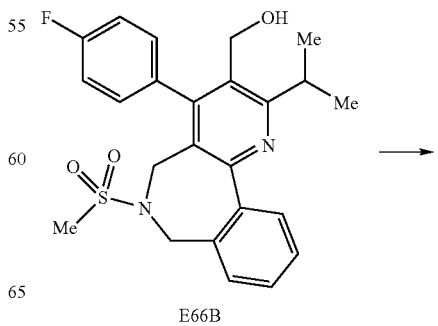

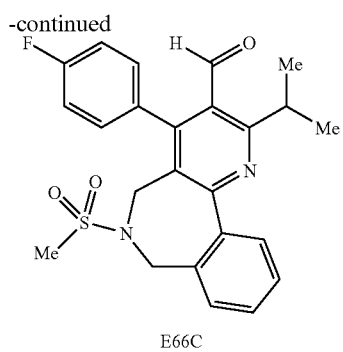

E66C

Dess-Martin periodinane (250 mg, 0.51 mmol) was added to a solution of E66B (130 mg, 0.28 mmol) in water-saturated dichloromethane (1.5 mL). The reaction was stirred at ambient temperature for 3 h and was diluted with ether. A solution of sodium thiosulfate (0.16 g) in saturated NaHCO$_3$ (7.5 mL) and water (2.5 mL) was added. The mixture was vigorously stirred for 10 min, and was transferred to a separatory funnel. The mixture was extracted with ether (2×30 mL). The combined organic layers were washed with saturated NaHCO$_3$, water, and brine, dried over MgSO$_4$ and concentrated to afford 88 mg of crude product. Purification of the residue over silica gel eluting with dichloromethane afforded E66C (35 mg, 27% yield): HPLC (method 7) $t_R$=2.0 min; LCMS (ESI, pos. ion spectrum) m/z 439 (M+H).

Part D:

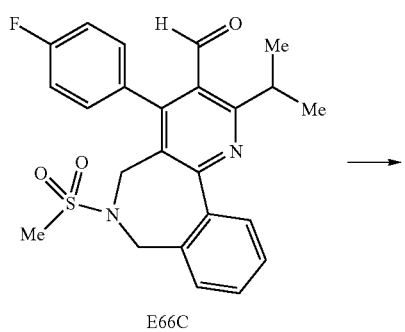

E66C

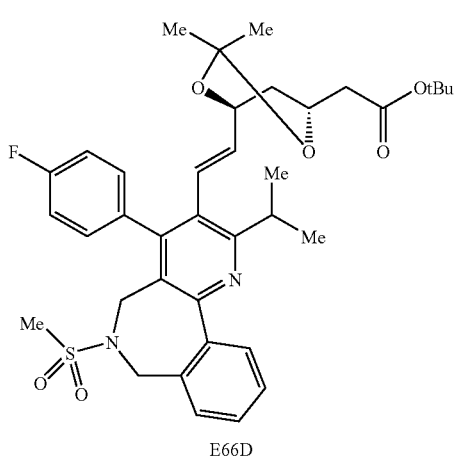

E66D

Lithium (bis)trimethylsilylamide (1.0 M in THF, 0.12 mL, 0.12 mmol) was added over 10 min to a solution of E66C (35 mg, 0.08 mmol) and E1D (44 mg, 0.097 mmol) in THF (0.85 mL) stirred at −78° C. After 1 h, the reaction was quenched with 25%-saturated ammonium chloride. The mixture was extracted with ethyl acetate. The combined organic layers were washed with saturated NaHCO$_3$ and brine, dried over MgSO$_4$ and concentrated to afford 64 mg of crude product. Purification of the residue over silica gel eluting with ethyl acetate/hexanes afforded E66D (45 mg, 85%): HPLC (method 7) $t_R$=2.7 min; LCMS (ESI, pos. ion spectrum) m/z 665 (M+H).

Part E:

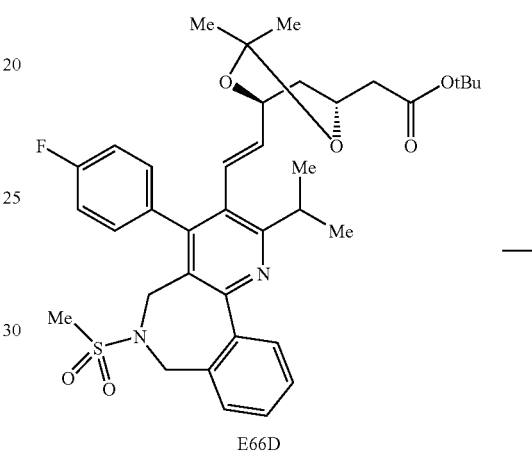

E66D

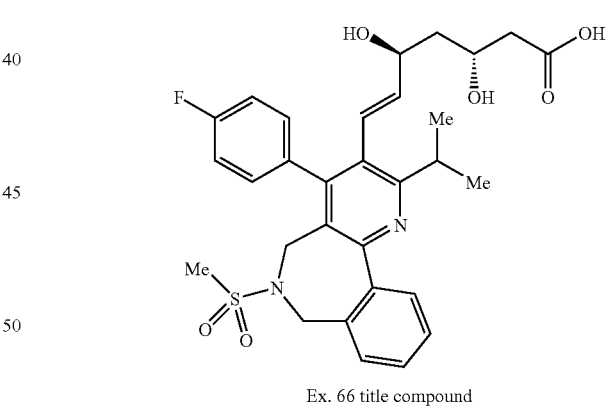

Ex. 66 title compound

A solution of E66D (45 mg, 0.068 mmol) and aqueous hydrochloric acid (6 N, 0.026 mL, 0.15 mmol) in THF (0.30 mL) was stirred at 0° C. for 1 h and then at ambient temperature for an additional 2 h. The reaction was cooled to 0° C. and aqueous sodium hydroxide (1 N, 0.29 mL, 0.29 mmol) and THF (0.7 mL) were added. The resultant mixture was stirred at ambient temperature for 3 h. The reaction was concentrated under reduced pressure and the residue was purified over C-18 silica gel to afford the title compound (22 mg, 56%) as the sodium salt: HPLC (method 3) $t_R$=2.1 min; LCMS (ESI, pos. ion spectrum) m/z 569 (M+H).

Example 67

6-Heptenoic acid, 7-[6-acetyl-4-(4-fluorophenyl)-6,7-dihydro-2-(1-methylethyl)-5H-pyrido[3,2-d][2]benzazepin-3-yl]-3,5-dihydroxy-, (3R,5S,6E)-

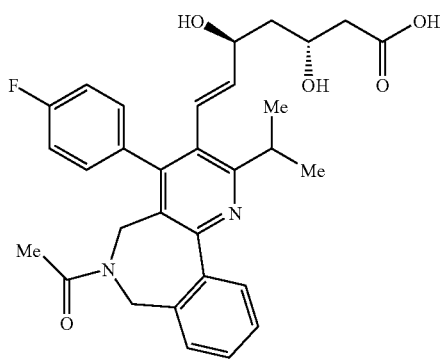

Part A:

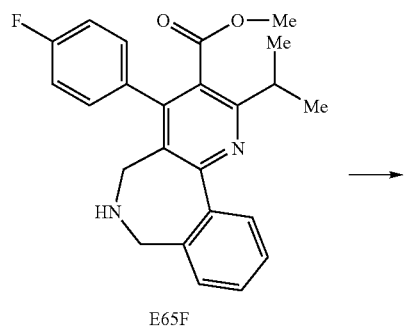

E65F

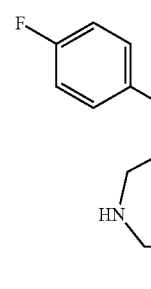

E67A

Diisobutylaluminum hydride (1.5 M in toluene, 30 mL, 45 mmol) was added dropwise over 1.5 h to a solution of E65F (2.3 g, 5.8 mmol) in dichloromethane (105 mL) stirred at −78° C. The reaction was stirred for an additional 1 h at −78° C. and was quenched with MeOH. Saturated Rochelle's salt (25 mL) and water (500 mL) were added. The mixture was stirred vigorously at ambient temperature until the layers separated. The mixture was transferred to a separatory funnel and extracted with dichloromethane (3×100 mL). The combined organic layers were dried over MgSO$_4$ and concentrated to afford E67A (1.9 g, 88% yield). This material was used in the next step without further purification.

Part B:

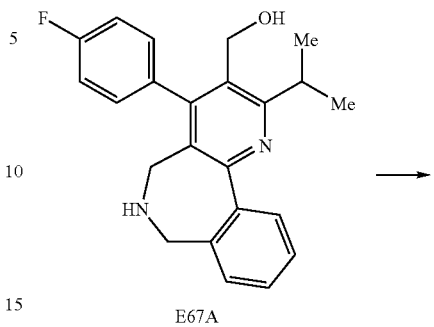

E67A

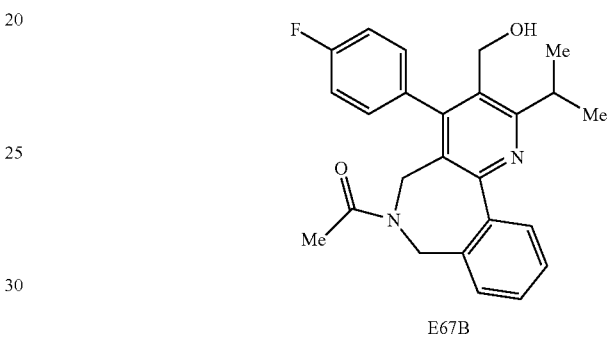

E67B

Acetyl chloride (38 mg, 0.034 mL, 0.49 mmol) and diisopropylethylamine (77 mg, 0.125 mL, 0.60 mmol) were sequentially added to a stirred suspension of E67A (0.15 g, 0.41 mmol) in dichloromethane (4 mL). After 1 h, the reaction was transferred to a separatory funnel with dichloromethane and water. The mixture was extracted with dichloromethane (2×20 mL). The combined organic layers were washed with water and brine, dried over MgSO$_4$ and concentrated to afford 0.17 g of crude product. Purification of the residue over silica gel eluting with ethyl acetate/dichloromethane afforded E67B (105 mg, 63%): HPLC (method 7) t$_R$=2.2 min; LCMS (ESI, pos. ion spectrum) m/z 405 (M+H).

Part C:

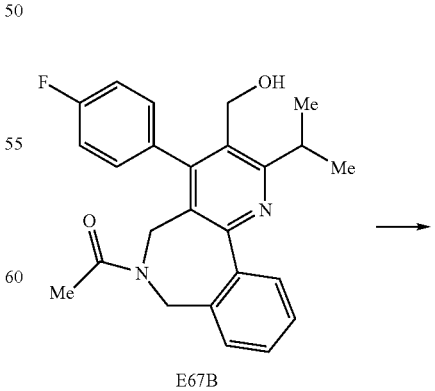

E67B

-continued

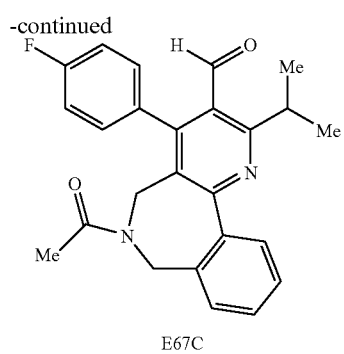
E67C

Dess-Martin periodinane (250 mg, 0.51 mmol) was added to a solution of E67B (105 mg, 0.26 mmol) in water-saturated dichloromethane (2.0 mL). After 1 h, the reaction was diluted with ether. A solution of sodium thiosulfate (0.14 g) in saturated NaHCO$_3$ (7.5 mL) and water (2.5 mL) was added. The mixture was stirred vigorously for 10 min and was transferred to a separatory funnel. The mixture was extracted with ether (2×30 mL). The combined organic layers were washed with saturated NaHCO$_3$, water, and brine, dried over MgSO$_4$ and concentrated to afford 120 mg of crude product. Purification of the residue over silica gel eluting with ethyl acetate/dichloromethane afforded E67C (93 mg, 89% yield): HPLC (method 7) t$_R$=2.4 min; LCMS (ESI, pos. ion spectrum) m/z 403 (M+H).

Part D:

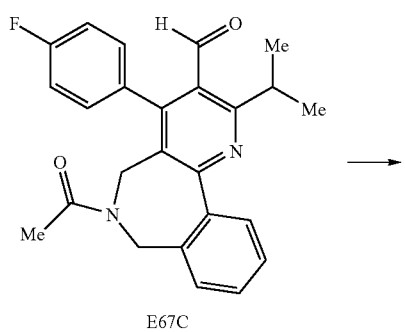
E67C

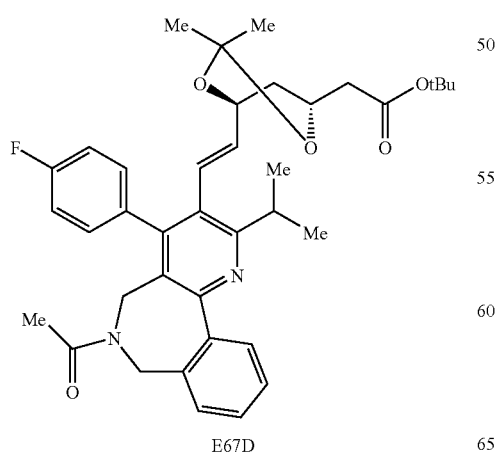
E67D

Lithium (bis)trimethylsilylamide (1.0 M in THF, 0.34 mL, 0.34 mmol) was added over 10 min to a solution of E67C (93 mg, 0.23 mmol) and E1D (124 mg, 0.27 mmol) in THF (2.4 mL) stirred at −78° C. After 1.5 h at −78° C., the reaction was quenched with 25%-saturated ammonium chloride. The mixture was extracted with ethyl acetate. The combined organic layers were washed with saturated NaHCO$_3$, water and brine, dried over MgSO$_4$ and concentrated to afford 190 mg of crude product. Purification of the residue over silica gel eluting with ethyl acetate/hexanes afforded E67D (107 mg, 74%): HPLC (method 7) t$_R$=2.7 min; LCMS (ESI, pos. ion spectrum) m/z 629 (M+H).

Part E:

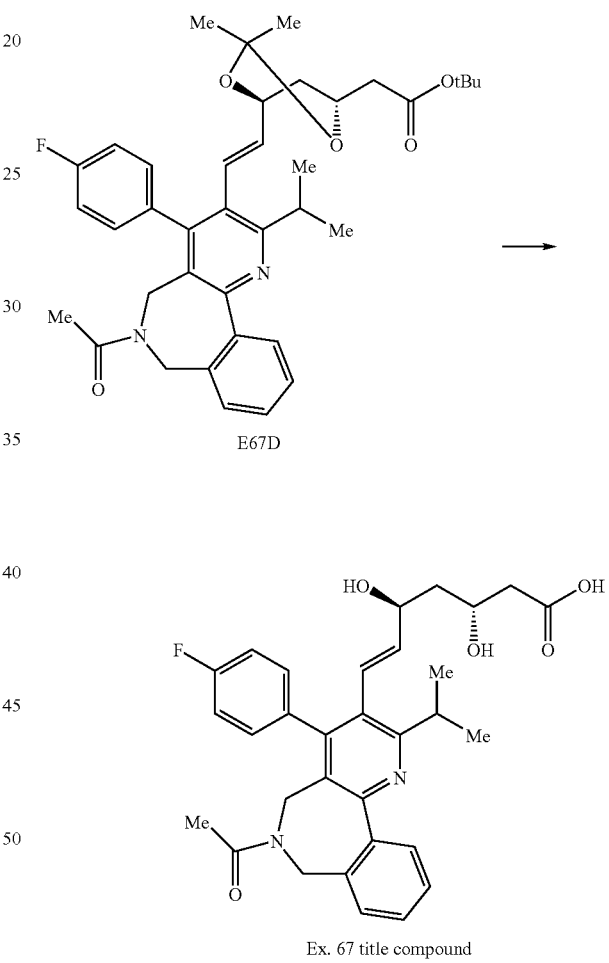

Ex. 67 title compound

A solution of E67D (107 mg, 0.17 mmol) and aqueous hydrochloric acid (6 N, 0.078 mL, 0.47 mmol) in THF (0.74 mL) was stirred at ambient temperature for 1.5 h. Aqueous sodium hydroxide (1 N, 0.70 mL, 0.70 mmol) was added. The resultant mixture was stirred vigorously at ambient temperature for 2.5 h. After evaporation in vacuo, the residue was purified over C-18 silica gel to afford the title compound as the sodium salt (67 mg, 68%): HPLC (method 3) t$_R$=2.15 min; LCMS (ESI, pos. ion spectrum) m/z 533 (M+H).

Example 68

6-Heptenoic acid, 7-[4-(4-fluorophenyl)-6,7-dihydro-2-(1-methylethyl)-7-oxo-5H-pyrido[3,2-d][2]benzazepin-3-yl]-3,5-dihydroxy-, (3R,5S,6E)-

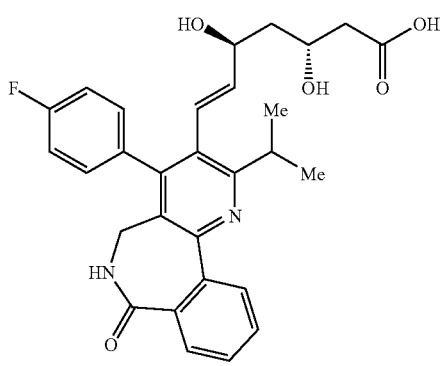

Part A:

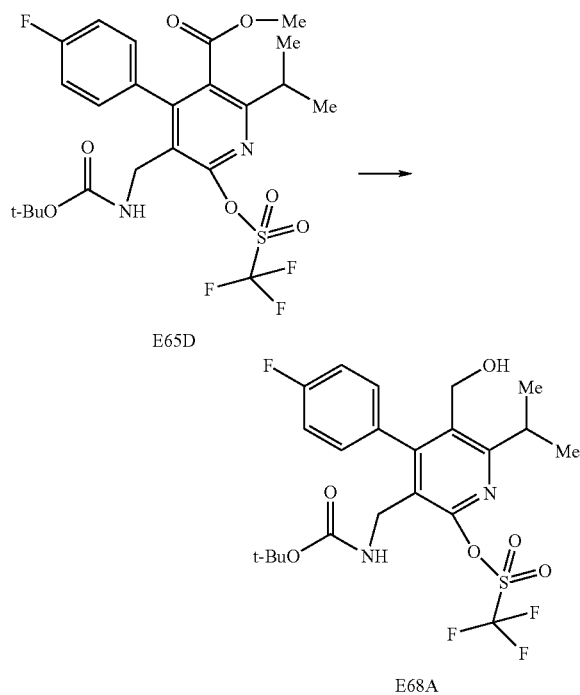

Diisobutylaluminum hydride (1.5 M in toluene, 1.8 mL, 2.7 mmol) was added dropwise over 10 min to a solution of E65D (0.26 g, 0.47 mmol) in dichloromethane (8 mL) stirred at −78° C. After 1 h, the reaction was quenched with MeOH. Saturated Rochelle's salt (0.64 mL) and water (13 mL) were added. The mixture was stirred vigorously at ambient temperature until the layers separated. The reaction was transferred to a separatory funnel and extracted with dichloromethane (3×30 mL). The combined organic layers were dried over MgSO$_4$ and concentrated to afford 0.26 g of crude product. Purification of the residue over silica gel eluting with ethyl acetate/dichloromethane afforded E68A (0.16 g, 67% yield): LCMS (ESI, pos. ion spectrum) m/z 523 (M+H).

Part B:

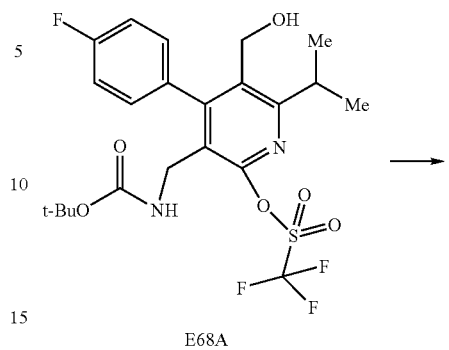

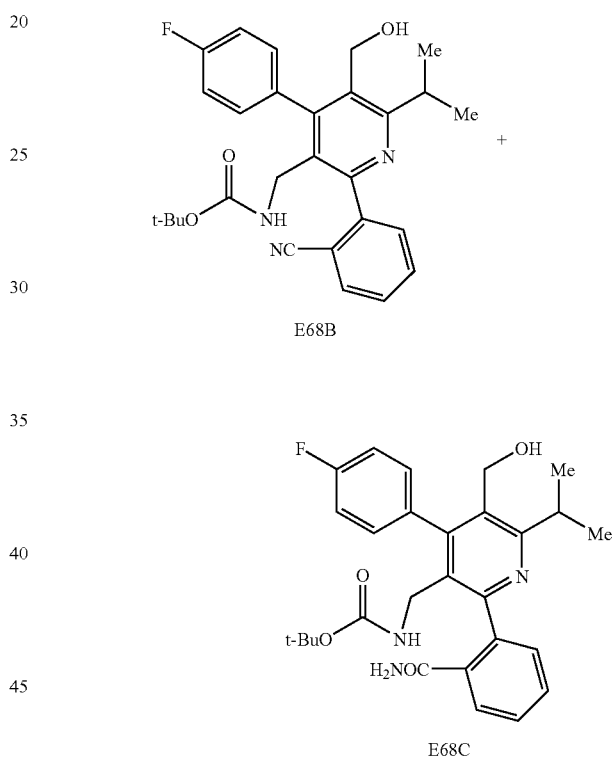

Nitrogen was bubbled through a mixture of E68A (0.16 g, 0.30 mmol), 2 M K$_2$CO$_3$ (0.61 mL, 1.2 mmol), LiCl (25 mg), and 2-cyanobenzeneboronic acid (0.088 g, 0.60 mmol) in dioxane (7.5 mL) for 15 min. Bis(triphenylphosphine)palladium dichloride (30 mg) was then added and the solution was refluxed. After 2 h, the reaction was cooled to room temperature and transferred to a separatory funnel with ethyl acetate and water. The mixture was extracted with ethyl acetate (2×30 mL). The combined organic layers were washed with brine, dried over MgSO$_4$ and concentrated to afford 0.23 g of crude product. Purification of the residue over silica gel eluting with ethyl acetate/dichloromethane afforded E68B [HPLC (method 7) t$_R$=2.21 min; LCMS (ESI, pos. ion spectrum) m/z 476 (M+H)] and E68C [HPLC (method 7) t$_R$=1.98 min, LCMS (ESI, pos. ion spectrum) m/z 494 (M+H)] (0.12 g combined yield). This mixture was used in the next step without further purification.

Part C:

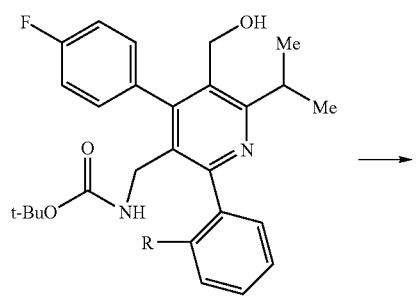

R = CN and CONH₂

E68B + E68C

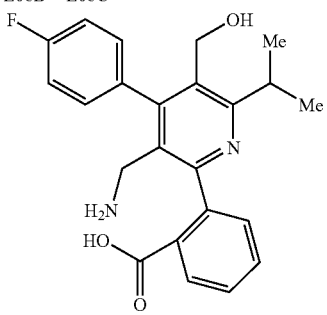

+

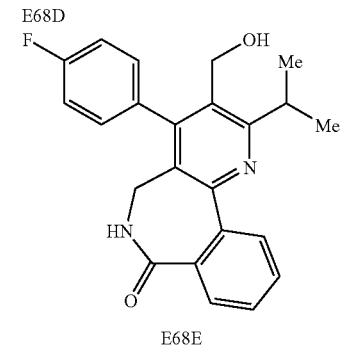

E68E

The product mixture from Part B (0.12 g, ~0.22 mmol) was refluxed in 6 N HCl (20 ml) After 4 h, the reaction was neutralized to pH 6 and evaporated in vacuo. The residue was purified over C-18 silica gel to afford E68D (25 mg, 29%) [HPLC (method 3) $t_R$=1.4 min; LCMS (ESI, pos. ion spectrum) m/z 395 (M+H)] and E68E (13 mg, 16%) [HPLC (method 3) $t_R$=2.2 min; LCMS (ESI, pos. ion spectrum) m/z 377 (M+H)].

Part D:

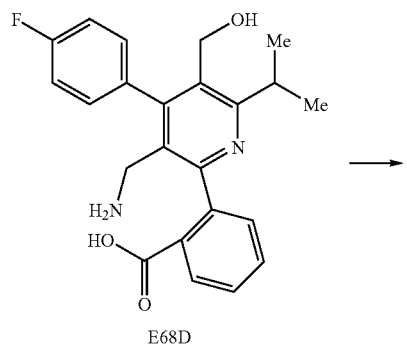

E68D

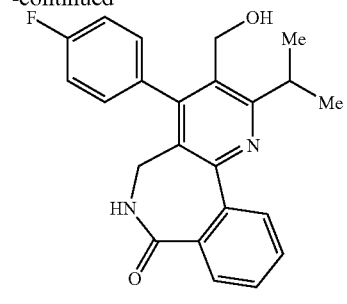

E68E

1-Hydroxybenzotriazole hydrate (15 mg, 0.063 mmol) and WSC (33 mg, 0.098 mmol) were added to a solution of E68D (25 mg, 0.063 mmol) in dichloromethane (2.0 mL). After 1 h, the reaction was chromatographed on a silica gel column eluting with ethyl acetate/dichloromethane to afford E68E (18.5 mg, 78%): HPLC (method 3) $t_R$=2.2 min; LCMS (ESI, pos. ion spectrum) m/z 377 (M+H).

Part E:

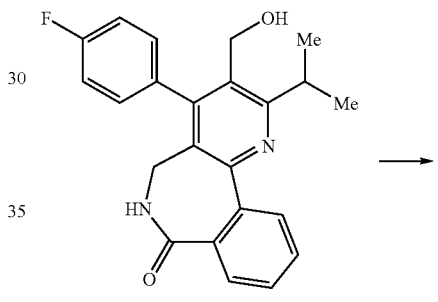

E68E

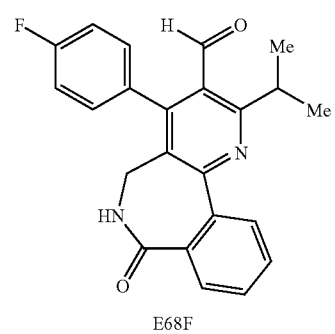

E68F

Dess-Martin periodinane (44 mg, 0.085 mmol) was added to a solution of E68E (33 mg, 0.092 mmol) in water-saturated dichloromethane (1.0 mL). After 1.3 h, the reaction was diluted with ether. A solution of sodium thiosulfate (0.16 g) in saturated NaHCO₃ (7.5 mL) and water (2.5 mL) was added. The mixture was stirred vigorously for 10 min and was transferred to a separatory funnel. The mixture was extracted with ether (2×30 mL). The combined organic layers were washed with saturated NaHCO₃, water, and brine, dried over MgSO₄ and concentrated to afford 30 mg of crude product. Purification of the residue over silica gel eluting with ethyl acetate/dichloromethane afforded E68F (25 mg, 77% yield). HPLC (method 7) $t_R$=2.33 min; LCMS (ESI, pos. ion spectrum) m/z 375 (M+H).

Part F:

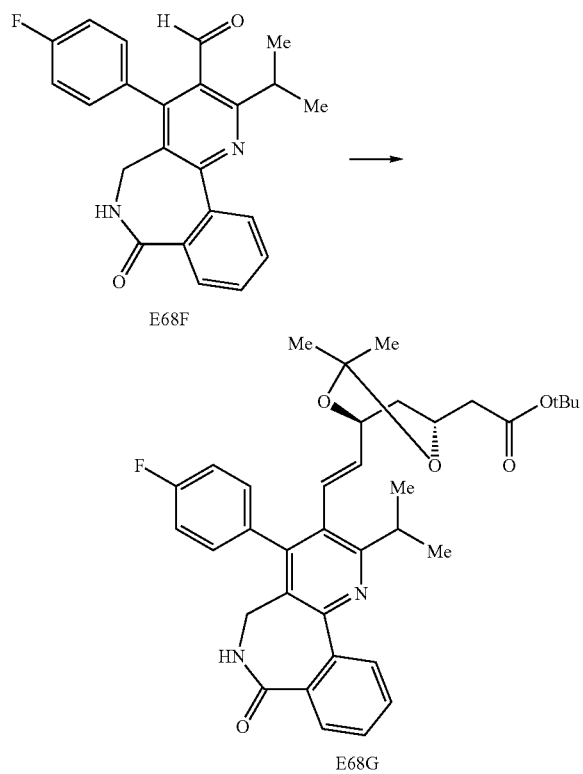

Lithium (bis)trimethylsilylamide (1.0 M in THF, 0.097 mL, 0.097 mmol) was added over 10 min to a solution of E68F (25 mg, 0.065 mmol) and E1D (35 mg, 0.078 mmol) in THF (0.7 mL) stirred at −78° C. After 2 h at −78° C., the reaction was quenched with 25%-saturated ammonium chloride. The mixture was extracted with ethyl acetate. The combined organic layers were washed with saturated NaHCO$_3$, water and brine, dried over MgSO$_4$ and concentrated to afford 70 mg of crude product. Purification of the residue over silica gel eluting with ethyl acetate/hexane afforded E68G (16 mg, 42%): HPLC (method 7) t$_R$=2.59 min; LCMS (ESI, pos. ion spectrum) m/z 601 (M+H).

Part G:

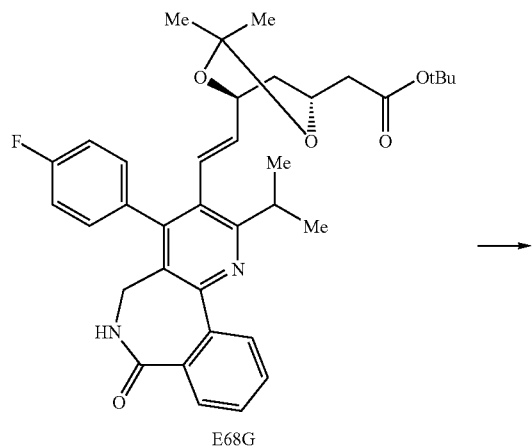

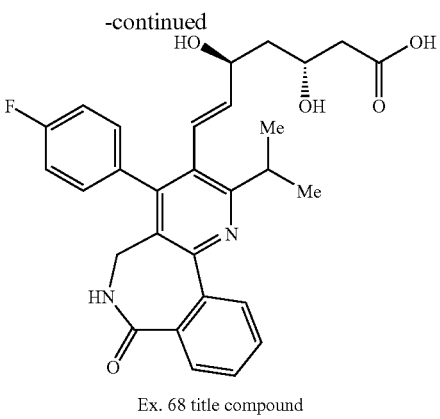

A solution of E68G (16 mg, 0.027 mmol) and aqueous hydrochloric acid (6 N, 0.012 mL, 0.072 mmol) in THF (0.15 mL) was stirred at ambient temperature for 1.5 h. Aqueous sodium hydroxide (1 N, 0.14 mL, 0.14 mmol) and THF (0.35 mL) were added. The resultant mixture was stirred vigorously at ambient temperature for 2.5 h. After evaporation in vacuo, the residue was purified over C-18 silica gel to afford the title compound as the sodium salt (9.8 mg, 69%): HPLC (method 3) t$_R$=2.14 min; LCMS (ESI, pos. ion spectrum) m/z 505 (M+H).

Example 69

6-Heptenoic acid, 7-[6-(aminocarbonyl)-4-(4-fluorophenyl)-6,7-dihydro-2-(1-methylethyl)-5H-pyrido[3,2-d][2]benzazepin-3-yl]-3,5-dihydroxy-, (3R,5S, 6E)-

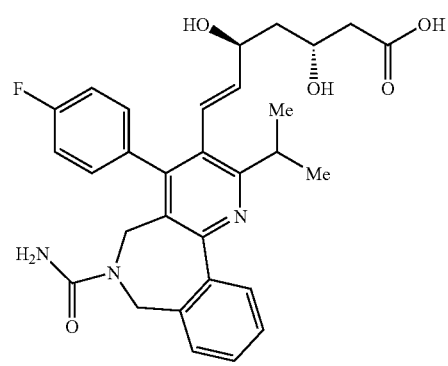

Part A:

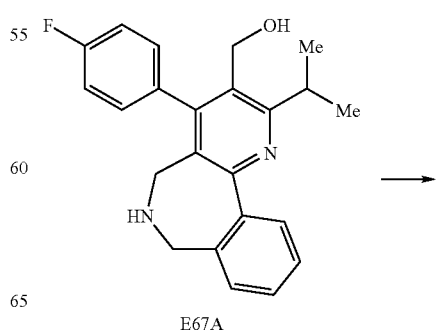

-continued

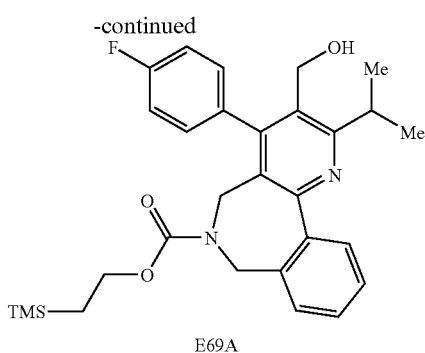

E69A 2-(Trimethylsilyl)ethyl 4-nitrophenyl carbonate (8.94 g, 31.6 mmol) was added to a solution of E67A (11.4 g, 31.5 mmol) and diisopropylethylamine (4.06 g, 5.50 mL, 31.6 mmol) in THF (55 mL) stirred at 0° C. After 15 min, the ice bath was removed. After 1d, additional 2-(trimethylsilyl) ethyl 4-nitrophenyl carbonate (2.72 g, 9.6 mmol) and diisopropylethylamine (1.65 mL, 9.6 mmol) were added and the reaction was stirred for an additional 3 d. The reaction was transferred to a separatory funnel with dichloromethane and water. The mixture was extracted with dichloromethane (2×). The combined organic layers were washed with water, dried over MgSO$_4$ and concentrated to afford 24.1 g of crude product. Purification of the residue over silica gel eluting with ethyl acetate/dichloromethane afforded E69A (11.2 g, 70% yield): HPLC (method 7) t$_R$=2.20 min; LCMS (ESI, pos. ion spectrum) m/z 507 (M+H).

Part B:

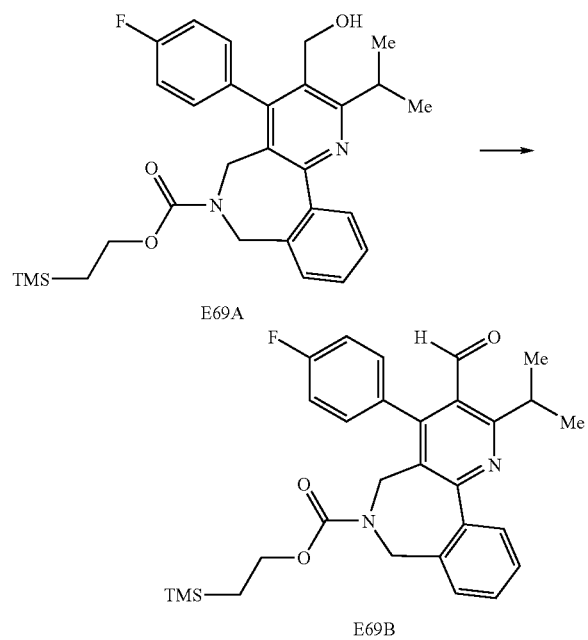

Dess-Martin periodinane (12.75 g, 26.5 mmol) was added to a solution of E69A (11.2 g, 22.1 mmol) in water-saturated dichloromethane (82 mL). The reaction was stirred at ambient temperature for 1 h and was diluted with ether. A solution of sodium thiosulfate (9.3 g) in saturated NaHCO$_3$ (16 mL) and water (8 mL) was added. The mixture was stirred vigorously for 30 min and the reaction mixture was transferred to a separatory funnel. The mixture was extracted with ether (2×500 mL). The combined organic layers were washed with saturated NaHCO$_3$, water, and brine, dried over MgSO$_4$ and concentrated to afford 15.5 g of crude product. Purification of the residue over silica gel eluting with ethyl acetate/dichloromethane afforded E69B (10.4 g, 93% yield): HPLC (method 7) t$_R$=2.83 min; LCMS (ESI, pos. ion spectrum) m/z 505 (M+H).

Part C:

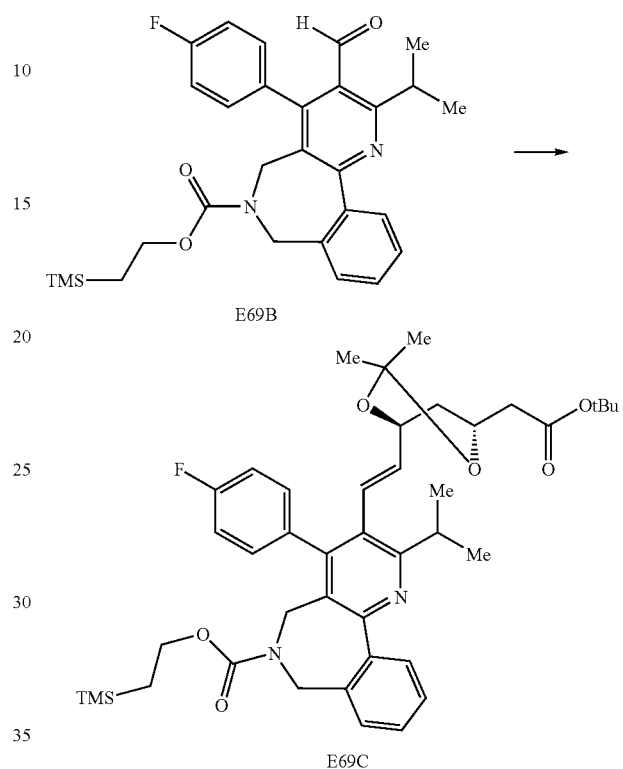

Lithium (bis)trimethylsilylamide (1.0 M in THF, 28.8 mL, 28.8 mmol) was slowly added over 10 min to a solution of E69B (10.4 g, 20.6 mmol) and E1D (11.2 g, 24.9 mmol) in THF (225 mL) stirred at −78° C. After 35 min at −78° C., the reaction was quenched with 25%-saturated ammonium chloride. The mixture was extracted with ethyl acetate. The combined organic layers were washed with saturated NaHCO$_3$, water and brine, dried over MgSO$_4$ and concentrated to afford 18.6 g of crude product. Purification of the residue over silica gel eluting with ethyl acetate/dichloromethane afforded E69C (15.2 g, 100%): HPLC (method 7) t$_R$=3.28 min; LCMS (ESI, pos. ion spectrum) m/z 731 (M+H).

Part D:

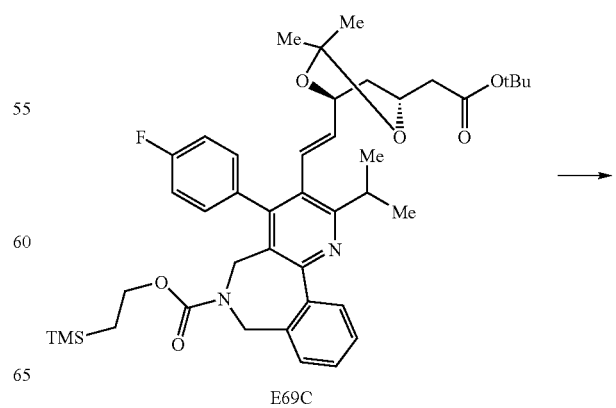

E69C

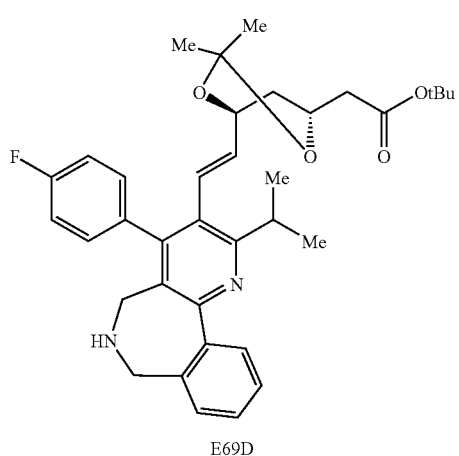

E69D

Tetrabutylammonium fluoride (1 M in THF, 50 mL, 50 mmol) was added to a solution of E69C (15.2 g, 20.6 mmol) in THF (50 mL). After 1 h, additional tetrabutylammonium fluoride (50 mL, 50 mmol) was added and the reaction was stirred at ambient temperature for an additional 30 min. The reaction was quenched with water and transferred to a separatory funnel. The mixture was extracted with ethyl acetate (2×300 mL). The combined organic layers were washed with water and brine, dried over MgSO$_4$ and concentrated to afford 14.0 g of crude product. Purification of the residue over silica gel eluting with MeOH/dichloromethane afforded E69D (12.0 g, 99%): HPLC (method 7) t$_R$=2.23 min; LCMS (ESI, pos. ion spectrum) m/z 587 (M+H).

Part E:

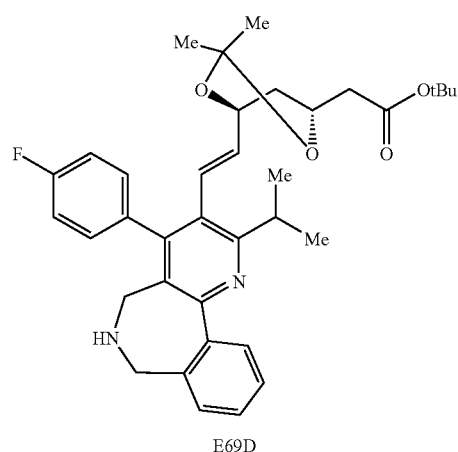

E69D

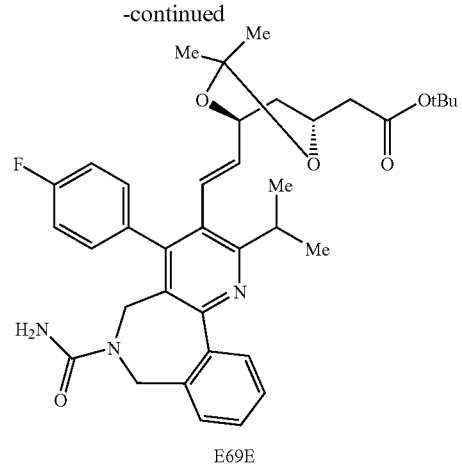

E69E

Trimethylsilyl isocyanate (11.4 mg, 0.013 mL, 0.083 mmol) was added to a stirred solution of E69D (27 mg, 0.046 mmol) in dichloromethane (0.5 mL). After 1.5 h, the reaction was transferred to a separatory funnel with dichloromethane and water. The mixture was extracted with dichloromethane (3×20 mL). The combined organic layers were dried over MgSO$_4$ and concentrated to afford E69E (30 mg, 100%). This was used in the next step without further purification.

Part F:

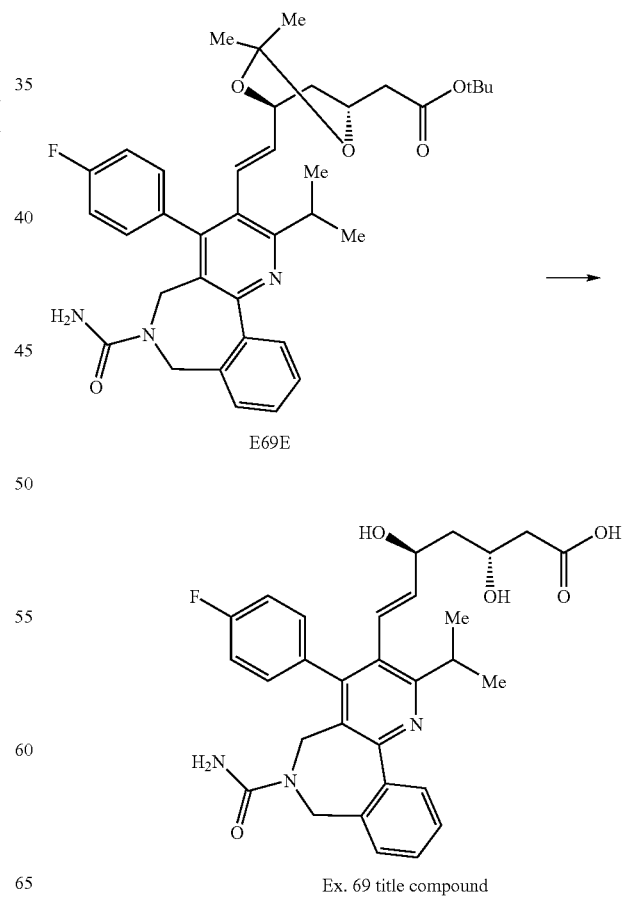

E69E

Ex. 69 title compound

A solution of E69E (30 mg, 0.047 mmol) and aqueous hydrochloric acid (6 N, 0.018 mL, 0.11 mmol) in THF (0.20 mL) was stirred at 0° C. for 1 h and then at ambient temperature for an additional 2 h. The reaction was cooled again to 0° C. and aqueous sodium hydroxide (1 N, 0.20 mL, 0.20 mmol) and THF (0.50 mL) were added. The resultant mixture was stirred vigorously at ambient temperature for 1.25 h. The reaction was evaporated and the residue was purified over C-18 silica gel to afford the title compound as the sodium salt (10.7 mg, 43%): HPLC (method 3) $t_R$=1.92 min; LCMS (ESI, pos. ion spectrum) m/z 534 (M+H).

Example 70

6-Heptenoic acid, 7-[6-[(dimethylamino)carbonyl]-4-(4-fluorophenyl)-6,7-dihydro-2-(1-methylethyl)-5H-pyrido[3,2-d][2]benzazepin-3-yl]-3,5-dihydroxy-, (3R,5S,6E)-

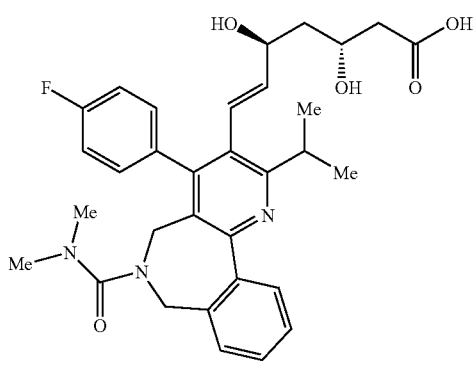

Part A:

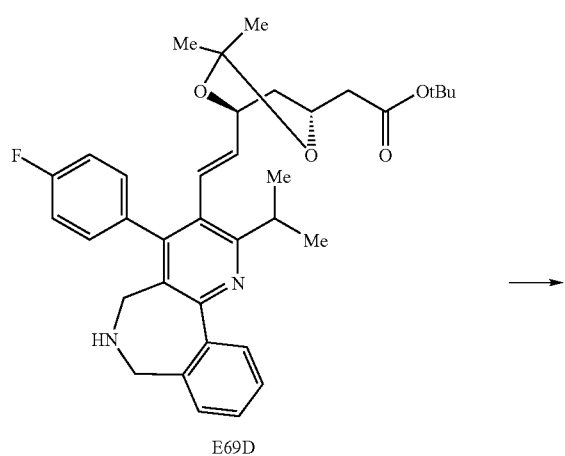

E69D

-continued

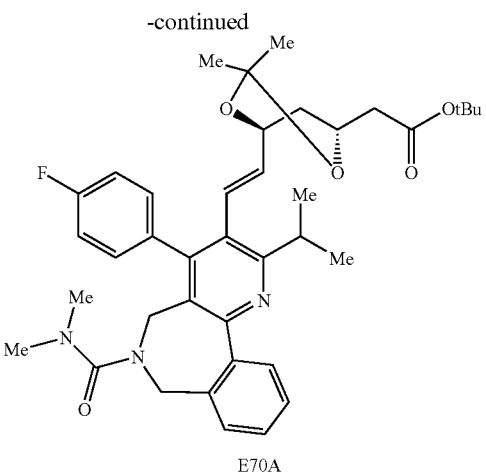

E70A

Dimethylcarbamoyl chloride (42 mg, 0.036 mL, 0.39 mmol) and diisopropylethylamine (66 mg, 0.089 mL, 0.51 mmol) were sequentially added to a stirred solution of E69D (150 mg, 0.25 mmol) in dichloromethane (2.5 mL). After 3 h, the reaction was transferred to a separatory funnel with dichloromethane and water. The mixture was extracted with dichloromethane (2×40 mL). The combined organic layers were dried over MgSO$_4$ and concentrated to afford 188 mg of crude product. Purification of the residue over silica gel eluting with ethyl acetate/dichloromethane provided E70A (174 mg, 100%). HPLC (method 3) $t_R$=2.66 min; LCMS (ESI, pos. ion spectrum) m/z 658 (M+H).

Part B:

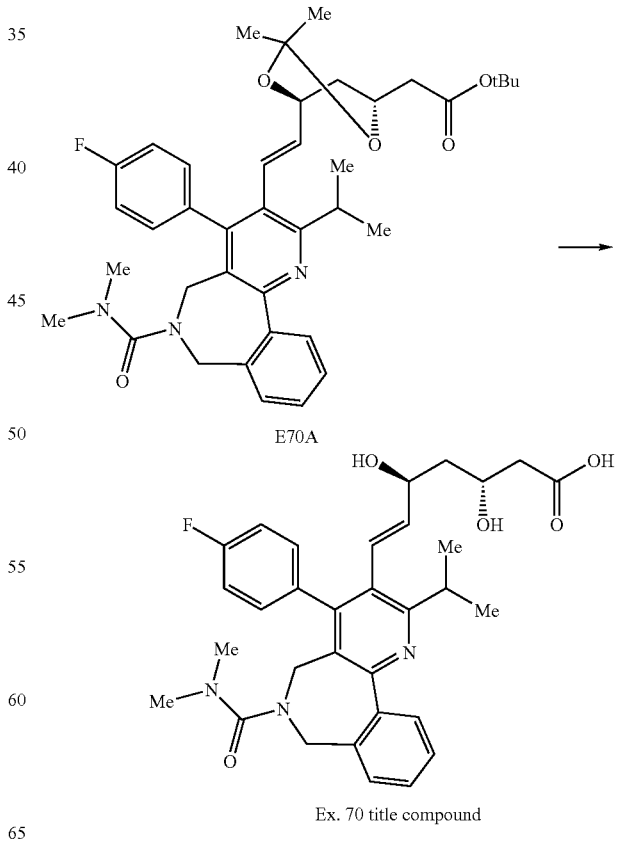

Ex. 70 title compound

A solution of E70A (174 mg, 0.25 mmol) and aqueous hydrochloric acid (6 N, 0.096 mL, 0.58 mmol) in THF (1.0 mL) was stirred at ambient temperature for 1.5 h. Aqueous sodium hydroxide (1 N, 1.1 mL, 1.1 µmol) and THF (2.7 mL) were added. The resultant mixture was stirred vigorously at ambient temperature for 1 h and evaporated. The residue was purified over C-18 silica gel to afford the title compound as the sodium salt (102 mg, 73%): HPLC (method 3) $t_R$=2.17 min; LCMS (ESI, pos. ion spectrum) m/z 562 (M+H).

Example 71

6-Heptenoic acid, 7-[4-(4-fluorophenyl)-6,7-dihydro-6-(hydroxyacetyl)-2-(1-methylethyl)-5H-pyrido[3,2-d][2]benzazepin-3-yl]-3,5-dihydroxy-, (3R,5S,6E)-

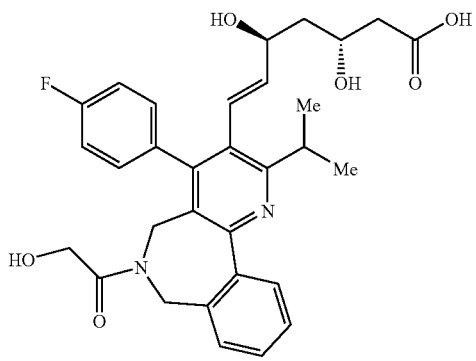

Part A:

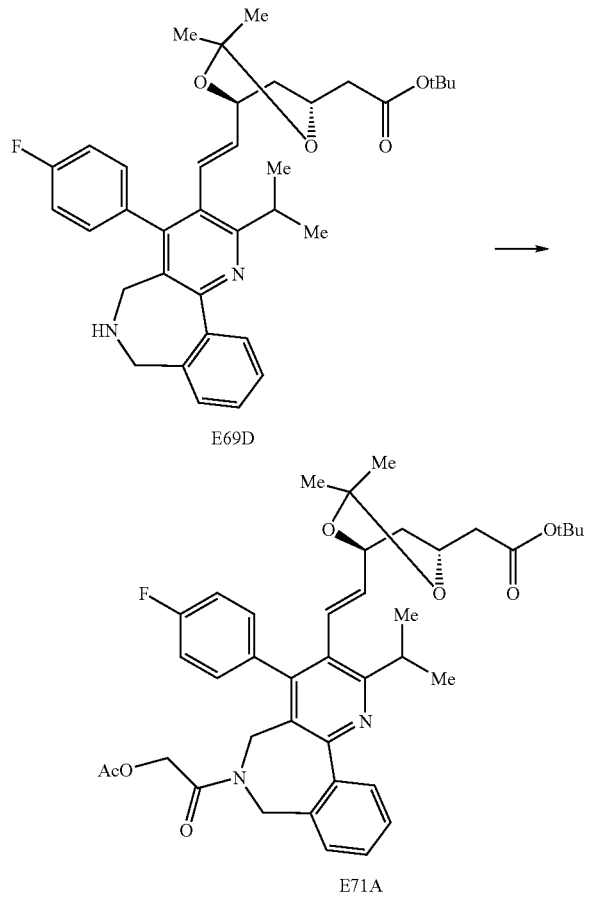

E69D

E71A

Acetoxyacetyl chloride (53 mg, 0.042 mL, 0.39 mmol) and diisopropylethylamine (66 mg, 0.089 mL, 0.51 mmol) were sequentially added to a stirred solution of E69D (150 mg, 0.25 mmol) in dichloromethane (2.5 mL). After 2 h, the reaction was transferred to a separatory funnel with dichloromethane and water. The mixture was extracted with dichloromethane (2×40 mL). The combined organic layers were dried over MgSO$_4$ and concentrated to afford 191 mg of crude product. Purification over silica gel eluting with ethyl acetate/dichloromethane provided E71A (171 mg, 100%): HPLC (method 3) $t_R$=2.64 min; LCMS (ESI, pos. ion spectrum) m/z 687 (M+H).

Part B:

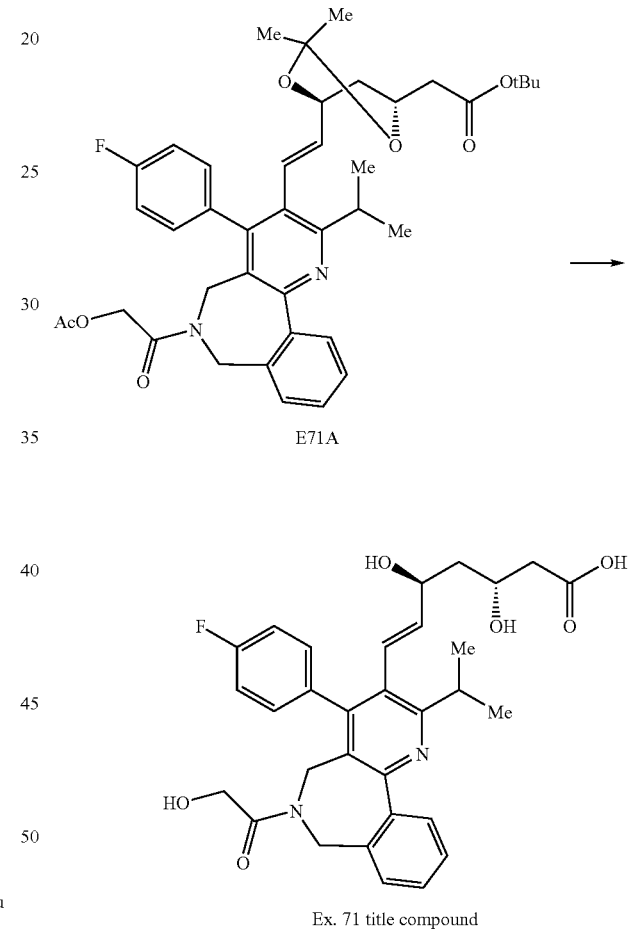

E71A

Ex. 71 title compound

A solution of E71A (171 mg, 0.25 mmol) and aqueous hydrochloric acid (6 N, 0.096 mL, 0.58 mmol) in THF (1.0 mL) was stirred at ambient temperature for 1.5 h. Aqueous sodium hydroxide (1 N, 1.1 mL, 1.1 mmol) and THF (2.7 mL) were added. The resultant mixture was stirred vigorously at ambient temperature for 1.5 h. The mixture was concentrated and the residue was purified over C-18 silica gel to afford the title compound as the sodium salt (71 mg, 53%): HPLC (method 3) $t_R$=2.04 min; LCMS (ESI, pos. ion spectrum) m/z 549 (M+H).

Example 72

6-Heptenoic acid, 7-[4-(4-fluorophenyl)-6-(2-furanylcarbonyl)-6,7-dihydro-2-(1-methylethyl)-5H-pyrido[3,2-d][2]benzazepin-3-yl]-3,5-dihydroxy-, (3R,5S,6E)-

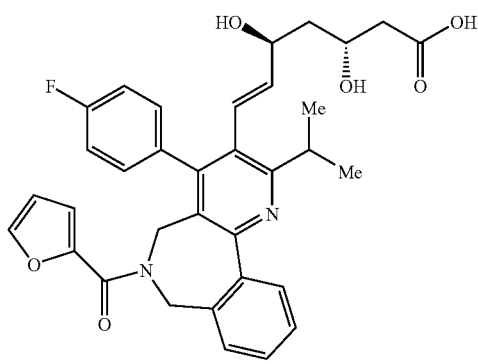

Part A:

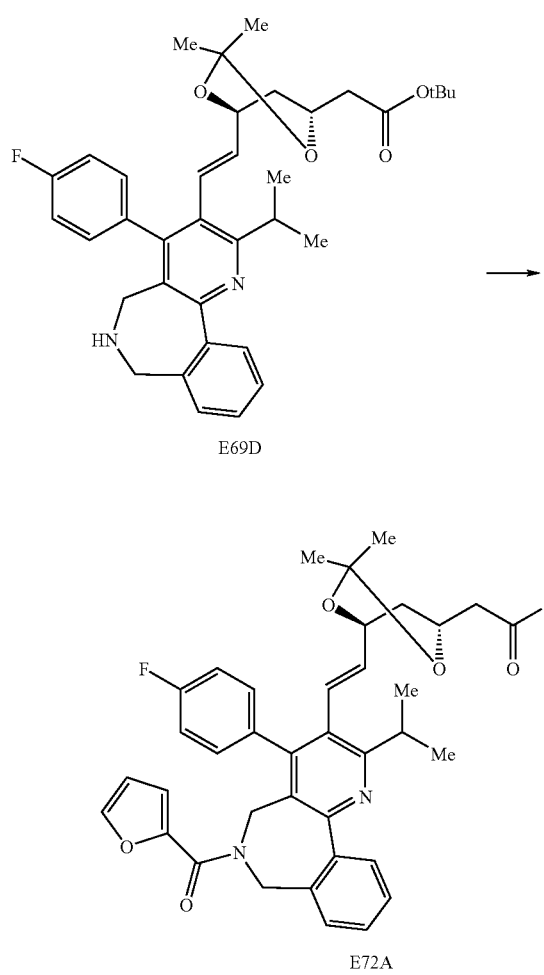

2-Furoyl chloride (51 mg, 0.038 mL, 0.39 mmol) and diisopropylethylamine (66 mg, 0.089 mL, 0.51 mmol) were sequentially added to a stirred solution of E69D (150 mg, 0.25 mmol) in dichloromethane (2.5 mL). After 2 h, the reaction was transferred to a separatory funnel with dichloromethane and water. The mixture was extracted with dichloromethane (2×40 mL). The combined organic layers were dried over MgSO$_4$ and concentrated to afford 199 mg of crude product. Purification over silica gel eluting with ethyl acetate/dichloromethane provided E72A (158 mg, 93%): HPLC (method 3) t$_R$=2.71 min; LCMS (ESI, pos. ion spectrum) m/z 681 (M+H).

Part B:

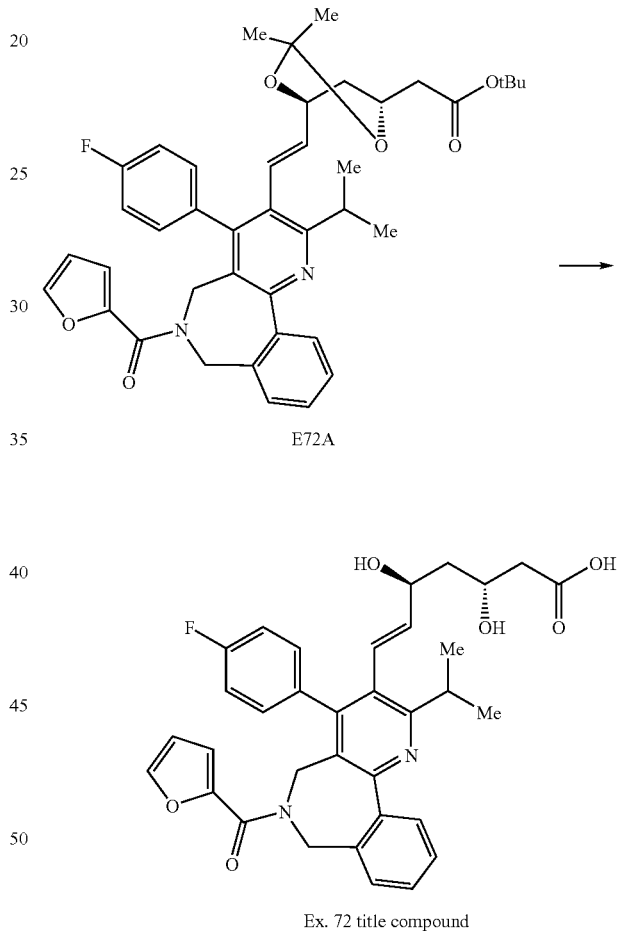

A solution of E72A (158 mg, 0.23 mmol) and aqueous hydrochloric acid (6 N, 0.096 mL, 0.58 mmol) in THF (1.0 mL) was stirred at ambient temperature for 2 h. Aqueous sodium hydroxide (1 N, 1.1 mL, 1.1 mmol) and THF (2.7 mL) were added. The resultant mixture was stirred vigorously at ambient temperature for 1.5 h. The mixture was concentrated and the residue was purified over C-18 silica gel to afford the title compound as the sodium salt (115 mg, 85%): HPLC (method 3) t$_R$=2.25 min; LCMS (ESI, pos. ion spectrum) m/z 585 (M+H).

Example 73

6-Heptenoic acid, 7-[4-(4-fluorophenyl)-6,7-dihydro-6-(methoxyacetyl)-2-(1-methylethyl)-5H-pyrido[3,2-d][2]benzazepin-3-yl]-3,5-dihydroxy-, (3R,5S,6E)-

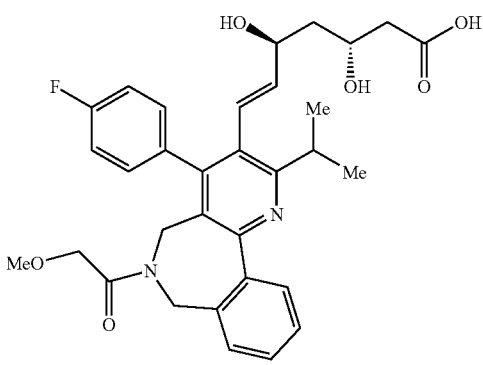

Part A:

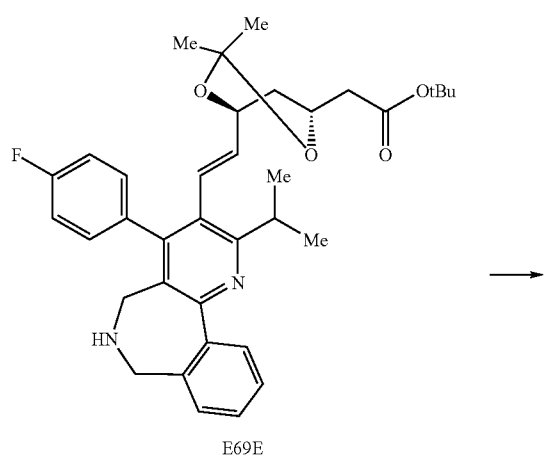

E69E

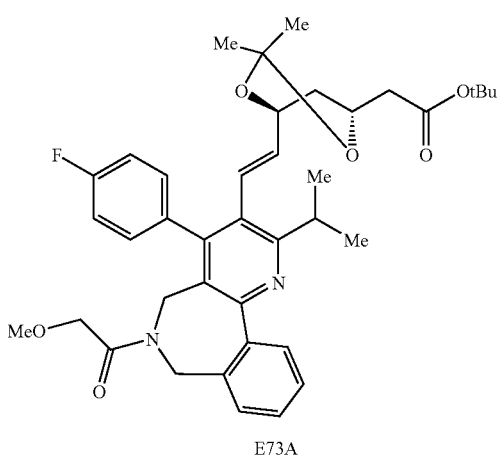

E73A

Methoxyacetyl chloride (42 mg, 0.036 mL, 0.39 mmol) and diisopropylethylamine (66 mg, 0.089 mL, 0.51 mmol) were sequentially added to a stirred solution of E69E (150 mg, 0.25 mmol) in dichloromethane (2.5 mL). After 1.5 h, the reaction was transferred to a separatory funnel with dichloromethane and water. The mixture was extracted with dichloromethane (2×40 mL). The combined organic layers were dried over MgSO$_4$ and concentrated to afford 187 mg of crude product. Purification over silica gel eluting with ethyl acetate/dichloromethane provided E73A (162 mg, 98%): HPLC (method 3) t$_R$=2.66 min; LCMS (ESI, pos. ion spectrum) m/z 659 (M+H).

Part B:

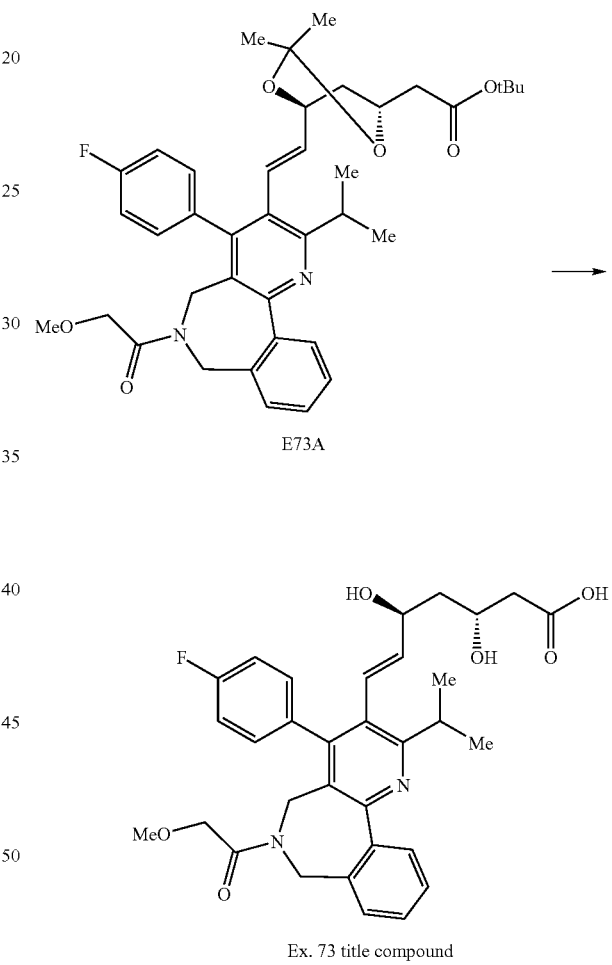

Ex. 73 title compound

A solution of E73A (162 mg, 0.24 mmol) and aqueous hydrochloric acid (6 N, 0.096 mL, 0.58 mmol) in THF (1.0 mL) was stirred at ambient temperature for 2.0 h. Aqueous sodium hydroxide (1 N, 1.1 mL, 1.1 mmol) and THF (2.7 mL) were added. The resultant mixture was stirred vigorously at ambient temperature for 1.8 h. The mixture was evaporated and the residue was purified over C-18 silica gel to afford the title compound as the sodium salt (111 mg, 82%): HPLC (method 3) t$_R$=2.13 min; LCMS (ESI, pos. ion spectrum) m/z 563 (M+H).

Example 74

Benzoic acid, 5-[6,7-dihydro-2-(1-methylethyl)-3-[(E)-2-[(2S,4R)-tetrahydro-4-hydroxy-6-oxo-2H-pyran-2-yl]ethenyl]-5H-benzo[6,7]cyclohepta[1,2-b]pyridin-4-yl]-2-fluoro-

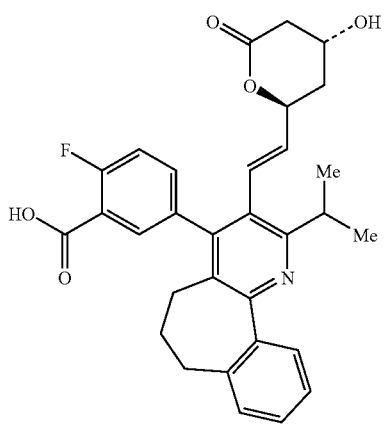

Part A:

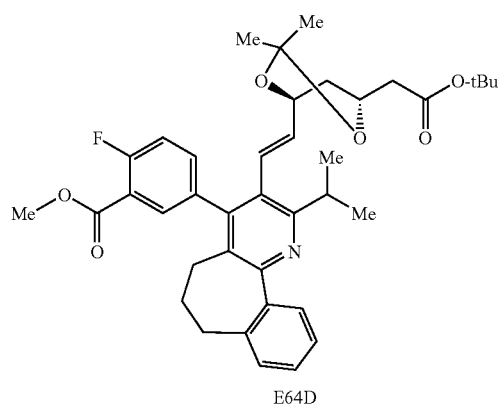

E64D

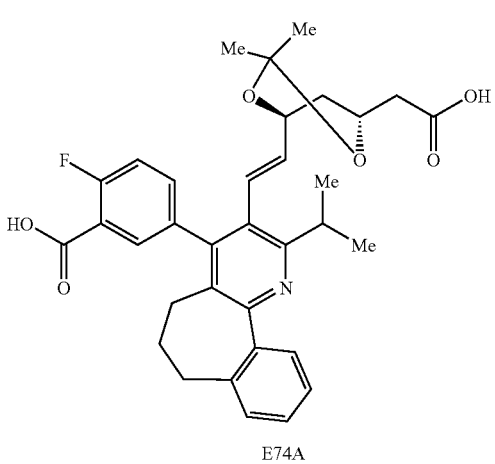

E74A

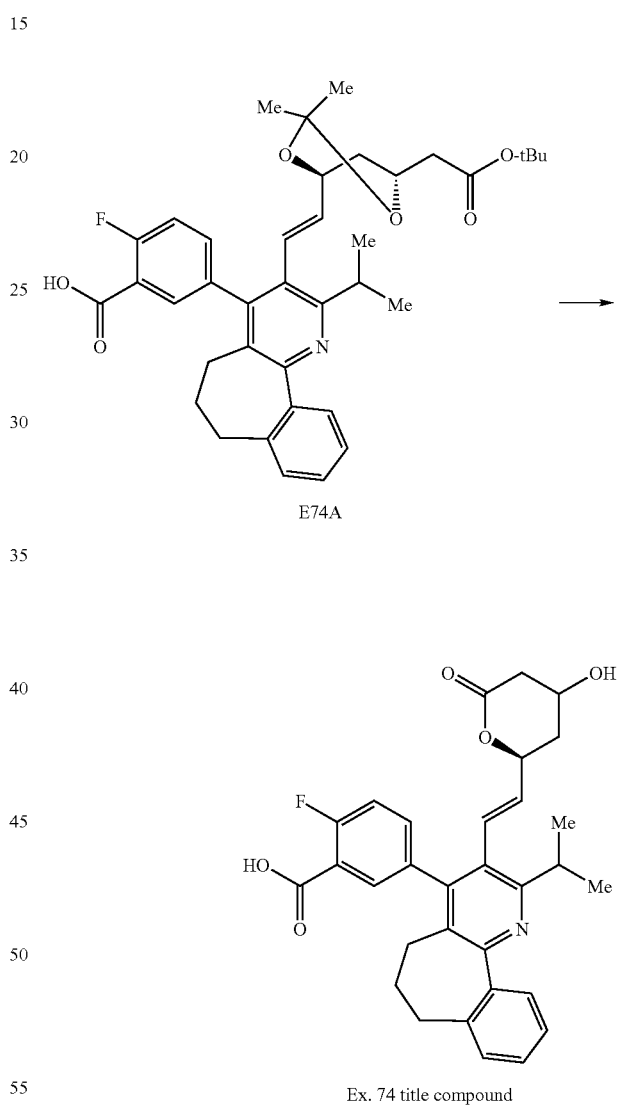

E74A

A solution of E64D (75 mg, 0.12 mmol) in THF (1.2 mL) and 2.5 N NaOH (0.23 mmol, 0.58 mmol) was stirred at 30° C. for 4 days. The reaction was transferred to a separatory funnel with ethyl acetate and water. The aqueous layer was adjusted to pH 5.0 with 1 N HCl. The mixture was extracted with ethyl acetate. The combined organic layers were washed with brine, dried over MgSO$_4$ and concentrated to afford E74A (25 mg, 34% yield): HPLC (method 7) $t_R$=2.6 min; LCMS (ESI, pos. ion spectrum) m/z 630 (M+H).

Part B:

Ex. 74 title compound

Trifluoroacetic acid (0.25 mL) was added to a solution of E74A (25 mg, 0.04 mmol) in CH$_2$Cl$_2$ (0.5 mL) stirred at 0° C. After 75 min, the reaction mixture was transferred to a separatory funnel with saturated NaHCO$_3$ and ethyl acetate. The mixture was extracted with ethyl acetate (2×15 mL). The combined organic layers were washed with 1 N NaHCO$_3$ and brine, dried over MgSO$_4$ and concentrated to afford Ex. 74 title compound as the sodium salt (18 mg, 80% yield): HPLC (method 7) $t_R$=2.17 min; LCMS (ESI, pos. ion spectrum) m/z 516 (M+H).

Example 75

Alternate Preparation of E65D

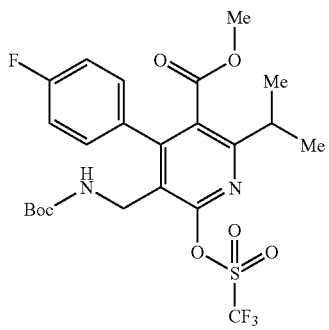
E65D

Part A:

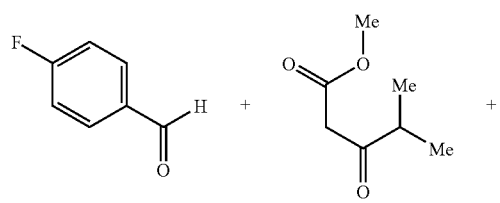

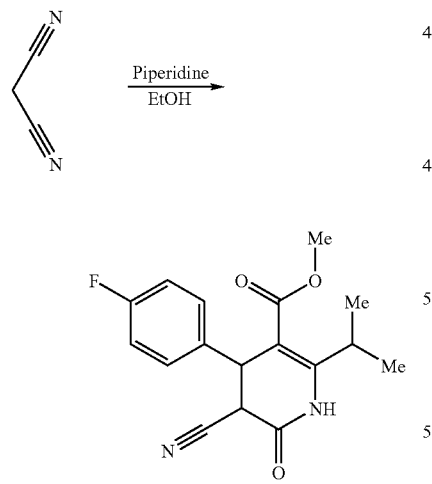

To a 2-L round-bottomed flask was added ethanol (1 L), 4-fluorobenzaldehyde (112 g, 0.9 mol), methyl isobutyrylacetate (130 g, 0.9 mol), malononitrile (59.5 g, 0.9 mol) and piperidine (2 g, 23 mmol). The reaction was stirred at 76° C. for 1 h and cooled to room temperature. The precipitate was collected by filtration, washed with ethanol and dried at 60° C. to provide compound E75A as a mixture of olefinic isomers (265 g, 93%).

Part B:

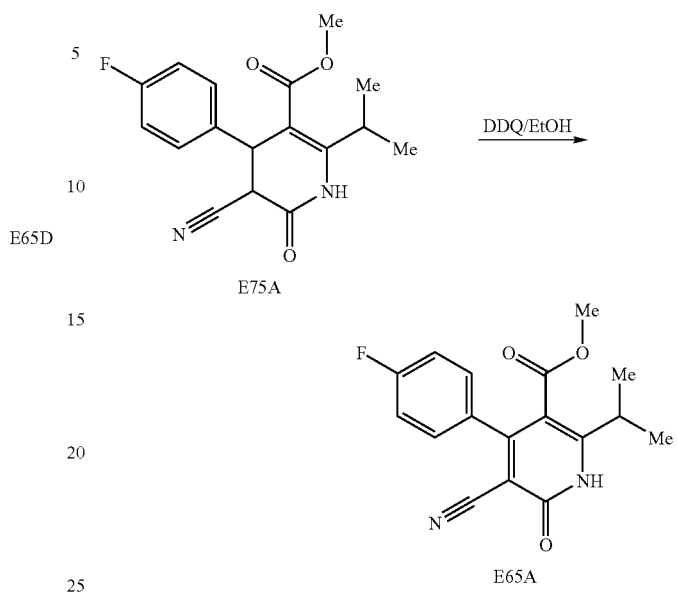

To a 3-L round-bottomed flask was added E75A (265 g, 0.84 mol) and ethanol (2 L). The mixture was stirred at 74° C. for 5 min to provide a yellow homogenous solution. The resultant solution was cooled to 60° C. and 2,3-dichloro-5,6-dicyano-1,4-benzoquinone (DDQ, 209 g, 0.92 mol) was added in portions at 60° C. The reaction was stirred at 60° C. for 15 min and cooled to −10° C. The precipitate was collected by filtration, washed with ethanol and dried to provide compound E65A as white crystals: (206 g, 78%).

Part C:

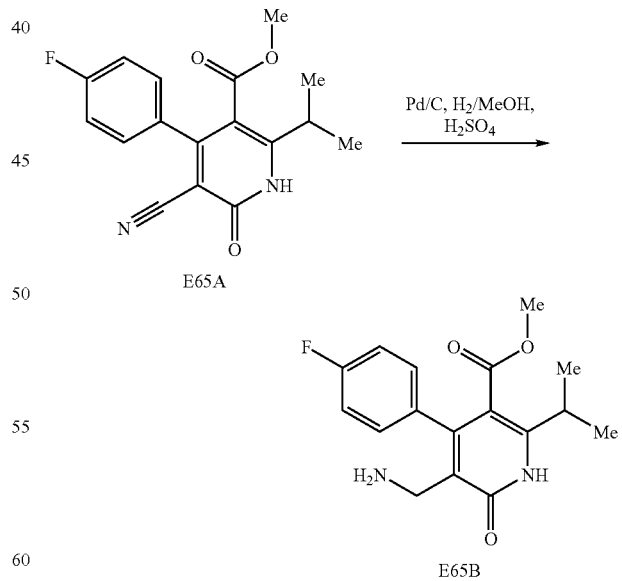

To a 2-L pressure bottle was added E65A (31.4 g, 0.1 mol), methanol (500 mL), concentrated sulfuric acid (3 mL) and 5% palladium on activated carbon powder (1.5 g). The reaction was stirred under hydrogen at 60 psig for 3 h. The reaction mixture was filtered and the filtrate was concentrated.

The residue was stirred in ethanol. The solid was collected by filtration and dried to provide E65B as a white salt (41.6 g, 100%).

Part D:

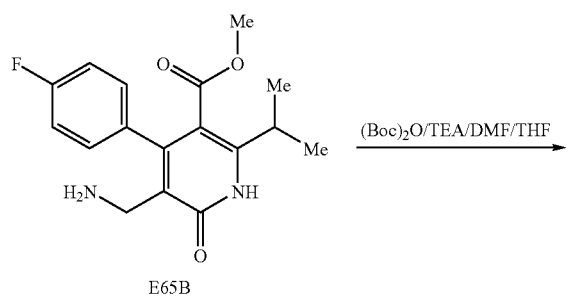

E65B

To a solution of E65B (28.8 g, 0.09 mol) in DMF (150 mL) and THF (150 mL) in a 1-L round-bottomed flask was added di-tert-butyl dicarbonate (21.9 g, 0.1 mol) and triethylamine (16 mL). The reaction was stirred at room temperature for 30 min and quenched with water (1 L). The precipitate was collected by filtration, washed with water and dried to provide compound E65C as white crystals (36.35 g, 98%).

Part E:

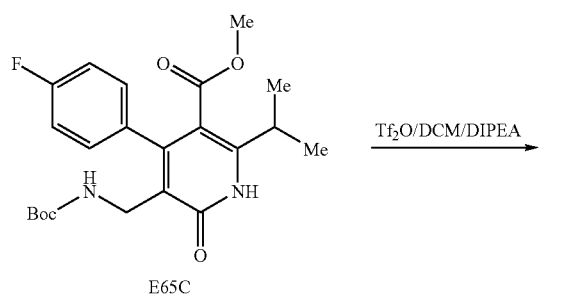

E65C

To a 3-L three-necked round-bottomed flask was added E65C (117.76 g, 0.28 mol), dichloromethane (1 L), diisopropylethylamine (80 g, 0.62 mol) and triflic anhydride (52 mL, 0.31 mol) at −70° C. The reaction was stirred at −60° C. for 10 min and was quenched with ethanol (300 mL) and sodium dihydrogen phosphate solution (50 mL). The reaction was warmed to room temperature. The organic solvent was removed under reduced pressure. The precipitate was collected by filtration, washed with ethanol/water (1:1) and dried to provide E65D as a white solid (147.2 g, 95%).

Example 76

6-Heptenoic acid, 7-[4-(4-fluorophenyl)-5,11-dihydro-2-(1-methylethyl)-11-(methylsulfonyl)pyrido[3,2-c][1,5]benzoxazepin-3-yl]-3,5-dihydroxy-, (3R,5S,6E)-

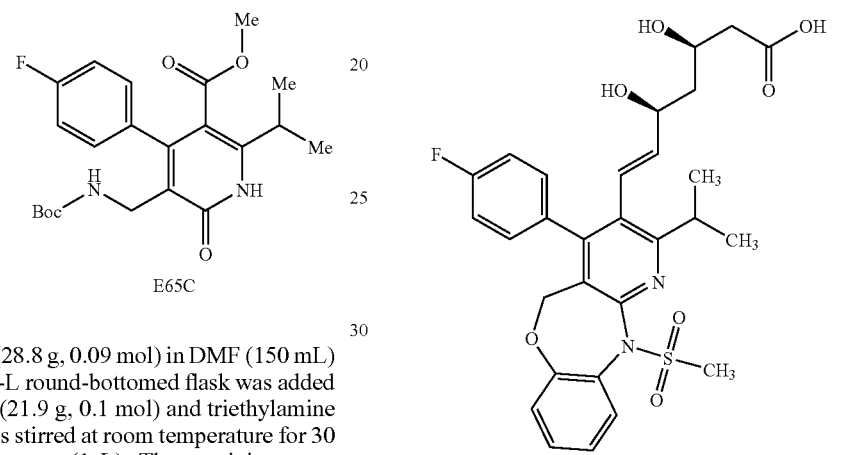

Part A:

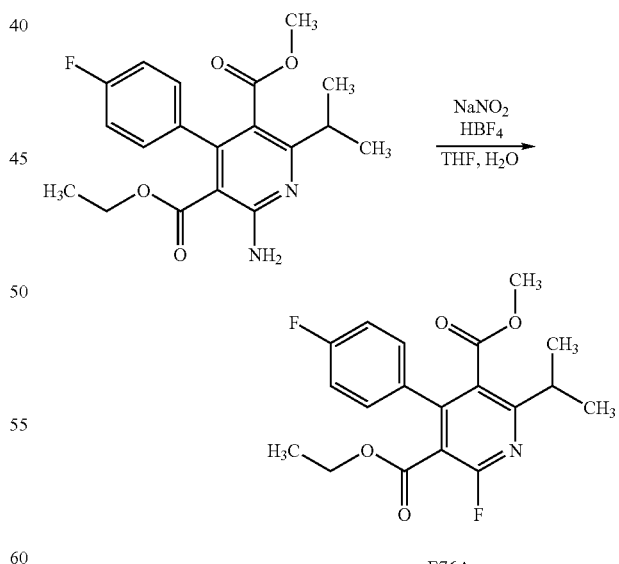

E76A

To 3-ethyl 5-methyl 2-amino-4-(4-fluorophenyl)-6-(1-methylethyl)-3,5-pyridinedicarboxylate (12.61 g, 35 mmol) in 70 mL of tetrahydrofuran at 0° C., was added tetrafluoroboric acid (48% wt. in water, 150 mL). A solution of sodium nitrite (14.5 g, 210 mmol) in 30 mL water was added slowly to this mixture. The mixture was stirred at 0° C. for 2 h. The reaction mixture was neutralized with sodium hydrogencarbonate, and the mixture was extracted with ethyl acetate. The combined extracts were washed with water and brine, dried over magnesium sulfate and concentrated. The residue was chromatographed on silica gel eluting with hexanes/ethyl acetate to provide compound E76A (8.63 g, 68%): HPLC (Method 8) $t_R$=3.78 min.

Part B:

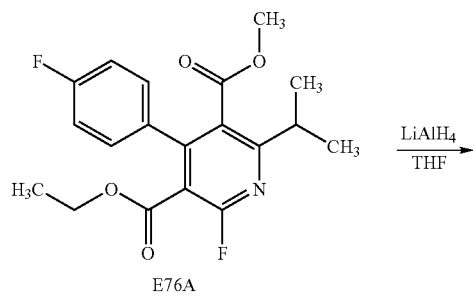

To E76A (8.63 g, 23.75 mmol) in 119 mL of tetrahydrofuran at −78° C., was added lithium aluminum hydride (1 M in tetrahydrofuran, 52.25 mL, 52.25 mmol). The mixture was stirred at −78° C. to −55° C. for 2.5 h and then at 0° C. for 30 min. The reaction mixture was quenched with saturated sodium ammonium chloride and extracted with ethyl acetate. The extracts were passed through a short silica gel column to provide compound E76B (7.21 g, 82% pure, 77%): HPLC (method 8) $t_R$=3.16 min.

Part C:

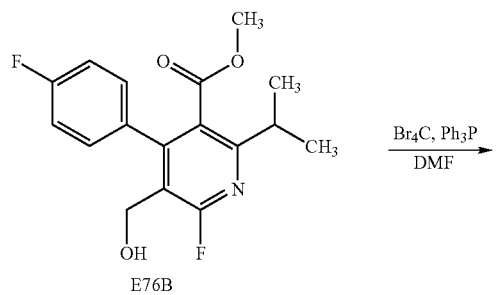

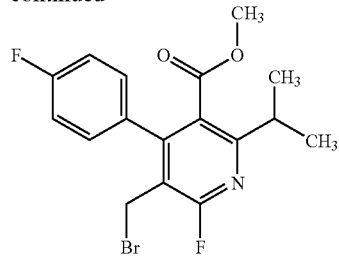

To E76B (5.91 g, 18.39 mmol) in 100 mL of N,N-dimethylformamide at 0° C. were sequentially added carbon tetrabromide (14.74 g, 44.43 mmol) and triphenylphosphine (11.65 g, 44.43 mmol). The reaction was stirred at 0° C. for 5 h. The reaction mixture was diluted with ethyl acetate, washed with water and brine, dried over magnesium sulfate, and concentrated. The residue was chromatographed on silica gel eluting with hexanes/ethyl acetate to provide E76C (5.1 g, 72%) as a solid.

Part D:

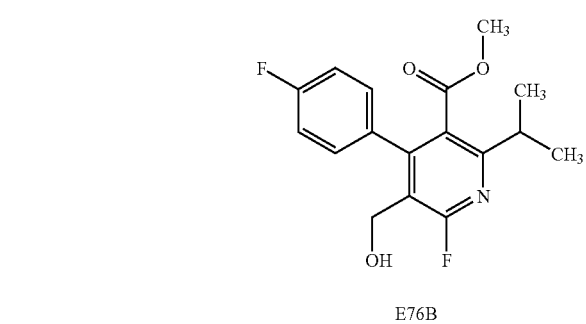

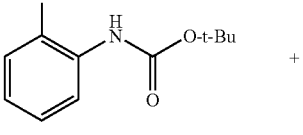

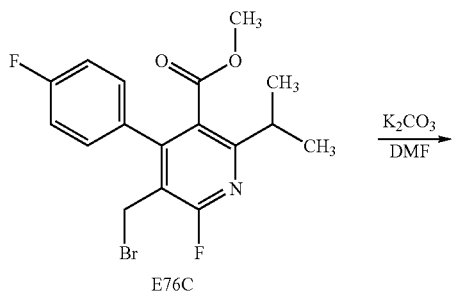

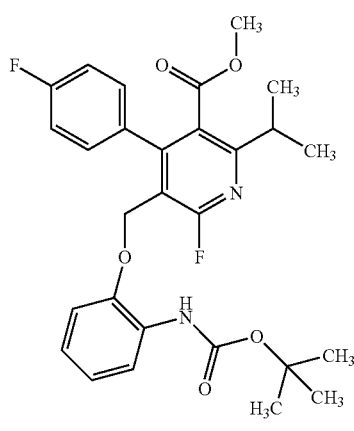

To tert-butyl (2-hydroxyphenyl)carbamate (428 mg, 2.04 mmol) and E76C (748 mg, 1.95 mmol) in 3.9 mL of N,N-dimethylformamide was added potassium carbonate (807 mg, 5.84 mmol). The reaction was stirred at room temperature for 3 h. The mixture was diluted with ethyl acetate, washed with water and brine, dried over magnesium sulfate and concentrated. The residue was chromatographed on silica gel eluting with hexanes/ethyl acetate to provide E76D as a white solid (1.00 g, 100%); HPLC (Method 8) $t_R$=4.21 min.

Part E:

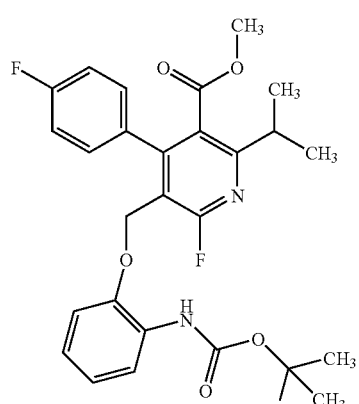

E76D

To E76D (1.00 g, 1.95 mmol) in 8 mL of N,N-dimethylformamide at 0° C. was added sodium hydride (60% in mineral oil, 148 mg, 3.70 mmol). The reaction was stirred at room temperature for 2.5 h and then was quenched with saturated aqueous ammonium chloride. The mixture was diluted with ethyl acetate, washed with water and brine, dried over magnesium sulfate and concentrated. The residue was chromatographed on silica gel eluting with hexanes/ethyl acetate to provide E76E as a white solid (950 mg, 99%): HPLC (Method 8) $t_R$=4.10 min.

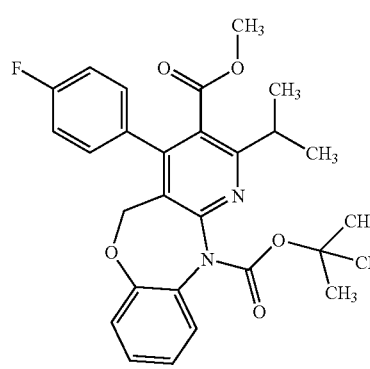

E76E

Part F:

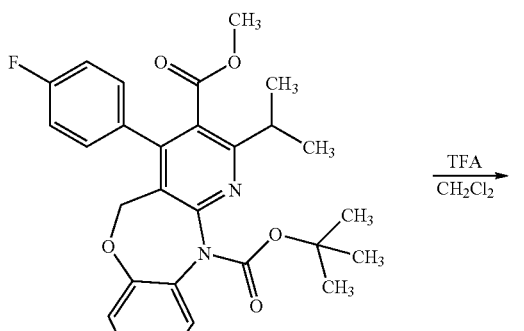

E76E

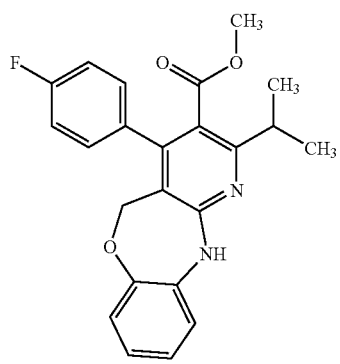

E76F

To E76E (950 mg, 1.93 mmol) in 5 mL of dichloromethane was added 5 mL of trifluoroacetic acid. The reaction was stirred at 35° C. for 90 min. The mixture was concentrated in vacuo, diluted with ethyl acetate, washed with aqueous sodium bicarbonate and brine, dried over magnesium sulfate and concentrated to provide E76F as an off-white solid (664 mg, 88%): HPLC (Method 8) $t_R$=4.07 min.

Part G:

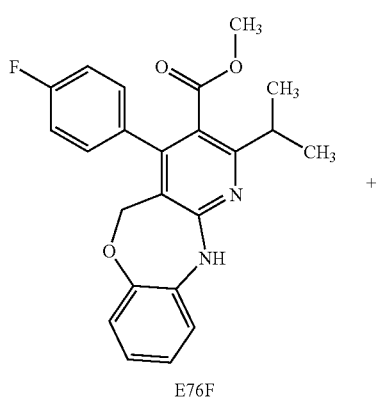

E76F

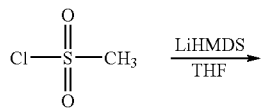

-continued

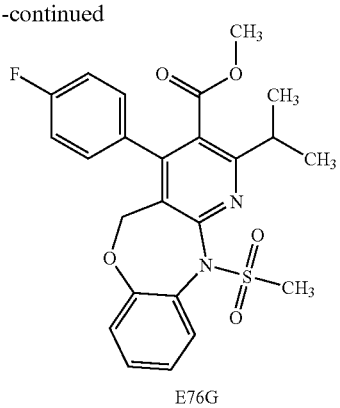

E76G

To E76F (603 mg, 1.54 mmol) in 10 mL of tetrahydrofuran at −78° C. was added lithium bis(trimethylsilyl)amide (1 M in tetrahydrofuran, 2 mL, 2.0 mmol). The mixture was stirred at −78° C. for 10 min. To this mixture was added methanesulfonyl chloride (265 mg, 0.18 mL, 2.31 mmol). The reaction was stirred at −78° C. to −60° C. for 1 h. The reaction mixture was quenched with saturated aqueous ammonium chloride, and diluted with ethyl acetate. The organic layer was washed with water and brine, dried over magnesium sulfate and concentrated. The residue was chromatographed on silica gel eluting with hexanes/ethyl acetate to provide E76G (588 mg, 81%): HPLC (Method 8) $t_R$=3.76 min.

Part H:

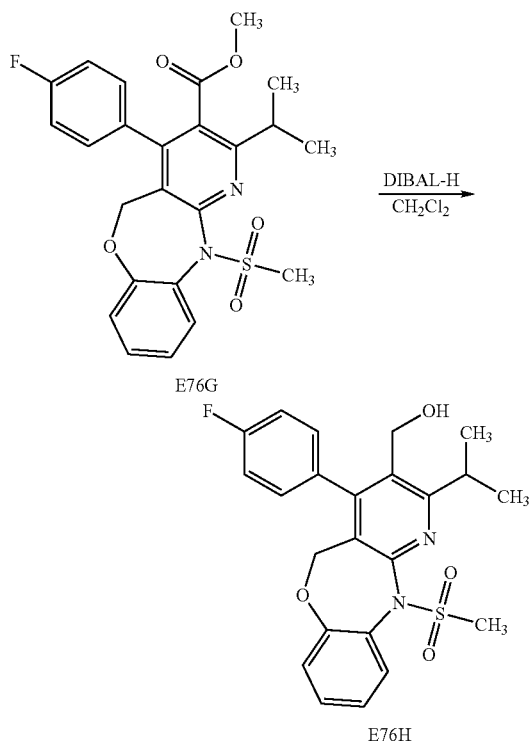

To E76G (588 mg, 1.25 mmol) in 12.5 mL of dichloromethane at −78° C. was added, dropwise, diisobutylaluminum hydride (1 M in dichloromethane, 3.12 mL, 3.12 mmol). After stirring at room temperature for 1 h, the reaction was cooled to 0° C. and quenched with saturated aqueous ammonium chloride. The mixture was diluted with ethyl acetate. The organic layer was washed with water and brine, dried over magnesium sulfate and concentrated. to provide E76H as a solid (518 mg, 94%): HPLC (Method 8) $t_R$=3.51 min.

Part I:

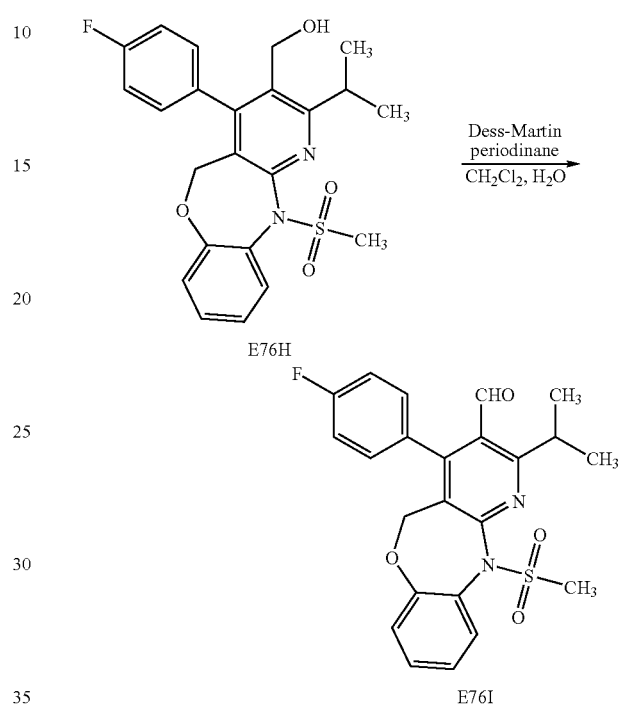

To E76H (518 mg, 1.17 mmol) and 0.023 mL of water in 11.7 mL of dichloromethane, was added, portionwise, Dess-Martin periodinane (744 mg, 1.76 mmol). The reaction was stirred at room temperature for 1 h. To the reaction mixture were added 10 mL of 10% sodium thiosulfate and 10 mL of saturated aqueous sodium bicarbonate. The mixture was stirred for 10 min and diluted with ethyl acetate. The organic layer was washed with water and brine, dried over magnesium sulfate and concentrated. The residue was chromatographed on silica gel eluting with hexanes/ethyl acetate to provide E76I as a solid (400 mg, 78%): HPLC (Method 8) $t_R$=3.78 min.

Part J:

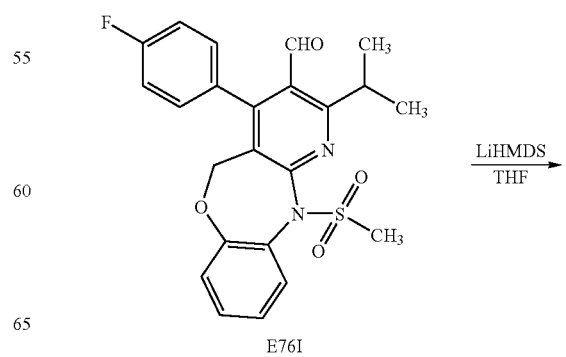

E76I

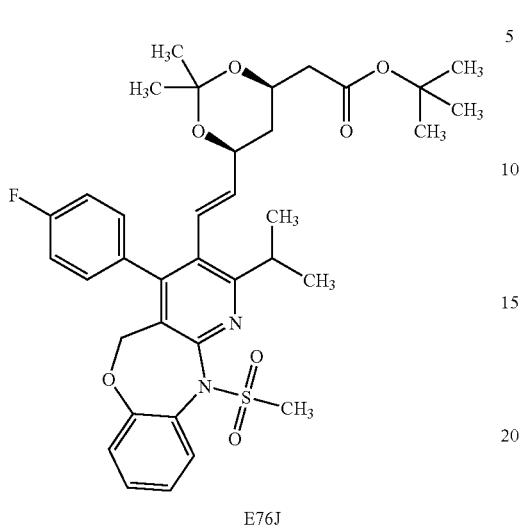

E76J

To E1D (267 mg, 0.59 mmol) in 3 mL of tetrahydrofuran at −78° C. was added lithium bis(trimethylsilyl)amide (1 M in tetrahydrofuran, 0.59 mL, 0.59 mmol). The mixture was stirred at −78° C. for 10 min and a solution of E76I (200 mg, 0.45 mmol) in 2 mL of tetrahydrofuran was added. The reaction was stirred at −78° C. for 2 h and quenched with aqueous ammonium chloride. The mixture was diluted with ethyl acetate. The organic layer was washed with water and brine, dried over magnesium sulfate and concentrated. The residue was chromatographed on silica gel eluting with hexanes/ethyl acetate to provide E76J (180 mg, 60%): HPLC (Method 8) $t_R$=4.27 min.

Part K:

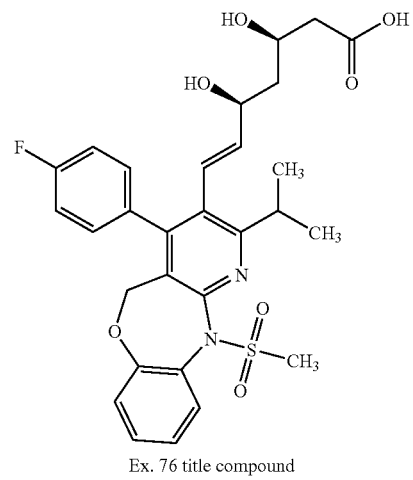

Ex. 76 title compound

To E76J (180 mg, 0.27 mmol) in 4 mL of tetrahydrofuran and 3 mL methanol at room temperature, was added 0.18 mL 6 N hydrochloric acid. The reaction was stirred at room temperature for 80 min and was cooled to 0° C. Sodium hydroxide (0.743 mL, 2 N) was added. The mixture was stirred for an additional 50 min and concentrated in vacuo. The residue was purified on a C18 silica column eluting with water and then water/methanol to provide the title compound as the sodium salt as a white solid (169 mg, 100%): LRMS (ESI, pos. ion spectrum) m/z 483 (M+H); HPLC (Method 8) $t_R$=3.28 min.

Example 77

6-Heptenoic acid, 7-[4-(4-fluorophenyl)-6,7,9,10-tetrahydro-2,10-bis(1-methylethyl)-9-oxo-5H-imidazo[1,5-a]pyrido[2,3-c]azepin-3-yl]-3,5-dihydroxy-, (3R,5S,6E)-

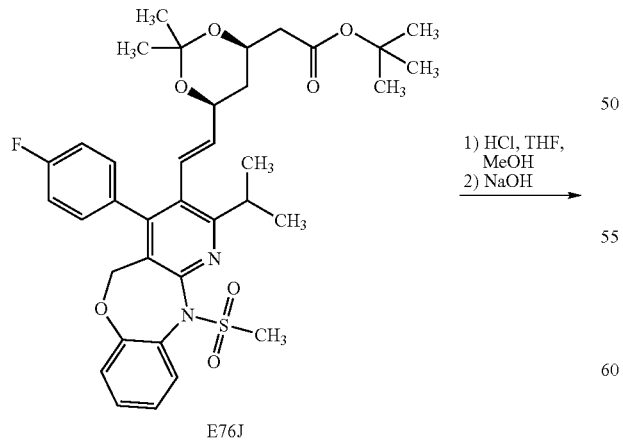

E76J

1) HCl, THF, MeOH
2) NaOH

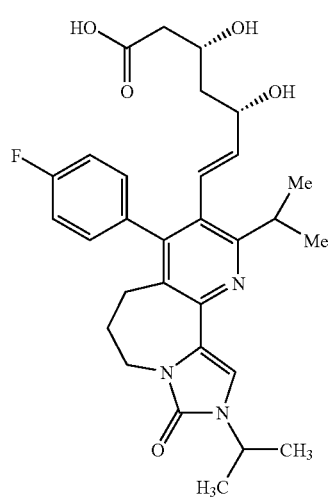

Part A:

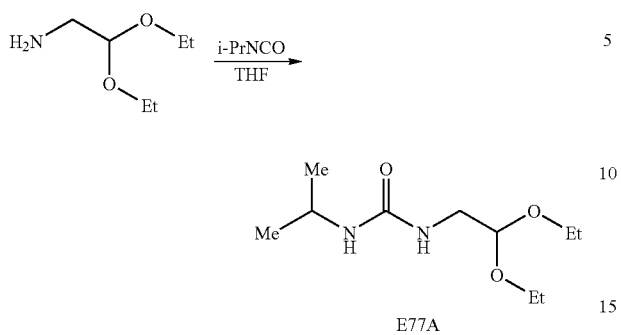

E77A

To a stirred, cooled (0° C.) solution of 6.66 mL (50.0 mmol) of aminoacetaldehyde dimethyl acetal in 40 mL of tetrahydrofuran was added isopropyl isocyanate. Stirring was continued for 30 min while the reaction was allowed to warm to room temperature. Removal of solvent under reduced pressure and concentrated to afford 9.9 g (91%) of E77A as a colorless solid: $^1$H NMR (DMSO-$d_6$, 300 MHz) δ 5.83 (d, 1H, J=7.7 Hz), 5.63 (t, 1H, J=5.8 Hz), 4.39 (t, 1H, J=5.5 Hz), 3.29-3.71 (m, 5H), 3.05 (t, 2H, J=5.7 Hz), 1.12 (t, 6H, J=7.0 Hz), 1.01 (d, 6H, J=6.2 Hz); $R_f$ (ethyl acetate) 0.57.

Part B:

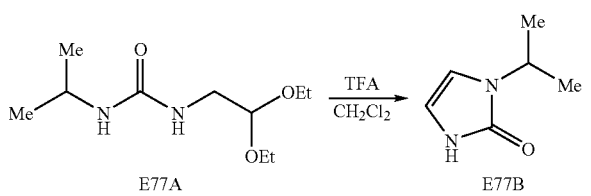

E77A → E77B

To a stirred solution of 1.09 g (5.00 mmol) of E77A in 5 mL of $CH_2Cl_2$ was added 5 mL of trifluoroacetic acid. The solution was stirred for 1 h, and concentrated under reduced pressure. The residue was passed through silica gel (eluting with ether then 10% methanol-ether). Concentration of the product-containing fractions provided an oil which was coevaporated twice with benzene and evacuated at 0.05 torr overnight to afford 600 mg (95%) of E77B as a waxy solid: $^1$H NMR ($CDCl_3$, 300 MHz) δ 10.7 (br.s, 1H), 6.30 (d, 1H, J=2.6 Hz), 6.23 (d, 1H, J=2.4 Hz), 4.28-4.43 (m, 1H), 1.28 (d, 6H, J=6.6 Hz).

Part C:

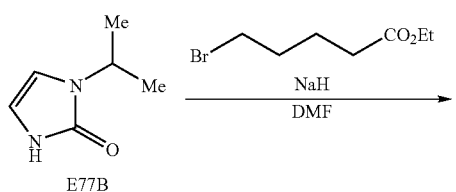

E77B

-continued

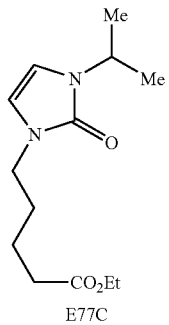

E77C

To a stirred solution of 2.90 g (23.0 mmol) of E77B in 40 mL of dimethylformamide was added 710 mg (40.0 mmol) of sodium hydride (60% dispersion in mineral oil). The suspension was stirred for 1 min, treated with 9.5 mL (60 mmol) of ethyl 5-bromopentanoate, and heated to reflux. The reaction was stirred overnight at reflux, quenched with aqueous acetic acid, and extracted with ethyl acetate. The organic extract was washed with aqueous sodium bicarbonate then brine, dried ($MgSO_4$), and concentrated under reduced pressure. Chromatography on silica gel (gradient elution with ethyl acetate then 20% methanol-ethyl acetate) afforded, after removal of solvent, 3.9 g (67%) of ester E77C as an amber oil: $^1$H NMR ($CDCl_3$, 300 MHz) δ 6.23 (d, 1H, J=3.3 Hz), 6.18 (d, 1H, J=2.9 Hz), 4.31-4.45 (m, 1H), 4.11 (q, 2H, J=7.1 Hz), 3.61 (t, 2H, J=6.8 Hz), 2.33 (t, 2H, J=7.2 Hz), 1.58-1.77 (m, 4H), 1.28 (d, 6H, J=6.6 Hz), 1.24 (t, 3H, J=7.2 Hz).

Part D:

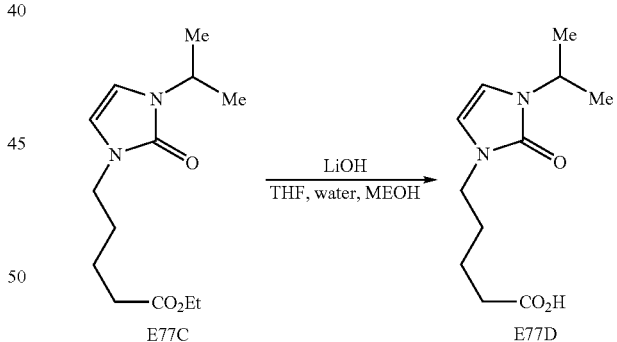

E77C → E77D

To a stirred solution of 3.26 g (12.8 mmol) of E77C in 20 mL of tetrahydrofuran and 2 mL of methanol was added 840 mg (20 mmol) of lithium hydroxide hydrate in 20 mL of water. The solution was stirred overnight at ambient temperature, quenched with 1 M aqueous HCl, and extracted with toluene. The organic extract was dried ($MgSO_4$) and concentrated under reduced pressure to afford 2.30 g (79%) of E77D as a waxy solid: $^1$H NMR ($CDCl_3$, 300 MHz) δ 6.27 (d, 1H, J=3.0 Hz), 6.22 (d, 1H, J=2.9 Hz), 4.33-4.48 (m, 1H), 3.66 (t, 2H, J=6.8 Hz), 2.38 (t, 2H, J=7.2 Hz), 1.58-1.78 (m, 4H), 1.29 (d, 6H, J=7.0 Hz).

Part E:

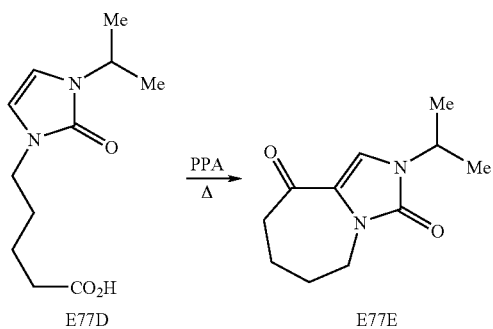

A mixture of 1.13 g of E77D in 10 g of polyphosphoric acid was heated for 6 h at 70-85° C., then overnight at 65° C., then for 1 h at 80° C. The reaction was cooled and quenched with half-saturated brine. This mixture was extracted with ethyl acetate, and the organic extract was dried (MgSO$_4$) and concentrated under reduced pressure. Chromatography on silica gel (gradient elution with 75% ethyl acetate-hexanes then ethyl acetate) and concentrated to afford a red oil which was crystallized from ethyl acetate-cyclohexane to afford 370 mg (36%) of E77E as a tan solid: $^1$H NMR (CDCl$_3$, 300 MHz) δ 7.13 (s, 1H), 4.34-4.48 (m, 1H), 3.92-3.99 (m, 2H), 2.66-2.71 (m, 2H), 1.84-2.04 (m, 4H), 1.32 (d, 6H, J=6.6 Hz); $^{13}$C NMR (CDCl$_3$, 75.4 MHz) δ 190.94, 152.21, 125.17, 115.56, 45.53, 41.65, 40.63, 26.87, 26.20, 21.97, 20.98.

Part F:

Tetrahydrofuran, 5 mL, was cooled to −78° C. and treated with 1.54 mL of a 1 M solution of sodium hexamethyldisilazide in THF. The solution was treated over 5 min with 292 mg (1.40 mmol) of E77E in 1 mL of tetrahydrofuran, stirred for an additional 5 min, and then treated with 420 mg (1.6 mmol) of ethyl 2-[(4-fluorophenyl)methylene]-4-methyl-3-oxo-pentanoic acid over 2 min. The resulting solution was stirred for 1.5 h at −78° C. and warmed slightly over 3 min. The reaction was quenched with dilute aqueous acetic acid, and the resultant mixture was extracted with ether. The organic extract was washed with dilute aqueous sodium bicarbonate then brine, dried (MgSO$_4$) and concentrated under reduced pressure to afford an oil. This material was dissolved in 10 mL of absolute ethanol and treated with 440 mg of ammonium acetate, 320 mg of copper (II) bromide, and 12 mg of toluenesulfonic acid. The mixture was stirred for 16 h at reflux, cooled, and treated with 20 mL of conc. ammonium hydroxide. The mixture was diluted with water and extracted twice with ether. The combined organic extracts were washed with water then brine, dried (MgSO$_4$) and concentrated under reduced pressure. The crude product was purified by chromatography on silica gel (gradient elution with 50% ether-hexanes then ether) to afford 632 mg (43%) of E77F as an amorphous solid: LRMS m/z 484 (M+Na)$^+$; HPLC (method 3) t$_R$=4.21 min.

Part G:

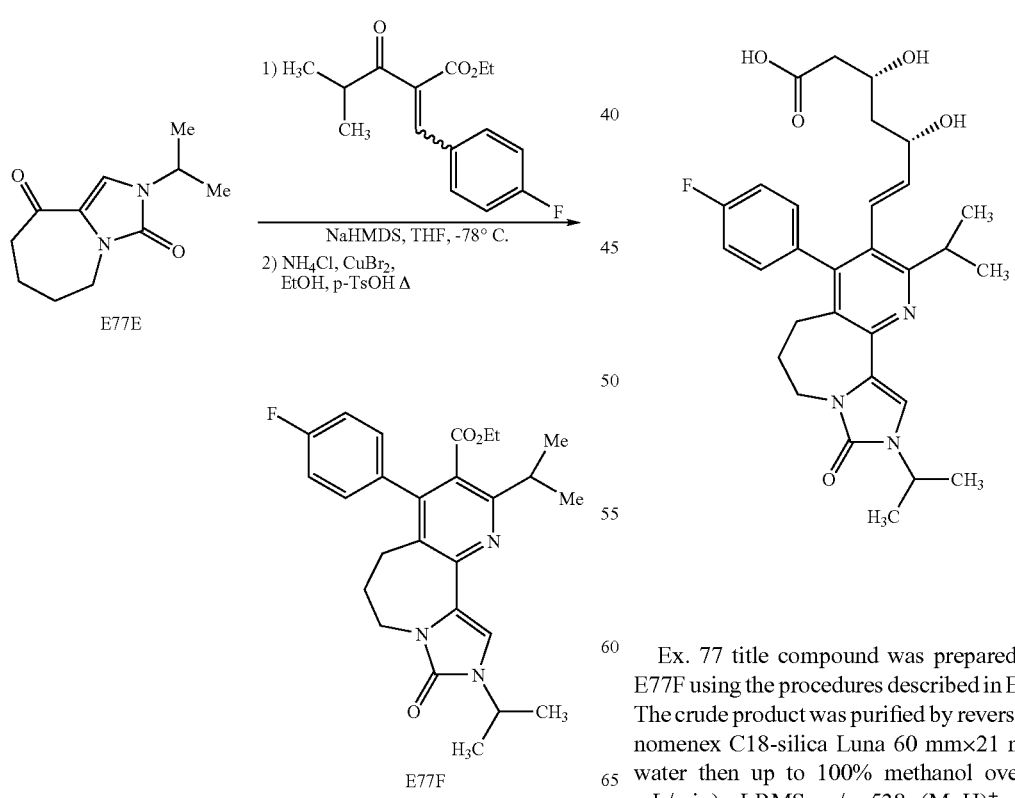

Ex. 77 title compound was prepared in 23% yield from E77F using the procedures described in Example 5 Parts B-D. The crude product was purified by reverse-phase HPLC (Phenomenex C18-silica Luna 60 mm×21 mm; 20% methanol-water then up to 100% methanol over 4 min; Flow=9.9 mL/min): LRMS m/z 538 (M+H)$^+$; HPLC (method 3) t$_R$=3.43 min.

Example 78

6-Heptenoic acid, 7-[4-(4-fluorophenyl)-6,7,9,10-tetrahydro-2-(1-methylethyl)-9-oxo-10-(phenylmethyl)-5H-imidazo[1,5-a]pyrido[2,3-c]azepin-3-yl]-3,5-dihydroxy-, (3R,5S,6E)-

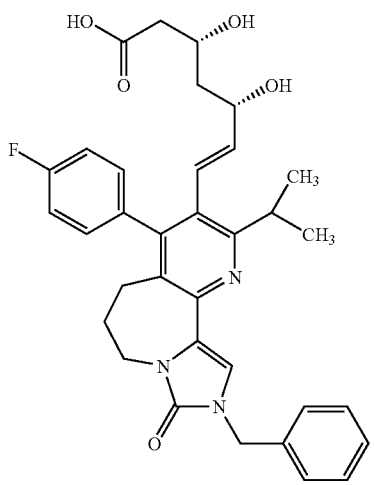

Part A:

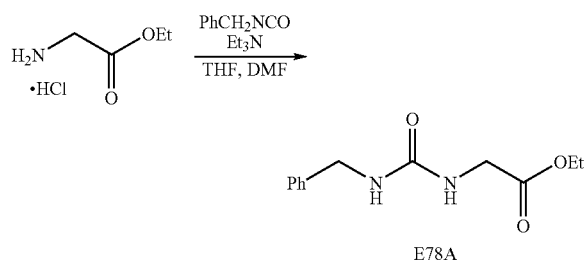

To a stirred suspension of 14 g (100 mmol) of glycine ethyl ester hydrochloride in 50 mL of tetrahydrofuran was added 12 mL of dimethylformamide followed by 17.4 mL (125 mmol) of triethylamine The mixture was treated with 12.4 mL (100 mmol) of benzyl isocyanate and heated to reflux with a heat pistol. Most of the insoluble material dissolved. The mixture was allowed to cool to ambient temperature. After stirring for 1 h, the reaction was treated with 30 mL of 1 M aqueous HCl then 350 mL of water. The mixture was stirred under a stream of nitrogen which resulted in the formation of a white precipitate which was collected by filtration and rinsed with water and then 20% ether-hexanes. The solid was vacuum-dried to afford 18.7 g (79%) of E78A as a colorless solid: LRMS m/z 237 (M+H)$^+$; HPLC (method 3) $t_R$=2.45 min.

Part B:

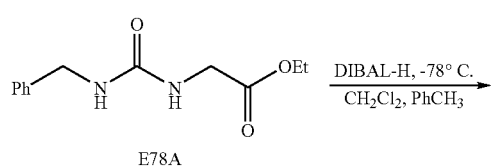

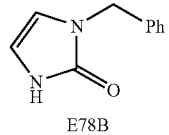

To a stirred, cooled (−78° C.) suspension of 9.45 g (40.0 mmol) of E78A in 80 mL of $CH_2Cl_2$ was added 33.3 mL (50.0 mmol) of a 1.5 M solution of diisobutylaluminum hydride in toluene. The mixture was warmed to nearly ambient temperature, recooled to 0° C., and stirred for 40 min The solution was allowed to warm for 5 min, and was quenched with ethyl acetate, then methanol, and then saturated aqueous sodium potassium tartrate. The biphasic mixture was stirred for 1 h and then extracted with ether. The organic extract was washed with water and then shaken vigorously for 2 min with 4 M aqueous HCl to ensure complete dehydration to imidazolone. The organic extract was then washed with water and brine, dried ($MgSO_4$), and concentrated under reduced pressure to afford a waxy solid. Crystallization from ethyl acetate-cyclohexane and concentrated to afford 2.48 g (36%) of E78B as an off-white solid. LRMS 175 (M+H)$^+$; HPLC (method 3) $t_R$=2.23 min.

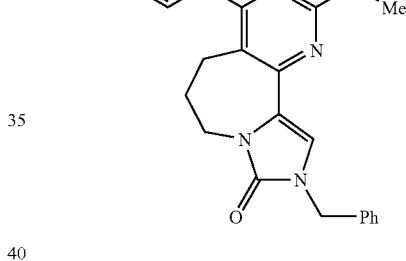

Part C:

E78C was prepared in 15% yield from E78B using the procedures described in Example 77 Parts C-F: LRMS m/z 500 (M+H)$^+$; HPLC (method 3): $t_R$=4.49 min.

Part D:

Ex. 78 title compound

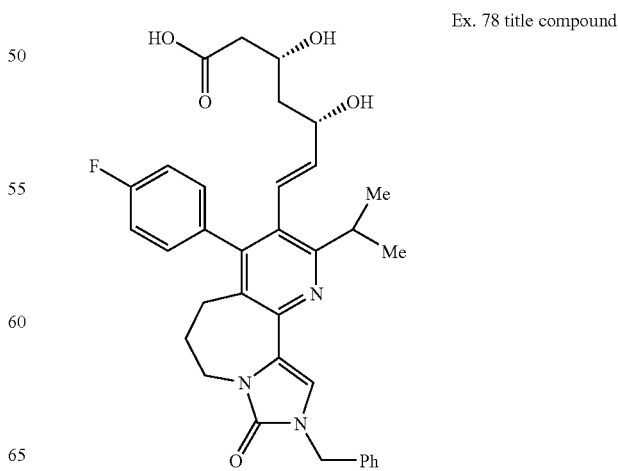

Ex. 78 title compound was prepared in 8% yield from E78C using the procedures described in Example 1 Parts C-D: LRMS m/z 586 (M+H)+; HPLC (method 3) $t_R$=3.79 min.

Example 79

6-Heptenoic acid, 7-[4-(4-fluorophenyl)-6,7-dihydro-2-(1-methylethyl)-5H-cyclohepta[2,1-b:3,4-b']dipyridin-3-yl]-3,5-dihydroxy-, (3R,5S,6E)-

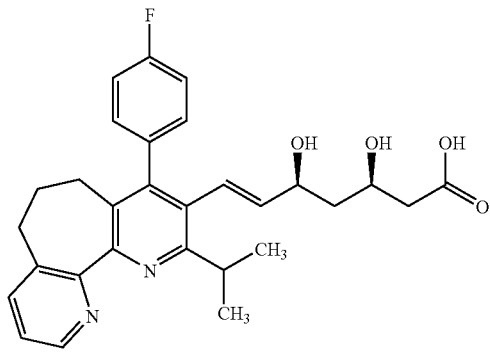

Part A:

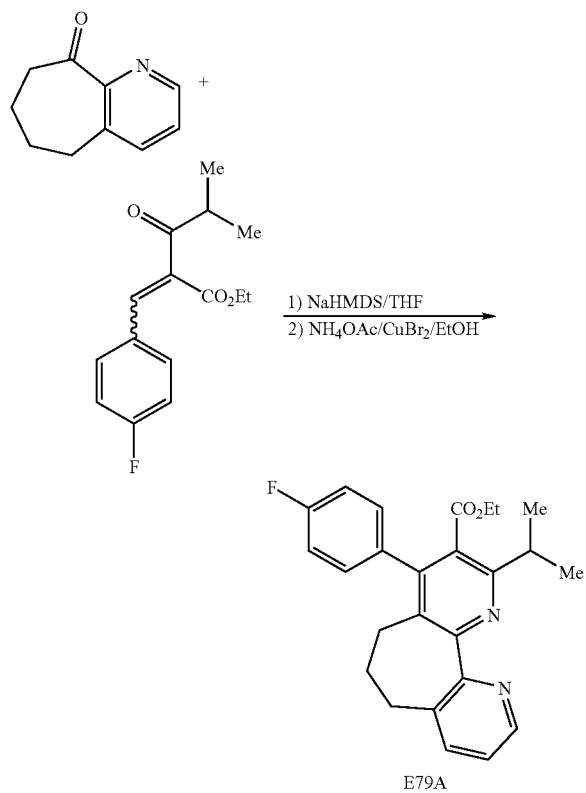

To a flame-dried flask charged with a 0.5 M solution of NaHMDS (19.86 mL, 9.86 mmol) in THF was added solution of 5,6,7,8-tetrahydrocyclohepta[b]pyridin-9-one (1.46 g, 4.55 mmol) in 1.0 mL THF dropwise at −78° C. under a $N_2$ atmosphere. The reaction was stirred at −78° C. for 45 min and was further treated with solution of ethyl 2-[(4-fluorophenyl)methylene]-4-methyl-3-oxo-pentanoate (2.00 g, 7.58 mmol) in 2.0 mL of THF dropwise at −78° C. The reaction was stirred for an additional 3 h at −78° C. The reaction was treated with 20.0 mL of saturated $NH_4Cl$ at −78° C. After warming to room temperature, the reaction was extracted with ethyl acetate (3×50 mL). The combined organic phases were dried over magnesium sulfate and concentrated in vacuo. A solution of the residue in 10.0 mL of EtOH was treated with $CuBr_2$ (3.4 g, 15.0 mmol), $NH_4OAc$ (4.6 g, 60.64 mmol), and p-TsOH (72 mg, 0.37 mmol). The reaction was stirred at reflux for 18 h. The EtOH was removed under reduced pressure. The residue was treated with ethyl acetate (100 mL) and 1:1 conc. ammonium hydroxide:water (50 mL). The mixture was stirred at room temperature for 1 h. The two phases were separated. The organic phase was washed with water (100 mL), brine (75 mL), dried over $MgSO_4$ and concentrated. Flash chromatography of the residue (silica, 30% ethyl acetate/hexanes) yielded E79A (1.3 g, 42%): LRMS (API, pos. ion spectrum) m/z 404 (M+H).

Part B:

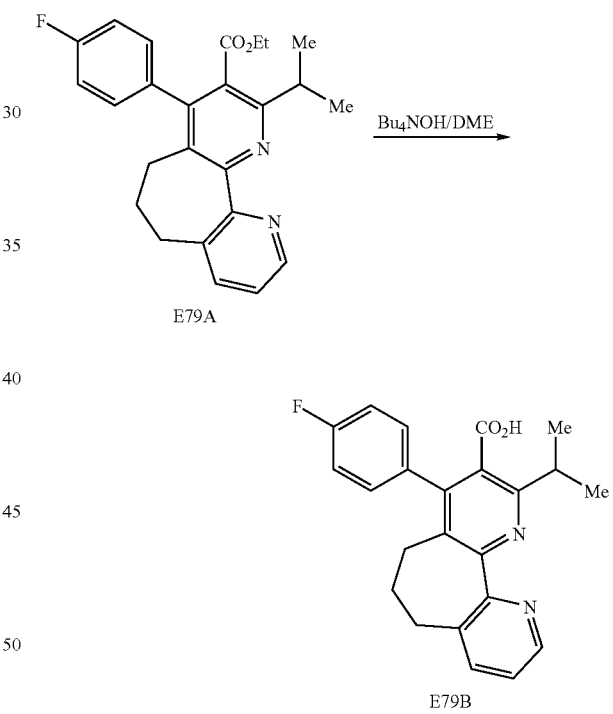

The water present in 40% tetrabutylammonium hydroxide (6.3 mL) was removed azeotropically with toluene. The residual oil was treated with E79A (650 mg, 1.6 mmol) and ethylene glycol dimethyl ether (10.0 mL). The reaction was stirred at refluxing temperature for 4 h. Aqueous NaOH (1.0 N, 10.0 mL) was added to the reaction mixture at room temperature. The mixture was washed with $Et_2O$ (3×10 mL), neutralized with HCl (1.0 N) to pH 6.0 and extracted with ethyl acetate (3×15 mL). The combined ethyl acetate layers were dried over $MgSO_4$ and concentrated to provide E79B (500 mg, 83%): LRMS (API, pos. ion spectrum) m/z 377 (M+H).

Part C:

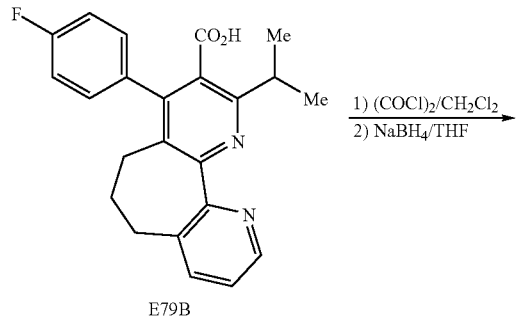

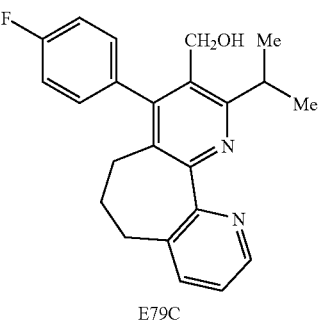

To a solution of E79B (400.0 mg, 1.02 mmol) in methylene chloride (5.0 mL) was added oxalyl chloride (0.34 mL, 3.98 mmol) and 1 drop of DMF. The reaction was stirred at ambient temperature under $N_2$ for 18 h and was then concentrated. Residual oxalyl chloride was removed by coevaporation with toluene under reduced pressure. The brown residue was dissolved in THF (5.0 mL) and was treated with sodium borohydride (500 mg, 13.0 mmol). After stirring at room temperature for 3 h, aqueous HCl (1.0 N) was added dropwise until gas evolution ceased. The reaction mixture was neutralized with aqueous NaOH (1.0 N) to pH 9, and extracted with ethyl acetate (3×10.0 mL). The combined organic layers were dried over $MgSO_4$ and concentrated. Flash chromatography of the residue (silica, 50% ethyl acetate/hexanes) provided E79C (172 mg, 47%): LRMS (API, pos. ion spectrum) m/z 363 (M+H).

Part D:

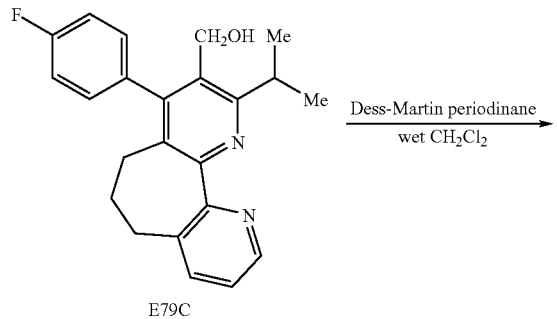

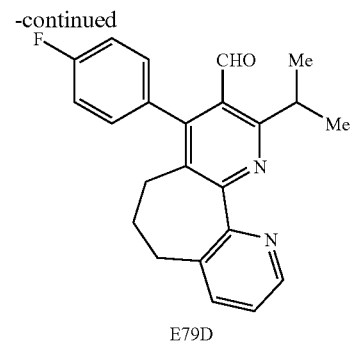

To a solution of E79C (100 mg, 0.28 mmol) in methylene chloride (8.0 ml) was added Dess-Martin periodinane (129 mg, 0.29 mmol). To the reaction was added well-mixed methylene chloride (2.0 mL) and water (0.005 mL, 0.31 mmol) dropwise over 5 min. The reaction was diluted with diethyl ether (10 mL), and concentrated. The residue was dissolved in ethyl acetate (10 mL), washed with aqueous 10% $Na_2S_2O_3$ (15 mL), saturated $NaHCO_3$ (15 mL), brine (10 mL), dried over $MgSO_4$ and concentrated. Flash chromatography of the residue (silica, 30% ethyl acetate/hexanes) yielded aldehyde E79D (75.8 mg, 75%): LRMS (API, pos. ion spectrum) m/z 361 (M+H).

Part E:

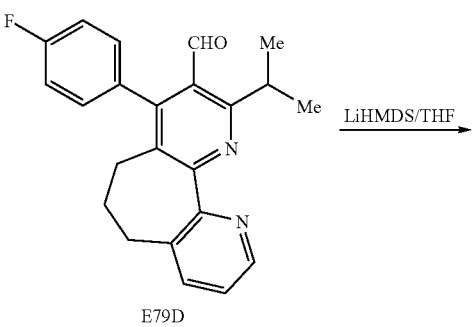

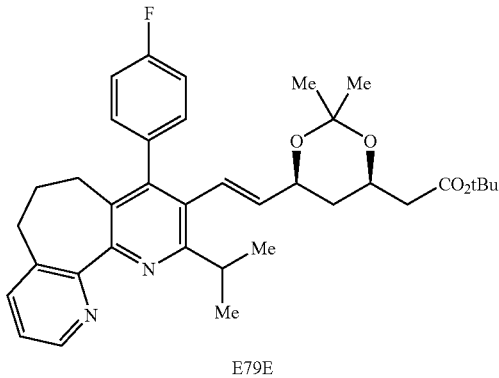

To a solution of E79D (30.0 mg, 0.083 mmol) and E1D (45.0 mg, 0.10 mmol) in THF (0.5 mL) was added LiHMDS (1.0 M in THF, 0.1 mL, 0.10 mmol) dropwise at −78° C. The reaction was stirred at the same temperature for 1 h. After stirring at −30° C. for an additional 1 h, saturated $NH_4Cl$ solution (2 mL) was added. The reaction mixture was extracted with ethyl acetate (3×5 mL). The combined organic layers were dried over $MgSO_4$ and concentrated. Flash chromatography of the residue (silica, 50% ethyl acetate/hexanes) yielded E79E (40.0 mg, 82%): LRMS (API, pos. ion spectrum) m/z 587 (M+H).

Part F:

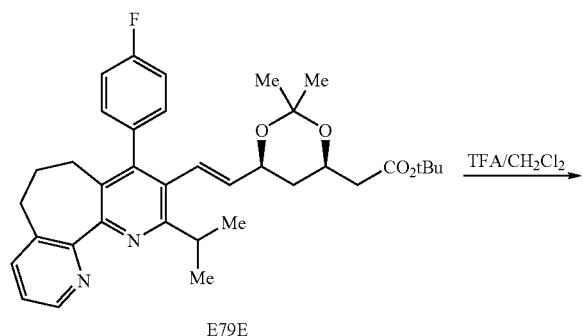

E79E

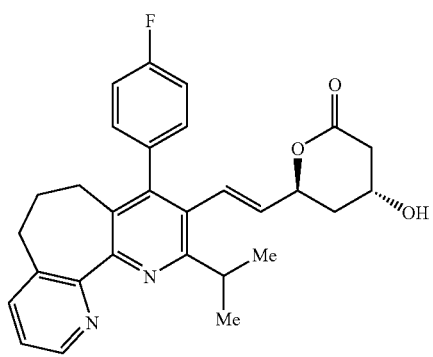

E79F

To a solution of E79E (40.0 mg, 0.068 mmol) in methylene chloride (1.0 mL) was added trifluoroacetic acid (1.0 mL). After stirring at room temperature for 2 h, the reaction was concentrated. The residue was dissolved in ethyl acetate (2.0 mL), and the solution was washed with saturated sodium bicarbonate (2.0 mL), dried over MgSO₄ and concentrated. Flash chromatography (silica, 10% MeOH/CH₂Cl₂) yielded lactone E79F (27.5 mg, 85%): LRMS (API, pos. ion spectrum) m/z 473 (M+H).

Part G:

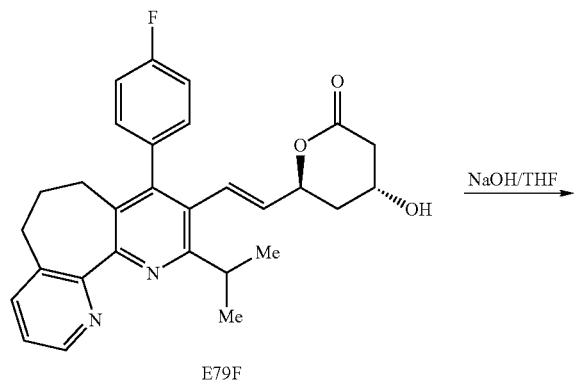

E79F

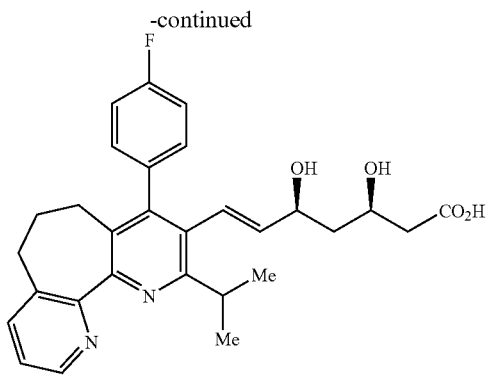

Ex. 79 title compound

To a solution of E79F (27.0 mg, 0.057 mmol) in THF (1.0 mL) was added NaOH (1.0 N, 0.085 mL, 0.085 mmol). After stirring at room temperature for 45 min, the THF was removed under reduced pressure. Reversed phase chromatography (C₁₈-silica, 100% water to 50% MeOH/water gradient) and concentrated to afford the title compound as the sodium salt as a white solid (10.0 mg, 34%): HRMS (ESI, pos. ion spectrum) m/z calcd for $C_{29}H_{32}FN_2O_4$: 491.2346, found: 491.2349 (M+H).

Example 80

6-Heptenoic acid, 7-[4-(4-fluorophenyl)-6,7-dihydro-9-methoxy-2-(1-methylethyl)-5H-cyclohepta[2,1-b:3,4-c']dipyridin-3-yl]-3,5-dihydroxy-, (3R,5S,6E)-

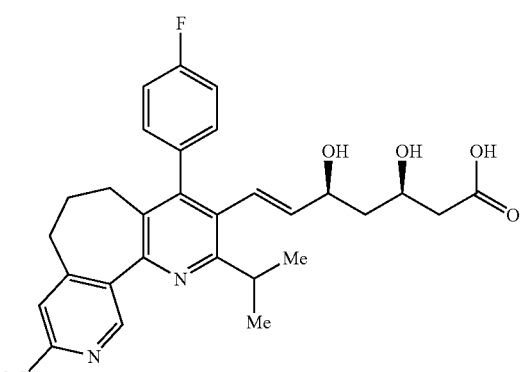

Part A:

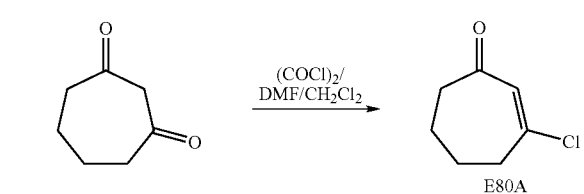

E80A

To a solution of 1,3-cycloheptanedione (43.0 g, 0.34 mol), and DMF (26.3 mL, 0.34 mol) in methylene chloride (1000.0 mL) was added oxalyl chloride (35.7 mL, 0.41 mol) dropwise at 0° C. After stirring at 0° C. for 15 min, the reaction mixture was washed with water (3×500 mL). The aqueous phase was then extracted with diethyl ether (4×300 mL). The combined methylene chloride and diethyl ether phases were dried over MgSO₄ and concentrated to yield E80A (49.0 g 100%) as a brown liquid.

Part B:

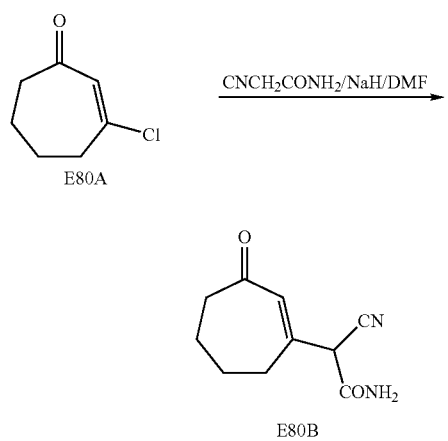

To a solution of 2-cyanoacetamide (57.1 g, 0.68 mol) in DMF (600 mL) was added NaH (60% in mineral oil, 29.0 g, 0.71 mol) in one portion at 0° C. After stirring at 0° C. for 30 min, a solution of E80A (49.0 g, 0.34 mol) in DMF (200 mL) was added dropwise. The reaction mixture was stirred at room temperature for 30 min and DMF was removed under reduced pressure. The residue was dissolved in water (350 mL). The solution was washed with ethyl acetate (3×150 mL), neutralized with 3.0 N aqueous HCl to pH 2-3 and extracted with 10% MeOH/CH₂Cl₂ (6×200 mL). The latter combined extracts were dried over MgSO₄ and concentrated. Flash chromatography of the residue (silica, 75% ethyl acetate/hexanes) yielded E80B (60.6 g, 93%) as a orange solid: LRMS (API, pos. ion spectrum) m/z 193 (M+H).

Part C:

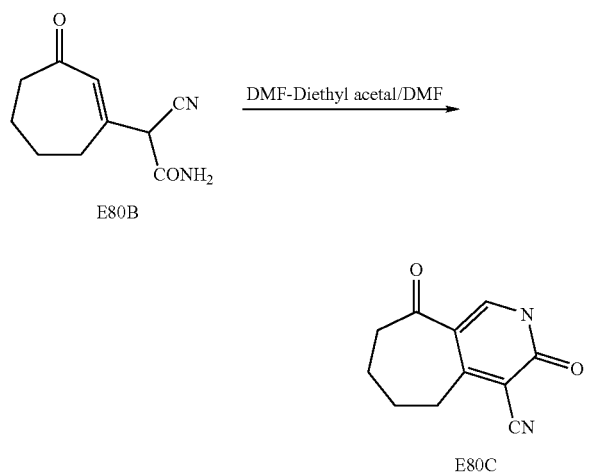

To a solution of E80B (60.2 g, 0.31 mol) in DMF (300 mL) was added dimethylformamide diethyl acetal (62.5 mL, 0.41 mol) dropwise over 1.5 h. The reaction mixture was stirred at room temperature for 18 h and concentrated under reduced pressure. The resulting brown oil was dissolved in aqueous NaOH (1.0 N, 500 mL), washed with chloroform (5×200 mL) and acidified with HCl (6.0 N) slowly at 0° C. to pH 2-3. The brown solid, E80C, was collected by filtration and dried in vacuo (55.0 g, 88%): LRMS (API, pos. ion spectrum) m/z 203 (M+H).

Part D:

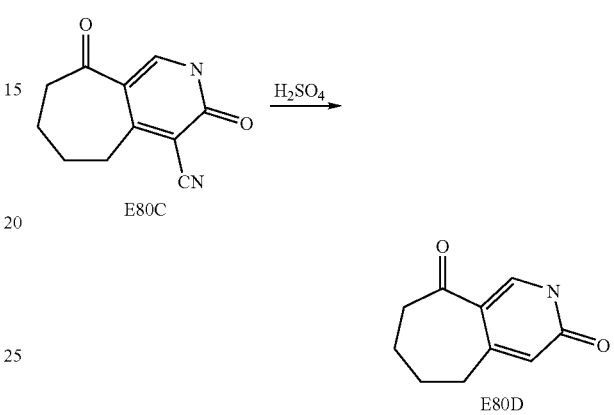

A solution of E80C (55.0 g, 0.27 mol) in 50% conc. sulfuric acid (300 mL) was stirred at 140° C. for 4.5 h. The reaction mixture was neutralized with 50% sodium hydroxide slowly at 0° C. to pH 7-8. The water was removed under reduced pressure. The residue was dissolved into warm chloroform and an insoluble solid was removed by filtration. The filtrate was concentrated. Flash chromatography of the residue (silica, 5% MeOH/CH₂Cl₂) yielded E80D (36.5 g, 76%) as a tan solid: LRMS (API, pos. ion spectrum) m/z 192 (M+H).

Part E:

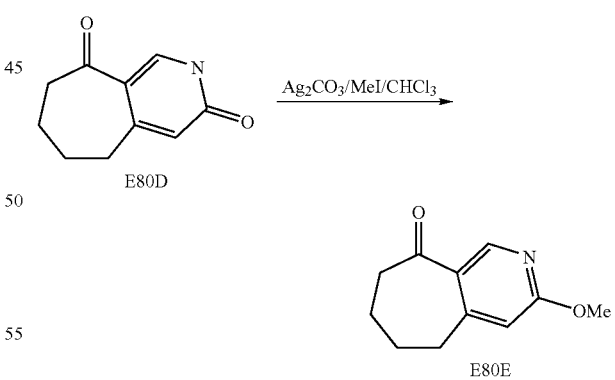

To an amber round-bottomed flask was added E80D (36.5 g, 0.21 mol), silver carbonate (85.3 g, 0.31 mol), iodomethane (78.4 mL, 1.26 mol) and chloroform (500 mL). The reaction mixture was stirred at room temperature for 18 h. The solid was removed by filtration. The filtrate was concentrated. Flash chromatography of the residue (silica, 2.5% ethyl acetate/hexanes) yielded E80E (39.5 g, 97%) as a yellow liquid: LRMS (API, pos. ion spectrum) m/z 178 (M+H).

Part F:

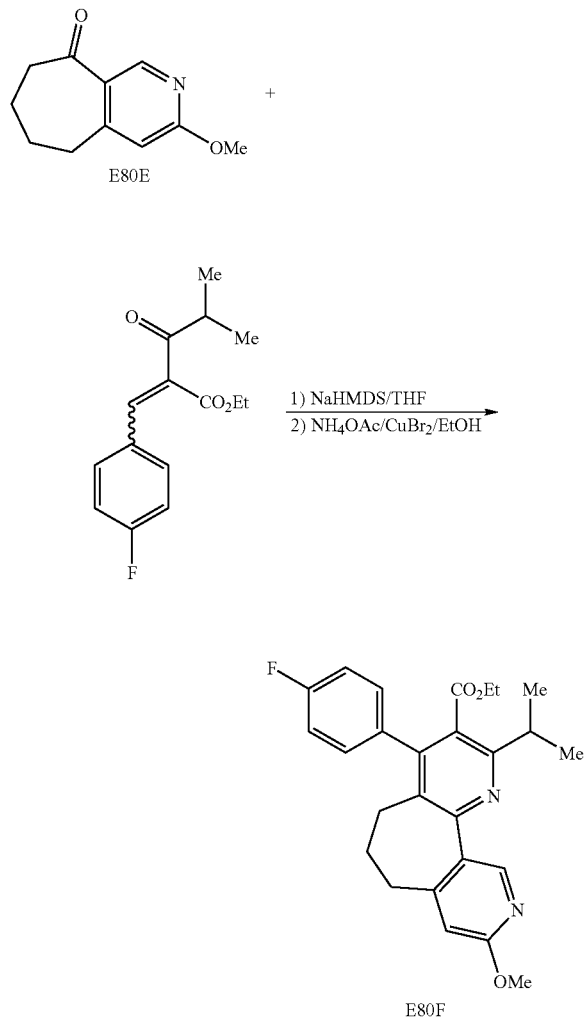

Compound E80F was prepared from E80E and ethyl 2-[(4-fluorophenyl)methylene]-4-methyl-3-oxo-pentanoate utilizing the procedure as described in Example 79 Part A.

Part G:

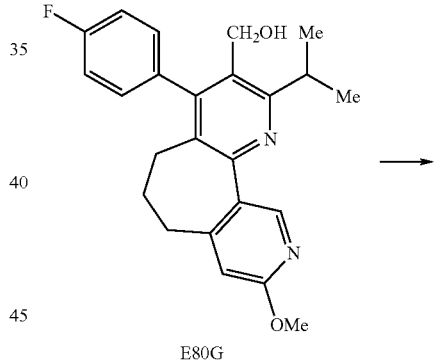

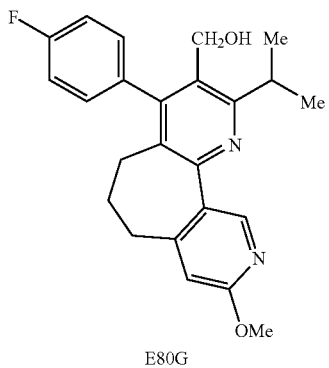

To a solution of E80F (505 mg, 1.16 mmol) in THF (10 mL) was added LAH (1.0 M in THF, 7.0 mL, 7.00 mmol) dropwise under $N_2$ at room temperature. After stirring at room temperature for 18 h, water (0.28 mL), then NaOH (1.0 N, 0.6 mL), and again water (0.9 mL) were added dropwise. The solid was removed by filtration and washed with THF. The combined filtrates were dried over $MgSO_4$ and concentrated. Flash chromatography of the residue (silica, 20% ethyl acetate/hexanes) yielded E80G (333 mg, 73%): LRMS (API, pos. ion spectrum) m/z 393 (M+H).

Part H:

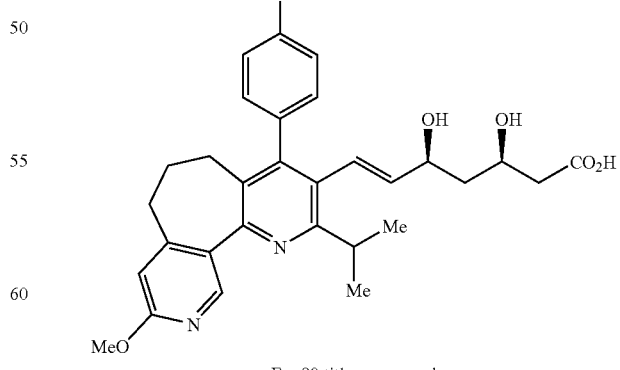

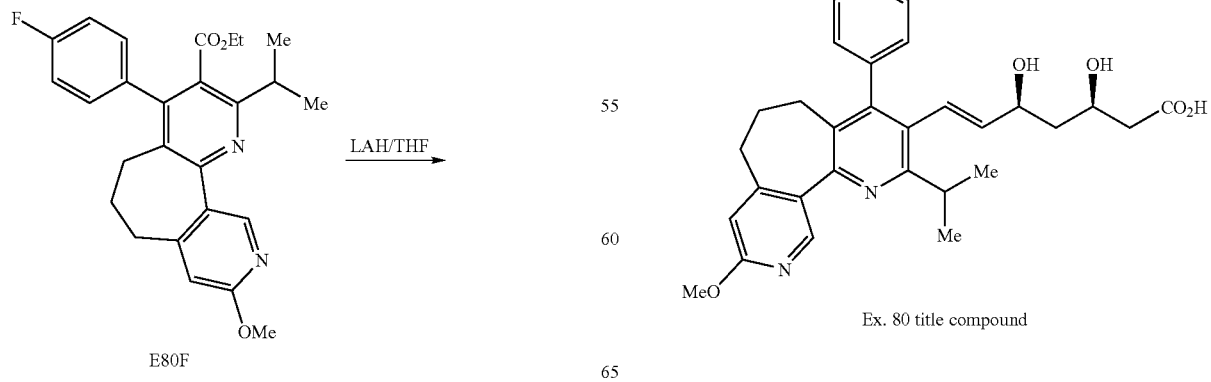

Ex. 80 title compound

The title compound was prepared as the sodium salt from E80G utilizing the procedures as described in Example 79 parts D-G: HRMS (ESI, pos. ion spectrum) m/z calcd for C$_{30}$H$_{34}$FN$_2$O$_5$: 521.2452, found: 577.3192; HPLC (method 3) t$_R$=3.53 min.

Example 81

6-Heptenoic acid, 7-[4-(4-fluorophenyl)-6,7,9,10-tetrahydro-2-(1-methylethyl)-9-oxo-5H-cyclohepta[2,1-b:3,4-c']dipyridin-3-yl]-3,5-dihydroxy-, (3R,5S,6E)-

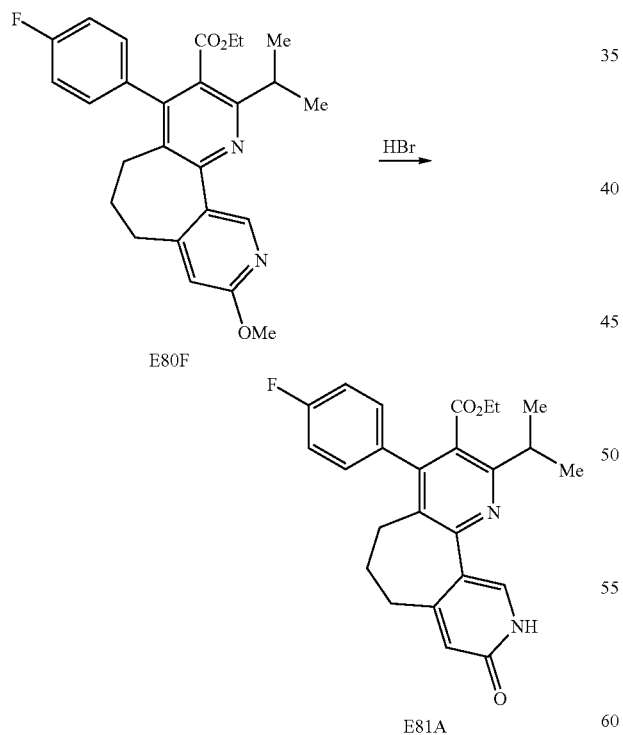

Part A:

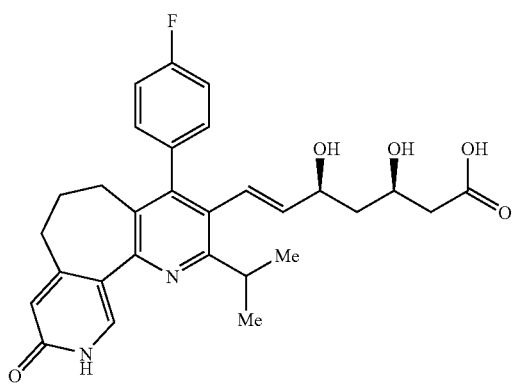

A solution of E80F (100 mg, 0.23 mmol) in 48% HBr (2.0 mL) was stirred at 90° C. for 2 h. The reaction mixture was poured onto ice and extracted with ethyl acetate (3×10 mL). The combined organic layers were dried over MgSO$_4$ and concentrated. Flash chromatography of the residue (silica, 100% ethyl acetate) yielded E81A (55.6 mg, 58%): LRMS (ESI, pos. ion spectrum) m/z 421 (M+H).

Part B:

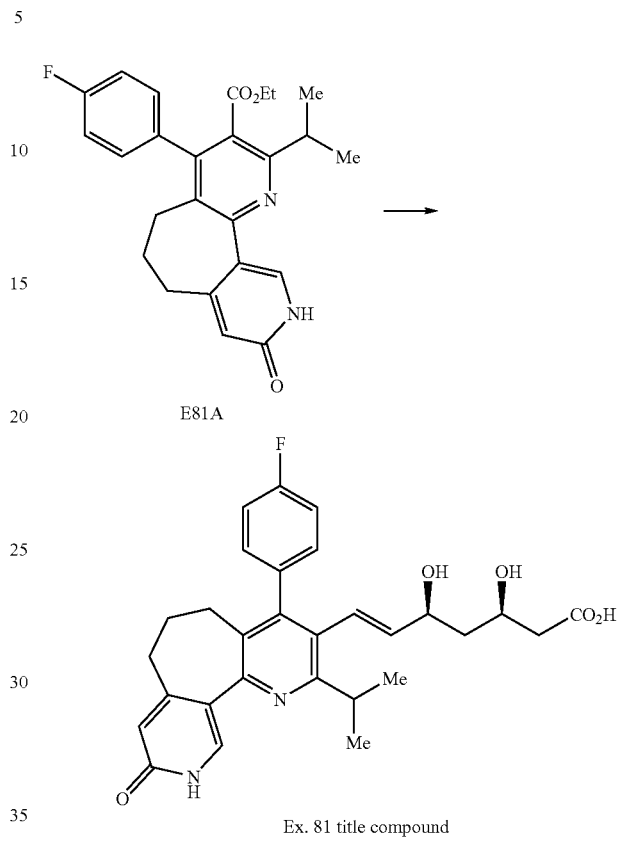

Ex. 81 title compound

The title compound was prepared as the sodium salt from compound E81A utilizing the procedures described in Example 80 Parts G-H: HRMS (ESI, pos. ion spectrum) m/z calcd for C$_{29}$H$_{32}$FN$_2$O$_5$: 507.2295, found: 507.2293 (M+H).

Example 82

6-Heptenoic acid, 7-[4-(4-fluorophenyl)-6,7-dihydro-2-(1-methylethyl)-5H-cyclohepta[2,1-b:3,4-c']dipyridin-3-yl]-3,5-dihydroxy-, (3R,5S,6E)-

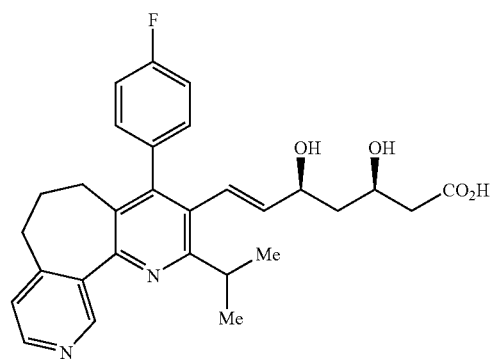

Part A:

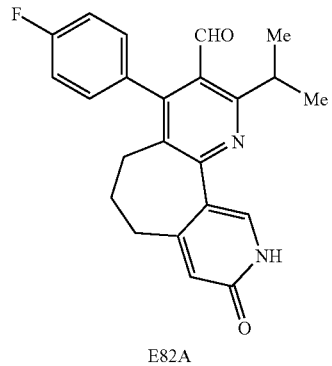

E82A (TfO)₂O/pyridine/CH₂Cl₂ →

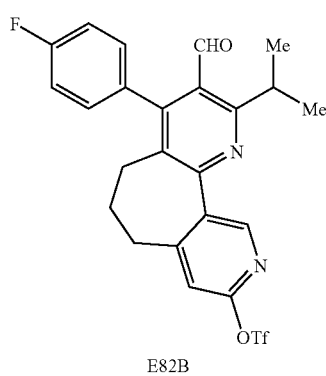

E82B

To a solution of E82A (prepared from E81A using the procedures described in Example 81, 700 mg, 1.86 mmol) and pyridine (0.18 mL, 2.23 mmol) in methylene chloride (5.0 mL) was added trifluoromethanesulfonic anhydride (0.38 mL, 2.23 mmol) dropwise at 0° C. After stirring 1.5 h at 0° C., the reaction was diluted with ethyl acetate (15 mL), washed with water (10 mL), brine (10 mL), dried over MgSO₄ and concentrated. Flash chromatography of the residue (silica, 10% ethyl acetate/hexanes) yielded E82B (660.0 mg, 70%): LRMS (ESI, pos. ion spectrum) m/z 509 (M+H).

Part B:

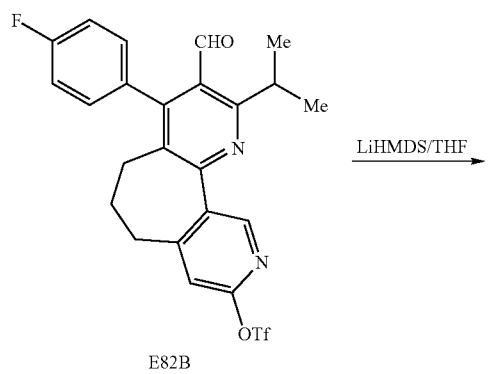

E82B

LiHMDS/THF →

-continued

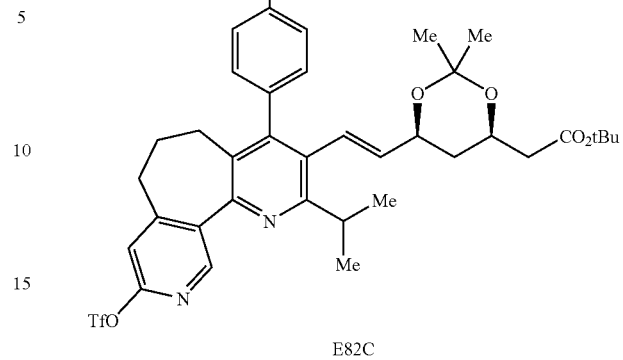

E82C

Compound E82C was prepared from compound E82B utilizing the procedure described in Example 79 Part E: LRMS (ESI, pos. ion spectrum) m/z 735 (M+H).

Part C:

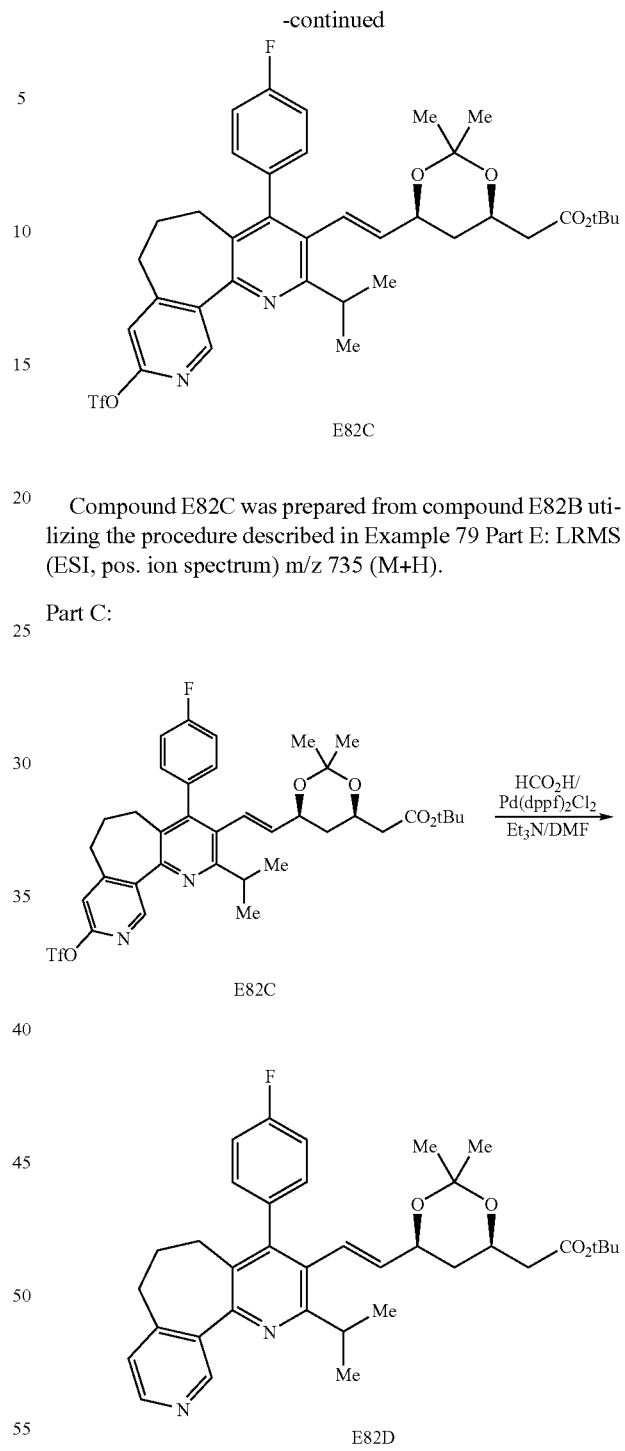

E82C

HCO₂H/ Pd(dppf)₂Cl₂ / Et₃N/DMF →

E82D

A mixture of E82C (80.0 mg, 0.11 mmol), triethylamine (0.046 mL, 0.33 mmol), and formic acid (0.008 mL, 0.22 mmol) in DMF (0.5 mL) was purged with N₂ and Pd(dppf)₂Cl₂ (9.0 mg, 0.011 mmol) was added. The reaction was stirred at 70° C. for 1.5 h, diluted with ethyl acetate (3.0 mL), washed with water (2×5 mL), dried over MgSO₄ and concentrated. Flash chromatography of the residue (silica, 20% ethyl acetate/hexanes) yielded E82D (51.0 mg, 79%): LRMS (ESI, pos. ion spectrum) m/z 587 (M+H).

Part D:

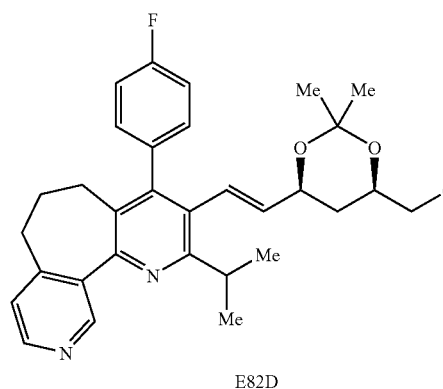

E82D

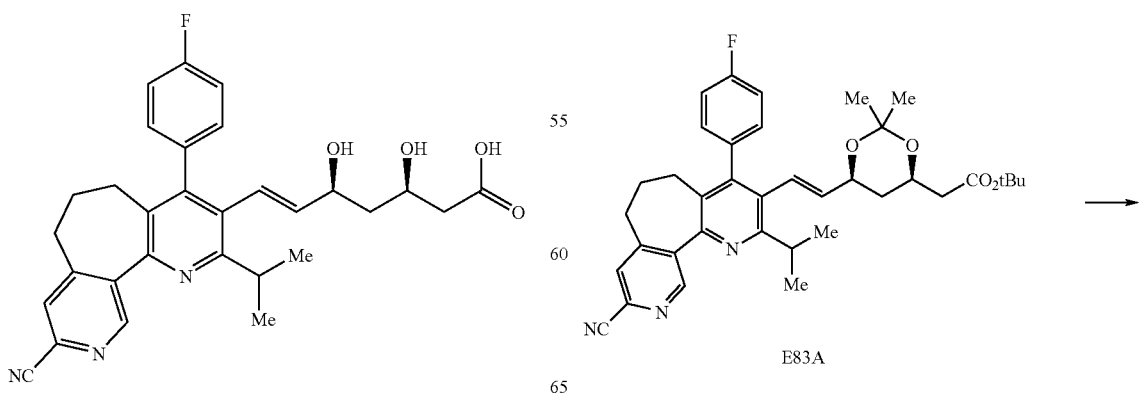

Ex. 82 title compound

The title compound was prepared as the sodium salt from E82D utilizing the procedure described in Example 79 Parts F-G: HRMS (ESI, pos. ion spectrum) m/z calcd for $C_{29}H_{32}FN_2O_4$: 491.2346, found: 491.2354 (M+H).

Example 83

6-Heptenoic acid, 7-[9-cyano-4-(4-fluorophenyl)-6,7-dihydro-2-(1-methylethyl)-5H-cyclohepta[2,1-b:3,4-c']dipyridin-3-yl]-3,5-dihydroxy-, (3R,5S,6E)-

Part A:

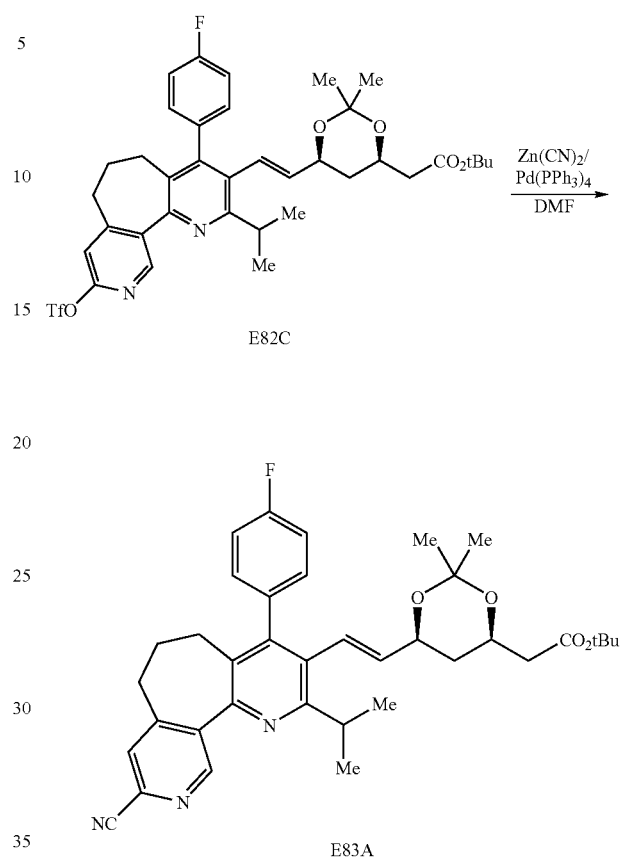

After purging a mixture of E82C (100.0 mg, 0.14 mmol), and $Zn(CN)_2$ (20.8 mg, 0.18 mmol) in DMF (1.0 mL) with argon three times, $Pd(PPh_3)_4$ (16.2 mg, 0.014 mmol) was added. The reaction was stirred at 90° C. for 18 h, diluted with ethyl acetate (3.0 mL), washed with water (2×5 mL), dried over $MgSO_4$ and concentrated. Flash chromatography of the residue (silica, 10% ethyl acetate/hexanes) yielded E83A (26.5 mg, 31%): LRMS (ESI, pos. ion spectrum) m/z 612 (M+H).

Part B:

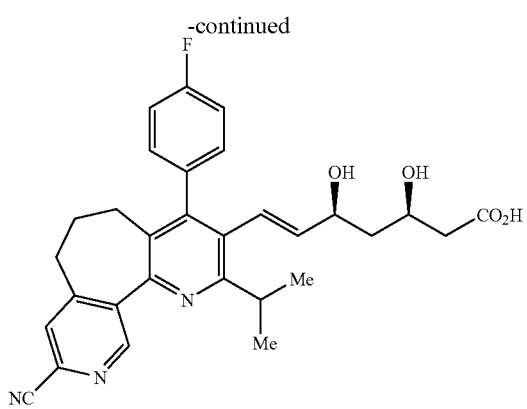

Ex. 83 title compound

The title compound was prepared as the sodium salt from compound E83A utilizing the procedure described in Example 79 Parts F-G: HRMS (ESI, pos. ion spectrum) m/z calcd for $C_{30}H_{31}FN_3O_4$: 516.2299, found: 516.2284 (M+H).

Example 84

6-Heptenoic acid, 7-[4-(4-fluorophenyl)-6,7,8,9-tetrahydro-2-(1-methylethyl)-9-oxo-5H-cyclohepta[2,1-b:4,3-b']dipyridin-3-yl]-3,5-dihydroxy-, (3R,5S,6E)-

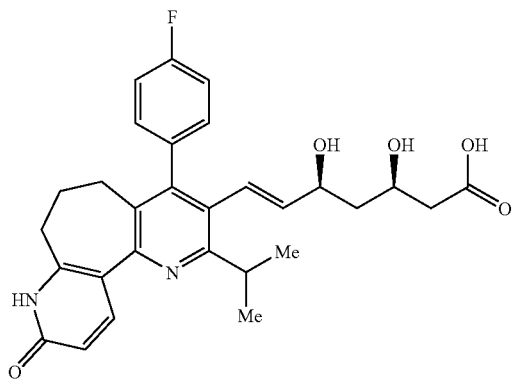

Part A:

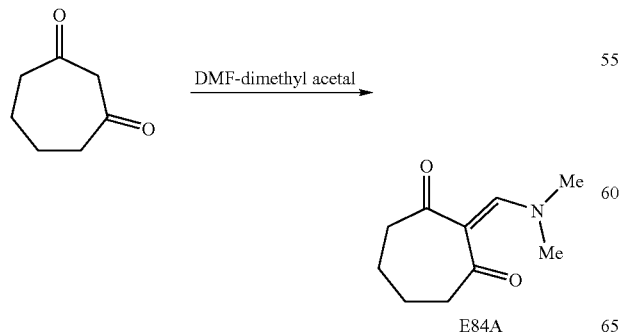

A solution of 1,3-cycloheptanedione (14.0 g, 0.11 mol) in dimethylformamide dimethyl acetal (50 mL) was stirred at refluxing temperature for 3 h. The reaction mixture was concentrated under reduced pressure to yield E84A (20.0 g, 100%) as a yellow solid: LRMS (API, pos. ion spectrum) m/z 182 (M+H).

Part B:

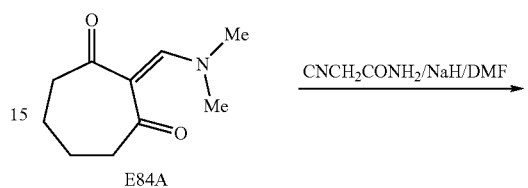

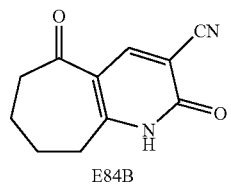

To a solution of 2-cyanoacetamide (23.2 g, 0.28 mol) in DMF (150 mL) was added NaH (60% in mineral oil, 11.8 g, 0.29 mol) in one portion at 0° C. After stirring at 0° C. for 30 min, a solution of E84A (25.0 g, 0.14 mol) in DMF (200 mL) was added dropwise. The reaction mixture was stirred at room temperature for 18 h, and DMF was removed under reduced pressure. The residue was dissolved in water (350 mL), washed with ethyl acetate (3×150 mL), and neutralized with 1.0 N aqueous HCl to pH 2-3. The yellow precipitate was collected by filtration and dried in vacuo to yield E84B (25.0 g, 88%): LRMS (API, pos. ion spectrum) m/z 405 (2M+H).

Part C:

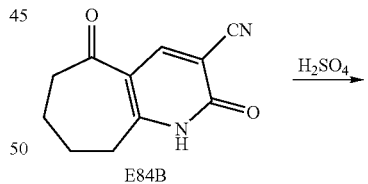

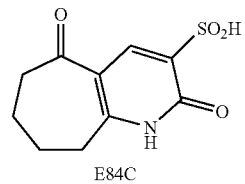

A solution of E84B (25.0 g, 0.12 mol) in 50% sulfuric acid (200 mL) was stirred at 130° C. for 2 h. The reaction mixture was poured onto ice and the resultant white precipitate was collected by filtration and dried in vacuo to yield E84C (26.5 g, 100%): LRMS (API, pos. ion spectrum) m/z 443 (2M+H).

309

Part D:

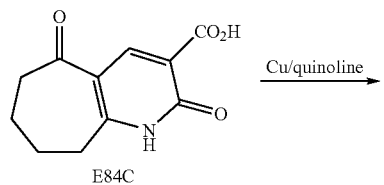

A mixture of E84C (25.0 g, 0.11 mol), copper powder (2.09 g, 0.33 mol) and quinoline (100 mL) was stirred at 240° C. for 2 h. The black semi-solid was dissolved in chloroform (300 mL) and washed with 1.0 N aqueous HCl (5×200 mL), dried over MgSO$_4$ and concentrated. The brown solid residue was washed with warm 50% Et$_2$O/ethyl acetate (2×100 mL) to yield E84D (15.0 g 77%) as a tan solid: LRMS (API, pos. ion spectrum) m/z 178 (M+H).

Part E:

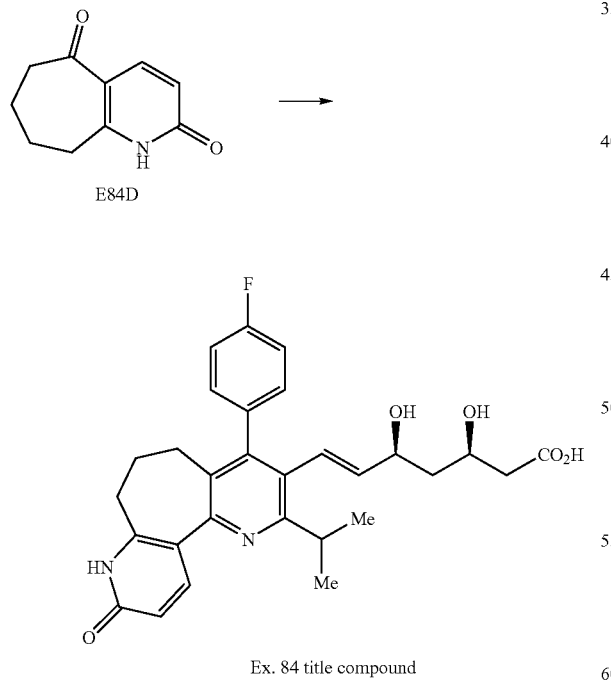

The title compound was prepared as the sodium salt from E84D utilizing procedures described in Example 80 Parts E-H: HRMS (ESI, pos. ion spectrum) m/z calcd for C$_{29}$H$_{32}$FN$_2$O$_5$: 507.2295, found: 507.2321 (M+H); HPLC (method 3) t$_R$=2.78 min.

310

Example 85

5H-Cyclohepta[2,1-b:4,3-b']dipyridine-9-carboxylic acid, 3-[(1E,3S,5R)-6-carboxy-3,5-dihydroxy-1-hexenyl]-4-(4-fluorophenyl)-6,7-dihydro-2-(1-methylethyl)-

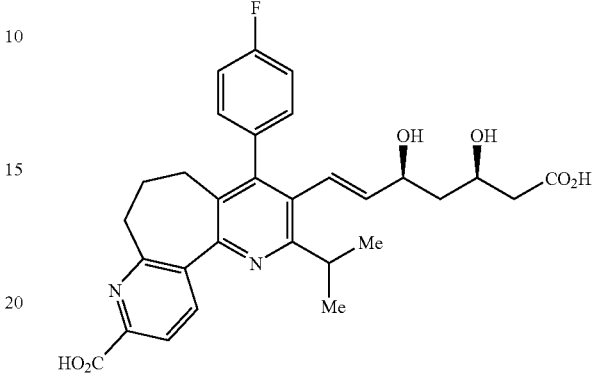

Part A:

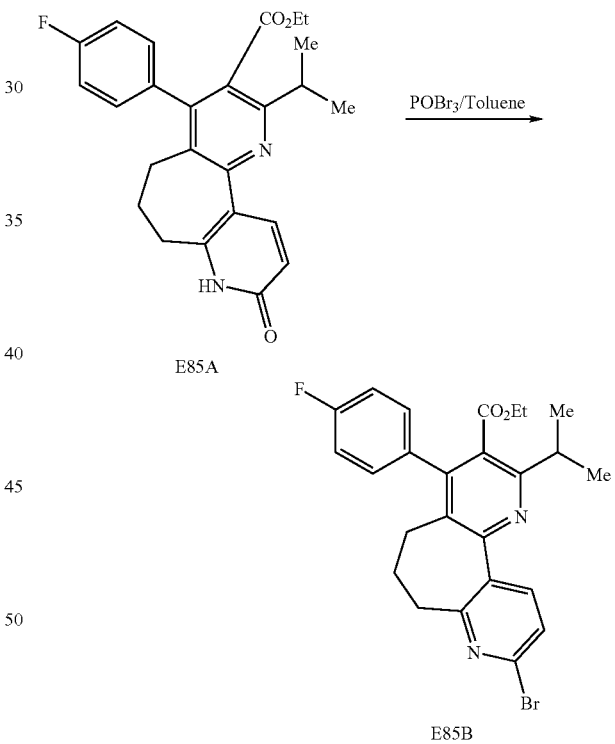

To a slurry of E85A (prepared using the procedures described in Example 80 Parts E-F and Example 81 Part A, 12.0 g, 28.6 mmol) in toluene (200 mL) was added phosphorus oxybromide (24.6 g, 85.8 mmol). The reaction was stirred at refluxing temperature for 3 h, poured onto ice and neutralized with 1.0 N aqueous sodium hydroxide to pH 7-8. The mixture was extracted with ethyl acetate (3×200 mL). The combined organic layers were dried over MgSO$_4$ and concentrated. Flash chromatography of the residue (silica, 10% ethyl acetate/hexanes) yielded E85B (11.2 g, 81%) as a white solid: LRMS (API, pos. ion spectrum) m/z 483/485 (M+H).

Part B:

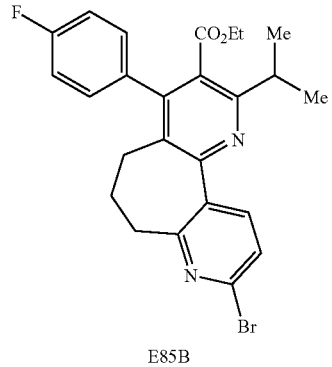

E85B

DIBAL-H/CH$_2$Cl$_2$ →

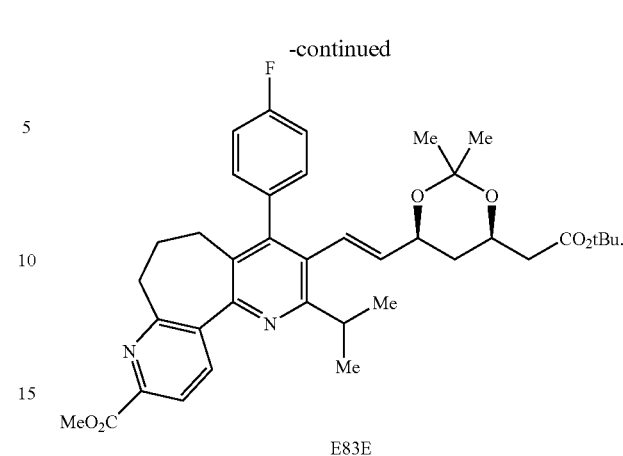

E83E

A slurry of E85D (prepared from E85C using the procedures described in Example 79 Parts D-E, 200.0 mg, 0.30 mmol), dppf (17.0 mg, 0.03 mmol), Pd(OAc)$_2$ (3.4 mg, 0.015 mmol), Et$_3$N (0.083 mL, 0.60 mmol) in MeOH (2.0 mL) and DMF (5.0 mL) was purged with CO three times. The reaction mixture was stirred at 60° C. under CO (1 atm) for 18 h. The reaction was diluted with ethyl acetate (10.0 mL), washed with water (2×20 mL), dried over MgSO$_4$ and concentrated. Flash chromatography of the residue (silica, 20% ethyl acetate/hexanes) yielded E85E (127.5 mg, 66%): LRMS (API, pos. ion spectrum) m/z 645 (M+H).

Part D:

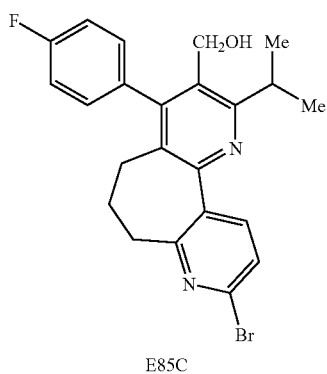

E85C

To a solution of E85B (11.0 g, 22.8 mmol) in methylene chloride (200 mL) was added DIBAL-H (1.0 M in hexanes, 80.0 mL, 80.0 mmol) dropwise at −78° C. under N$_2$. The reaction was stirred for 45 min at −78° C., and was then diluted with diethyl ether (300 mL). Saturated Rochelle's salt (100 mL) was added. The mixture was stirred for 1 h at room temperature. The organic phase was dried over MgSO$_4$ and concentrated. Flash chromatography of the residue (silica, 20% ethyl acetate/hexanes) yielded E85C (8.9 g, 89%) as a white solid: LRMS (API, pos. ion spectrum) m/z 441/443 (M+H).

Part C:

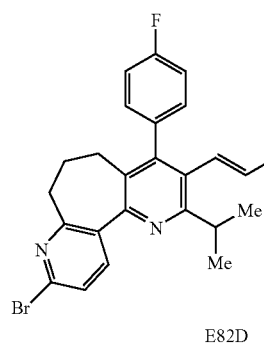

E82D

Pd(OAc)$_2$/ dppf CO/ MeOH/ DMF →

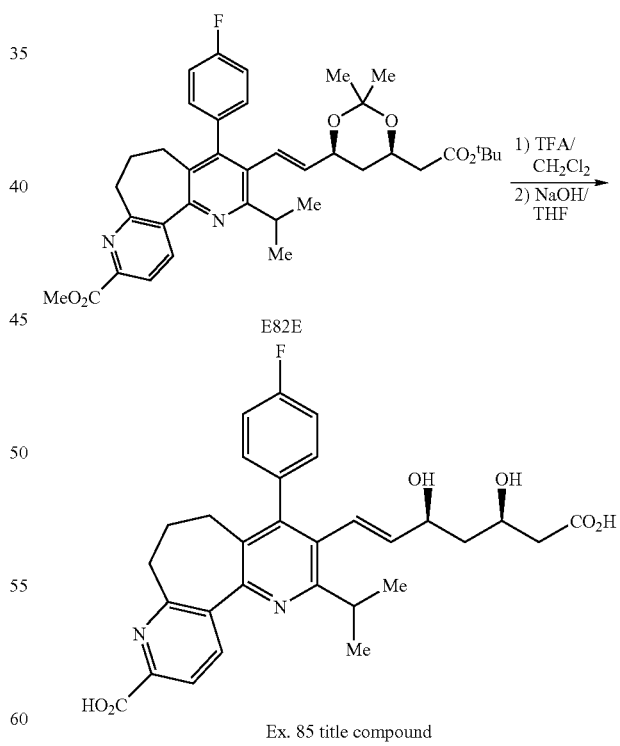

E82E

Ex. 85 title compound

The title compound was prepared as the disodium salt from compound E85E utilizing the procedures described in Example 79 Parts F-G: HRMS (ESI, pos. ion spectrum) m/z calcd for C$_{30}$H$_{32}$FN$_2$O$_6$: 535.2244, found: 535.2243 (M+H); HPLC (method 3) $t_R$=3.37 min.

Example 86

5H-Cyclohepta[2,1-b:3,4-c']dipyridine-9-carboxylic acid, 3-[(1E,3S,5R)-6-carboxy-3,5-dihydroxy-1-hexenyl]-4-(4-fluorophenyl)-6,7-dihydro-2-(1-methylethyl)-

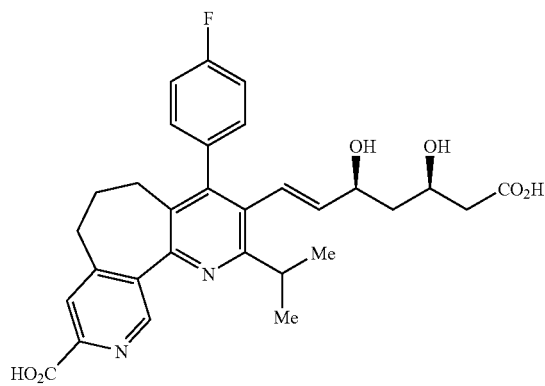

E81A

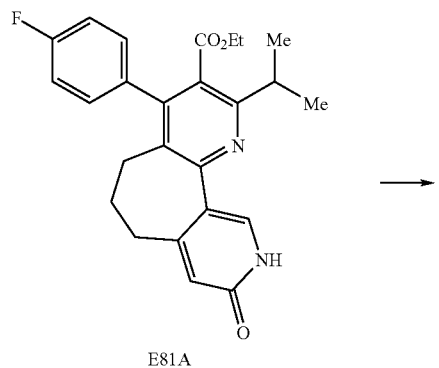

Ex. 86 title compound

The title compound was prepared from E81A utilizing the procedures described in Example 85: HRMS (ESI, pos. ion spectrum) m/z calcd for $C_{30}H_{32}FN_2O_6$: 535.2244, found: 535.2264 (M+H); HPLC (method 3) $t_R$=3.21 min.

Example 87

6-Heptenoic acid, 7-[9-(aminocarbonyl)-4-(4-fluorophenyl)-6,7-dihydro-2-(1-methylethyl)-5H-cyclohepta[2,1-b:3,4-c']dipyridin-3-yl]-3,5-dihydroxy-, (3R,5S,6E)-

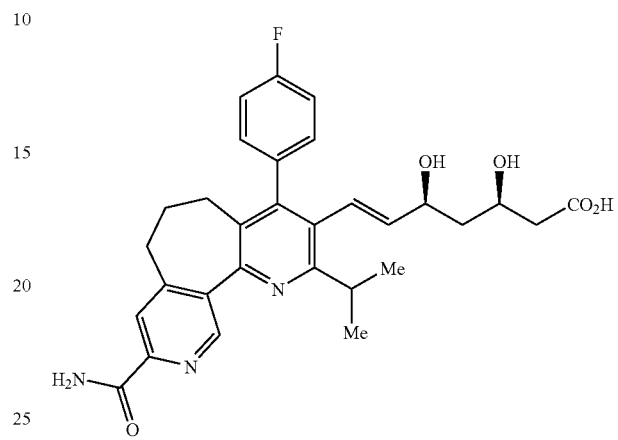

Part A:

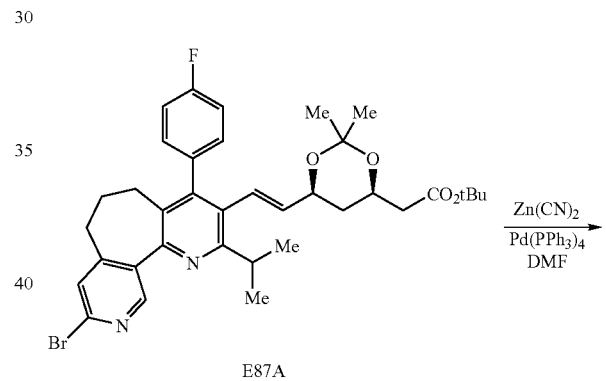

E87A

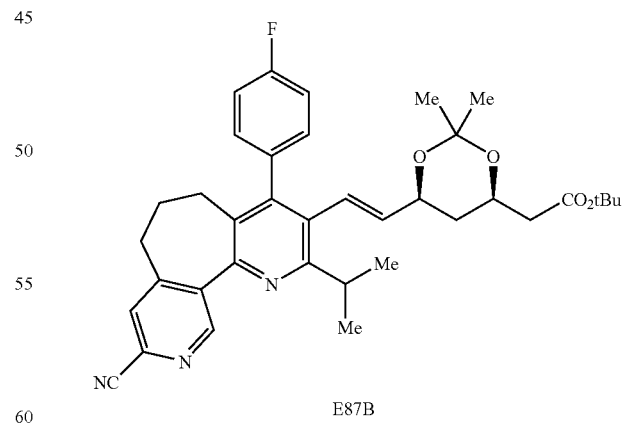

E87B

A suspension of E87A (prepared using the procedures describe in Example E85, 300 mg, 0.46 mmol), and $Zn(CN)_2$ (81.0 mg, 0.69 mmol) in DMF (5.0 mL) was degassed three times and $Pd(PPh_3)_4$ was added. The reaction mixture was stirred at 90° C. for 3 h. The DMF was removed under reduced pressure. Flash chromatography of the residue (silica, 10% ethyl acetate/hexanes) yielded E87B (220.0 mg, 78%) as a white solid: LRMS (API, pos. ion spectrum) m/z 612 (M+H).

Part B:

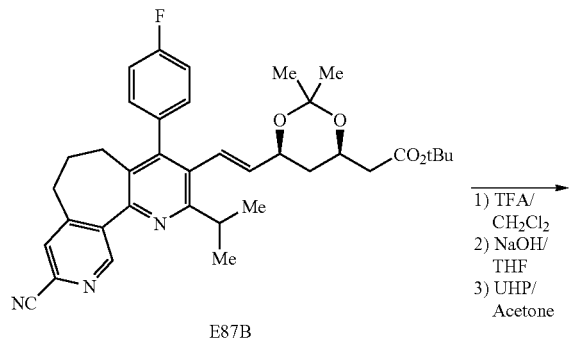

E87B

1) TFA/CH₂Cl₂
2) NaOH/THF
3) UHP/Acetone

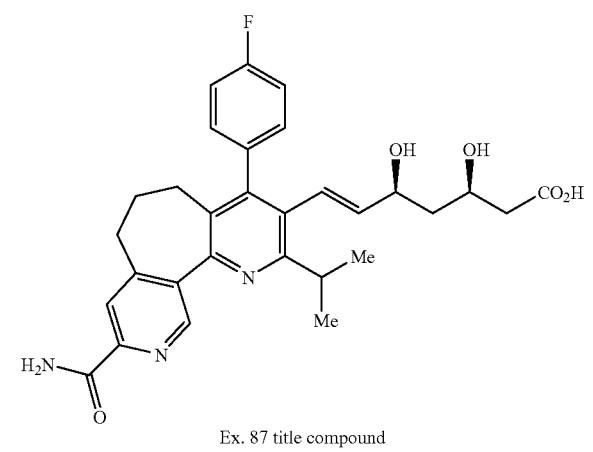

Ex. 87 title compound

To a solution of E87B (120 mg, 0.20 mmol) in methylene chloride was added TFA (1.0 mL). The mixture was stirred at ambient temperature for 1 h. The reaction was concentrated and excess TFA was removed by coevaporation with methylene chloride three times. The residue was dissolved in THF (1.5 mL) and treated with aqueous NaOH (1.0 N, 1.37 mL, 1.37 mmol). The reaction was stirred for 30 min and treated with urea hydrogen peroxide (110.6 mg, 1.18 mmol) followed by acetone (3.0 mL). The reaction was stirred at ambient temperature for 2 h and concentrated. Reversed-phase HPLC purification (Phenomenex C18 Luna 60 mm×21 mm; 3% methanol-water for 3 min then up to 100% methanol over 6 min; Flow=9.9 mL/min) yielded the title compounds as the sodium salt (68.0 mg, 63%) as a white powder: HRMS (ESI, pos. ion spectrum) m/z calcd for $C_{30}H_{33}FN_3O_5$: 534.2404, found: 534.2417 (M+H). HPLC (method 3) $t_R$=3.46 min.

Example 88

6-Heptenoic acid, 7-[9-(aminocarbonyl)-4-(4-fluorophenyl)-6,7-dihydro-2-(1-methylethyl)-5H-cyclohepta[2,1-b:4,3-b']dipyridin-3-yl]-3,5-dihydroxy-, (3R,5S,6E)-

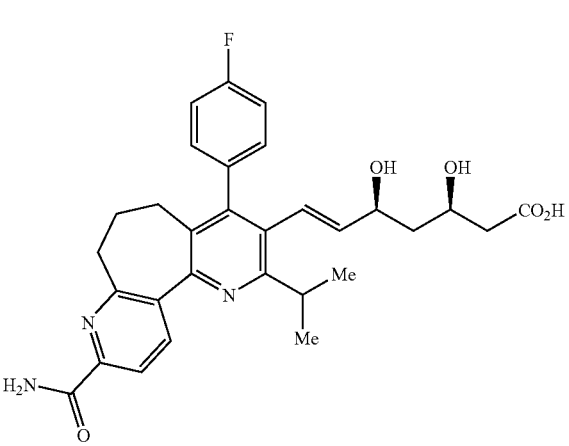

The title compound was prepared from compound E85D using the procedures described in preparation of compound Ex 87. The reversed-phase HPLC purification (Phenomenex C18 Luna 60 mm×21 mm; 2% methanol-water for 3 min. then up to 90% methanol over 5 min. Flow=9.9 mL/min) yielded the title compound as the sodium salt (53%) as a white powder: HRMS (ESI, pos. ion spectrum) m/z calcd for $C_{30}H_{33}FN_3O_5$: 534.2404, found: 534.2430 (M+H). HPLC (method 3) $t_R$=3.50 min.

Example 89

6-Heptenoic acid, 7-[9-[[[3-(dimethylamino)propyl]amino]carbonyl]-4-(4-fluorophenyl)-6,7-dihydro-2-(1-methylethyl)-5H-cyclohepta[2,1-b:4,3-b']dipyridin-3-yl]-3,5-dihydroxy-, (3R,5S,6E)-

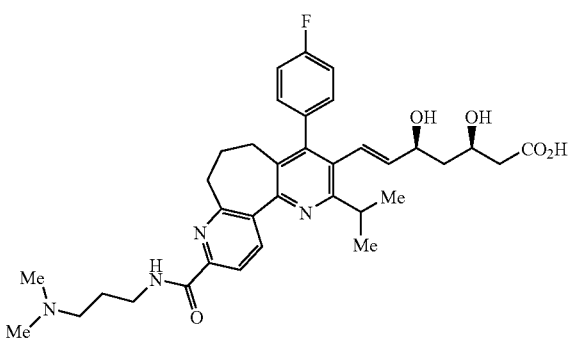

Part A:

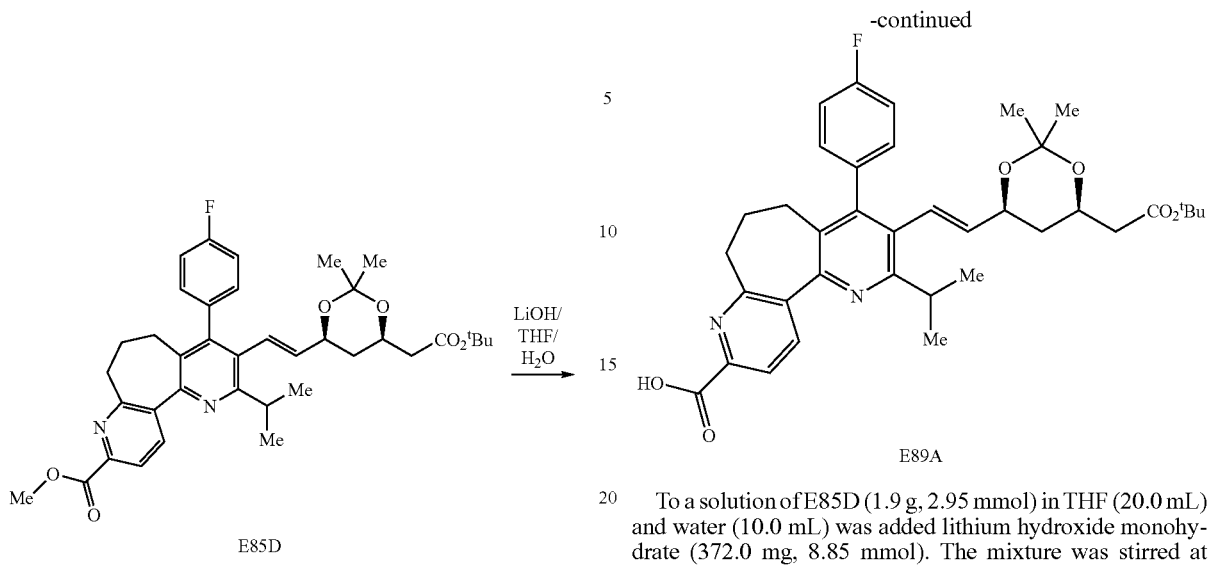

To a solution of E85D (1.9 g, 2.95 mmol) in THF (20.0 mL) and water (10.0 mL) was added lithium hydroxide monohydrate (372.0 mg, 8.85 mmol). The mixture was stirred at ambient temperature for 45 min and was then neutralized with 1.0 N aqueous HCl to pH 6 and extracted with ethyl acetate (3×75 mL). The combined organic layers were dried over $MgSO_4$ and concentrated to yield E89A (1.8 g, 97%) as a white solid: LRMS (API, pos. ion spectrum) m/z 631 (M+H).

Part B:

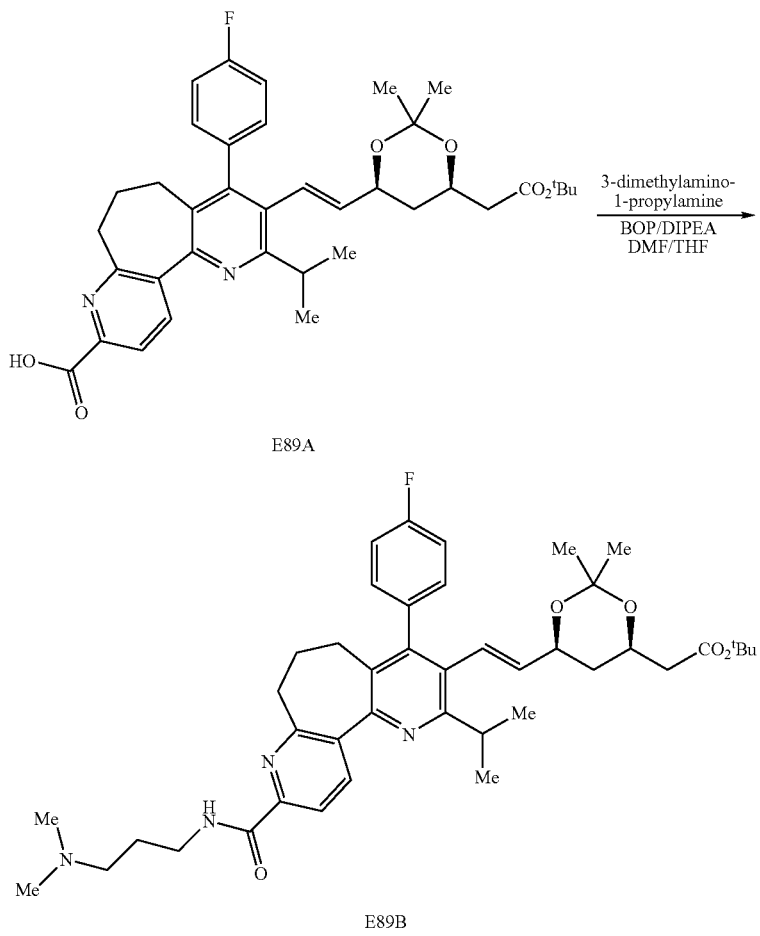

Compound E89B was prepared from Compound E89A utilizing the procedure described in Example 11 Part F. Flash chromatography (silica, 90:10:1 chloroform-methanol-ammonium hydroxide) of the crude product yielded E89B (77%) as a white solid: LRMS (API, pos. ion spectrum) m/z 715 (M+H).
Part C:
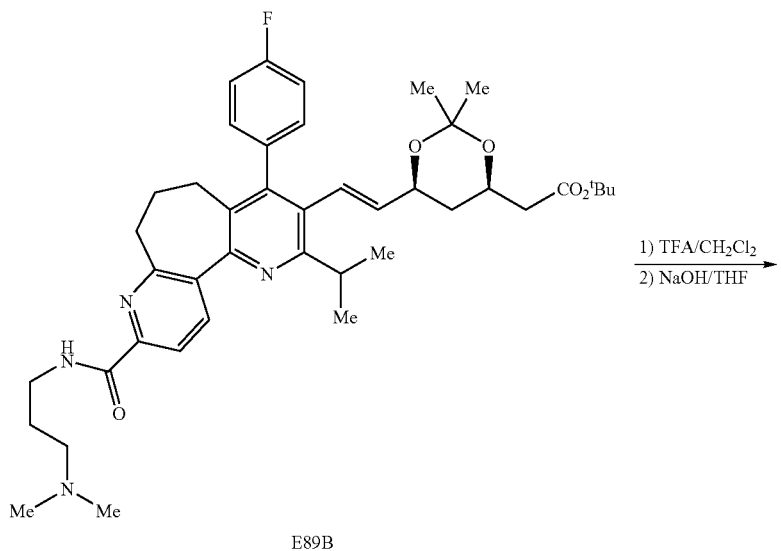
E89B
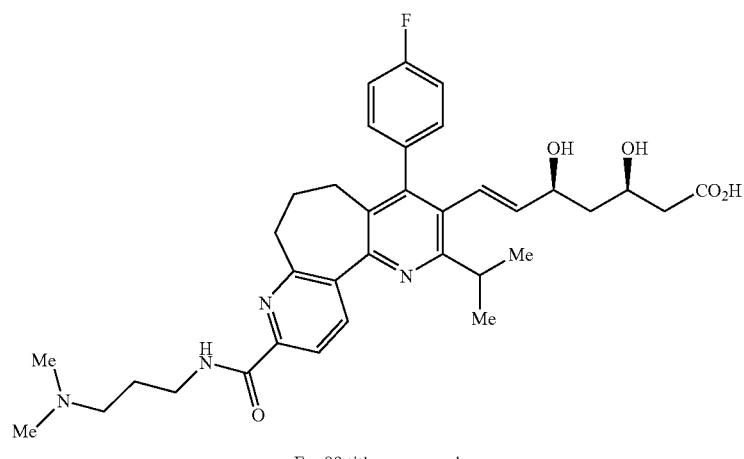
Ex. 89 title compound The title compound was prepared from E89B utilizing the procedure described in Example 79 Parts F-G. Reversed-phase HPLC purification (Phenomenex C18 Luna 60 mm×21 mm; 20% methanol-water then up to 100% methanol over 6 min; Flow=9.9 mL/min) yielded the title compound as the sodium salt (60%) as a white powder: HRMS (ESI, pos. ion spectrum) m/z calcd for $C_{35}H_{44}FN_4O_5$: 619.3296, found: 619.3272 (M+H).

Example 90

6-Heptenoic acid, 7-[9-amino-4-(4-fluorophenyl)-6,7-dihydro-2-(1-methylethyl)-5H-cyclohepta[2,1-b:4,3-b']dipyridin-3-yl]-3,5-dihydroxy-, (3R,5S,6E)-

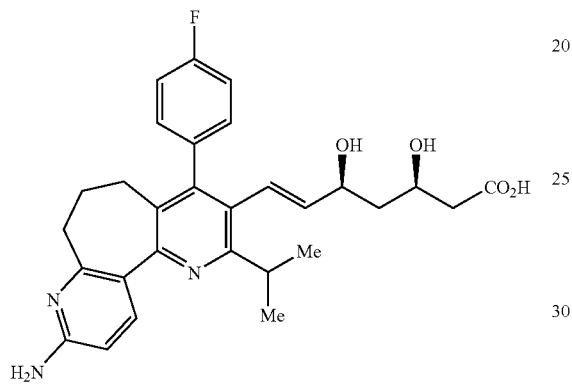

Part A:

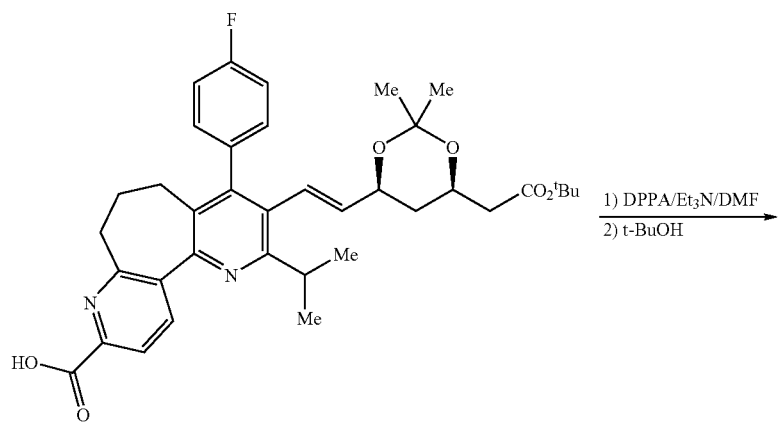

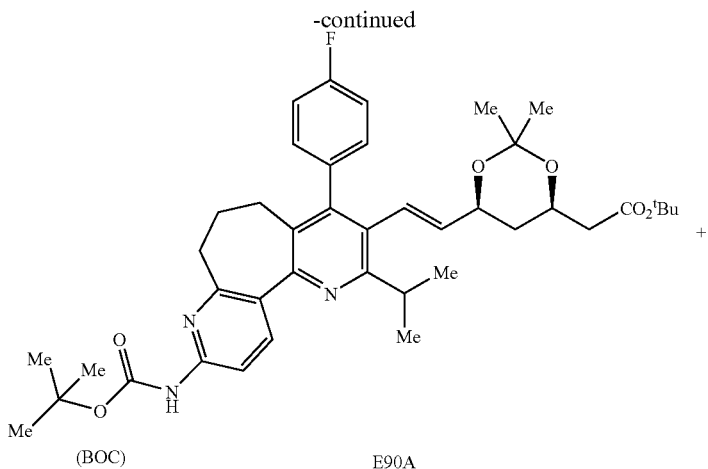

(BOC)     E90A

+

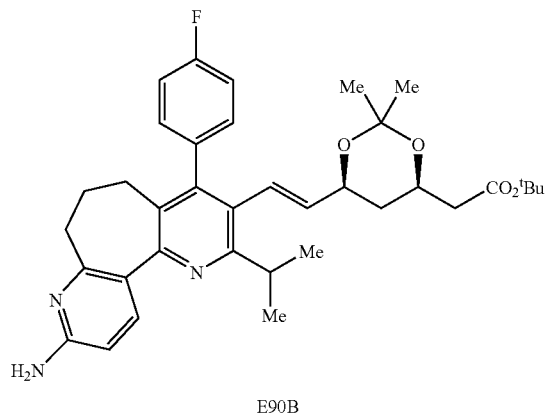

E90B

To a solution of E89A (150.0 mg, 0.24 mmol) in DMF (2.0 mL) were sequentially added triethylamine (0.050 mL, 0.36 mmol) and diphenylphosphoryl azide (0.077 mL, 0.36 mmol). The reaction was stirred at ambient temperature for 30 min and tert-butanol (3.0 mL) was added to the very thick mixture. The reaction mixture was then stirred at 90° C. for 3 h and cooled to ambient temperature. The reaction was diluted with diethyl ether (10 mL); washed with saturated sodium bicarbonate and water; dried over dried over MgSO$_4$ and concentrated. Flash chromatography (silica, 10% ethyl acetate/hexanes then 100% ethyl acetate) yielded E90A (higher R$_f$, 100.0 mg, 59%) as a white solid [LRMS (ESI, pos. ion spectrum) m/z 702 (M+H)], and E90B (lower R$_f$, 70.0 mg, 48%) as a yellow solid: LRMS (API, pos. ion spectrum) m/z 602 (M+H).

Part B:

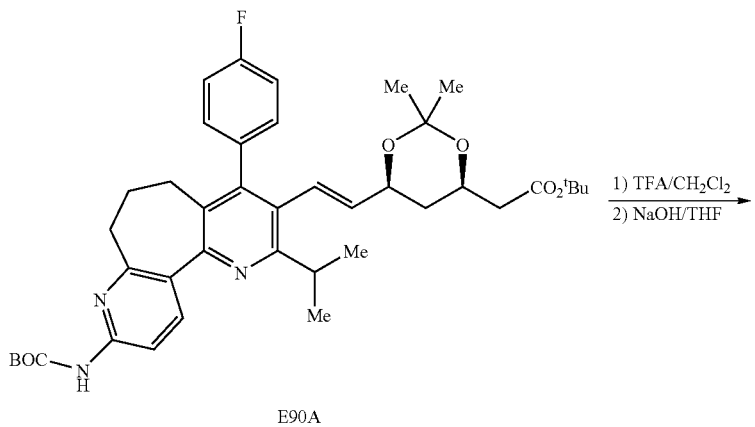

E90A

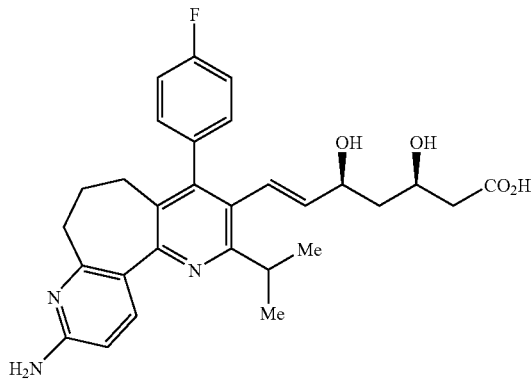

Ex. 90 title compound

The title compound was prepared from compound E90A utilizing the procedure described in Example 79 Parts F-G. Reversed-phase HPLC purification (Phenomenex C18 Luna 60 mm×21 mm; 20% methanol-water then up to 100% methanol over 6 min; Flow=9.9 mL/min) yielded the title compound as the sodium salt (35%) as a white powder: HRMS (ESI, pos. ion spectrum) m/z calcd for $C_{29}H_{33}FN_3O_4$: 506.2455, found: 506.2452 (M+H).

Example 91

6-Heptenoic acid, 7-[9-[[2-(dimethylamino)ethyl]amino]-4-(4-fluorophenyl)-6,7-dihydro-2-(1-methylethyl)-5H-cyclohepta[2,1-b:4,3-b']dipyridin-3-yl]-3,5-dihydroxy-, (3R,5S,6E)-

Part A:

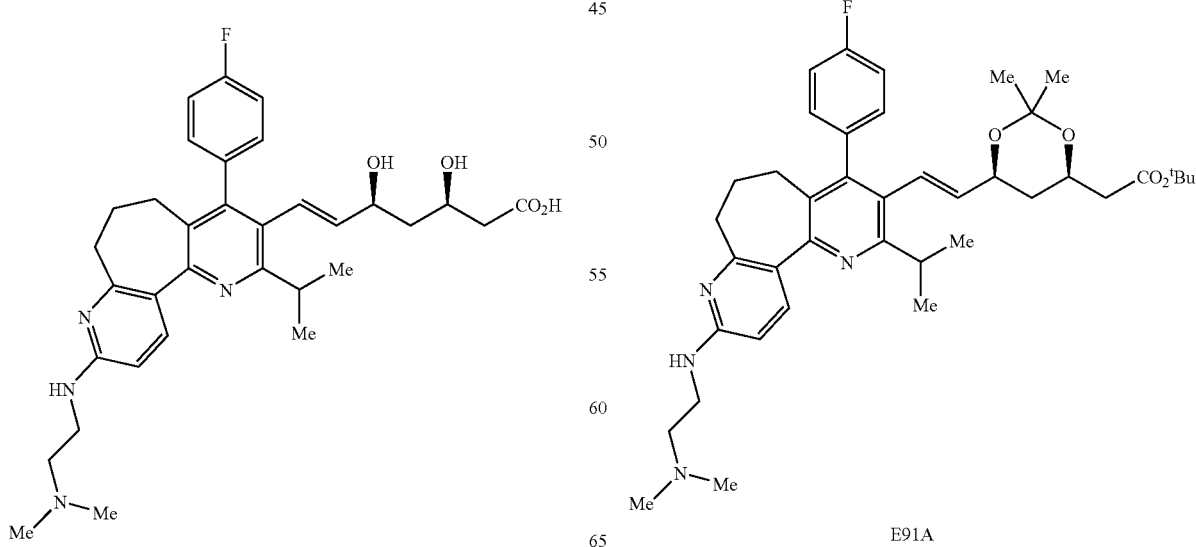

To a suspension of E85D (100.0 mg, 0.15 mmol) in toluene (1.0 mL) was added N,N-dimethylethylenediamine (0.019 mL, 0.18 mmol), cesium carbonate (68.4 mg, 0.21 mmol), tris(dibenzylideneacetone)dipalladium(0) (6.8 mg, 0.0075 mmol) and (±)-2,2'-bis(diphenylphosphino)-1,1'-binaphthalene (7.0 mg, 0.0112 mmol) sequentially. The reaction mixture was degassed three times and stirred at 90° C. for 18 h. The solvent was removed under reduced pressure. Flash chromatography of the residue (silica, 10:90 ethyl acetate-hexanes, then ethyl acetate, then 90:10:1 chloroform-methanol-ammonium hydroxide) yielded E91A (49.0 mg, 49%) as a brown solid: LRMS (ESI, pos. ion spectrum) m/z 673 (M+H).

Part B:

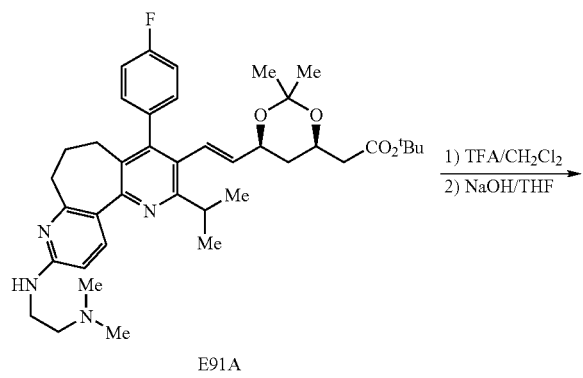

E91A

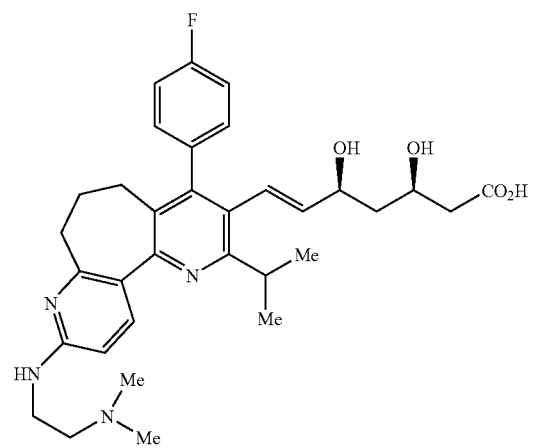

Ex. 91 title compound

The title compound was prepared from compound E91A utilizing the procedure as described in Example 79 Part F-G. Reversed-phase HPLC purification (Phenomenex C18 Luna 60 mm×21 mm; 5% methanol-water for 3 min then up to 100% methanol over 6 min; Flow=9.9 mL/min) yielded the title compound as the sodium salt (52%%) as a white powder: HRMS (ESI, pos. ion spectrum) m/z calcd for $C_{33}H_{42}FN_4O_4$: 577.3190, found: 577.3192 (M+H).

Example 92

6-Heptenoic acid, 7-[4-(4-fluorophenyl)-6,7-dihydro-2-(1-methylethyl)-9-(4-methyl-1-piperazinyl)-5H-cyclohepta[2,1-b:4,3-b']dipyridin-3-yl]-3,5-dihydroxy-, (3R,5S,6E)-

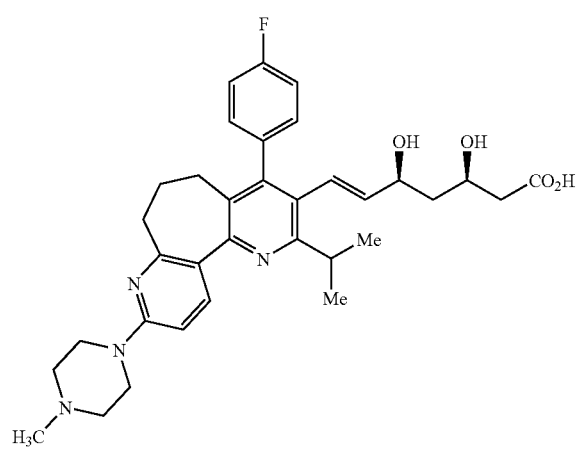

The title compound was prepared from compound E87A using similar procedures as described in Example 91. Reversed-phase HPLC purification (Phenomenex C18 Luna 60 mm×21 mm; 15% methanol-water for 3 min. then up to 100% methanol over 6 min; Flow=9.9 mL/min) yielded the title compound as the sodium salt as a white powder: HRMS (ESI, pos. ion spectrum) m/z calcd for $C_{34}H_{42}FN_4O_4$: 589.3190, found: 589.3199 (M+H).

Example 93

6-Heptenoic acid, 7-[4-(4-fluorophenyl)-6,7-dihydro-2-(1-methylethyl)-9-[(methylsulfonyl)amino]-5H-cyclohepta[2,1-b:4,3-b']dipyridin-3-yl]-3,5-dihydroxy-, (3R,5S,6E)-

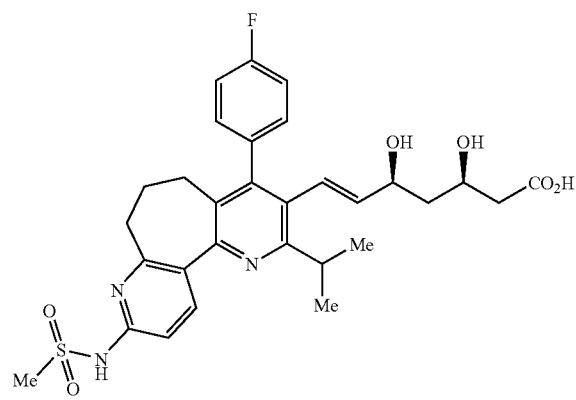

Part A:

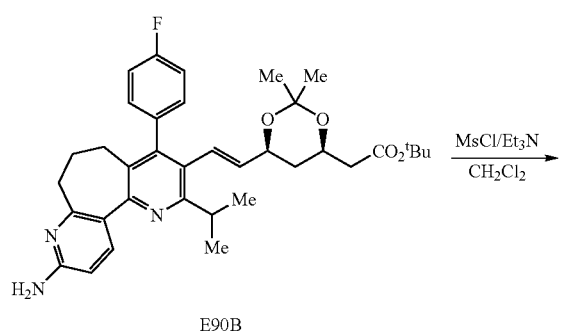

E90B

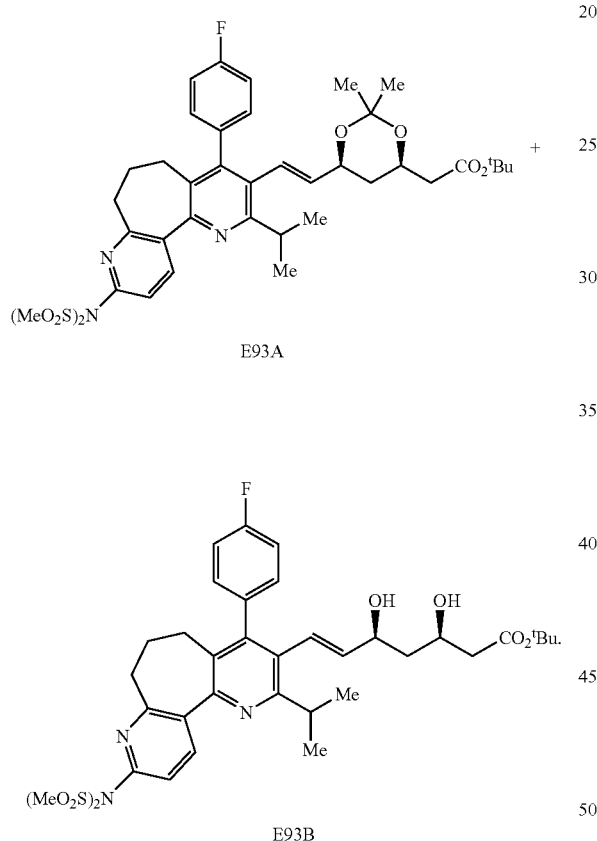

E93A

E93B

Part B:

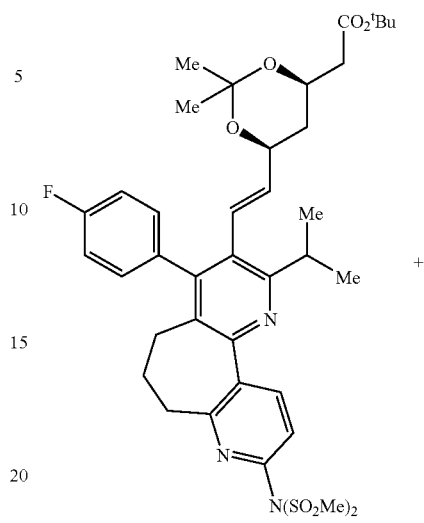

E93A

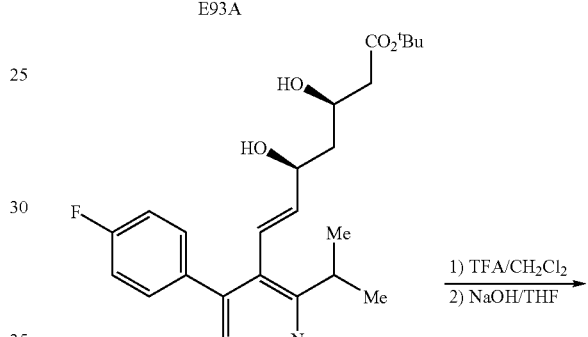

E93B

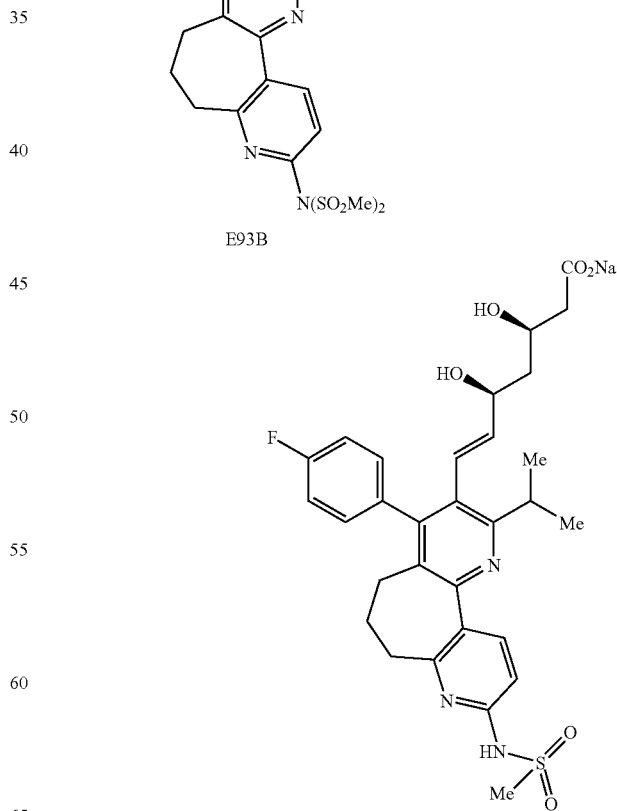

Ex. 93 title compound

To a solution of E90B (70.0 mg, 0.12 mmol) in methylene chloride (1.0 mL) were sequentially added triethylamine (0.021 mL, 0.15 mmol) and methasulfonyl chloride (0.011 mL, 0.14 mmol) dropwise at 0° C. After stirring for 1 h at 0° C., the reaction was diluted with methylene chloride (2.0 mL), washed with saturated sodium bicarbonate (5 mL) and water (5 mL), dried over MgSO$_4$ and concentrated. Flash chromatography of the residue (silica, 50% ethyl acetate/hexanes then ethyl acetate) yielded a mixture (13.6 mg) of E93B [LRMS (API, pos. ion spectrum) m/z 718 (M+H)] and E93A [LRMS (API, pos. ion spectrum) m/z 758 (M+H)].

The title compound was prepared from the mixture of E93A and E93B utilizing the procedure described in Example 79 Parts G-H. Reversed-phase HPLC purification (Phenomenex C18 Luna 60 mm×21 mm; 15% methanol-water for 3 min then up to 100% methanol over 6 min; Flow=9.9 mL/min) yielded the title compound as the sodium salt as a white powder: HRMS (ESI, pos. ion spectrum) m/z calcd for $C_{30}H_{35}FSN_3O_6$: 584.2231, found: 584.2248 (M+H).

Example 94

6-Heptenoic acid, 7-[9-[[[[4-(dimethylamino)butyl]amino]carbonyl]amino]-4-(4-fluorophenyl)-6,7-dihydro-2-(1-methylethyl)-5H-cyclohepta[2,1-b:4,3-b']dipyridin-3-yl]-3,5-dihydroxy-, (3R,5S,6E)-

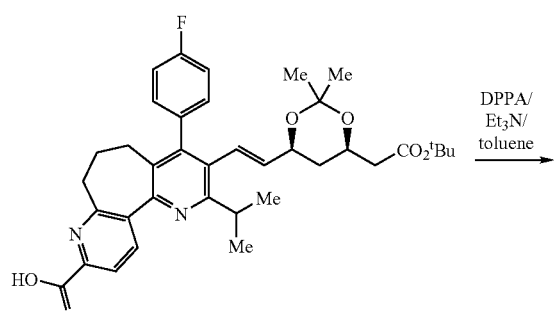

Part A:

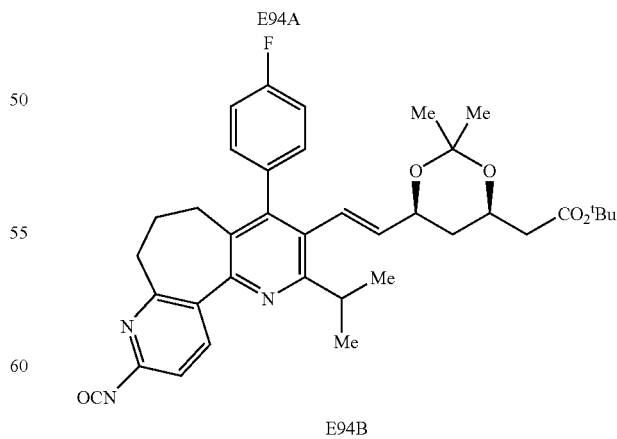

To a suspension of E89A (100.0 mg, 0.16 mmol) in toluene (1.0 mL) were sequentially added triethylamine (0.052 mL, 0.24 mmol) and diphenylphosphoryl azide (0.033 mL, 0.24 mmol). The reaction mixture was stirred at ambient temperature under nitrogen for 4 h. The toluene was removed under reduced pressure. Flash chromatography of the residue (silica, 20% ethyl acetate/hexanes) yielded E94A (83.0 mg, 85%) as a white solid: LRMS (ESI, pos. ion spectrum) m/z 628.

Part B:

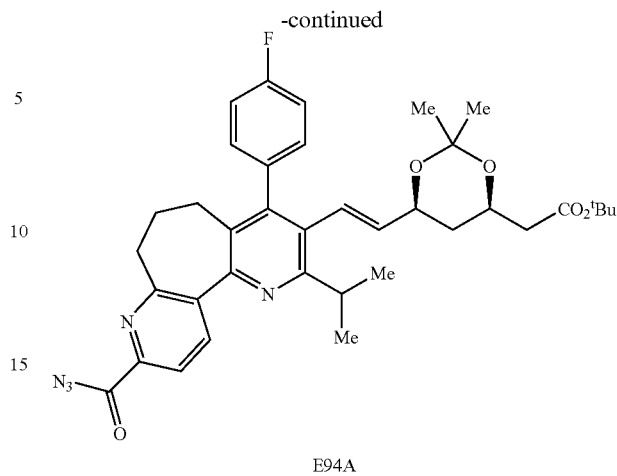

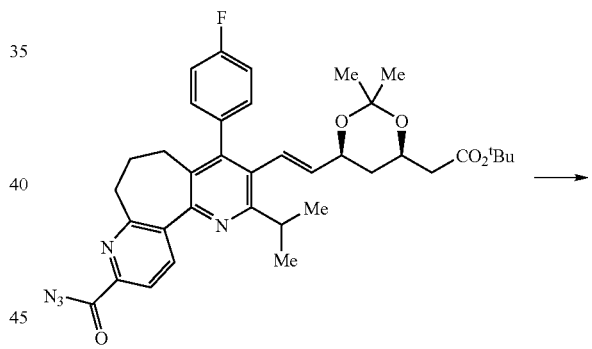

A solution of E94A (400.0 mg, 0.61 mmol) in toluene (50.0 mL) was stirred at refluxing temperature for 2 h. The toluene was removed under reduced pressure. Flash chromatography of the residue (silica, 5% MeOH/CH$_2$Cl$_2$) yielded E94B (120.0 mg, 31%) as a yellow solid: LRMS (ESI, pos. ion spectrum) m/z 628 (M+H).

Part C:

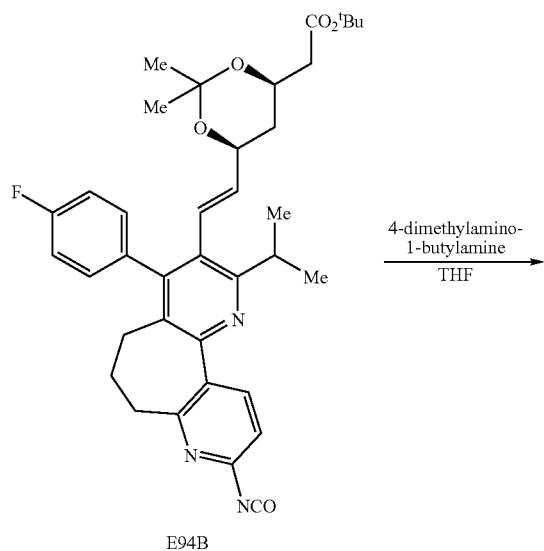

E94B

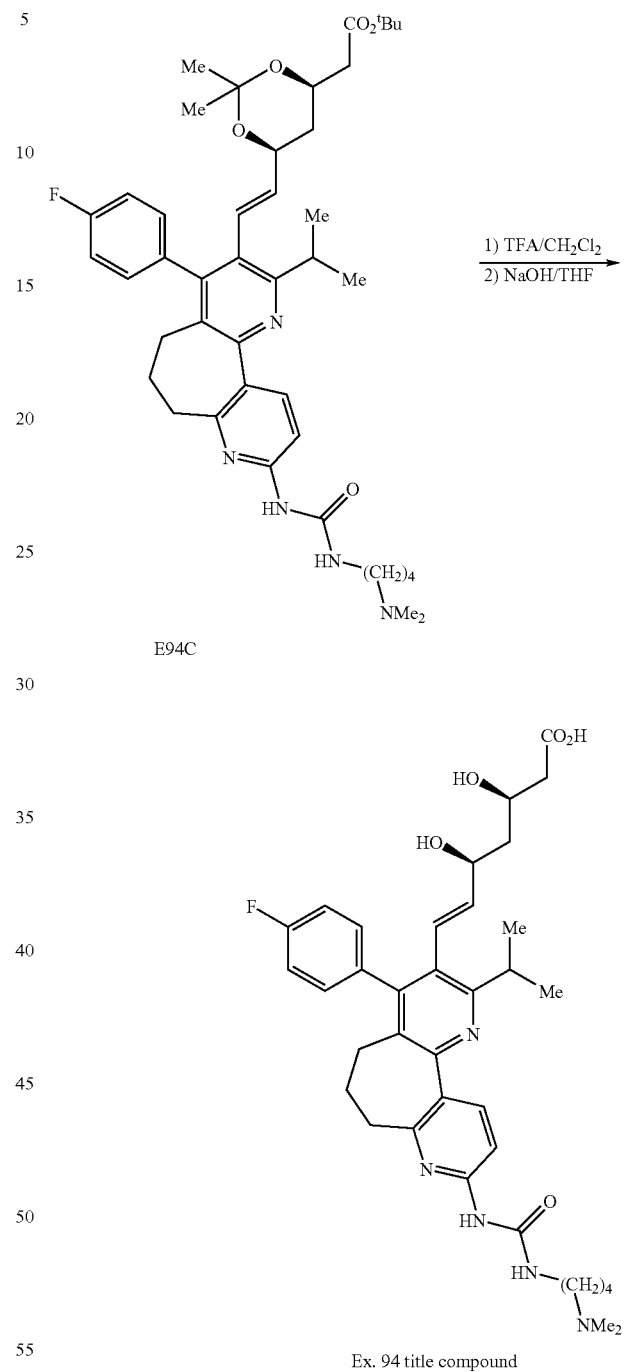

E94C

Ex. 94 title compound

Part D:

To a solution of E94B (120.0 mg, 0.19 mmol) in THF (1.0 mL) was added 4-dimethylamino-1-butylamine (34.0 mg, 0.29 mmol). The reaction was stirred at ambient temperature for 2 h and the THF was removed under reduced pressure. Flash chromatography of the residue (silica, 5% MeOH/CH$_2$Cl$_2$) yielded E94C (24.0 mg, 17%): LRMS (ESI, pos. ion spectrum) m/z 744 (M+H).

The title compound was prepared from compound E94C utilizing the procedure described in Example 79 Parts G-H. Reversed-phase HPLC purification (Phenomenex C18 Luna 60 mm×21 mm; 15% methanol-water for 3 min then up to 100% methanol over 6 min; flow=9.9 mL/min) yielded the title compound as a sodium salt (7.0 mg, 54%) as a white powder: HRMS (ESI, pos. ion spectrum) m/z calcd for C$_{36}$H$_{47}$FN$_5$O$_5$: 648.3561, found: 648.3576 (M+H).

Examples 95 to 101

Using the procedure described for Example 89 the following Examples were prepared:

| Ex. | Structure | Characterization |
|---|---|---|
| 95 | 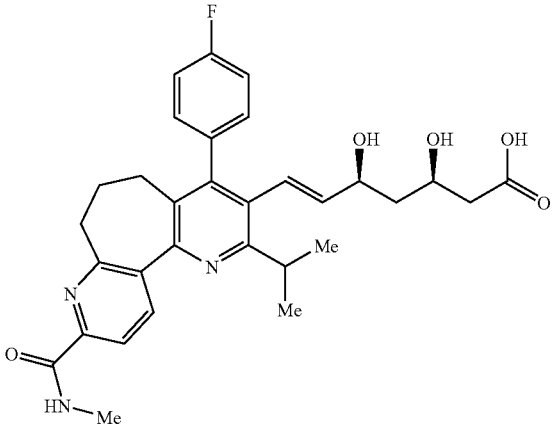<br>6-Heptenoic acid, 7-[4-(4-fluorophenyl)-6,7-dihydro-9-[(methyl-amino)carbonyl]-2-(1-methylethyl)-5H-cyclo-hepta[2,1-b:4,3-b']dipyridin-3-yl]-3,5-dihydroxy-, (3R,5S,6E)- | HPLC (method 3) $t_R$ = 3.63 min<br>HRMS (ESI$^+$) m/z<br>$C_{31}H_{35}FN_3O_5$<br>Calcd: 548.2561 (M + H)<br>Found: 548.2565 (M + H) |
| 96 | 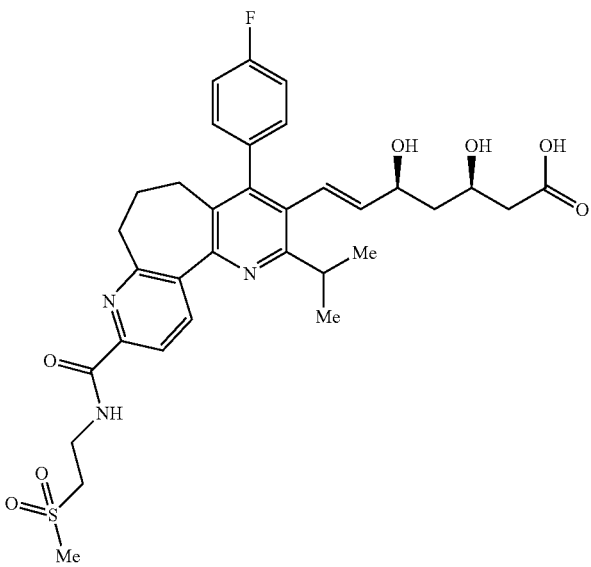<br>6-Heptenoic acid, 7-[4-(4-fluorophenyl)-6,7-dihydro-2-(1-methyl-ethyl)-9-[[[2-(methylsulfonyl)ethyl]amino]carbonyl]-5H-cyclo-hepta[2,1-b:4,3-b']dipyridin-3-yl]-3,5-dihydroxy-, [3R,5S,6E)- | HPLC (method 3) $t_R$ = 3.40 min<br>HRMS (ESI$^+$) m/z<br>$C_{33}H_{39}FN_3O_7$<br>Calcd: 640.2493 (M + H)<br>Found: 640.2502 (M + H) |

-continued

| Ex. | Structure | Characterization |
|---|---|---|
| 97 | 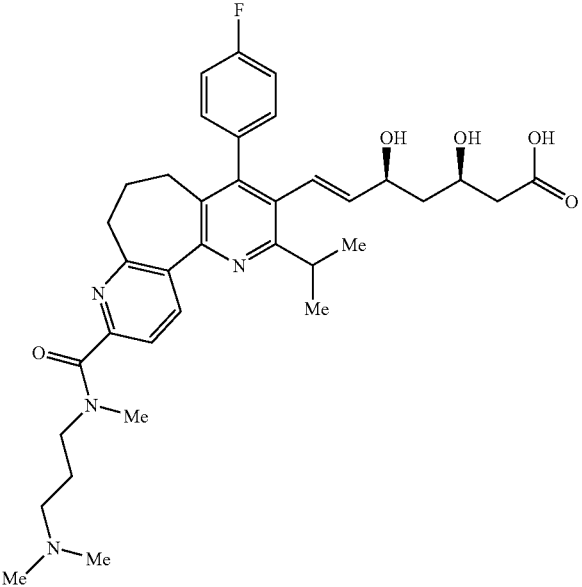<br>6-eptenoic acid, 7-[9-[[[3-(di-methylamino)propyl]methylamino]carbonyl]-4-(4-fluoro-phenyl)-6,7-dihydro-2-(1-methylethyl)-5H-cyclo-hepta[2,1-b:4,3-b']dipyridin-3-yl]-3,5-dihydroxy-, (3R,5S,6E)- | HPLC (method 3) $t_R$ = 2.79 min<br>HRMS (ESI$^+$) m/z<br>$C_{36}H_{46}FN_4O_5$<br>Calcd: 633.3452<br>(M + H)<br>Found: 633.3464<br>(M + H) |
| 98 | 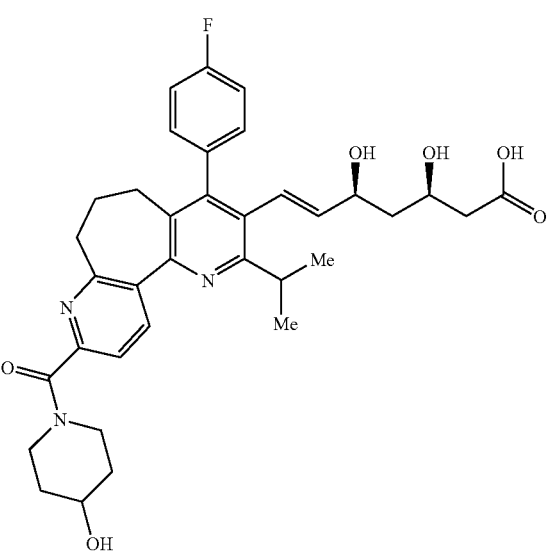<br>6-Heptenoic acid, 7-[4-(4-fluorophenyl)-6,7-dihydro-9-[(4-hy-droxy-1-piperidinyl)carbonyl]-2-(1-methylethyl)-5H-cyclo-hepta[2,1-b:4,3-b']dipyridin-3-yl]-3,5-di-hydroxy-, (3R,5S,6E)- | HPLC (method 3) $t_R$ = 3.14 min<br>HRMS (ESI$^+$) m/z<br>$C_{35}H_{40}FN_3O_6$<br>Calcd: 640.2799<br>(M + H)<br>Found: 640.2820<br>(M + H) |

| Ex. | Structure | Characterization |
|---|---|---|
| 99 | 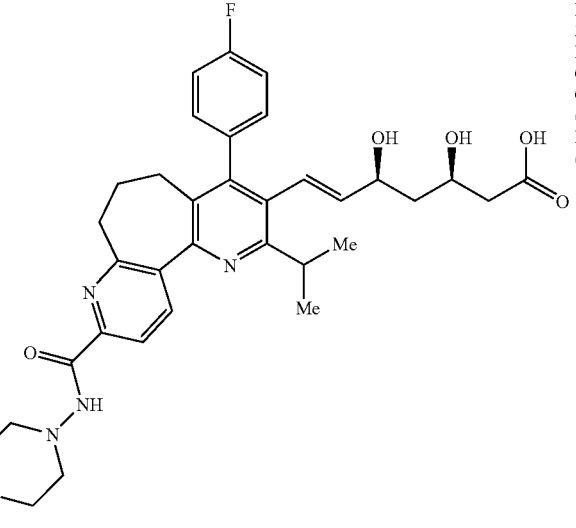<br>6-Heptenoic acid, 7-[4-(4-fluorophenyl)-6,7-dihydro-2-(1-methyl-ethyl)-9-[[(4-methyl-1-pipera-zinyl)amino]carbonyl]-5H-cyclohepta[2,1-b:4,3-b′]di-pyridin-3-yl]-3,5-dihydroxy-, (3R,5S,6E)- | HPLC (method 3) $t_R$ = 3.00 min<br>HRMS (ESI$^+$) m/z<br>$C_{35}H_{43}FN_5O_5$<br>Calcd: 632.3248<br>(M + H)<br>Found: 632.3269<br>(M + H) |
| 100 | 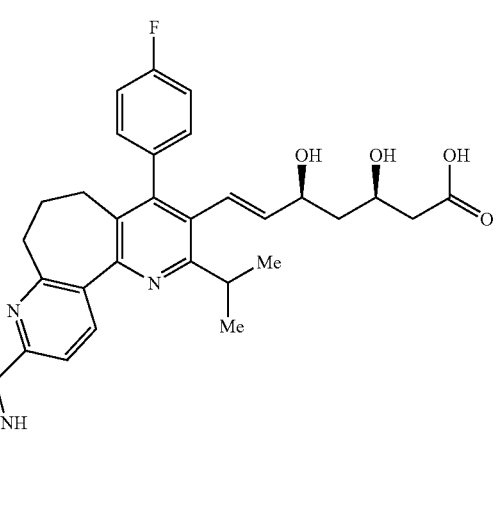<br>6-Heptenoic acid, 7-[4-(4-fluorophenyl)-6,7-dihydro-9-[[(2-hydroxy-ethyl)amino]carbonyl]-2-(1-methylethyl)-5H-cyclo-hepta[2,1-b:4,3-b′]dipyridin-3-yl]-3,5-di-hydroxy-, (3R,5S,6E)- | HPLC (method 3) $t_R$ = 3.40 min<br>LRMS (ESI$^+$) m/z<br>578 (M + H) |

| Ex. | Structure | Characterization |
|---|---|---|
| 101 | 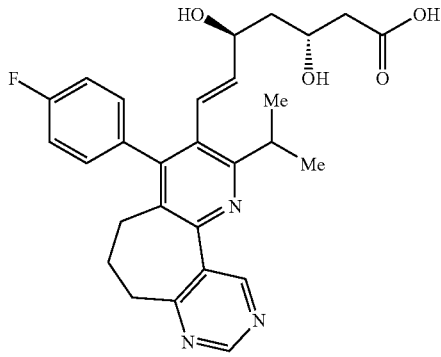

6-Heptenoic acid, 7-[4-(4-fluorophenyl)-6,7-dihydro-9-[[(3-hydroxy-propyl)amino]carbonyl]-2-(1-methylethyl)-5H-cyclo-hepta[2,1-b:4,3-b']dipyridin-3-yl]-3,5-di-hydroxy-, (3R,5S,6E)- | LRMS (ESI⁺) m/z 592 (M + H) |

Example 102

6-Heptenoic acid, 7-[4-(4-fluorophenyl)-6,7-dihydro-2-(1-methylethyl)-5H-pyrido[2',3':3,4]cyclohepta[1,2-d]pyrimidin-3-yl]-3,5-dihydroxy-, (3R,5S,6E)-

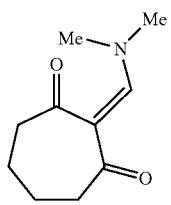

Part A:

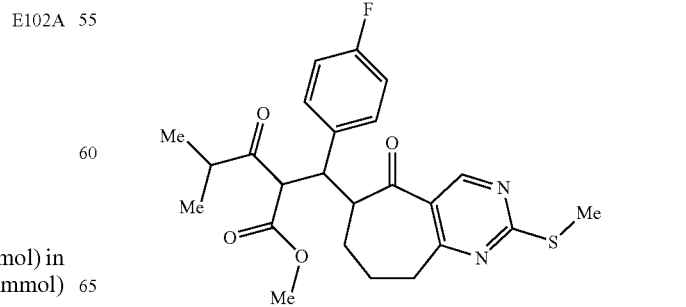

A solution of 1,3-cycloheptanedione (15.1 g, 120 mmol) in N,N-dimethylformamide dimethyl acetal (48 mL, 360 mmol) was heated to 100° C. for 3 h. The reaction mixture was concentrated in vacuo, then dried under high vacuum overnight to afford E102A as an amber solid (20.6 g, 95%); HPLC (method 9)>95%, $t_R$=0.56 min; LCMS (method 1) m/z 182.

Part B:

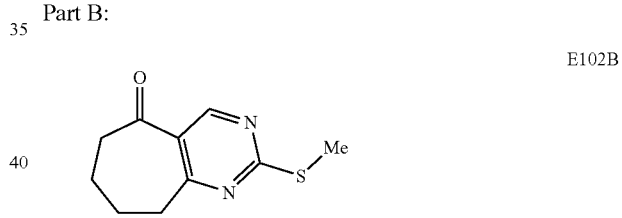

A solution of E102A (20.6 g, 114 mmol) in methanol (1140 mL) was treated successively with triethylamine (63.6 mL, 456 mmol) and S-methylisothiouronium sulfate (38.1 g, 137 mmol). After 30 min, the reaction mixture was concentrated in vacuo. Purification of the residue by flash chromatography (SiO₂, eluting with 2% acetone/dichloromethane) afforded E102B as an amber solid (21.1 g, 89%): LRMS (ESI, M+H) m/z 209; HPLC (method 9)>99%, $t_R$=1.2 min.

Part C:

A solution of NaHMDS (1.0M in THF, 120 mL, 120 mmol) was added to THF (333 mL) and the mixture was cooled to −78° C. A solution of E102B (20.8 g, 100 mmol) in THF (333 mL) was added dropwise over 50 min. After 30 min, a solution of methyl 2-[(4-fluorophenyl)methylene]-4-methyl-3-oxo-pentanoate (30.0 g, 120 mmol) in THF (333 mL) was added dropwise over 50 min. After 1 h, the reaction was quenched by the slow addition of HOAc/THF (1:1, 40 mL) and was then warmed to room temperature. The reaction mixture was diluted with ethyl acetate, washed (50% saturated aqueous NH₄Cl, saturated aqueous NH₄Cl), dried (brine, Na₂SO₄), then concentrated in vacuo. Purification of the residue by flash chromatography (SiO₂, eluting with 10-30% ethyl acetate/hexanes) afforded E102C as a pale yellow foam and as a mixture of diastereomers (44.7 g, 97%): LRMS (ESI, M+H) m/z 459; HPLC (method 9), 90%, $t_R$=1.9 and 2.1 min.

Part D:

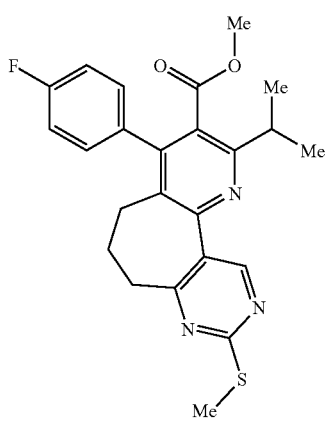

E102D

D1. To a solution of E102C (7.70 g, 16.8 mmol) in HOAc (168 mL) was added NH₄OAc (6.475 g, 84 mmol) and Cu(OAc)₂.H₂O (13.4 g, 67.2 mmol). The resulting mixture was heated to reflux. After 16 h, the reaction mixture was poured into 0° C. aqueous NH₄OH (200 mL of concentrated NH₄OH and 400 mL of H₂O). The mixture was then extracted with diethyl ether. The combined extracts were washed with H₂O, dried (brine, Na₂SO₄) then concentrated in vacuo. Purification of the residue by flash chromatography (SiO₂, eluting with 2% acetone/dichloromethane), then repurification by flash chromatography (SiO₂, eluting with 10-20% ethyl acetate/hexanes) afforded E102D as a white solid (1.082 g, 15%): LRMS (ESI, M+H) m/z 438; HPLC (method 9)>95%, $t_R$=2.1 min.

OR

D2. To a solution of E102C (4.586 g, 10.0 mmol) in ethanol (50 mL) was added NH₄OAc (4.625 g, 60 mmol) and CuBr₂ (2.233 g, 10.0 mmol). The mixture was heated to reflux. After 16 h, ~90% of the ethanol was removed in vacuo and the resulting slurry was diluted with methyl tert-butyl ether. The resulting solution was filtered through Celite®. The pad was rinsed with additional methyl tert-butyl ether. The filtrate was washed (H₂O, saturated aqueous NaHCO₃, H₂O), dried (brine, Na₂SO₄), and then concentrated in vacuo. Purification of the residue by flash chromatography (SiO₂, eluting with 2% acetone/dichloromethane), then repurification by flash chromatography (SiO₂, eluting with 10-20% ethyl acetate/hexanes) afforded E102D as a pale yellow solid (2.045 g, 47%): LRMS (ESI, M+H) m/z 438; HPLC (method 9)>99%, $t_R$=2.1 min.

Part E:

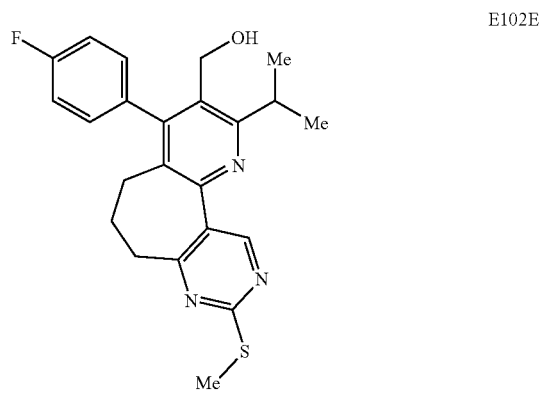

E102E

A solution of E102D (2.0 g, 4.6 mmol) in dichloromethane (35 mL) was cooled to −78° C. A solution of DIBAL-H (11.0M in dichloromethane, 11.5 mL, 11.5 mmol) was added dropwise over 20 min. After 30 min, the reaction was slowly quenched with methanol (1 mL) and then warmed to room temperature. Aqueous Rochelle's salt (25% saturated, 400 mL) was added, and the resulting mixture was stirred vigorously overnight. The dichloromethane layer was separated, dried (brine, Na₂SO₄), then concentrated in vacuo. Purification of the residue by flash chromatography (SiO₂, 20-30% ethyl acetate/hexanes) afforded E102E as an off white solid (1.783 g, 95%): LRMS (ESI, M+H) m/z 410; HPLC (method 9)>99%, $t_R$=1.9 min.

Part F:

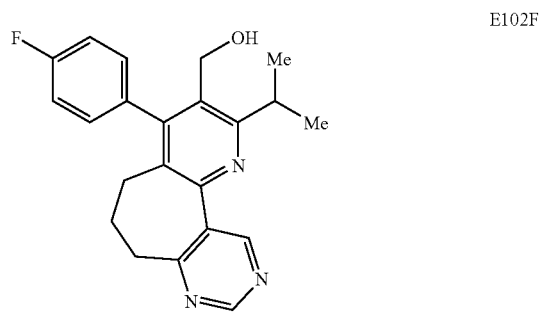

E102F

To a solution of E102E (204.8 mg, 0.5 mmol) in ethanol (5 mL) was added Raney 2800 Nickel (slurry in H₂O, 4.1 g, 20 weight equivalents) and the resulting mixture was heated to reflux. After 2 h, the reaction was cooled to room temperature, then filtered through Celite®. The solids were rinsed with ethyl acetate. The filtrate was dried (Na₂SO₄) and then concentrated in vacuo to afford E102F as a white solid (101.0 mg, 56%): LRMS (ESI, M+H) m/z 364; HPLC (method 9)>95%, $t_R$=1.7 min).

Part G:

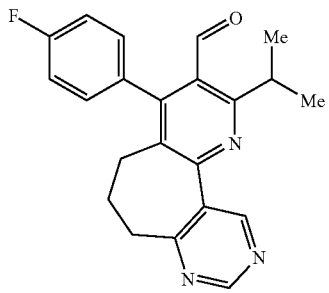
E102G

To a 0° C. solution of E102F (101.0 mg, 0.28 mmol) in ethyl acetate (2.8 mL) was added TEMPO (0.5 mg, 0.0028 mmol) and potassium bromide (3.3 mg, 0.028 mmol). Commercial bleach solution (Clorox®, ~1 M sodium hypochlorite, buffered to pH 9.3-9.5 with NaHCO₃, 1.4 mL, 1.4 mmol) was added dropwise, keeping the internal reaction temperature <5° C. After 30 min, the organic layer was separated, washed (10% aqueous Na₂S₂O₃, 1 N NaOH, H₂O), dried (brine, Na₂SO₄), and then concentrated in vacuo to afford E102G as an off-white foam (84.3 mg, 83%): LRMS (ESI, M+H) m/z 362; HPLC (method 9)>95%, $t_R$=1.9 min.

E102H

[Structure of E102H]

Part H:
A solution of E102G (83.1 mg, 0.23 mmol) and 1,1-dimethylethyl 2,4,6-trideoxy-3,5-O-(1-methylethylidene)-6-[(1-phenyl-1H-tetrazol-5-yl)sulfonyl]-D-erythro-hexonate (156.1 mg, 0.345 mmol) in THF (2.3 mL) was cooled to −78° C. A solution of LiHMDS (1.0 M in THF, 0.345 mL, 0.345 mmol) was added dropwise over 10 min. After 30 min, the reaction was quenched with 25%-saturated aqueous NH₄Cl and then warmed to room temperature. The reaction mixture was diluted with ethyl acetate, washed (saturated aqueous NaHCO₃), dried (brine, Na₂SO₄), then concentrated in vacuo. Purification by flash chromatography (SiO₂, eluting with 10-20% acetone/dichloromethane) afforded E102H as a white foam (108.6 mg, 80%): LRMS (ESI, M+H) 588; HPLC (method 9), >95%, $t_R$=2.2 min.

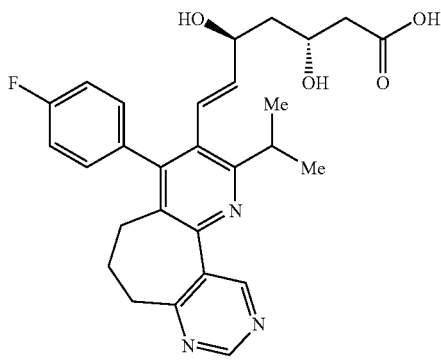
Ex. 102 title compound

Part I:
To a solution of E102H (105.7 mg, 0.18 mmol) in THF (1.8 mL) was added 6 N HCl (0.090 mL, 0.54 mmol). After 2 h, 1 N NaOH (0.900 mL, 0.90 mmol) was added and the resulting mixture was stirred vigorously. After 1 h, methyl tert-butyl ether (10 mL) was added, and after 10 min of stirring, the aqueous phase was collected. The pH of the aqueous phase was adjusted to 8 with 1 N HCl. The solution was loaded onto a C₁₈ cartridge (UCT CLEAN-UP®, 10 g, prewashed with methanol and then H₂O). The cartridge was flushed with H₂O and the product was eluted with acetonitrile/H₂O (1:1). The product-containing fractions were combined and concentrated. The residue was redissolved in H₂O, frozen (−78° C.) and then lyophilized to afford the title compound as a white lyophilate (67.7 mg, 73%): LRMS (ESI, M+H) m/z 492; HPLC (method 9)>99%, $t_R$=1.6 min.

Example 103

2H-Pyran-2-one, 6-[(E)-2-[4-(4-fluorophenyl)-5,6,7,8-tetrahydro-8-methyl-2-(1-methylethyl)pyrazolo[3',4':6,7]cyclohepta[1,2-b]pyridin-3-yl]ethenyl]tetrahydro-4-hydroxy-, (4R,6S)-

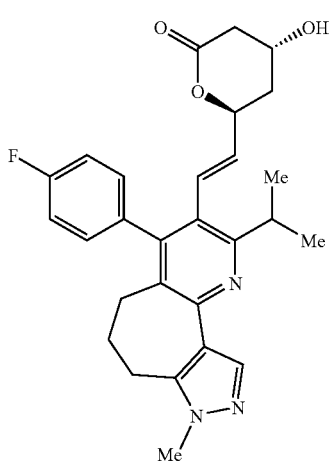

Part A:

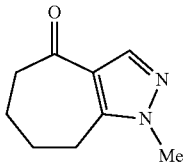

E103A

To a solution of E102A (4.17 g, 23.0 mmol) in methanol (184 mL) which had been cooled to 0° C. was added a solution of methylhydrazine (1.35 mL, 25.3 mmol) in methanol (46 mL) over 5 min. After 30 min, the reaction mixture was concentrated in vacuo. The crude product (2.953 g, regioselectivity=5:1) was combined with the crude product from another identical reaction (1.700 g, regioselectivity=5:1) and purified by flash chromatography (SiO$_2$, eluting with 10-20% acetone/dichloromethane). The resulting amber solid (4.653 g, regioselectivity=5:1) was dissolved in warm ethyl acetate (40 mL). Hexanes (120 mL) and then a seed crystal were added. The resulting solution was placed in a −20° C. freezer overnight. The resulting solid was filtered and was dried in vacuo to afford E103A as pale-yellow feathery needles (3.384 g, 73% recovery, regioselectivity>99:1): LRMS (ESI, M+H) m/z 165; HPLC (method 10)>99%, t$_R$=1.7 min.

Part B:

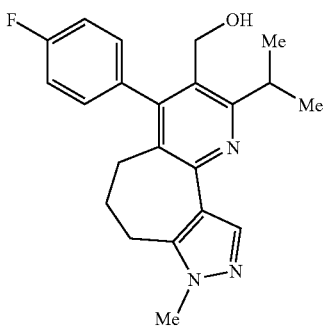

E103B

E103B was prepared from E103A using the procedure described in Example 102 Parts B-E (employing Pyridine Formation Procedure D1) as a white foam: LRMS (ESI, M+H) m/z 366; HPLC (method 9)>99%, t$_R$=1.2 min.

Part C:

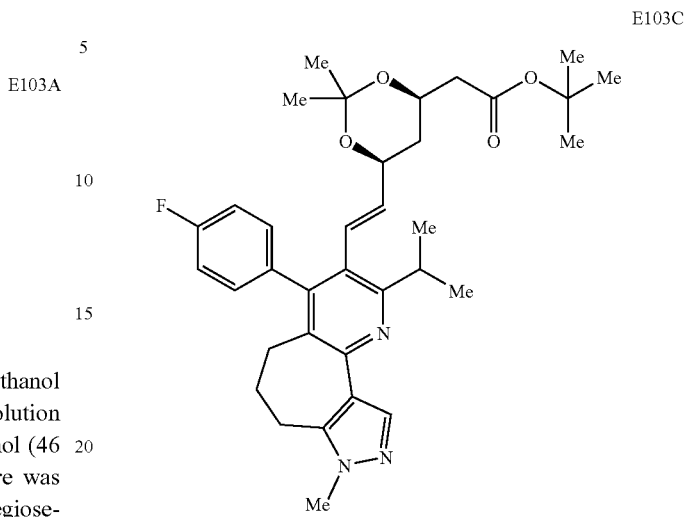

E103C

E103C was prepared as a white solid from E103B using the procedure described in Example 102 Parts G-H: LRMS (ESI, M+H) m/z 590; HPLC (method 9) 94%, t$_R$=2.0 min.

Part D:

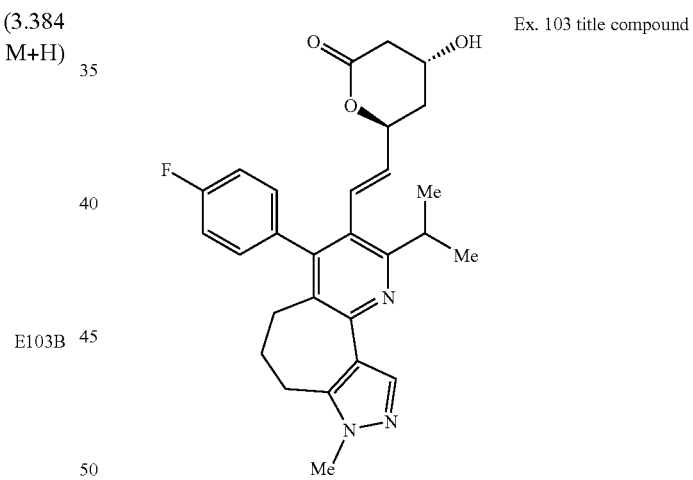

Ex. 103 title compound

A solution of E103C (112.1 mg, 0.19 mmol) in dichloromethane (1.9 mL) was cooled to 0° C. and then TFA (1.9 mL) was added. After 10 min, the cooling bath was removed and the reaction mixture was warmed to room temperature. After 2 h, the reaction mixture was poured into saturated aqueous NaHCO$_3$ and then extracted with ethyl acetate. The combined extracts were washed (1 M NaHCO$_3$), dried (brine, Na$_2$SO$_4$), and then concentrated in vacuo. Purification of the residue by flash chromatography (SiO$_2$, 10-20% acetone/dichloromethane) afforded the title compound as the sodium salt as a white solid (73.9 mg, 82%): LRMS (ESI, M+H) m/z 476; HPLC (method 9)>99%, t$_R$=1.2 min.

Example 104

6-Heptenoic acid, 7-[4-(4-fluorophenyl)-5,6,7,8-tetrahydro-8-methyl-2-(1-methylethyl)pyrazolo[3',4':6,7]cyclohepta[1,2-b]pyridin-3-yl]-3,5-dihydroxy-, (3R,5S,6E)-

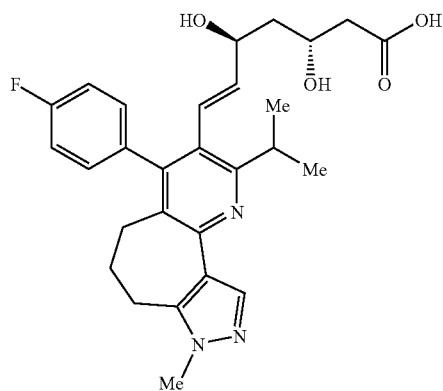

To a solution of Example 103 title compound (61.8 mg, 0.13 mmol) in THF (1.3 mL) was added 1 N NaOH (0.163 mL, 0.163 mmol) and the resulting mixture was stirred at room temperature. After 1 h, the reaction mixture was diluted with methanol/H$_2$O (1:19, 20 mL), then loaded on to a C$_{18}$ cartridge (UCT CLEAN-UP®, 10 g, prewashed with methanol and then H$_2$O). The cartridge was flushed with H$_2$O, and then the product was eluted with acetonitrile/H$_2$O (1:1). The product-containing fractions were combined, and concentrated. The residue was redissolved in H$_2$O and then lyophilized to afford the title compound as a white lyophilate (62.3 mg, 93%): LRMS (ESI, M+H) m/z 494; HPLC (method 9)>95%, t$_R$=1.1 min.

Example 105

6-Heptenoic acid, 7-[4-(4-fluorophenyl)-5,6,7,9-tetrahydro-9-methyl-2-(1-methylethyl)pyrazolo[3',4':6,7]cyclohepta[1,2-b]pyridin-3-yl]-3,5-dihydroxy-, (3R,5S,6E)-

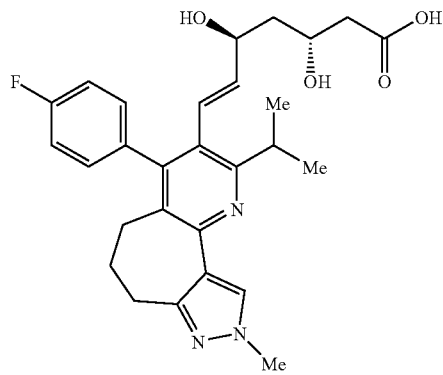

Part A:

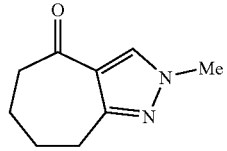

E105A

To a solution of E102A (5.074 g, 28.0 mmol) in methanol (224 mL) cooled to −78° C. was added a solution of methylhydrazine (1.639 mL, 30.8 mmol) in methanol (56 mL) over 5 min. After 2 h, the reaction mixture was concentrated in vacuo (regioselectivity=3:1). Purification of the residue by flash chromatography (SiO$_2$, eluting with 10-20% acetone/dichloromethane) afforded an amber solid (4.093 g, 89%) which was dissolved in warm ethyl acetate (15 mL). Hexanes (60 mL) and then a seed crystal of E103A were added and the resulting solution was then placed in a −20° C. freezer overnight. The next morning, a light-red solid was filtered, the filtrate concentrated in vacuo, and the recrystallization procedure was repeated. The resulting solid was filtered, then dried in vacuo to afford E105A as a yellow solid (2.262 g, 49%, regioselectivity 19:1): LRMS (ESI, M+H) m/z 165; HPLC (method 10)>99%, t$_R$=2.2 min.

Part B:

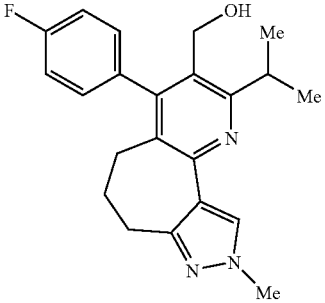

E105B

E105B was prepared from E105A using the procedure described in Example 102 Parts C-E (using Pyridine Formation Procedure D1) as a white foam: LRMS (ESI, M+H) m/z 366; HPLC (method 4) 98%, t$_R$=2.3 min.

Part C:

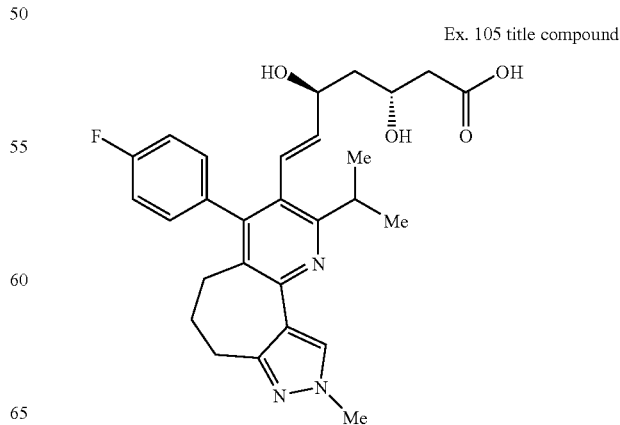

Ex. 105 title compound

The title compound was prepared as the sodium salt from E105B using the procedure described in Example 103 Parts C-D as a white lyophilate: LRMS (ESI, M+H) m/z 494; HPLC (method 9)>95%, $t_R$=1.1 min.

Example 106

Pyrazolo[3',4':6,7]cyclohepta[1,2-b]pyridine-9(5H)-acetic acid, 3-[(1E,3S,5R)-6-carboxy-3,5-dihydroxy-1-hexenyl]-4-(4-fluorophenyl)-6,7-dihydro-2-(1-methylethyl)-

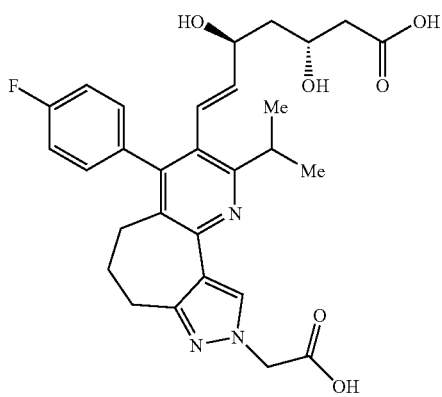

Part A:

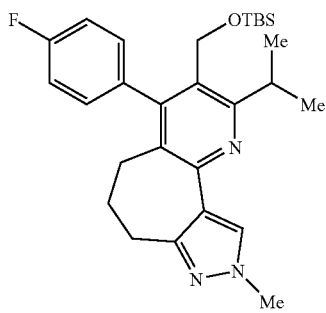

E106A

To a solution of E105B (730.9 mg, 2.0 mmol) in dichloromethane (20 mL) cooled to 0° C. was added 4-(dimethylamino)pyridine (24.4 mg, 0.2 mmol), triethylamine (696.9 mL, 5.0 mmol), and then TBS-Cl (602.9 mg, 4.0 mmol). The cooling bath was removed after 10 min. After 16 h, the reaction mixture was concentrated in vacuo. The residue was purified by flash chromatography (SiO$_2$, eluting with 5-10% acetone/dichloromethane) to afford E106A as a white solid (674.5 mg, 70%): LRMS (ESI, M+H) m/z 480; HPLC (method 10)>99%, $t_R$=2.1 min.

Part B:

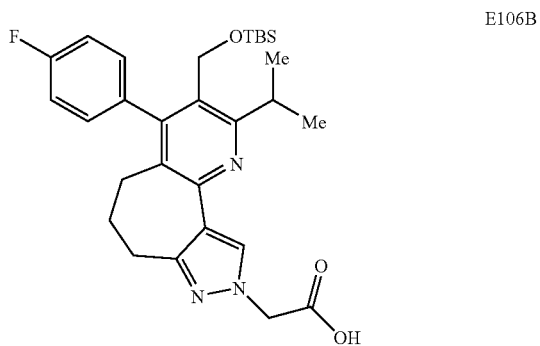

E106B

To a solution of E106A (191.9 mg, 0.4 mmol) in THF (4 mL) cooled to −78° C. was added n-BuLi (1.6 M in hexanes, 0.3 mL, 0.48 mmol) dropwise over 10 min. After 1 h, CO$_2$ (g) was blown onto the surface for 5 min. After 15 min, 1 N NaOH (5 mL) and methyl tert-butyl ether (5 mL) were added and the resulting mixture was stirred vigorously for 15 min. The aqueous phase was separated, the pH was adjusted to 2 with 6 N HCl, and the mixture was then extracted with ethyl acetate. The combined extracts were dried (Na$_2$SO$_4$) and concentrated in vacuo to afford E106B as a white foam (97.1 mg, 46%): LRMS (ESI, M+H) m/z 524; HPLC (method 10) 93%, $t_R$=2.2 min.

Part C:

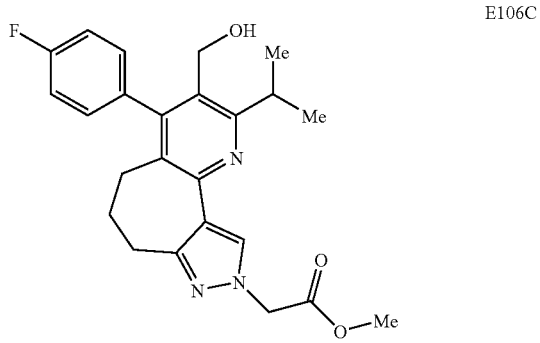

E106C

To a solution of E106B (94.3 mg, 0.18 mmol) in methanol (3.6 mL) was added one drop of conc. H$_2$SO$_4$ and the resulting solution was heated to reflux. After 2 h, the reaction mixture was concentrated in vacuo to provide E106C which was used in the next step without further purification or characterization.

Part D:

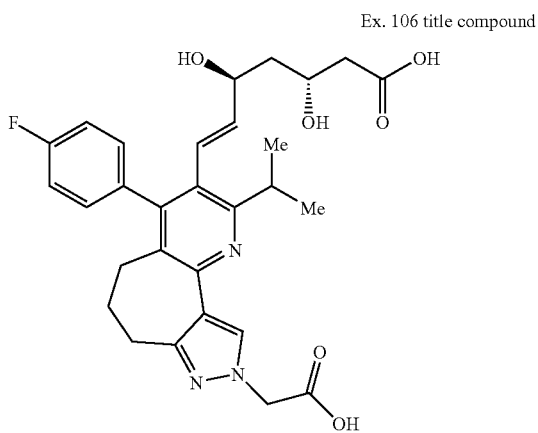

Ex. 106 title compound

The title compound was prepared as the disodium salt from E106C using the procedure described in Example 102 Parts G-I as a white lyophilate: LRMS (ESI, M+H) m/z 538; HPLC (method 9)>95%, $t_R$=1.1 min.

Example 107

6-Heptenoic acid, 7-[4-(4-fluorophenyl)-6,7-dihydro-9-methyl-2-(1-methylethyl)-5H-pyrido[2',3':3,4]cyclohepta[1,2-d]pyrimidin-3-yl]-3,5-dihydroxy-, (3R,5S,6E)-

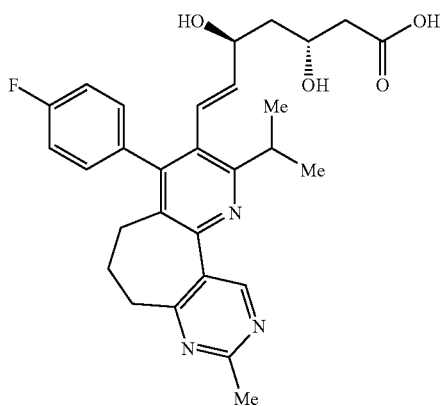

Part A:

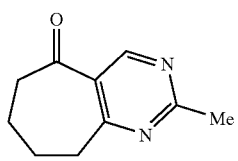

E107A

To a solution of E102A (3.081 g, 17.0 mmol) in methanol (170 mL) cooled to 0° C. were added, sequentially, triethylamine (7.108 mL, 51.0 mmol) and acetamidine hydrochloride (4.822 g, 51.0 mmol). After 10 min, the cooling bath was removed. After 16 h, the reaction mixture was concentrated in vacuo and the residue was purified by flash chromatography (SiO$_2$, eluting with 5-10% acetone/dichloromethane) to afford E107A as a yellow solid (2.338 g, 78%): LRMS (ESI, M+H) m/z 177; HPLC (method 9)>99%, $t_R$=0.75 min.

Part B:

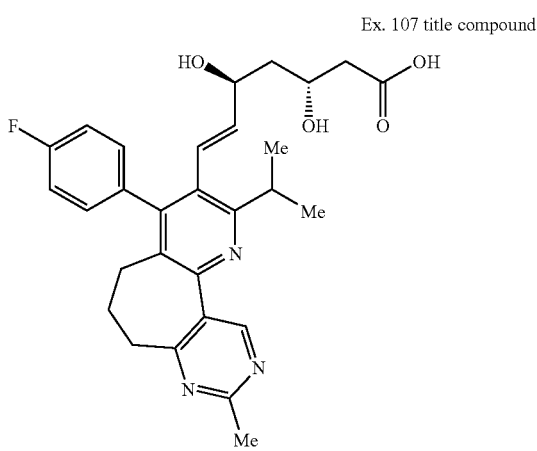

Ex. 107 title compound

The title compound was prepared as the sodium salt from E107A using the procedure described in Example 102 Parts C—I (using Pyridine Formation Procedure D1) as a white lyophilate: LRMS (ESI, M+H) m/z 506; HPLC (method 9) 99%, $t_R$=1.6 min.

Example 108

6-Heptenoic acid, 7-[9-(dimethylamino)-4-(4-fluorophenyl)-6,7-dihydro-2-(1-methylethyl)-5H-pyrido[2',3':3,4]cyclohepta[1,2-d]pyrimidin-3-yl]-3,5-dihydroxy-, (3R,5S,6E)-

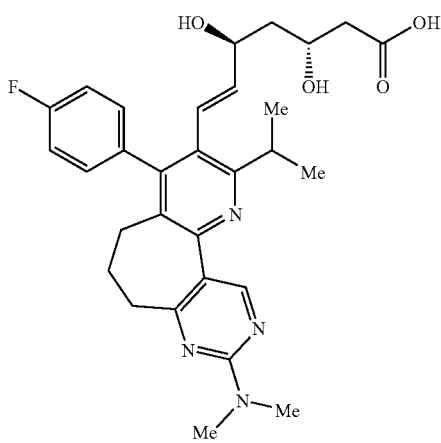

Part A:

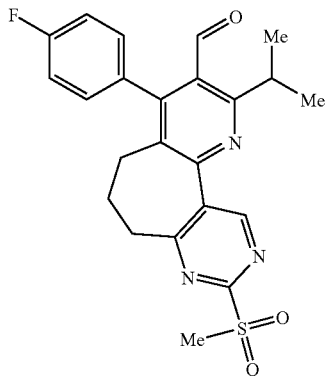
E108A

E108A was prepared from E102E using the procedure described in Example 102 Part G as an off-white foam: LRMS (ESI, M+H) m/z 440; HPLC (method 9) 92%, $t_R$=1.8 min.

Part B:

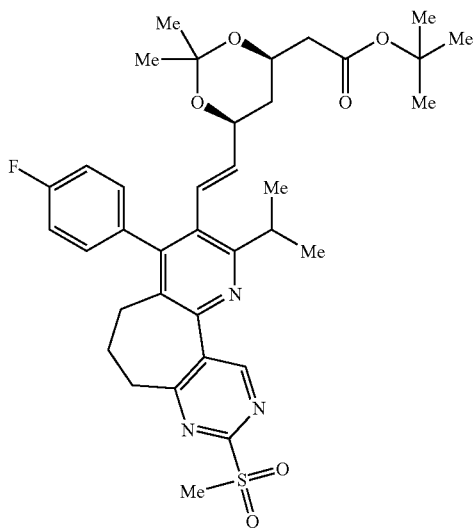
E108B

E108B was prepared from E108A using the procedure described in Example 102 Part H as an off-white foam: LCMS (ESI, M+H, $t_R$=2.1 min) m/z 666.

Part C:

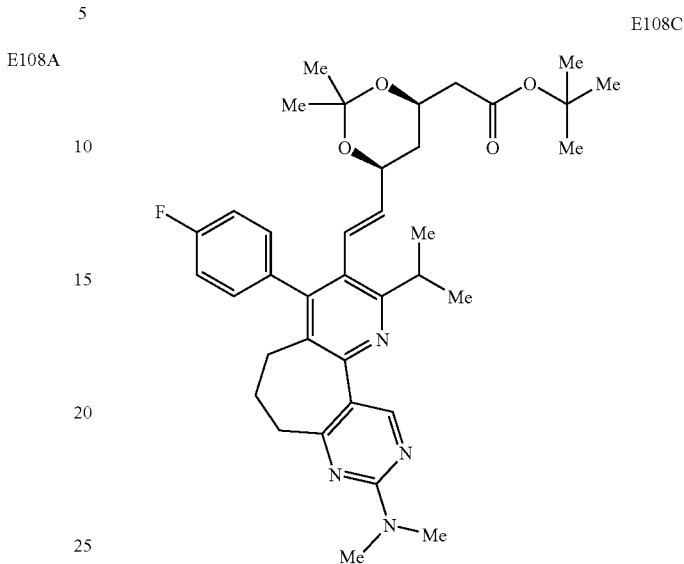
E108C

To a solution of E108B (59.9 mg, 0.09 mmol) in methanol (0.9 mL) in a screw-capped vial was added dimethylamine (2.0 M in methanol, 0.180 mL, 0.36 mmol). After 18 h, the reaction mixture was concentrated in vacuo. The residue was purified by flash chromatography (SiO$_2$, eluting with 0%, 2%, then 5% acetone/dichloromethane) to afford E108C as a white solid (37.8 mg, 67%): LRMS (ESI, M+H) m/z 631; HPLC (method 9)>99%, $t_R$=2.2 min.

Part D:

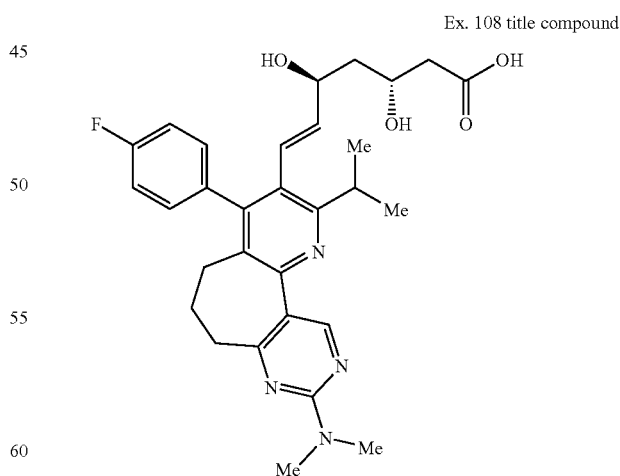
Ex. 108 title compound

The title compound was prepared from E108C using the procedure described in Example 102 Part I: LRMS (ESI, M+H) m/z 535; HPLC (method 9)>99%, $t_R$=1.4 min.

Example 109

6-Heptenoic acid, 7-[4-(4-fluorophenyl)-6,7-dihydro-9-(methylamino)-2-(1-methylethyl)-5H-pyrido[2',3':3,4]cyclohepta[1,2-d]pyrimidin-3-yl]-3,5-dihydroxy-, (3R,5S,6E)-

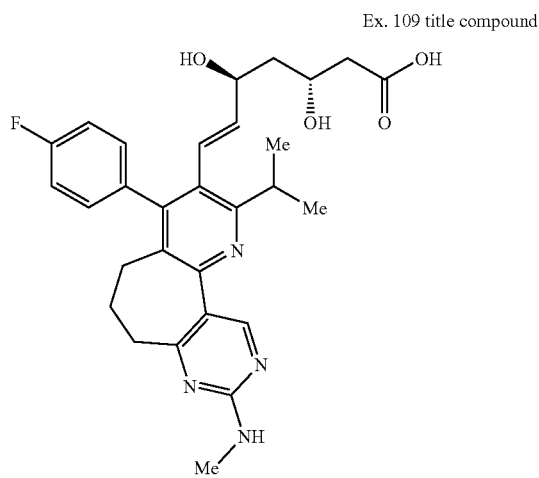

Ex. 109 title compound

The title compound was prepared as the sodium salt from methylamine and E108B using the procedure described in Example 108 Parts C-D: LRMS (ESI, M+H) m/z 521; HPLC (method 9)>99%, $t_R$=1.2 min.

Example 110

6-Heptenoic acid, 7-[9-(cyanoamino)-4-(4-fluorophenyl)-6,7-dihydro-2-(1-methylethyl)-5H-pyrido[2',3':3,4]cyclohepta[1,2-d]pyrimidin-3-yl]-3,5-dihydroxy-, (3R,5S,6E)-

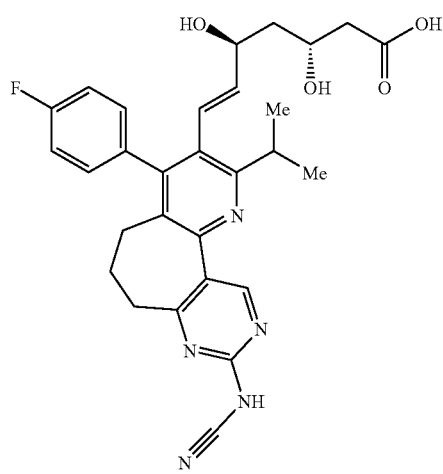

Part A:

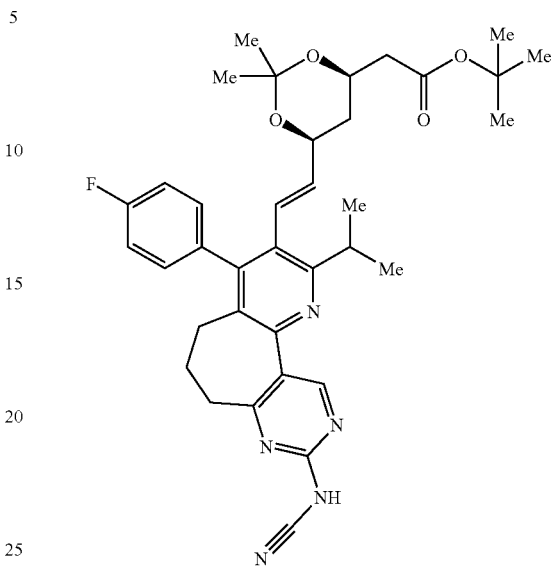

E110A

To a solution of E108B (79.9 mg, 0.12 mmol) in THF (1.2 mL) was added sodium hydrogen cyanamide (76.8 mg, 1.2 mmol). After 16 h, the reaction mixture was partitioned between saturated aqueous NH$_4$Cl and ethyl acetate. The organic phase was separated, dried (brine, Na$_2$SO$_4$), and concentrated in vacuo. Purification of the residue by flash chromatography (SiO$_2$, 20-30% acetone/dichloromethane) afforded E110A as an off-white solid (23.5 mg, 31%): LRMS (ESI, M+H) m/z 628; HPLC (method 9)>99%, $t_R$=2.1 min.

Part B:

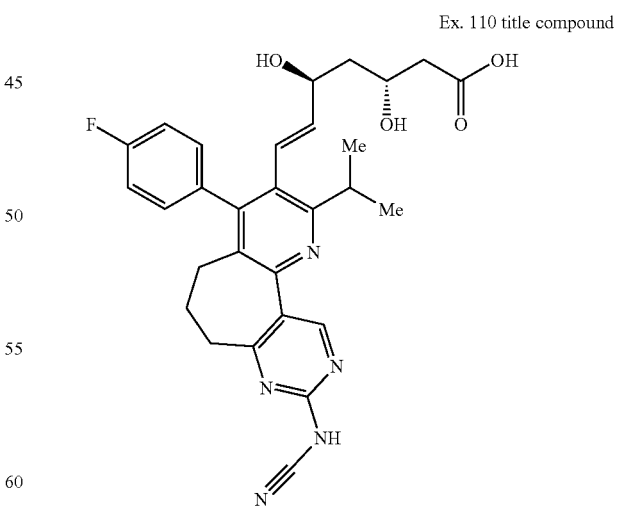

Ex. 110 title compound

The title compound was prepared as the sodium salt as a white lyophilate from E110A using the procedure described in Example 102 Part I; LRMS (ESI, M+H) m/z 532; HPLC (method 9) 98%, $t_R$=1.4 min.

Example 111

6-Heptenoic acid, 7-[4-(4-fluorophenyl)-6,7,9,10-tetrahydro-2-(1-methylethyl)-9-oxo-5H-pyrido[2',3':3,4]cyclohepta[1,2-d]pyrimidin-3-yl]-3,5-dihydroxy-, (3R,5S,6E)-

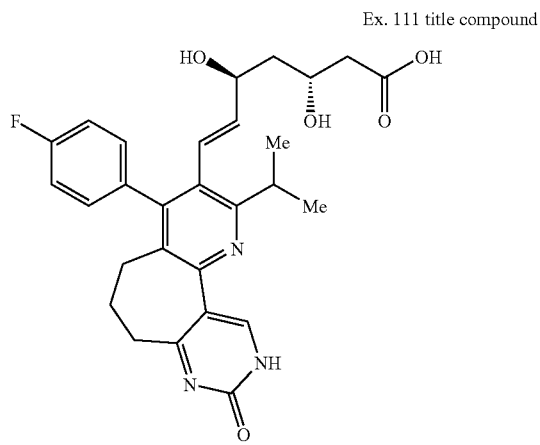

Ex. 111 title compound

To a solution of E108B (99.9 mg, 0.15 mmol) in THF (1.5 mL) was added aqueous NaOH (1 N, 0.300 mL, 0.30 mmol). After 3 h, aqueous HCl (6 N, 0.125 mL, 0.75 mmol) was added. After 3 h, aqueous NaOH (1 N, 1.05 mL, 1.05 mmol) was then added. After 10 min, the THF was removed in vacuo. The pH of the aqueous phase was adjusted to 7 with 1 N HCl. The mixture was then loaded on to a $C_{18}$ cartridge (UCT CLEAN-UP®, 10 g, prewashed with methanol and then $H_2O$). The cartridge was flushed with $H_2O$ and then the column was eluted with 10%, 20%, 40%, then 60% methanol/$H_2O$. The product-containing fractions were combined and concentrated. The residue was redissolved in $H_2O$, frozen (−78° C.) and then lyophilized to afford the title compound as the sodium salt as a white lyophilate (50.7 mg, 64%): LRMS (ESI, M+H) m/z 508) HPLC (method 9) 99%, $t_R$=1.1 min.

Example 112

6-Heptenoic acid, 7-[4-(4-fluorophenyl)-6,7-dihydro-9-[(methylamino)carbonyl]-2-(1-methylethyl)-5H-pyrido[2',3':3,4]cyclohepta[1,2-d]pyrimidin-3-yl]-3,5-dihydroxy-, (3R,5S,6E)-

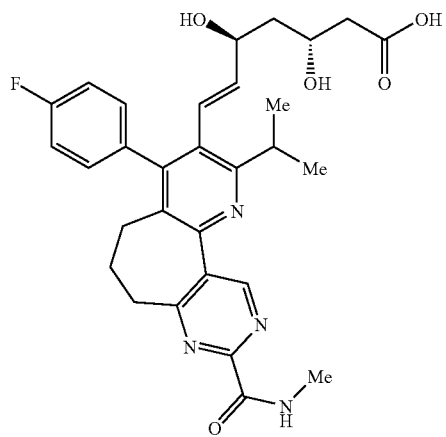

Part A:

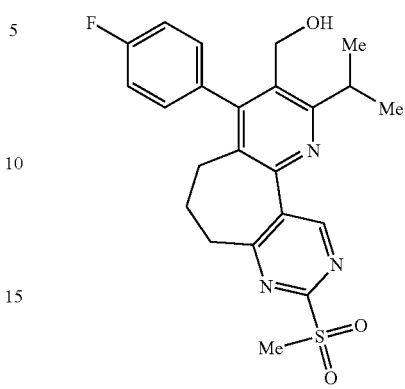

E112A

To a solution of E102E (819.0 mg, 2.0 mmol) in dichloromethane (20 mL) cooled to 0° C. was added MCPBA (70%, 1.085 g, 4.4 mmol). After 10 min, the cooling bath was removed. After 30 min, the reaction mixture was diluted with dichloromethane, washed with 1 N $NaHCO_3$, dried ($Na_2SO_4$), and then concentrated in vacuo. Purification of the residue by flash chromatography ($SiO_2$, 10-20% acetone/dichloromethane) afforded E112A as a white foam (845.2 mg, 96%): LRMS (ESI, M+H) m/z 442; HPLC (method 9)>99%, $t_R$=1.6 min.

Part B:

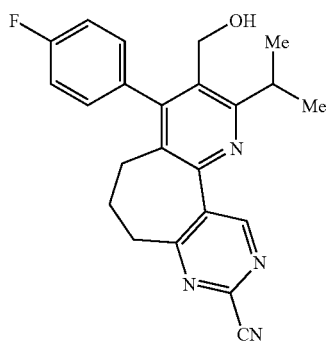

E112B

To a solution of E112A (838.9 mg, 1.9 mmol) in dimethylformamide (19 mL) was added potassium cyanide (247.5 mg, 3.8 mmol). After 30 min, $H_2O$ (200 mL) and diethyl ether (200 mL) were added, and the resulting mixture was stirred vigorously until two clear phases emerged. The organic phase was separated, and the aqueous phase was extracted with diethyl ether. The combined organics were washed with $H_2O$, dried (brine, $Na_2SO_4$), and then concentrated in vacuo. Purification by flash chromatography ($SiO_2$, 2% acetone/dichloromethane) afforded E112B as a white foam (650.6 mg, 88%): LRMS (ESI, M+H) m/z 389; HPLC (method 9)>99%, $t_R$=1.8 min.

Part C:

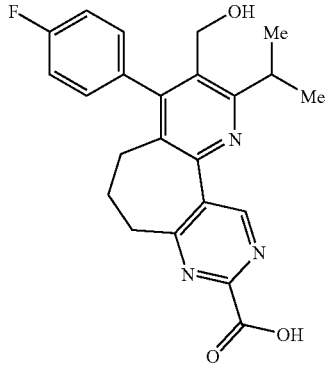

E112B (419.5 mg, 1.08 mmol) was suspended in aqueous NaOH (2 N, 10.8 mL, 21.6 mmol) and heated to 100° C. After 3 h, the reaction mixture was cooled to room temperature, diluted with $H_2O$ (50 mL) and then extracted with diethyl ether. The pH of the aqueous phase was adjusted to 2 with 1 N HCl and the mixture was then extracted with ethyl acetate. The combined ethyl acetate extracts were dried (brine, $Na_2SO_4$) and concentrated in vacuo to afford E112C as a white foam (338.3 mg, 77%): LRMS (ESI, M+H) m/z 408; HPLC (method 9) 99%, $t_R$=1.5 min.

Part D:

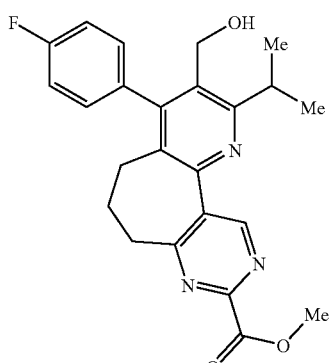

To a solution of E112C (203.7 mg, 0.5 mmol) in methanol (5 mL) was added one drop of concentrated $H_2SO_4$. The resulting mixture was heated to reflux. After 4 h, the reaction mixture was concentrated in vacuo and the residue was partitioned between ethyl acetate and 1 N $NaHCO_3$. The organic phase was separated, dried (brine, $Na_2SO_4$), and then concentrated in vacuo to afford E112D as a white solid (199.4 mg, 95%): LRMS (ESI, M+H) m/z 422; HPLC (method 9)>99%, $t_R$=1.6 min.

Part E:

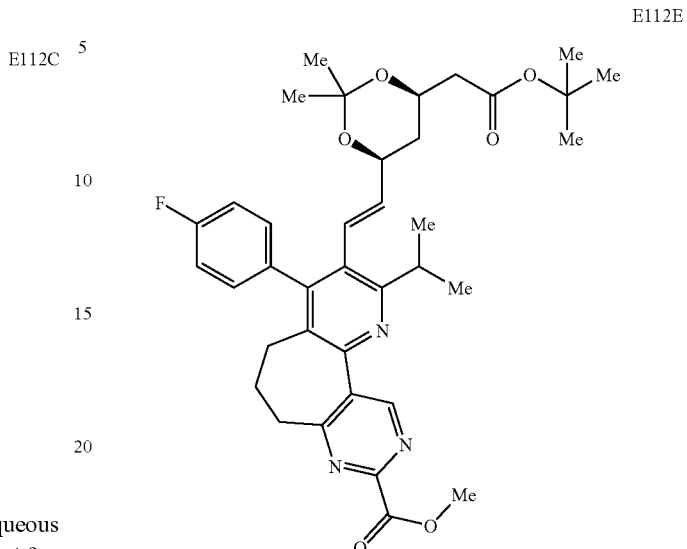

E112E was prepared from E112D using the procedure described in Example 102 Parts G-H as a white foam: LCMS (ESI, M+H, $t_R$=2.2) m/z 646.

Part F:

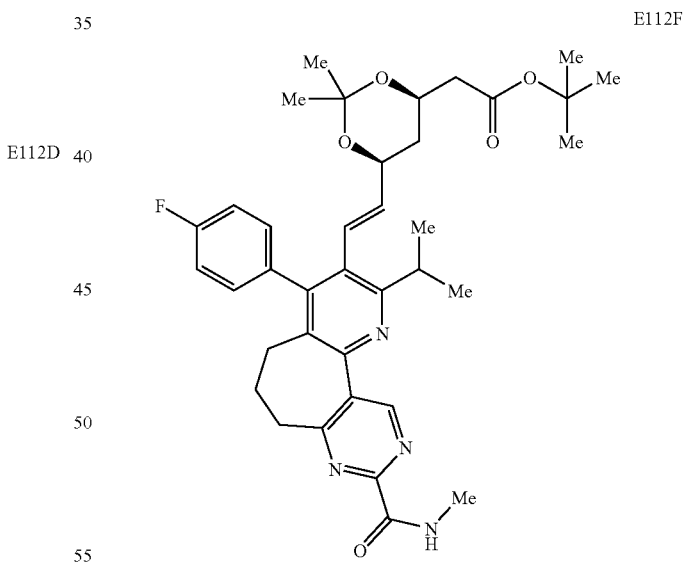

To a solution of methylamine in THF (2.0 M, 3.10 mL, 6.2 mmol) was added E112E (40.0 mg, 0.062 mmol) and the resulting solution was stirred at room temperature. After 14 h, the reaction mixture was concentrated in vacuo. The residue was dissolved in ethyl acetate, the mixture was filtered through a small pad of $SiO_2$, and the filtrate was concentrated in vacuo to afford E112F as a pale-yellow solid (31.0 mg, 78%): LCMS (ESI, M+H, $t_R$=2.2) m/z 645.

Part G:

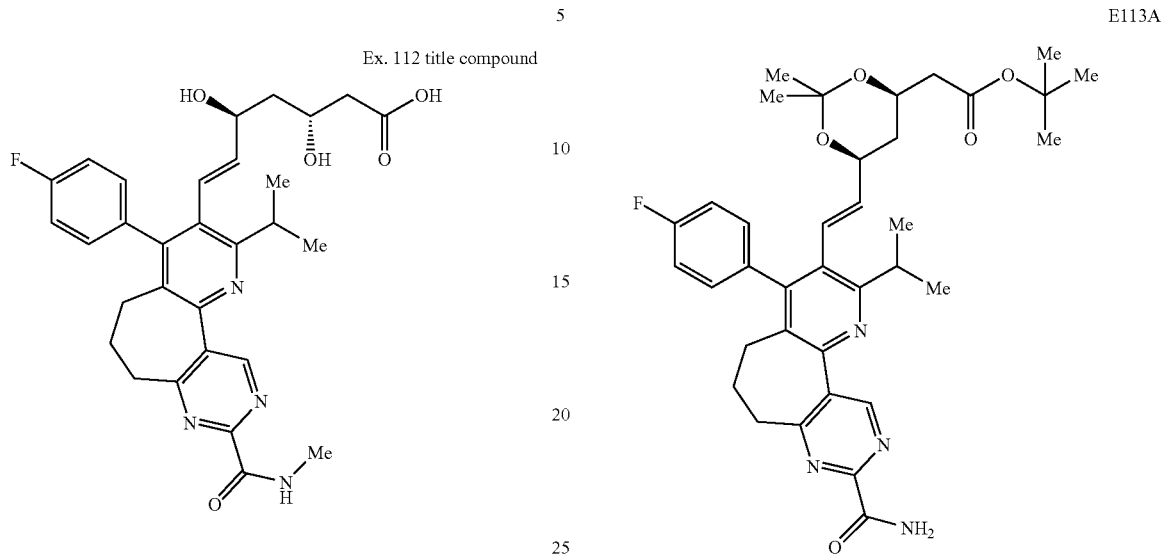

Ex. 112 title compound

The title compound was prepared as the sodium salt from E112F using the procedure described in Example 102 Part I as a white lyophilate: LRMS (ESI, M+H) m/z 549; HPLC (method 9) 98%, $t_R$=1.5 min.

Example 113

6-Heptenoic acid, 7-[9-(aminocarbonyl)-4-(4-fluorophenyl)-6,7-dihydro-2-(1-methylethyl)-5H-pyrido[2′,3′:3,4]cyclohepta[1,2-d]pyrimidin-3-yl]-3,5-dihydroxy-, (3R,5S,6E)-

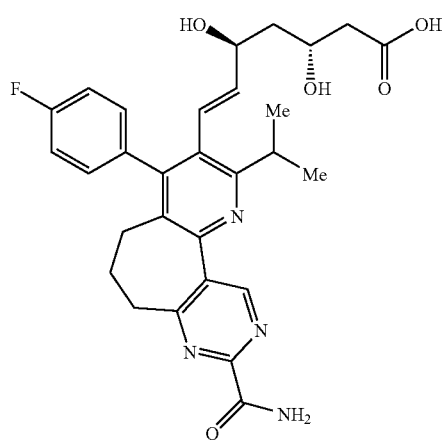

Part A:

E113A

To a solution of ammonia in methanol (2.0 M, 3.10 mL, 6.2 mmol) was added E112E (40.0 mg, 0.062 mmol), and the resulting mixture was heated to 40° C. After 16 h, the reaction mixture was concentrated in vacuo. The residue was dissolved in ethyl acetate and washed (saturated aqueous NH$_4$Cl), dried (Na$_2$SO$_4$) and then concentrated in vacuo to afford E113A as an off-white solid (35.1 mg, 91%): LCMS (ESI, M+H, $t_R$=2.1) m/z 631.

Part B:

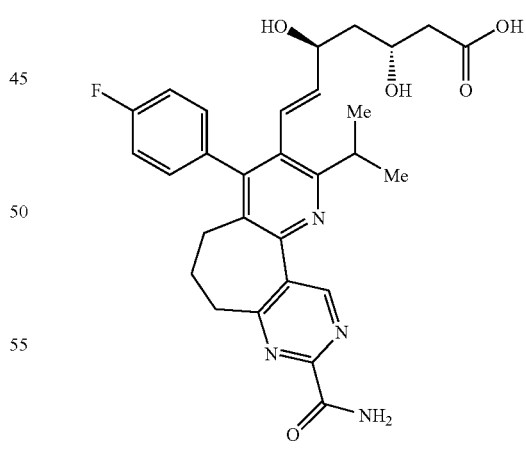

Ex. 113 title compound

The title compound was prepared as the sodium salt as a white lyophilate from E113A using the procedure described in Example 102 Part I: LRMS (ESI, M+H) m/z 535; HPLC (method 9)>99%, $t_R$=1.4 min.

Example 114

6-Heptenoic acid, 7-[9-[(dimethylamino)carbonyl]-4-(4-fluorophenyl)-6,7-dihydro-2-(1-methylethyl)-5H-pyrido[2',3':3,4]cyclohepta[1,2-d]pyrimidin-3-yl]-3,5-dihydroxy-, (3R,5S,6E)-

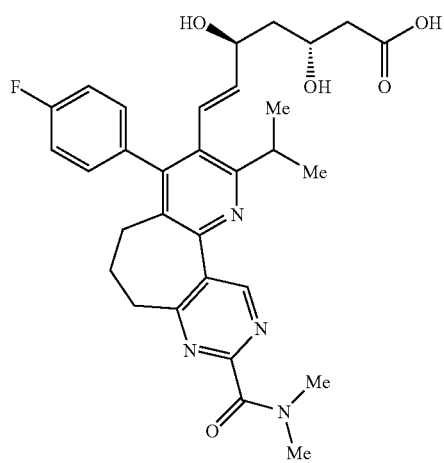

Ex. 114 title compound

The title compound was prepared as the sodium salt as a white lyophilate from E112E using the procedure described in Example 112 Parts F-G: LRMS (ESI, M+H) m/z 563; HPLC (method 9)>99%, $t_R$=1.4 min.

Example 115

6-Heptenoic acid, 7-[4-(4-fluorophenyl)-6,7-dihydro-9-methoxy-2-(1-methylethyl)-5H-pyrido[2',3':3,4]cyclohepta[1,2-d]pyrimidin-3-yl]-3,5-dihydroxy-, (3R,5S,6E)-

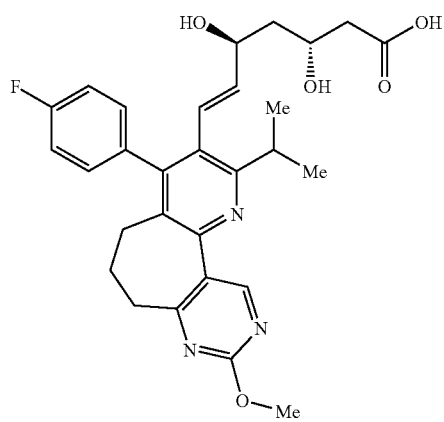

Part A:

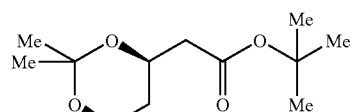

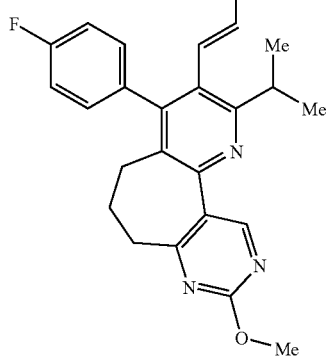

To a solution of E108B (99.9 mg, 0.15 mmol) in THF (1.5 mL) and methanol (1.5 mL) was added $K_2CO_3$ (103.7 mg, 0.75 mmol). The resulting mixture was stirred at room temperature. After 10 min, the reaction mixture was partitioned between ethyl acetate and saturated aqueous $NH_4Cl$. The organic layer was separated, dried (brine, $Na_2SO_4$), and then concentrated in vacuo to afford E115A as an off-white foam (89.8 mg, 97%): LCMS (ESI, M+H, $t_R$=2.2) m/z 618.

Part B:

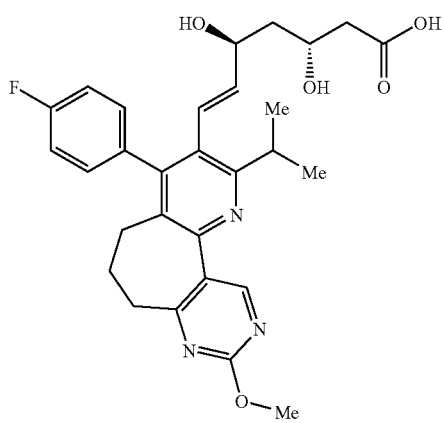

Ex. 115 title compound

The title compound was prepared as the sodium salt as a white lyophilate from E115A using the procedure described in Example 102 Part I: LRMS (ESI, M+H) m/z 522; HPLC (method 9) 96%, $t_R$=1.6 min.

Example 116

6-Heptenoic acid, 7-[4-(4-fluorophenyl)-5,6,9,10-tetrahydro-2-(1-methylethyl)-10-oxo-1,9-phenanthrolin-3-yl]-3,5-dihydroxy-, (3R,5S,6E)-

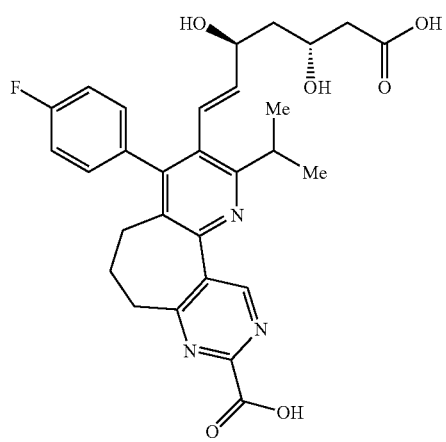

The title compound was prepared from E112E using the procedure described in Example 102 part I as the disodium salt as a white lyophilate: LRMS (ESI, M+H) m/z 536; HPLC (method 9)>99%, $t_R$=1.4 min.

Example 117

6-Heptenoic acid, 7-[(7aR)-4-(4-fluorophenyl)-7a,8,9,10-tetrahydro-2-(1-methylethyl)-10-oxo-5H,7H-pyrido[2,3-e]pyrrolo[2,1-c][1,4]oxazepin-3-yl]-3,5-dihydroxy-, (3R,5S,6E)-

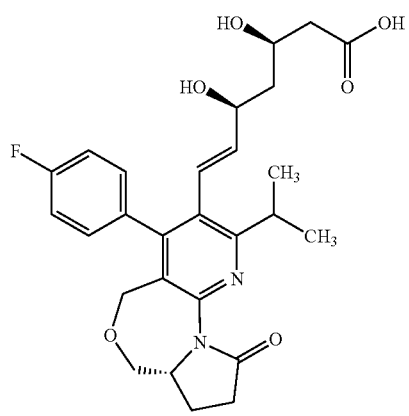

Part A:

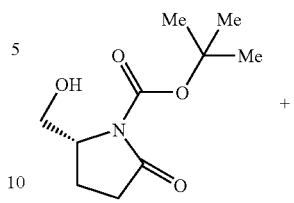

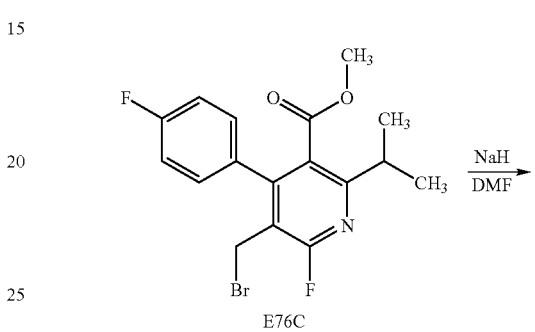

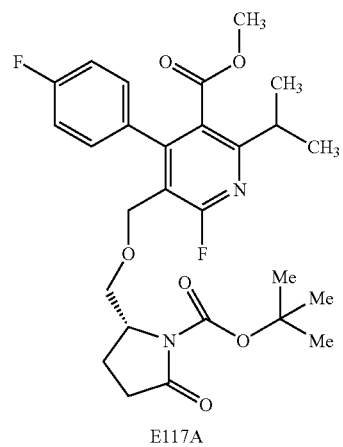

To tert-butyl (R)-2-(hydroxymethyl)-5-oxopyrrolidine-1-carboxylate (412 mg, 1.91 mmol) in 3 mL of N,N-dimethylformamide at 0° C., was added sodium hydride (60% in mineral oil, 80 mg, 2.00 mmol). After stirring at room temperature for 15 min, the mixture was cooled to 0° C. and a solution of E76C (700 mg, 1.82 mmol) in 1 mL of N,N-dimethylformamide was added. The reaction was stirred at 0° C. for 10 min and then at room temperature for 1 h. The reaction mixture was quenched with saturated aqueous ammonium chloride and diluted with ethyl acetate. The organic layer was washed with water and brine, dried over magnesium sulfate and concentrated in vacuo. The residue was chromatographed on silica gel using hexanes/ethyl acetate to provide E117A as a white gum (785 mg, 83%): HPLC (Method 8) $t_R$=3.69 min.

Part B:

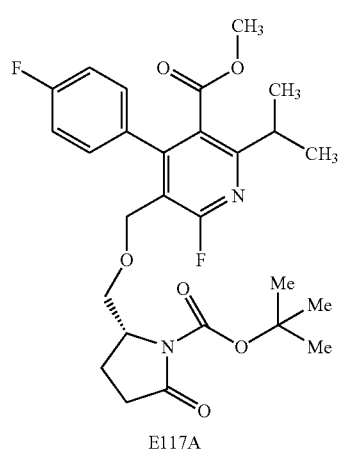

E117A

1) TFA, CH$_2$Cl$_2$
2) NaH, DMF

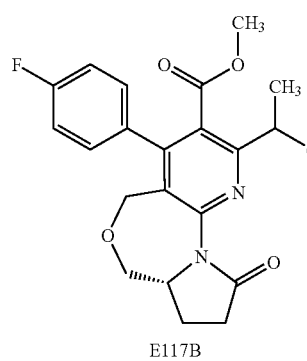

E117B

Part C:

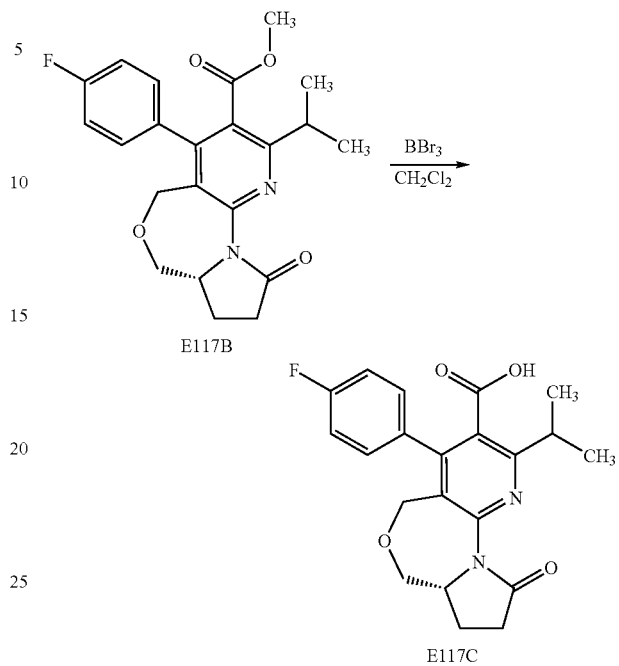

To E117B (545 mg, 1.37 mmol) in 39 mL of dichloromethane at −78° C. was added dropwise boron tribromide (1 M in dichloromethane, 16.41 mL, 16.41 mmol) in 30 min. The reaction was stirred at −78° C. for 5 min and then at room temperature for 22 h. The reaction mixture was concentrated. To the residue at 0° C. was added 2 g of ice followed by 25 mL of methanol. The mixture was filtered and the filtrate was concentrated. The residue was purified by gradient preparative RP-HPLC to provide E117C as a white solid.

Part D:

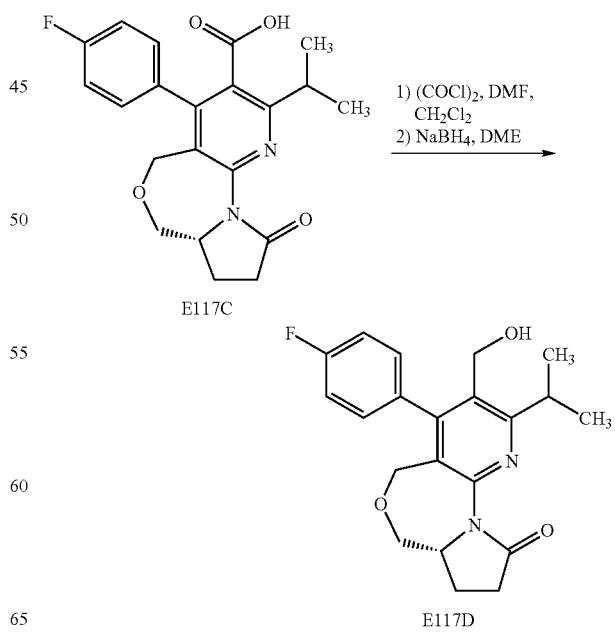

To a solution of E117A (785 mg, 1.51 mmol) in 5 mL of dichloromethane at 0° C. was added 3 mL of trifluoroacetic acid, dropwise. The reaction was stirred at 0° C. for 90 min and concentrated in vacuo. The residue was diluted with ethyl acetate, washed with aqueous sodium bicarbonate and brine, dried over magnesium sulfate and concentrated in vacuo. The residue was dissolved in 5 mL of N,N-dimethylformamide, and sodium hydride (60% in mineral oil, 121 mg, 3.03 mmol) was added at 0° C. After stirring at room temperature for 2 h, the reaction mixture was cooled to 0° C., quenched with saturated aqueous ammonium chloride, and diluted with ethyl acetate. The organic layer was washed with water and brine, dried over magnesium sulfate and concentrated. The residue was chromatographed on silica gel using hexanes/ethyl acetate to provide E117B as a solid (545 mg, 90%): HPLC (Method 8) t$_R$=2.96 min.

To E117C and 0.05 mL N,N-dimethylformamide in 25 mL of dichloromethane at room temperature was added dropwise oxalyl chloride (2 M in dichloromethane, 1.37 ml, 2.74 mmol). The reaction was stirred at room temperature for 90 min and concentrated in vacuo. The residue was dissolved in 10 mL of 1,2-dimethoxyethane and sodium borohydride (207 mg, 5.47 mmol) was added at 0° C. The reaction was stirred at room temperature for 50 min and then quenched with 5 mL water at 0° C. The mixture was extracted with ethyl acetate and the combined extracts were washed with water and brine, dried and concentrated. The residue was chromatographed on silica gel using hexanes/ethyl acetate to provide E117D as a solid (186 mg, 37% from E117B): HPLC (Method 8) $t_R$=2.40 min.

Part E:

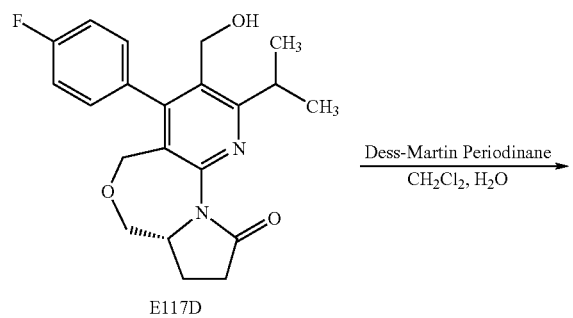

E117D

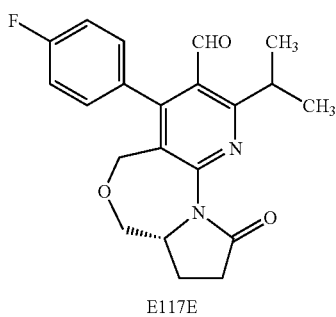

E117E

To E117D (186 mg, 0.50 mmol) and 0.01 mL of water in 5 mL of dichloromethane was added, in portions, Dess-Martin periodinane (319 mg, 0.753 mmol). The reaction was stirred at room temperature for 45 min. To the reaction mixture were added 3 mL of 10% sodium thiosulfate and 3 mL of saturated aqueous sodium bicarbonate. The mixture was stirred for 10 min and diluted with ethyl acetate. The organic layer was washed with water and brine, dried over magnesium sulfate and concentrated. The residue was chromatographed on silica gel using hexanes/ethyl acetate to provide E117E as a solid (156 mg, 84%): HPLC (Method 8) $t_R$=2.97 min.

Part F:

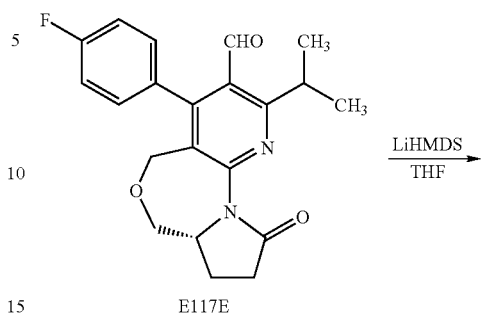

E117E

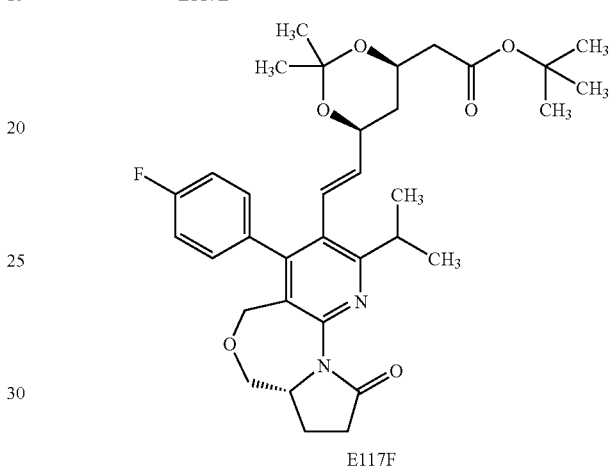

E117F

To E117E (156 mg, 0.42 mmol) and E1D (268 mg, 0.59 mmol) in 5.3 mL of tetrahydrofuran at −78° C. was added lithium bis(trimethylsilyl)amide (1 M in tetrahydrofuran, 0.61 mL, 0.61 mmol). The reaction was stirred at −78° C. for 1 h and quenched with aqueous ammonium chloride. The mixture was diluted with ethyl acetate. The organic layer was washed with water and brine, dried over magnesium sulfate and concentrated. The residue was chromatographed on silica gel using hexanes/ethyl acetate to provide E117F as a solid (220 mg, 87%): HPLC (Method 8) $t_R$=3.89 min.

Part G:

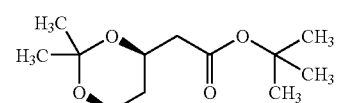

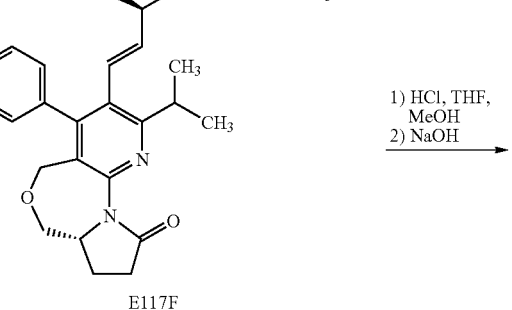

E117F

-continued

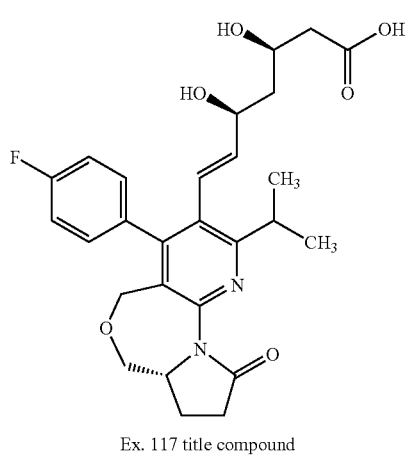

Ex. 117 title compound

To E117F (220 mg, 0.37 mmol) in 5 mL of tetrahydrofuran and 4 mL of methanol at room temperature was added 0.247 mL of 6 N hydrochloric acid. The reaction was stirred at room temperature for 75 min and cooled to 0° C. Sodium hydroxide (0.925 mL, 2 N) was added. The mixture was stirred for additional 70 min and concentrated in vacuo. The residue was purified on a 10 g C18-silica column eluting with water and then water/methanol to provide the title compound as the sodium salt as a white solid (160 mg, 83%): LRMS (ESI, pos. ion spectrum) m/z 499 (M+H); HPLC (Method 8) $t_R$=2.29 min.

Example 118

Using the procedures described in Example 117, the following Example was prepared:

| Ex. | Structure | Characterization |
|---|---|---|
| 118 | 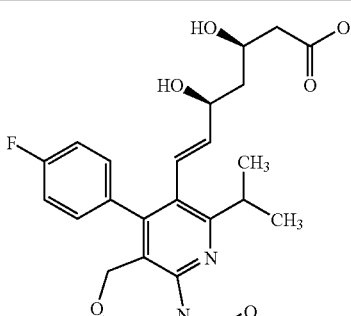<br>6-Heptenoic acid, 7-[(7aS)-4-(4-fluorophenyl)-7a,8,9,10-tetrahydro-2-(1-methylethyl)-10-oxo-5H,7H-pyrido[2,3-e]pyrrolo[2,1-c][1,4]oxazepin-3-yl]-3,5-dihydroxy-, (3R,5S,6E)- | HPLC (Method 8) $t_R$ = 2.26 min LRMS (ESI, pos, ion spectrum) m/z 499 (M + H) |

Example 119

6-Heptenoic acid, 7-[7-(4-fluorophenyl)-9-(1-methylethyl)-4H,6H-pyrido[2,3-e][1,2,4]triazolo[5,1-c][1,4]oxazepin-8-yl]-3,5-dihydroxy-, (3R,5S,6E)-

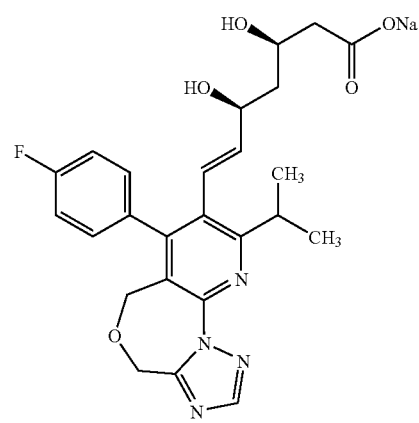

Part A:

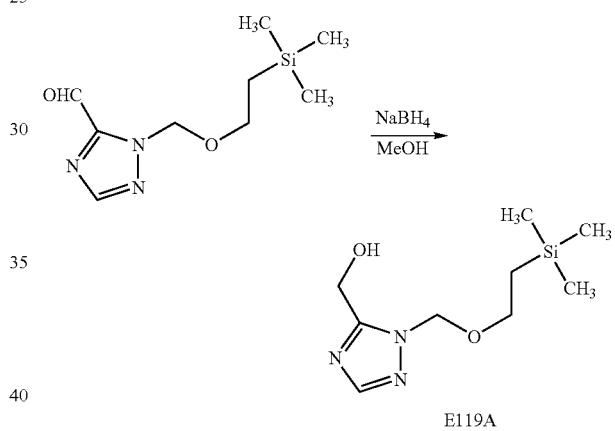

E119A

To 2-((2-(trimethylsilyl)ethoxy)methyl)-2H-1,2,4-triazole-3-carboxaldehyde (5.05 g, 22.21 mmol) in 74 mL of methanol was added sodium borohydride (1.09 g, 28.88 mmol) in portions. The reaction mixture was stirred at room temperature for 1 h and concentrated in vacuo. The residue was diluted with ethyl acetate and the resultant mixture washed with water and brine, dried over magnesium sulfate and concentrated in vacuo to provide E119A as a colorless oil (4.88 g, 96%).

Part B:

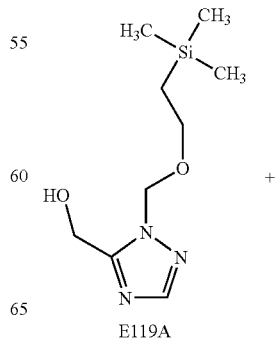

E119A

-continued

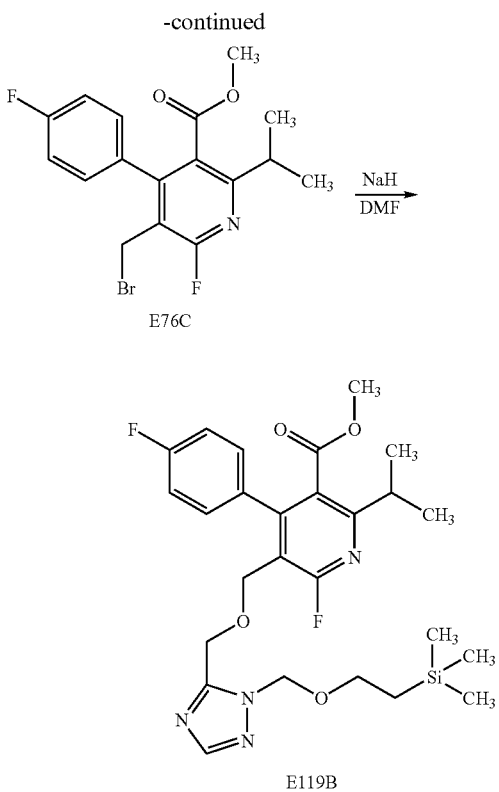

E76C

E119B

E119B

To E119A (1.08 g, 4.72 mmol) in 6 mL of N,N-dimethylformamide at 0° C. was added sodium hydride (60% in mineral oil, 198 mg, 4.96 mmol). The reaction was stirred at room temperature for 15 min, cooled to 0° C. and solid E76C (1.82 g, 4.73 mmol) was added. The reaction was stirred at room temperature for 40 min and quenched with saturated ammonium chloride. The mixture was diluted with ethyl acetate and the organic layer was washed with water and brine, dried over magnesium sulfate and concentrated. The residue was chromatographed on silica gel using hexanes/ethyl acetate to provide E119B (1.68 g, 67%): HPLC (Method 8) $t_R$=4.00 min.

Part C:

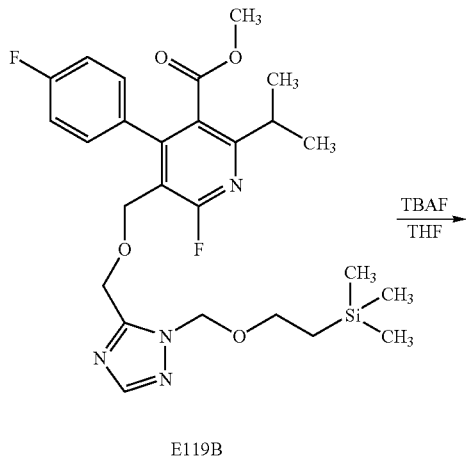

E119B

-continued

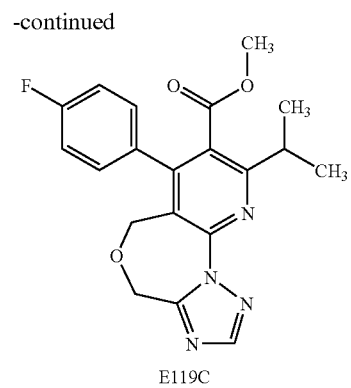

E119C

To E119B (1.68 g, 3.15 mmol) in 16 mL of tetrahydrofuran was added dropwise tetra-n-butylammonium fluoride (1 M in tetrahydrofuran, 18.9 mL, 18.9 mmol). The mixture was heated at 60° C. for 2.5 h and concentrated. The residue was chromatographed on silica gel using hexanes/ethyl acetate to provided E119C as a solid (579 mg, 48%): HPLC (Method 8) $t_R$=3.21 min.

Part D:

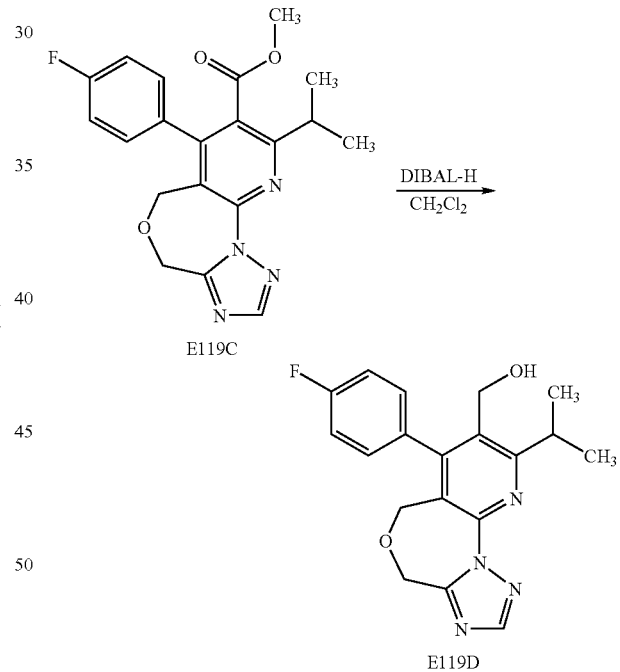

E119C

E119D

To E119C (579 mg, 1.51 mmol) in 15 mL of dichloromethane at −78° C. was added diisobutylaluminum hydride (1 M in dichloromethane, 3.63 mL, 3.63 mmol) dropwise. After stirring at room temperature for 1 h, the reaction was cooled to 0° C. and quenched with saturated aqueous ammonium chloride. The mixture was diluted with ethyl acetate. The organic layer was washed with water and brine, dried over magnesium sulfate and concentrated. The residue was chromatographed on silica gel using hexanes/ethyl acetate to provide E119D as a solid (246 mg, 46%); HPLC (Method 8) $t_R$=2.82 min.

Part E:

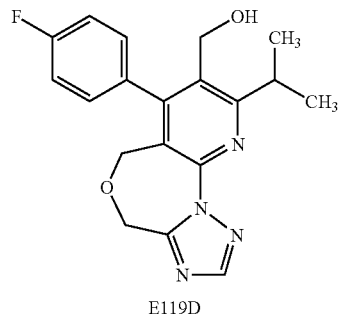

E119D

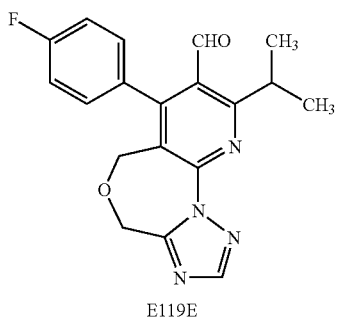

E119E

To E119D (246 mg, 0.69 mmol) and 0.014 mL of water in 20 mL of dichloromethane was added Dess-Martin periodinane (500 mg, 1.18 mmol) in portions. The reaction was stirred at room temperature for 110 min. To the reaction mixture were added 4 mL of 10% sodium thiosulfate and 4 mL of saturated aqueous sodium bicarbonate. The mixture was stirred for 10 min and diluted with ethyl acetate. The organic layer was washed with water and brine, dried over magnesium sulfate and concentrated. The residue was chromatographed on silica gel using hexanes/ethyl acetate to provide E119E as a solid (185 mg, 76%): HPLC (Method 8) $t_R$=3.21 min.

Part F:

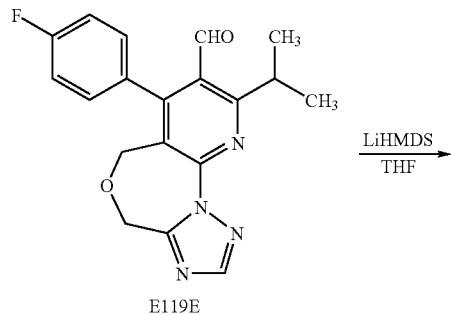

E119E

-continued

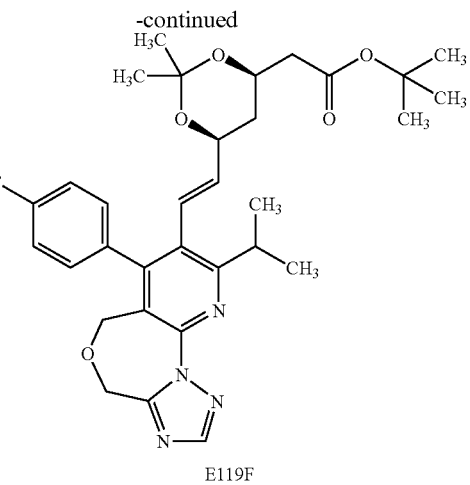

E119F

To E119E (185 mg, 0.53 mmol) and E1D (404 mg, 0.89 mmol) in 5.3 mL of tetrahydrofuran at −78° C. was added lithium bis(trimethylsilyl)amide (1 M in tetrahydrofuran, 0.92 mL, 0.92 mmol). The reaction was stirred at −78° C. for 1 h and was quenched with saturated aqueous ammonium chloride. The mixture was diluted with ethyl acetate. The organic layer was washed with water and brine, dried over magnesium sulfate and concentrated. The residue was chromatographed on silica gel using hexanes/ethyl acetate to provide E119F as a solid (208 mg, 68%): HPLC (Method 8) $t_R$=4.00 min.

Part G:

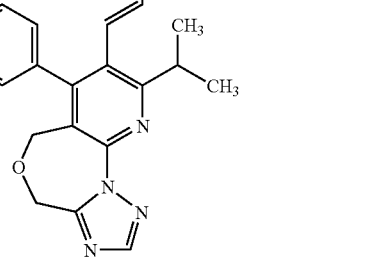

E119F

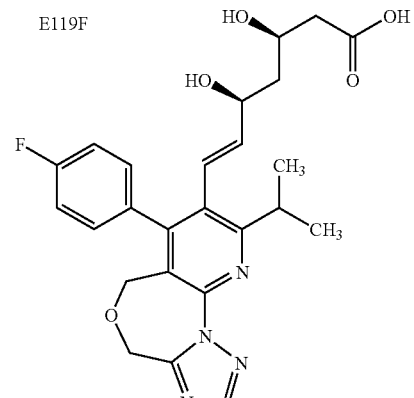

Ex. 119 title compound

To E119F (204 mg, 0.36 mmol) in 6.5 mL of tetrahydrofuran and 5 mL of methanol at room temperature, was added 0.235 mL 6 N hydrochloric acid. The reaction was stirred at room temperature for 90 min and cooled to 0° C. Sodium hydroxide (0.968 mL, 2 N) was added to the mixture. The mixture was stirred for additional 70 min and concentrated in vacuo. The residue was purified by chromatography on a 10-g C18-silica column eluting with water and then water/methanol to provide the title compound as the sodium salt as a white solid (173 mg, 96%): LRMS (ESI, pos. ion spectrum) m/z 483 (M+H); HPLC (Method 8) $t_R$=2.67 min.

Example 120

Using the procedures described in Example 119, the following Example was prepared:

| Ex. | Structure | Characterization |
|---|---|---|
| 120 | 6-Heptenoic acid, 7-[7-(4-fluorophenyl)-9-(1-methylethyl)-4H,6H-pyrazolo[5,1-c]pyrido[2,3-e][1,4]oxazepin-8-yl]-3,5-dihydroxy-, (3R,5S,6E)- | HPLC (Method 8) $t_R$ = 2.82 min LRMS (ESI, pos, ion spectrum) m/z 482 (M + H) |

Examples 121 to 122

Using the procedures described in Example 81, the following Examples were prepared

| Ex. | Structure | Characterization |
|---|---|---|
| 121 | 6-Heptenoic acid, 7-[4-(4-fluorophenyl)-5,6,8,9-tetrahydro-2-(1-methylethyl)-8-oxo-1,9-phenanthrolin-3-yl]-3,5-dihydroxy-, (3R,5S,6E)- | HPLC (Method 8) $t_R$ = 2.87 min LRMS (ESI, pos, ion spectrum) m/z 493 (M + H) |
| 122 | 6-Heptenoic acid, 7-[6-(4-fluorophenyl)-4,5-dihydro-8-(1-methylethyl)[1,2,5]oxadiazolo[3,4-h]quinolin-7-yl]-3,5-dihydroxy-, (3R,5S,6E)- | HPLC (Method 8) $t_R$ = 3.16 min LRMS (ESI, pos, ion spectrum) m/z 490 (M + H) |

Example 123

6-Heptenoic acid, 7-[8-(4-fluorophenyl)-6,7-dihydro-5-methyl-10-(1-methylethyl)-5H-pyrazino[2,3-b]pyrido[2,3-d]azepin-9-yl]-3,5-dihydroxy-, (3R,5S,6E)-

Part A:

4-Methylamino-butyric acid hydrochloride
Et₃N, EtOH, reflux

-continued

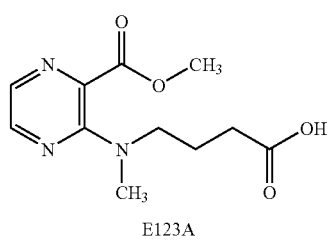
E123A

A solution of methyl 3-bromopyrazine-2-carboxylate (7.87 g, 36.5 mmol), 4-(methylamino)butanoic acid hydrochloride (6.17 g, 40.2 mmol) and triethylamine (16.1 mL, 116 mmol) in absolute ethanol (15 mL) was heated at reflux under nitrogen for 8 h. The reaction was cooled to room temperature and filtered. The filtrate was concentrated. Flash chromatography of the residue on a silica gel column with 50-100% ethyl acetate/hexanes as the eluant provided 9.03 g (98% yield) of compound E123A: LCMS (method 2; ESI, pos. ion spectrum) $t_R$=1.8 min, m/z 254.

Part B:

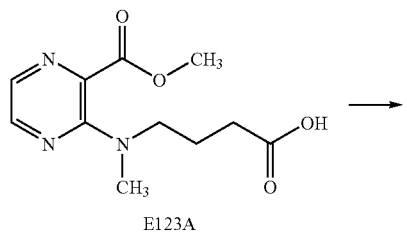
E123A

→

To a solution of E123A (9.03 g, 35.7 mmol) in dry methylene chloride (100 mL) and dry methanol (1 mL) at 0° C. was added a solution of trimethylsilyldiazomethane in hexanes (53.5 mL, 107 mmol) dropwise over 15 min. The reaction was warmed to room temperature and stirred for an additional 1 h. The reaction was quenched by the dropwise addition of acetic acid until gas evolution ceased. The mixture was concentrated and the residue was chromatographed on a silica gel column with 20-30% ethyl acetate/hexanes as the eluant to provide 9.05 g (95% yield) of E123B: HPLC (method 3) $t_R$=2.8 min; LRMS (method 2; ESI, pos. ion spectrum) $t_R$=2.0 min, m/z 268.

Part C:

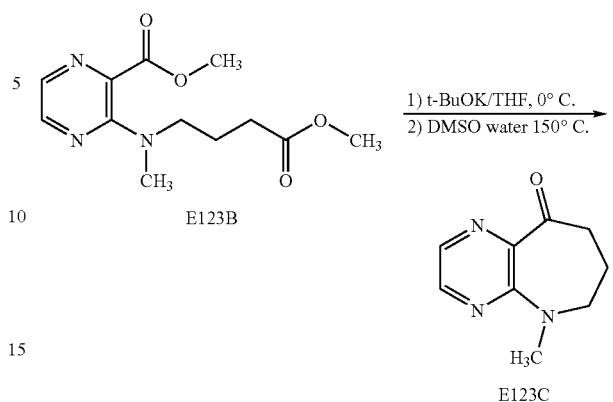

To a solution of E123B (9.05 g, 33.9 mmol) in THF (350 mL) at 0° C. was added a solution of potassium tert-butoxide in THF (40.7 mL, 40.7 mmol) over 30 min. The reaction was stirred at 0° C. for an additional 30 min, quenched with saturated aqueous ammonium chloride solution and neutralized to approximately pH 5 with aqueous 1 N HCl solution. The mixture was extracted with ethyl acetate (3×100 mL). The combined organic fractions were washed with saturated aqueous sodium chloride solution (100 mL), dried over magnesium sulfate, filtered and concentrated. A solution of the residue in DMSO (50 mL) and water (2 mL) and was heated to 150° C. under nitrogen for 8 h. After cooling to room temperature, the reaction was diluted with saturated aqueous sodium chloride solution (100 mL) and extracted with ethyl acetate (10×100 mL). The organic fractions were combined, dried over magnesium sulfate, filtered and concentrated to afford crude E123C. Flash chromatography on a silica gel column with 50-100% ethyl acetate/hexanes as the eluant provided 4.43 g (74% yield) of E123C: LCMS (method 2; ESI, pos. ion spectrum) $t_R$=1.4 min, m/z 178.

Part D:

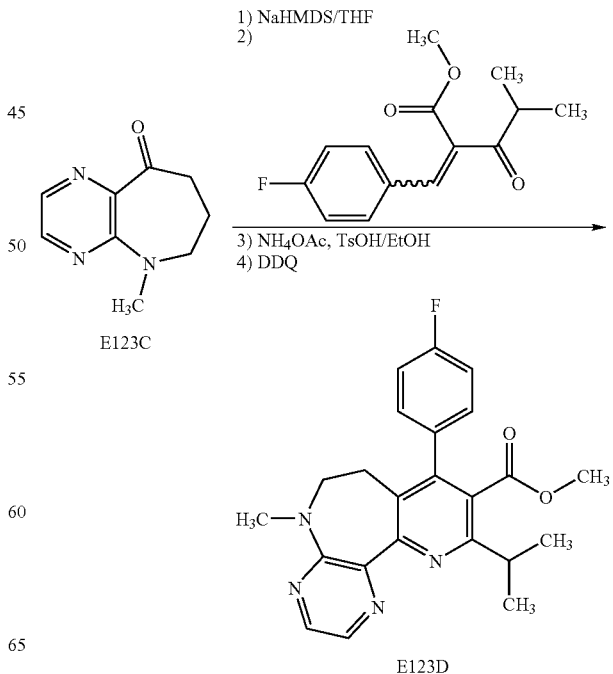

383

A THF solution of NaHMDS (30 mL, 1.0 M, 30 mmol) was diluted with 20 mL of dry THF and the mixture was cooled to −78° C. A solution of E123C (4.43 g, 25 mmol) in 30 mL of dry THF was added dropwise over a 10 min period. After the addition, the mixture was stirred at −78° C. for 30 min. A solution of methyl 2-[(4-fluorophenyl)methylene]-4-methyl-3-oxo-pentanoate (18.8 g, 75.1 mmol) in 50 mL of dry THF which had been precooled to −78° C. was quickly added to the mixture via a cannula. The reaction mixture was stirred at −78° C. for 4 h and was quenched with a solution of acetic acid (15 mL, 262 mmol) in 10 mL of THF. After warming to room temperature, the reaction was diluted with saturated aqueous ammonium chloride solution (100 mL) and was extracted with ethyl acetate (4×100 mL). The organic fractions were combined, washed with saturated aqueous sodium chloride solution (100 mL), dried over magnesium sulfate, filtered and concentrated. Flash chromatography on a silica gel column with 10-50% ethyl acetate/hexanes as the eluant provided 10.7 g (100% yield) of a yellow oil: LCMS (method 1, ESI, pos. ion spectrum) $t_R$=1.9 and 1.7 min, m/z 428.

To a solution of the preceding yellow oil in 100 mL of absolute ethanol was added ammonium acetate (15.4 g, 200 mmol) and p-toluenesulfonic acid monohydrate (237 mg, 1.2 mmol). The reaction was refluxed for 14 h and the solvent was removed in vacuo. The white residue was dissolved in 40 mL of methylene chloride and filtered. The filtrate was concentrated to afford a brown solid.

To a solution of the preceding brown solid in methylene chloride (200 mL) at 0° C. was added 2,3-dichloro-5,6-dicyano-1,4-benzoquinone (6.24 g, 27.5 mmol). The reaction was stirred for 2 h at room temperature, diluted with 100 mL of methylene chloride, and washed with saturated aqueous sodium bicarbonate solution (100 mL). The organic layer was dried over magnesium sulfate, filtered and concentrated. Flash chromatography of the residue on a silica gel column with 10-50% ethyl acetate/hexanes as the eluant provided 8.7 g (86% yield) of E123D: LCMS (method 1; ESI, pos. ion spectrum) $t_R$=1.6 min, m/z 407.

Part E:

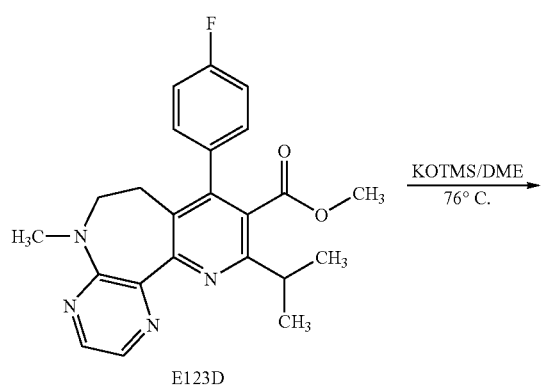

E123D

384

-continued

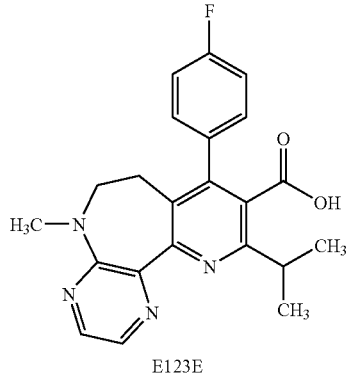

E123E

To a solution of E123D (7.82 g, 19.3 mmol) in 150 mL of dry 1,2-dimethoxyethane was added potassium trimethylsilanolate (4.12 g, 90%, 29 mmol). The mixture was heated at 76° C. under nitrogen for 6 h. The reaction was cooled to room temperature and quenched with water (50 mL). The mixture was extracted with ethyl acetate (3×100 mL). The organic fractions were combined and washed with saturated aqueous sodium chloride solution (100 mL), dried over magnesium sulfate, filtered and concentrated to afford the 3.8 g of E123D. The aqueous fraction was neutralized to pH 3-5 with 1 N HCl aqueous solution, saturated with solid sodium chloride, and extracted with ethyl acetate (4×100 mL). The organic fractions were combined, dried over magnesium sulfate, filtered and concentrated to afford 3.8 g of E123E: LCMS (method 1; ESI, pos. ion spectrum) $t_R$=1.1 min, m/z 393.

Part F:

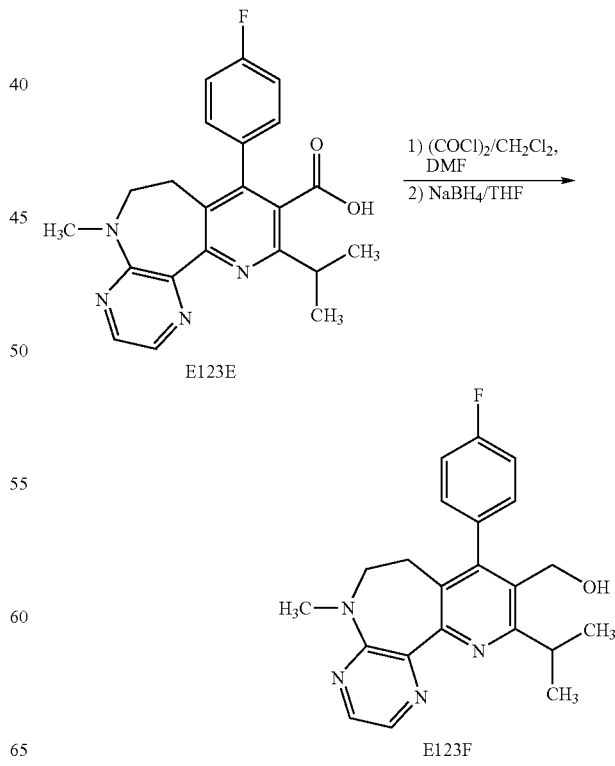

To a solution of E123E (6.8 g, 17.3 mmol) in 150 mL of dry methylene chloride at 0° C. were added a solution of oxalyl chloride (11.3 mL, 2.0 M, 22.5 mmol) in dichloromethane and a catalytic amount of DMF (0.010 mL). The mixture was warmed to room temperature, stirred for 20 min, and concentrated to dryness on a rotary evaporator. The residue was dissolved in dry 1,2-dimethoxyethane (80 mL) and the mixture was cooled to 0° C. Sodium borohydride (86.7 mL, 0.5 M in DME, 43.3 mmol) was added dropwise over 30 min. The reaction was stirred at 0° C. for 1 h and then at room temperature for 6 h. The reaction was cooled to 0° C., quenched by the dropwise addition of water (50 mL), and extracted with ethyl acetate (3×150 mL). The organic fractions were combined, washed with saturated aqueous sodium chloride solution (100 mL), dried over magnesium sulfate, filtered and concentrated to afford the crude product. Flash chromatography on a silica gel column with 50% ethyl acetate/hexanes as the eluant to afford 4.0 g (57% yield from E123D) of E123F as a yellow solid: LCMS (method 1; ESI, pos. ion spectrum) $t_R$=1.2 min, m/z 379.

Part G:

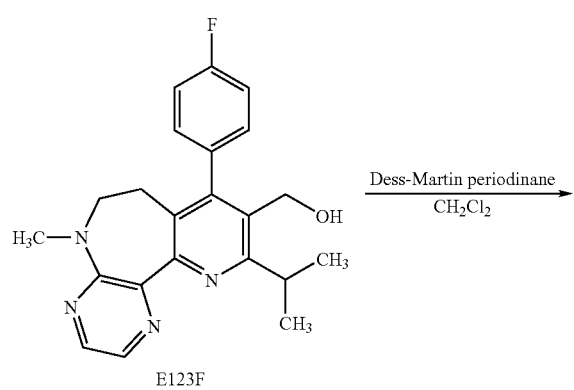

To a solution of E123F (3.7 g, 9.8 mmol) in 100 mL of wet methylene chloride was added Dess-Martin periodinane (8.32 g, 19.6 mmol). The reaction was stirred for 2.5 h. The reaction was diluted with water (100 mL) and methylene chloride (200 mL). The organic layer was separated and washed with water (100 mL), dried over magnesium sulfate, filtered and concentrated to afford the crude product. Flash chromatography on a silica gel column with 20-40% ethyl acetate/hexanes as the eluant provided 3.4 g (92% yield) of E123G as a yellow solid: LCMS (method 1; ESI, pos. ion spectrum) $t_R$=1.4 min, m/z 377.

Part H:

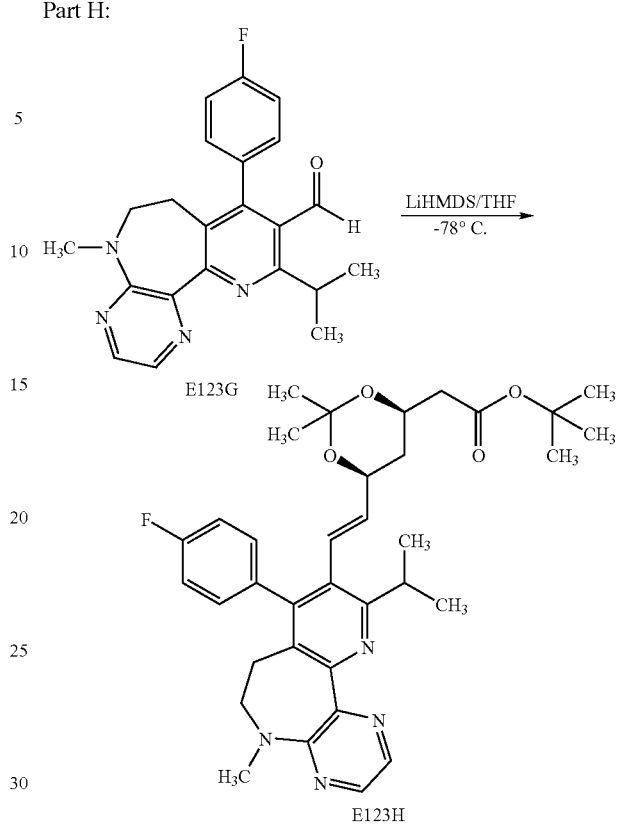

To a solution of E123G (3.38 g, 8.99 mmol) and E1D (6.1 g, 13.5 mmol) in THF (150 mL) at −78° C. was added LiHMDS (17.9 mL, 1.0 M in THF, 17.9 mmol) dropwise over 10 min. After 1 h, the reaction was quenched at −78° C. by the addition of 100 mL of saturated aqueous ammonium chloride solution followed by the addition of ethyl acetate (100 mL). The aqueous layer was extracted with an additional 200 mL of ethyl acetate. The organic fractions were combined, washed with saturated aqueous sodium chloride solution (100 mL), dried with magnesium sulfate, filtered, and concentrated to afford crude E123H. Purification by flash chromatography on a silica gel column with 20-50% ethyl acetate/hexanes as the eluant provided 4.6 g (85% yield) of E123H as a yellow foam: LCMS (method 1; ESI, pos. ion spectrum) $t_R$=1.8 min, m/z 603.

Part I:

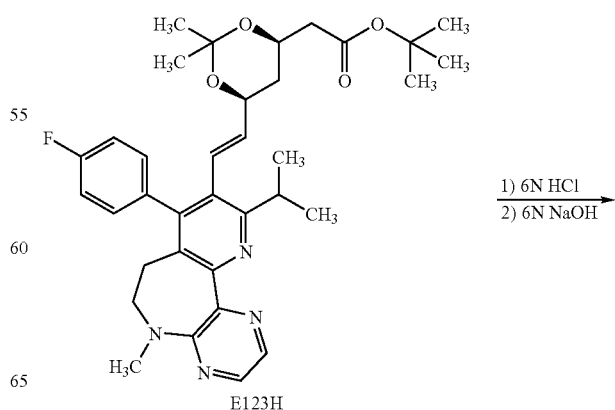

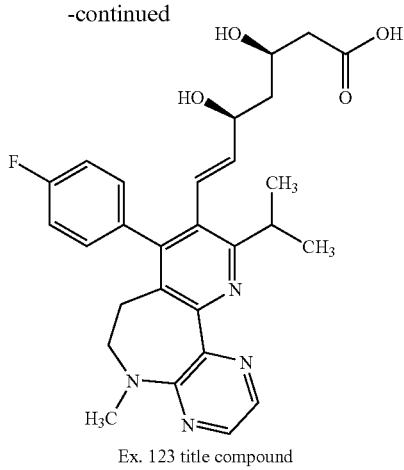

Ex. 123 title compound

To a stirred solution of E123H (4.56 g, 7.58 mmol) in tetrahydrofuran (60 mL) was added aqueous HCl (4.3 mL, 6.0 N, 25.8 mmol). After 90 min, aqueous NaOH (6.18 mL, 6.0 N, 37.1 mmol) was added. Methanol (10 mL) was then added in to ensure that the reaction mixture was homogeneous. After stirring for 30 min, the mixture was neutralized with aqueous HCl (1.0 N) solution to pH ~8. The organic solvent was removed in vacuo to yield a thick, pale-yellow slurry. This material was dissolved in 200 mL of water and loaded on a 40 μm C-18 silica gel column (J. T. Baker catalog #7025-00, 300 g, 55 mm id×200 mm, which had been prewashed with 500 mL of MeOH and 500 mL of deionized water). The column was eluted consecutively with water (1000 mL), 5% methanol in water (1000 mL), 10% methanol in water (2000 mL), 20% methanol in water (1000 mL), 30% methanol in water (1000 mL) and then 50% methanol in water (2000 mL). The product-containing fractions (which eluted between 10-30% methanol in water) were combined and concentrated in vacuo to dryness. The residue was dissolved in methanol (50 mL) and filtered through a sintered funnel. The filtrate was concentrated to dryness. The residue was dissolved in 30 mL of water and lyophilized to afford the title compound as the sodium salt (3.51 g, 88% yield) as a yellow solid: HPLC (method 3) $t_R$=2.5 min; LCMS (method 1; ESI, pos. ion spectrum) $t_R$=1.2 min, m/z 507.

Example 124

6-Heptenoic acid, 7-[8-(4-fluorophenyl)-6,7-dihydro-10-(1-methylethyl)-5H-pyrido[2,3-c]tetrazolo[1,5-a]azepin-9-yl]-3,5-dihydroxy-, (3R,5S,6E)-

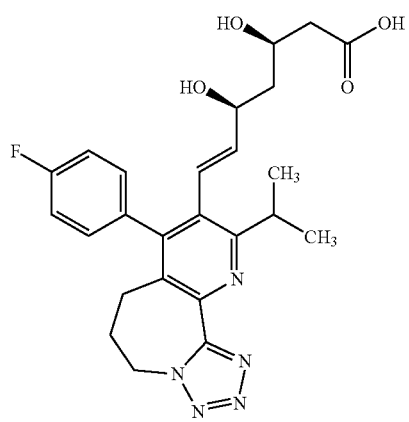

Part A:

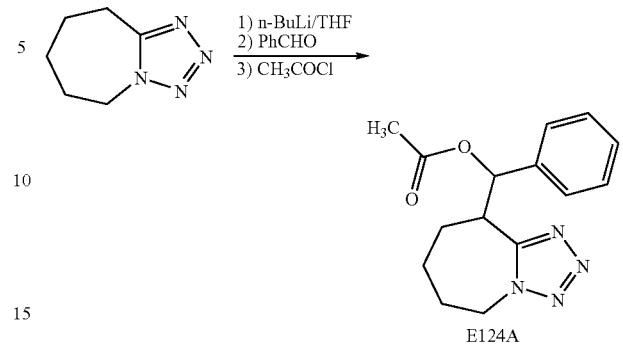

A solution of 6,7,8,9-tetrahydro-5H-tetrazolo[1,5-a]azepine (30 g, 218 mmol) in dry tetrahydrofuran (800 mL) was cooled to −78° C. A 2.5 M solution of n-BuLi in hexanes (88 mL, 220 mmol) was added to the reaction dropwise over 20 min, and the resulting reddish solution was stirred for 30 min. Freshly-distilled benzaldehyde (22.2 mL, 218 mmol) was added dropwise to the reaction over 20 min. The resulting colorless solution was stirred for an additional 20 min at −78° C. Freshly-distilled acetyl chloride (15.7 mL, 220 mmol) was added to the mixture over 15 min. The reaction was warmed to room temperature over a 30 min period. The mixture was diluted with saturated aqueous ammonium chloride solution (200 mL) and extracted with ethyl acetate (3×200 mL). The organic fractions were combined, washed with saturated aqueous sodium chloride solution (100 mL), dried over magnesium sulfate, filtered and concentrated to provide an off-white solid. Recrystallization of this residue from ethyl acetate and hexanes afford 25.4 g of E124A. The mother liquors were concentrated and chromatographed to provide an additional 20 g of E124A (73% yield): LCMS (method 1; ESI, pos. ion spectrum) $t_R$=1.3 min, m/z 287.

Part B:

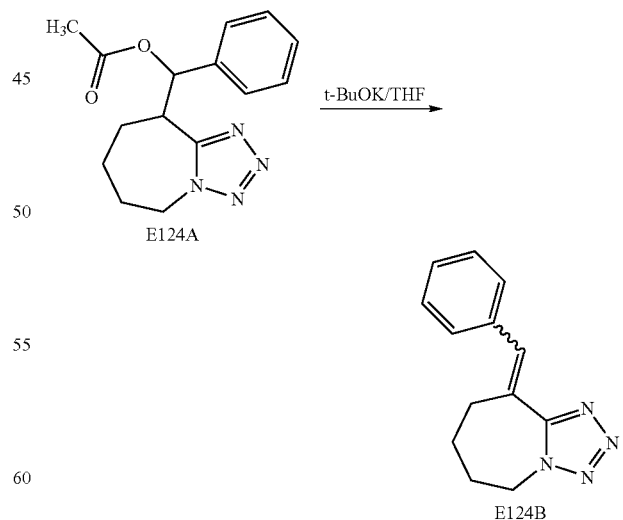

To a solution of E124A (25.4 g, 88.8 mmol) in dry tetrahydrofuran (800 mL) at 0° C. was added potassium tert-butoxide in THF (98 mL, 1.0 M, 98 mmol) over 10 min. The reaction was stirred at 0° C. for an additional 30 min and then at room temperature for 30 min. The resulting yellowish solution was quenched with saturated aqueous sodium bicarbonate solution (100 mL) and extracted with ethyl acetate (3×300 mL). The organic fractions were combined, washed with saturated aqueous sodium chloride solution (200 mL), dried over magnesium sulfate, filtered and concentrated to afford the crude product. Recrystallization from ethyl acetate and hexanes afforded 20 g (99% yield) of E124B as a white solid: LCMS (method 1; ESI, pos. ion spectrum) $t_R$=1.7 min, m/z 227.

Part C:

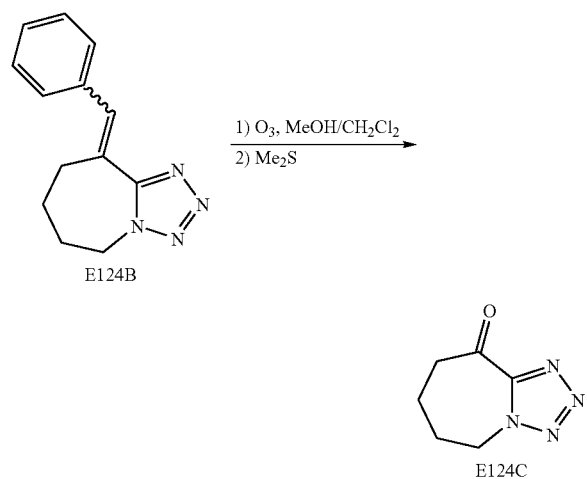

A solution of E124B (24 g, 106 mmol) in methanol (500 mL) and methylene chloride (400 mL) was cooled to −78° C. Ozone was passed through the solution until the blue-purple color persisted. Nitrogen was then passed through the reaction mixture to remove the excess ozone. Dimethyl sulfide (20 ml) was added and the reaction was warmed to room temperature and stirred overnight. The mixture was concentrated. The residue was chromatographed on a silica gel column with 50-80% ethyl acetate/hexanes as the eluant to afford 13 g (81% yield) of E124C as a white solid: LCMS (method 1; ESI, pos. ion spectrum) $t_R$=0.5 min, m/z 153.

Part D:

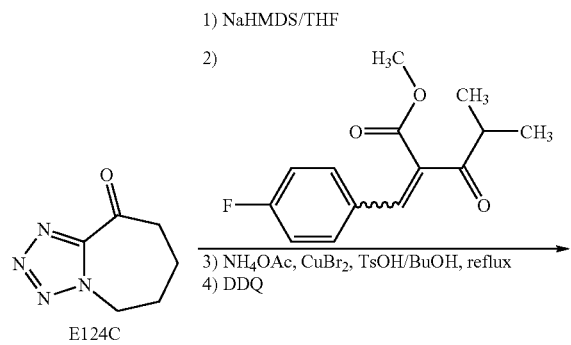

-continued

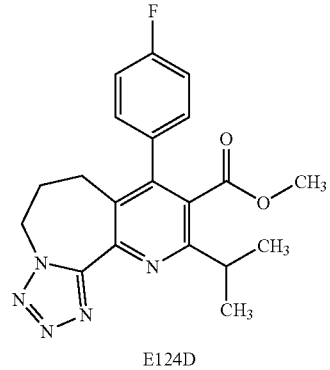

E124D

A NaHMDS solution in THF (80 mL, 1.0 M, 80 mmol) was diluted with 50 mL of dry THF and the mixture was cooled to −78° C. A solution of E124C (11 g, 72.4 mmol) in 200 mL of dry THF was added in dropwise over 1 h. After the addition, the mixture was stirred at −78° C. for 30 min. A solution of methyl 2-[(4-fluorophenyl)methylene]-4-methyl-3-oxo-pentanoate (37.2 g, 149 mmol) in 150 mL of dry THF which had been precooled to −78° C. was quickly added via a cannula. The reaction mixture was stirred at −78° C. for 4 h and was quenched with a solution of acetic acid (8.3 mL, 145 mmol) in 10 mL of THF. After warming to room temperature, the reaction was diluted with water (100 mL), neutralized to approximately pH 6 with 1 N hydrochloric acid and extracted with ethyl acetate (3×200 mL). The organic fractions were combined, washed with saturated aqueous sodium chloride solution (100 mL), dried over magnesium sulfate, filtered and concentrated. Flash chromatography of the residue on a silica gel column with 10-50% ethyl acetate/hexanes as the eluant provided 24 g (82% yield) of a yellow oil: LCMS (method 1; ESI, pos. ion spectrum) $t_R$=1.5 and 1.6 min, m/z 403.

To a solution of the preceding yellow oil (23.2 g, 57.8 mmol) in 300 mL of n-BuOH was added ammonium acetate (35.65 g, 412.5 mmol), copper bromide (25.84 g, 115.6 mmol), and p-toluenesulfonic acid monohydrate (550 mg, 2.9 mmol). The reaction was refluxed for 16 h and the solvent was removed in vacuo. The residue was suspended in 200 mL of methylene chloride and 2,3-dichloro-5,6-dicyano-1,4-benzoquinone (5 g, 22 mmol) was added. After stirring for 30 min at room temperature, the solvent was removed in vacuo. The residue was suspended in water (100 mL) and ethyl acetate (200 mL) and the mixture was neutralized with 1 N ammonium hydroxide solution until all the solid dissolved. The organic layer was separated, and the aqueous layer was further extracted with ethyl acetate (3×200 mL). The organic fractions were combined, washed with saturated aqueous sodium chloride solution (100 mL), dried over magnesium sulfate, filtered and concentrated to afford the crude product. Flash chromatography of the residue on a silica gel column with a 20% ethyl acetate/hexanes to ethyl acetate gradient as the eluant provided 11 g (50% yield) of E124D [LCMS (method 1; ESI, pos. ion spectrum) $t_R$=1.6 min, m/z 382] and 2.5 g of the primary carboxamide derivative of E124D which was characterized by single crystal x-ray analysis.

Part E:

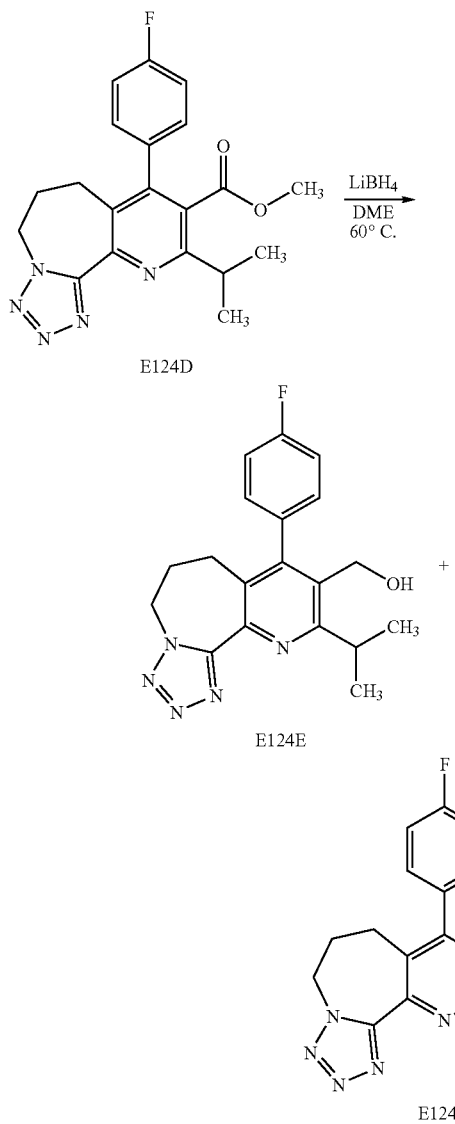

To a solution of E124D (10 g, 26.3 mmol) in 80 mL of dry 1,2-dimethoxyethane was added lithium borohydride (4.6 g, 95%, 201 mmol) in three portions. The mixture was heated to 60° C. under nitrogen for 72 h. The reaction was cooled to 0° C. and quenched by the careful addition of water (50 mL). The mixture was extracted with ethyl acetate (3×100 mL). The organic fractions were combined, washed with saturated aqueous sodium chloride solution (100 mL), dried over magnesium sulfate, filtered and concentrated. Flash chromatography of the residue on a silica gel column with 20-50% ethyl acetate/hexanes as the eluant provided 3.7 g of E124E. The combined aqueous fractions were neutralized to pH 3-5 with aqueous 1 N HCl solution, saturated with solid sodium chloride and extracted with ethyl acetate (4×100 mL). The organic fractions were combined, dried over magnesium sulfate, filtered and concentrated to afford 3.85 g of E124F: LCMS (method 1) $t_R$=1.4 min; (ESI, pos. ion spectrum) m/z 368.

Part F:

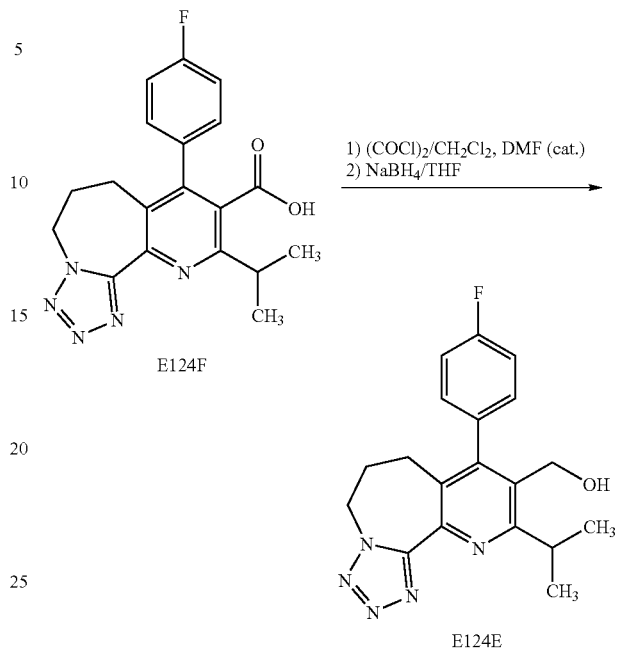

To a solution of E124F (3.85 g, 10.5 mmol) in 100 mL of dry methylene chloride at 0° C. were added a solution of oxalyl chloride (50 mL, 2.0 M, 100 mmol) in dichloromethane and a catalytic amount of DMF (0.04 mL). The mixture was warmed to room temperature, stirred for 20 min and then concentrated to dryness on a rotary evaporator. The residue was dissolved in dry tetrahydrofuran (80 mL) and cooled to 0° C. Sodium borohydride (3.81 g, 101 mmol) was added to the solution. The reaction was stirred at 0° C. for 4 h and then overnight at room temperature. The reaction was cooled to 0° C., quenched by the dropwise addition of water, and extracted with ethyl acetate (3×100 mL). The organic fractions were combined, washed with saturated aqueous sodium chloride solution (100 mL), dried over magnesium sulfate, filtered and concentrated. Flash chromatography of the residue on a silica gel column with 20-50% ethyl acetate/hexanes as the eluant afforded 3.7 g of E124E as a white solid: LCMS (method 1; ESI, pos. ion spectrum) $t_R$=1.5 min, m/z 354.

Part G:

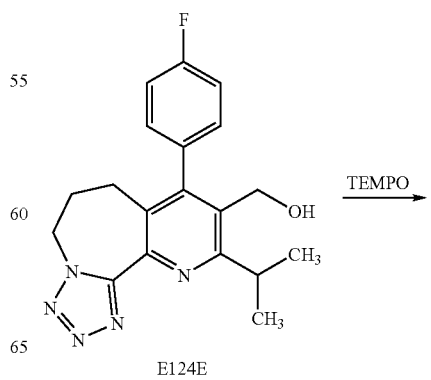

-continued

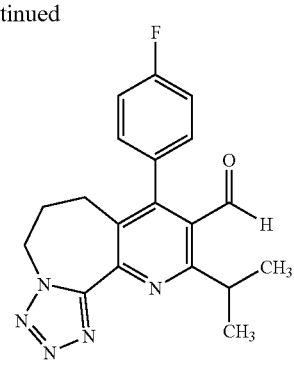

E124G

To a solution of E124E (6.76 g, 19.1 mmol) in ethyl acetate (150 mL) was added KBr (227 mg, 1.9 mmol) and TEMPO (30 mg, 0.19 mmol). The solution was cooled to 0° C. and 40.1 mL of buffered bleach (1.0 M, Clorox® adjusted to pH 9.5 with solid NaHCO$_3$) was added over 10 min. The reaction was stirred at 0° C. for 3 h and was quenched with 50 mL of half-saturated Na$_2$S$_2$O$_3$ in water. The organic layer was washed successively with 50 mL of 1 N NaOH, 100 mL of water, and 100 mL of saturated aqueous sodium chloride solution, dried over magnesium sulfate, filtered and concentrated. Flash chromatography of the residue on a silica gel column with 40% ethyl acetate/hexanes as the eluant provided 5.85 g of E124G (87% yield) as a white solid: LCMS (method 1; ESI, pos. ion spectrum) $t_R$=1.6 min, m/z 352.

Part H:

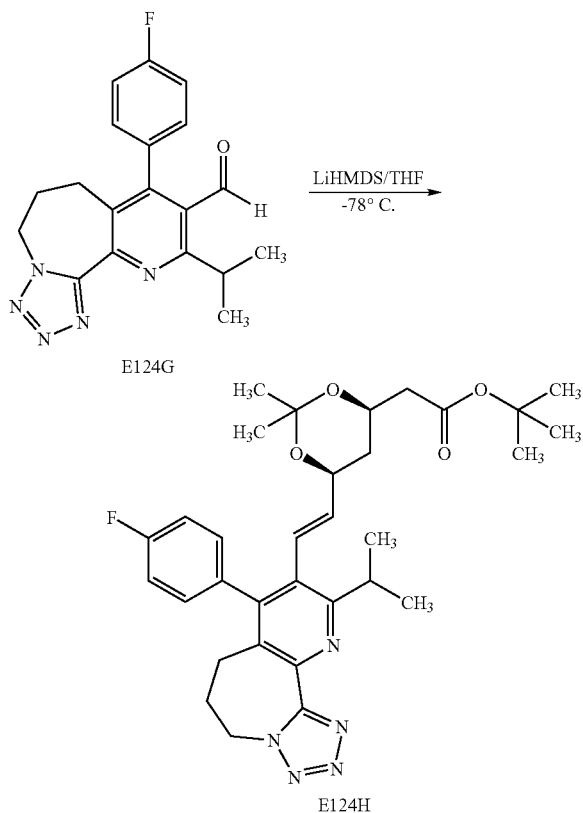

To a solution of E124G (5.85 g, 16.7 mmol) and E1D (15.1 g, 33.3 mmol) in THF (150 mL) at −78° C. was added LiHMDS (33.4 mL, 1.0 M in THF, 33.4 mmol) dropwise over 10 min. After 1 h, the reaction was quenched at −78° C. by the addition of 100 mL of saturated aqueous ammonium chloride solution followed by the addition of ethyl acetate (100 mL). The aqueous layer was extracted with an additional 200 mL of ethyl acetate. The organic fractions were combined, washed with saturated aqueous sodium chloride solution (100 mL), dried with magnesium sulfate, filtered, and concentrated. Purification of the residue by flash chromatography on a silica gel column with 20-50% ethyl acetate/hexanes as the eluant provided 8.43 g (88% yield) of E124H as a white foam: LCMS (method 1; ESI, pos. ion spectrum) $t_R$=2.0 min, m/z 578.

Part I:

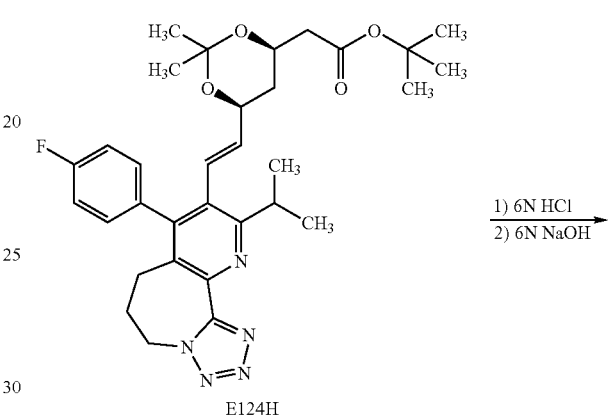

To a stirred solution of E124H (8.2 g, 14.2 mmol) in tetrahydrofuran (80 mL) was added aqueous HCl (7.1 mL, 6.0 N, 42.6 mmol). After 90 min, aqueous NaOH (11.5 mL, 6.0 N, 68.7 mmol) was added. After stirring for 2.5 h, the mixture was neutralized with aqueous HCl (1.0 N) to approximately pH 8-9. The organic solvent was removed in vacuo to yield a thick pale-yellow slurry. This material was dissolved in 200 mL of water and loaded on a 40 μm C-18 silica gel column (J. T. Baker catalog #7025-00, 300 g, 55 mm id×200 mm, which had been prewashed with 500 mL of MeOH and 500 mL of deionized water). The column was eluted consecutively with water (1000 mL), 5% methanol in water (1000 mL), 10% methanol in water (2000 mL), 20% methanol in water (1000 mL), 30% methanol in water (1000 mL) and then 50% methanol in water (2000 mL). The product-containing fractions (fractions between 10-30% methanol in water) were combined and concentrated in vacuo to dryness. The residue was dissolved in methanol (50 mL) and filtered through a sintered

Example 125

6-Heptenoic acid, 7-[7-(4-fluorophenyl)-5,6-dihydro-9-(1-methylethyl)tetrazolo[1,5-h][1,7]naphthyridin-8-yl]-3,5-dihydroxy-, (3R,5S,6E)-

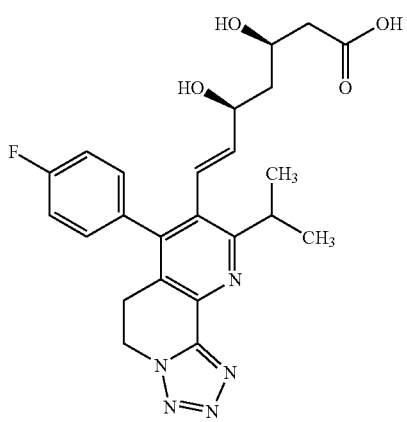

Part A:

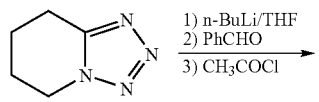

A solution of 5,6,7,8-tetrahydrotetrazolo[1,5-a]pyridine (1.09 g, 8.8 mmol) in dry tetrahydrofuran (50 mL) was cooled to −78° C. A 2.5 M solution of n-BuLi in hexanes (3.6 mL, 9.0 mmol) was added dropwise over 2 min, and the resulting orange solution was stirred for 5 min. Freshly-distilled benzaldehyde (0.89 mL, 8.75 mmol) was added dropwise over 2 min. The resulting solution was stirred for additional 20 min at −78° C. Freshly-distilled acetyl chloride (0.75 mL, 10.5 mmol) was added over 2 min. The reaction was warmed to room temperature over a 30 min period and then stirred at room temperature for an additional 1 h. The reaction was diluted with saturated aqueous ammonium chloride solution (30 mL) and extracted with ethyl acetate (3×50 mL). The organic fractions were combined, washed with saturated funnel. The filtrate was concentrated to dryness, redissolved in 30 mL of water and lyophilized to afford the title compound as the sodium salt (6.8 g, 95% yield) as a white solid: HPLC (method 3) $t_R$=3.0 min; LCMS (method 1; ESI, pos. ion spectrum) $t_R$=1.3 min, m/z 482.

aqueous sodium chloride solution (50 mL), dried over magnesium sulfate, filtered and concentrated. Chromatography of the residue on a silica gel column with 30% ethyl acetate/hexanes as the eluant to afford 1.86 g (78% yield) of E125A as a white solid: LCMS (method 1; ESI, pos. ion spectrum) $t_R$=1.3 min, m/z 273.

Part B:

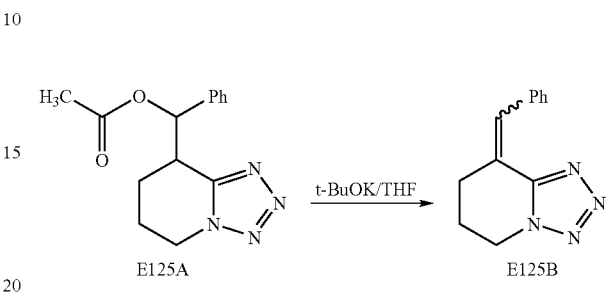

To a solution of E125A (1.86 g, 6.84 mmol) in dry tetrahydrofuran (20 mL) at room temperature was added a solution of potassium tert-butoxide in THF (7.52 mL, 7.52 mmol) dropwise over 10 min. The reaction was stirred at room temperature for 30 min. The resulting slightly brown solution was quenched with saturated aqueous sodium bicarbonate solution (10 mL) at 0° C. and extracted with ethyl acetate (3×50 mL). The organic fractions were combined, washed with saturated aqueous sodium chloride solution (30 mL), dried over magnesium sulfate, filtered and concentrated. Chromatography of the residue on a silica gel column with 20-50% ethyl acetate/hexanes as the eluant and concentrated to afford 1.2 g (83% yield) of E125B as a white solid: LCMS (method 1; ESI, pos. ion spectrum) $t_R$=1.4 min, m/z 213.

Part C:

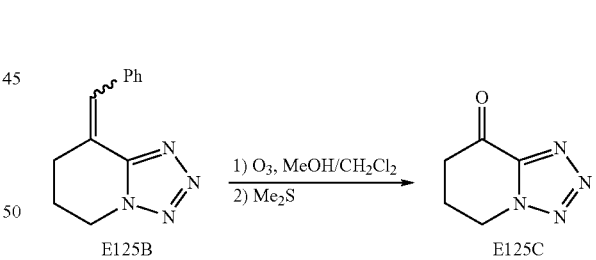

A solution of E125B (1.1 g, 5.2 mmol) in methanol (20 mL) and methylene chloride (20 mL) was cooled −78° C. Ozone was passed through the reaction until the blue-purple color persisted. Nitrogen was then passed through the reaction mixture to remove the excess ozone. Dimethyl sulfide (2 ml) was added and the reaction was warmed to room temperature and stirred overnight. The mixture was concentrated and the residue was chromatographed on a silica gel column with 50-80% ethyl acetate/hexanes as the eluant to afford 550 mg (77% yield) of E125C as a white solid: LCMS (method 1; ESI, pos. ion spectrum) $t_R$=0.4 min, m/z 139.

Part D:

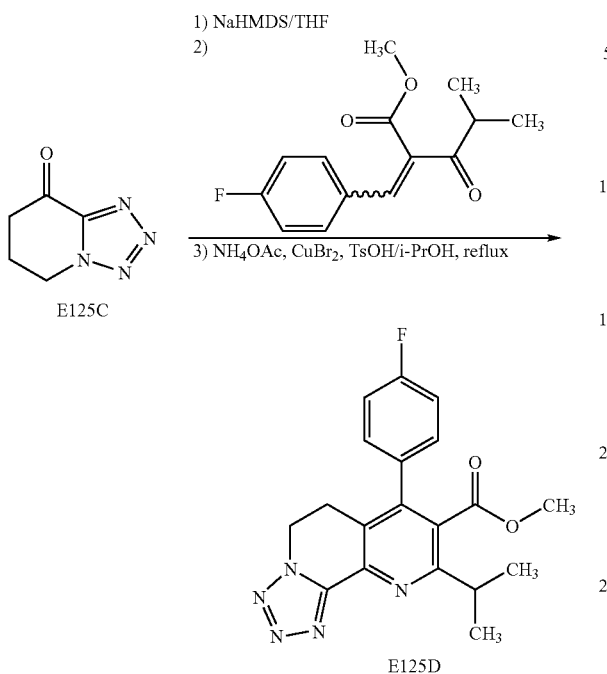

To a NaHMDS solution in THF (3.75 mL, 1.0 M, 3.75 mmol) was added 3 mL of dry THF. The mixture was cooled to −78° C. A solution of E125C (398 mg, 2.88 mmol) in 5 mL of dry THF was added in dropwise over 5 min. After the addition, the mixture was stirred at −78° C. for 30 min. A solution of methyl 2-[(4-fluorophenyl)methylene]-4-methyl-3-oxo-pentanoate (2.16 g, 8.65 mmol) in 10 mL of dry THF which had been precooled to −78° C. was quickly transferred into the reaction via a cannula. The reaction mixture was stirred at −78° C. for 6 h and was quenched with a solution of acetic acid (0.5 mL, 8.65 mmol) in 2 mL of THF. After warming to room temperature, the reaction was diluted with water (10 mL), neutralized to pH 6 with 1 N hydrochloric acid, and extracted with ethyl acetate (3×20 mL). The organic fractions were combined, washed with saturated aqueous sodium chloride solution (30 mL), dried over magnesium sulfate, filtered and concentrated. Flash chromatography of the residue on a silica gel column with 10-50% ethyl acetate/hexanes as the eluant provided 0.91 g (82% yield) of a yellow oil. LCMS (method 1; ESI, pos. ion spectrum) $t_R$=1.3 min, m/z 389.

To a solution of the preceding yellow oil (0.91 g, 2.34 mmol) in 30 mL of isopropanol was added ammonium acetate (1.45 g, 18.8 mmol), copper bromide (1.1 g, 4.9 mmol), and p-toluenesulfonic acid monohydrate (22 mg, 0.12 mmol). The reaction was heated for 16 h at 80° C. and the solvent was evaporated to dryness in vacuo. The residue was suspended in water (30 mL) and ethyl acetate (30 mL) and neutralized with 1 N ammonium hydroxide solution to approximately pH 9 at 0° C. The organic layer was separated, and the aqueous layer was further extracted with ethyl acetate (3×30 mL). The organic fractions were combined, washed with saturated aqueous sodium chloride solution (30 mL), dried over magnesium sulfate, filtered and concentrated. Flash chromatography of the residue on a silica gel column with 20-50% ethyl acetate/hexanes as the eluant provided 0.42 g (49% yield) of E125D: LCMS (method 1; ESI, pos. ion spectrum) $t_R$=1.4 min, m/z 368.

Part E:

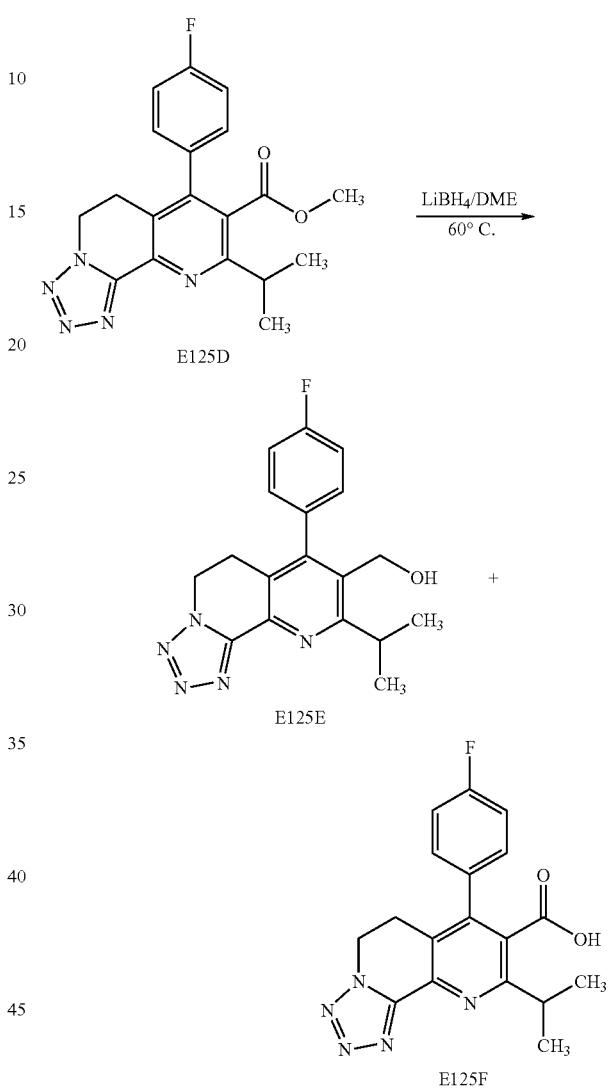

To a solution of E125D (205 mg, 0.56 mmol) in 5 mL of dry 1,2-dimethoxyethane was added lithium borohydride (90 mg, 95%, 3.1 mmol) in two portions. The mixture was heated to 60° C. under nitrogen for 48 h. The reaction was cooled to 0° C. and quenched by the careful addition of water (5 mL). The mixture was extracted with ethyl acetate (3×10 mL). The organic fractions were combined and washed with saturated aqueous sodium chloride solution (30 mL), dried over magnesium sulfate, filtered and concentrated to afford the E125E (20 mg). The aqueous fraction was neutralized to approximately pH 3-5 with 1 N hydrochloric acid, and was extracted with ethyl acetate (3×30 mL). The organic fractions were combined, washed with saturated aqueous sodium chloride solution (30 mL), dried over magnesium sulfate, filtered and concentrated to afford E125F (122 mg): LCMS (method 1; ESI, pos. ion spectrum) $t_R$=1.3 min, m/z 354.

Part F:

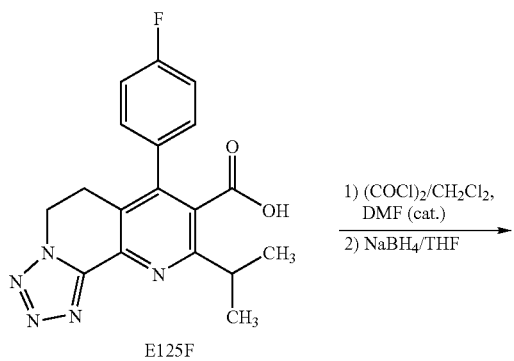

To a solution of E125F (122 mg, 0.35 mmol) in 5 mL of dry methylene chloride at 0° C. were added a solution of oxalyl chloride (0.43 mL, 2.0 M, 0.86 mmol) in dichloromethane and a catalytic amount of DMF (0.005 mL). The mixture was warmed to room temperature, stirred for 1 h and concentrated to dryness on a rotary evaporator. The residue was dissolved in dry 1,2-dimethoxyethane (2 mL) and cooled to 0° C. Sodium borohydride in 1,2-dimethoxyethane (0.7 mL, 0.5 M, 0.35 mmol) was added. The reaction was stirred at 0° C. for 10 min. The reaction was quenched by the dropwise addition of water and was extracted with ethyl acetate (3×10 mL). The organic fractions were combined, washed with saturated aqueous sodium chloride solution (10 mL), dried over magnesium sulfate, filtered and concentrated to afford 105 mg of E125E: LCMS (method 1; ESI, pos. ion spectrum) $t_R$=1.4 min, m/z 340.

Part G:

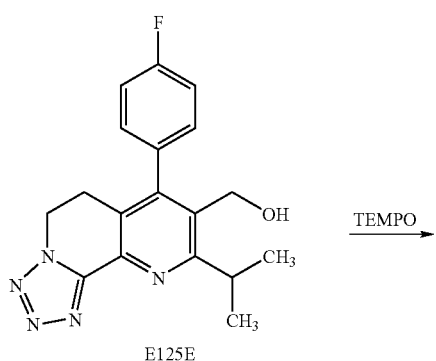

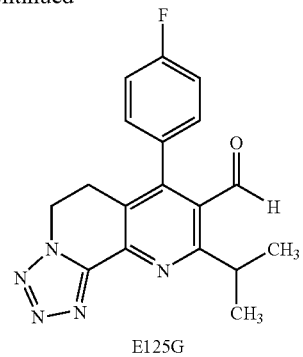

To a solution of E125E (125 mg, 0.37 mmol) in ethyl acetate (10 mL) was added KBr (4.4 mg, 0.037 mmol) and TEMPO (1 mg, 0.006 mmol). The solution was cooled to 0° C. and 1.5 mL of buffered bleach (1.0 M, Clorox® adjusted to pH 8.5 with solid NaHCO₃) was added over 2 min. The reaction was stirred at 0° C. for 10 min and was quenched with 2 mL of half-saturated Na₂S₂O₃ in water. The organic layer was washed successively with 3 mL of 1 N NaOH, 3 mL of water, and 3 mL of saturated aqueous sodium chloride solution; dried over magnesium sulfate; filtered and concentrated to afford E125G as a white solid (124 mg, 100% yield): LCMS (method 1; ESI, pos. ion spectrum) $t_R$=1.6 min, m/z 338.

Part H:

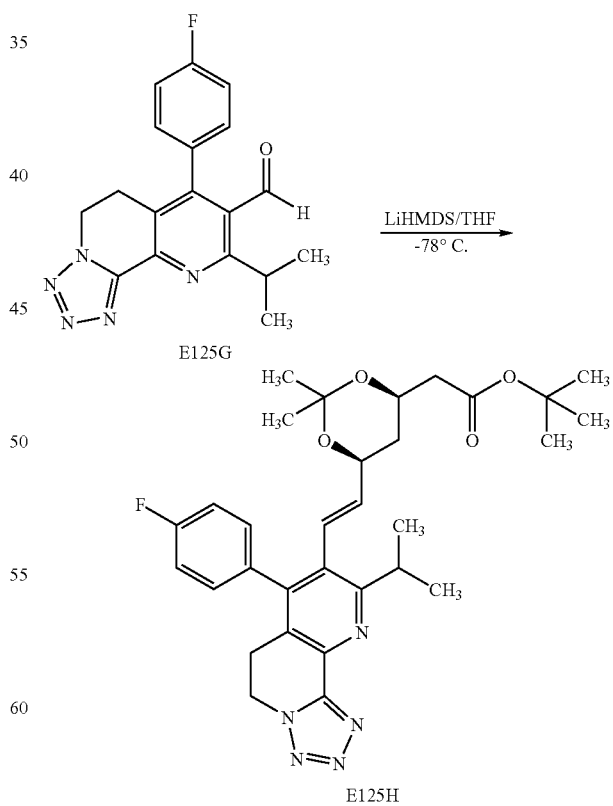

To a solution of E125G (156 g, 0.46 mmol) and E1D (251 mg, 0.56 mmol) in THF (3 mL) at −78° C. was added LiH- MDS (0.56 mL, 1.0 M in THF, 0.56 mmol) dropwise. After 1 h, the reaction was quenched at −78° C. by the addition of 5 mL of saturated aqueous ammonium chloride solution followed by the addition of ethyl acetate (10 mL). The organic layer was separated, and the aqueous layer was extracted with an additional 10 mL of ethyl acetate. The organic fractions were combined, washed with saturated aqueous sodium chloride solution (5 mL), dried with magnesium sulfate, filtered, and concentrated. Purification of the residue by flash chromatography on a silica gel column with ethyl acetate/dichloromethane/hexanes (1:1:7 to 1:1:1) as the eluant provided 180 mg (82% yield) of E125H as a white foam: LCMS (method 1; ESI, pos. ion spectrum) $t_R$=2.0 min, m/z 564.

Part I:

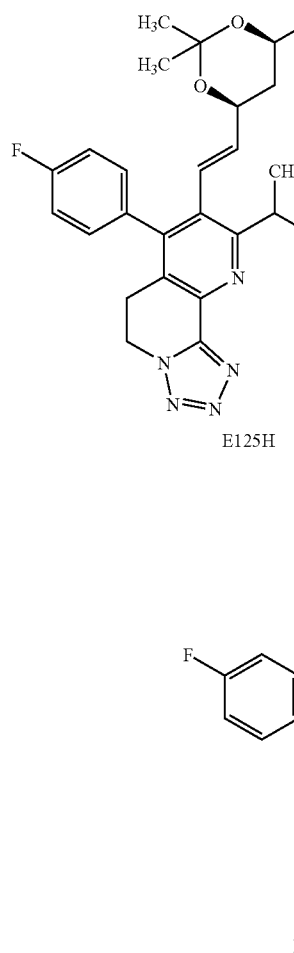

Ex. 125 title compound

To a stirred solution of E125H (58 mg, 0.1 mmol) in tetrahydrofuran (2 mL) was added aqueous HCl (0.05 mL, 6.0 N, 0.30 mmol). After 2 h, aqueous NaOH (0.1 mL, 6.0 N, 0.60 mmol) was added. After stirring for 2.5 h, the mixture was neutralized with aqueous HCl (1.0 N) to pH 8-9. The organic solvent was removed in vacuo to yield a thick pale yellow slurry. This material was dissolved in 20 mL of water and loaded on a 40 μm C-18 silica gel column (40 g, which had been prewashed with 50 mL of MeOH and 50 mL of deionized water). The column was eluted consecutively with water (100 mL), 5% methanol in water (100 mL), 10% methanol in water (100 mL), 20% methanol in water (100 mL), and 30% methanol in water (100 mL). The product-containing fractions (fractions between 10-20% methanol in water) were combined and concentrated in vacuo to dryness. The residue was dissolved in methanol (10 mL) and filtered through a sintered funnel. The filtrate was concentrated to dryness, redissolved in 10 mL of water and lyophilized to afford the title compound as the sodium salt (27 mg, 56% yield) as a white solid: HPLC (method 3) $t_R$=2.9 min; LCMS (method 1; ESI, pos. ion spectrum) $t_R$=1.3 min, m/z 467.

Example 126

6-Heptenoic acid, 7-[9-(4-fluorophenyl)-5,6,7,8-tetrahydro-11-(1-methylethyl)pyrido[2,3-c]tetrazolo[1,5-a]azocin-10-yl]-3,5-dihydroxy-, (3R,5S,6E)-

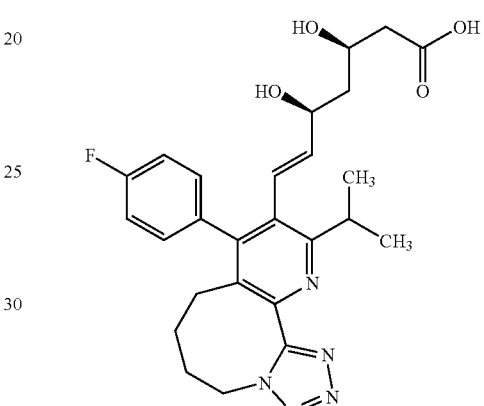

Part A:

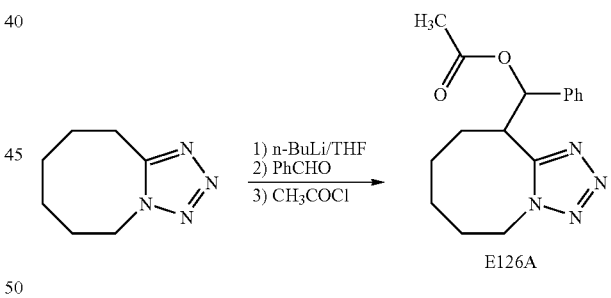

A solution of 5,6,7,8,9,10-hexahydrotetrazolo[1,5-a]azocine (11.6 g, 76.3 mmol) in dry tetrahydrofuran (200 mL) was cooled to −78° C. A 2.5 M solution of n-BuLi in hexanes (32.1 mL, 80.1 mmol) was added dropwise over 10 min, and the resulting orange solution was stirred for 10 min. Freshly-distilled benzaldehyde (8.53 mL, 84 mmol) was added dropwise over 5 min. The resulting solution was stirred for additional 30 min at −78° C. Freshly-distilled acetyl chloride (6.51 mL, 91.6 mmol) was added. The reaction was warmed to room temperature over a 30 min period and stirred at room temperature for 1 h. The reaction was diluted with saturated aqueous ammonium chloride solution (100 mL) and extracted with ethyl acetate (3×100 mL). The organic fractions were combined, washed with saturated aqueous sodium chloride solution (50 mL), dried over magnesium sulfate, filtered and concentrated to provide an off-white solid. Recrystallization from ethyl acetate and hexanes afforded 8.02 g of E126A. The mother liquors were concentrated and chromatographed on a silica gel column with 10-20% ethyl acetate/hexanes to provide an additional 4.55 g of E126A (55% combined yield) as a white solid: LCMS (method 1; ESI, pos. ion spectrum) $t_R$=1.4 min, m/z 301.

Part B:

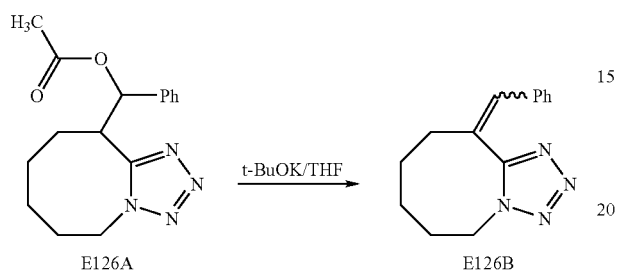

To a solution of E126A (8.02 g, 26.73 mmol) in dry tetrahydrofuran (100 mL) at room temperature was added a solution of potassium tert-butoxide in THF (29.4 mL, 29.4 mmol) dropwise over 5 min. The reaction was stirred at room temperature for 30 min. The resulting slightly-colored solution was quenched with saturated aqueous sodium bicarbonate solution (10 mL) at 0° C. and extracted with ethyl acetate (3×50 mL). The organic fractions were combined, washed with saturated aqueous sodium chloride solution (50 mL), dried over magnesium sulfate, filtered and concentrated to afford E126B (5.1 g, 80% yield) as a white solid: LCMS (method 1; ESI, pos. ion spectrum) $t_R$=1.5 and 1.6 min, m/z 241.

Part C:

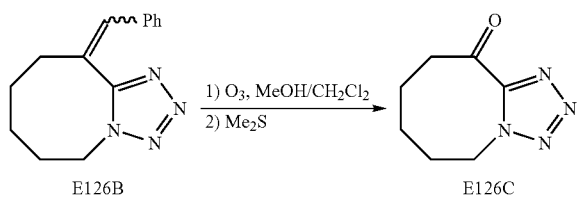

A solution of E126B (500 mg, 2.08 mmol) in methanol (20 mL) and methylene chloride (20 mL) was cooled −78° C. Ozone was passed through the reaction until the blue-purple color persisted. Nitrogen was then passed through the reaction mixture to remove the excess ozone. Dimethyl sulfide (2 ml) was added and the reaction was warmed to room temperature and stirred overnight. The mixture was concentrated and the residue was chromatographed on a silica gel column with 50-80% ethyl acetate/hexanes as the eluant to afford 266 mg (77% yield) of E126C as a white solid: LCMS (method 1; ESI, pos. ion spectrum) $t_R$=0.5 min, m/z 167.

Part D:

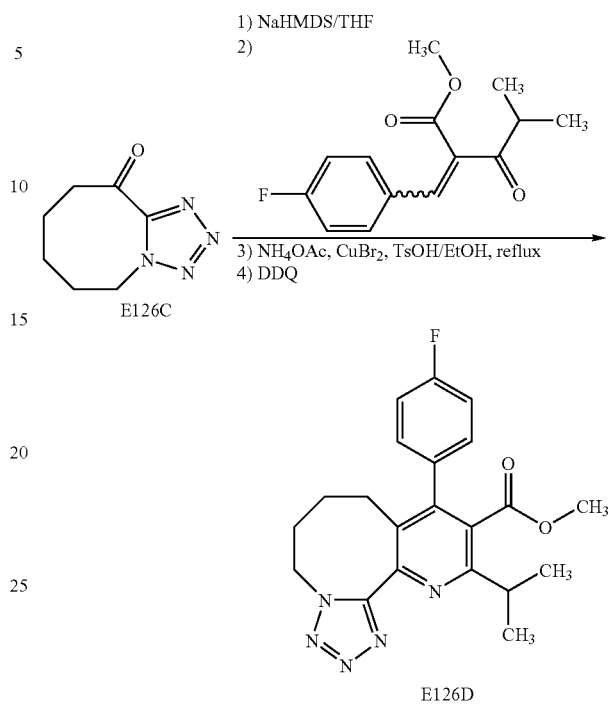

A NaHMDS solution in THF (1.2 mL, 1.0 M, 1.2 mmol) was cooled to −78° C. A solution of E126C (133 mg, 0.8 mmol) in 2 mL of dry THF was added dropwise over 5 min. After the addition, the mixture was stirred at −78° C. for 10 min. A solution of methyl 2-[(4-fluorophenyl)methylene]-4-methyl-3-oxo-pentanoate (0.6 g, 2.4 mmol) in 2 mL of dry THF which had been precooled to −78° C. was quickly transferred via a cannula. The reaction mixture was stirred at −78° C. for 6 h and was quenched with a solution of acetic acid (0.14 mL, 2.4 mmol) in 1 mL of THF. After warming to room temperature, the reaction was diluted with water (2 mL) and extracted with ethyl acetate (3×10 mL). The organic fractions were combined, washed with saturated aqueous sodium chloride solution (10 mL), dried over magnesium sulfate, filtered and concentrated. Flash chromatography of the residue on a silica gel column with 20% ethyl acetate/hexanes as the eluant provided 0.33 g (99% yield) of a yellow oil: LCMS (method 1; ESI, pos. ion spectrum) $t_R$=1.7 min, m/z 417.

To a solution of the preceding yellow oil (0.33 g, 0.79 mmol) in 7 mL of ethanol were added ammonium acetate (0.37 g, 4.8 mmol), copper bromide (357 mg, 1.6 mmol), and p-toluenesulfonic acid monohydrate (7.6 mg, 0.04 mmol). The reaction was heated for 18 h at 80° C. and the solvent was evaporated in vacuo. The residue was suspended in 10 mL of methylene chloride and 2,3-dichloro-5,6-dicyano-1,4-benzoquinone (272 mg, 0.8 mmol) was added. After stirring for 30 min at room temperature, the solvent was evaporated to dryness in vacuo. The residue was suspended in water (5 mL) and ethyl acetate (10 mL) and neutralized with 1 N ammonium hydroxide solution until the aqueous layer become pale blue (approximately pH 8). The organic layer was separated, and the aqueous layer was further extracted with ethyl acetate (3×10 mL). The organic fractions were combined, washed with saturated aqueous sodium chloride solution (10 mL), dried over magnesium sulfate, filtered and concentrated. Flash chromatography of the residue on a silica gel column with 20-40% ethyl acetate/hexanes as the eluant provided 26 mg (8.3% yield) of E126D: LCMS (method 1; ESI, pos. ion spectrum) $t_R$=1.6 min, m/z 396.

Part E:

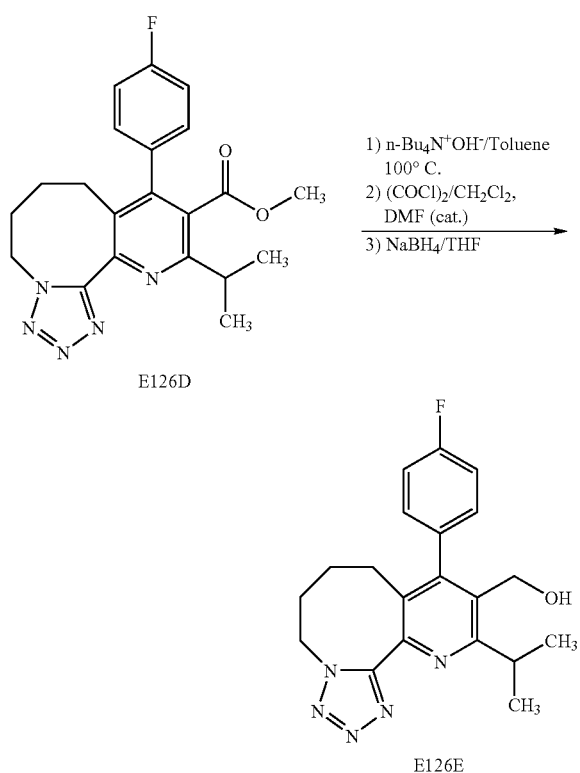

E126D (26 mg, 0.066 mmol) and tetrabutylammonium hydroxide solution (40% in water, 0.43 mL, 0.66 mmol) were coevaporated with toluene at 100° C. (3×10 mL). The reaction was diluted with water (3 mL), acidified with 1 N hydrochloric acid to approximately pH 4 and extracted with ethyl acetate (5×5 mL). The organic fractions were combined and washed with saturated aqueous sodium chloride solution (10 mL), dried over magnesium sulfate, filtered and concentrated. The residue was coevaporated with toluene (2×3 mL) and dissolved in dichloromethane (1 mL). A solution of oxalyl chloride (0.1 mL, 2.0 M, 0.2 mmol) in dichloromethane and a catalytic amount of dimethylformamide (0.005 mL) were added. The reaction was stirred for 30 min and concentrated in vacuo to remove the solvent and excess oxalyl chloride. The residue was dissolved in dry 1,2-dimethoxyethane (2 ml) and cooled to 0° C. Sodium borohydride in 1,2-dimethoxyethane (0.33 mL, 0.5 M, 0.17 mmol) was added. The reaction was stirred at 0° C. for 30 min. The reaction was quenched by the dropwise addition of water and the mixture was extracted with ethyl acetate (3×10 mL). The organic fractions were combined, washed with saturated aqueous sodium chloride solution (10 mL), dried over magnesium sulfate, filtered and concentrated to afford E126E (24 mg): LCMS (method 1; ESI, pos. ion spectrum) $t_R$=1.4 min, m/z 368.

Part F:

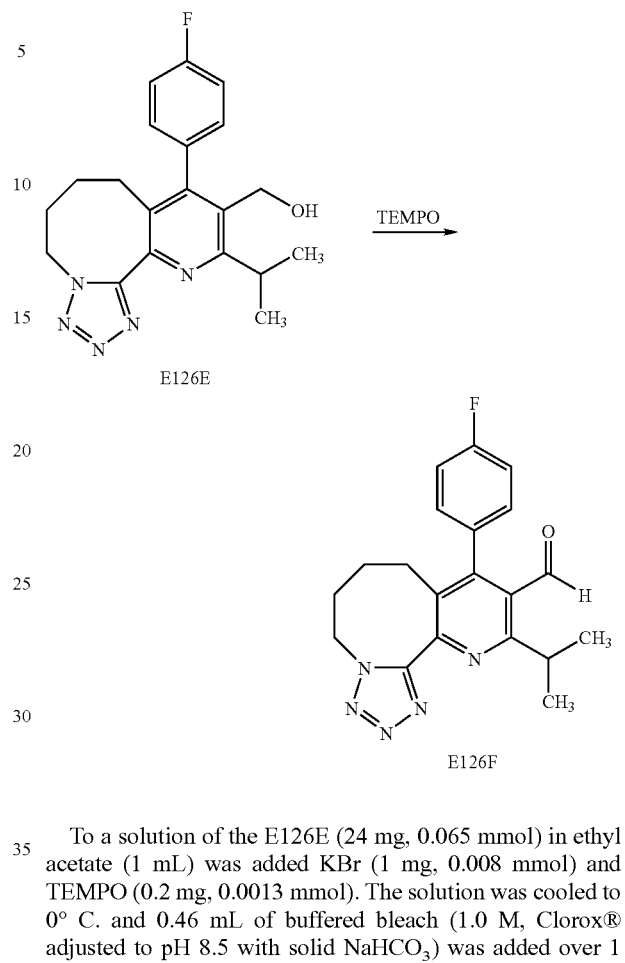

To a solution of the E126E (24 mg, 0.065 mmol) in ethyl acetate (1 mL) was added KBr (1 mg, 0.008 mmol) and TEMPO (0.2 mg, 0.0013 mmol). The solution was cooled to 0° C. and 0.46 mL of buffered bleach (1.0 M, Clorox® adjusted to pH 8.5 with solid $NaHCO_3$) was added over 1 minute. The reaction was stirred at 0° C. for 1 h and was quenched with 1 mL of aqueous $Na_2S_2O_3$. The reaction was diluted with ethyl acetate (10 mL) and the aqueous layer was separated. The organic layer was then washed successively with 2 mL of 1 N NaOH, 2 mL of water, and 2 mL of saturated aqueous sodium chloride solution; dried over magnesium sulfate; filtered; and concentrated to afford E126F as a white solid (23 mg, 97% yield): LCMS (method 1; ESI, pos. ion spectrum) $t_R$=1.6 min, m/z 366.

Part G:

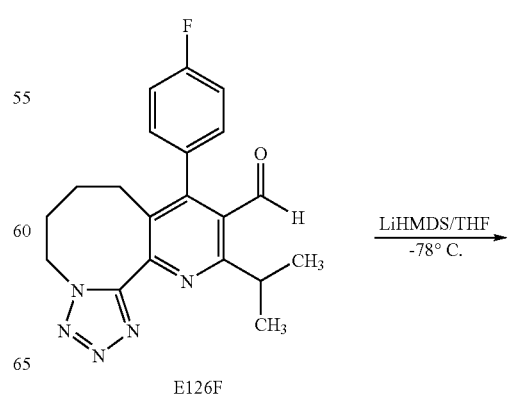

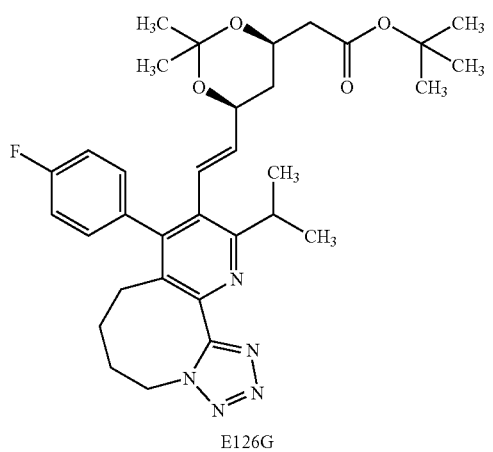

E126G

To a solution of E126F (23 mg, 0.063 mmol) and E1D (57 mg, 0.13 mmol) in THF (1.5 mL) at −78° C. was added LiHMDS (0.13 mL, 1.0 M in THF, 0.13 mmol) dropwise. After 30 min, the reaction was quenched at −78° C. by the addition of saturated aqueous ammonium chloride solution (2 mL) followed by the addition of ethyl acetate (10 mL). The aqueous layer was extracted with an additional 10 mL of ethyl acetate. The organic fractions were combined, washed with saturated aqueous sodium chloride solution (5 mL), dried with magnesium sulfate, filtered, and concentrated. Purification of the residue by flash chromatography on a silica gel column with 20-50% ethyl acetate/hexanes as the eluant provided 11 mg (30% yield) of E126G as a white foam: LCMS (method 1; ESI, pos. ion spectrum) $t_R$=2.1 min, m/z 592.

Part H:

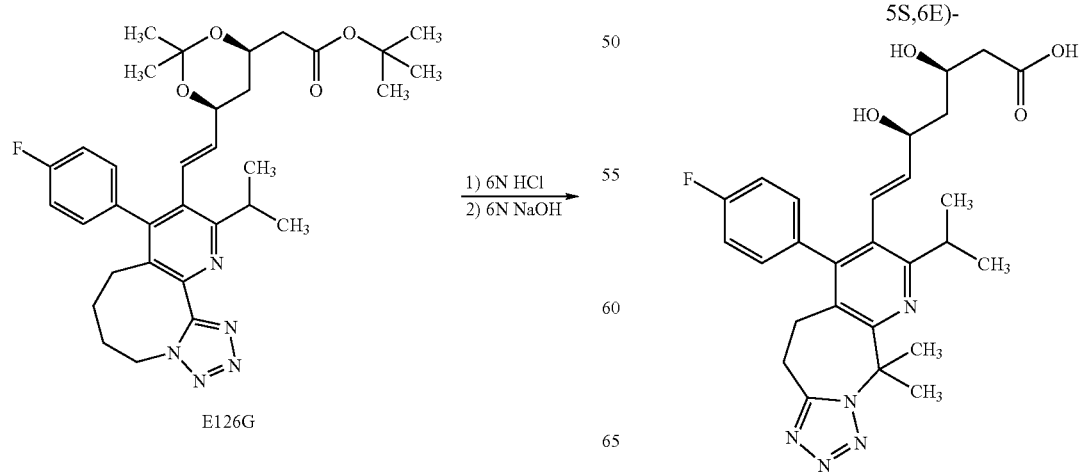

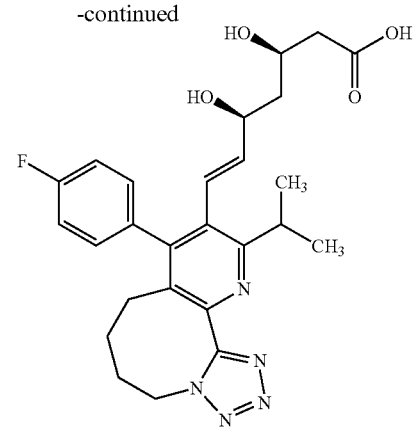

Ex. 126 title compound

To a stirred solution of compound E126G (11 mg, 0.019 mmol) in tetrahydrofuran (1 mL) was added aqueous HCl (0.01 mL, 6.0 N, 0.06 mmol). After 2 h, aqueous NaOH (0.019 mL, 6.0 N, 0.11 mmol) was added. After stirring for 3 h, the mixture was neutralized with aqueous HCl (1.0 N) to pH 8-9. The organic solvent was removed in vacuo to yield a thick pale-yellow slurry. This material was dissolved in 2 mL of water and loaded onto a 40 μm C-18 silica gel column (60 g, which was prewashed with 50 mL of MeOH and 50 mL of deionized water). The column was eluted consecutively with water (100 mL), 5% methanol in water (100 mL), 10% methanol in water (100 mL), 20% methanol in water (100 mL), 30% methanol in water (100 mL) and 40% methanol in water (100 mL). The product-containing fractions (fractions between 30-40% methanol in water) were combined and concentrated in vacuo to dryness. The residue was dissolved in methanol (3 mL) and filtered through a sintered funnel. The filtrate was concentrated to dryness, redissolved in 3 mL of water, and lyophilized to afford the title compound (5.6 mg, 57% yield) as a white solid: HPLC (method 2) $t_R$=3.1 min; LCMS (method 1; ESI, pos. ion spectrum) $t_R$=1.4 min, m/z 496.

Example 127

6-Heptenoic acid, 7-[9-(4-fluorophenyl)-10,11-dihydro-5,5-dimethyl-7-(1-methylethyl)-5H-pyrido[3,2-e]tetrazolo[1,5-a]azepin-8-yl]-3,5-dihydroxy-, (3R, 5S,6E)-

Part A:

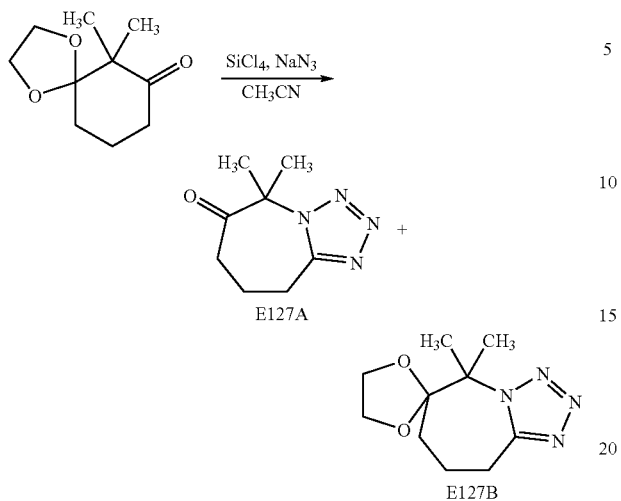

A solution of 6,6-dimethyl-1,4-dioxaspiro[4.5]decan-7-one (4.34 g, 23.6 mmol) in dry acetonitrile (20 mL) was added dropwise to a suspension of silicon tetrachloride (5.4 mL, 47.2 mmol) and sodium azide (9.19 g, 141 mmol) in dry acetonitrile (100 mL) over a 10 min period. The reaction was stirred at room temperature for 48 h. The reaction was quenched by pouring the mixture into ice (100 mL). The mixture was neutralized with saturated aqueous sodium bicarbonate solution to approximately pH 8. The slurry was filtered through a pad of Celite®. The filtrate was concentrated to remove the acetonitrile. The aqueous concentrate was extracted with dichloromethane (3×100 mL). The combined organic layers were dried over magnesium sulfate, filtered and concentrated to provide an off-white solid. This material was chromatographed on a silica gel column with 20-60% ethyl acetate in hexanes to afford 1.6 g of E127B and 426 mg of E127A (40% combined yield).

Part B:

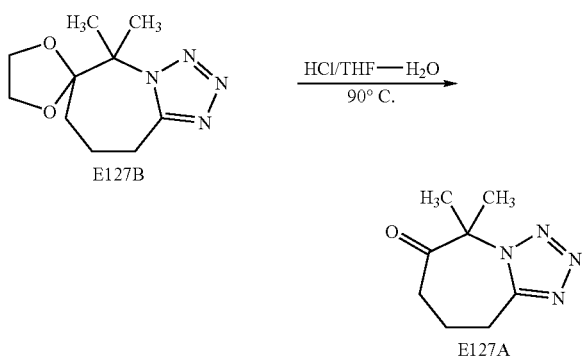

A tetrahydrofuran solution (5 mL) containing E127B (1.1 g, 4.9 mmol) and 8 N hydrochloric acid (5 mL) was heated to reflux under nitrogen for 6 h. The reaction was cooled to room temperature and extracted with ethyl acetate (3×10 mL). The combined organic layers were dried over magnesium sulfate, filtered and concentrated. The residue was chromatographed on a silica gel column with 20-60% ethyl acetate in hexanes to afford 617 mg E127A and 300 mg of E127B (97% combined yield): LCMS (method 1; ESI, pos. ion spectrum) $t_R$=0.7 min, m/z 181.

Part C:

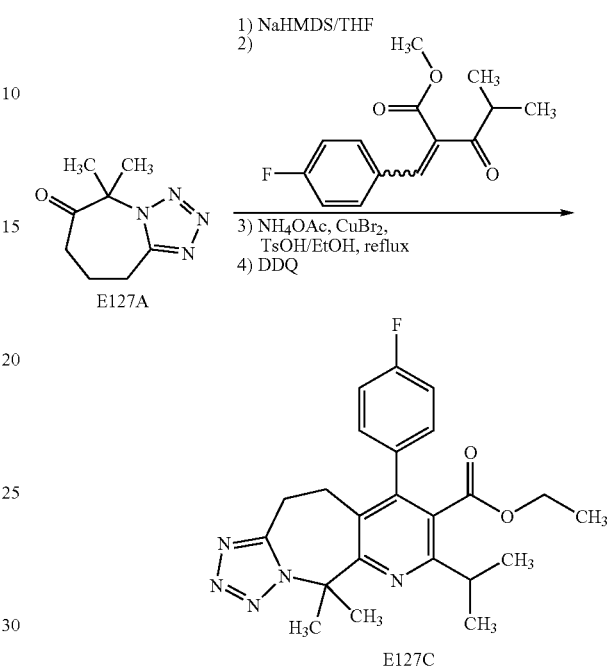

To a NaHMDS solution in THF (2.72 mL, 1.0 M, 2.72 mmol) was added 3 mL of dry THF. The mixture was cooled to −78° C. A solution of E127A (326 mg, 1.81 mmol) in 5 mL of dry THF was added dropwise over 5 min. After the addition, the mixture was stirred at −78° C. for 10 min. A solution of methyl 2-[(4-fluorophenyl)methylene]-4-methyl-3-oxo-pentanoate (1.36 g, 5.4 mmol) in 5 mL of dry THF which had been precooled to −78° C. was transferred quickly via a cannula. The reaction mixture was stirred at −78° C. for 6 h and was quenched with a solution of acetic acid (0.31 mL, 5.4 mmol) in 2 mL of THF. After warming to room temperature, the reaction was diluted with water (5 mL) and extracted with ethyl acetate (3×20 mL). The organic fractions were combined, washed with saturated aqueous sodium chloride solution (20 mL), dried over magnesium sulfate, filtered and concentrated. Flash chromatography of the residue on a silica gel column with 10-20% ethyl acetate/hexanes as the eluant provided 659 mg (85% yield) of a yellow oil. LCMS (method 1; ESI, pos. ion spectrum) $t_R$=1.8 min, m/z 431.

To a solution of the preceding yellow oil (659 mg, 1.53 mmol) in 15 mL of ethanol were added ammonium acetate (945 mg, 12.3 mmol), copper bromide (684 mg, 3.06 mmol), and p-toluenesulfonic acid monohydrate (15 mg, 0.08 mmol). The reaction was refluxed for 18 h and the solvent was evaporated in vacuo. The residue was suspended in 15 mL of dichloromethane and 2,3-dichloro-5,6-dicyano-1,4-benzoquinone (417 mg, 1.84 mmol) was added. After stirring for 18 h at room temperature, the solvent was evaporated in vacuo. The residue was suspended in water (15 mL) and ethyl acetate (50 mL) and neutralized with 1 N ammonium hydroxide solution until all the solids dissolved. The organic layer was separated, and the aqueous layer was further extracted with ethyl acetate (3×50 mL). The organic fractions were combined, washed with saturated aqueous sodium chloride solution (50 mL), dried over magnesium sulfate, filtered and concentrated. Flash chromatography of the residue on a silica gel column with 20-60% ethyl acetate/hexanes as the eluant provided 100 mg (16% yield) of E127C as a white solid: LCMS (method 1; ESI, pos. ion spectrum) $t_R$=2.0 min, m/z 424.

Part D:

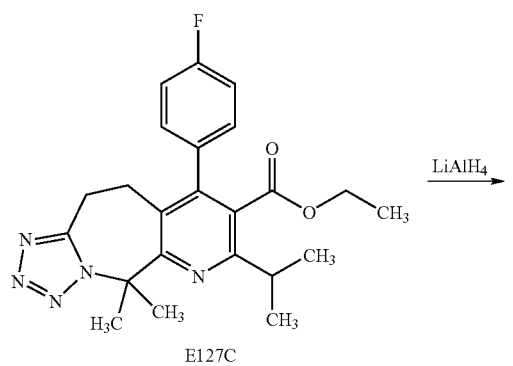

E127C

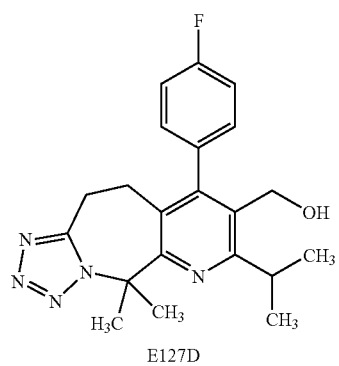

E127D

To a solution of E127C (95 mg, 0.23 mmol) in 5 mL of dry 1,2-dimethoxyethane was added lithium aluminum hydride (0.44 mL, 1.0 M in THF, 0.44 mmol). The mixture was heated to 80° C. under nitrogen for 3 h. The reaction was cooled to 0° C. and quenched by the careful addition of water (1 mL). The mixture was extracted with ethyl acetate (3×10 mL). The organic fractions were combined and washed with saturated aqueous sodium chloride solution (10 mL), dried over magnesium sulfate, filtered and concentrated to afford E127D (23 mg, 26% yield): LCMS (method 1; ESI, pos. ion spectrum) $t_R$=1.8 min, m/z 382.

Part E:

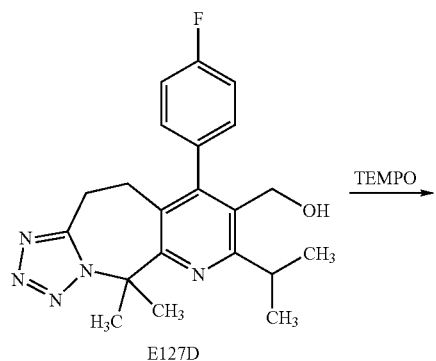

E127D

-continued

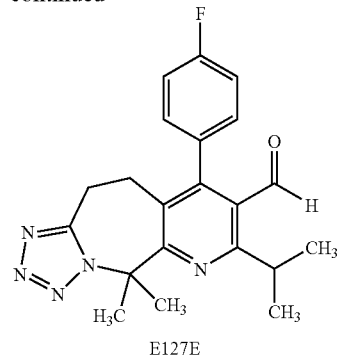

E127E

To a solution of E127D (23 mg, 0.06 mmol) in ethyl acetate (2 mL) was added KBr (2.4 mg, 0.02 mmol) and TEMPO (0.3 mg, 0.002 mmol). The solution was cooled to 0° C. and buffered bleach (1.0 mL, 1.0 M, Clorox® adjusted to pH 8.5 with solid NaHCO$_3$) was added. The reaction was stirred at 0° C. for 30 min and was quenched with 2 mL of Na$_2$S$_2$O$_3$ in water. The reaction was diluted with ethyl acetate (5 mL). The organic layer was then washed successively with 2 mL of 1 N NaOH, 3 mL of water, 3 mL of saturated aqueous sodium chloride solution; dried over magnesium sulfate; filtered and concentrated to afford E127E (20 mg, 88% yield) as a white solid: LCMS (method 1; ESI, pos. ion spectrum) $t_R$=1.9 min, m/z 380.

Part F:

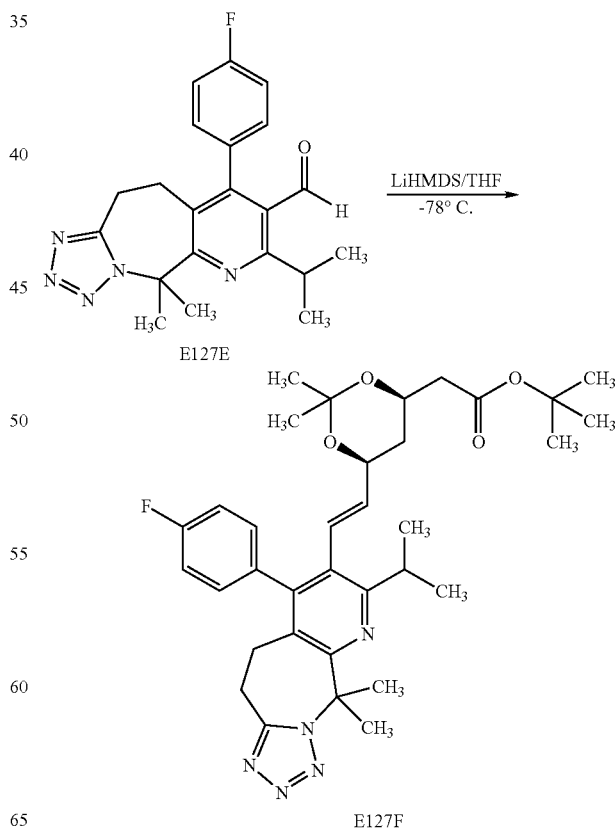

E127F

To a solution of E127E (20 mg, 0.053 mmol) and E1D (135 mg, 0.30 mmol) in THF (2 mL) at −78° C. was added LiHMDS (0.3 mL, 1.0 M in THF, 0.3 mmol) dropwise. After 1 h, the reaction was quenched at −78° C. by the addition of 1 mL of saturated aqueous ammonium chloride solution followed by the addition of ethyl acetate (10 mL). The aqueous layer was extracted with an additional 10 mL of ethyl acetate. The organic fractions were combined, washed with saturated aqueous sodium chloride solution (5 mL), dried with magnesium sulfate, filtered, and concentrated. Purification of the residue by flash chromatography on a silica gel column with 20-50% ethyl acetate/hexanes as the eluant provided 18.2 mg (56% yield) of E127F as a white foam: LCMS (method 1; ESI, pos. ion spectrum) $t_R$=2.2 min, m/z 606.

Part G:

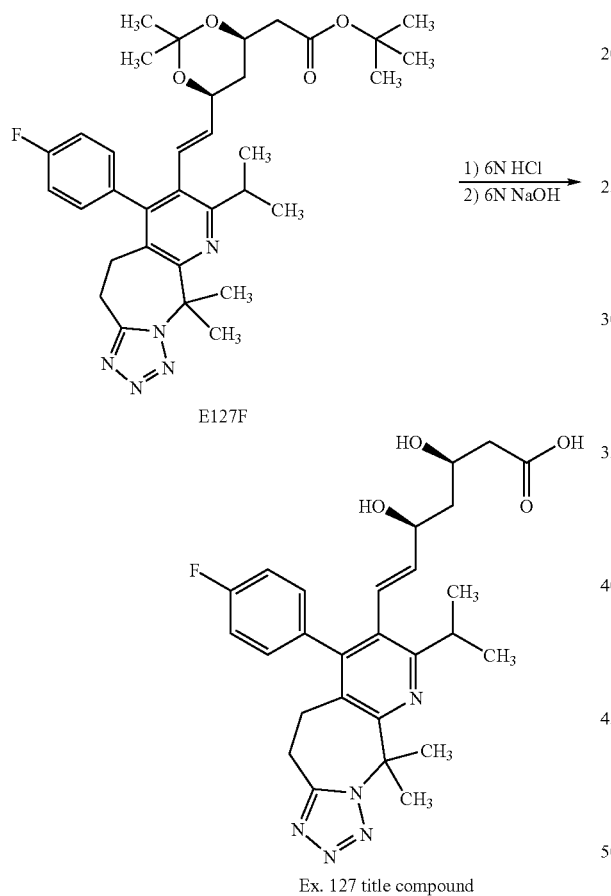

To a stirred solution of E127F (18.2 mg, 0.03 mmol) in tetrahydrofuran (0.5 mL) was added aqueous HCl (0.015 mL, 6.0 N, 0.09 mmol). After 2 h, aqueous NaOH (0.03 mL, 6.0 N, 0.18 mmol) was added. After stirring for 3 h, the mixture was neutralized with hydrochloric acid (1.0 N) solution to pH 8-9. The organic solvent was removed in vacuo to yield a thick pale-yellow slurry. This material was dissolved in 3 mL of water and loaded onto a 40 μm C-18 silica gel column (60 g, which was prewashed with 50 mL of MeOH and 50 mL of deionized water). The column was eluted consecutively with water (100 mL), 5% methanol in water (100 mL), 10% methanol in water (100 mL), 15% methanol in water (100 mL), 20% methanol in water (100 mL), 25% methanol in water (100 mL), 30% methanol in water (100 mL) and 40% methanol in water (100 mL). The product-containing fractions (fractions between 30-40% methanol in water) were combined and concentrated in vacuo to dryness. The residue was dissolved in methanol (3 mL) and filtered through a sintered funnel. The filtrate was concentrated to dryness. The residue was dissolved in 3 mL of water and lyophilized to afford the title compound as the sodium salt (11.8 mg, 76% yield) as a white solid: HPLC (method 3) $t_R$=3.7 min; LCMS (method 1; ESI, pos. ion spectrum) $t_R$=1.2 min, m/z 510.

Example 128

6-Heptenoic acid, 7-[8-(4-fluorophenyl)-6,7-dihydro-5,5-dimethyl-10-(1-methylethyl)-5H-pyrido[2,3-c]tetrazolo[1,5-a]azepin-9-yl]-3,5-dihydroxy-, (3R,5S,6E)-

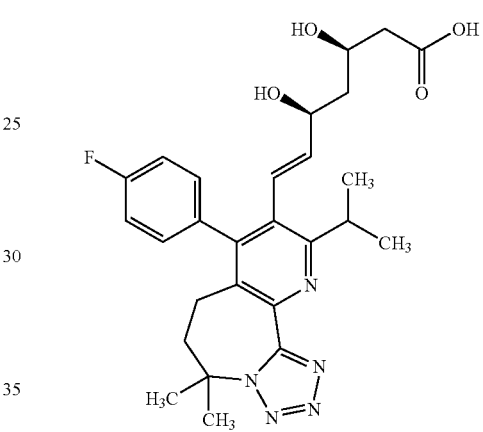

Part A:

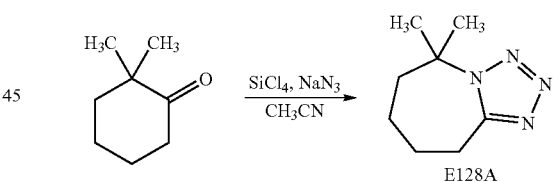

A solution of 2,2-dimethylcyclohexanone (5.0 g, 39.7 mmol) in dry acetonitrile (40 mL) was added dropwise to a suspension of silicon tetrachloride (10.2 mL, 89.2 mmol) and sodium azide (17.4 g, 268 mmol) in dry acetonitrile (120 mL). The reaction was stirred at room temperature for 7 days. The reaction was poured into ice (200 mL) and neutralized with saturated aqueous sodium bicarbonate solution to approximately pH 8. The slurry was filtered through a pad of Celite®. The filtrate was concentrated to remove the acetonitrile. The aqueous concentrate was extracted with dichloromethane (3×200 mL). The combined organic layers were dried over magnesium sulfate, filtered and concentrated to provide an off-white solid. This solid was chromatographed on a silica gel column with 20-60% ethyl acetate in hexanes to afford 2.90 g of E128A: LCMS (method 1; ESI, pos. ion spectrum) $t_R$=1.0 min, m/z 167.

Part B:

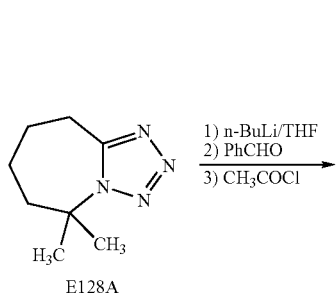

A solution of E128A (2.90 g, 17.5 mmol) in dry tetrahydrofuran (75 mL) was cooled to −78° C. A 2.5 M solution of n-BuLi in hexanes (7.2 mL, 18 mmol) was added dropwise over 10 min, and the resulting orange solution was stirred for 30 min. Freshly distilled benzaldehyde (2.13 mL, 21 mmol) was added dropwise over 2 min. The resulting colorless solution was stirred for additional 20 min at −78° C. Freshly distilled acetyl chloride (1.61 mL, 22.7 mmol) was added. The reaction was warmed to room temperature within 30 min, diluted with saturated aqueous ammonium chloride solution (50 mL) and extracted with ethyl acetate (3×100 mL). The organic fractions were combined, washed with saturated aqueous sodium chloride solution (100 mL), dried over magnesium sulfate, filtered and concentrated to provide an off white solid. Chromatography of the residue on a silica gel column with 20% ethyl acetate in hexanes afforded 4.39 g of E128B (80% yield): LCMS (method 1; ESI, pos. ion spectrum) $t_R$=1.5 min, m/z 315.

Part C:

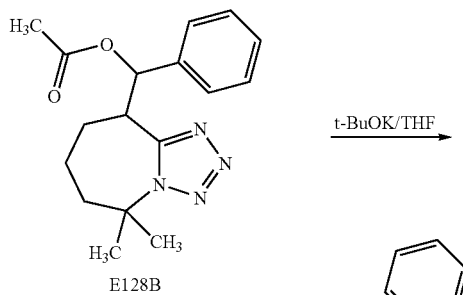

To a solution of E128B (4.05 g, 12.9 mmol) in dry tetrahydrofuran (100 mL) at 0° C. was added potassium tert-butoxide in THF (14.2 mL, 14.2 mmol) over 30 min. The reaction was stirred at room temperature for 30 min. The resulting yellowish solution was quenched with saturated aqueous ammonium chloride solution (40 mL) and extracted with ethyl acetate (3×100 mL). The organic fractions were combined, washed with saturated aqueous sodium chloride solution (100 mL), dried over magnesium sulfate, filtered and concentrated. Chromatography of the residue on a silica gel column with 20% ethyl acetate in hexanes afforded 2.45 g of E128C (75% yield) as a white solid: LCMS (method 1; ESI, pos. ion spectrum) $t_R$=1.6 min, m/z 255.

Part D:

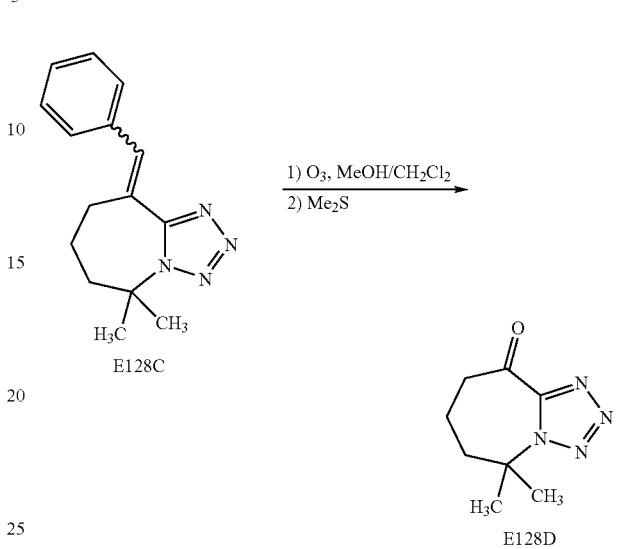

A solution of E128C (2.45 g, 9.65 mmol) in methanol (50 mL) and methylene chloride (50 mL) was cooled −78° C. Ozone was passed through the mixture until the blue-purple color persisted. Nitrogen was then passed through the reaction mixture to remove the excess ozone. Dimethyl sulfide (2 ml) was added and the reaction was warmed to room temperature and stirred overnight. The mixture was concentrated and the residue was chromatographed on a silica gel column with 20-70% ethyl acetate/hexanes as the eluant to afford 1.51 g (87% yield) of E128D as a white solid: LCMS (method 1; ESI, pos. ion spectrum) $t_R$=0.89 min, m/z 181.

Part E:

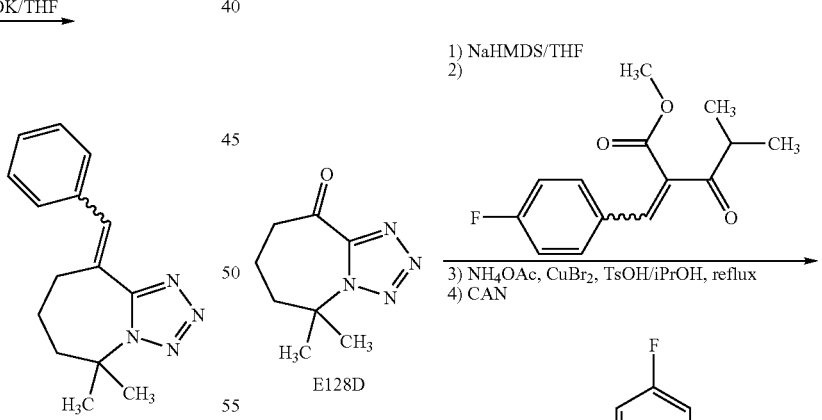

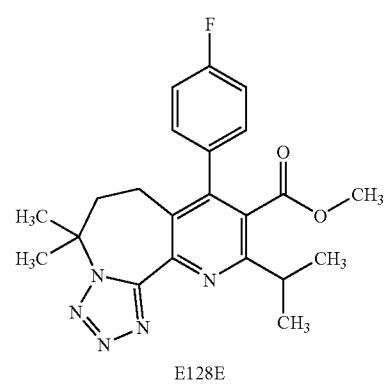

Preparation of E128E. To a NaHMDS solution in THF (10.1 mL, 1.0 M, 10.1 mmol) was added 8 mL of dry THF. The mixture was cooled to −78° C. A solution of E128D (1.51 g, 8.39 mmol) in 10 mL of dry THF was added dropwise over 5 min. After the addition, the mixture was stirred at −78° C. for 30 min. A solution of methyl 2-[(4-fluorophenyl)methylene]-4-methyl-3-oxo-pentanoate (6.29 g, 25.2 mmol) in 10 mL of dry THF which had been precooled to −78° C. was quickly transferred via a cannula. The reaction mixture was stirred at −78° C. for 3 h and was quenched with a solution of acetic acid (1.5 mL, 26.2 mmol) in 3 mL of THF. After warming to room temperature, the reaction was diluted with water (10 mL) and extracted with ethyl acetate (3×20 mL). The organic fractions were combined, washed with saturated aqueous sodium chloride solution (20 mL), dried over magnesium sulfate, filtered and concentrated. Flash chromatography of the residue on a silica gel column with 10-40% ethyl acetate/hexanes as the eluant provided 1.89 g (53% yield) of a yellow oil: LCMS (method 1; ESI, pos. ion spectrum) $t_R$=1.7 min, m/z 431.

To a solution of the preceding yellow oil (1.89 g, 4.39 mmol) in 15 mL of isopropanol were added ammonium acetate (2.70 g, 35.1 mmol), copper bromide (2.05 g, 9.2 mmol), and p-toluenesulfonic acid monohydrate (42 mg, 0.22 mmol). The reaction was heated at 80° C. for 3 h and the solvent was evaporated in vacuo. The residue was suspended in 50 mL of tetrahydrofuran. An aqueous ammonium cesium (IV) nitrate solution (12 g, 22 mmol in 25 mL of water) was added. After stirring for 20 min at room temperature, the reaction was extracted with ethyl acetate (3×50 mL). The organic fractions were combined, washed with saturated aqueous sodium chloride solution (50 mL), dried over magnesium sulfate, filtered and concentrated. Flash chromatography of the residue on a silica gel column with 20-60% ethyl acetate/hexanes as the eluant provided 490 mg (27% yield) of E128E: LCMS (method 1; ESI, pos. ion spectrum) $t_R$=1.8 min, m/z 410.

Part F:

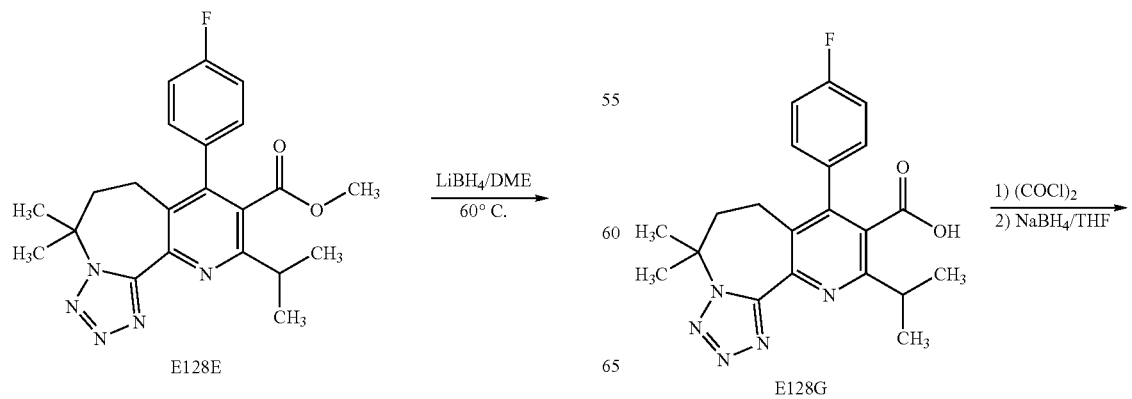

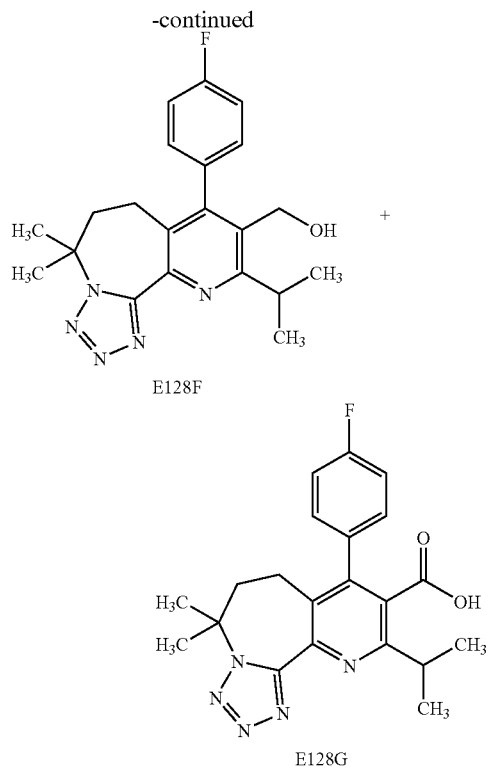

To a solution of E128E (490 mg, 1.2 mmol) in 30 mL of dry 1,2-dimethoxyethane was added lithium borohydride (215 mg, 95%, 7.3 mmol) in three portions. The mixture was heated to 80° C. under nitrogen for 26 h. The reaction was cooled to 0° C. and quenched by the careful addition of water (10 mL). The mixture was extracted with ethyl acetate (2×20 mL). The organic fractions were combined and washed with 1 N sodium hydroxide solution and saturated aqueous sodium chloride solution (10 mL), dried over magnesium sulfate, filtered and concentrated to afford E128F.

The aqueous fraction was neutralized to pH 3-5 with 1 N HCl solution, saturated with solid sodium chloride and extracted with ethyl acetate (4×30 mL). The organic fractions were combined, dried over magnesium sulfate, filtered and concentrated to afford the 117 mg of E128G: LCMS (method 1; ESI, pos. ion spectrum) $t_R$=1.6 min, m/z 396.

Part G:

-continued

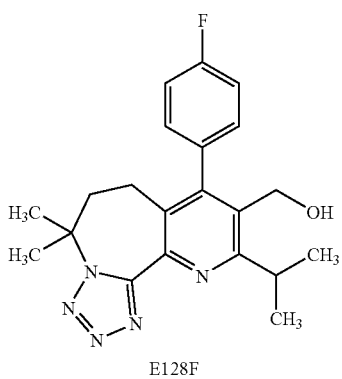

E128F

To a solution of E128G (117 mg, 0.30 mmol) in 3 mL of dry dichloromethane at 0° C. were added a solution of oxalyl chloride (0.37 mL, 2.0 M in dichloromethane, 0.74 mmol) in dichloromethane and a catalytic amount of DMF (0.005 mL). The mixture was warmed to room temperature, stirred for 1 h and concentrated to dryness on a rotary evaporator. The residue was dissolved in dry 1,2-dimethoxyethane (2 mL) and cooled to 0° C. Sodium borohydride (0.65 mL, 0.5 M in 1,2-dimethoxyethane was added. The reaction was stirred at 0° C. for 20 min, quenched by dropwise addition of water and extracted with ethyl acetate (3×10 mL). The organic fractions were combined, washed with saturated aqueous sodium chloride solution (10 mL), dried over magnesium sulfate, filtered and concentrated. The combined residue from this step and that from Example 128 Part F was purified on a silica gel column with 30-50% ethyl acetate/hexanes as the eluant to afford 140 mg of E128F as a white solid: LCMS (method 1; ESI, pos. ion spectrum) $t_R$=1.6 min, m/z 382.

Part H:

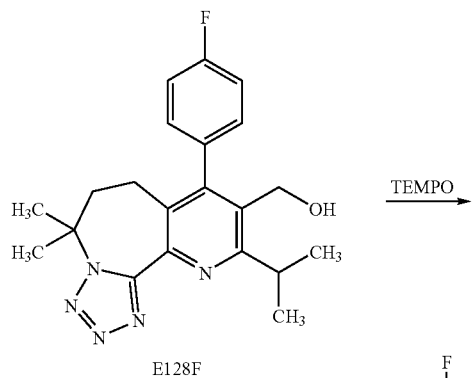

To a solution of E128F (140 mg, 0.37 mmol) in ethyl acetate (5 mL) was added KBr (4 mg, 0.04 mmol) and TEMPO (4 mg, 0.02 mmol). The solution was cooled to 0° C. and buffered bleach (1.56 mL, 1.0 M, Clorox® adjusted to pH 8.5 with solid NaHCO$_3$) was added. The reaction was stirred at 0° C. for 30 min and was quenched with 2 mL of aqueous Na$_2$S$_2$O$_3$. The reaction was diluted with ethyl acetate (5 mL). The organic layer was washed successively with 2 mL of 1 N NaOH, 3 mL of water, and 3 mL of saturated aqueous sodium chloride solution; dried over magnesium sulfate; filtered and concentrated to afford E128H (90 mg, 64% yield) as a white solid: LCMS (method 1; ESI, pos. ion spectrum) $t_R$=1.8 min, m/z 380.

Part I:

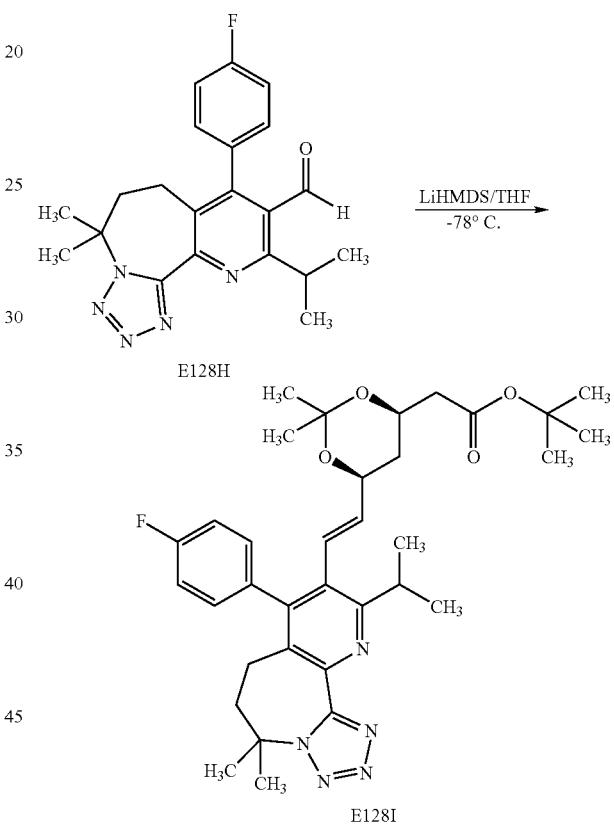

To a solution of E128H (90 mg, 0.24 mmol) and E1D (161 mg, 0.36 mmol) in THF (5 mL) at −78° C. was added LiHMDS (0.36 mL, 1.0 M in THF, 0.36 mmol) dropwise. After 1 h, the reaction was quenched at −78° C. by the addition of 1 mL of saturated aqueous ammonium chloride followed by the addition of ethyl acetate (10 mL). The aqueous layer was extracted with an additional 10 mL of ethyl acetate. The organic fractions were combined, washed with saturated aqueous sodium chloride solution (5 mL), dried with magnesium sulfate, filtered, and concentrated. Purification of the residue by flash chromatography on a silica gel column with dichloromethane/ethyl acetate/hexanes (5:1:4) as the eluant provided 117 mg (81% yield) of E128I as a white foam: LCMS (method 1; ESI, pos. ion spectrum) $t_R$=2.1 min, m/z 606.

Part J:

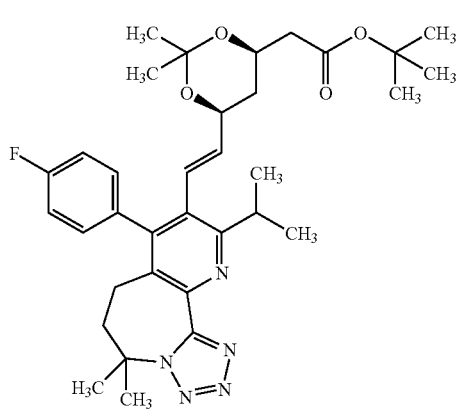

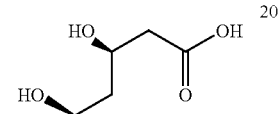

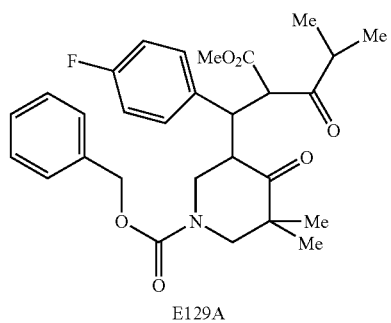

Ex. 128 title compound

To a stirred solution of E128I (117 mg, 0.19 mmol) in tetrahydrofuran (1 mL) was added aqueous HCl (0.097 mL, 6.0 N, 0.58 mmol). After 40 min, aqueous NaOH (0.19 mL, 6.0 N, 1.14 mmol) was added. After stirring for 30 min, methanol (1 mL) was added in to make a homogeneous solution. After stirring for additional 5 min, the organic solvent was removed in vacuo to yield a thick pale-yellow slurry. This material was dissolved in 10 mL of water, and loaded onto a 40 μm C-18 silica gel column (60 g, which was prewashed with 50 mL of MeOH and 50 mL of deionized water). The column was eluted consecutively with water (100 mL), 5% methanol in water (100 mL), 10% methanol in water (100 mL), 15% methanol in water (100 mL), 20% methanol in water (100 mL), 25% methanol in water (100 mL), 30% methanol in water (100 mL), and 50% methanol in water (100 mL). The product-containing fractions (fractions between 15-25% methanol in water) were combined and concentrated in vacuo to dryness. The residue was dissolved in methanol (5 mL) and filtered through a sintered funnel. The filtrate was concentrated to dryness. The residue was redissolved in 10 mL of water and lyophilized to afford the title compound as the sodium salt (65.1 mg, 65% yield) as a white solid: HPLC (method 3) $t_R$=3.4 min; LCMS (method 1; ESI, pos. ion spectrum) $t_R$=1.6 min, m/z 510.

Example 129

6-Heptenoic acid, 7-[6-acetyl-4-(4-fluorophenyl)-5,6,7,8-tetrahydro-8,8-dimethyl-2-(1-methylethyl)-1,6-naphthyridin-3-yl]-3,5-dihydroxy-, (3R,5S,6E)-

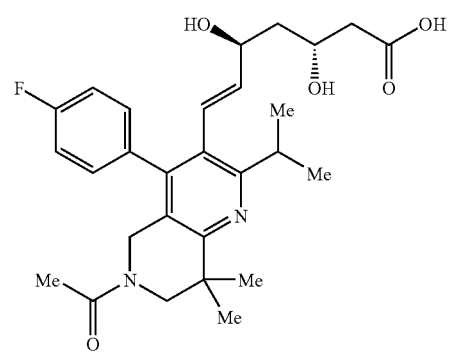

Part A:

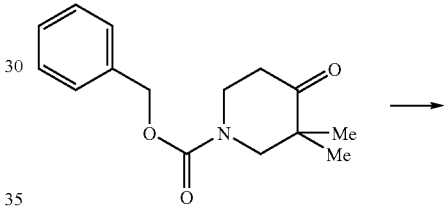

Phenylmethyl 3,3-dimethyl-4-oxo-1-piperidinecarboxylate, (7.0 g, 27 mmol) in THF (91 mL) was added over 45 min to a stirred −78° C. solution of sodium (bis)trimethylsilylamide (1.0 M in THF, 34 mL, 34 mmol) in THF (91 mL). After 30 min, methyl 2-[(4-fluorophenyl)methylene]-4-methyl-3-oxo-pentanoate (8.4 g, 7.6 mL, 34 mmol) in THF (91 mL) was added over 25 min. After 2 h, the reaction was quenched with glacial acetic acid (1.5 mL). The reaction mixture was warmed to room temperature, diluted with ethyl acetate, washed with saturated ammonium chloride solution and brine, dried over MgSO₄ and concentrated to afford E129A (17 g).

Part B:

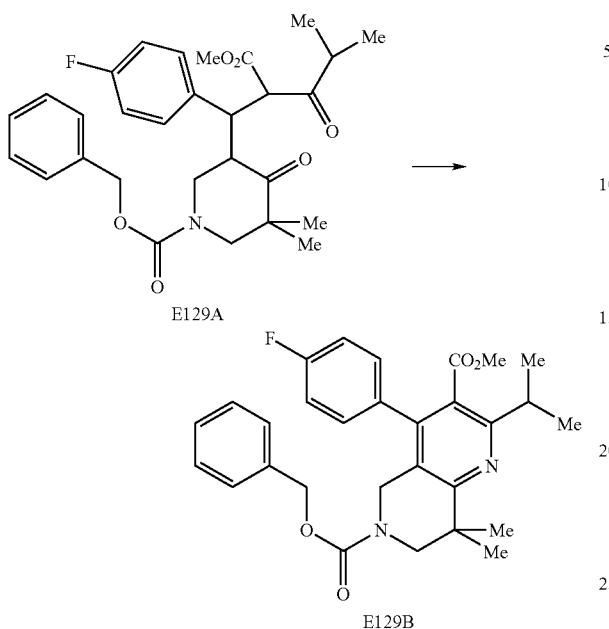

A mixture of E129A from the preceding step (17 g), ammonium acetate (16 g, 200 mmol), and copper (II) bromide (15 g, 68 mmol) in ethanol (170 mL) was stirred at 80° C. overnight. The reaction was then evaporated in vacuo. Ether was added to the residue and the resulting mixture was filtered through Celite®. The filtrate was washed with water, saturated sodium bicarbonate, water, and brine; dried over $MgSO_4$; and concentrated. Purification of the residue over silica gel afforded E129B (4.4 g, 33% yield): HPLC (method 5) $t_R$=2.7 min; LCMS (ESI, pos. ion spectrum) m/z 491 (M+H).

Part C:

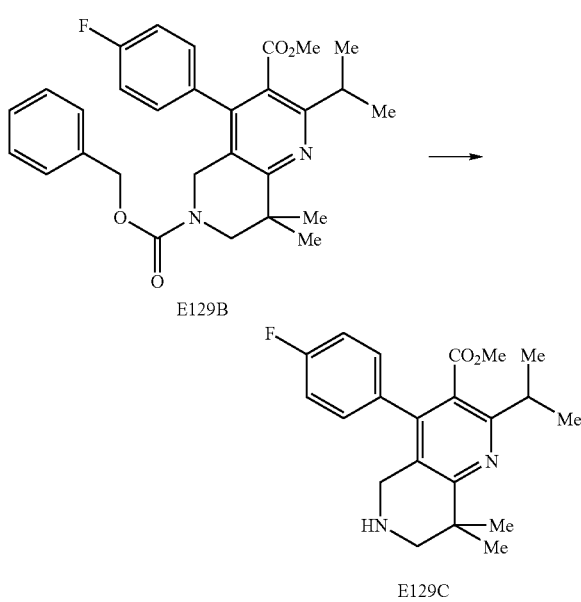

Palladium on carbon (10%, 4.5 g) was added to a solution of E129B (4.4 g, 9.0 mmol) and 1,4-cyclohexadiene (6.7 g, 8.5 mL, 90 mmol) in ethanol (36 mL). A strong exotherm ensued and some gas evolution occurred. The reaction was stirred at ambient temperature under nitrogen for 75 min and then was filtered through Celite® The solids were rinsed with methanol and the combined filtrates were evaporated to afford E129C (3.0 g, 95%): HPLC (method 5) $t_R$=2.0 min; LCMS (ESI, pos. ion spectrum) m/z 357 (M+H).

Part D:

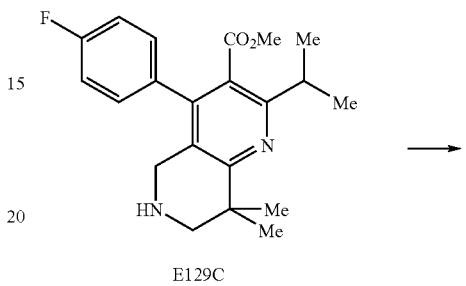

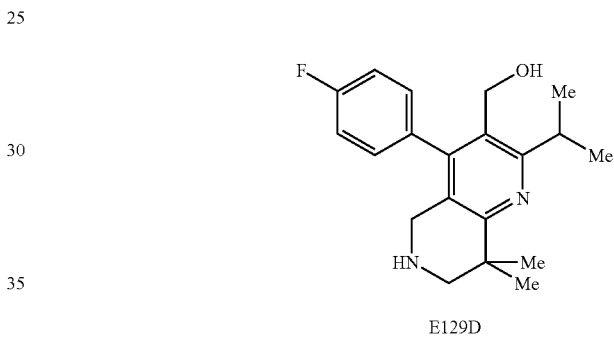

Diisobutylaluminum hydride (1.0 M in methylene chloride, 54 mL, 54 mmol) was added over 1.5 h to E129C (3.0 g, 8.6 mmol) at −78° C. After an additional 25 min, the reaction was quenched with a few drops of methanol. A saturated solution of Rochelle's salt (11 mL) and water (250 mL) were added to the reaction and the mixture was stirred vigorously for 2 h. The mixture was extracted with methylene chloride. The organic phase was dried over $MgSO_4$ and concentrated to afford E129D (95% pure by HPLC, 2.7 g, 96% yield): HPLC (method 5) $t_R$=1.8 min; LCMS (ESI, pos. ion spectrum) m/z 329 (M+H).

Part E:

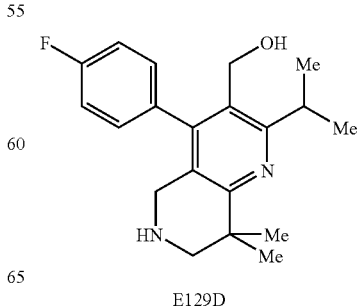

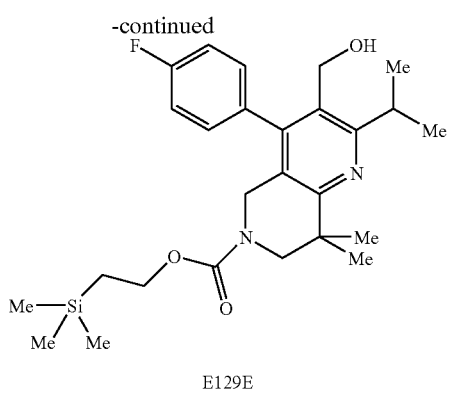

E129E 2-(Trimethylsilyl)ethyl 4-nitrophenyl carbonate (8.2 g, 24 mmol) was added to a stirred 0° C. solution of E129D (7.6 g, 20 mmol) and diisopropylethylamine (3.1 g, 4.1 mL, 24 mmol) in THF (62 mL). After 5 h, additional 2-(trimethylsilyl)ethyl p-nitrophenyl carbonate (2.0 g, 5.8 mmol) and diisopropylethylamine (1 mL, 5.8 mmol) were added. After 3 days, the reaction mixture was transferred to a separatory funnel with water and was extracted with methylene chloride. The organic layer was dried over MgSO₄ and concentrated to afford 19 g of residue. Purification of the residue over silica gel afforded E129E (9.2 g, 98%): HPLC (method 5) $t_R$=2.7 min; LCMS (ESI, pos. ion spectrum) m/z 473 (M+H).

Part F:

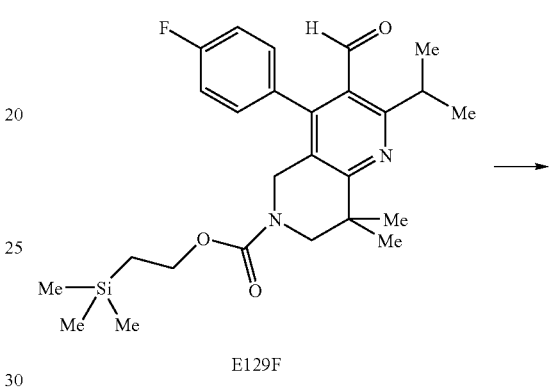

E129E

E129F

Dess-Martin periodinane (11 g, 23 mmol) was added to a solution of E129E (9.2 g, 19 mmol) in water-saturated methylene chloride (80 mL). After 40 min, the reaction was diluted with ether. A solution of sodium thiosulfate (8 g) dissolved in saturated NaHCO₃ (14 mL) and water (7 mL) were added and the mixture was stirred vigorously for 40 min. The mixture was extracted with ether. The combined organic layers were washed with saturated NaHCO₃, water, and brine; dried over MgSO₄ and concentrated to afford 13 g of residue. Purification of the residue over silica gel afforded E129F (7.8 g, 85%): HPLC (method 5) $t_R$=2.8 min; LCMS (ESI, pos. ion spectrum) m/z 471 (M+H).

Part G:

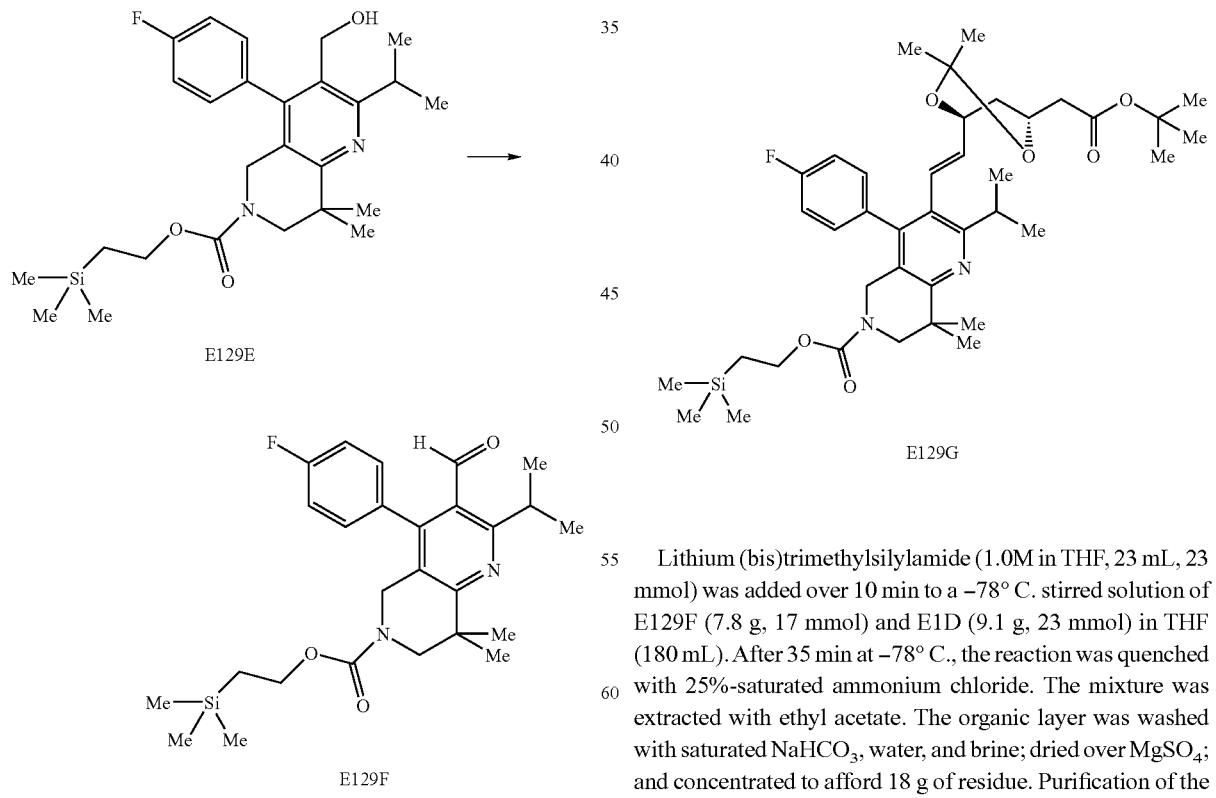

E129F

E129G

Lithium (bis)trimethylsilylamide (1.0M in THF, 23 mL, 23 mmol) was added over 10 min to a −78° C. stirred solution of E129F (7.8 g, 17 mmol) and E1D (9.1 g, 23 mmol) in THF (180 mL). After 35 min at −78° C., the reaction was quenched with 25%-saturated ammonium chloride. The mixture was extracted with ethyl acetate. The organic layer was washed with saturated NaHCO₃, water, and brine; dried over MgSO₄; and concentrated to afford 18 g of residue. Purification of the residue over silica gel afforded E129G (8.5 g, 74%): HPLC (method 5) $t_R$=3.7 min; LCMS (ESI, pos. ion spectrum) m/z 697 (M+H).

Part H:

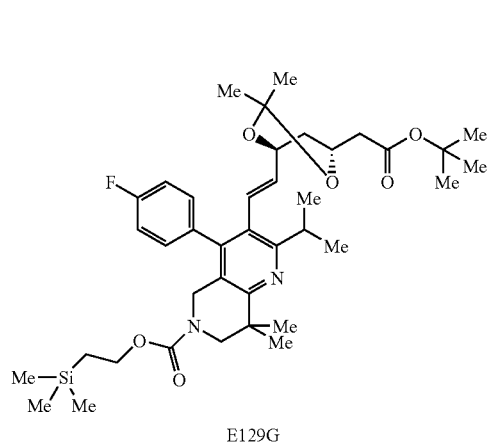

E129G

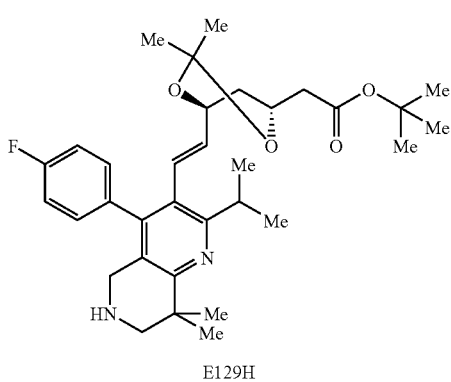

E129H

Tetrabutylammonium fluoride (1.0 M in THF, 120 mL) was added to a solution of E129G (8.5 g, 12 mmol) in THF (120 mL). After stirring at ambient temperature for 30 min, the reaction was quenched with water. The mixture was extracted with ethyl acetate. The combined organic layers were washed with water and brine dried over $MgSO_4$ and concentrated to afford 9.3 g of residue. Purification of the residue over silica gel afforded E129H (6.2 g, 92%) HPLC (method 5) $t_R$=2.4 min; LCMS (ESI, pos. ion spectrum) m/z 553 (M+H).

Part I:

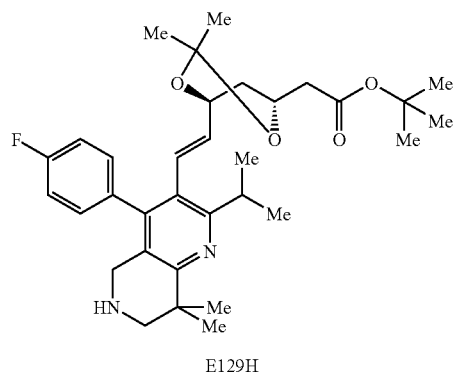

E129H

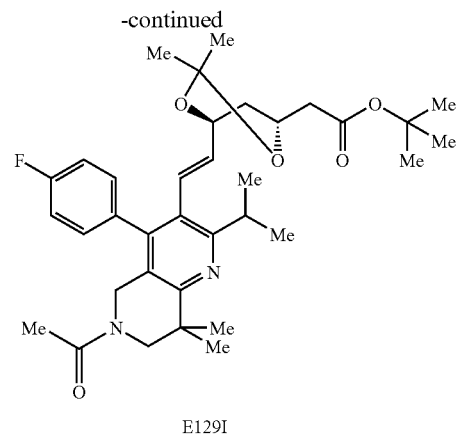

E129I

Acetyl chloride (31 mg, 0.028 mL, 0.39 mmol) and diisopropylethylamine (66 mg, 0.089 mL, 0.51 mmol) were sequentially added to a solution of E129H (140 mg, 0.25 mmol) in methylene chloride (2.5 mL). After stirring at ambient temperature for 1 h, the reaction was transferred to a separatory funnel with methylene chloride and water. The layers were separated and the aqueous phase was extracted with methylene chloride. The combined organic layers were dried over $MgSO_4$ and concentrated to afford 160 mg of residue. Purification of the residue over silica gel afforded E129I (142 mg, 96%): HPLC (method 5) $t_R$=2.7 min; LCMS (ESI, pos. ion spectrum) m/z 595 (M+H).

Part J:

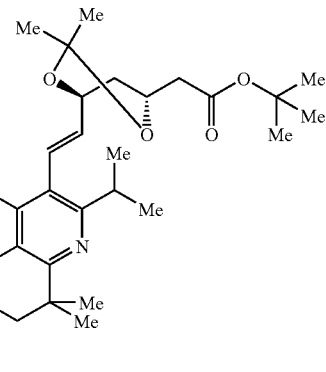

E129I

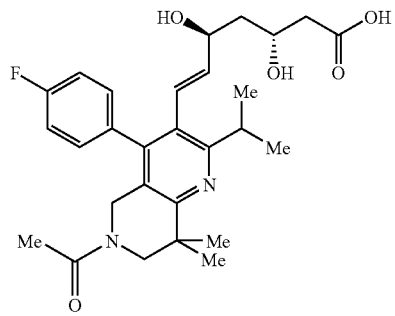

Ex. 129 title compound

A solution of E129I (142 mg, 0.23 mmol) and aqueous hydrochloric acid (6 N, 0.10 mL, 0.66 mmol) in THF (1 mL)

was stirred at ambient temperature for 75 min. Aqueous sodium hydroxide (1 N, 0.98 mL, 0.98 mmol) was then added and the resultant mixture was stirred vigorously for 2 h. The reaction mixture was evaporated in vacuo. The residue was purified over C-18 silica gel to afford the title compound as the sodium salt (90 mg, 75%): HPLC (method 5) $t_R$=2.0 min; LCMS (ESI, pos. ion spectrum) m/z 499 (M+H).

Example 130

6-Heptenoic acid, 7-[4-(4-fluorophenyl)-5,6,7,8-tetrahydro-8,8-dimethyl-2-(1-methylethyl)-6-(methylsulfonyl)-1,6-naphthyridin-3-yl]-3,5-dihydroxy-, (3R,5S,6E)-

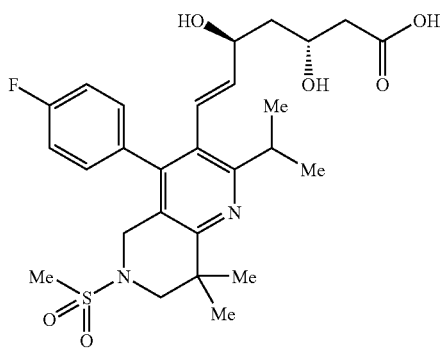

Part A:

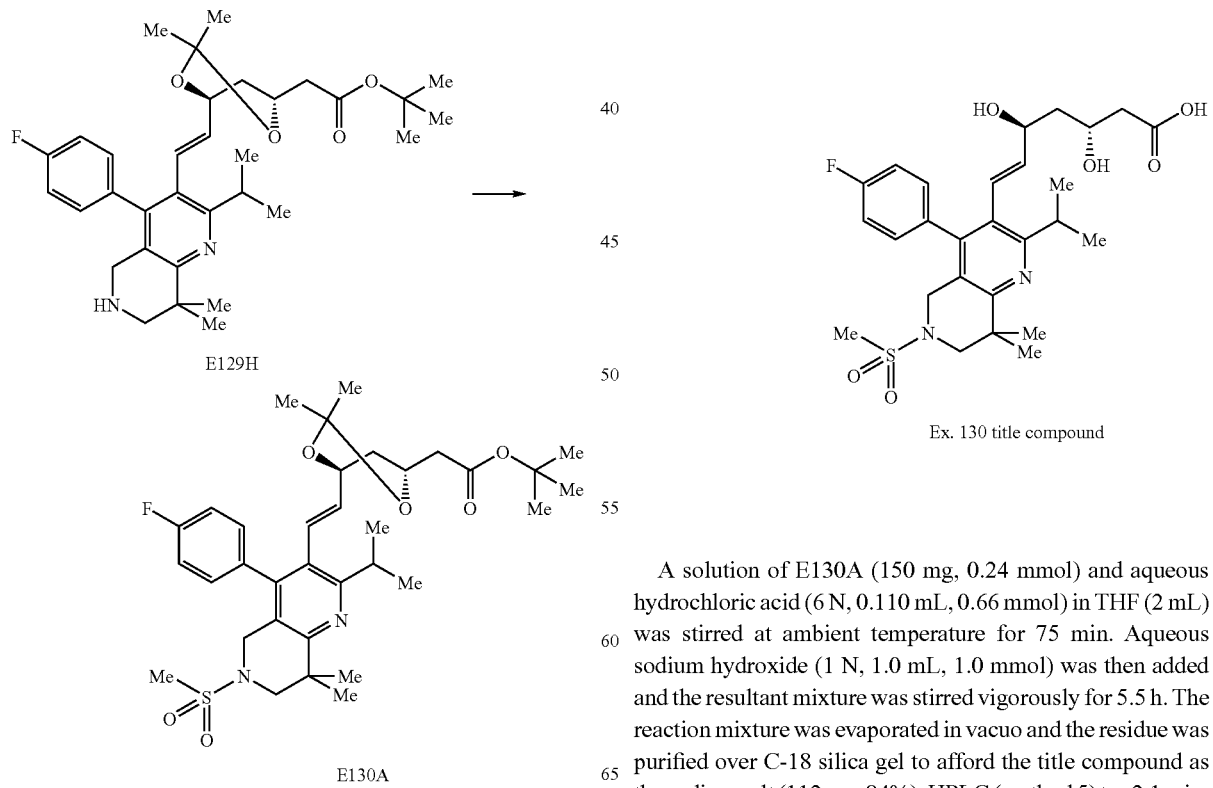

Methanesulfonyl chloride (88 mg, 0.059 mL, 0.75 mmol) and then pyridine (73 mg, 0.073 mL, 0.92 mmol) were added to a solution of E129H (140 mg, 0.25 mmol) in methylene chloride (2.5 mL). After 2.5 h, the reaction was transferred to a separatory funnel with methylene chloride and water. The aqueous layer was extracted with methylene chloride. The combined organic layers were washed with water, dried over MgSO$_4$ and concentrated to afford 232 mg of a residue. Purification of the residue over silica gel afforded E130A (150 mg, 95%): HPLC (method 5) $t_R$=2.7 min; LCMS (ESI, pos. ion spectrum) m/z 631 (M+H).

Part B:

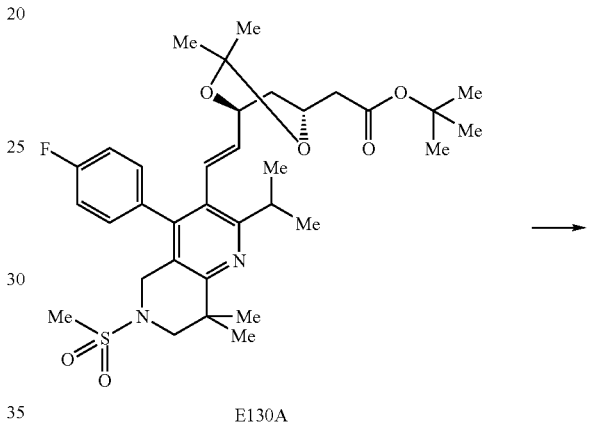

E130A

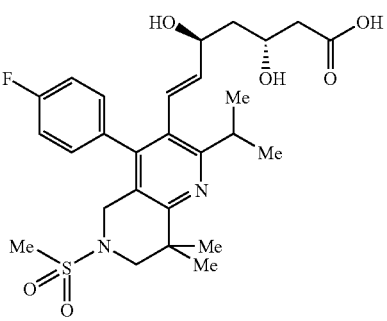

Ex. 130 title compound

A solution of E130A (150 mg, 0.24 mmol) and aqueous hydrochloric acid (6 N, 0.110 mL, 0.66 mmol) in THF (2 mL) was stirred at ambient temperature for 75 min. Aqueous sodium hydroxide (1 N, 1.0 mL, 1.0 mmol) was then added and the resultant mixture was stirred vigorously for 5.5 h. The reaction mixture was evaporated in vacuo and the residue was purified over C-18 silica gel to afford the title compound as the sodium salt (112 mg, 84%): HPLC (method 5) $t_R$=2.1 min; LCMS (ESI, pos. ion spectrum) m/z 535 (M+H).

Example 131

6-Heptenoic acid, 7-[4-(4-fluorophenyl)-5,6,7,8-tetrahydro-6-(hydroxyacetyl)-8,8-dimethyl-2-(1-methylethyl)-1,6-naphthyridin-3-yl]-3,5-dihydroxy-, (3R,5S,6E)-

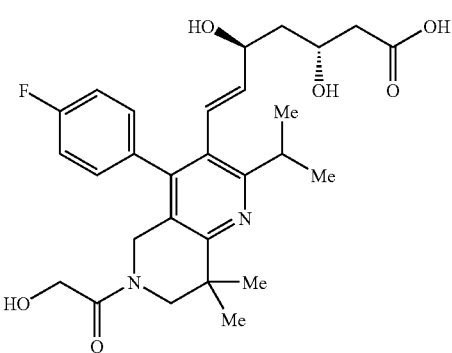

Part A:

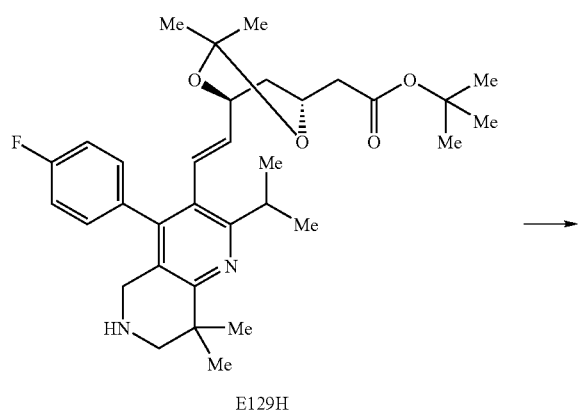

E129H

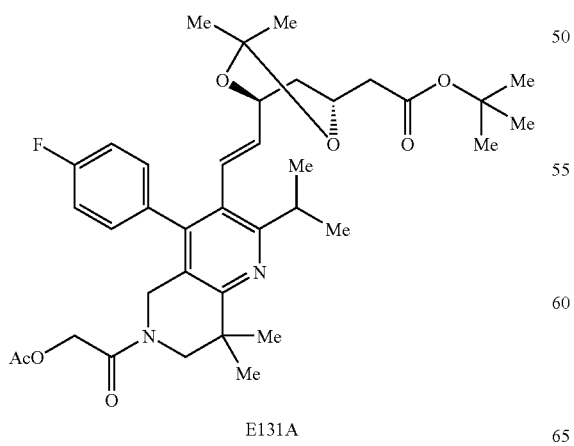

E131A

Acetoxyacetyl chloride (53 mg, 0.042 mL, 0.39 mmol) and then diisopropylethylamine (66 mg, 0.089 mL, 0.51 mmol) were added to a solution of E129H (140 mg, 0.25 mmol) in methylene chloride (2.5 mL). After 1 h, the reaction was transferred to a separatory funnel with methylene chloride and water. The aqueous layer was extracted with methylene chloride. The combined organic layers were dried over MgSO$_4$ and concentrated to afford 186 mg of residue. Purification of the residue over silica gel afforded 167 mg (99%) of E131A: HPLC (method 5) $t_R$=2.7 min; LCMS (ESI, pos. ion spectrum) m/z 653 (M+H).

Part B:

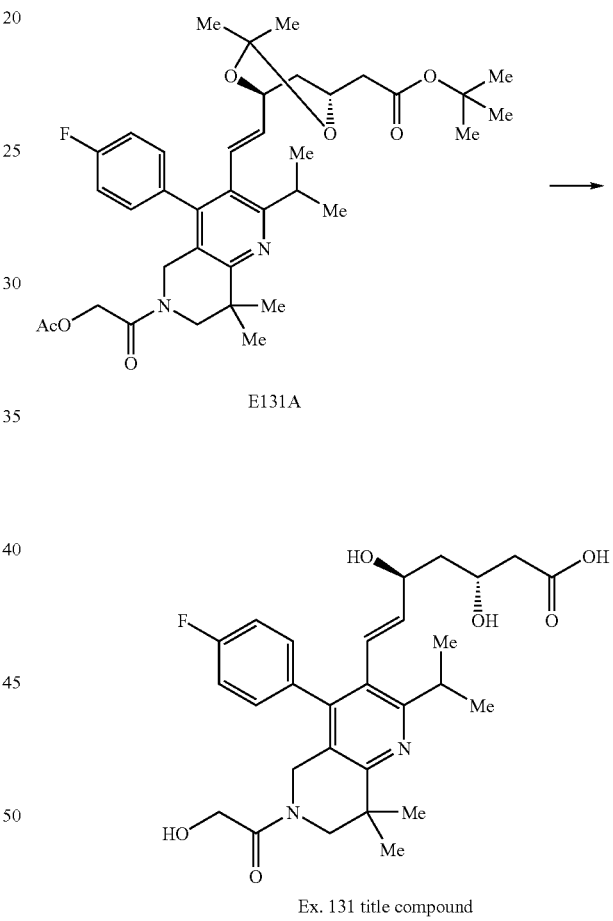

E131A

Ex. 131 title compound

A solution of E131A (167 mg, 0.25 mmol) and aqueous hydrochloric acid (6 N, 0.110 mL, 0.66 mmol) in THF (1 mL) was stirred at ambient temperature for 75 min. Aqueous sodium hydroxide (1 N, 1.2 mL, 1.2 mmol) was then added and the resultant mixture was stirred vigorously for 2 h. The reaction mixture was evaporated in vacuo and the residue was purified over C-18 silica gel to afford the title compound as the sodium salt (96 mg, 71%): HPLC (method 5) $t_R$=1.9 min; LCMS (ESI, pos. ion spectrum) m/z 515 (M+H).

Example 132

6-Heptenoic acid, 7-[4-(4-fluorophenyl)-5,6,7,8-tetrahydro-6-(methoxyacetyl)-8,8-dimethyl-2-(1-methylethyl)-1,6-naphthyridin-3-yl]-3,5-dihydroxy-, (3R,5S,6E)-

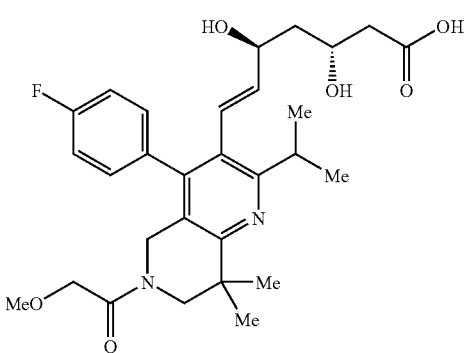

Part A:

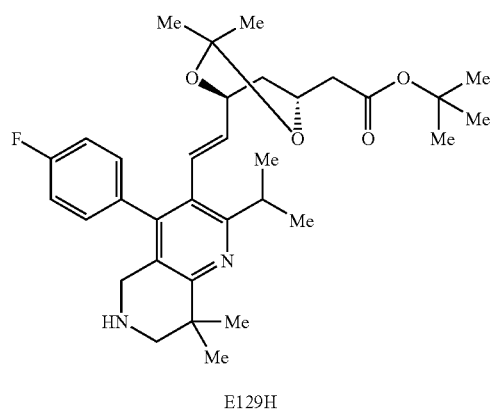
E129H

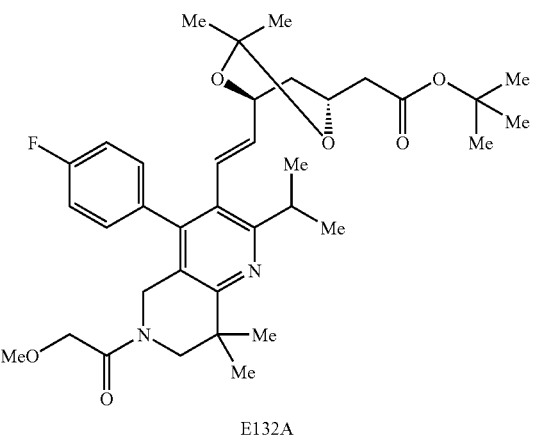
E132A

Methoxyacetyl chloride (42 mg, 0.036 mL, 0.39 mmol) and then diisopropylethylamine (66 mg, 0.089 mL, 0.51 mmol) were added to a solution of E129H (140 mg, 0.25 mmol) in methylene chloride (2.5 mL). After stirring at ambient temperature for 2 h, the reaction was transferred to a separatory funnel with methylene chloride and water. The aqueous layer was extracted with methylene chloride. The combined organic layers were dried over MgSO$_4$ and concentrated to afford 179 mg of a residue. Purification of the residue over silica gel afforded E132A (155 mg, 99%): HPLC (method 5) t$_R$=2.7 min; LCMS (ESI, pos. ion spectrum) m/z 625 (M+H).

Part B:

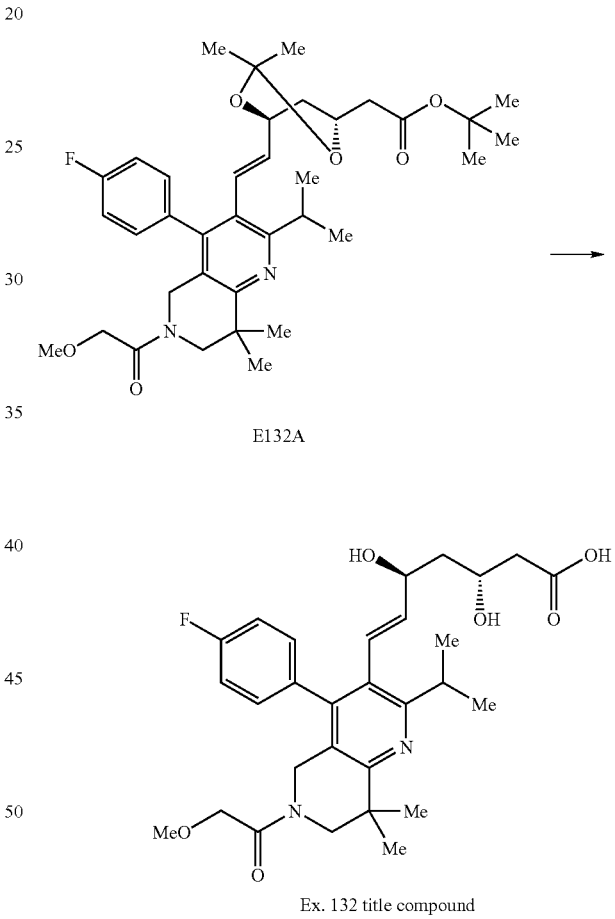

A solution of E132A (155 mg, 0.25 mmol) and aqueous hydrochloric acid (6 N, 0.110 mL, 0.66 mmol) in THF (1 mL) was stirred at ambient temperature for 75 min. Aqueous sodium hydroxide (1 N, 1.0 mL, 1.0 mmol) was then added and the resultant mixture was stirred vigorously for 2 h. The reaction mixture was evaporated in vacuo and the residue was purified over C-18 silica gel to afford the title compound as the sodium salt (78 mg, 57%): HPLC (method 5) t$_R$=2.1 min; LCMS (ESI, pos. ion spectrum) m/z 529 (M+H).

Example 133

6-Heptenoic acid, 7-[4-(4-fluorophenyl)-5,6,7,8-tetrahydro-2-(1-methylethyl)-6-(methylsulfonyl)-1,6-naphthyridin-3-yl]-3,5-dihydroxy-, (3R,5S,6E)-

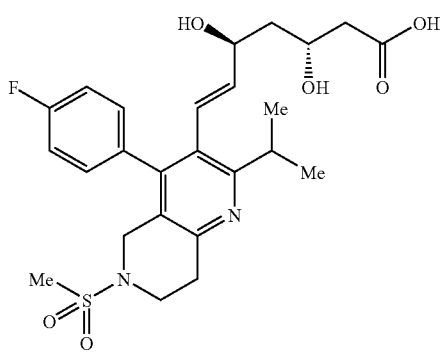

The title compound was prepared from phenylmethyl 4-oxo-1-piperidinecarboxylic acid using the same procedures described in Examples 129 Parts A-H and Example 130 Parts A-B: HPLC (method 5) $t_R$=1.3 min; LCMS (ESI, pos. ion spectrum) m/z 507 (M+H).

Example 134

6-Heptenoic acid, 7-[4-(4-fluorophenyl)-7,8-dihydro-2-(1-methylethyl)-6,6-dioxido-5H-thiopyrano[4,3-b]pyridin-3-yl]-3,5-dihydroxy-, (3R,5S,6E)-

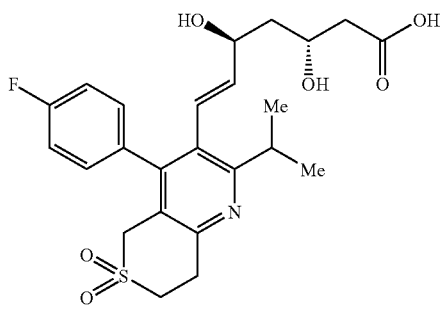

Part A:

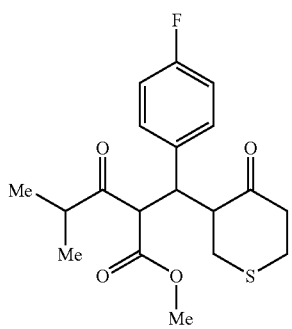

E134A was prepared from tetrahydrothiopyran-4-one using the procedure described in Example 102 Part C. E134A was used without further purification or characterization.

Part B:

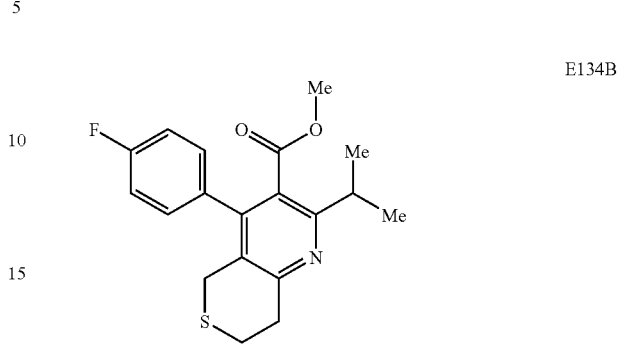

E134B was prepared as a yellow solid from E134A using the procedure described in E102 Part D: HPLC (method 9)>99%, $t_R$=1.8 min; LRMS (ESI, M+H) m/z 346.

Part C:

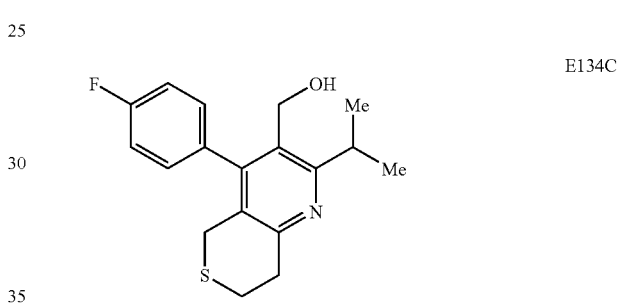

E134C was prepared as a yellow solid from E134B using the procedure described in Example 102 Part E: HPLC (method 9) 97%, $t_R$=0.9 min; LRMS (ESI, M+H) m/z 318.

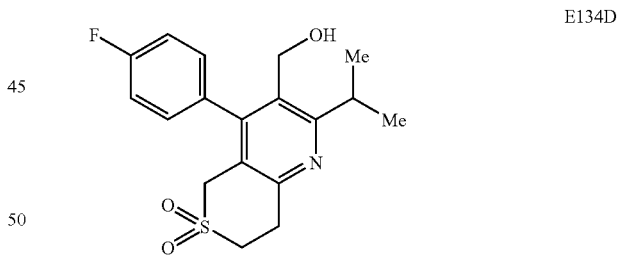

Part D:

To a solution of E134C (317.4 mg, 1.0 mmol) in dichloromethane (10 mL) cooled to 0° C. was added MCPBA (70%, 616.3 mg, 2.5 mmol). After 15 min, dichloromethane (10 mL) and 1 M NaHCO$_3$ (20 mL) were added, and the resulting mixture was stirred vigorously while warming to room temperature until two clear phases emerged. The organic phase was separated, washed (1 M NaHCO$_3$, saturated NaHCO$_3$), dried (Na$_2$SO$_4$), and then concentrated in vacuo. Purification of the residue by flash chromatography (SiO$_2$, 5%, 10%, then 15% acetone/dichloromethane) afforded E134D as a white solid (290.4 mg, 83%): HPLC (method 9)>95%, $t_R$=0.8 min; LRMS (ESI, M+H) m/z 350.

Part E:

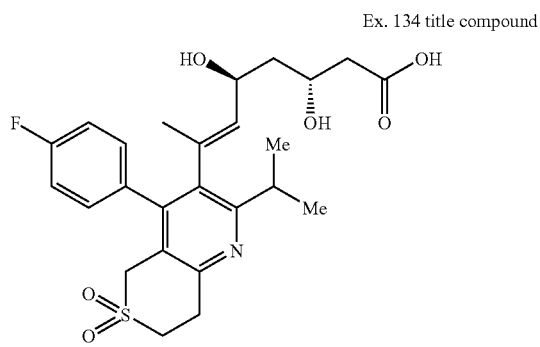

Ex. 134 title compound

The title compound was prepared as the sodium salt as a white lyophilate from E134D using the procedures described in Example 102 Parts G-I: HPLC (method 9)>99%, $t_R$=0.8 min; LRMS (ESI, M+H) m/z 478.

Example 135

6-Heptenoic acid, 7-[4-(4-fluorophenyl)-6,7,8,9-tetrahydro-9,9-dimethyl-2-(1-methylethyl)-7-oxo-5H-pyrido[2,3-c]azepin-3-yl]-3,5-dihydroxy-, (3R, 5S,6E)-

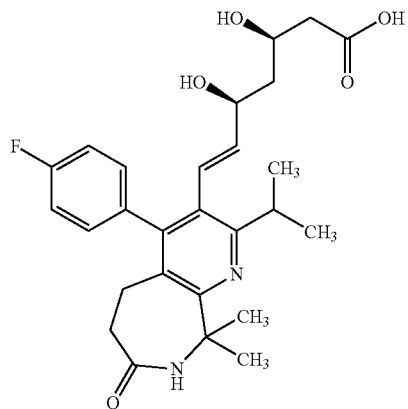

Part A:

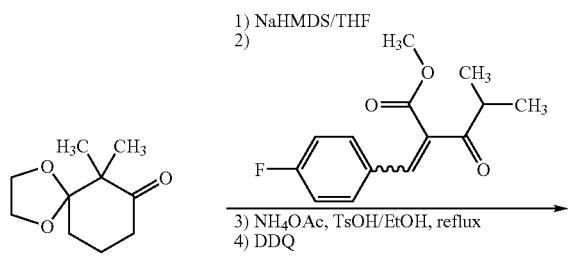

-continued

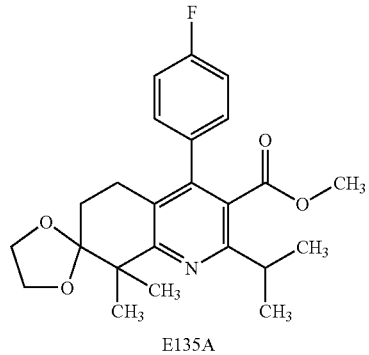

E135A

A NaHMDS solution in THF (65 mL, 1.0 M, 65 mmol) was diluted with 30 mL of dry THF and the mixture was cooled to −78° C. A solution of 6,6-dimethyl-1,4-dioxaspiro[4.5]decan-7-one (7.8 g, 42.4 mmol) in 20 mL of dry THF was added dropwise to the reaction over 10 min. After the addition, the mixture was stirred at −78° C. for 30 min. A solution of methyl 2-[(4-fluorophenyl)methylene]-4-methyl-3-oxo-pentanoate (13 g, 52 mmol) in 20 mL of dry THF which had been precooled −78° C. was transferred quickly via a cannula. The reaction mixture was stirred at −78° C. for 2 h and was quenched with a solution of acetic acid (24 mL, 419 mmol) in 30 mL of THF. After warming to room temperature, the reaction was diluted with saturated ammonium chloride solution (30 mL) and extracted with ethyl acetate (3×100 mL). The organic fractions were combined, washed with saturated aqueous sodium chloride solution (100 mL), dried over magnesium sulfate, filtered and concentrated to provide a yellow oil (18.4 g, 100% yield): LCMS (method 1; ESI, pos. ion spectrum) $t_R$=1.9 min, m/z 435.

To a solution of the preceding yellow oil (18.4 g, 42.4 mmol) in 200 mL of absolute ethanol were added ammonium acetate (26.5 g, 344 mmol) and p-toluenesulfonic acid monohydrate (41 mg, 0.22 mmol). The reaction was heated at 80° C. for 12 h and cooled to room temperature. The excess ammonium acetate was removed by filtration and was washed with 100 mL of dichloromethane. The combined filtrates were concentrated to an oily residue The preceding oily residue was dissolved in 100 ml of 1,2-dichloroethane, and 2,3-dichloro-5,6-dicyano-1,4-benzoquinone (10.7 g, 47.1 mmol) was added. The dark solution was stirred for 3 h at room temperature. The solvent was evaporated in vacuo. The residue was dissolved in 20 mL of dichloromethane and purified by flash chromatography on a silica gel column with 5-20% ethyl acetate/hexanes as the eluant to provide 14 g (80% yield) of E135A as a white solid: HPLC (method 3) $t_R$=4.2 min; LCMS (method 1; ESI, pos. ion spectrum) $t_R$=2.1 min, m/z 414.

Part B:

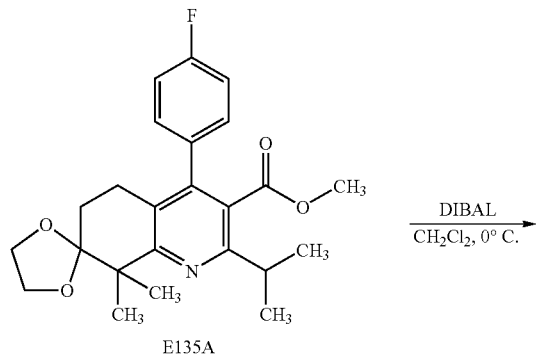
E135A

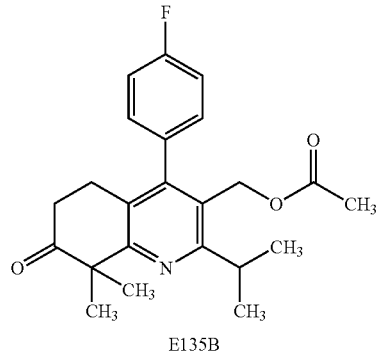
E135B

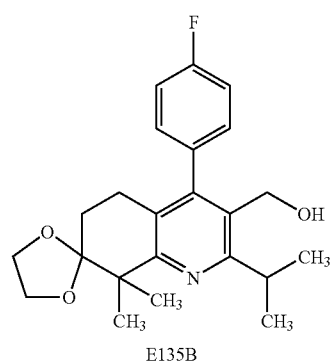
E135B

To a solution of E135A (12.34 g, 29.9 mmol) in dry dichloromethane (150 mL) at 0° C. was added dropwise a DIBAL solution (68 mL, 1.0 M in dichloromethane, 68 mmol). After 1 h at 0° C., the reaction was quenched by careful addition of methanol (5 mL). The mixture was diluted with 100 mL of 25%-saturated aqueous potassium sodium tartrate and the mixture was stirred at room temperature for 3 h. The organic layer was separated, dried over magnesium sulfate, filtered and concentrated. Flash chromatography of the residue on a silica gel column with 20-50% ethyl acetate/hexanes as the eluant provided 10.9 g (95% yield) of E135B as a white solid: HPLC (method 3) $t_R$=3.9 min; LCMS (method 1; ESI, pos. ion spectrum) $t_R$=1.7 min, m/z 386.

Part C:

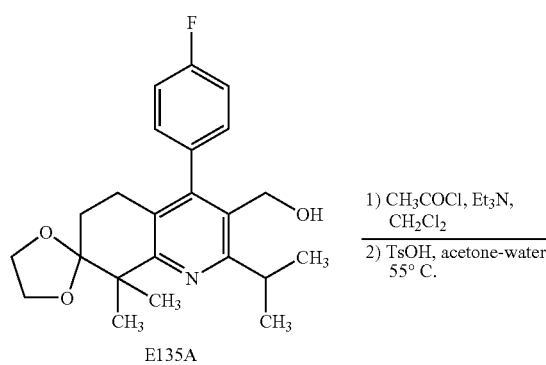
E135A

To a solution of E135B (10.9 g, 28.3 mmol) in dry dichloromethane (100 mL) at 0° C. were added triethylamine (6.78 mL, 48.8 mmol) and acetyl chloride (3.47 mL, 48.8 mmol). The reaction was stirred room temperature for 30 min and quenched with saturated aqueous sodium bicarbonate solution (50 mL). The organic layer was separated. The aqueous layer was extracted with dichloromethane (2×100 mL). The organic fractions were combined, washed with saturated aqueous sodium chloride solution (100 mL), dried over magnesium sulfate, filtered and concentrated to afford an oil: LCMS (method 1; ESI, pos. ion spectrum) $t_R$=2.1 min, m/z 428. The preceding oil was dissolved in acetone (130 mL) and water (5 mL). p-Toluenesulfonic acid monohydrate (2.64 g, 13.9 mmol) was added. The mixture was heated to 51° C. for 14 h and 55° C. for 24 h. The solvent was removed in vacuo and the residue was chromatographed on a silica gel column with 10-20% ethyl acetate in hexanes to afford 6.5 g of E135C as a white solid: LCMS (method 1; ESI, pos. ion spectrum) $t_R$=2.0 min, m/z 384.

Part D:

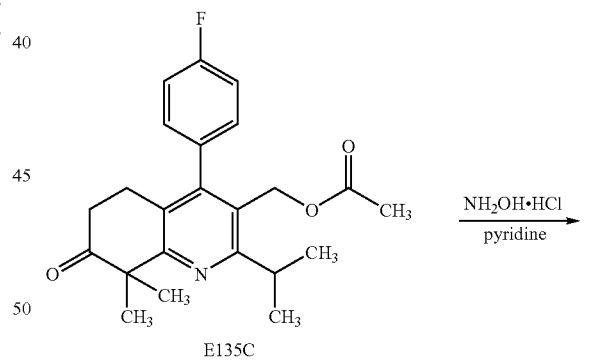
E135C

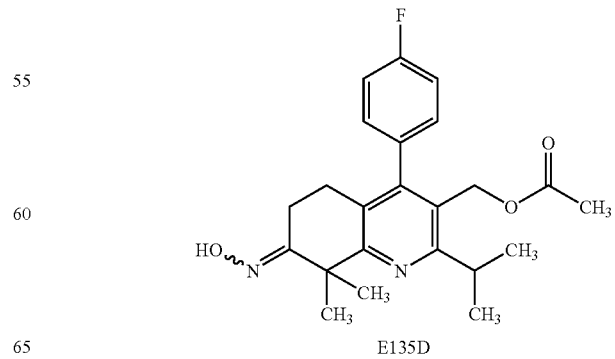
E135D

A solution of E135C (1.2 g, 3.13 mmol) and hydroxylamine hydrochloride (0.65 g, 9.4 mmol) in dry ethanol (4 mL) and pyridine (4 mL) was heated at 90° C. for 2 h. The solvent was evaporated and the residue was taken up in ethyl acetate (30 mL) and water (10 mL). The organic layer was separated, washed with water (2×10 mL) and saturated aqueous sodium chloride solution (10 mL), dried over magnesium sulfate, filtered, and concentrated to afford E135D (1.25 g, 100% yield) as a white solid: LCMS (method 1; ESI, pos. ion spectrum) $t_R$=1.9 min, m/z 399.

Part E:

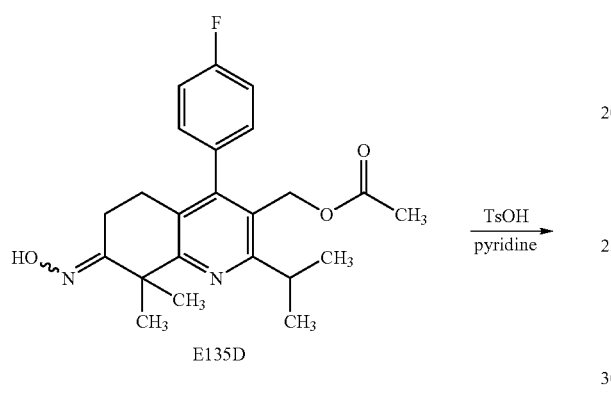

A solution in E135D (343 mg, 0.862 mmol) in dry pyridine (3 mL) was cooled to 0° C. p-Toluenesulfonic acid monohydrate (222 mg, 1.16 mmol) was added. The mixture was stirred at 0° C. for 20 min and at room temperature for 2 h, and was then heated to 90° C. for 14 h. The reaction was cooled to room temperature, diluted with saturated aqueous sodium bicarbonate solution (10 mL) and extracted with ethyl acetate (3×20 mL). The organic fractions were combined, washed with saturated aqueous sodium chloride (10 mL), dried over magnesium sulfate, filtered and concentrated. Preparative HPLC purification of the residue afforded 100 mg (29% yield) of E135E as a white solid: HPLC (method 3) $t_R$=3.9 min; LCMS (method 1; ESI, pos. ion spectrum) $t_R$=1.9 min, m/z 399.

Part F:

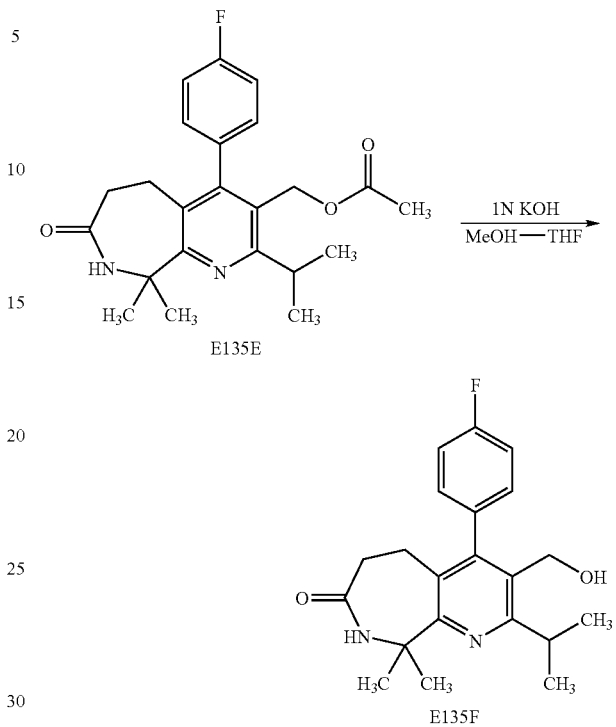

To a solution of E135E (100 mg, 0.25 mmol) in 3 mL of dry tetrahydrofuran was added potassium hydroxide solution (2 mL, 1.0 N, 2 mmol) and methanol (1 mL). The mixture was stirred at room temperature for 2 h and concentrated in vacuo to remove the organic solvent. The residue was diluted with saturated aqueous sodium bicarbonate solution (5 mL) and extracted with ethyl acetate (3×10 mL). The organic fractions were combined, washed with saturated aqueous sodium chloride solution (10 mL), dried over magnesium sulfate, filtered and concentrated. Chromatography of the residue on a silica gel column with 30-50% ethyl acetate/hexanes as the eluant afforded 85 mg (95% yield) of E135F as a white solid: HPLC (method 3) $t_R$=3.6 min; LCMS (method 1; ESI, pos. ion spectrum) $t_R$=1.7 min, m/z 357.

Part G:

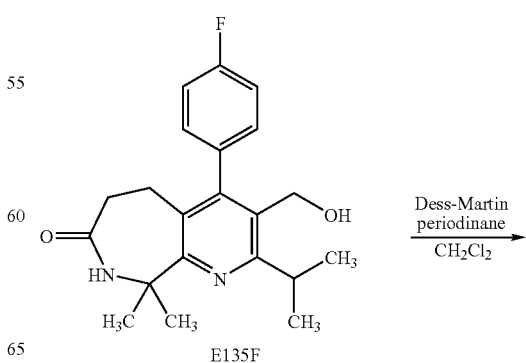

-continued

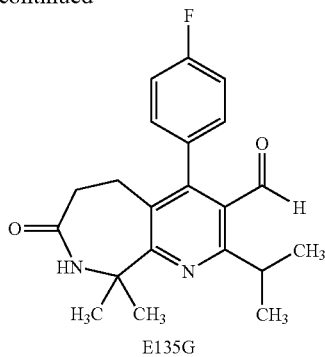

E135G

To a solution of E135F (35.6 mg, 0.10 mmol) in 2 mL of methylene chloride was added Dess-Martin periodinane (171 mg, 0.40 mmol). The reaction was stirred for 1 h and was diluted with water (2 mL) and methylene chloride (10 mL). The organic layer was separated, washed water (2 mL), dried over magnesium sulfate, filtered and concentrated. Flash chromatography of the residue on a silica gel column with 30-50% ethyl acetate/hexanes as the eluant provided 34 mg (96% yield) of E135G: HPLC (method 3) $t_R$=4.0 min; LCMS (method 1; ESI, pos. ion spectrum) $t_R$=1.9 min, m/z 355.

Part H:

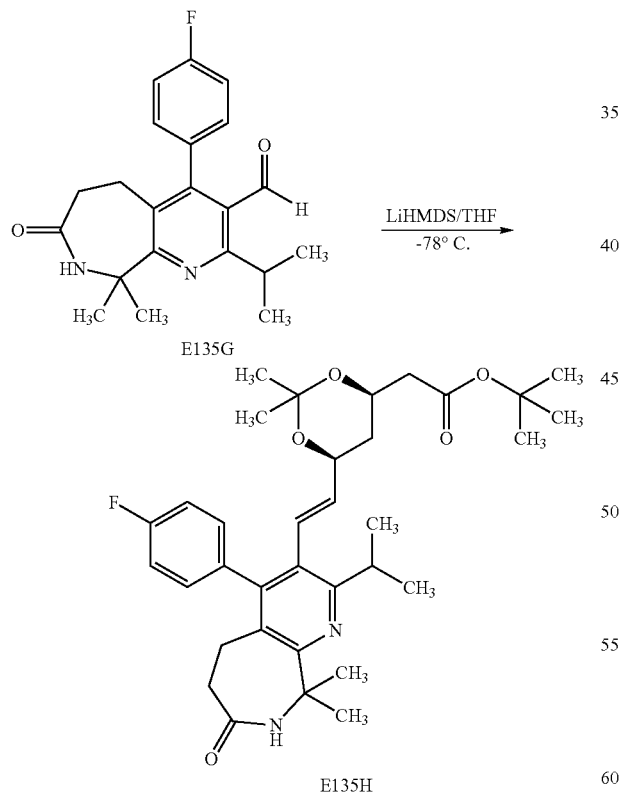

E135H

To a solution of E135G (34 mg, 0.096 mmol) and E1D (43 mg, 0.10 mmol) in THF (2 mL) at −78° C. was added LiHMDS (0.38 mL, 1.0 M in THF, 0.38 mmol) dropwise. After 1 h, the reaction was quenched at −78° C. by the addition of 2 mL of saturated aqueous ammonium chloride solution followed by the addition of ethyl acetate (10 mL). The aqueous layer was extracted with an additional 10 mL of ethyl acetate. The organic fractions were combined, washed with saturated aqueous sodium chloride solution (5 mL), dried with magnesium sulfate, filtered, and concentrated. Purification of the residue by flash chromatography on a silica gel column with 10-30% ethyl acetate/hexanes as the eluant provided 55 mg (99% yield) of E135H as an oil: HPLC (method 3) $t_R$=4.6 min; LCMS (method 1; ESI, pos. ion spectrum) $t_R$=2.2 min, m/z 581.

Part I:

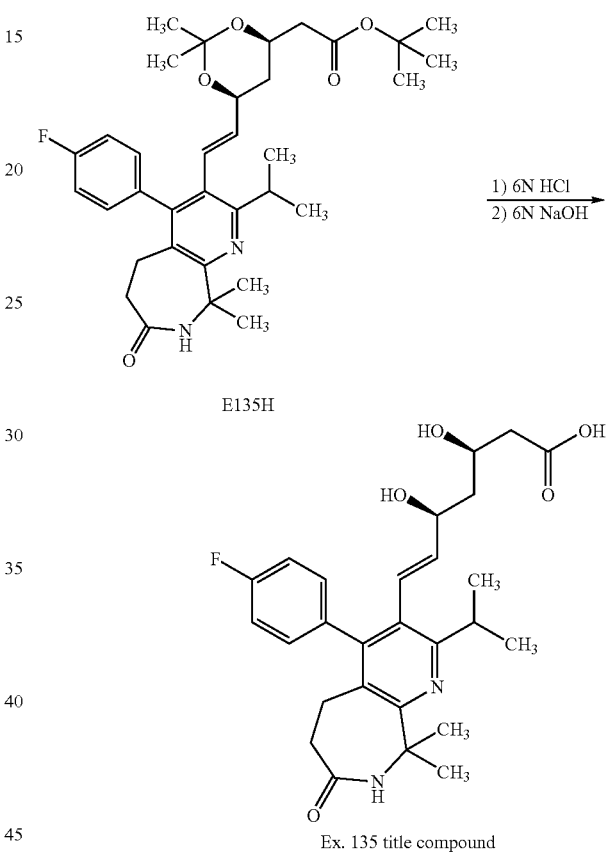

Ex. 135 title compound

To a stirred solution of E135H (55 mg, 0.095 mmol) in tetrahydrofuran (1 mL) was added aqueous HCl (0.057 mL, 6.0 N, 0.34 mmol). After 20 min, aqueous NaOH (0.115 mL, 6.0 N, 0.69 mmol) was added. After 30 min, methanol (1 mL) was added to make a homogeneous solution. After an additional 15 min, the organic solvent was removed in vacuo to yield a thick pale-yellow slurry. This material was dissolved in 10 mL of water and was loaded onto a 40 μm C-18 silica gel column (60 g, which was prewashed with 50 mL of MeOH and 50 mL of deionized water). The column was eluted consecutively with water (100 mL), 5% methanol in water (100 mL), 10% methanol in water (100 mL), 20% methanol in water (100 mL), 25% methanol in water (100 mL), 30% methanol in water (100 mL), 40% methanol in water (100 mL), and 50% methanol in water (100 mL). The product-containing fractions (fractions between 40-50% methanol in water) were combined and concentrated in vacuo to dryness. The residue was dissolved in methanol (5 mL) and filtered through a sintered funnel and the filtrate was concentrated to dryness. The residue was dissolved in 5 mL of water and lyophilized to afford the title compound (20 mg, 44% yield) as a white solid: HPLC (method 3) $t_R$=3.4 min; LCMS (method 1; ESI, pos. ion spectrum) $t_R$=1.6 min, m/z 485.

Example 136

2H-pyran-2-one, 6-[(E)-2-[8-(4-fluorophenyl)-6,7-dihydro-10-(1-methylethyl)-5H-pyrido[2,3-c]tetrazolo[1,5-a]azepin-9-yl]ethenyl]tetrahydro-4-hydroxy-, (4R,6S)-

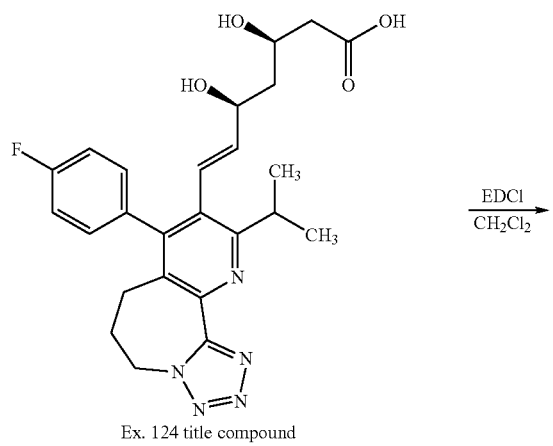

Ex. 124 title compound $\xrightarrow{\text{EDCl}}{\text{CH}_2\text{Cl}_2}$

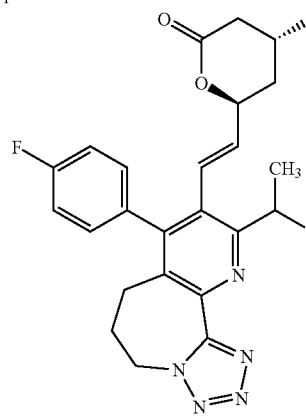

To a stirred suspension of Example 124 title compound (1.4 g, 2.78 mmol) in methylene chloride (100 mL) was added 1-(3-dimethylaminopropyl)-3-ethylcarbodiimide hydrochloride (586 mg, 3.05 mmol). After 4 h, the reaction was diluted with water (20 mL) and filtered. The white solid was washed with water (100 mL) and dried in vacuo to afford the title compound (870 mg, 68% yield) as a white solid: HPLC (method 3) $t_R$=3.1 min; LCMS (method 1; ESI, pos. ion spectrum) $t_R$=1.4 min, m/z 464.

What is claimed is:

1. A compound having the structure

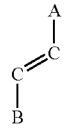

wherein A is selected from

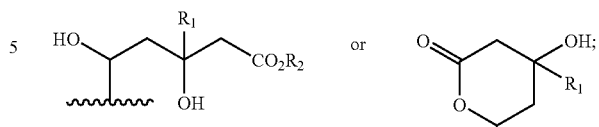

wherein
$R_1$ and $R_2$ are the same or different and are independently selected from H or lower alkyl;
B is

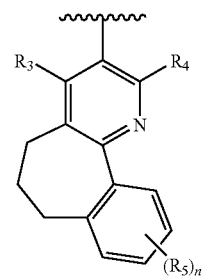

B1 wherein
n is 1 or 2;
$R_6$ (a substituent in the benzo ring) is, when n=1,
  nitro,
  —N(H)C(O)NR$_8$R$_9$,
  —N(H)C(O)CH$_2$NMe$_2$,
  —N(H)C(O)NH$_2$
  tetrazole linked through its carbon atom and which is optionally substituted by methyl,
  methyl substituted with N(H)SO$_2$Me or N(H)C(O)N-HMe,
  SO$_2$N(H)R$_{10}$,
  C(O)N(H)R$_{11}$,
  —N=C(NH$_2$)NH$_2$ or

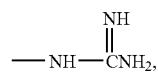

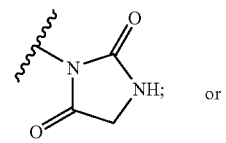

or
$R_6$ is identical at each occurrence and is, when n=2,
  CN,
  CO$_2$H,
  COOMe; or
$R_6$ is, when $R_3$ is 3-carboxy-4-fluorophenyl and n=1 or 2,
  H,
  alkyl,
  alkenyl, alkynyl,
cycloalkyl,
aryl,
heterocyclo, or
an alkyl substituent;
  wherein each of the above $R_6$ groups may be independently substituted with a member selected from the group consisting of halogen, nitro, cyano, $OR_{22}$, alkyl, alkenyl, alkynyl, cycloalkyl, aryl or heterocyclo;
  wherein $R_{22}$ is selected from the group consisting of H, $C_1$-$C_8$alkyl, $C_2$-$C_8$alkenyl, $C_2$-$C_8$alkynyl, $C_3$-$C_8$cycloalkyl, $C_6$-$C_{10}$aryl or $C_3$-$C_9$heterocyclo;
$R_3$ and $R_4$ are the same or different and are independently selected from
H,
alkyl,
alkenyl,
alkynyl,
cycloalkyl,
aryl, or
heterocyclo (wherein the attachment atom in the heterocyclo group is a carbon);
  wherein each of the above $R_3$ and $R_4$ groups may be independently substituted with a member selected from the group consisting of halogen, nitro, cyano, $OR_{22}$, alkyl, alkenyl, alkynyl, cycloalkyl, aryl or heterocyclo;
  wherein $R_{22}$ is selected from the group consisting of H, $C_1$-$C_8$alkyl, $C_2$-$C_8$alkenyl, $C_2$-$C_8$alkynyl, $C_3$-$C_8$cycloalkyl, $C_8$-$C_{10}$aryl or $C_3$-$C_9$heterocyclo;
$R_8$ is H, or methyl;
$R_9$ is
  a) alkyl which is optionally substituted by one or more groups independently selected from
    carboxy,
    methylamino,
    dimethylamino,
    aminoalkyl,
    and/or hydroxyl,
  b) alkyl substituted by carboxy and amino, or
  c) heterocyclo;
  wherein each of the above $R_9$ groups may be independently substituted with a member selected from the group consisting of halogen, nitro, cyano, $OR_{22}$, alkyl, alkenyl, alkynyl, cycloalkyl, aryl or heterocyclo;
  wherein $R_{22}$ is selected from the group consisting of H, $C_1$-$C_8$alkyl, $C_2$-$C_8$alkenyl, $C_2$-$C_8$alkynyl, $C_3$-$C_8$cycloalkyl, $C_8$-$C_{10}$aryl or $C_3$-$C_9$heterocyclo;
$R_{10}$ is
  H, or
  alkyl which is optionally substituted with one or more groups independently selected from
    hydroxy,
    dimethylamino and/or 4-morpholino,
    $SO_2Me$, $C(O)Me$, or
    $C(O)NHMe$;
$R_{11}$ is
  alkyl (which is optionally substituted with dimethylamino),
  MeO,
  $SO_2Me$, or
  heterocyclo;

or a pharmaceutically acceptable salt thereof, or an ester thereof, a prodrug ester thereof, and all stereoisomers thereof.

2. The compound as defined in claim 1 where the A group is in the form of a free acid, a physiologically acceptable and hydrolyzable ester or δ lactone thereof, or an alkali metal salt, alkaline earth metal salt or an amino acid salt.

3. The compound as defined in claim 1 wherein
$R_1$ is H;
the A group is a free acid, a physiologically acceptable and hydrolyzable ester or δ lactone thereof, or an alkali metal salt, alkaline earth metal salt or an amine salt or an amino acid salt;
C=C is trans;
$R_3$ is aryl; and
$R_4$ is alkyl or cycloalkyl,
  wherein each of the above $R_3$ and $R_4$ groups may be independently substituted with a member selected from the group consisting of halogen, nitro, cyano, $OR_{22}$, alkyl, alkenyl, alkynyl, cycloalkyl, aryl or heterocyclo;
  wherein $R_{22}$ is selected from the group consisting of H, $C_1$-$C_8$alkyl, $C_2$-$C_8$alkenyl, $C_2$-$C_8$alkynyl, $C_3$-$C_8$cycloalkyl, $C_8$-$C_{10}$aryl or $C_3$-$C_9$heterocyclo.

4. The compound as defined in claim 1 having the structure

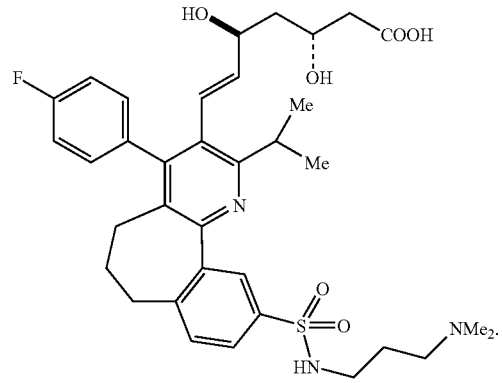

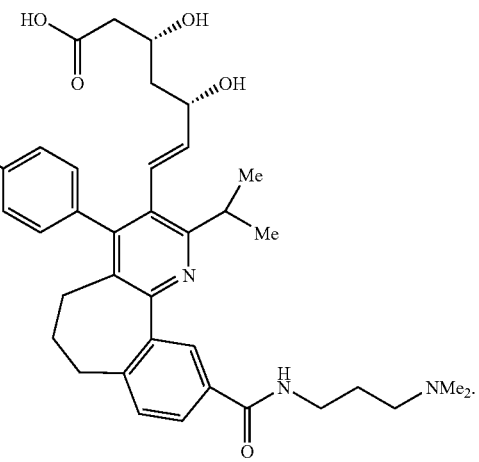

-continued

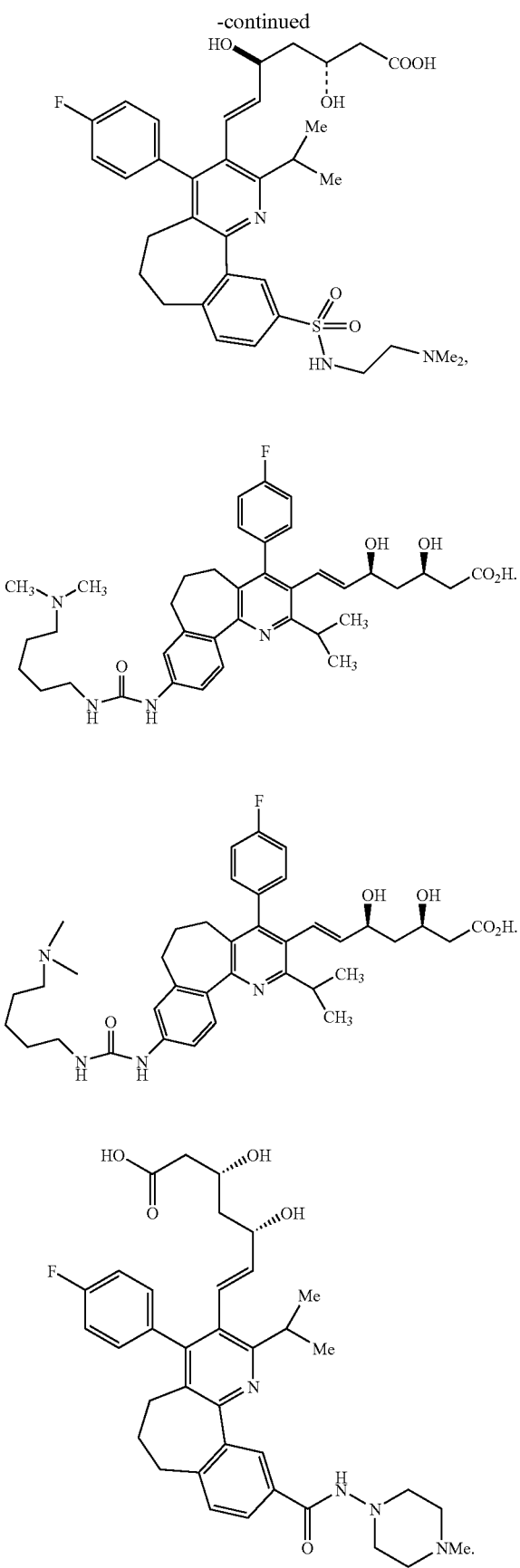

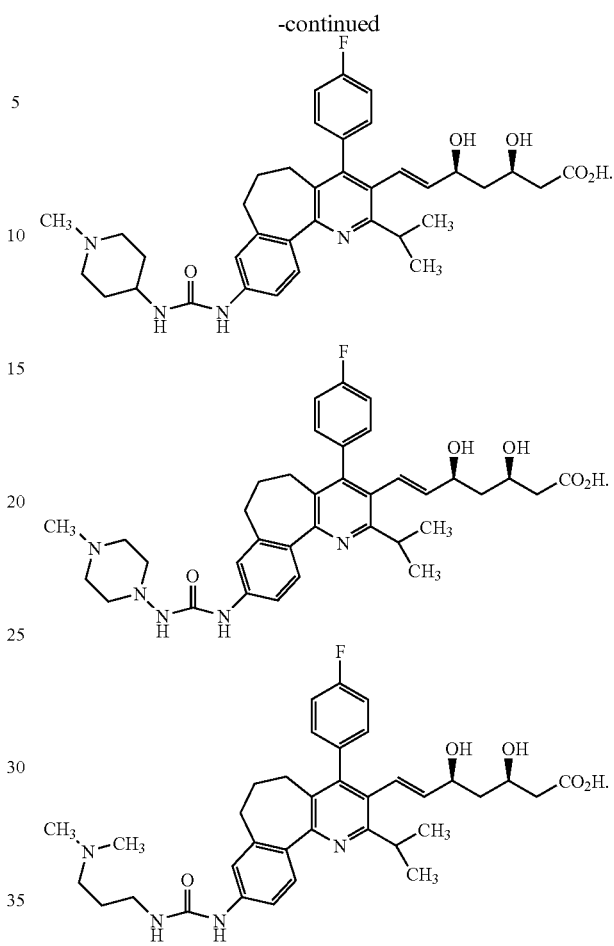

5. A pharmaceutical composition comprising a compound as defined in claim 1 and a pharmaceutically acceptable carrier therefor.

6. A pharmaceutical combination comprising the HMG CoA reductase inhibitor compound as defined in claim 1 and an antidiabetic agent which is 1, 2, 3 or more of metformin, glyburide, glimepiride, glipyride, glipizide, chlorpropamide, gliclazide, acarbose, miglitol, pioglitazone, troglitazone, rosiglitazone, muraglitazar, insulin, Gl-262570, isaglitazone, JTT-501, N,N-2344, L895645, YM-440, R-119702, AJ9677, repaglinide, nateglinide, KAD1129, GW-409544, KRP297, AC2993, LY315902, P32/98 and/or NVP-DPP-728A, or an anti-obesity agent which is orlistat, ATL-962, AJ9677, L750355, CP331648, sibutramine, topiramate, human Ciliary neurotrophic factor with a 15 amino acid truncation of the C-terminus and 2 amino acid substitutions, dexamphetamine, phentermine, phenylpropanolamine, and/or mazindol, P57 or CP-644673 (Pfizer); or an antihypertensive agent which is an ACE inhibitor which is captopril, fosinopril, enalapril, lisinopril, quinapril, benazepril, fentiapril, ramipril or moexipril;

an NEP/ACE inhibitor which is omapatrilat, gemopatrilat, or CGS 30440;

an angiotensin II receptor antagonist which is irbesartan, losartan or valsartan;

amlodipine besylate, prazosin HCl, verapamil, nifedipine, nadolol, propranolol, or clonidine HCl, carvediol; atenolol, hydrochlorothiazide, torasemide, furosemide, spironolactone or indapamide; and the lipid modulating agent is pravastatin, lovastatin, simvastatin, atorvastatin, cerivastatin, fluvastatin, pitavastatin, rosuvastatin, fenofibrate, gemfibrozil, clofibrate, avasimibe, TS-962, MD-700, cholestagel, niacin, and/or LY295427;

or which is an anti-Alzheimer's agent which is tacrine HCl, donepezil;

an antiosteoporosis agent, which is parathyroid hormone, alendronate, coenzyme $Q_{10}$;

a chondroprotective compound which is polysulfated glycosaminoglycan (PSGAG), glucosamine, chondroitin sulfate (CS), hyaluronic acid (HA), pentosan polysulfate (PPS), doxycycline or minocycline;

a cyclooxygenase (COX)-2 inhibitor, which is celecoxib or rofecoxib.

7. The combination as defined in claim 6 wherein the HMG CoA reductase inhibitor is in combination with a platelet aggregation inhibitor which is aspirin, clopidogrel, ticlopidine, dipyridamole, ifetroban, abciximab, tirofiban, eptifibatide, or anagrelide.

8. The combination as defined in claim 7 wherein the platelet inhibitor is clopidogrel, aspirin or a combination of clopidogrel and aspirin.

* * * * *

UNITED STATES PATENT AND TRADEMARK OFFICE
CERTIFICATE OF CORRECTION

PATENT NO. : 7,659,281 B2
APPLICATION NO. : 11/789335
DATED : February 9, 2010
INVENTOR(S) : Philip D. Stein et al.

It is certified that error appears in the above-identified patent and that said Letters Patent is hereby corrected as shown below:

In the Claims:

Claim 4:

Column 448, line 44, change "." to -- , --.

Column 448, line 64, change "." to -- , --.

Column 449, line 25, change "." to -- , --.

Column 449, lines 34 to 46, change " 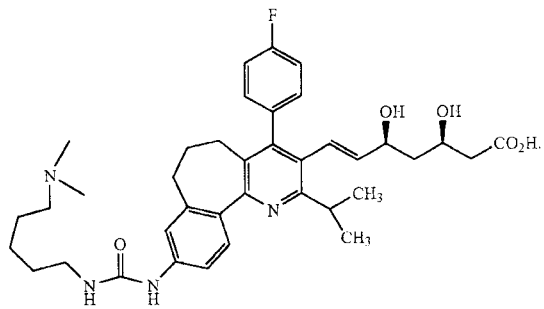 " to

-- 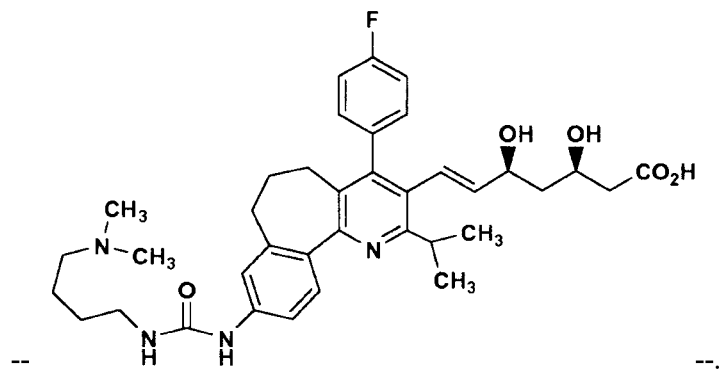 --.

Signed and Sealed this
Eighth Day of November, 2011

David J. Kappos
*Director of the United States Patent and Trademark Office*

CERTIFICATE OF CORRECTION (continued)
U.S. Pat. No. 7,659,281 B2

In the Claims:

Claim 4 (continued):

Column 449, line 66, change "." to -- , --.

Column 450, line 8, change "." to -- , --.

Column 450, line 19, change "." to -- , --.

Claim 6:

Column 450, line 48, change "N,N-2344" to -- NN-2344 --.

Column 450, line 65, change "carvediol;" to -- carvediol, --.